US007511062B2

(12) United States Patent
Kuang et al.

(10) Patent No.: US 7,511,062 B2
(45) Date of Patent: Mar. 31, 2009

(54) SUBSTITUTED 2-QUINOLYL-OXAZOLES USEFUL AS PDE4 INHIBITORS

(75) Inventors: Rongze Kuang, Green Brook, NJ (US); David Blythin, North Caldwell, NJ (US); Neng-Yang Shih, Warren, NJ (US); Ho-Jane Shue, Las Vagas, NV (US); Xiao Chen, Edison, NJ (US); Jianhua Cao, Edison, NJ (US); Danlin Gu, Kirkland, WA (US); Ying Huang, Berkeley Heights, NJ (US); John H. Schwerdt, Lake Hiawatha, NJ (US); Pauline C. Ting, New Providence, NJ (US); Shing-Chun Wong, Union, NJ (US); Li Xiao, Cranbury, NJ (US)

(73) Assignee: Schering Corporation, Kenilworth, NJ (US)

( * ) Notice: Subject to any disclaimer, the term of this patent is extended or adjusted under 35 U.S.C. 154(b) by 568 days.

(21) Appl. No.: 11/130,359

(22) Filed: May 16, 2005

(65) Prior Publication Data
US 2006/0106062 A1    May 18, 2006

Related U.S. Application Data

(60) Provisional application No. 60/572,266, filed on May 18, 2004.

(51) Int. Cl.
*C07D 215/38* (2006.01)
*A61K 31/44* (2006.01)
(52) U.S. Cl. .................. 514/312; 514/314; 546/153; 546/159
(58) Field of Classification Search .............. 546/153, 546/159; 514/312, 314
See application file for complete search history.

(56) References Cited

U.S. PATENT DOCUMENTS

| 5,804,588 | A | 9/1998 | Dyke et al. |
|---|---|---|---|
| 5,834,485 | A | 11/1998 | Dyke et al. |
| 6,069,151 | A | 5/2000 | Dyke et al. |
| 6,313,116 | B1 | 11/2001 | Dyke et al. |
| 6,787,552 | B2 | 9/2004 | Sakuma et al. |
| 2004/0152744 | A1 | 8/2004 | Sakuma et al. |
| 2008/0027101 | A1* | 1/2008 | Ting et al. .................. 514/314 |

FOREIGN PATENT DOCUMENTS

| CA | 2489902 A1 | 12/2003 |
|---|---|---|
| WO | WO 98/20007 | 5/1998 |
| WO | WO 00/58303 | 10/2000 |
| WO | WO 01/46172 A1 | 6/2001 |

OTHER PUBLICATIONS

Prabhakar, et al., Characterization of cAMP-Dependent Inhibition . . . , Int. J. Immunopharmac., 16, 10 (1994) p. 805-816.
Mann, et al., New Oxazole-Based Peptidomimetics: Usefule Building Blocks . . . , Organic Letters, 5, 24 (2003) p. 4567-4570.
Grabowska, et al., 5-(Hydroxymethyl)oxazoles: Versatile Scaffolds for Combinatorial . . . , J. Comb. Chem. 2 (2000) p. 475-490.
Billah, Motasim, et al., Synthesis and Profile of SCH351591, a Novel PDE4 Inhibitor, Bioorganic & Medicinal Chemistry Letters 12 (2002) p. 1621-1623.

* cited by examiner

*Primary Examiner*—D. Margaret Seaman
(74) *Attorney, Agent, or Firm*—Anita W. Magatti; Serena I. Farquharson-Torres; Gerard E. Reinhardt

(57) ABSTRACT

The invention claims compounds of the formula

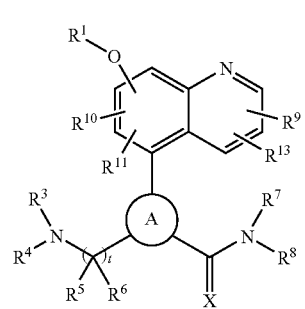

wherein

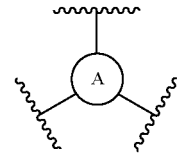

is a 5-membered heteroaryl;
X is S or O;
$R^1$ is H, alkyl, cycloalkyl, cylcoalkylalkyl-, —$CH_2F$, —$CHF_2$, —$CF_3$, —C(O)alkyl or —C(O)$NR^{18}R^{19}$;
$R^3$ and $R^4$ H, alkyl, hydroxyalkyl or —C(O)Oalkyl;
$R^5$ and $R^6$ are H, alkyl, hydroxyalkyl, alkoxyalkyl, mercaptoalkyl, —$CH_2F$, —$CHF_2$, —$CF_3$, —C(O)OH or —C(O)Oalkyl;
$R^7$ is H, alkyl, alkenyl, hydroxyalkyl, cycloalkyl, alkoxyalkyl, aminoalkyl, ($R^{17}$-phenyl)alkyl or —$CH_2$—C(O)—O-alkyl; and $R^8$ comprises alkyl, heteroaryl, phenyl or cycloalkyl, or heterocycloalkyl, all optionally substituted, or a cycloalkyl- or heterocycloalkyl-substituted amide; or
$R^7$ and $R^8$ and the nitrogen to which they are attached together form an optionally substituted ring; and the remaining variables are as defined in the specification. Also claimed are pharmaceutical compositions, the use of the compounds as PDE4 inhibitors, and combinations with other actives.

29 Claims, No Drawings

SUBSTITUTED 2-QUINOLYL-OXAZOLES USEFUL AS PDE4 INHIBITORS

CROSS REFERENCE TO RELATED APPLICATION

This application claims the benefit of U.S. Provisional Application 60/572,266, filed May 18, 2004.

FIELD OF THE INVENTION

The present invention relates to substituted 2-quinolyl-oxazoles, thiazoles, imidazoles and pyrazoles, pharmaceutical compositions comprising them, and their use as PDE4 inhibitors for treating a variety of diseases such as allergic and inflammatory diseases, CNS diseases and diabetes. Combinations with other agents useful in the treatment of several diseases are also claimed.

BACKGROUND

Phosphodiesterases are known to regulate cyclic AMP, and phosphodiesterase 4 (PDE4) has been shown to be the predominant regulator of cyclic AMP in respiratory smooth muscle and inflammatory cells. Inhibitors of PDE4 are useful in treating a variety of diseases, including allergic and inflammatory diseases, diabetes, central nervous system diseases, pain, and viruses that produce TNF.

Amino-substituted quinolyl PDE4 inhibitors are disclosed in U.S. Pat. No. 5,804,588; sulfonamide-substituted quinolyl PDE4 inhibitors are disclosed in U.S. Pat. No. 5,834,485; and (benzo-fused)heteroaryl-substituted PDE4 inhibitors are disclosed in U.S. Pat. No. 6,069,151.

SUMMARY OF THE INVENTION

The present invention relates to a compound having the structural formula I

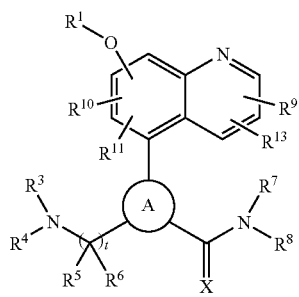

I or a pharmaceutically acceptable salt or solvate thereof, wherein

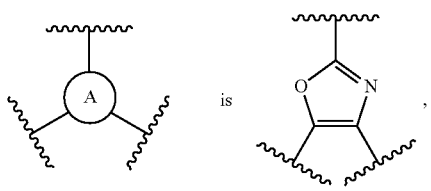

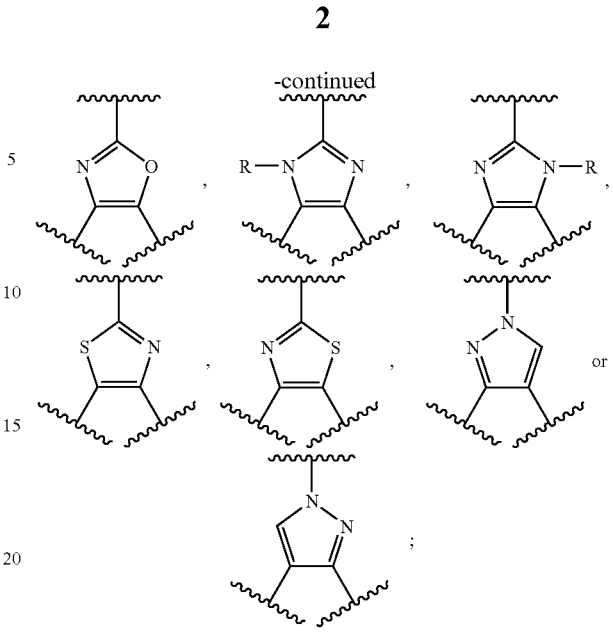

R is H or alkyl;

X is O or S;

$R^1$ is H, alkyl, cycloalkyl, cycloalkyl($C_1$-$C_4$)alkyl-, —$CH_2F$, —$CHF_2$, —$CF_3$, —C(O)alkyl or —C(O)$NR^{18}R^{19}$;

$R^3$ and $R^4$ are independently selected from the group consisting of H, alkyl, hydroxyalkyl and —C(O)Oalkyl;

$R^5$ and $R^6$ are independently selected from the group consisting of H, alkyl, hydroxyalkyl, alkoxyalkyl, mercaptoalkyl, —$CH_2F$, —$CHF_2$, —$CF_3$, —C(O)OH, —C(O)Oalkyl and —C(O)$NR^{43}R^{44}$;

t is 1 or 2;

$R^7$ is H, alkyl, alkenyl, hydroxyalkyl, cycloalkyl, alkoxyalkyl, aminoalkyl, ($R^{17}$-phenyl)alkyl or —$CH_2$—C(O)—O-alkyl;

$R^8$ is H, alkyl, alkenyl, alkoxy, alkoxyalkyl, hydroxyalkyl, dihydroxyalkyl, alkyl-$NR^{18}R^{19}$, cyanoalkyl, haloalkyl, $R^{23}$-heteroaryl, $R^{23}$-heteroarylalkyl, $R^{36}$-heterocycloalkyl, ($R^{36}$-heterocycloalkyl)alkyl, $R^{17}$-phenyl, ($R^{17}$-phenyl)alkyl, $R^{17}$-naphthyl, ($R^{17}$-naphthyl)alkyl, $R^{17}$-benzyloxy, -alkyl-C(O)—$NR^{18}R^{19}$, -alkyl-C(O)—N($R^{30}$)—($R^{23}$-heteroaryl), -alkyl-C(O)—($R^{17}$-phenyl), -alkyl-C(O)—($R^{36}$-heterocycloalkyl); -alkyl-N($R^{30}$)—C(O)Oalkyl, -alkyl-N($R^{30}$)—C(O)—$NR^{18}R^{19}$, -alkyl-N($R^{30}$)—C(O)alkyl, -alkyl-N($R^{30}$)—C(O)-(fluoroalkyl), -alkyl-N($R^{30}$)—C(O)—($R^{39}$-cycloalkyl), -alkyl-N($R^{30}$)—C(O)—($R^{17}$-phenyl), -alkyl-N($R^{30}$)—C(O)—($R^{23}$-heteroaryl), -alkyl-N($R^{30}$)—C(O)-alkylene-($R^{23}$-heteroaryl), -alkyl-NH—$SO_2$—$NR^{18}R^{19}$, -alkyl-N($R^{30}$)—($R^{17}$-phenyl), -alkyl-N($R^{30}$)—($R^{23}$-heteroaryl), -alkyl-O—($R^{17}$-phenyl), -alkyl-O—($R^{23}$-heteroaryl), -alkyl-N($R^{30}$)—$SO_2$-alkyl, alkylthioalkyl-, alkyl-$SO_2$-alkyl-, ($R^{35}$-phenylalkyl)-S-alkyl-, (hydroxyalkyl)-S-alkyl-, (alkoxyalkyl)-S-alkyl-, -alkyl-$CO_2$-alkyl, $R^{45}$-hydroxyalkyl, dihydroxyalkyl substituted by $R^{17}$-benzyloxy, dihydroxyalkyl substituted by $R^{17}$-phenyl, alkoxyalkyl substituted by $R^{17}$-phenyl, ($R^{17}$-phenyl)alkyl substituted by —$CO_2$alkyl, ($R^{17}$-phenyl)alkyl substituted by —C(O)N($R^{30}$)$_2$, alkyl substituted by ($R^{23}$-heteroaryl) and —C(O)$NR^{37}R^{38}$, haloalkyl substituted by $CO_2$alkyl, $R^{12}$-cycloalkyl, ($R^{12}$-cycloalkyl)alkyl,

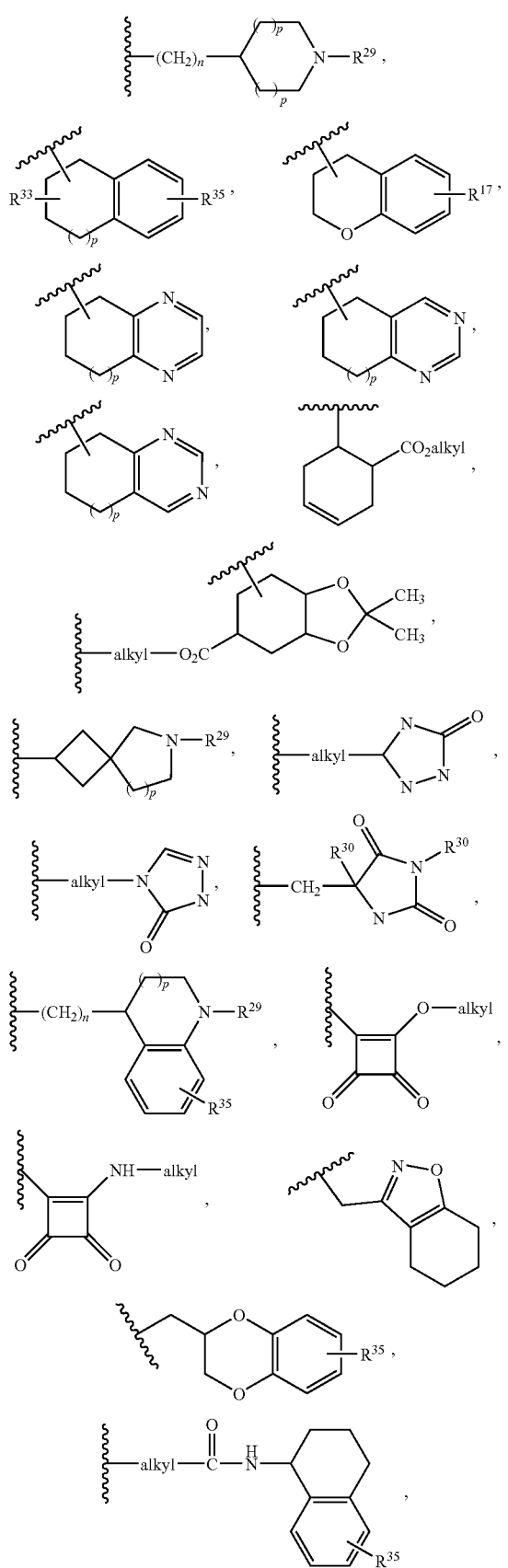
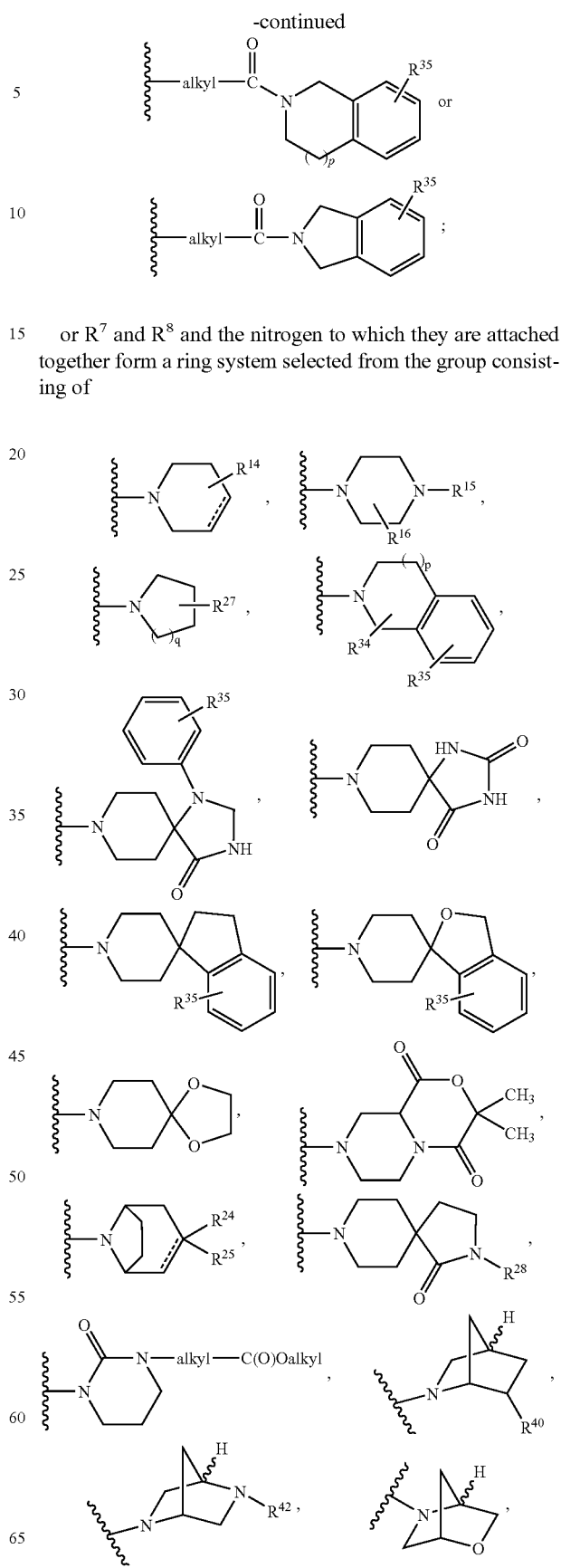
or $R^7$ and $R^8$ and the nitrogen to which they are attached together form a ring system selected from the group consisting of

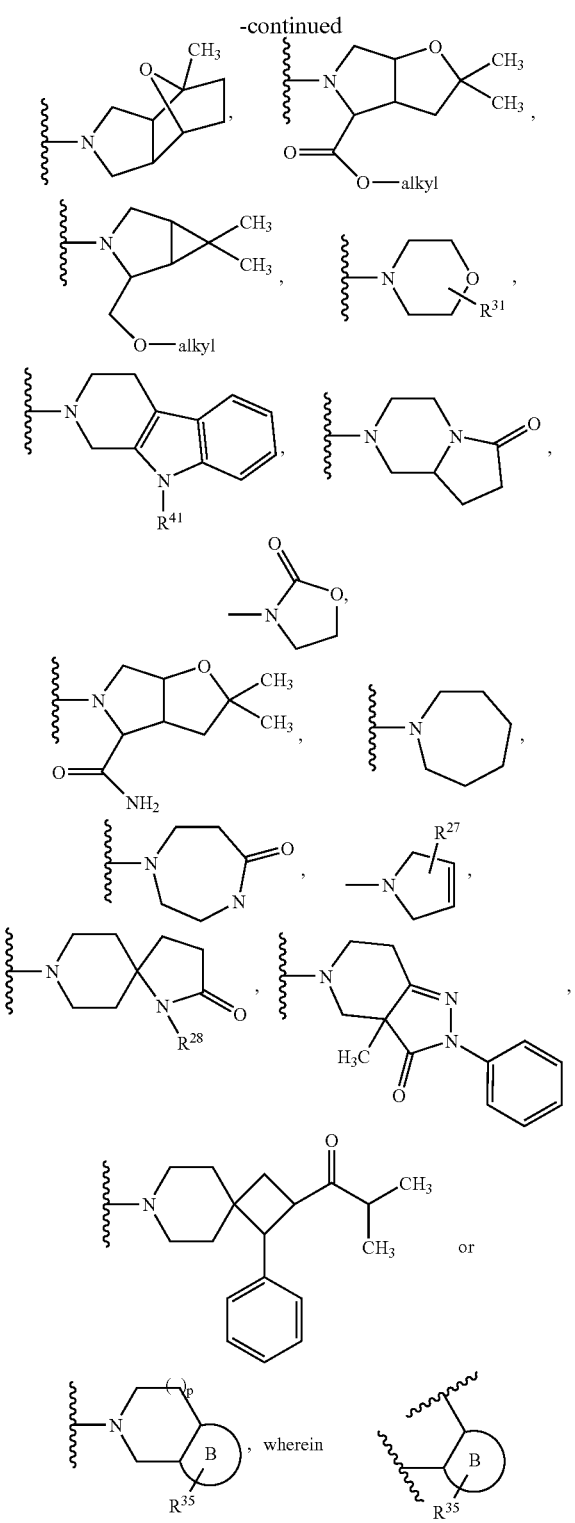

comprises an $R^{35}$-substituted 5 or 6-membered heteroaryl group fused to the piperidinyl or pyrrolidinyl ring;

p is 0 or 1;
q is 0 or 1;
the dotted line represents an optional double bond;
$R^9$ is H, halo, alkyl, cycloalkyl, —CH$_2$F, —CHF$_2$ or CF$_3$;

$R^{10}$, $R^{11}$, and $R^{13}$ are independently selected from the group consisting of H and halo;

$R^{12}$ is 1-3 substituents independently selected from the group consisting of H, alkyl, hydroxy, alkoxy, hydroxyalkyl, alkoxyalkyl, —C(O)Oalkyl, —(CH$_2$)$_n$—N(R$^{30}$)—C(O)-cycloalkyl, —(CH$_2$)$_n$—N(R$^{30}$)—C(O)alkyl, —(CH$_2$)$_n$—N(R$^{30}$)—C(O)Oalkyl, —(CH$_2$)$_n$—N(R$^{30}$)—(R$^{23}$-heteroaryl), —(CH$_2$)$_n$—N(R$^{30}$)—C(O)—NR$^{18}$R$^{19}$, —(CH$_2$)$_n$—C(O)—NR$^{18}$R$^{19}$, R$^{17}$-phenyl, R$^{35}$-heteroarylalkyl, R$^{35}$-heteroaryloxy, —C(O)-heterocycloalkyl, —O—C(O)-heterocycloalkyl, —O—C(O)—NR$^{18}$R$^{19}$, —NH—SO$_2$-alkyl, —NH—C(=NH)NH$_2$, and

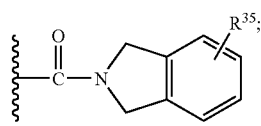

or two R$^{12}$ substituents on the same carbon form =O, =NOR$^{30}$ or =CH$_2$;

$R^{14}$ is 1 or 2 substituents independently selected from the group consisting of H, OH, halo, alkyl, alkoxy, hydroxyalkyl, alkoxyalkyl, —CF$_3$, CN, R$^{17}$-phenyl, (R$^{17}$-phenyl)alkyl, —NR$^{18}$R$^{19}$, alkyl-NR$^{18}$R$^{19}$, —(CH$_2$)$_n$—C(O)OH, —(CH$_2$)$_n$—C(O)Oalkyl, —(CH$_2$)$_n$—C(O)alkyl, —(CH$_2$)$_n$—C(O)(R$^{35}$-phenyl), —(CH$_2$)$_n$—C(O)(R$^{23}$-heteroaryl), —(CH$_2$)$_n$—C(O)NR$^{18}$R$^{19}$, —(CH$_2$)$_n$—C(O)N(R$^{30}$)—(CH$_2$)$_n$—(R$^{23}$-heteroaryl), —(CH$_2$)$_n$—N(R$^{30}$)—C(O)alkyl, —(CH$_2$)$_n$—N(R$^{30}$)—C(O)-(fluoroalkyl), —(CH$_2$)$_n$—N(R$^{30}$)—C(O)-(cycloalkyl), —(CH$_2$)$_n$—N(R$^{30}$)—C(O)(R$^{35}$-phenyl), —(CH$_2$)$_n$—N(R$^{30}$)—C(O)(R$^{23}$-heteroaryl), —(CH$_2$)$_n$—N(R$^{30}$)C(O)NR$^{18}$R$^{19}$, —(CH$_2$)$_n$—N(R$^{30}$)—C(O)Oalkyl, —(CH$_2$)$_n$—N(R$^{30}$)cycloalkyl, —(CH$_2$)$_n$—N(R$^{30}$)(R$^{17}$-phenyl), —(CH$_2$)$_n$—N(R$^{30}$)(R$^{23}$-heteroaryl), —(CH$_2$)$_n$—N(R$^{18}$)SO$_2$alkyl, —(CH$_2$)$_n$—N(R$^{20}$)SO$_2$—(R$_{17}$-phenyl), —(CH$_2$)$_n$—N(R$^{30}$)SO$_2$—CF$_3$, —CH$_2$S(O)$_{0-2}$(R$^{35}$-phenyl), —(CH$_2$)$_n$—OC(O)N(R$^{30}$)alkyl, R$^{23}$-heteroaryl, (R$^{23}$-heteroaryl)alkyl, (R$^{23}$-heteroaryl)oxy, (R$^{23}$-heteroaryl)amino, —CH(OH)—(R$^{17}$-phenyl), —CH(OH)—(R$^{23}$-heteroaryl), —C(=NOR$^{30}$)—(R$^{17}$-phenyl), —C(=NOR$^{30}$)—(R$^{23}$-heteroaryl), morpholinyl, thiomorpholinyl,

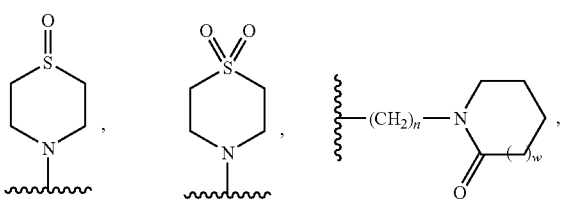

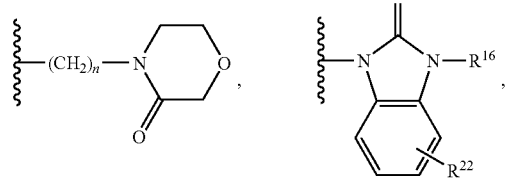

w is 0 or 1;

or two $R^{14}$ substituents and the carbon to which they are both attached form —C(=NOR$^{30}$)— or —C(O)—;

each n is independently 0, 1, 2 or 3;

$R^{15}$ is H, alkyl, cycloalkyl, (cycloalkyl)alkyl, hydroxyalkyl, alkoxyalkyl, haloalkyl, —C(O)Oalkyl, —C(O)O(R$^{30}$-cycloalkyl), -alkyl-C(O)O-alkyl, —C(O)O-alkylene-(R$^{35}$-phenyl), R$^{17}$-phenyl, (R$^{17}$-phenyl)alkyl, —CH—(R$^{17}$-phenyl)$_2$, R$^{23}$-heteroaryl, —(CH$_2$),—C(O)NR$^{18}$R$^{19}$, —SO$_2$-alkyl, —SO$_2$-cycloalkyl, —SO$_2$—CF$_3$, —SO$_2$—(R$^{35}$-phenyl), —SO$_2$—NR$^{18}$R$^{19}$, —C(O)alkyl, —C(O)-(fluoroalkyl), —C(O)—C(CH$_3$)(CF$_3$)$_2$, —C(O)—(R$^{17}$-phenyl), —C(O)—(R$^{23}$-heteroaryl), —C(O)-hydroxyalkyl, —C(O)-alkoxyalkyl, —C(O)—(R$^{39}$-cycloalkyl), —C(O)-alkylene-(R$^{17}$-phenyl), —C(O)-alkylene-(R$^{23}$-heteroaryl), —C(O)-alkylene-S—C(O)alkyl, —C(=S)—(R$^{17}$-phenyl), hydroxyalkyl substituted by R$^{17}$-phenyl, hydroxyalkyl substituted by R$^{23}$-heteroaryl, alkoxyalkyl substituted by R$^{17}$-phenyl, alkoxyalkyl substituted by R$^{23}$-heteroaryl, wherein z is 0, 1 or 2;

$R^{16}$ is 1 to 4 substituents independently selected from the group consisting of H, alkyl, R$^{17}$-phenyl, (R$^{17}$-phenyl)alkyl, (R$^{23}$-heteroaryl)alkyl, hydroxyalkyl, alkoxyalkyl and —C(O)Oalkyl, or two R$^{16}$ groups and the carbon to which they are both attached form —C(O)—;

$R^{17}$ is 1 to 3 substituents independently selected from the group consisting of H, halo, alkyl, cycloalkyl, —OH, hydroxyalkyl, alkoxy, alkoxyalkyl, —CN, —CF$_3$, —OCF$_3$, —OCHF$_2$, —OCH$_2$F, —C(O)OH, —C(O)Oalkyl, —C(O)O—(R$^{35}$-phenyl), —C(O)alkyl, —C(O)—(R$^{35}$-phenyl), —SOalkyl, —SO$_2$alkyl, —SO$_2$—CF$_3$, alkylthio, —NR$^{43}$R$^{44}$, -alkyl-NR$^{43}$R$^{44}$, R$^{35}$-phenyl, R$^{35}$-phenoxy, R$^{35}$-heteroaryl, R$^{35}$-heteroaryloxy, R$^{36}$-heterocycloalkyl, —C(O)—(R$^{36}$-heterocycloalkyl), hydroxyalkyl-NH—, —C(O)N(R$^{30}$)$_2$, —N(R$^{43}$)—(R$^{35}$-cycloalkyl) and —C(=NOR$^{30}$); or two R$^{17}$ substituents on adjacent carbon atoms together form —O—CH$_2$—O—, —O—(CH$_2$)$_2$—O—, —(CH$_2$)$_2$—O— or —O—CH$_2$—O—CH$_2$—;

$R^{18}$ and $R^{19}$ are independently selected from the group consisting of H, alkyl, hydroxyalkyl, alkoxyalkyl, haloalkyl, R$^{17}$-phenyl, (R$^{17}$-phenyl)alkyl, naphthyl and cycloalkyl;

$R^{20}$ is H, alkyl, or cycloalkyl;

$R^{22}$ is 1 to 4 substituents independently selected from the group consisting of H, alkyl, hydroxy, alkoxy, halo, —CF$_3$, —NH$_2$ and R$^{35}$-phenyl;

$R^{23}$ is 1 to 4 substituents independently selected from the group consisting of H, alkyl, hydroxy, alkoxy, halo, —CF$_3$, —NR$^{18}$R$^{19}$, —CN, —C(O)Oalkyl, —SO$_2$-alkyl, —NHSO$_2$-alkyl, R$^{35}$-phenyl, R$^{35}$-heteroaryl, morpholinyl, and —(CH$_2$)$_n$—C(O)—N(R$^{30}$)$_2$;

$R^{24}$ is H, OH or alkoxy; or when the optional double bond is present, R$^{24}$ and the adjacent carbon atom form the double bond;

$R^{25}$ is H or R$^{35}$-phenyl;

$R^{27}$ is 1 to 3 substituents independently selected from the group consisting of H, halo, OH, alkyl, alkoxy, hydroxyalkyl, alkoxyalkyl, haloalkyl, —CN, —C(O)OH, —C(O)Oalkyl, —C(O)N(R$^{30}$)(R$^{18}$), —C(O)—(R$^{36}$-hetercycloalkyl), R$^{17}$-phenyl, (R$^{17}$-phenyl)-alkyl, R$^{23}$-heteroaryl, (R$^{23}$-heteroaryl)alkyl, (R$^{23}$-heteroaryl)oxy, (R$^{23}$-heteroaryl)amino NR$^{18}$R$^{19}$, NR$^{18}$R$^{19}$-alkyl, —(CH$_2$)$_n$—N(R$^{30}$)—C(O)alkyl, —(CH$_2$)$_n$N(R$^{30}$)—C(O)-(fluoroalkyl), —(CH$_2$)$_n$—N(R$^{30}$)—C(O)alkoxyalkyl, —(CH$_2$)$_n$—N(R$^{30}$)—C(O)(cycloalkyl), —(CH$_2$)$_n$—N(R$^{30}$)—(R$^{23}$-heteroaryl), —(CH$_2$)$_n$—N(R$^{30}$)—C(O)—(R$^{23}$-heteroaryl), —(CH$_2$)$_n$—N(R$^{30}$)—C(O)O-alkyl, —(CH$_2$)$_n$—N(R$^{30}$)—C(O)O—(CF$_3$-alkyl), —(CH$_2$)$_n$—N(R$^{30}$)—C(O)O—(R$^{39}$-cycloalkyl), —(CH$_2$)$_n$—N(R$^{30}$)—C(O)O-alkylene-cycloalkyl, —(CH$_2$)$_n$—N(R$^{30}$)—C(O)—N(R$^{30}$)(R$^{20}$), —(CH$_2$)$_n$—N(R$^{30}$)—SO$_2$-alkyl, —(CH$_2$)$_n$—N(R$^{30}$)—SO$_2$—CF$_3$, —(CH$_2$)$_n$—N(R$^{30}$)—SO$_2$—N(R$^{30}$)$_2$ and

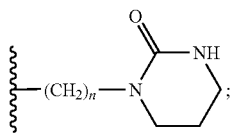

or two $R^{27}$ groups and the carbon to which they are both attached form —C(=NOR$^{30}$)— or —C(O)—;

$R^{28}$ is H, alkyl, $R^{35}$-benzyl or -alkyl-C(O)O-alkyl;

$R^{29}$ is alkyl, haloalkyl, —C(O)Oalkyl, —C(O)alkyl, —C(O)CF$_3$, —C(O)—($R^{12}$-cycloalkyl), —C(O)—($R^{17}$-phenyl), —C(O)—($R^{23}$-heteroaryl), —C(O)—($R^{36}$-hetercycloalkyl), —SO$_2$-alkyl, —SO$_2$—($R^{35}$-phenyl), —C(O)NR$^{18}$R$^{19}$, $R^{35}$-phenyl, ($R^{35}$-phenyl)alkyl or $R^{23}$-heteroaryl;

$R^{30}$ is independently selected from the group consisting of H, alkyl, $R^{35}$-benzyl and $R^{35}$-phenyl;

$R^{31}$ is H, alkyl, $R^{35}$-benzyl or phenoxyalkyl;

$R^{33}$ is H, OH or alkoxy;

$R^{34}$ is H, alkyl, hydroxyalkyl, alkoxyalkyl or —C(O)Oalkyl;

$R^{35}$ is 1 to 3 substituents independently selected from the group consisting of H, halo, alkyl, OH, —CF$_3$, alkoxy, —CO$_2$alkyl and —N($R^{43}$)($R^{44}$);

$R^{36}$ is 1 or 2 substituents independently selected from the group consisting of H, alkyl, $R^{17}$-phenyl, —OH, hydroxyalkyl, alkoxyalkyl, —C(O)Oalkyl and —NR$^{18}$R$^{19}$; or two $R^{36}$ groups and the carbon to which they are both attached form —C(=NOR$^{30}$)— or —C(O)—;

$R^{37}$ and $R^{38}$ are independently selected from the group consisting of H and alkyl, or $R^{37}$ and $R^{38}$ together are —(CH$_2$)$_3$— or —(CH$_2$)$_4$—, and together with the nitrogen to which they are attached, form a ring;

$R^{39}$ is H, OH, alkyl, alkoxy, or CF$_3$;

$R^{40}$ is —OR$^{30}$ or —NHC(O)alkyl;

$R^{41}$ is H or —SO$_2$alkyl;

$R^{42}$ is —(CH$_2$)$_n$—($R^{35}$-phenyl), —(CH$_2$)$_n$—($R^{23}$-heteroaryl), —C(O)Oalkyl or —C(O)alkyl;

$R^{43}$ and $R^{44}$ are independently selected from the group consisting of H and alkyl; and $R^{45}$ is 1 or 2 substituents independently selected from the group consisting of halo, alkoxyalkyl, —CO$_2$alkyl, $R^{17}$-phenyl, $R^{23}$-heteroaryl and cycloalkyl.

This invention also provides a method of treating diseases mediated by PDE 4, including allergic and inflammatory diseases, CNS diseases, and diabetes comprising administering an effective amount of at least one compound of formula I to a patient in need of such treatment.

In particular, this invention also provides a method of treating a PDE4 mediated disease or condition selected from the group consisting of: pain (e.g., acute pain, acute inflammatory pain, chronic inflammatory pain, and neuropathic pain), acute inflammation, chronic inflammation, rheumatoid arthritis, psoriasis, atopic dermatitis, asthma, COPD, adult respiratory disease, arthritis, inflammatory bowel disease, Crohn's disease, ulcerative colitis, septic shock, endotoxic shock, gram negative sepsis, toxic shock syndrome, stroke, ischemia reperfusion injury, renal reperfusion injury, glomerulonephritis, Parkinson's disease, Alzheimer's disease, mild cognitive impairment (MCI), depression, anxiety, graft vs. host reaction (i.e., graft vs. host disease), allograft rejections (e.g., acute allograft rejection, and chronic allograft rejection), acute respiratory distress syndrome, delayed type hypersensitivity reaction, atherosclerosis, cerebral ischemia, osteoarthritis, multiple sclerosis, angiogenesis, osteoporosis, gingivitis, respiratory viruses, herpes viruses, hepatitis viruses, HIV, Kaposi's sarcoma associated virus (i.e., Kaposi's sarcoma), meningitis, cystic fibrosis, pre-term labor, cough, pruritis, multi-organ dysfunction, psoriatic arthritis, herpes, encephalitis, traumatic brain injury, CNS tumors, interstitial pneumonitis, hypersensitivity, crystal induced arthritis, acute pancreatitis, chronic pancreatitis, acute alcoholic hepatitis, necrotizing enterocolitis, chronic sinusitis, ocular inflammation, corneal neovascularization, polymyositis, acne, esophagitis, glossitis, airflow obstruction, airway hyperresponsiveness (i.e., airway hyperreactivity), bronchiectasis, bronchiolitis, bronchiolitis obliterans (i.e., bronchiolitis obliterans syndrome), chronic bronchitis, dyspnea, emphysema, hypercapnea, hyperinflation, hypoxemia, hyperoxia-induced inflammations, hypoxia, pulmonary fibrosis, pulmonary hypertension, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, periodontitis, cancer, transplant reperfusion injury, early transplantation rejection (e.g., acute allograft rejection), airway hyperreactivity, allergic contact dermatitis, allergic rhinitis, alopecia areata, autoimmune deafness (including, for example, Meniere's disease), autoimmune hemolytic syndromes, autoimmune hepatitis, autoimmune neuropathy, autoimmune ovarian failure, autoimmune orchitis, autoimmune thrombocytopenia, chronic inflammatory demyelinating polyneuropathy, cirrhosis, dermatomyositis, diabetes, drug-induced autoimmunity, endometriosis, fibrotic diseases, gastritis, Goodpasture's syndrome, Graves' disease, Gullain-Barre disease, Hashimoto's thyroiditis, hepatitis-associated autoimmunity, HIV-related autoimmune syndromes and hematologic disorders, hypophytis, interstitial cystitis, juvenile arthritis, Langerhans' cell histiocytitis, lichen planus, metal-induced autoimmunity, myocarditis (including viral myocarditis), myositis, neuropathies (including, for example, IgA neuropathy, membranous neuropathy and idiopathic neuropathy), nephritic syndrome, optic neuritis, pancreatitis, post-infectious autoimmunity, primary biliary cirrhosis, reactive arthritis, ankylosing spondylitis, Reiter's syndrome, reperfusion injury, scleritis, scleroderma, secondary hematologic manifestation of autoimmune diseases (such as anemias), silicone implant associated autoimmune disease, Sjogren's syndrome, systemic lupus erythematosus, transverse myelitis, tubulointerstitial nephritis, uveitis, and vitiglio in a patient in need of such treatment comprising administering to said patient an effective amount of at least one compound of formula I, or a pharmaceutically acceptable salt or solvate thereof.

Compounds of formula I are preferably useful in treating pain (e.g., acute pain, acute inflammatory pain, chronic inflammatory pain, and neuropathic pain), acute inflammation, chronic inflammation, rheumatoid arthritis, psoriasis, atopic dermatitis, asthma, COPD, arthritis, inflammatory bowel disease, Crohn's disease, ulcerative colitis, septic shock, endotoxic shock, gram negative sepsis, toxic shock syndrome, stroke, ischemia reperfusion injury, glomerulonephritis, Parkinson's disease, Alzheimer's disease, mild cognitive impairment, depression, anxiety, graft vs. host reaction (i.e., graft vs. host disease), allograft rejections (e.g., acute allograft rejection, and chronic allograft rejection), delayed type hypersensitivity reaction, osteoarthritis, multiple sclerosis, angiogenesis, osteoporosis, HIV, cough, psoriatic arthritis, CNS tumors, necrotizing enterocolitis, airflow obstruction, airway hyperresponsiveness (i.e., airway hyperreactivity), bronchiolitis, chronic bronchitis, emphysema, pulmonary fibrosis, pulmonary hypertension, small airway disease, wheeze, lupus, cancer, transplant reperfusion injury, early transplantation rejection (e.g., acute allograft rejection), airway hyperreactivity, allergic contact dermatitis, allergic rhinitis, diabetes, juvenile arthritis, reactive arthritis, ankylosing spondylitis, reperfusion injury, and systemic lupus erythematosus.

More preferably, compounds of formula I are useful for treating COPD, asthma, IBD, dermatitis, MS, arthritis, Parkinson's disease, Alzheimer's disease, mild cognitive impairment, depression and anxiety.

Preferred veterinary uses for compounds of formula I include the treatment of dermatitis in dogs and the treatment of recurrent airway disease in horses.

This invention also provides a method of treating a PDE4 mediated disease or condition in a patient in need of such treatment comprising administering to said patient at least one compound of formula I, or a pharmaceutically acceptable salt or solvate thereof, in combination with at least one other medicament (e.g., a drug, agent or therapeutic) selected from the group consisting of:
  a) disease modifying antirheumatic drugs;
  b) nonsteroidal anitinflammatory drugs;
  c) COX-2 selective inhibitors;
  d) COX-1 inhibitors;
  e) immunosuppressives;
  f) steroids;
  g) biological response modifiers;
  h) other anti-inflammatory agents or therapeutics useful for the treatment of chemokine mediated diseases; and
  i) other agents or therapeutics useful for the treatment of depression, anxiety, Alzheimer's Disease or Parkinson's Disease.

This invention also provides a method of treating a pulmonary disease (e.g., COPD, asthma or cystic fibrosis) in a patient in need of such treatment comprising administering to said patient a therapeutically effective amount of at least one compound of formula I, or a pharmaceutically acceptable salt or solvate thereof, in combination with at least one compound selected from the group consisting of: glucocorticoids, 5-lipoxygenase inhibitors, $\beta$-2 adrenoceptor agonists, muscarinic M1 antagonists, muscarinic M3 antagonists, muscarinic M2 agonists, NK3 antagonists, LTB4 antagonists, cysteinyl leukotriene antagonists, bronchodilators, PDE4 inhibitors, PDE inhibitors, elastase inhibitors, MMP inhibitors, phospholipase A2 inhibitors, phospholipase D inhibitors, histamine H1 antagonists, histamine H3 antagonists, dopamine agonists, adenosine A2 agonists, NK1 and NK2 antagonists, GABA-b agonists, nociceptin agonists, expectorants, mucolytic agents, decongestants, antioxidants, anti-IL-8 antibodies, anti-IL-5 antibodies, anti-IgE antibodies, anti-TNF antibodies, IL-10, adhesion molecule inhibitors, and growth hormones.

This invention also provides a method of treating multiple sclerosis in a patient in need of such treatment comprising administering to said patient, a therapeutically effective amount of at least one compound of formula I, or a pharmaceutically acceptable salt or solvate thereof, in combination with at least one compound selected from the group consisting of glatiramer acetate, glucocorticoids, methotrexate, azothioprine, mitoxantrone, chemokine inhibitors, and CB2-selective agents.

This invention also provides a method of treating multiple sclerosis in a patient in need of such treatment comprising administering to said patient a therapeutically effective amount of at least one compound of formula I, or a pharmaceutically acceptable salt or solvate thereof, in combination with at least one compound selected from the group consisting of: methotrexate, cyclosporin, leflunimide, sulfasalazine, $\beta$-methasone, $\beta$-interferon, glatiramer acetate, and prednisone.

This invention also provides a method of treating rheumatoid arthritis in a patient in need of such treatment comprising administering to said patient a therapeutically effective amount of at least one compound of formula I, or a pharmaceutically acceptable salt or solvate thereof, in combination with at least one compound selected from the group consisting of COX-2 inhibitors, COX inhibitors, immunosuppressives (e.g., methotrexate, cyclosporin, leflunimide and sulfasalazine), steroids (e.g., betamethasone, cortisone and dexamethasone), anti-TNF-$\alpha$ compounds, MMP inhibitors, glucocorticoids, chemokine inhibitors, CB2-selective inhibitors, and other classes of compounds indicated for the treatment of rheumatoid arthritis.

This invention also provides a method of treating stroke and ischemia reperfusion injury in a patient in need of such treatment comprising administering to said patient a therapeutically effective amount of at least one compound of formula I, or a pharmaceutically acceptable salt or solvate thereof, in combination with at least one compound selected from the group consisting of thrombolitics (e.g., tenecteplase, TPA, alteplase), antiplatelet agents (e.g., gpIIb/IIIa), antagonists (e.g., abciximab and eftiifbatide), anticoagulants (e.g., heparin), and other compounds indicated for the treatment of rheumatoid arthritis.

This invention also provides a method of treating stroke and ischemia reperfusion injury in a patient in need of such treatment comprising administering to said patient a therapeutically effective amount of at least one compound of formula I, or a pharmaceutically acceptable salt or solvate thereof, in combination with at least one compound selected from the group consisting of tenecteplase, TPA, alteplase, abciximab, eftiifbatide, and heparin.

This invention also provides a method of treating psoriasis in a patient in need of such treatment comprising administering to said patient a therapeutically effective amount of at least one compound of formula I, or a pharmaceutically acceptable salt or solvate thereof, in combination with at least one compound selected from the group consisting of immunosuppressives (e.g., methotrexate, cyclosporin, leflunimide and sulfasalazine), steroids (e.g., $\beta$-methasone) and anti-TNF-$\alpha$ compounds (e.g., etonercept and infliximab).

This invention also provides a method of treating COPD in a patient in need of such treatment comprising administering to said patient a therapeutically effective amount of at least one compound of formula I, or a pharmaceutically acceptable salt or solvate thereof.

This invention also provides a method of treating arthritis in a patient in need of such treatment comprising administering to said patient a therapeutically effective amount of at least one compound of formula I, or a pharmaceutically acceptable salt or solvate thereof.

This invention also provides a method of treating osteoarthritis in a patient in need of such treatment comprising administering to said patient a therapeutically effective amount of at least one compound of formula I, or a pharmaceutically acceptable salt or solvate thereof.

This invention also provides a method of treating acute pain, acute inflammatory pain, chronic inflammatory pain, or neuropathic pain in a patient in need of such treatment comprising administering to said patient a therapeutically effective amount of at least one compound of formula I, or a pharmaceutically acceptable salt or solvate thereof.

This invention also provides a method of treating pain in a patient in need of such treatment comprising administering to said patient a therapeutically effective amount of at least one compound of formula I, or a pharmaceutically acceptable salt or solvate thereof, and administering a therapeutically effective amount of at least one medicament selected from the group consisting of: NSAIDs, COXIB inhibitors, anti-depressants, and anti-convulsants.

This invention also provides a pharmaceutical composition comprising at least one (e.g., 1-3, usually 1) compound of formula I, or a pharmaceutically acceptable salt or solvate thereof, and a pharmaceutically acceptable carrier. Preferred are oral dosage forms and dosage forms suitable for inhalation.

This invention also provides a pharmaceutical composition comprising at least one (e.g., 1-3, usually 1) compound of formula I, or a pharmaceutically acceptable salt or solvate thereof, and at least one (e.g., 1-3, usually 1) other agent, medicament, antibody and/or inhibitor disclosed above, and a pharmaceutically acceptable carrier.

DETAILED DESCRIPTION

Preferred compounds of formula I are those wherein the quinolyl portion has the structure

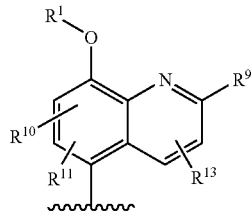

More preferred are compounds wherein $R^{10}$, $R^{11}$ and $R^{13}$ are each H. Also preferred are compounds wherein $R^1$ is H, alkyl, cycloalkyl or $CF_3$; more preferably, $R^1$ is alkyl, especially methyl. Also preferred are compounds wherein $R^9$ is H, alkyl or —$CF_3$, more preferably —$CF_3$.

In compounds of formula I, X is preferably O.

In compounds of formula I,

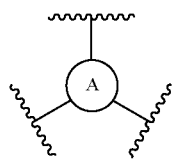

is preferably oxazolyl, more preferably

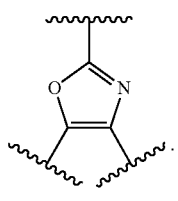

In compounds of formula I, $R^3$ is preferably H, alkyl, hydroxyalkyl or —C(O)Oalkyl, and $R^4$ is H or alkyl. More preferably, $R^3$ and $R^4$ are each independently H or alkyl.

In compounds of formula I, $R^5$ is preferably H, and $R^6$ is preferably H, alkyl or hydroxyalkyl. When $R^6$ is alkyl, it is preferably methyl, ethyl or isopropyl, more preferably methyl; when it is hydroxyalkyl, it is preferably hydroxymethyl or hydroxyethyl (i.e., —$(CH_2)_2OH$ or —$CH(OH)CH_3$). In a more preferred embodiment, $R^5$ is H and $R^6$ is H, methyl or hydroxymethyl. Preferably, t is 1. When t is 2, preferably both $R^5$ substituents and one $R^6$ substituent are H and one $R^6$ substituent is H or methyl.

Preferably, $R^5$ and $R^6$ have the following stereochemistry (i.e., $R^6$ is "S"):

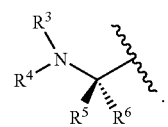

When $R^7$ and $R^8$ do not form a ring, the following definitions are preferred.

$R^7$ is preferably H, alkyl, cycloalkyl, hydroxyalkyl or alkoxyalkyl. More preferably, $R^7$ is H, alkyl, hydroxyalkyl, especially wherein alkyl is methyl or ethyl, and hydroxyalkyl is hydroxyethyl. Especially preferred are compounds wherein $R^7$ is H or alkyl, especially H, methyl or ethyl, with H being most preferred.

$R^8$ is preferably $R^{12}$-cycloalkyl, ($R^{12}$-cycloalkyl)alkyl, $R^{45}$-hydroxyalkyl, $R^{17}$-phenyl, ($R^{17}$-phenyl)alkyl, $R^{23}$-heteroaryl, ($R^{23}$-heteroaryl)alkyl, -alkyl-N($R^{30}$)—C(O)—$NR^{18}R^{19}$, -alkyl-N($R^{30}$)—C(O)alkyl, -alkyl-N($R^{30}$)—C(O)—($R^{17}$-phenyl), -alkyl-N($R^{30}$)—C(O)—($R^{23}$-heteroaryl), -alkyl-N($R^{30}$)—($R^{23}$-heteroaryl),

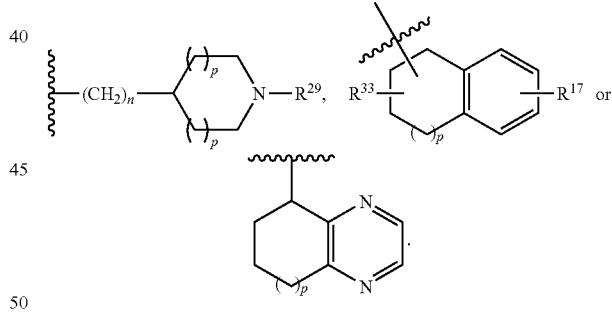

More preferably, $R^8$ is $R^{12}$-cycloalkyl, $R^{45}$-hydroxyalkyl, ($R^{17}$-phenyl)alkyl, $R^{23}$-heteroaryl, ($R^{23}$-heteroaryl)alkyl, -alkyl-N($R^{30}$)—($R^{23}$-heteroaryl), -alkyl-N($R^{30}$)—C(O)alkyl,

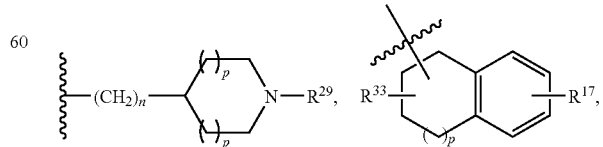

(especially where p is 0) or

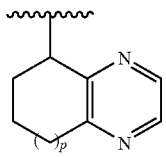

(especially where p is 1). Especially preferred are compounds wherein $R^8$ is $R^{12}$-cycloalkyl, $R^{45}$-hydroxyalkyl, ($R^{17}$-phenyl)alkyl, ($R^{23}$-heteroaryl)alkyl, -alkyl-N($R^{30}$)—C(O)-alkyl, -alkyl-N($R^{30}$)—($R^{23}$-heteroaryl) or

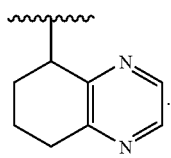

When $R^8$ comprises $R^{12}$-cycloalkyl, $R^{12}$ is preferably OH, —(CH$_2$)$_n$—N($R^{30}$)—C(O)-cycloalkyl or —(CH$_2$)$_n$—N($R^{30}$)—($R^{23}$-heteroaryl), especially OH. When $R^8$ is

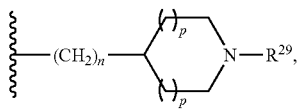

n is preferably 0 and $R^{29}$ is preferably heteroaryl, —C(O)alkyl or —C(O)cycloalkyl. When $R^8$ is $R^{45}$-hydroxyalkyl, $R^{45}$ is preferably $R^{17}$-phenyl.

$R^{30}$ is preferably H.

Preferred heteroaryl groups include pyrimidyl, benzothienyl, benzofuranyl, indolyl, pyridyl and pyrazinyl.

Especially preferred are compounds of formula I wherein $R^7$ is H and $R^8$ is ($R^{17}$-phenyl)alkyl, ($R^{23}$-heteroaryl)alkyl, $R^{45}$-hydroxyalkyl, -alkyl-N($R^{30}$)—($R^{23}$-heteroaryl) or

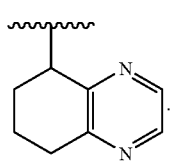

$R^{17}$ is preferably 1-3 substituents selected from the group consisting of halogen, OH, alkoxy and alkyl; $R^{23}$ is preferably 1 or 2 substituents independently selected from the group consisting of H, alkyl, alkoxy and halogen; $R^{45}$ is preferably $R^{17}$-phenyl, wherein $R^{17}$ is 1-3 substituents selected from the group consisting of halogen, OH, alkoxy and alkyl; heteroaryl is pyrimidyl, benzothienyl, benzofuranyl, indolyl, pyridyl or pyrazinyl, and $R^{30}$ is H.

Also preferred are compounds of formula I wherein $R^7$ and $R^8$ and the nitrogen to which they are attached form

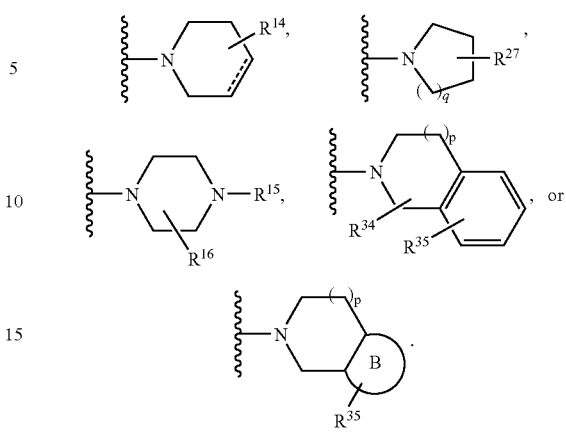

In the preferred compounds where $R^7$ and $R^8$ form

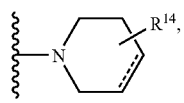

the optional double bond preferably is not present (i.e., a single bond is present). $R^{14}$ is preferably selected from H, OH, alkoxy, —(CH$_2$)$_n$—N($R^{30}$)($R^{23}$-heteroaryl), $R^{23}$-heteroaryl or ($R^{23}$-heteroaryl)-alkyl. In a further preferred embodiment, one $R^{14}$ is OH and the other $R^{14}$ is $R^{23}$-heteroaryl; in another embodiment, one $R^{14}$ is H and the other is ($R^{23}$-heteroaryl)-alkyl or —(CH$_2$)$_n$—N($R^{30}$)($R^{23}$-heteroaryl) (especially wherein n is 1).

In the preferred compounds where $R^7$ and $R^8$ form

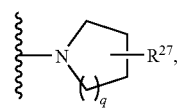

q is preferably 1. $R^{27}$ is preferably 1-3 substituents independently selected from the group consisting of H, OH, alkyl, alkoxy, alkoxyalkyl, $R^{17}$-phenyl, —C(O)OH, —C(O)Oalkyl, $R^{23}$-heteroaryl, ($R^{23}$-heteroaryl)amino and —(CH$_2$)$_n$—N($R^{30}$)—C(O)(cycloalkyl), wherein n is 0.

In the preferred compounds where $R^7$ and $R^8$ form

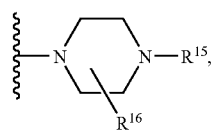

$R^{15}$ is preferably alkyl, $R^{17}$-phenyl, $R^{23}$-heteroaryl, —C(O)alkyl, —C(O)(fluoroalkyl), —C(O)—($R^{23}$-heteroaryl), —C(O)-alkoxyalkyl, —C(O)—($R^{38}$-cycloalkyl), —SO$_2$-alkyl, —SO$_2$—NR$^{18}$R$^{19}$ or

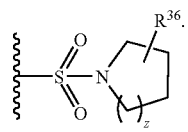

$R^{16}$ is preferably H, alkyl, or two $R^{16}$ groups and the carbon to which they are attached form —C(O)—.

In the preferred compounds where $R^7$ and $R^8$ form

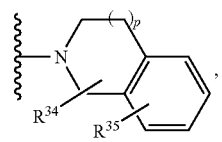

preferably p is 0, $R^{34}$ is hydrogen, and $R^{35}$ is 1 or 2 substituents independently selected from H, OH, halo and alkyl.

In the preferred compounds where $R^7$ and $R^8$ form

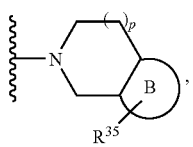

preferably p is 0, ring B is a pyrazolyl or thiazolyl ring, and $R^{35}$ is 1 or 2 substituents independently selected from H and alkyl.

As used above, and throughout the specification, the following terms, unless otherwise indicated, shall be understood to have the following meanings:

"Patient" includes both humans and animals.

"Mammal" means humans and other mammalian animals.

"Alkyl" means an aliphatic hydrocarbon group which may be straight or branched and comprising about 1 to about 6 carbon atoms in the chain. Branched means that one or more lower alkyl groups such as methyl, ethyl or propyl, are attached to a linear alkyl chain. Non-limiting examples of suitable alkyl groups include methyl, ethyl, n-propyl, isopropyl, n-butyl, t-butyl and n-pentyl.

"Alkenyl" means an aliphatic hydrocarbon group containing at least one carbon-carbon double bond and which may be straight or branched and comprising about 2 to about 6 carbon atoms in the chain. Branched means that one or more lower alkyl groups such as methyl, ethyl or propyl, are attached to a linear alkenyl chain. Non-limiting examples of suitable alkenyl groups include ethenyl, propenyl, n-butenyl, 3-methylbut-2-enyl and n-pentenyl.

"Alkylene" means a difunctional group obtained by removal of a hydrogen atom from an alkyl group that is defined above. Non-limiting examples of alkylene include methylene (i.e., —CH$_2$—), ethylene (i.e., —CH$_2$—CH$_2$—) and branched chains such as —CH(CH$_3$)—CH$_2$—.

"Heteroaryl" means a single ring, bicyclic or benzofused heteroaromatic group of 5 to 10 atoms comprised of 2 to 9 carbon atoms and 1 to 4 heteroatoms independently selected from the group consisting of N, O and S, provided that the rings do not include adjacent oxygen and/or sulfur atoms. N-oxides of the ring nitrogens are also included. Examples of single-ring heteroaryl groups are pyridyl, oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Examples of bicyclic heteroaryl groups are naphthyridyl (e.g., 1,5 or 1,7), imidazopyridyl, pyridopyrimidinyl and 7-azaindolyl. Examples of benzofused heteroaryl groups are indolyl, quinolyl, isoquinolyl, phthalazinyl, benzothienyl (i.e., thianaphthenyl), benzimidazolyl, benzofuranyl, benzoxazolyl, benzisoxazolyl, benzothiazolyl and benzofurazanyl. All positional isomers are contemplated, e.g., 2-pyridyl, 3-pyridyl and 4-pyridyl. The term $R^{23}$-heteroaryl refers to such groups wherein substitutable ring carbon atoms have a substituent as defined above. When the heteroaryl group is a benzofused ring, the substituents can be attached to either or both the phenyl ring portion and the heteroaromatic ring portion, and the heteroaryl group can be attached to the rest of the molecule either through the phenyl ring portion or the heteroaromatic ring portion.

"Cycloalkyl" means a non-aromatic mono- or multicyclic ring system comprising about 3 to about 10 carbon atoms, preferably about 3 to about 6 carbon atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like. Monocyclic rings are preferred.

"Halo" means fluoro, chloro, bromo, or iodo groups. Preferred are fluoro, chloro or bromo, and more preferred are fluoro and chloro.

"Haloalkyl" means an alkyl as defined above wherein one or more hydrogen atoms on the alkyl is replaced by a halo group defined above; in particular, fluoroalkyl refers to an alkyl chain substituted by one or more fluoro atoms.

"Aminoalkyl" means an alkyl as defined above wherein a hydrogen atom on the alkyl is replaced by an amino (i.e., —NH$_2$) group.

"Heterocycloalkyl" means a non-aromatic saturated monocyclic or multicyclic ring system comprising about 3 to about 10 ring atoms, preferably about 5 to about 10 ring atoms, in which one or more, preferably 1, 2, 3 or 4, of the atoms in the ring system is independently selected from an element other than carbon, for example nitrogen, oxygen or sulfur, alone or in combination. There are no adjacent oxygen and/or sulfur atoms present in the ring system. Preferred heterocycloalkyls contain 5 to 6 ring atoms. The prefix aza, oxa or thia before the heterocycloalkyl root name means that at least a nitrogen, oxygen or sulfur atom respectively is present as a ring atom. The nitrogen or sulfur atom of the heterocyclyl can be optionally oxidized to the corresponding N-oxide, S-oxide or S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. The heterocycloalkyl group can be attached to the parent moiety through a ring carbon or a ring nitrogen.

"(Heterocycloalkyl)alkyl" means a heterocycloalkyl-alkyl group in which the heterocycloalkyl and alkyl groups are as defined above. The bond to the parent is through the alkyl.

"(Heteroaryl)alkyl" means a heteroaryl-alkyl- group in which the heteroaryl and alkyl are as previously described. Non-limiting examples of suitable heteroarylalkyl groups include pyridylmethyl, 2-(furan-3-yl)ethyl and quinolin-3-ylmethyl. The bond to the parent moiety is through the alkyl.

"(Phenyl)alkyl and "(naphthyl)alkyl similarly mean phenyl-alkyl and naphthyl-alkyl groups wherein the bond to the parent moiety is through the alkyl.

"Hydroxyalkyl" means a HO-alkyl- group in which alkyl is as previously defined. Non-limiting examples of suitable hydroxyalkyl groups include hydroxymethyl and 2-hydroxyethyl. Similarly, "dihydroxyalkyl" refers to a straight or branched alkyl chain substituted by two hydroxy groups.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkylthio" means an alkyl-S— group in which the alkyl group is as previously described. Non-limiting examples of suitable alkylthio groups include methylthio, ethylthio and isopropylthio. The bond to the parent moiety is through the sulfur.

"Heteroarylamino" means an heteroaryl-NH— group in which the heteroaryl group is as previously described. Non-limiting examples of suitable heteroarylamino groups include pyrimidinyl-amino and pyrazinyl-amino. The bond to the parent moiety is through the amino nitrogen.

"Heteroaryloxy" means an heteroaryl-O— group in which the heteroaryl group is as previously described. Non-limiting examples of suitable heteroaryloxy groups include pyrimidinyl-O— and pyrazinyl-O—. The bond to the parent moiety is through the ether oxygen.

The term "hydroxyalkyl substituted by $CO_2$alkyl" means an alkyl chain substituted by a hydroxy group and a $CO_2$alkyl group. Similarly, terms such as "hydroxyalkyl substituted by $R^{17}$-phenyl" means an alkyl chain substituted by a hydroxy group and a $R^{17}$-phenyl group; "hydroxyalkyl substituted by $R^{17}$-phenyl and alkoxy" means an alkyl group substituted by a hydroxy group, a $R^{17}$-phenyl, and an alkoxy group. In each of these substituents and other similar substituents listed in the definitions, the alkyl chains can be branched.

Examples of moieties formed when two adjacent $R^{17}$ groups form a ring with the carbons on the phenyl ring to which they are attached are:

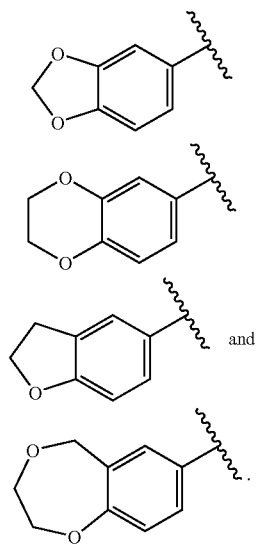
and

When $R^7$ and $R^8$ together form

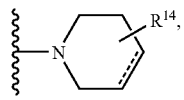

the dotted line indicates an optional double bond as defined above. When the double bond is absent, i.e., when a single bond is present, the one or two $R^{14}$ substituents can be attached to the same or different ring carbons. When the double bond is present, only one $R^{14}$ substituent can be attached to a carbon that is part of the double bond.

When $R^7$ and $R^8$ together form

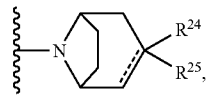

the dotted line indicates an optional double bond as defined above. When the double bond is absent, i.e., when a single bond is present, $R^{24}$ can be H, OH or alkoxy and $R^{25}$ can be H or $R^{35}$-phenyl, but when the double bond is present, $R^{24}$ forms the double bond with the adjacent carbon and $R^{25}$ is H or $R^{35}$-phenyl. That is, the moiety has the structural formula

When $R^7$ and $R^8$ together form

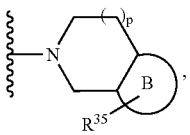

it means that an optionally substituted fused bicyclic ring is formed, wherein the

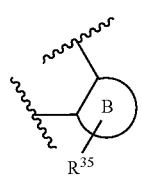

portion comprises an $R^{35}$-substituted 5 or 6-membered heteroaryl group fused to the piperidinyl ring.

Examples are:

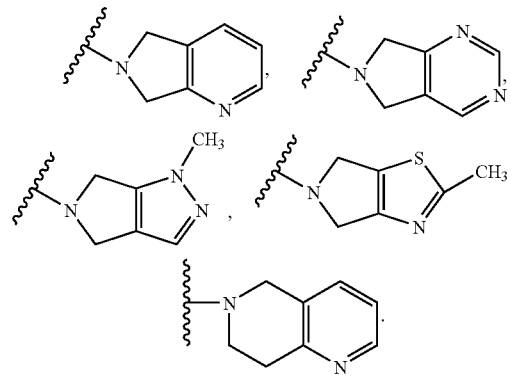

The term "optionally substituted" means optional substitution with the specified groups, radicals or moieties, in available position or positions.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

As used herein, the term "composition" is intended to encompass a product comprising the specified ingredients in the specified amounts, as well as any product which results, directly or indirectly, from combination of the specified ingredients in the specified amounts.

The wavy line ∿∿ as a bond generally indicates a mixture of, or either of, the possible isomers, e.g., containing (R)- and (S)-stereochemistry. For example,

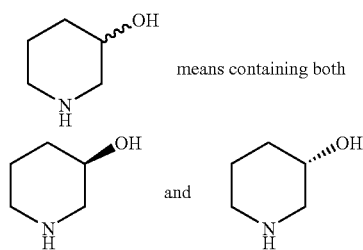

means containing both and

Lines drawn into the ring systems, such as, for example:

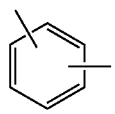

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

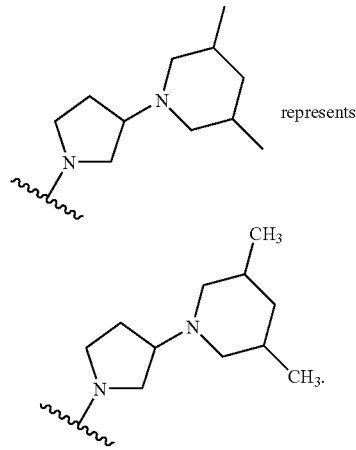

represents

It should also be noted that any carbon or heteroatom with unsatisfied valences in the text, schemes, examples, structural formulae, and any Tables herein is assumed to have the hydrogen atom or atoms to satisfy the valences.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting PDE4 and thus producing the desired therapeutic effect in a suitable patient.

The compounds of formula I form salts which are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalene-sulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Polymorphic forms of the compounds of Formula I, and of the salts, solvates and prodrugs of the compounds of Formula I, are intended to be included in the present invention.

This invention also includes the compounds of this invention in isolated and pure form.

Compounds of formula I can be prepared by known methods from starting materials either known in the art or prepared by methods known in the art. Non-limiting examples of suitable methods are illustrated in the following schemes.

In the schemes, the quinolyl portion is shown as the preferred structure, but those skilled in the art will recognize that other substitutions on the quinolyl portion can be made by these procedures. Also, one skilled in the art will recognize that the schemes show the significant steps of the procedures, and that the synthesis of compounds of formula I may require the need for the protection of certain functional groups during the preparation of the compounds; the synthesis of compounds also may require the reduction of a reducible functional group or the oxidation of an oxidizable functional group.

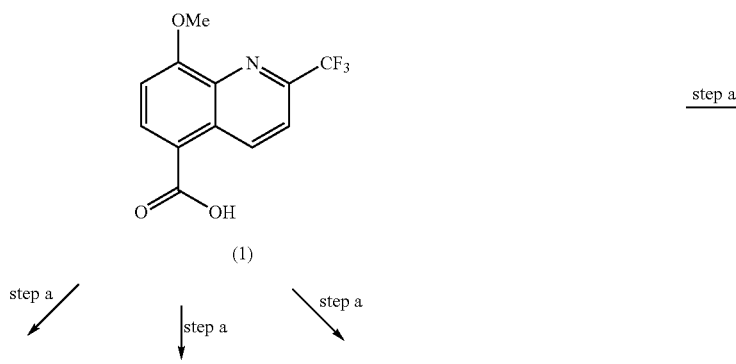

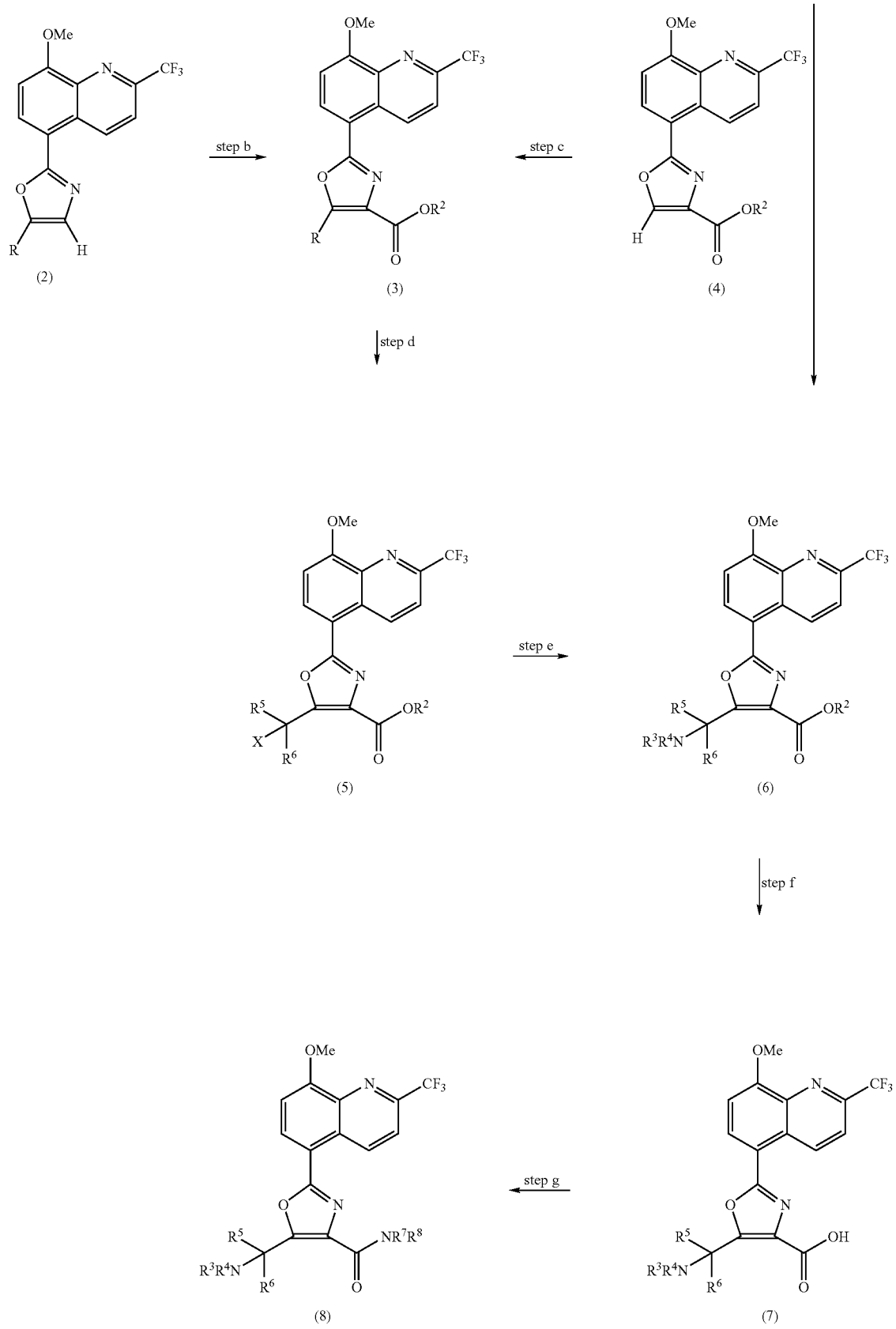

Step a
Formation of the oxazole ring can be accomplished by a number of methods including, but not limited to the following.
Method 1
(1) → 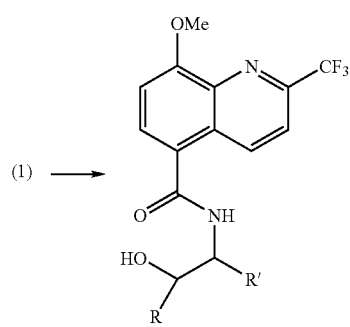 →
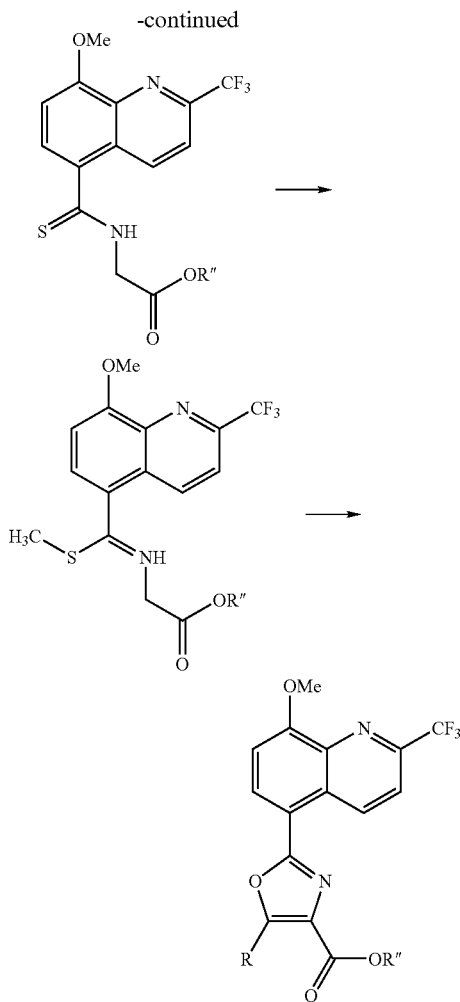
R' = H, COOR²
Method 2
(1) → 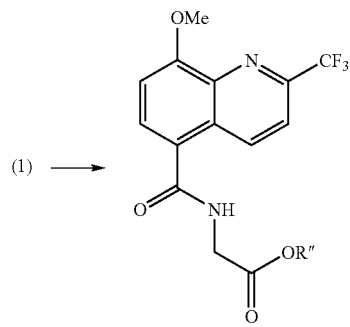 →
Method 3
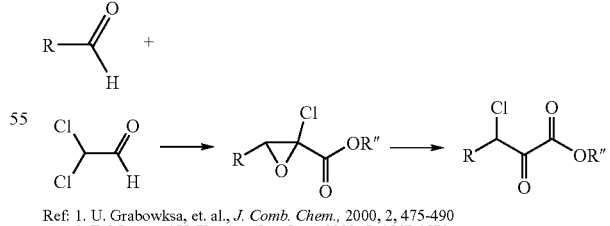
Ref: 1. U. Grabowksa, et. al., *J. Comb. Chem.*, 2000, 2, 475-490
2. E. Mann and H. Kessler, *Org. Lett.*, 2003, 5, 4567-4570.
Method 4
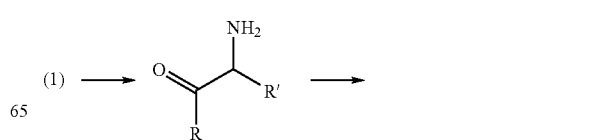

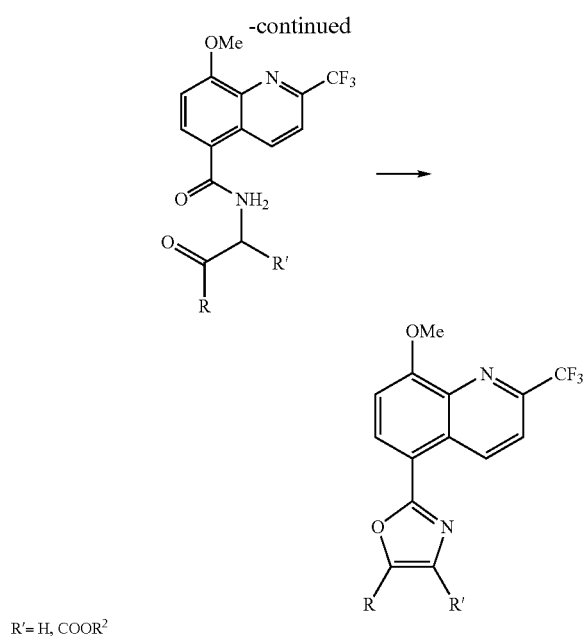

R' = H, COOR²

Using the appropriate starting materials, both the amine and ester functional groups can be incorporated when the oxazole ring is synthesized.

Step b

Introduction of the ester moiety COOR² can be accomplished stepwise by reaction with phosphorous oxychloride and subsequent oxidation of the intermediate aldehyde to the carboxylic acid and further esterification. Alternatively, reaction at this position can proceed with a Lewis acid such as zinc triflate and an acid chloride.

Step c

Introduction of the R moiety can be accomplished by deprotonation with a strong base such as n-butyl lithium, sec-butyl lithium, lithium diisopropylamine or lithium hexamethyldisilazide, followed by addition of an aldehyde or alkyl halide. This reaction can use a variety of solvents including diethyl ether, THF, dioxane, hexane, toluene, HMPA, DMPU and TMEDA.

Step d

Activation of the R moiety in (3) can be accomplished by several different methods. If R is an alkyl moiety, halogenation, for example with bromine or N-bromo-succinimide and an initiator such as benzoyl peroxide, AIBN or light in carbon tetrachloride as the solvent provides (5) as a halide. If R incorporates an ester or alcohol functional group, through appropriate oxidation or reduction reactions, the aldehyde or ketone functional group can be obtained for further reaction in Step e through a reductive amination reaction. If R incorporates an ester, ketone, or aldehyde functional group, appropriate reduction reaction with a hydride such as $NaBH_4$, $LiBH_4$, $LiAlH_4$, or diisobutylaluminum hydride will provide the alcohol moiety. This alcohol can be activated by conversion, for example, to the corresponding mesylate, tosylate, chloride, bromide or iodide.

Step e

Introduction of the amine moiety in (6) can be accomplished by an alkylation reaction on (5) if X is a leaving group such as chloride, bromide, mesylate or tosylate. This reaction can use a variety of bases including TEA, DIPEA, N-methyl morpholine, pyridine, dimethylaminopyridine, imidazole, $K_2CO_3$, $Cs_2CO_3$, potassium t-butoxide, and NaOH, and can be done in a variety of solvents including DMF, dimethylacetamide, THF, dioxane, $CH_3CN$, toluene, $CH_2Cl_2$ and dichloroethane. Alternatively, if the $—C(X)(R^5)(R^6)$ moiety incorporates a ketone or aldehyde functional group, the amine moiety can be introduced through a reductive amination reaction. Suitable reducing reagents for this reaction include $NaBH_3CN$, sodium triacetoxyborohydride in a mixture of solvents including THF, dioxane, $CH_3CN$, toluene, $CH_2Cl_2$, dichloroethane, methanol, ethanol, trifluoroethanol. The reductive amination reaction may require the addition of a drying agent such as sieves or $MgSO_4$, or azeotropic removal of water or the addition of a Lewis acid such as titanium isopropoxide. In addition, the ketone or aldehyde moiety can be converted into an oxime with hydroxylamine and a variety of bases such as pyridine, TEA, sodium acetate, and $Na_2CO_3$. The oxime can be reduced to an amine.

Step f

Hydrolysis of ester (6) to acid (7) can be accomplished with a suitable base such as NaOH, LiOH, sodium methoxide, sodium ethoxide, $K_2CO_3$, $Cs_2CO_3$, $BCl_3$, potassium t-butoxide, TEA, DBU and DIPEA in a mixture of solvents including water, methanol, ethanol, isopropanol, $CH_2Cl_2$, THF, diethyl ether and dioxane.

Step g

Amide bond formation to obtain (8) can be accomplished by formation of the acid chloride, a mixed anhydride, or activated ester and addition of the appropriate amine. A variety of suitable amide bond coupling reagents such as HATU, CDI, EDC, DCC, PyBOP, polymer supported CDI, polymer supported EDC and the like, with or without HOBt, can be used. These coupling reagents can be used with a suitable base such as TEA, DIPEA, N-methyl morpholine, pyridine, dimethylaminopyridine, DBU, imidazole and the like in a mixture of solvents including DMF, dimethylacetamide, THF, dioxane, $CH_3CN$, N-methylpyrrolidine, $CH_2Cl_2$, and dichloroethane.

Abbreviations used in the above general schemes and in the following examples, as well as throughout the specification, are as follows: Me (methyl); Bu (butyl); Et (ethyl); Ac (acetyl); Boc or BOC (t-butoxycarbonyl); DMF (dimethylformamide); THF (tetrahydrofuran); DIPEA (diisopropylethylamine); RT (room temperature); HOBt (hydroxybenzotriazole); TFA (trifluoroacetic acid); TEA (triethyl amine); KHMDS (potassium bis(trimethylsilyl)amide); TLC (thin layer chromatography); EDC (1-(3-dimethylaminopropyl)-3-ethyl-carbodiimide hydrochloride); HMPA (hexamethylphosphoramide); DMPU (1,3-dimethyl-3,4,5,6-tetrahydro-2(1H)-pyrimidinone); TMEDA (N,N,N',N'-tetramethyletheylenediamine); HATU (O-(7-azabenzotriazol-1-yl)-N,N,N',N'-tetramethyl uranium hexafluoro-phosphate); NBS (N-bromosuccinimide); DCC (1,3-dicyclohexylcarbodiimide); DEC (1,2-diethylaminoethyl chloride hydrochloride); TMSCN (trimethylsilylcyanide); CDI (carbonyldiimidazole); PyBOP (benzotriazol-1-yloxytripyrrolidinophosphonium hexafluorophosphate).

EXAMPLE 1

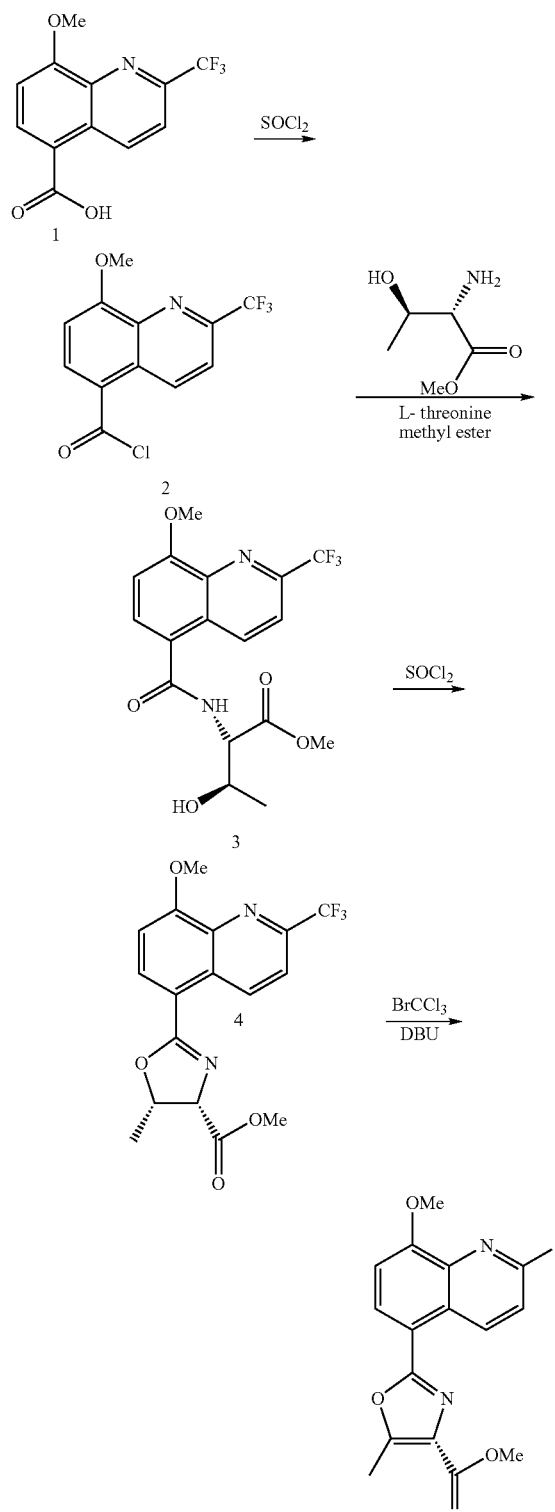

Step 1: SOCl$_2$ (26.7 ml, 367 mmol) was added to a mixture of compound 1 (40 g, 147 mmol) in dry toluene (300 ml) and DMF (0.4 ml). The mixture was heated at 70° C. for 2 h, then the excess of SOCl$_2$ and solvents were evaporated to dryness to obtain compound 2 as an off white-solid (41 g).

Step 2: A solution of compound 2 (41 g, 141 mmol) in CH$_2$Cl$_2$ (200 ml) was added slowly to a solution of L-threo-nine methyl ester HCl salt (29 g, 170 mmol) in CH$_2$Cl$_2$ (200 ml) and DIPEA (38 g, 296 mmol) at 0° C. The solution was stirred at 0° C., then warmed to RT over 3 h. After 3 h at RT, the mixture was washed with aqueous NH$_4$Cl solution, then the solid was precipitated in the organic layer and filtered off to give compound 3 (54 g) as a white solid. MS: C$_{17}$H$_{17}$F$_3$N$_2$O$_5$ [M+1]$^+$387.1.

Step 3: SOCl$_2$ (76.8 ml, 645 mmol) was added through a syringe to a suspension of compound 3 (50 g, 129 mmol) in dry CH$_2$Cl$_2$ (500 ml) cooled to −45 0° C. The mixture was stirred at −45° C. for 1 h, then warmed up to RT slowly. After the reaction was complete, solvent and excess SOCl$_2$ were evaporated. The residue was dissolved in CH$_2$Cl$_2$ (800 ml) and washed with saturated NaHCO$_3$ solution (3×600 ml), dried (Na$_2$SO$_4$), filtered and concentrated to give compound 4 as a beige solid (43 g, 120 mmol, 93%). MS: C$_{17}$H$_{15}$F$_3$N$_2$O$_4$ [M+1]$^+$369.1.

Step 4: DBU (13.9 ml, 93 mmol) was added via a syringe to a solution of compound 4 (31 g, 84 mmol) in dry CH$_2$Cl$_2$ (300 ml) at 0° C., followed by the addition of BrCCl$_3$ (9.1 ml, 93 mmol). The mixture was stirred at 0° C. for 2 h, then at RT overnight. The reaction was quenched with 0.15 N HCl (400 ml) and extracted with CH$_2$Cl$_2$ (2×100 ml). The organic layer was dried with Na$_2$SO$_4$, filtered and concentrated to give crude title compound 5 (35 g). The crude material was triturated with MeOH (200 ml) and 23.5 g of compound 5 was collected as a pale yellow solid. MS: C$_{17}$H$_{13}$F$_3$N$_2$O$_4$ [M+1]$^+$ 367.1.

EXAMPLE 2

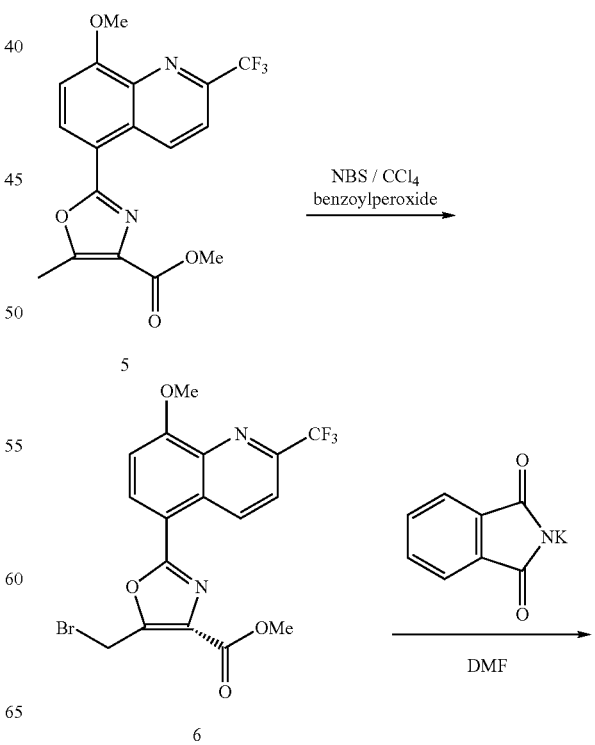

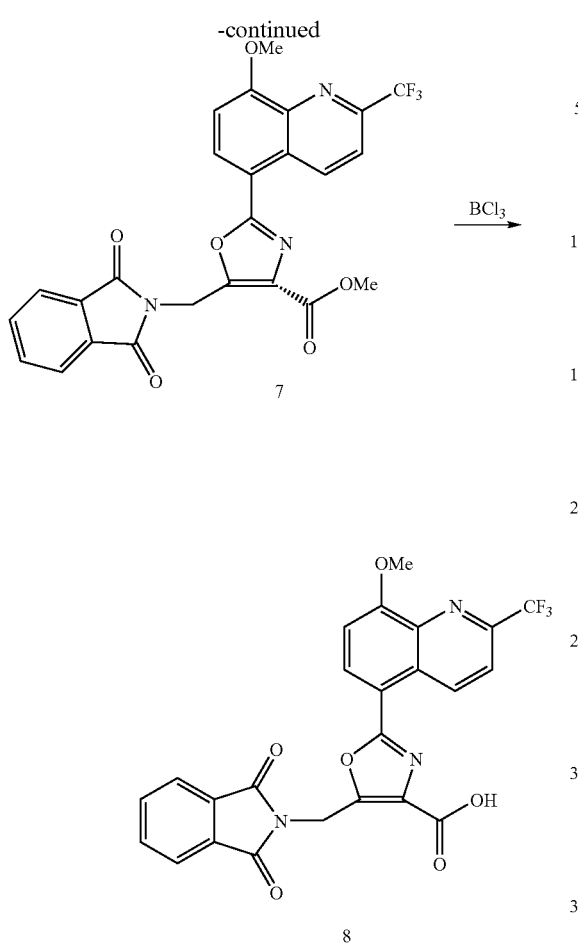

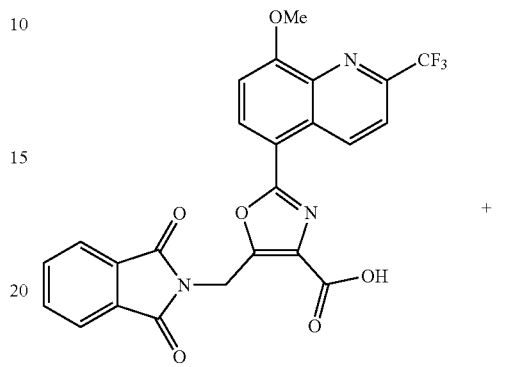

water, and dried (Na$_2$SO$_4$) to give the title compound 8 as a yellow solid (8.5 g, 17.1 mmol, 87%). MS: C$_{24}$H$_{14}$F$_3$N$_3$O$_6$ [M+1]$^+$498.1.

EXAMPLE 3

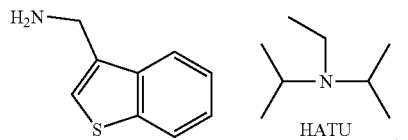

Step 1: NBS (23.5 g, 132 mmol) and benzoyl peroxide (1.4 g, 5.75 mmol) were added to a mixture of compound 5 (42 g, 115 mmol) in dry CCl$_4$ (550 ml). The mixture was refluxed for 3 h, then concentrated by evaporating off most of the solvent. Saturated NH$_4$Cl solution was added and the product was extracted from the aqueous layer with CH$_2$Cl$_2$ (2×300 ml). The organic fractions were combined, dried (Na$_2$SO$_4$), filtered and evaporated. The crude material was triturated with MeOH to give compound 6 as a white solid (49.5 g, 110 mmol, 96%). MS: C$_{17}$H$_{12}$F$_3$BrN$_2$O$_4$ [M+1]$^+$Br$^{79,81}$ 445.1, 447.1.

Step 2: Potassium phthalimide (20.6 g, 111 mmol) was added to a solution of compound 6 (49.5 g, 111 mmol) in dry DMF (650 ml) at RT. After stirring at RT for 2 h, the reaction mixture was poured into an ice water bath (1.5 L). The resultant yellow precipitate was collected, washed with water, and dried at 45° C. under vacuum to give compound 7 as a yellow solid (56 g, 110 mmol). MS: C$_{25}$H$_{16}$F$_3$N$_3$O$_6$ [M+1]$^+$512.0.

Step 3: BCl$_3$ (1 M in CH$_2$Cl$_2$, 78 ml, 78 mmol) solution was added to a solution of compound 7 (10 g, 19.57 mmol) in dry CH$_2$Cl$_2$ (400 ml) at −15° C. After the addition of BCl$_3$, the mixture turned yellow and precipitate started to form. The reaction was warmed to 0° C. After the reaction was complete (checked by TLC), the mixture was poured into ice-water (600 ml). The yellow precipitate was filtered, washed with

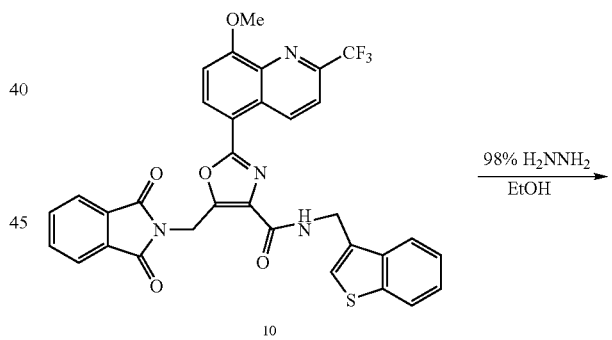

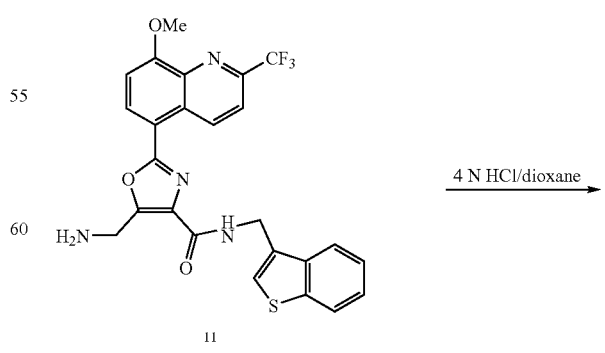

-continued

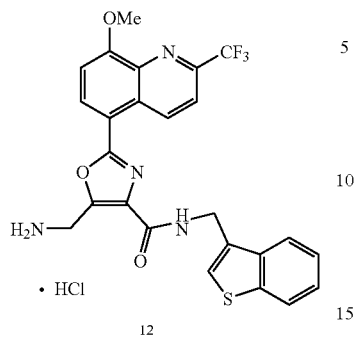
12

Step 1: To a suspension of compound 8 (0.35 g, 0.7 mmol) in dry DMF (16 ml), compound 9 (3-aminomethyl benzothiophene) (0.11 g, 0.7 mmol), DI PEA (0.18 g, 1.4 mmol) and HATU (0.53 g, 1.4 mmol) were added at RT. After 30 ml, the reaction mixture was poured into cold water (30 ml). The precipitate was filtered, washed with water and dried under vacuum to give crude compound 10 (0.45 g, 0.7 mmol) as a yellow solid.

Step 2: The crude material of compound 10 (0.45 g, 0.7 mmol) was treated with absolute EtOH (15 ml) and 98% hydrazine (0.22 g, 7 mmol) at RT overnight. The reaction mixture was evaporated and purified on a Biotage (40 M) system, eluting with 3% $NH_4OH:CH_3OH$ (1:9)/97% $CH_2Cl_2$. Compound 11 was obtained as a pure yellow solid (0.22 g, 0.43 mmol, 61% yield) which was converted to its HCl salt by treatment with 1.2 equivalent of 4 N HCl/dioxane in $CH_2Cl_2$. Compound 12 was obtained by evaporating off solvents and excess acid. MS (M+1): m/e. 513.

EXAMPLE 4

A series of aromatic or heteroaromatic amide analogs (compound 13) was made by methods analogous to those described for compound 12 in Example 3 or via an alternative coupling method by treatment of compound 8 (0.2 mmol) either with aromatic or heteroaromatic amine reagent (0.2 mmol), DEC (0.24 mmol), HOBT (0.24 mmol), and TEA (0.24 mmol) in DMF (2.5 ml) at RT overnight. Water (3 ml) was added to the reaction and precipitate was collected, rinsed with water, and vacuum dried at 40° C. The phthalamido protecting group of the coupled product was removed with 98% hydrazine in EtOH (as in step 2 of Example 3) and purified by silica gel chromatography [5% $NH_4OH$—$CH_3OH$ (1:9) in 95% $CH_2Cl_2$] or by preparative Gilson Prep column (XTerra RP $C_{18}$, 5 µm) chromatography, gradient eluted with 0.5% TFA in (9:1) ($H_2O$—$CH_3CN$) to 0.5% TFA in $CH_3CN:H_2O$ (8:2). Compound 13 was obtained as free form or as a TFA salt, depending on the method of purification. The free form of compound 13 was treated with 1.2 equivalent of HCl to give compound 13 as a HCl salt. The data for compound 13 analogs are listed as follows:

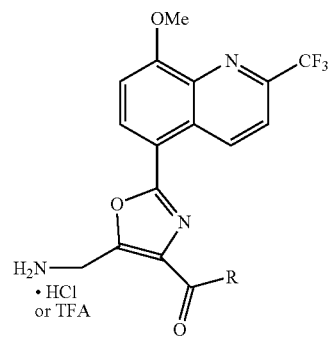
13

| Cpd. No. | Structure | MS (M + 1) |
|---|---|---|
| 13-1 | 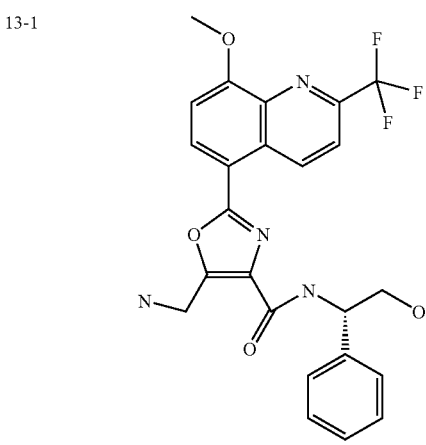 | 487 |
| 13-2 | 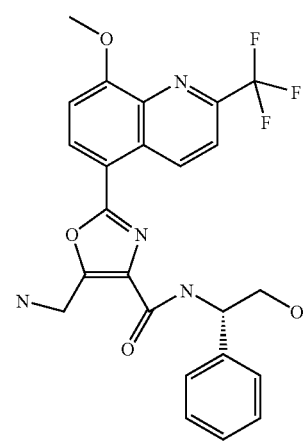 | 471 |

-continued
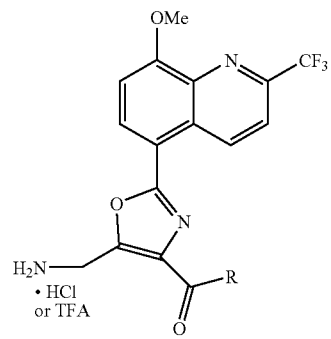
| Cpd. No. | Structure | MS (M + 1) |
|---|---|---|
| 13-3 | 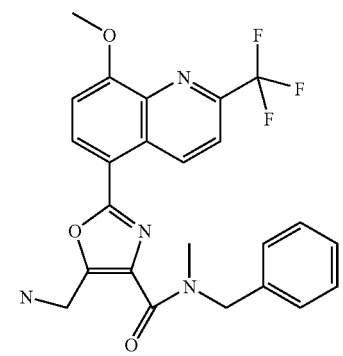 | 471 |
| 13-4 | 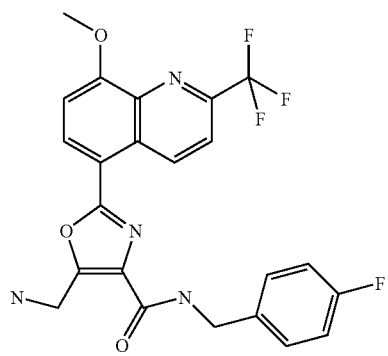 | 475 |
| 13-5 | 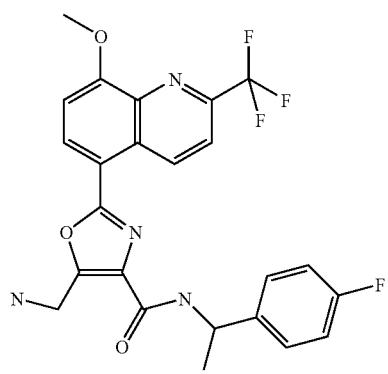 | 489 |
-continued
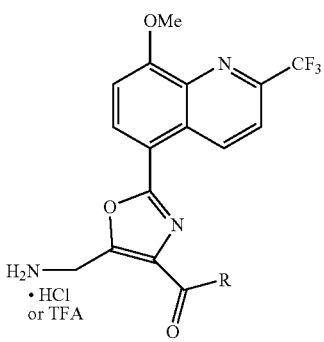
| Cpd. No. | Structure | MS (M + 1) |
|---|---|---|
| 13-6 | 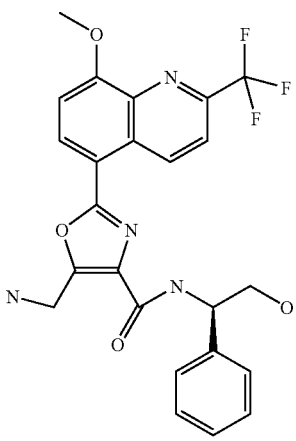 | 487 |
| 13-7 | 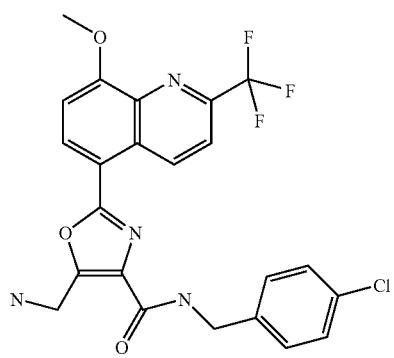 | 491 |
| 13-8 | 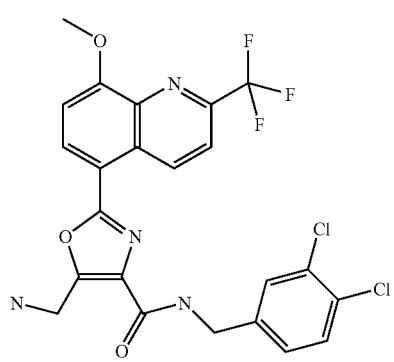 | 525 |

-continued
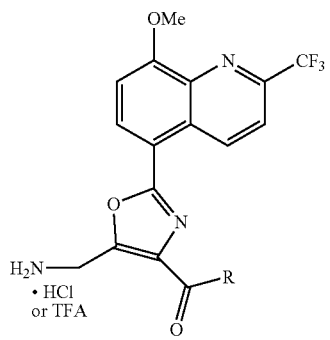
•HCl or TFA
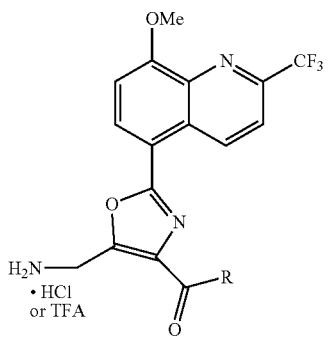
•HCl or TFA
| Cpd. No. | Structure | MS (M + 1) |
|---|---|---|
| 13-9 | 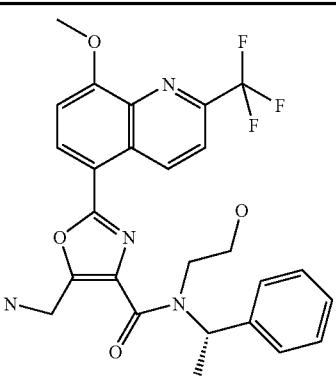 | 515 |
| 13-10 | 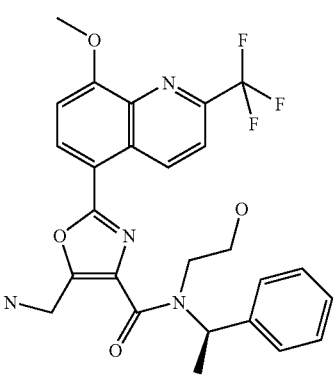 | 515 |
| 13-11 | 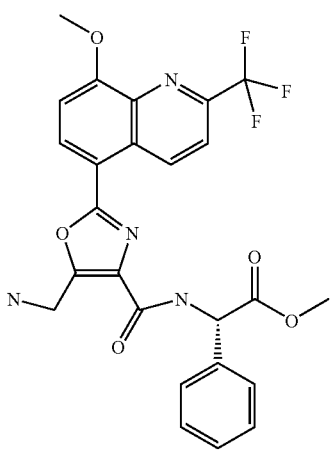 | 515 |
| Cpd. No. | Structure | MS (M + 1) |
|---|---|---|
| 13-12 | | 501 |
| 13-13 | 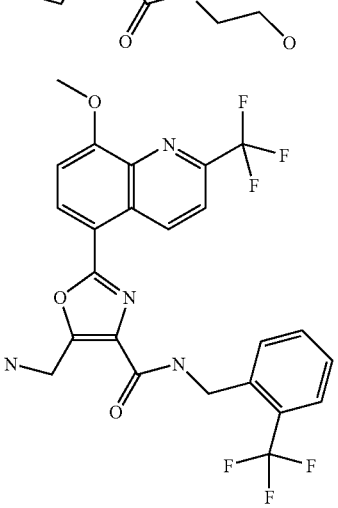 | 525 |
| 13-14 | | 475 |

-continued

| Cpd. No. | Structure | MS (M + 1) |
|---|---|---|
| 13-15 | 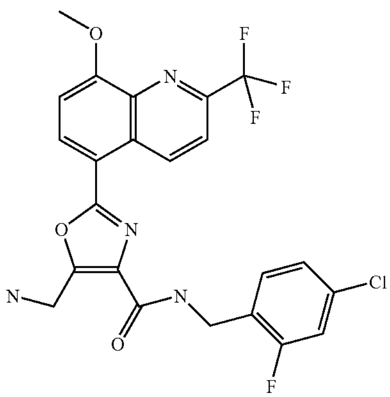 | 509 |
| 13-16 | 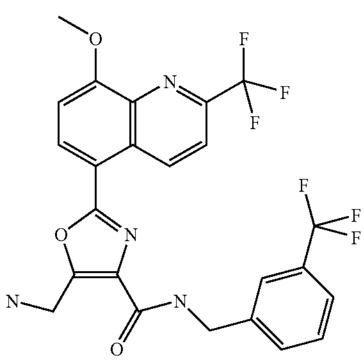 | 525 |
| 13-17 | 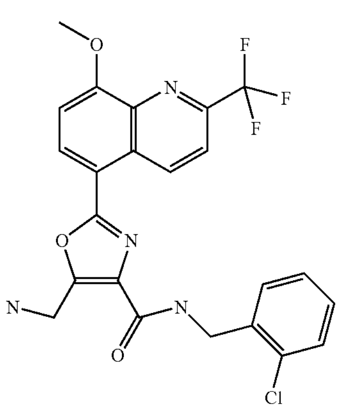 | 491 |
| 13-18 | | 475 |
| 13-19 | | 491 |
| 13-20 | | 525 |

-continued

13

[Structure: 8-methoxy-2-(trifluoromethyl)quinoline linked to oxazole with CH2NH2, HCl or TFA salt, and C(=O)R group]

| Cpd. No. | Structure | MS (M + 1) |
|---|---|---|
| 13-21 | 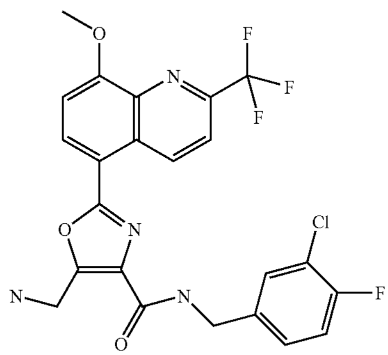 | 509 |
| 13-22 | 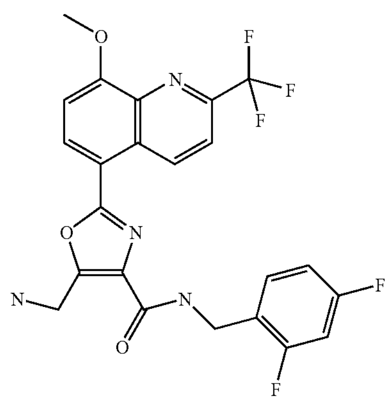 | 493 |
| 13-23 | 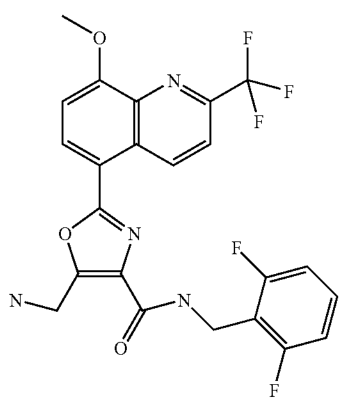 | 493 |
| 13-24 | | 493 |
| 13-25 | | 535 |
| 13-26 | | 487 |

| Cpd. No. | Structure | MS (M + 1) |
|---|---|---|
| 13-27 | 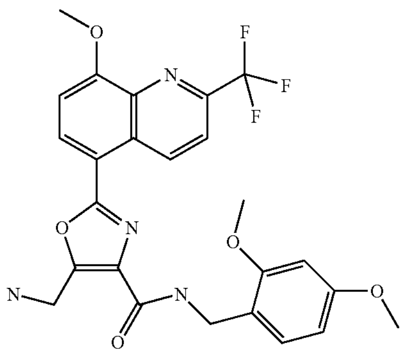 | 517 |
| 13-28 | 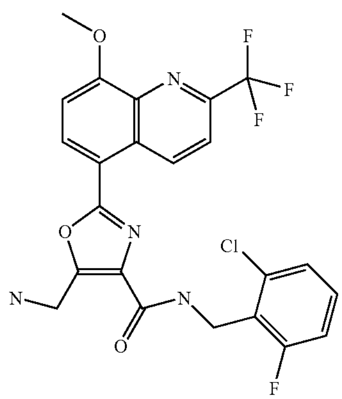 | 509 |
| 13-29 | 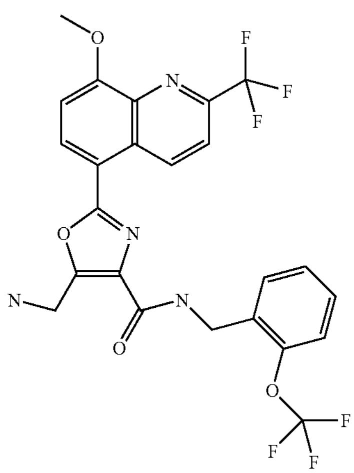 | 541 |
| 13-30 | | 523 |
| 13-31 | | 487 |
| 13-32 | | 505 |

-continued
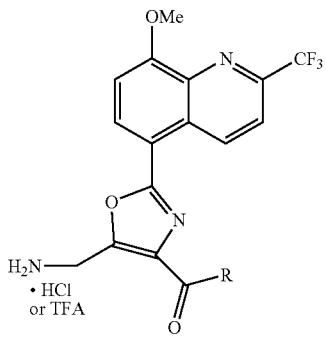
·HCl or TFA
| Cpd. No. | Structure | MS (M + 1) |
|---|---|---|
| 13-33 | 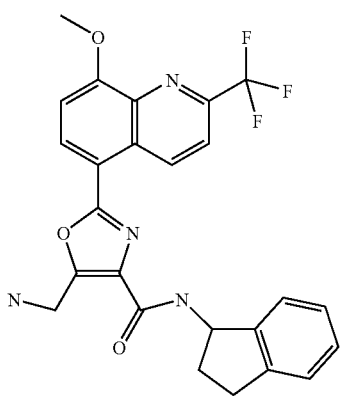 | 483 |
| 13-34 | 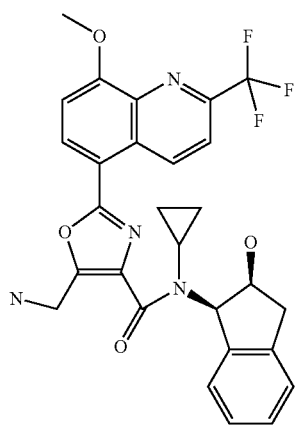 | 539 |
-continued
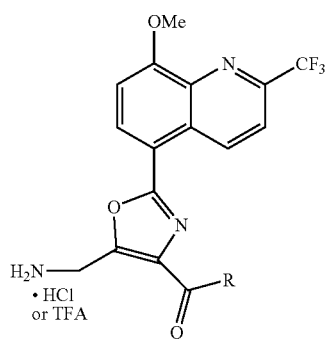
·HCl or TFA
| Cpd. No. | Structure | MS (M + 1) |
|---|---|---|
| 13-35 | 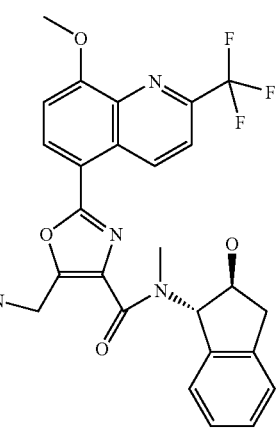 | 513 |
| 13-36 | 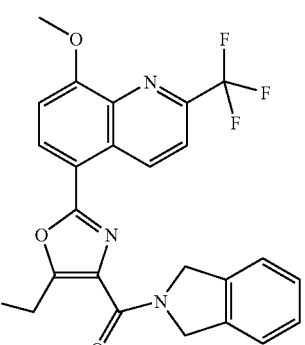 | 469 |
| 13-37 | 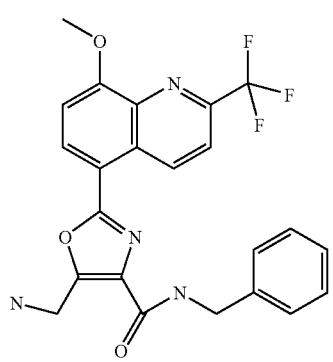 | 457 |

-continued

| Cpd. No. | Structure | MS (M + 1) |
|---|---|---|

13

[Structure: 8-methoxy-2-(trifluoromethyl)quinolin-5-yl oxazole with H₂N-CH₂ and C(=O)R groups; ·HCl or TFA]

| Cpd. No. | Structure | MS (M + 1) |
|---|---|---|
| 13-38 | [oxazole carboxamide with N-(3-methoxybenzyl)] | 487 |
| 13-39 | [oxazole carboxamide with N-(2-bromobenzyl)] | 537 |
| 13-40 | [oxazole carboxamide with N-(3,5-dimethoxybenzyl)] | 517 |

-continued

13

[Structure: 8-methoxy-2-(trifluoromethyl)quinolin-5-yl oxazole with H₂N-CH₂ and C(=O)R groups; ·HCl or TFA]

| Cpd. No. | Structure | MS (M + 1) |
|---|---|---|
| 13-41 | [oxazole carboxamide with N-(1,2,3,4-tetrahydronaphthalen-1-yl)] | 497 |
| 13-42 | [oxazole carboxamide with N-(2,6-dichlorobenzyl)] | 525 |
| 13-43 | [oxazole carboxamide with N-ethyl-N-(4-methylbenzyl)] | 499 |

51
-continued
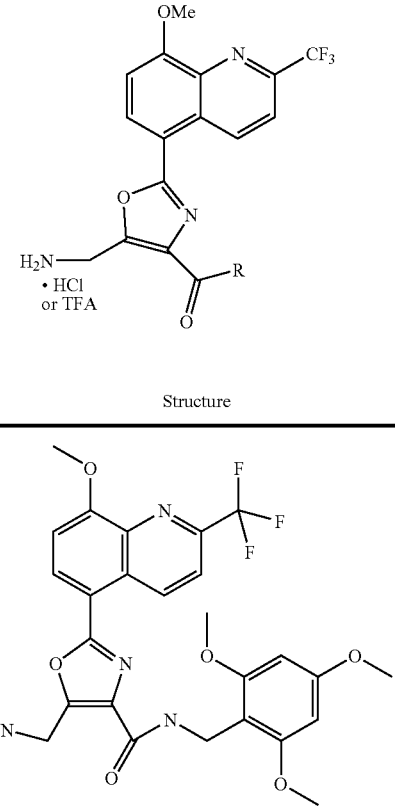
· HCl or TFA
| Cpd. No. | Structure | MS (M + 1) |
|---|---|---|
| 13-44 | 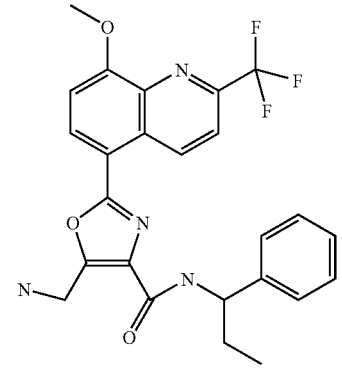 | 547 |
| 13-45 | 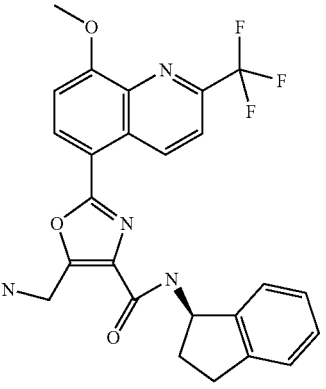 | 485 |
| 13-46 | 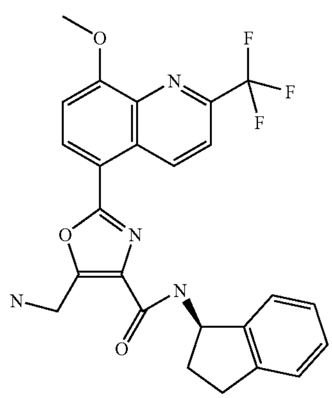 | 483 |
52
-continued
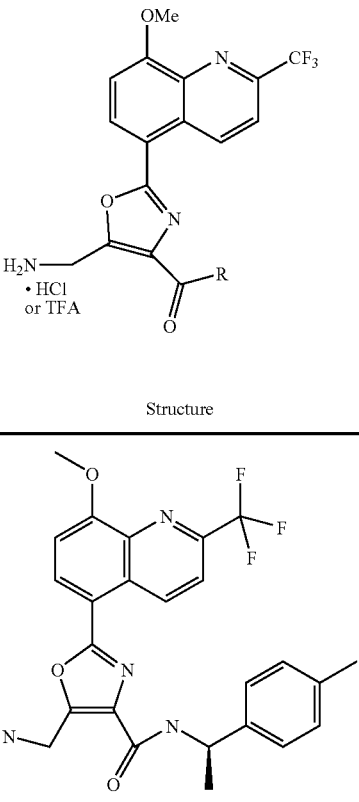
· HCl or TFA
| Cpd. No. | Structure | MS (M + 1) |
|---|---|---|
| 13-47 | 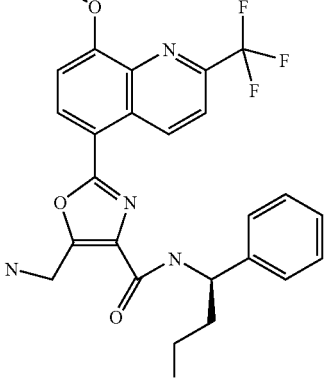 | 485 |
| 13-48 | 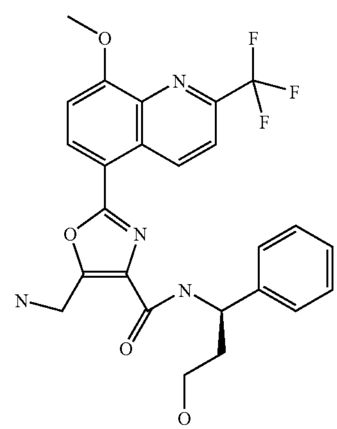 | 501 |
| 13-49 | 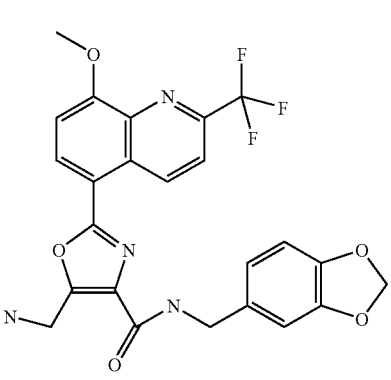 | 501 |

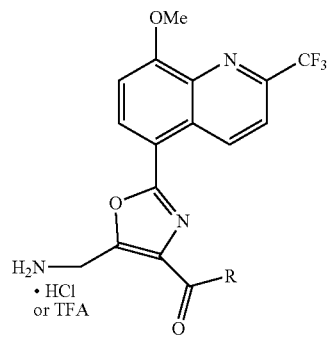
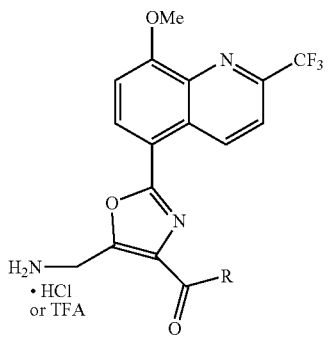
| Cpd. No. | Structure | MS (M + 1) |
|---|---|---|
| 13-50 | 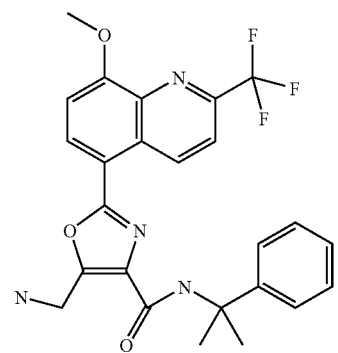 | 485 |
| 13-51 | 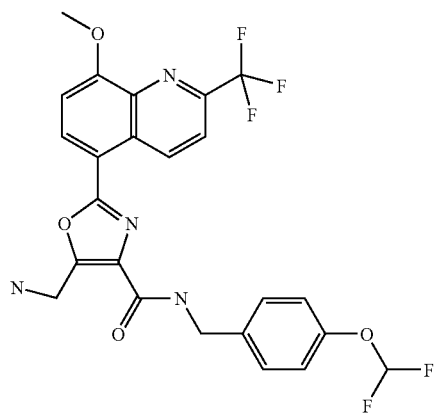 | 523 |
| 13-52 | 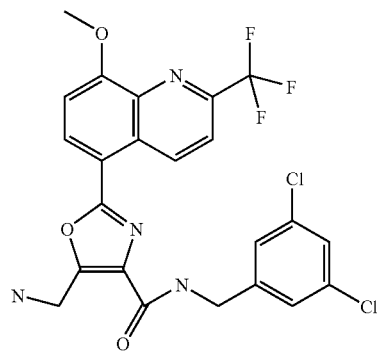 | 526 |
| Cpd. No. | Structure | MS (M + 1) |
|---|---|---|
| 13-53 | 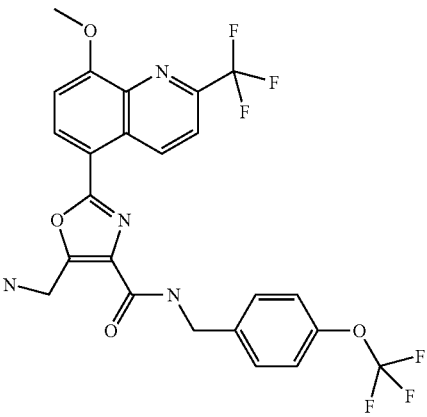 | 541 |
| 13-54 | 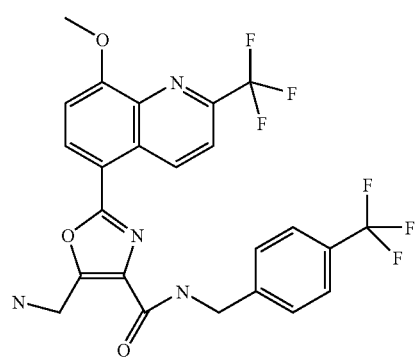 | 525 |
| 13-55 | 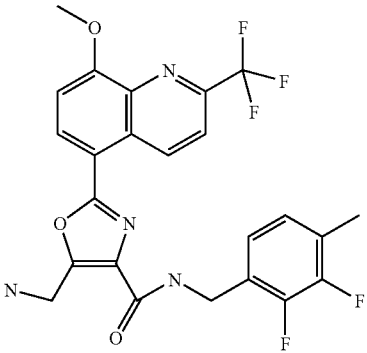 | 507 |

-continued
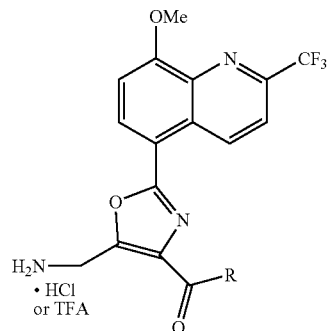
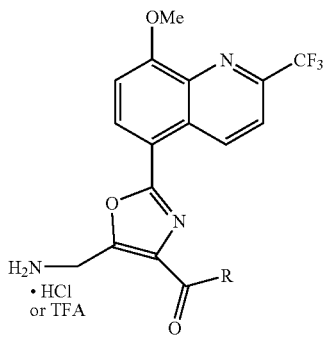
| Cpd. No. | Structure | MS (M + 1) |
|---|---|---|
| 13-56 | | 535 |
| 13-57 | | 515 |
| 13-58 | | 499 |
| Cpd. No. | Structure | MS (M + 1) |
|---|---|---|
| 13-59 | | 533 |
| 13-60 | | 503 |
| 13-61 | | 483 |

-continued
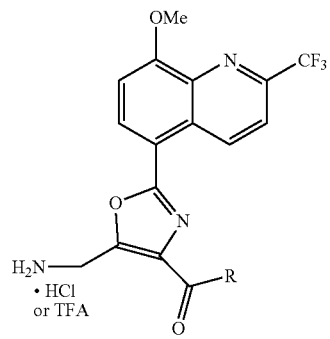
| Cpd. No. | Structure | MS (M + 1) |
|---|---|---|
| 13-62 | 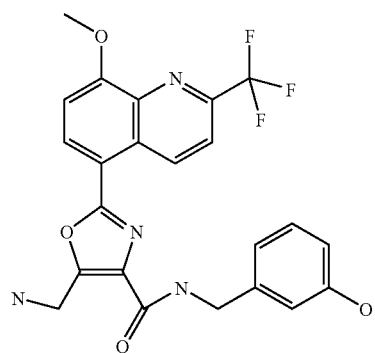 | 473 |
| 13-63 | 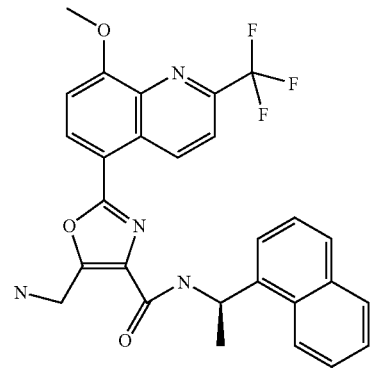 | 521 |
| 13-64 | 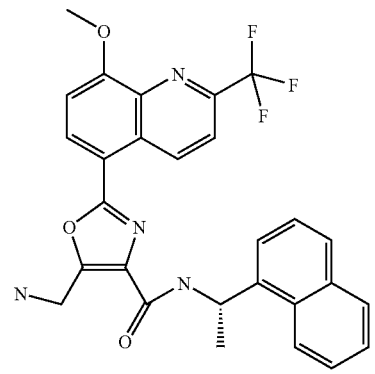 | 521 |
-continued
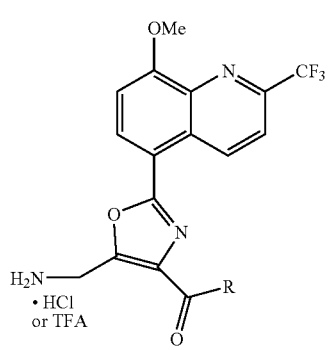
| Cpd. No. | Structure | MS (M + 1) |
|---|---|---|
| 13-65 | 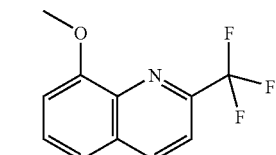 | 521 |
| | 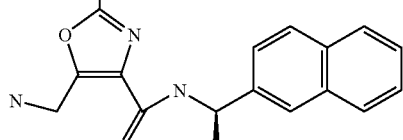 | |
| 13-66 | 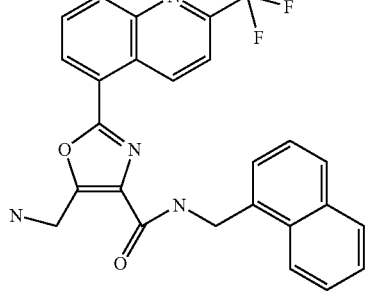 | 507 |
| 13-67 | 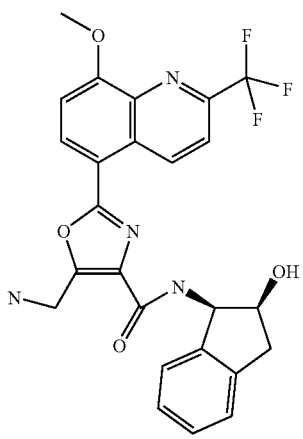 | 499 |

-continued

| Cpd. No. | Structure | MS (M + 1) |
|---|---|---|
| 13-68 | 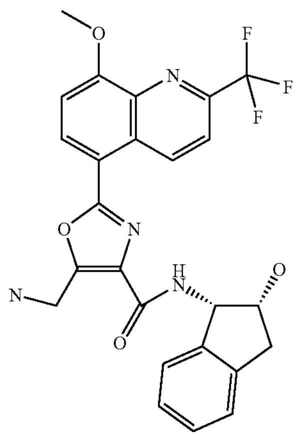 | 499 |
| 13-69 | 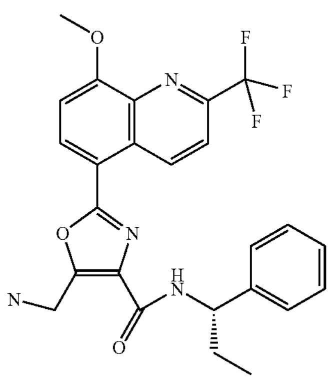 | 485 |
| 13-70 | 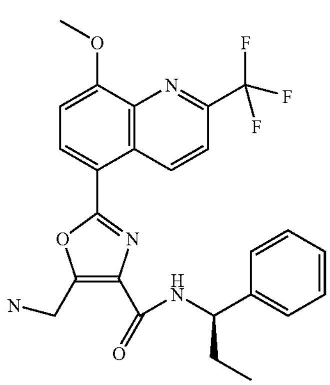 | 485 |
| 13-71 | | 485 |
| 13-72 | | 485 |
| 13-73 | | 538 |

-continued
| Cpd. No. | Structure | MS (M + 1) |
|---|---|---|
| 13-74 | 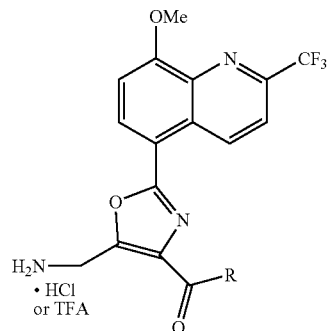 | 500 |
| 13-75 | 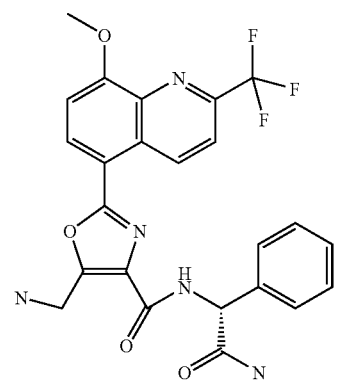 | 487 |
-continued
| Cpd. No. | Structure | MS (M + 1) |
|---|---|---|
| 13-76 | 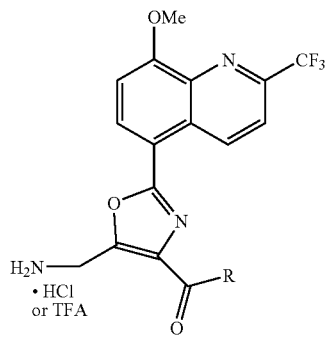 | 565 |
| 13-77 | 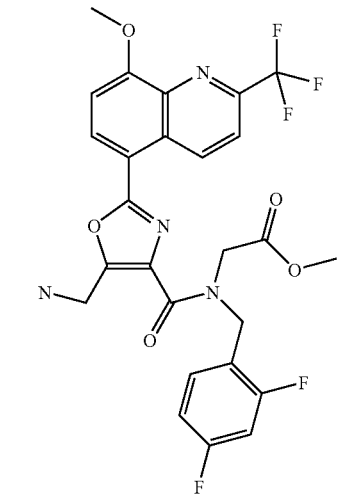 | 505 |

-continued

| Cpd. No. | Structure | MS (M + 1) |
|---|---|---|
| 13-78 | 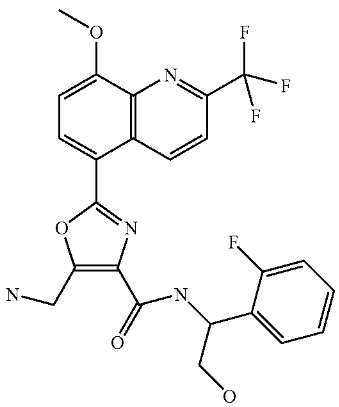 | 505 |
| 13-79 | 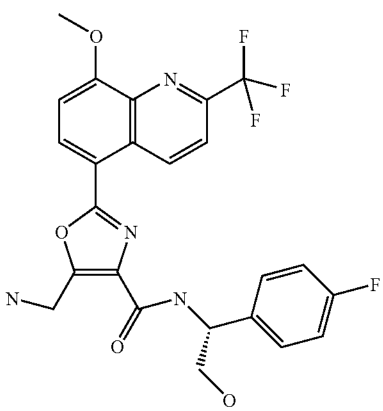 | 505 |
| 13-80 | 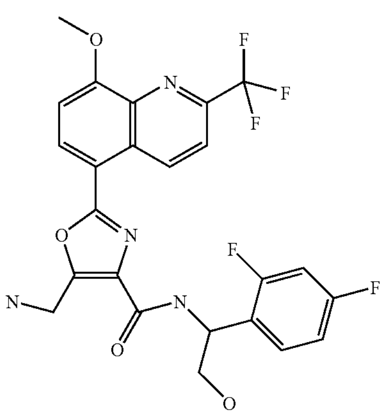 | 523 |
| 13-81 | | 527 |
| 13-82 | | 513 |
| 13-83 | | 527 |

-continued

| Cpd. No. | Structure | MS (M + 1) |
|---|---|---|
| 13-84 | | 527 |
| 13-85 | | 555 |
| 13-86 | 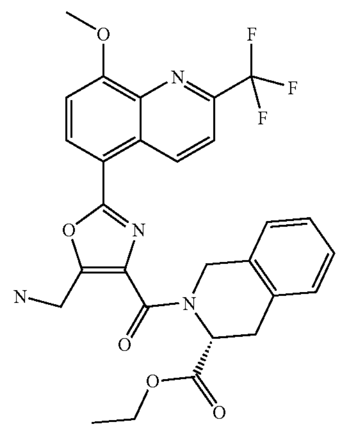 | 555 |
| 13-87 | 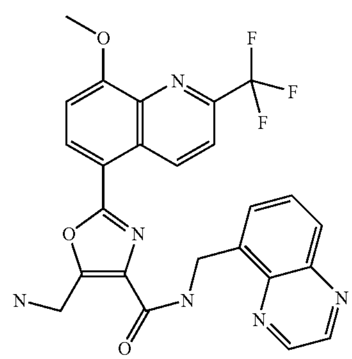 | 509 |
| 13-88 | 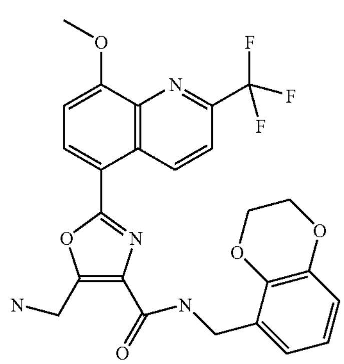 | 515 |

-continued
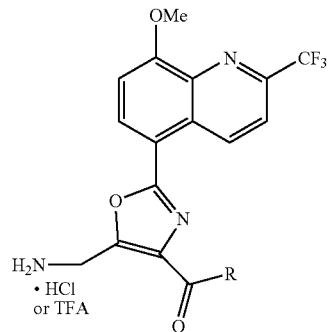
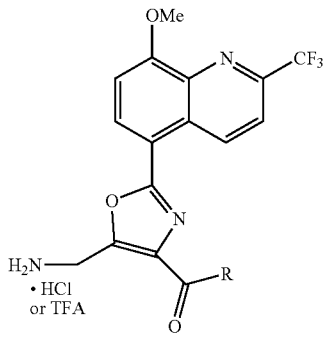
| Cpd. No. | Structure | MS (M + 1) |
|---|---|---|
| 13-89 | 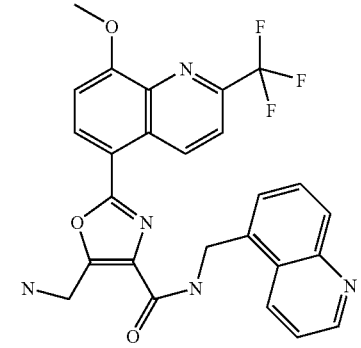 | 508 |
| 13-90 | 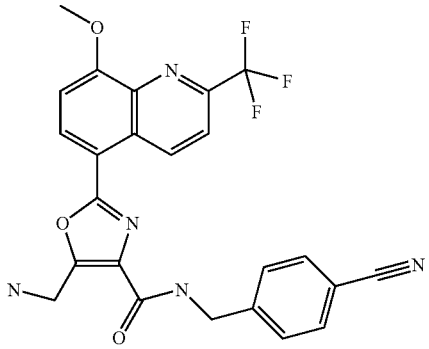 | 482 |
| 13-91 | 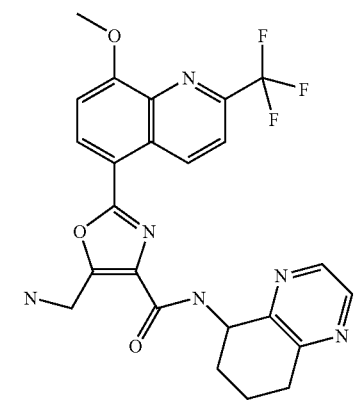 | 499 |
| Cpd. No. | Structure | MS (M + 1) |
|---|---|---|
| 13-92 | | 473 |
| 13-93 | 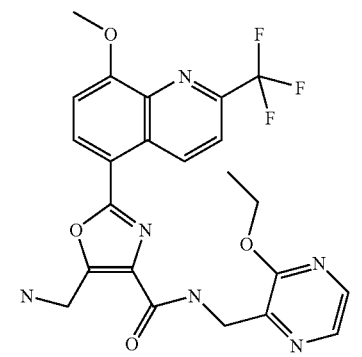 | 515 |
| 13-94 | | 503 |

-continued

| Cpd. No. | Structure | MS (M + 1) |
|---|---|---|
| 13-95 | 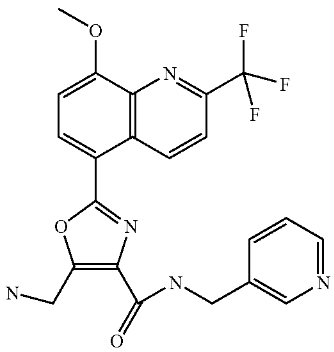 | 458 |
| 13-96 | 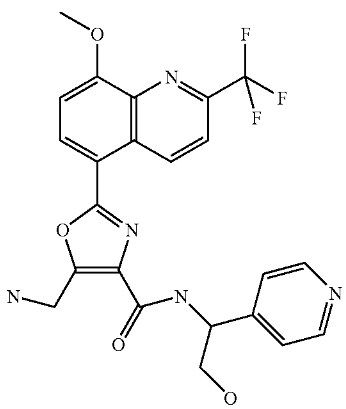 | 488 |
| 13-97 | 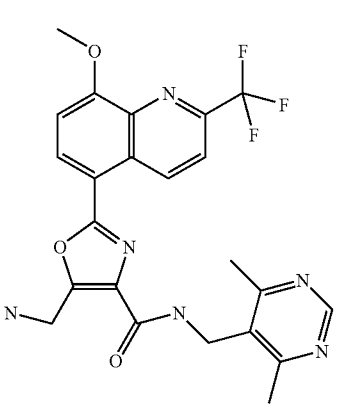 | 487 |
| 13-98 | | 499 |
| 13-99 | | 519 |
| 13-100 | | 527 |

-continued
| Cpd. No. | Structure | MS (M + 1) |
|---|---|---|
| 13-101 | 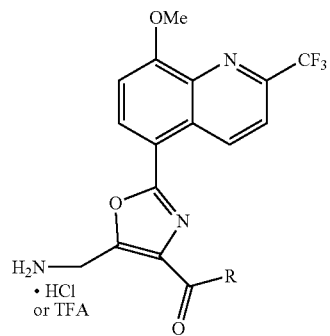 | 547 |
| 13-102 | 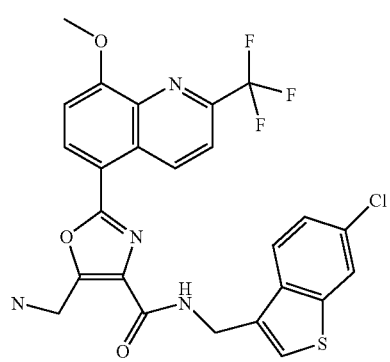 | 531 |
| 13-103 | 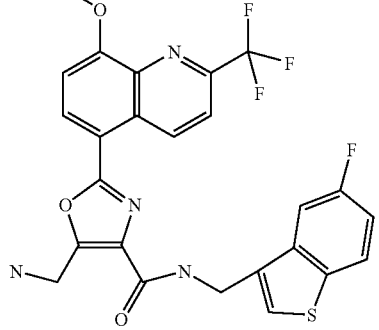 | 571 |
-continued
| Cpd. No. | Structure | MS (M + 1) |
|---|---|---|
| 13-104 | 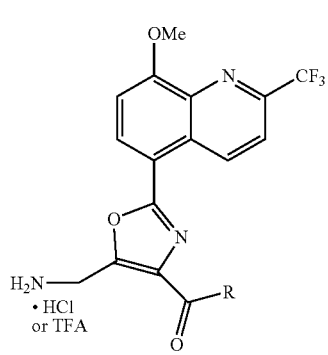 | 515 |
| 13-105 | 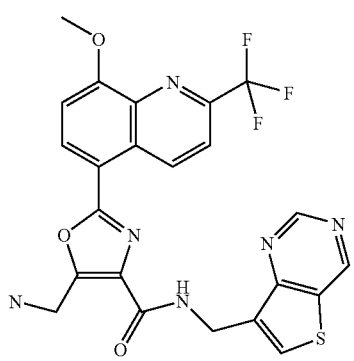 | 545 |
| 13-106 | 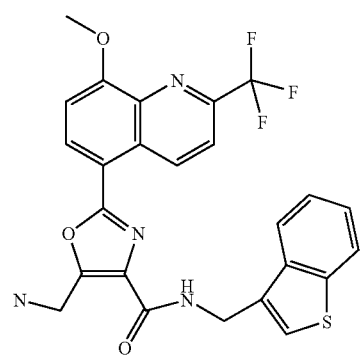 | |

-continued
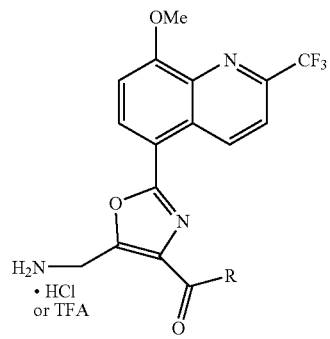
• HCl or TFA
| Cpd. No. | Structure | MS (M + 1) |
|---|---|---|
| 13-107 | 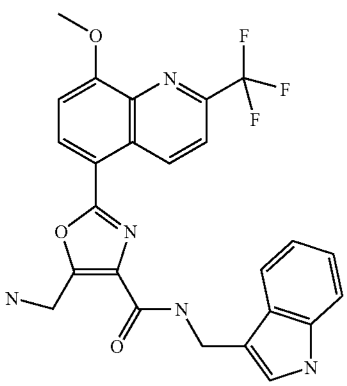 | 496 |
| 13-108 | 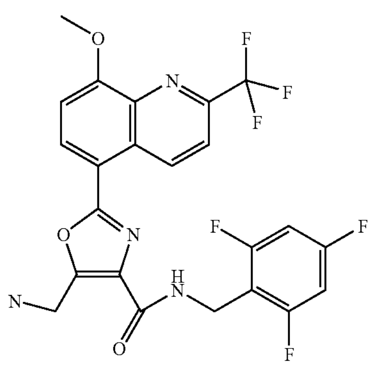 | 511 |
| 13-109 | 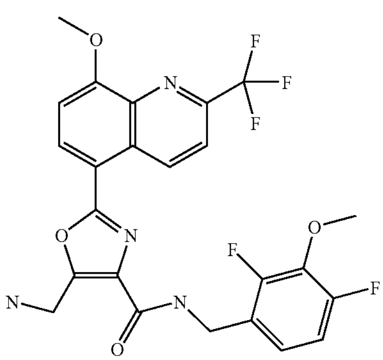 | 523 |
-continued
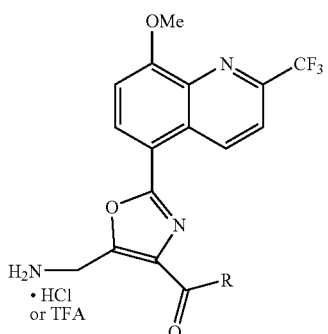
• HCl or TFA
| Cpd. No. | Structure | MS (M + 1) |
|---|---|---|
| 13-110 | 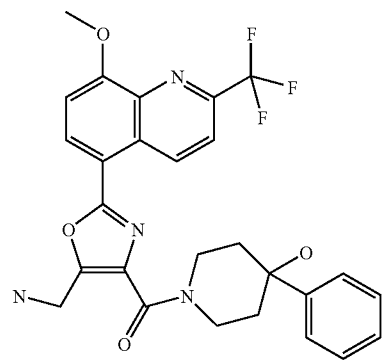 | 527 |
| 13-111 | 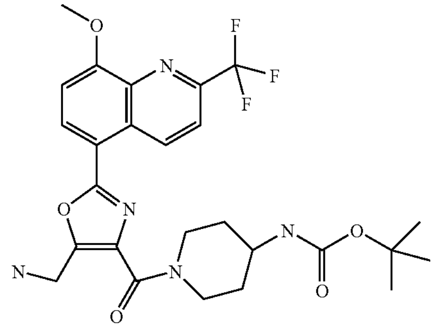 | 550 |
| 13-112 | 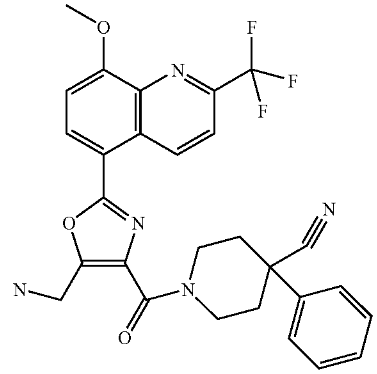 | 536 |

-continued
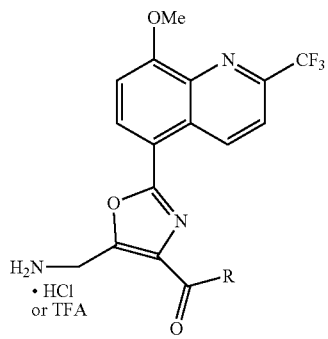
• HCl or TFA
| Cpd. No. | Structure | MS (M + 1) |
|---|---|---|
| 13-113 | 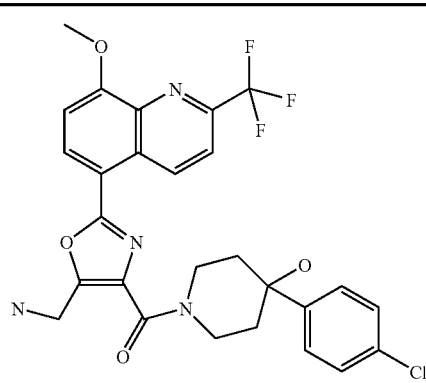 | 561 |
| 13-114 | 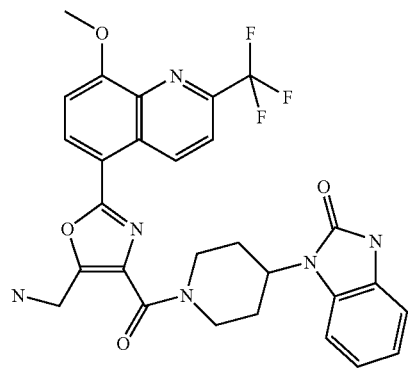 | 567 |
| 13-115 | 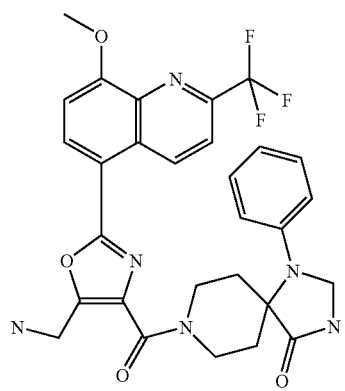 | 581 |
-continued
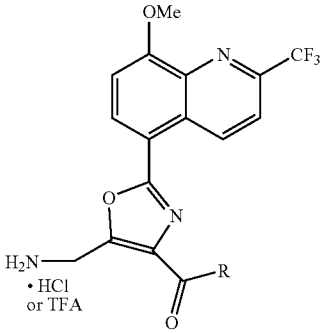
• HCl or TFA
| Cpd. No. | Structure | MS (M + 1) |
|---|---|---|
| 13-116 | 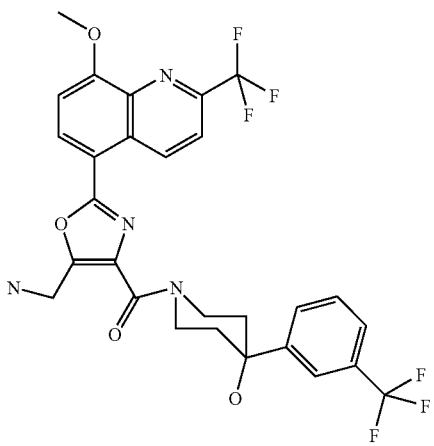 | 595 |
| 13-117 | 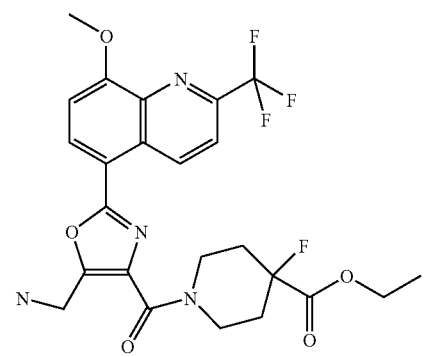 | 525 |
| 13-118 | 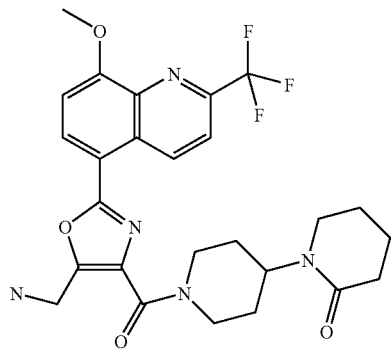 | 532 |

-continued
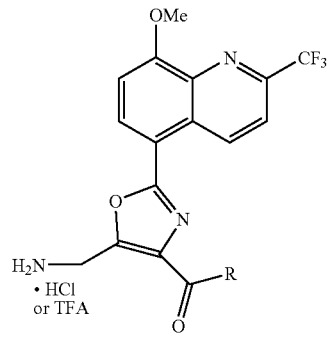
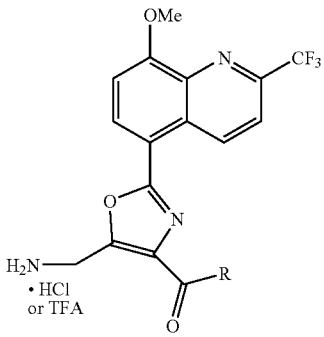
| Cpd. No. | Structure | MS (M + 1) |
|---|---|---|
| 13-119 | | 539 |
| 13-120 | | 569 |
| 13-121 | | 533 |
| Cpd. No. | Structure | MS (M + 1) |
|---|---|---|
| 13-122 | | 546 |
| 13-123 | | 555 |
| 13-124 | | 540 |

-continued
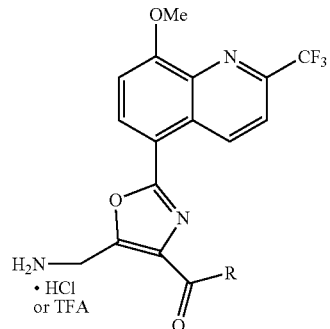
| Cpd. No. | Structure | MS (M + 1) |
|---|---|---|
| 13-125 | 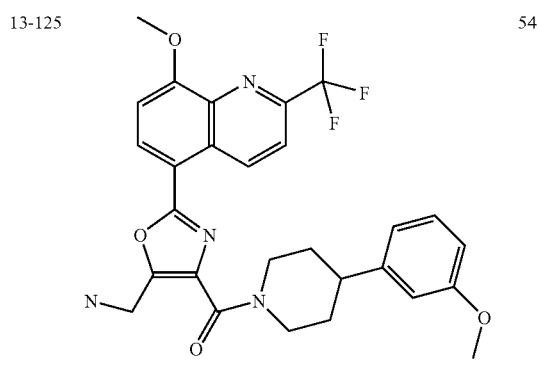 | 541 |
| 13-126 | 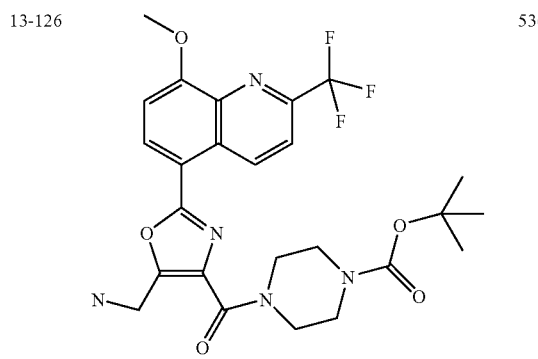 | 536 |
| 13-127 | 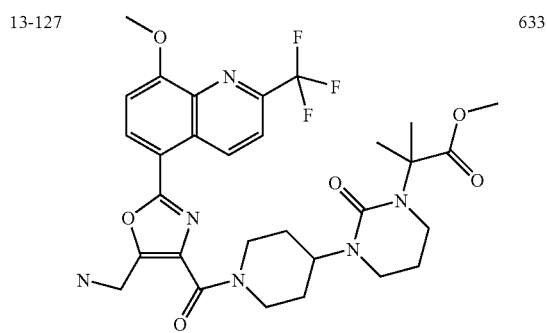 | 633 |
-continued
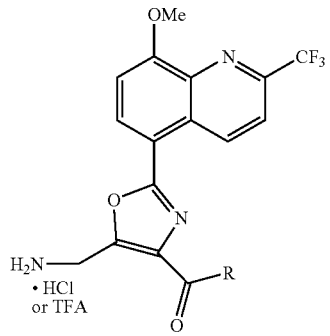
| Cpd. No. | Structure | MS (M + 1) |
|---|---|---|
| 13-128 | 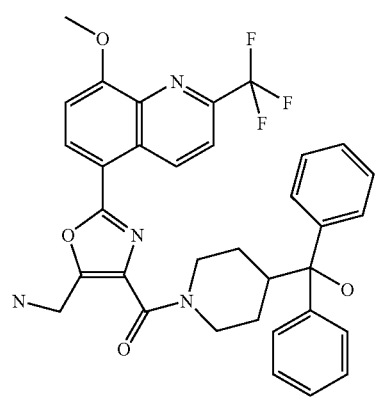 | 617 |
| 13-129 | 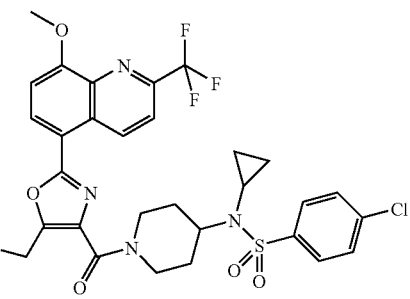 | 664 |
| 13-130 | 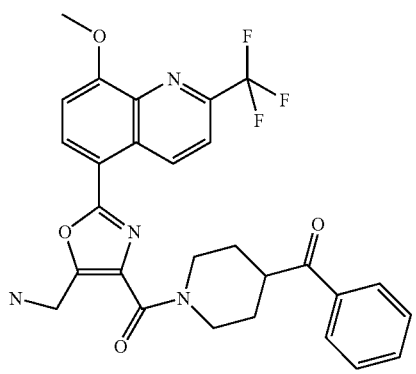 | 539 |

-continued
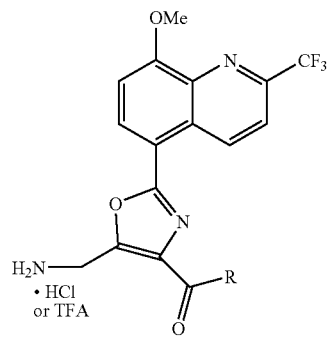
| Cpd. No. | Structure | MS (M + 1) |
|---|---|---|
| 13-131 | 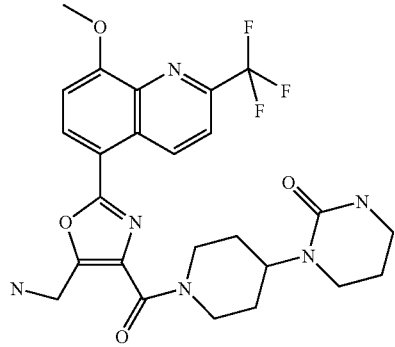 | 533 |
| 13-132 | 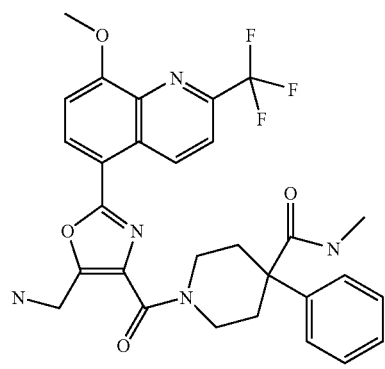 | 568 |
| 13-133 | 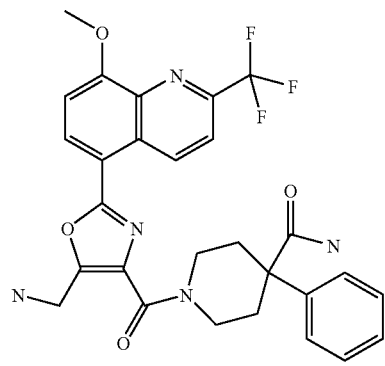 | 554 |
-continued
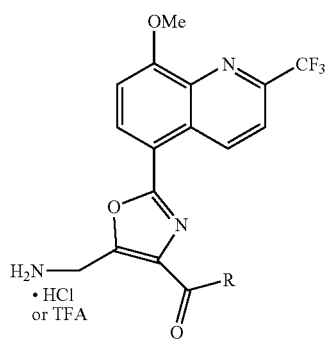
| Cpd. No. | Structure | MS (M + 1) |
|---|---|---|
| 13-134 | 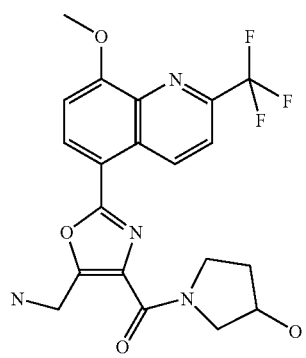 | 437 |
| 13-135 | 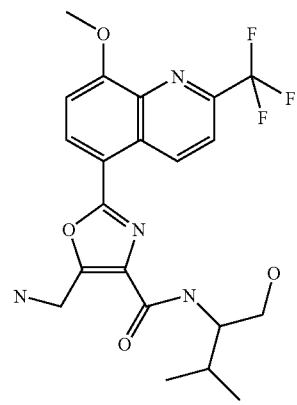 | 453 |
| 13-136 | 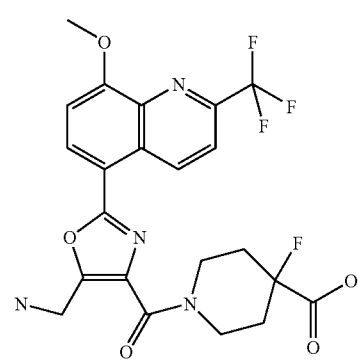 | 497 |

-continued
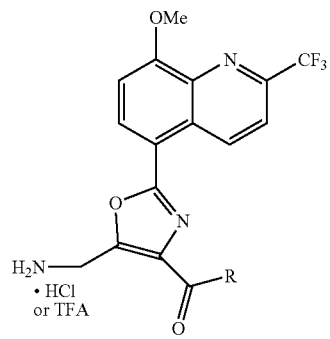
| Cpd. No. | Structure | MS (M + 1) |
|---|---|---|
| 13-137 | 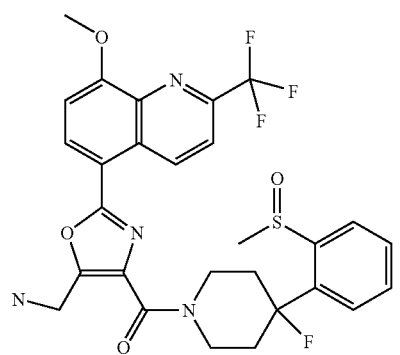 | 591 |
| 13-138 | 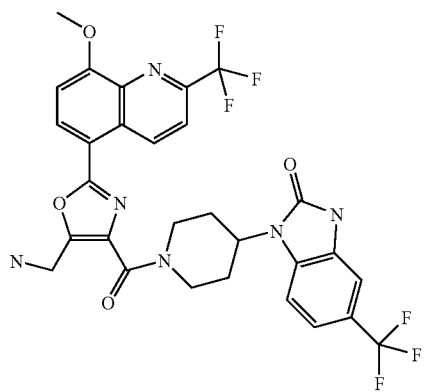 | 635 |
| 13-139 | 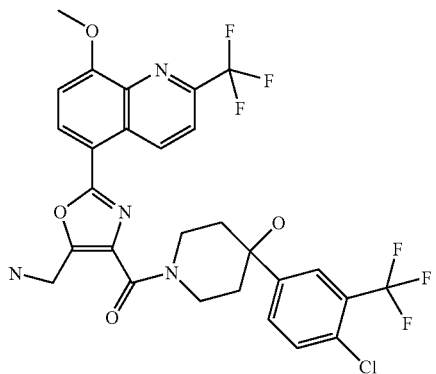 | 629 |
-continued
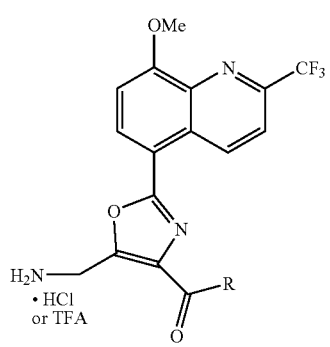
| Cpd. No. | Structure | MS (M + 1) |
|---|---|---|
| 13-140 | 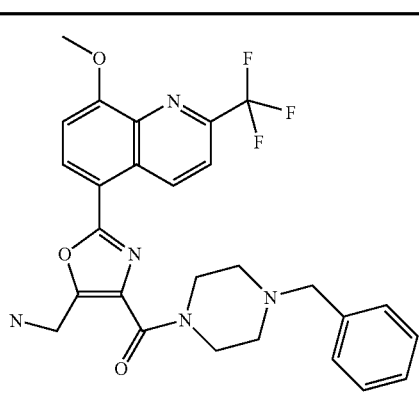 | 526 |
| 13-141 | 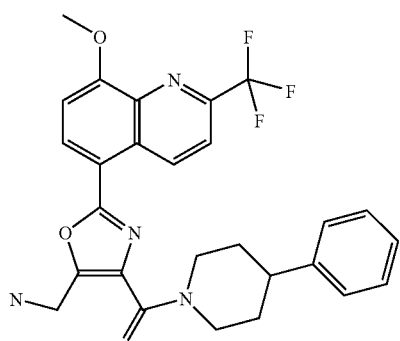 | 511 |
| 13-142 | 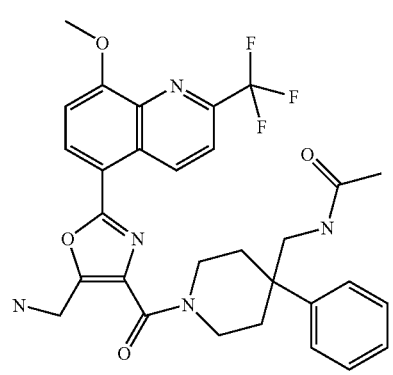 | 582 |

-continued
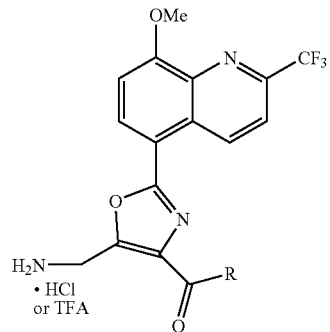
· HCl or TFA
| Cpd. No. | Structure | MS (M + 1) |
|---|---|---|
| 13-143 | 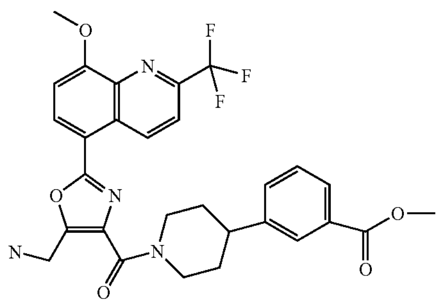 | 569 |
| 13-144 | 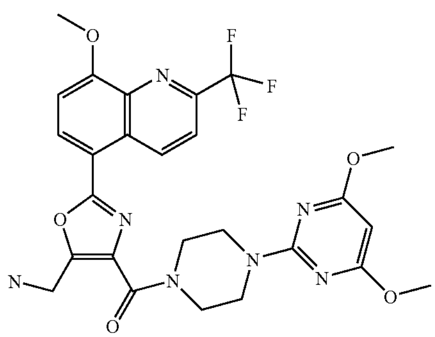 | 574 |
| 13-145 | 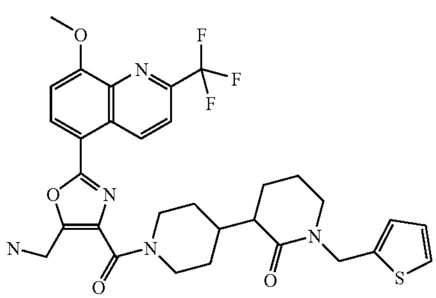 | 629 |
-continued
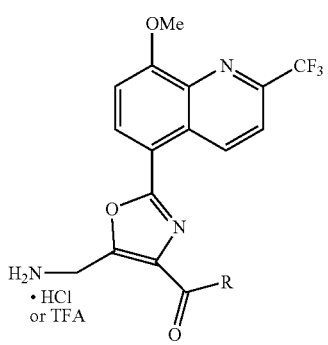
· HCl or TFA
| Cpd. No. | Structure | MS (M + 1) |
|---|---|---|
| 13-146 | 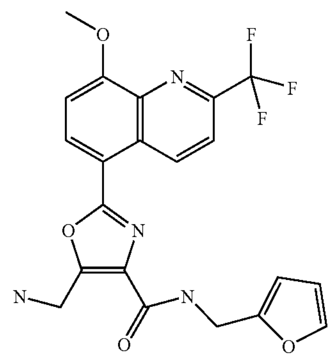 | 447 |
| 13-147 | 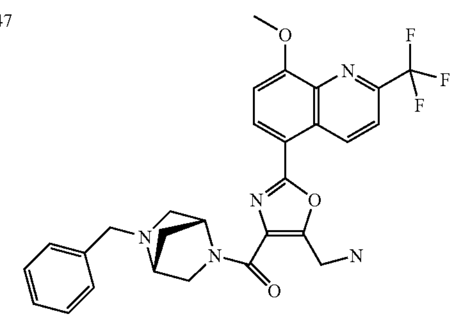 | 538 |
| 13-148 | 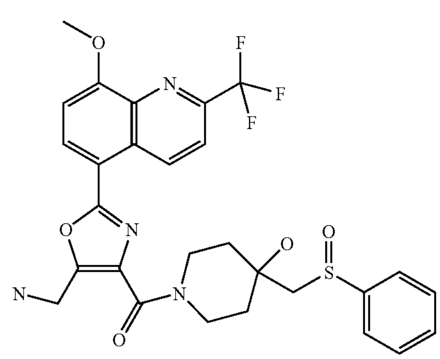 | 589 |

-continued
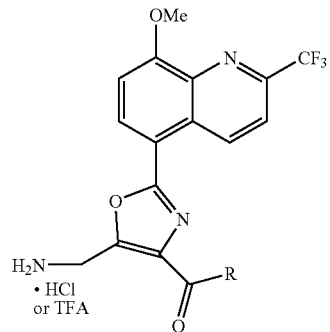
| Cpd. No. | Structure | MS (M + 1) |
|---|---|---|
| 13-149 | 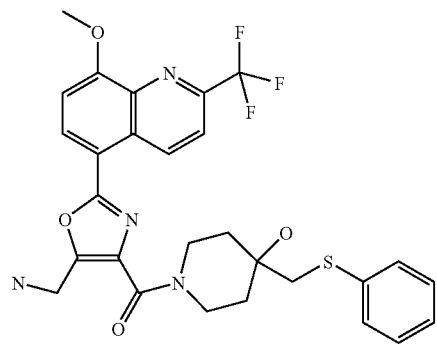 | 573 |
| 13-150 | 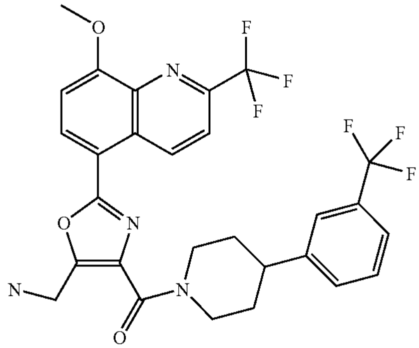 | 579 |
| 13-151 | 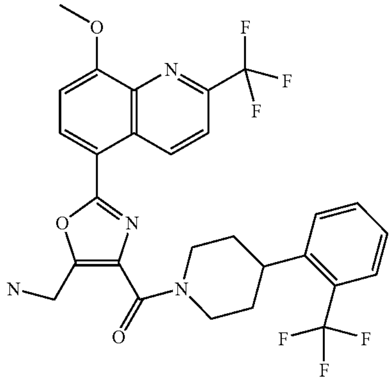 | 579 |
-continued
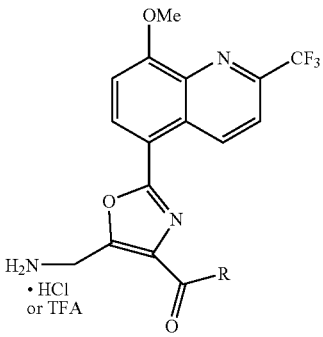
| Cpd. No. | Structure | MS (M + 1) |
|---|---|---|
| 13-152 | 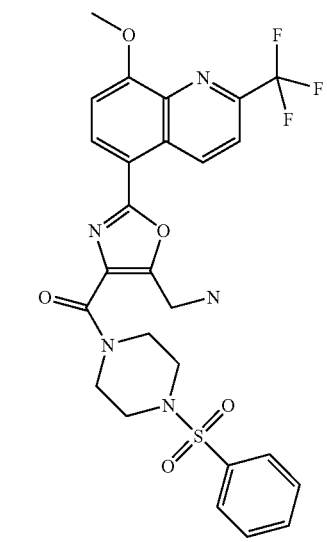 | 576 |
| 13-153 | 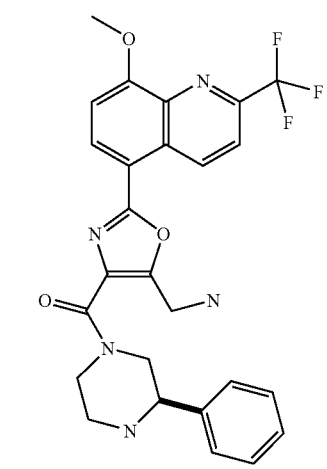 | 512 |

| Cpd. No. | Structure | MS (M + 1) |
|---|---|---|
| 13-154 | 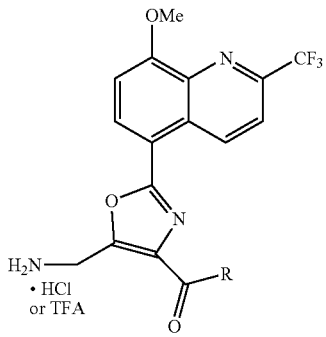 | 580 |
| 13-155 | 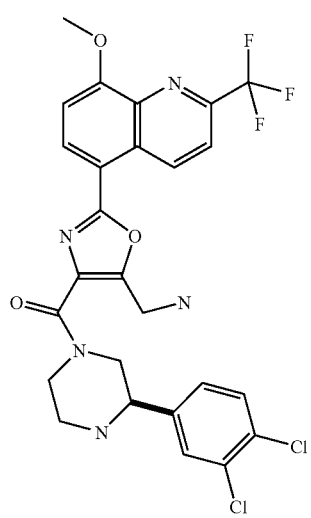 | 553 |
| Cpd. No. | Structure | MS (M + 1) |
|---|---|---|
| 13-156 | 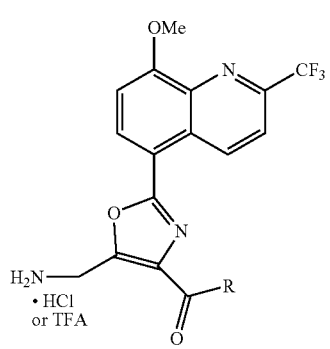 | 535 |
| 13-157 | 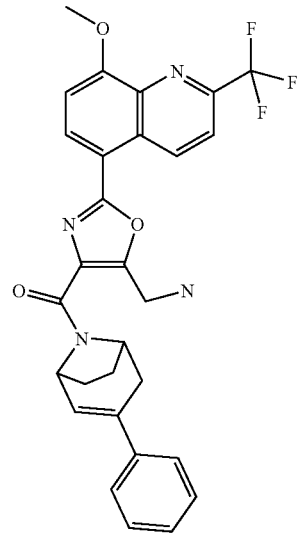 | 619 |

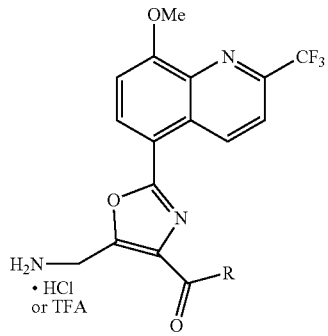

| Cpd. No. | Structure | MS (M+1) |
|---|---|---|
| 13-158 | 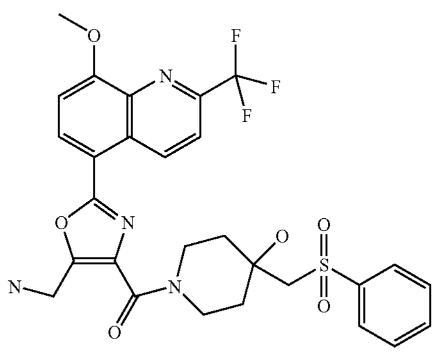 | 605 |
| 13-159 | 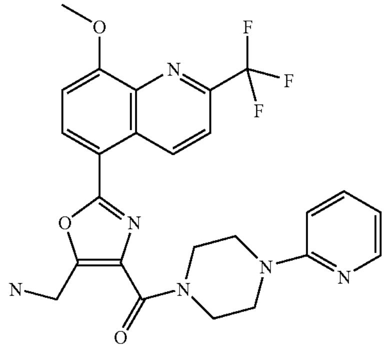 | 513 |
| 13-160 | 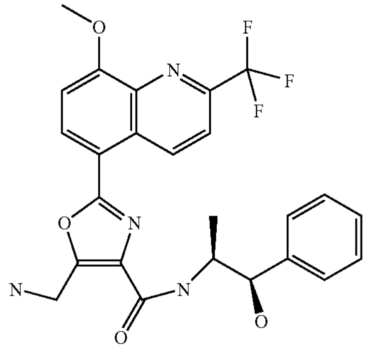 | 501 |
| 13-161 | | 501 |
| 13-162 | | 636 |

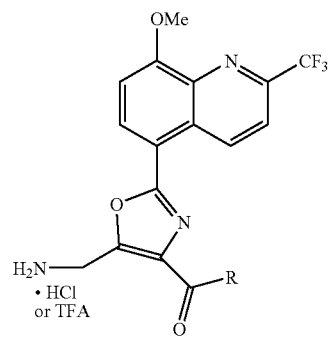
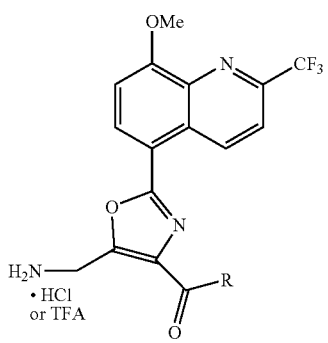
| Cpd. No. | Structure | MS (M + 1) |
|---|---|---|
| 13-163 | | 604 |
| 13-164 | | 473.5 |
| 13-165 | 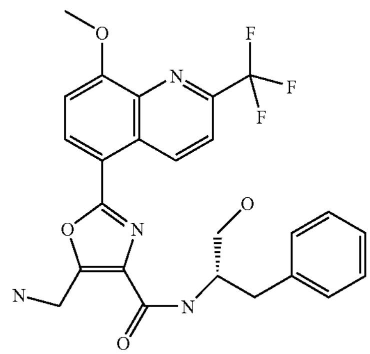 | 501 |
| 13-166 | 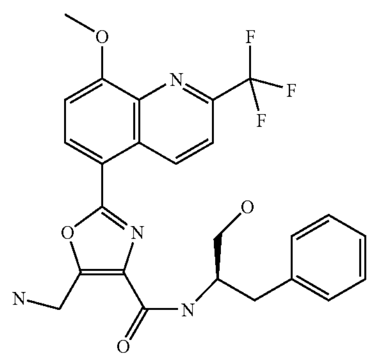 | 501 |
| 13-167 | 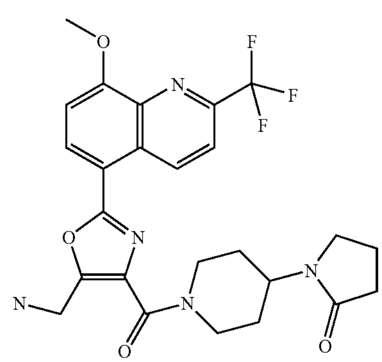 | 518 |

| Cpd. No. | Structure | MS (M + 1) |
|---|---|---|
| 13-168 | 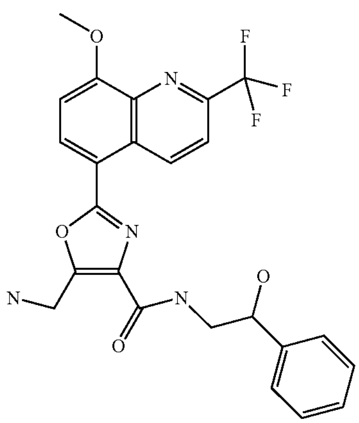 | 487 |
| 13-169 | 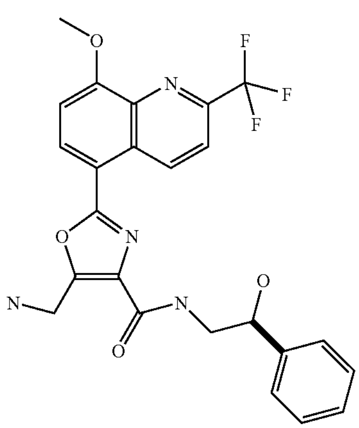 | 487 |
| 13-170 | | 601 |
| 13-171 | | 645 |

-continued
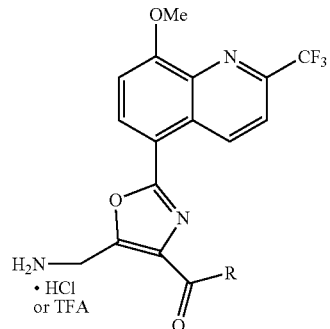
| Cpd. No. | Structure | MS (M + 1) |
|---|---|---|
| 13-172 | 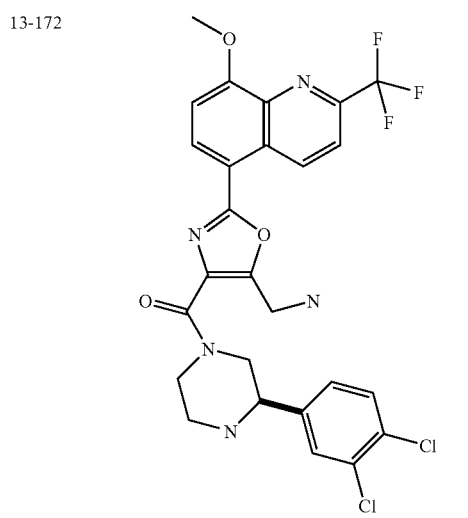 | 580 |
| 13-173 | 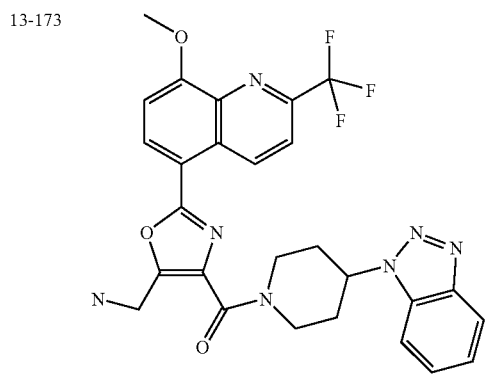 | 552 |
-continued
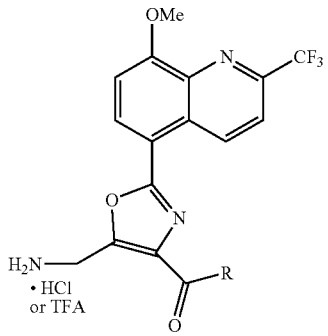
| Cpd. No. | Structure | MS (M + 1) |
|---|---|---|
| 13-174 | 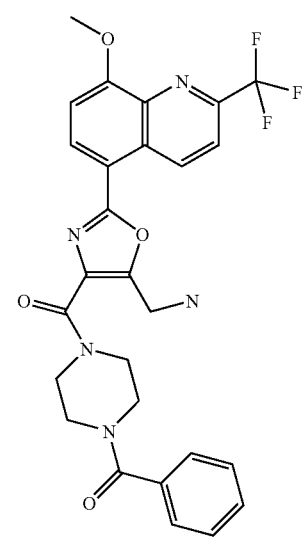 | 541 |
| 13-175 | 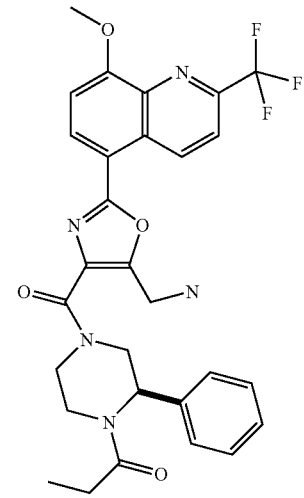 | 568 |

-continued
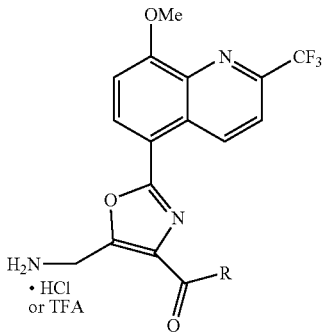
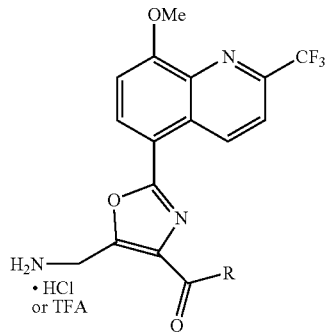
| Cpd. No. | Structure | MS (M + 1) |
|---|---|---|
| 13-176 | 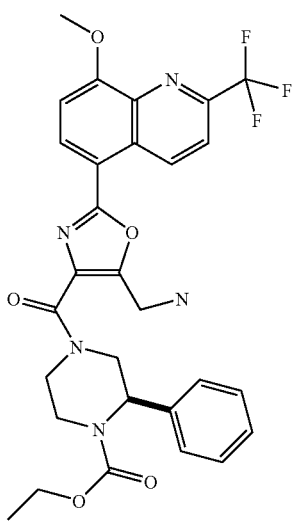 | 584 |
| Cpd. No. | Structure | MS (M + 1) |
|---|---|---|
| 13-178 | 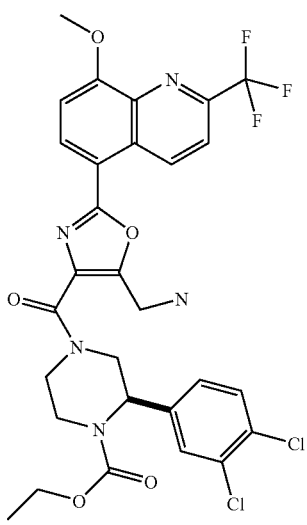 | 652 |
| 13-179 | 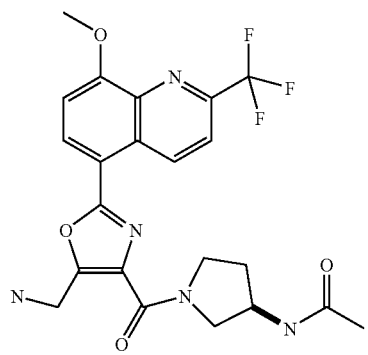 | 478 |
| 13-177 | 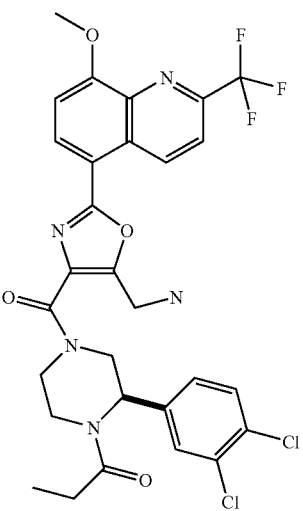 | 636 |

-continued

13

[Structure: 8-methoxy-2-(trifluoromethyl)quinoline linked to oxazole bearing CH2NH2·HCl or TFA and C(=O)R]

| Cpd. No. | Structure | MS (M + 1) |
|---|---|---|
| 13-180 | 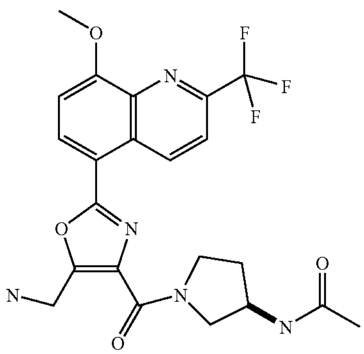 | 478 |
| 13-181 | 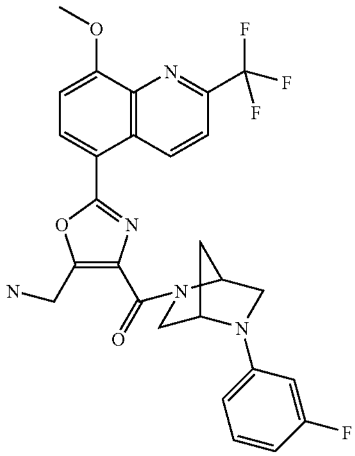 | 542 |

-continued

13

[Structure: 8-methoxy-2-(trifluoromethyl)quinoline linked to oxazole bearing CH2NH2·HCl or TFA and C(=O)R]

| Cpd. No. | Structure | MS (M + 1) |
|---|---|---|
| 13-182 | 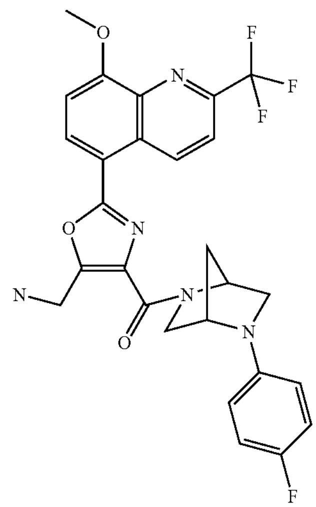 | 542 |
| 13-183 | 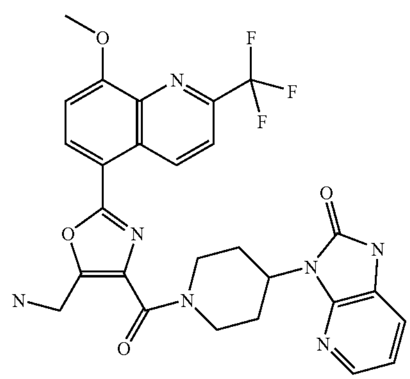 | 568 |

-continued
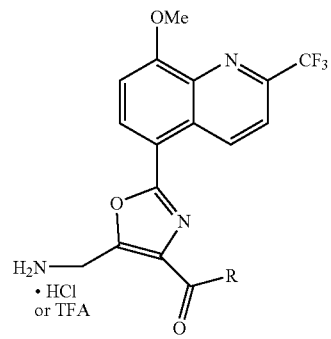
| Cpd. No. | Structure | MS (M + 1) |
|---|---|---|
| 13-184 | 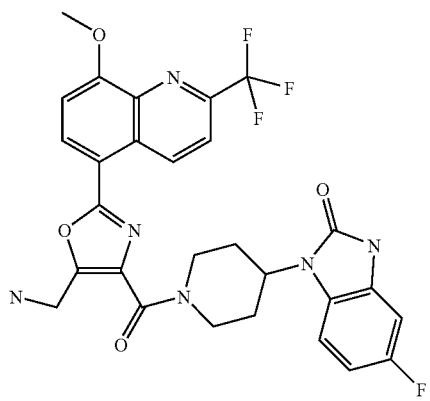 | 585 |
| 13-185 | 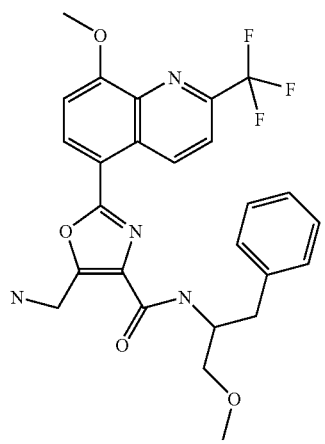 | 515 |
-continued
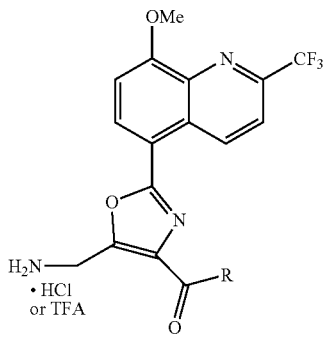
| Cpd. No. | Structure | MS (M + 1) |
|---|---|---|
| 13-186 | 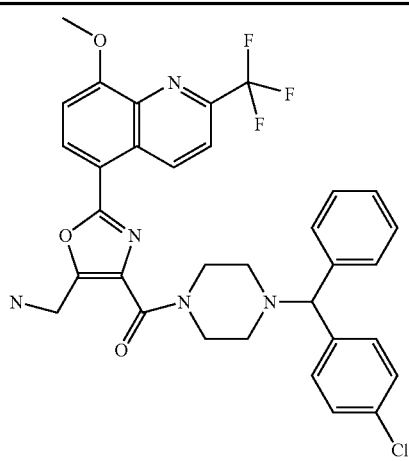 | 637 |
| 13-187 | 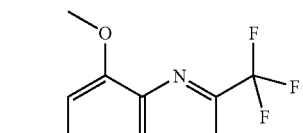 | 542 |
| 13-188 | 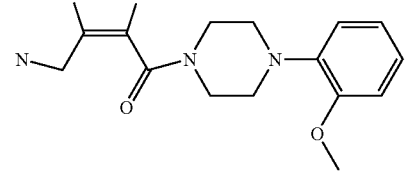 | 530 |

105
-continued
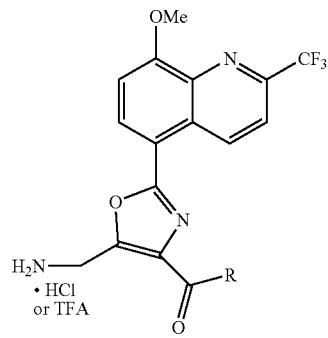
| Cpd. No. | Structure | MS (M + 1) |
|---|---|---|
| 13-189 | 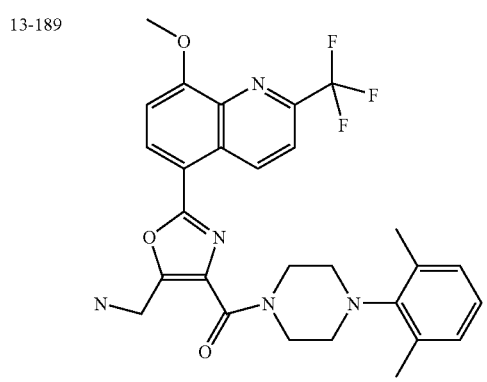 | 540 |
| 13-190 | 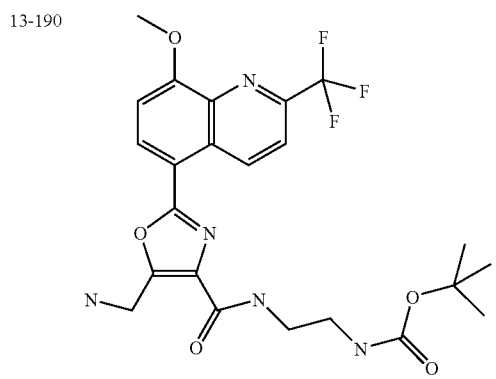 | 510 |
106
-continued
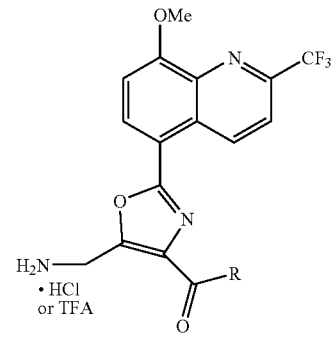
| Cpd. No. | Structure | MS (M + 1) |
|---|---|---|
| 13-191 | 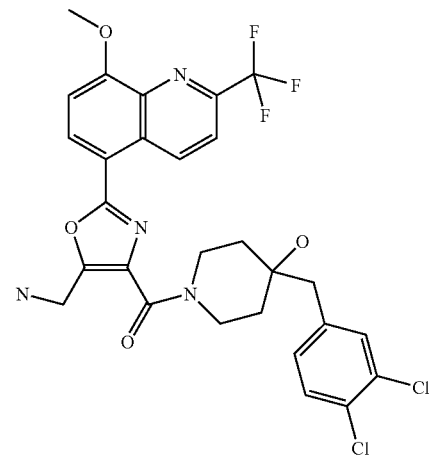 | 609 |
| 13-192 | 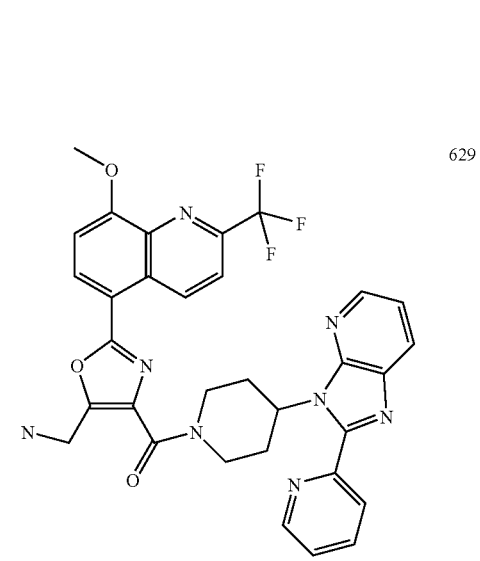 | 629 |

107
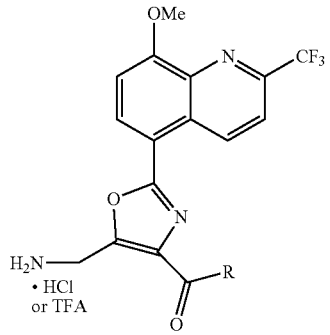
108
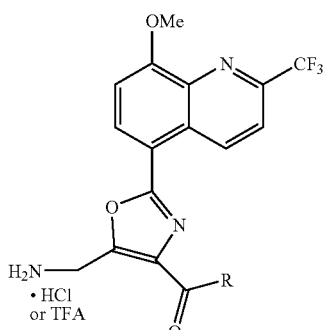
| Cpd. No. | Structure | MS (M + 1) |
|---|---|---|
| 13-193 | | 541 |
| 13-194 | | 482 |
| 13-195 | | 514 |
| Cpd. No. | Structure | MS (M + 1) |
|---|---|---|
| 13-196 | | 512 |
| 13-197 | | 517 |

| Cpd. No. | Structure | MS (M + 1) |
|---|---|---|
| 13-198 | 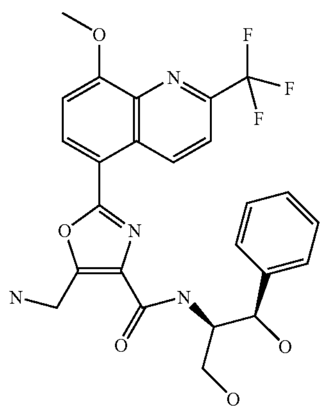 | 518 |
| 13-199 | 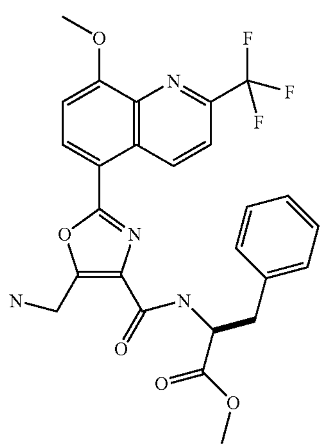 | 529 |
| 13-200 | 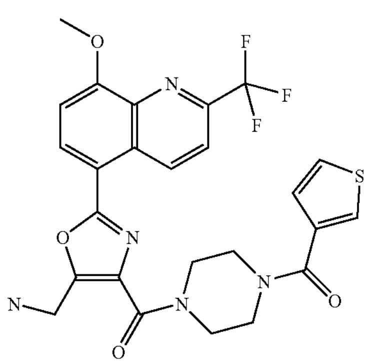 | 546 |
| 13-201 | | 568 |
| 13-202 | | 584 |
| 13-203 | | 543 |

-continued
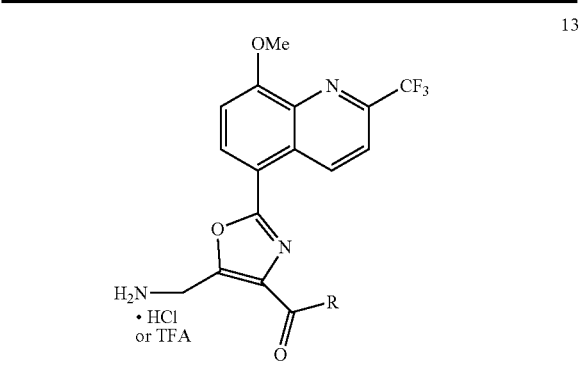
| Cpd. No. | Structure | MS (M + 1) |
|---|---|---|
| 13-204 | 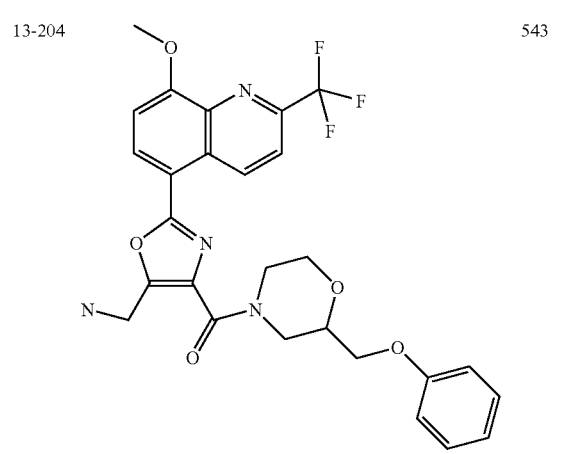 | 543 |
| 13-205 | 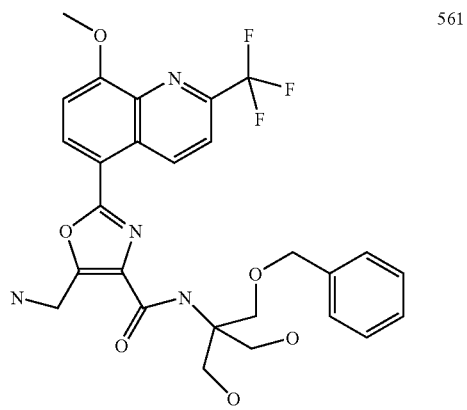 | 561 |
| 13-206 | 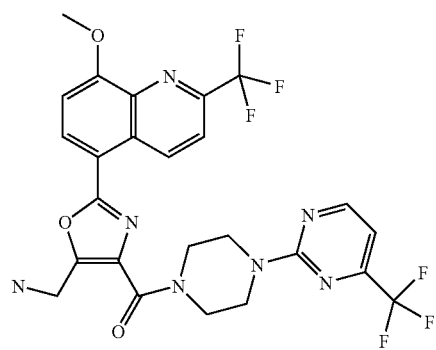 | 582 |
-continued
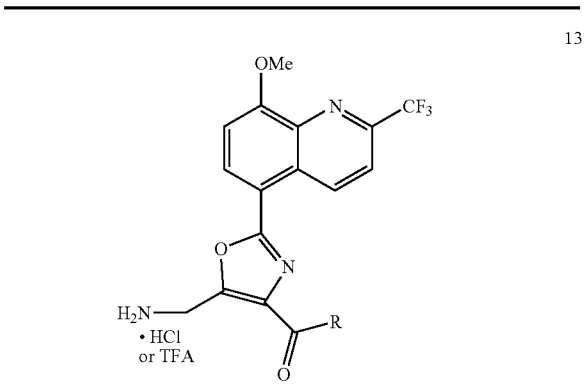
| Cpd. No. | Structure | MS (M + 1) |
|---|---|---|
| 13-207 | 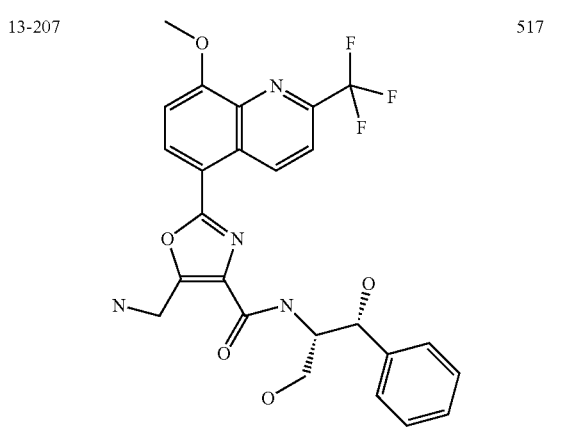 | 517 |
| 13-208 | 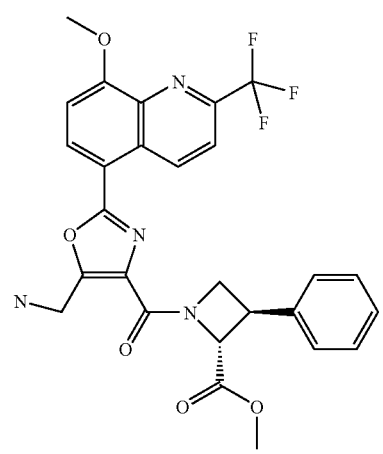 | 541 |

-continued

| Cpd. No. | Structure | MS (M+1) |
|---|---|---|
| 13-209 | 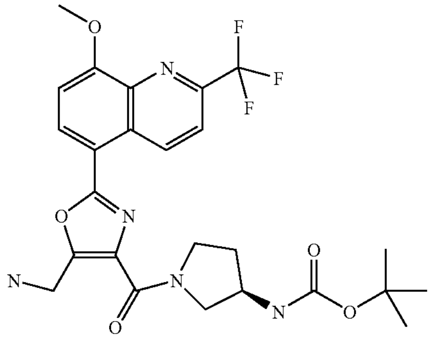 | 536 |
| 13-210 | 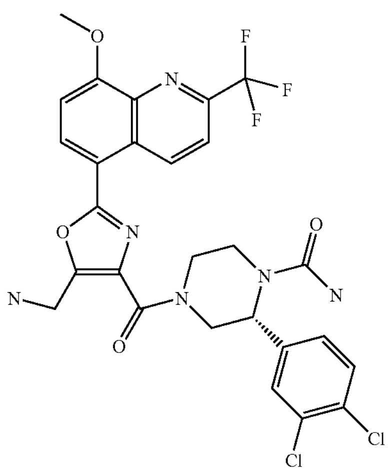 | 624 |
| 13-211 | 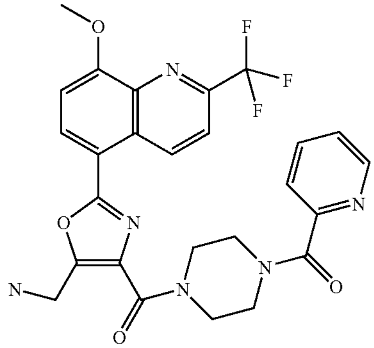 | 541 |
| 13-212 | | 554 |
| 13-213 | | 550 |
| 13-214 | | 550 |

US 7,511,062 B2

115                                    116

-continued                             -continued 13                                     13

[Structure: 8-methoxy-2-(trifluoromethyl)quinoline connected to oxazole bearing H₂N-CH₂- and C(O)-R groups; •HCl or TFA]

| Cpd. No. | Structure | MS (M + 1) |
|---|---|---|
| 13-215 | [quinoline-oxazole with 4-methyl-3-phenylpiperazine amide] | 526 |
| 13-216 | [quinoline-oxazole with piperazine-C(O)-pyridin-3-yl] | 529 |
| 13-217 | [quinoline-oxazole with piperazine-C(O)-(3,5-difluorophenyl)] | 576 |

| Cpd. No. | Structure | MS (M + 1) |
|---|---|---|
| 13-218 | [quinoline-oxazole with (3,4-dihydroxy-2-(4-methoxybenzyl)pyrrolidine) amide] | 573 |
| 13-219 | [quinoline-oxazole with proline tert-butyl ester] | 521 |

117 -continued
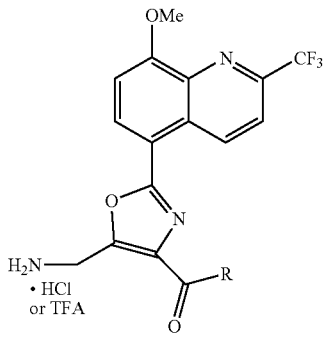
| Cpd. No. | Structure | MS (M + 1) |
|---|---|---|
| 13-220 | 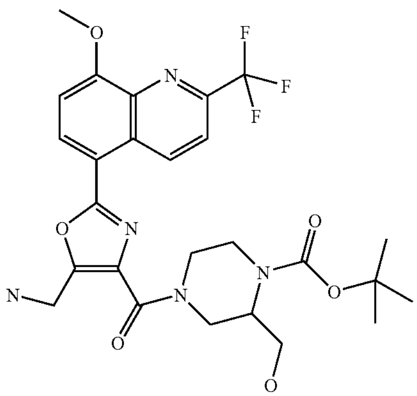 | 566 |
| 13-221 | 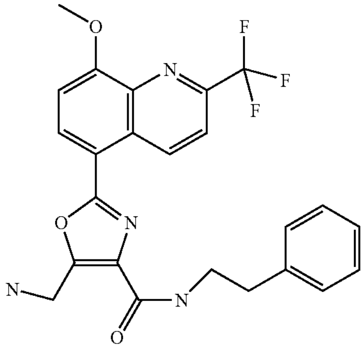 | 471 |
| 13-222 | 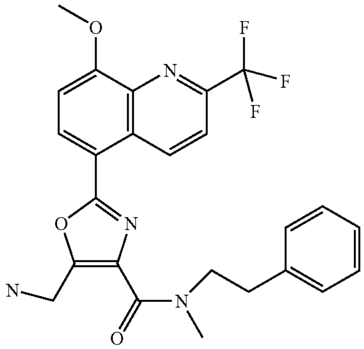 | 485 |
118 -continued
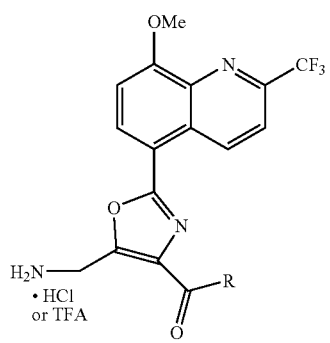
| Cpd. No. | Structure | MS (M + 1) |
|---|---|---|
| 13-223 | 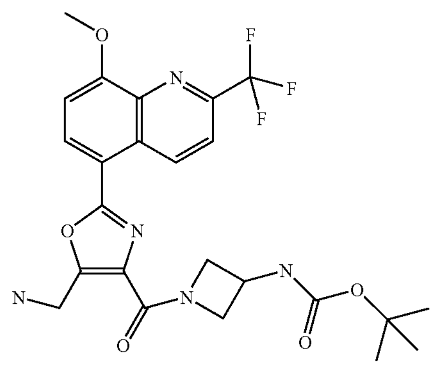 | 522 |
| 13-224 | 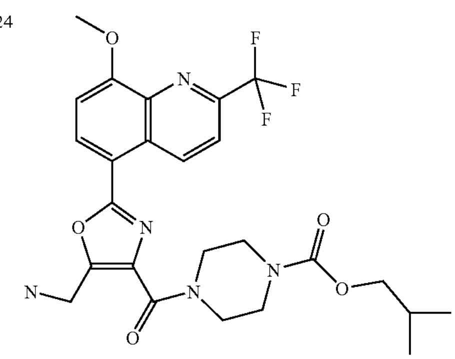 | 536 |
| 13-225 | 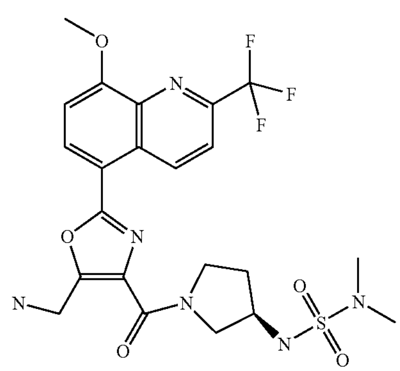 | 543 |

| Cpd. No. | Structure | MS (M + 1) |
|---|---|---|
| 13-226 | 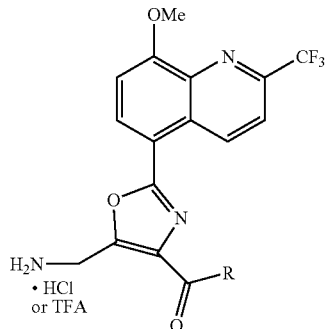 | 522 |
| 13-227 | 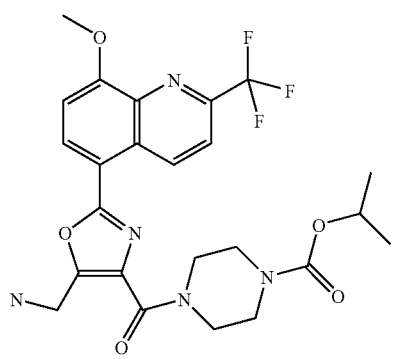 | 505 |
| 13-228 | 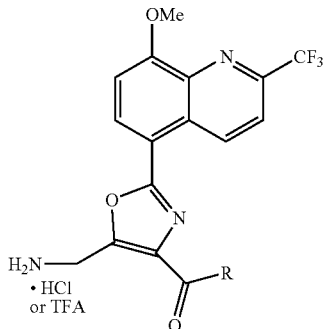 | 510 |
| 13-229 | 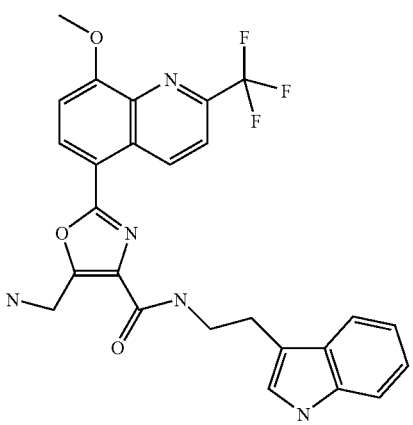 | 545 |

121
-continued
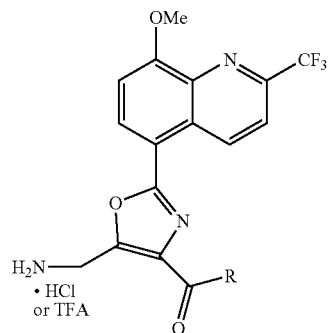
| Cpd. No. | Structure | MS (M + 1) |
|---|---|---|
| 13-230 | 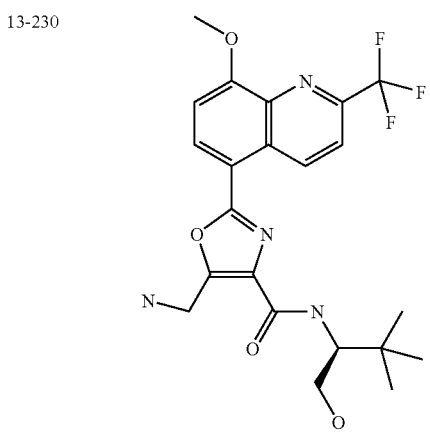 | 467 |
| 13-231 | 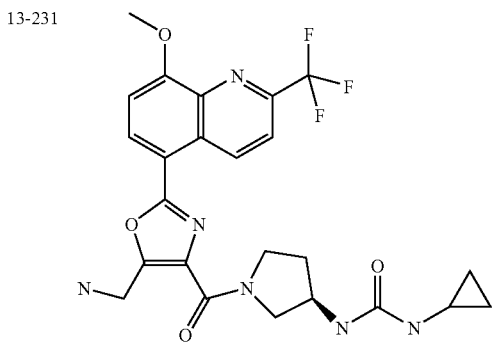 | 519 |
| 13-232 | 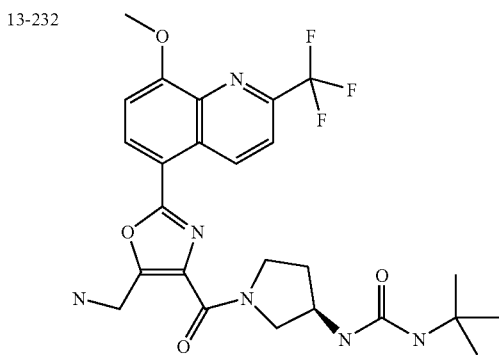 | 536 |
122
-continued
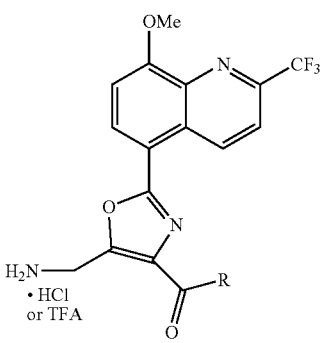
| Cpd. No. | Structure | MS (M + 1) |
|---|---|---|
| 13-233 | 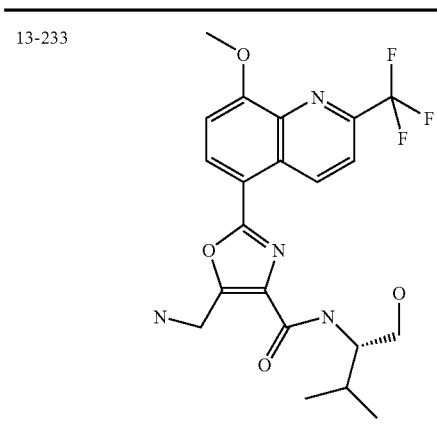 | 453 |
| 13-234 | 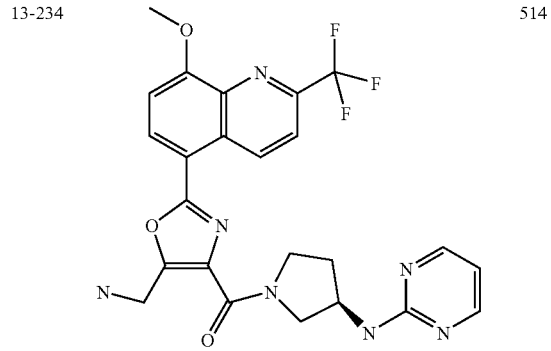 | 514 |
| 13-235 | 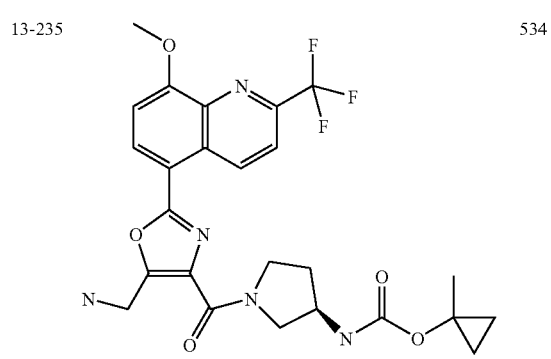 | 534 |

-continued
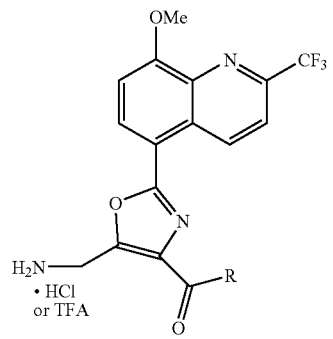
· HCl or TFA
| Cpd. No. | Structure | MS (M + 1) |
|---|---|---|
| 13-236 | 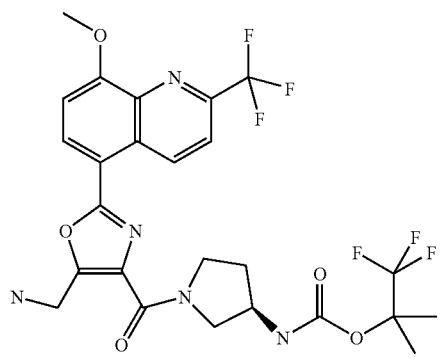 | 590 |
| 13-237 | 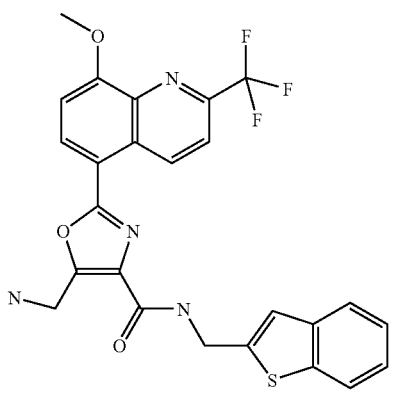 | 513 |
| 13-238 | 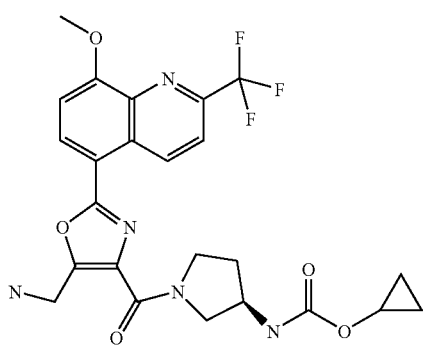 | 520 |
-continued
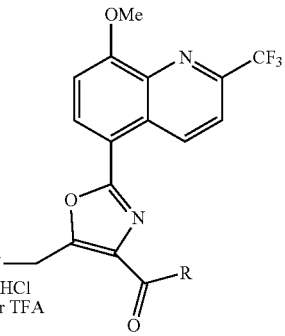
· HCl or TFA
| Cpd. No. | Structure | MS (M + 1) |
|---|---|---|
| 13-239 | 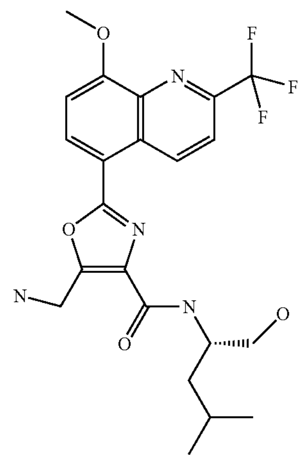 | 467 |
| 13-240 | 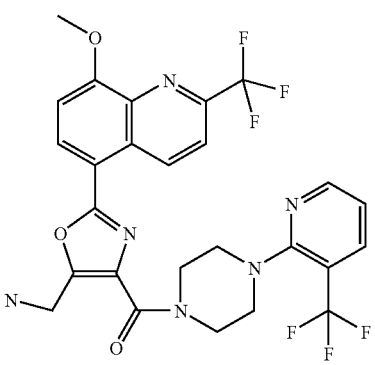 | 581 |
| 13-241 | 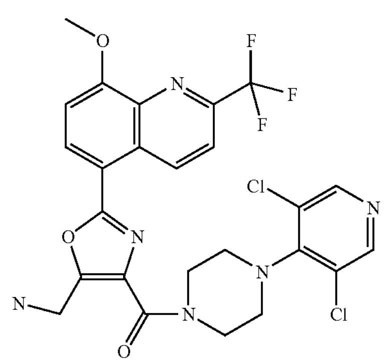 | 581 |

125 126
-continued
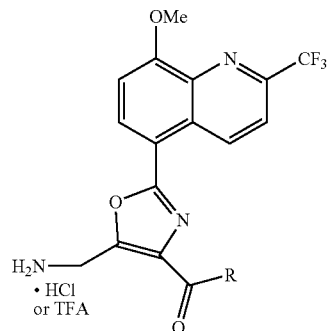
-continued
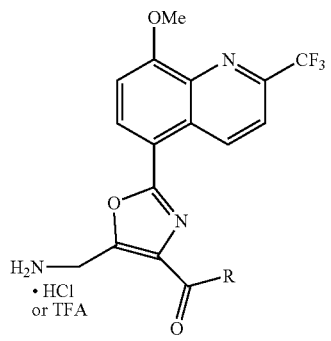
| Cpd. No. | Structure | MS (M + 1) |
|---|---|---|
| 13-242 | | 544 |
| 13-243 | | 529 |
| Cpd. No. | Structure | MS (M + 1) |
|---|---|---|
| 13-244 | | 477 |
| 13-245 | | 529 |
| 13-246 | | 520 |

| Cpd. No. | Structure | MS (M + 1) |
|---|---|---|
| 13-247 | | 534 |
| 13-248 | | 569 |
| 13-249 | | 542 |
| Cpd. No. | Structure | MS (M + 1) |
|---|---|---|
| 13-250 | | 507 |
| 13-251 | | 625 |
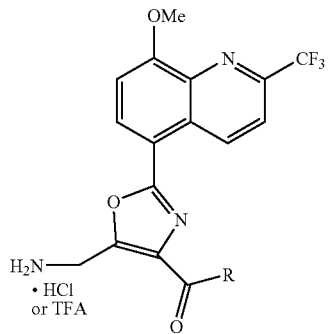

-continued
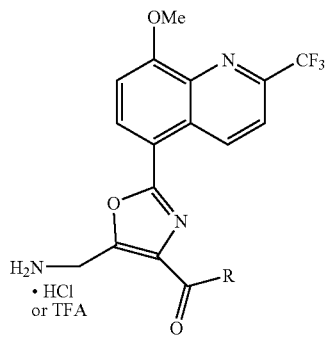
| Cpd. No. | Structure | MS (M + 1) |
|---|---|---|
| 13-252 | 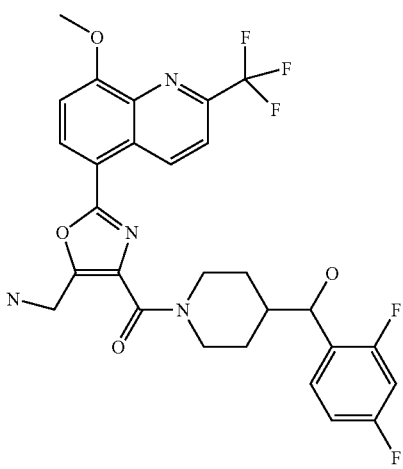 | 577 |
| 13-253 | 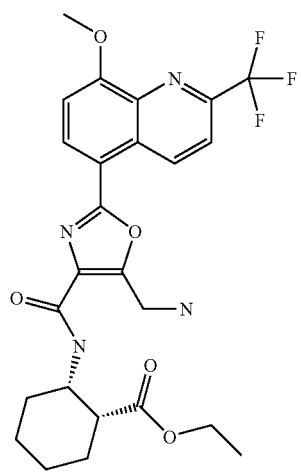 | 521 |
-continued
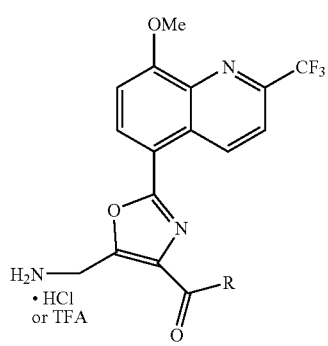
| Cpd. No. | Structure | MS (M + 1) |
|---|---|---|
| 13-254 | 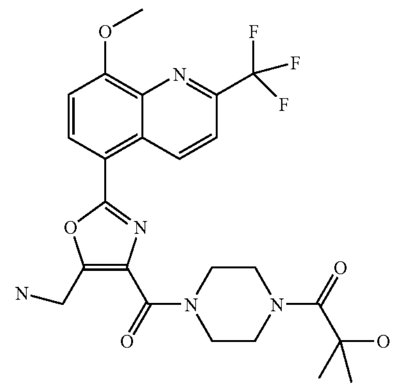 | 522 |
| 13-255 | 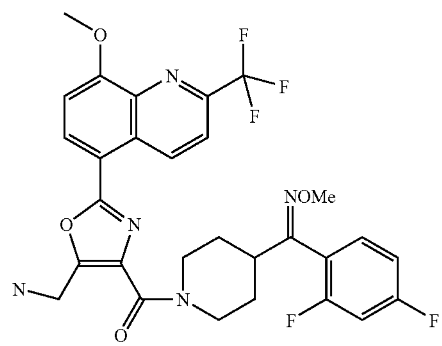 | 604 |
| 13-256 | 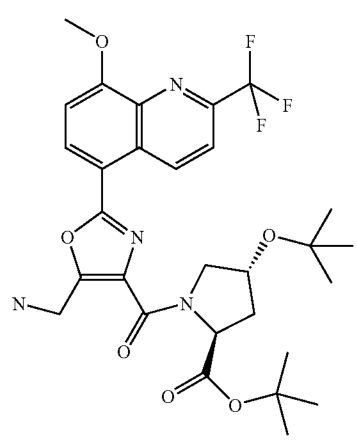 | 593 |

-continued
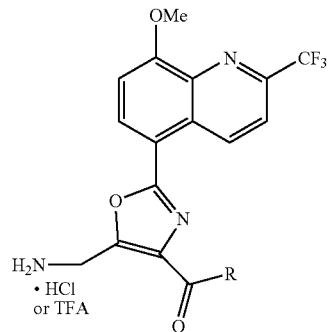
| Cpd. No. | Structure | MS (M + 1) |
|---|---|---|
| 13-257 | 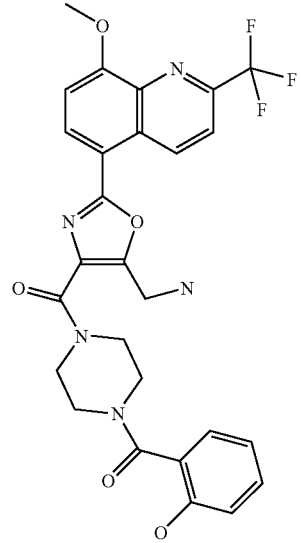 | 556 |
| 13-258 | 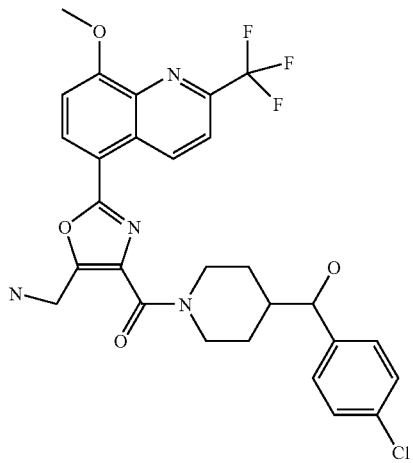 | 575 |
-continued
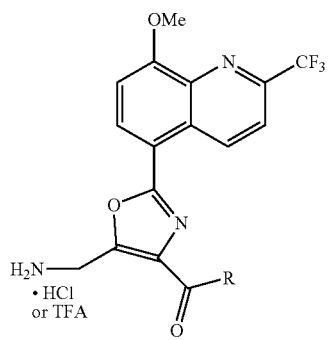
| Cpd. No. | Structure | MS (M + 1) |
|---|---|---|
| 13-259 | 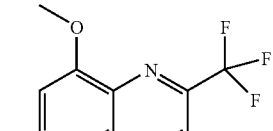 | 602 |
| 13-260 | 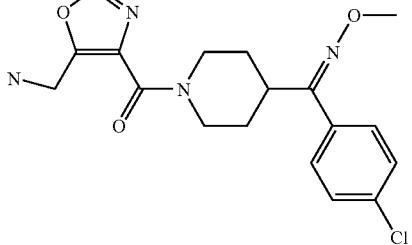 | 465 |
| 13-261 | 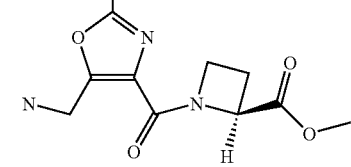 | 590 |

-continued

| Cpd. No. | Structure | MS (M+1) |
|---|---|---|
| 13-262 | 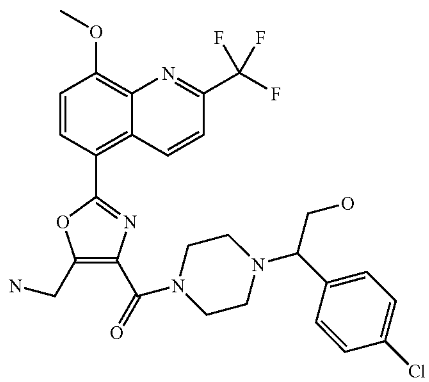 | 590 |
| 13-263 | 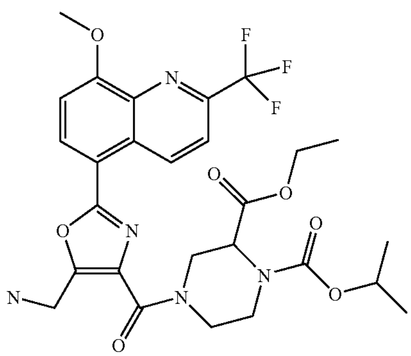 | 594 |
| 13-264 | 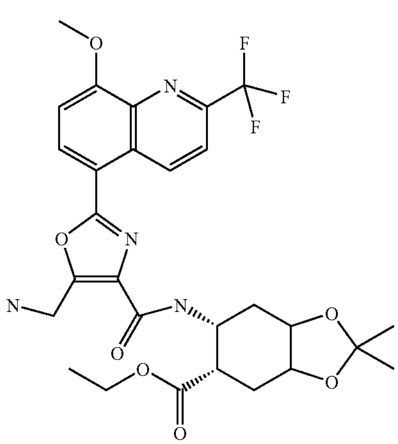 | 593 |
| 13-265 | | 542 |
| 13-266 | | 560 |
| 13-267 | | 587 |

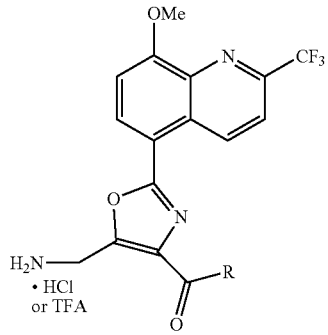
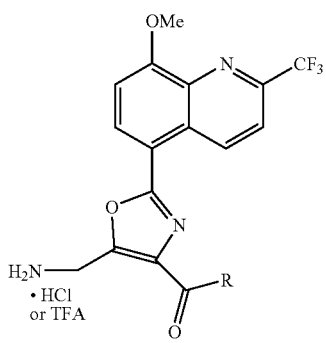
| Cpd. No. | Structure | MS (M + 1) |
|---|---|---|
| 13-268 | 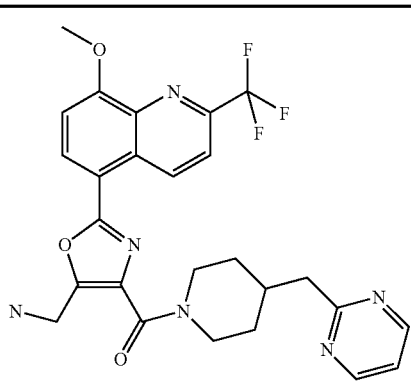 | 527 |
| 13-269 | 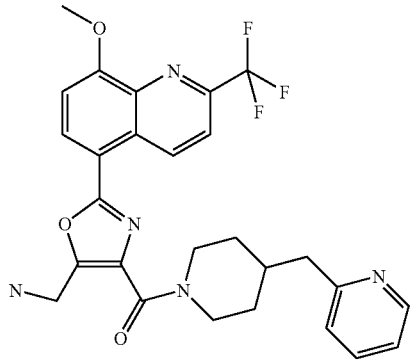 | 526 |
| 13-270 | 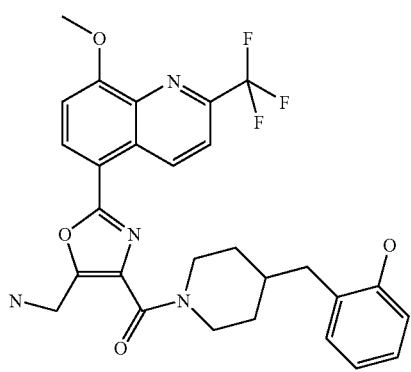 | 541 |
| Cpd. No. | Structure | MS (M + 1) |
|---|---|---|
| 13-271 | 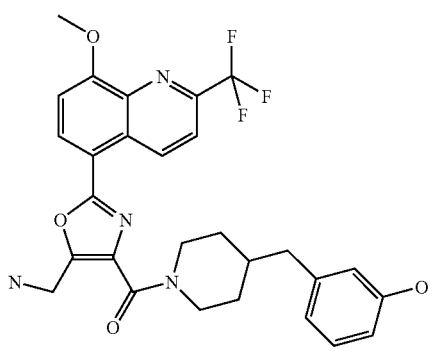 | 541 |
| 13-272 | 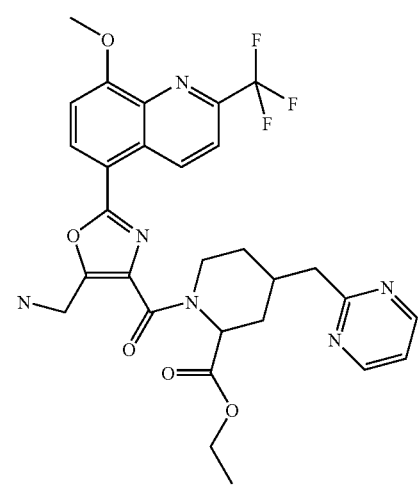 | 599 |

-continued
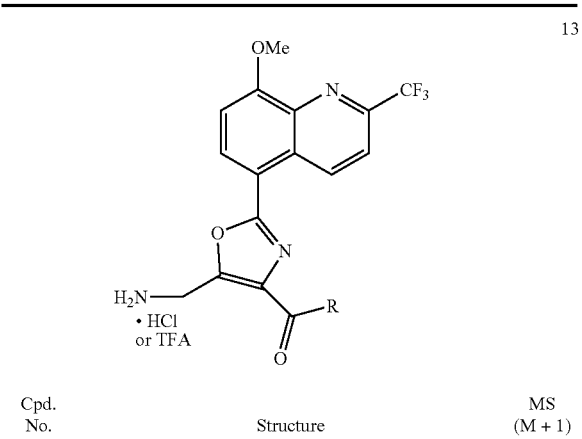
| Cpd. No. | Structure | MS (M + 1) |
|---|---|---|
| 13-273 | 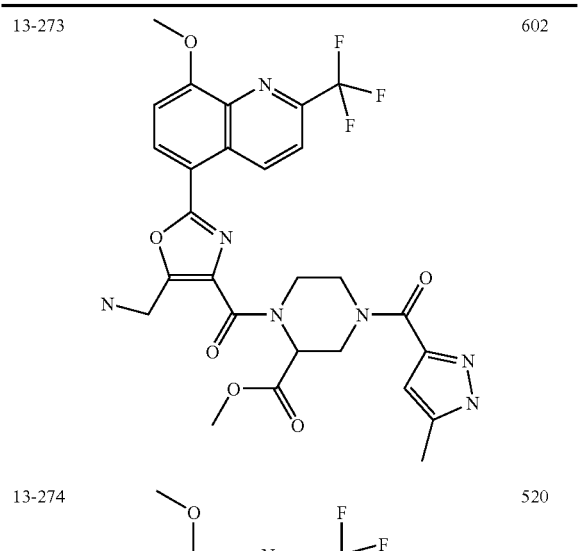 | 602 |
| 13-274 | 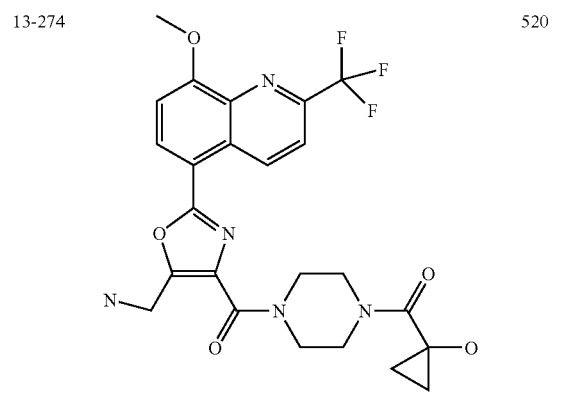 | 520 |
| 13-275 | 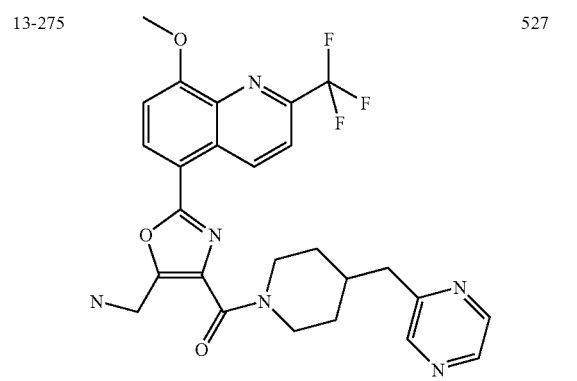 | 527 |
-continued
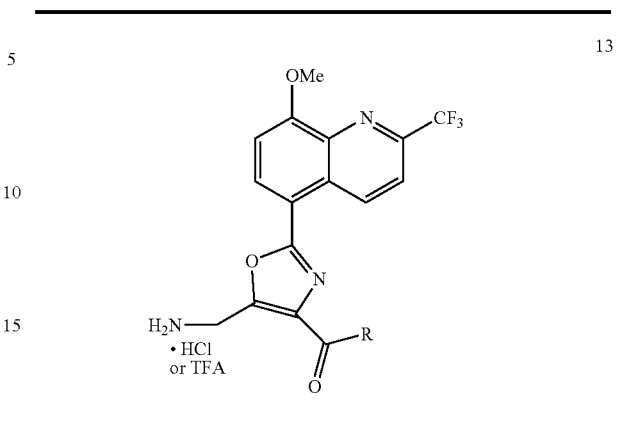
| Cpd. No. | Structure | MS (M + 1) |
|---|---|---|
| 13-276 | 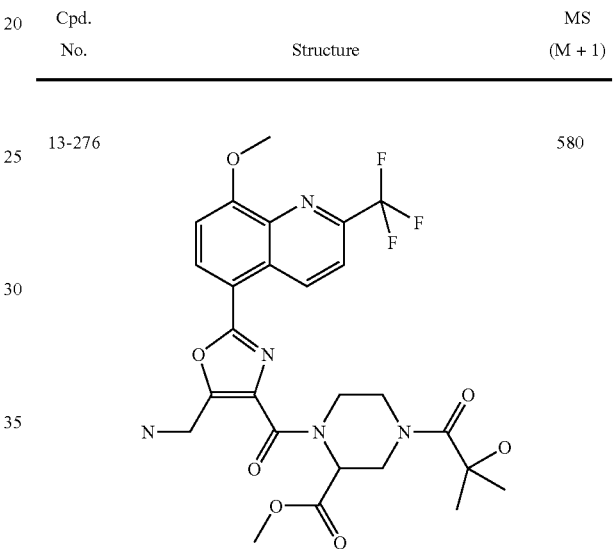 | 580 |
| 13-277 | 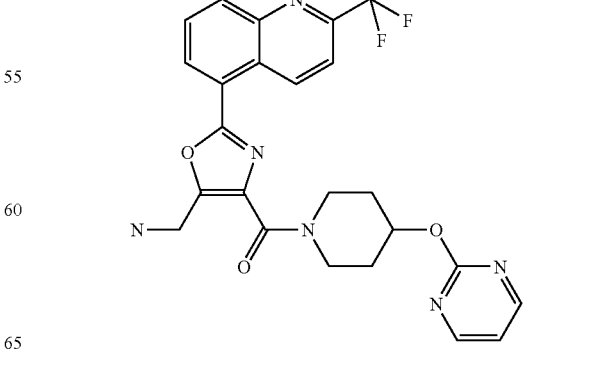 | 529 |

-continued
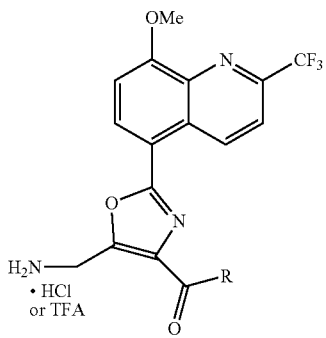
| Cpd. No. | Structure | MS (M + 1) |
|---|---|---|
| 13-278 | 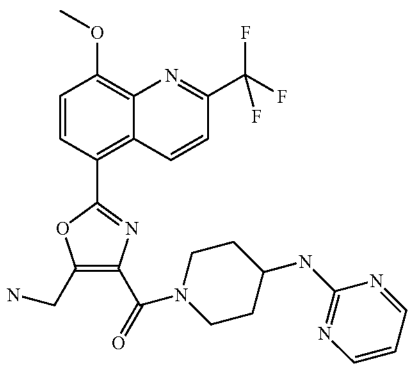 | 528 |
| 13-279 | 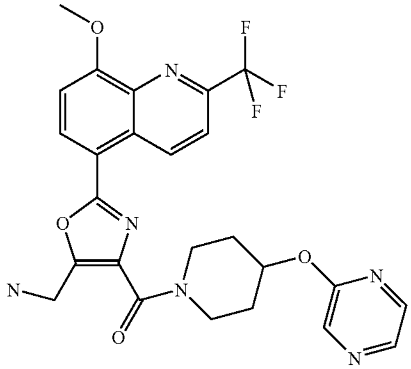 | 529 |
| 13-280 | 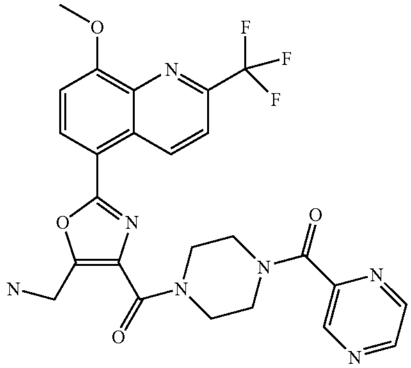 | 542 |
-continued
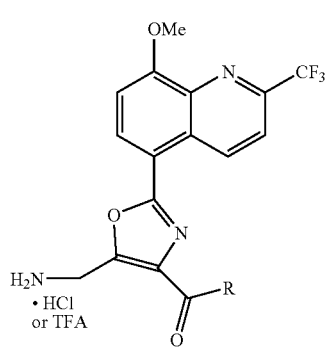
| Cpd. No. | Structure | MS (M + 1) |
|---|---|---|
| 13-281 | 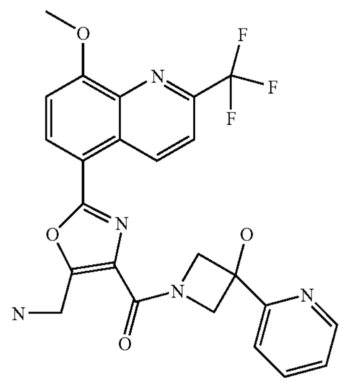 | 500 |
| 13-282 | 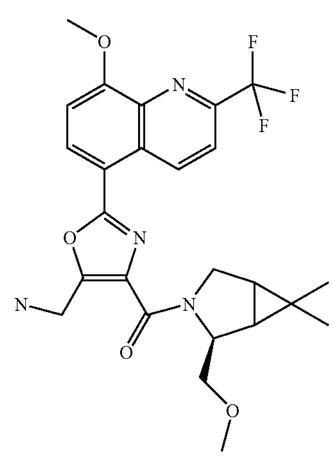 | 505 |

-continued
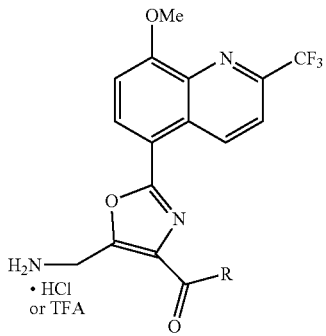
• HCl or TFA
| Cpd. No. | Structure | MS (M + 1) |
|---|---|---|
| 13-283 | 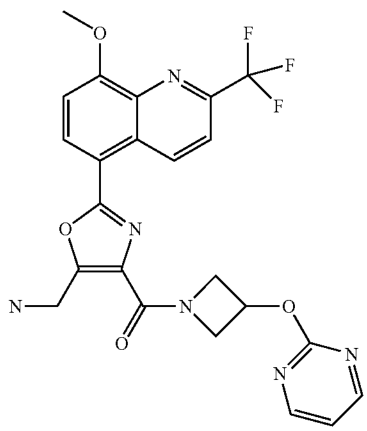 | 501 |
| 13-284 | 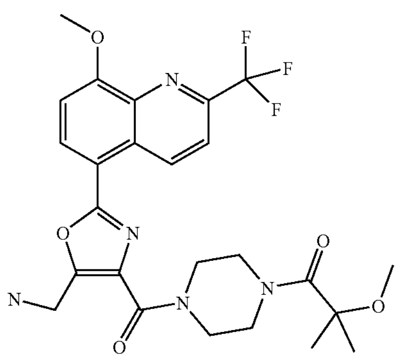 | 536 |
| 13-285 | 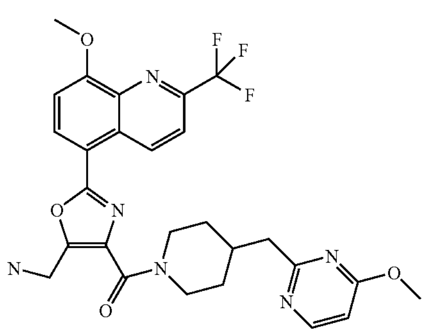 | 557 |
-continued
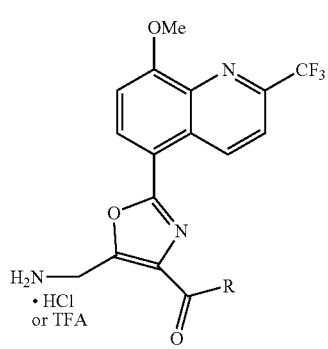
• HCl or TFA
| Cpd. No. | Structure | MS (M + 1) |
|---|---|---|
| 13-286 | 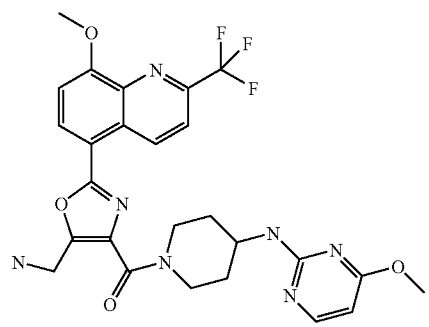 | 558 |
| 13-287 | 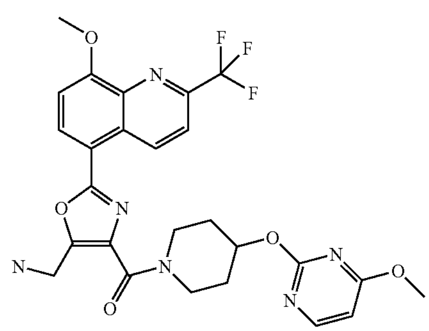 | 559 |
| 13-288 | 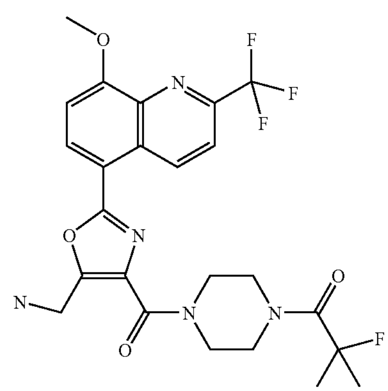 | 524 |

-continued
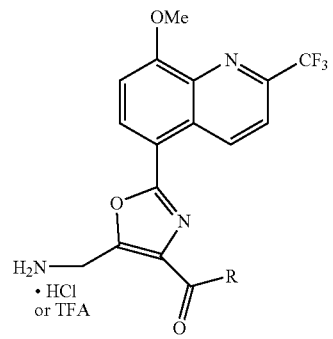
| Cpd. No. | Structure | MS (M + 1) |
|---|---|---|
| 13-289 | 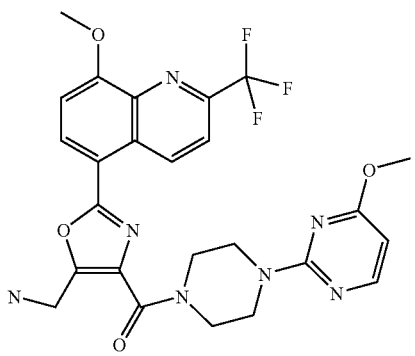 | 544 |
| 13-290 | 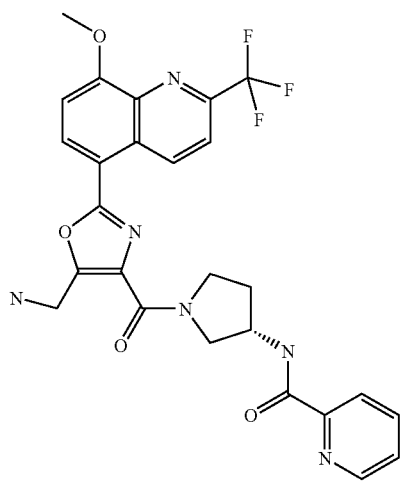 | 541 |
-continued
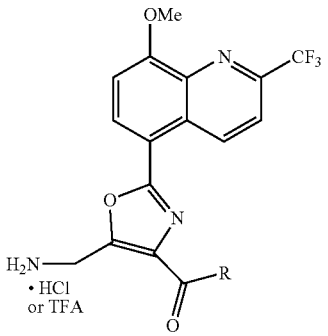
| Cpd. No. | Structure | MS (M + 1) |
|---|---|---|
| 13-291 | 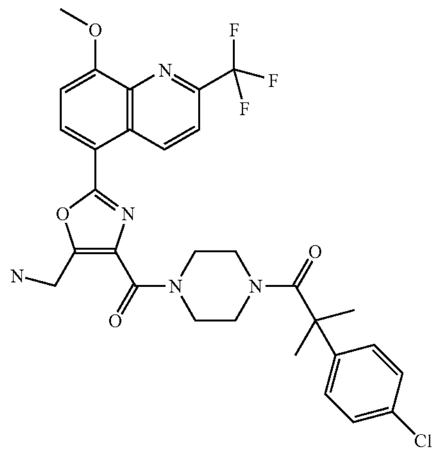 | 616 |
| 13-292 | 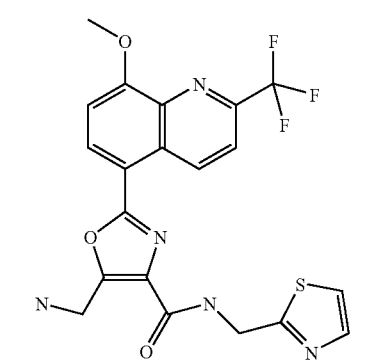 | 464 |
| 13-293 | 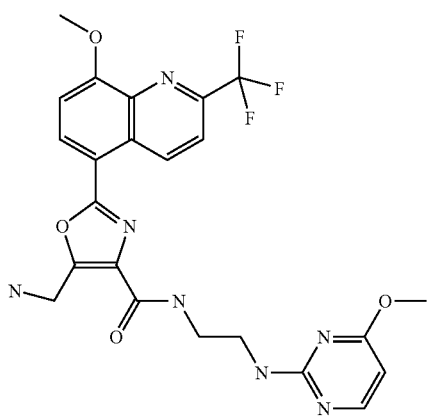 | 518 |

-continued
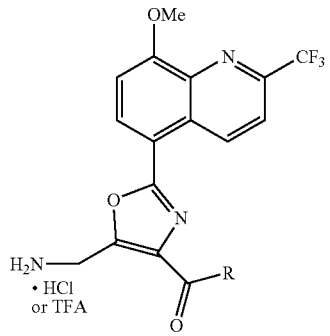
| Cpd. No. | Structure | MS (M + 1) |
|---|---|---|
| 13-294 | 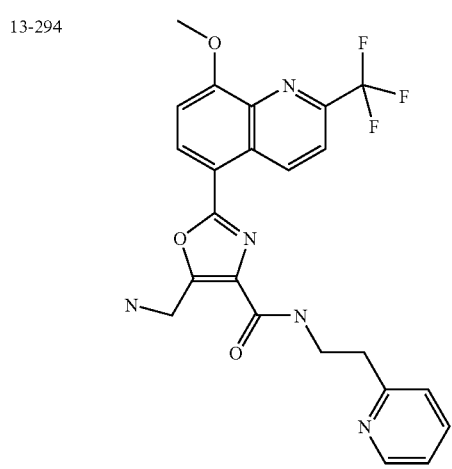 | 472 |
| 13-295 | 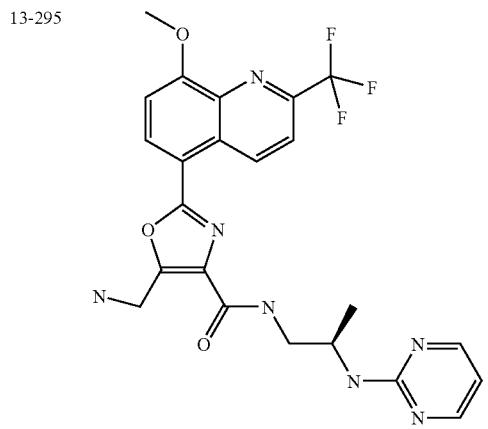 | 502 |
-continued
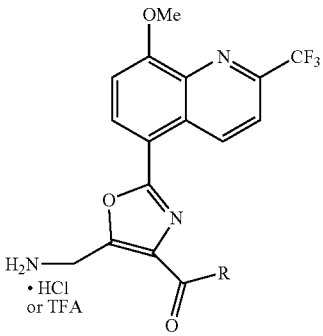
| Cpd. No. | Structure | MS (M + 1) |
|---|---|---|
| 13-296 | 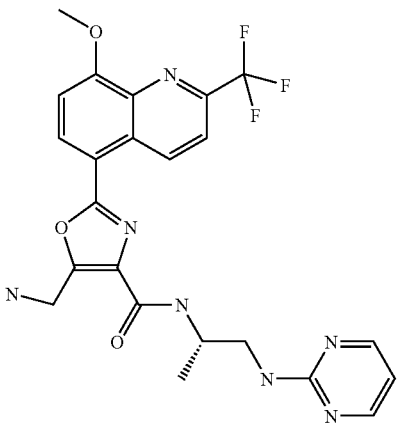 | 502 |
| 13-297 | 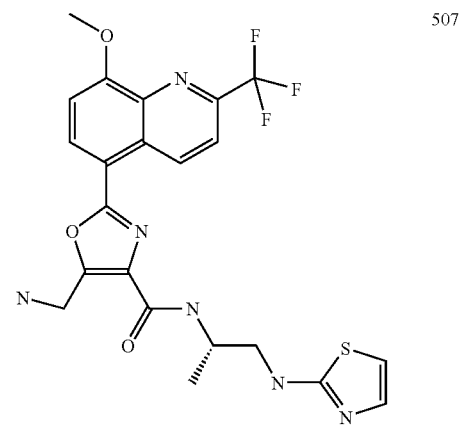 | 507 |

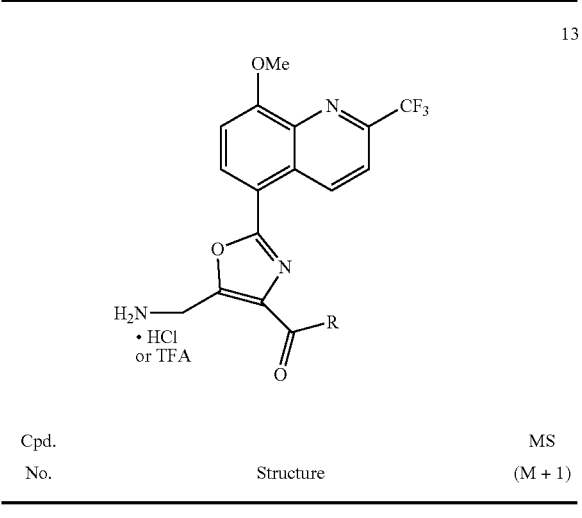
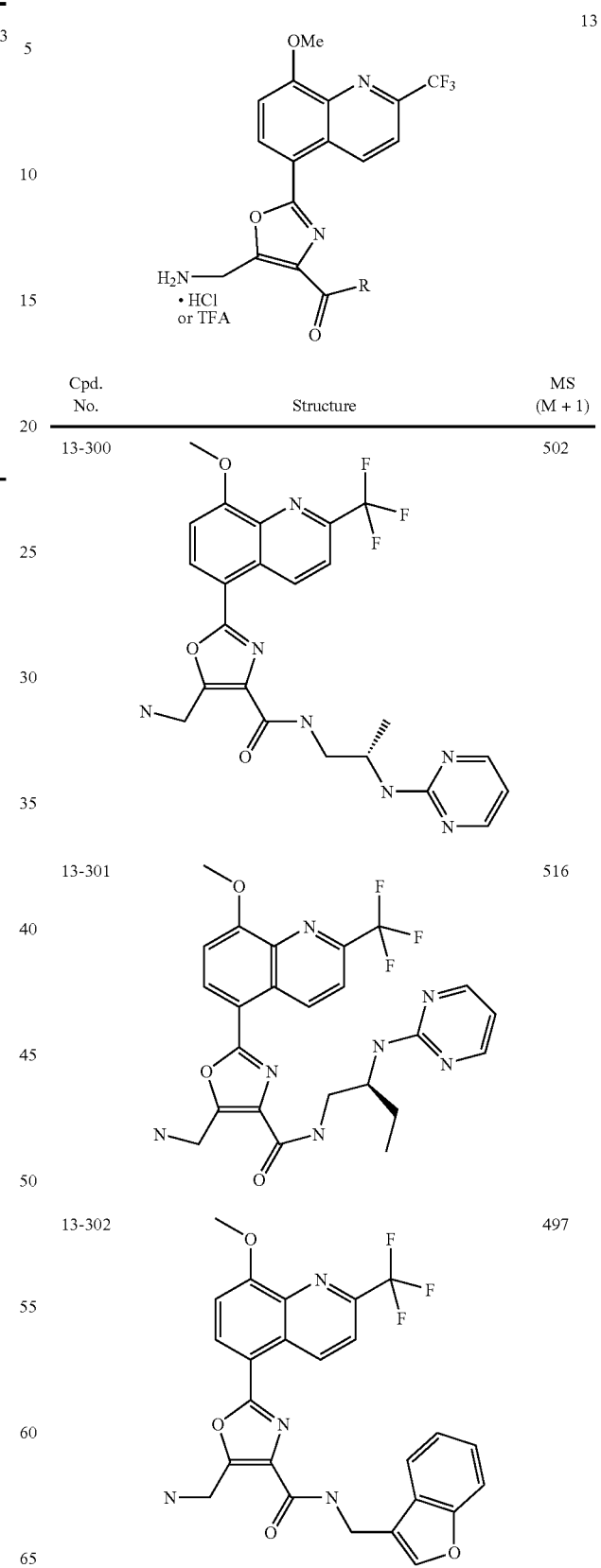
| Cpd. No. | Structure | MS (M + 1) |
|---|---|---|
| 13-298 | | 586 |
| 13-299 | | 516 |
| 13-300 | 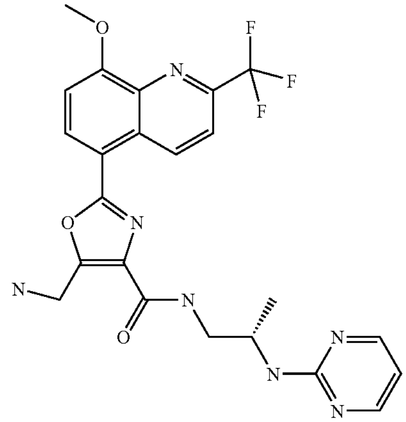 | 502 |
| 13-301 | 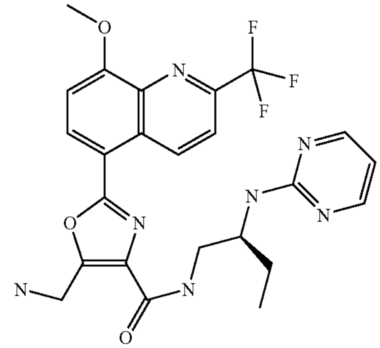 | 516 |
| 13-302 | 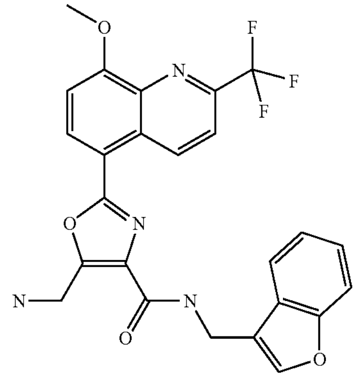 | 497 |

-continued
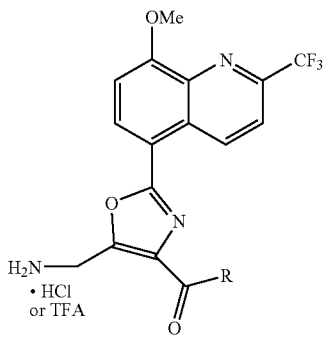
·HCl or TFA
| Cpd. No. | Structure | MS (M + 1) |
|---|---|---|
| 13-303 | 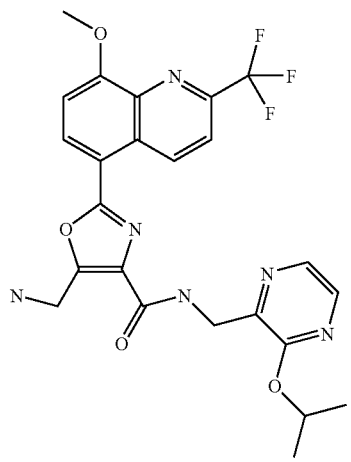 | 517 |
| 13-304 | 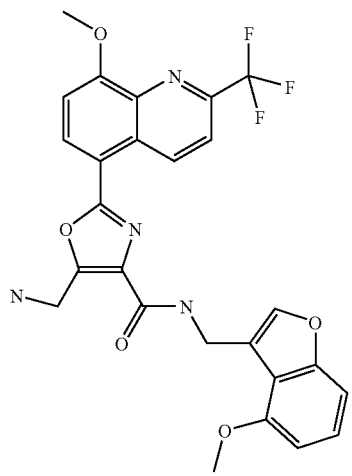 | 527 |
-continued
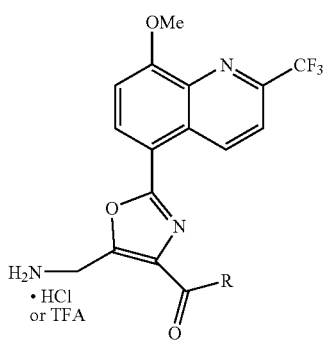
·HCl or TFA
| Cpd. No. | Structure | MS (M + 1) |
|---|---|---|
| 13-305 | 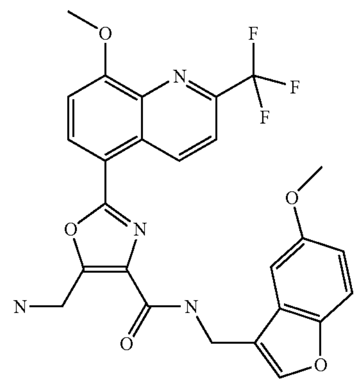 | 527 |
| 13-306 | 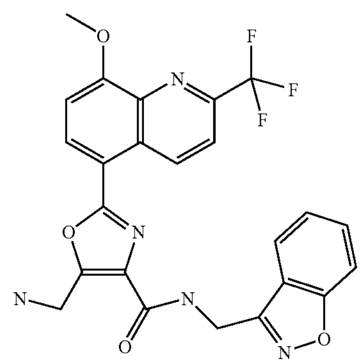 | 498 |
| 13-307 | 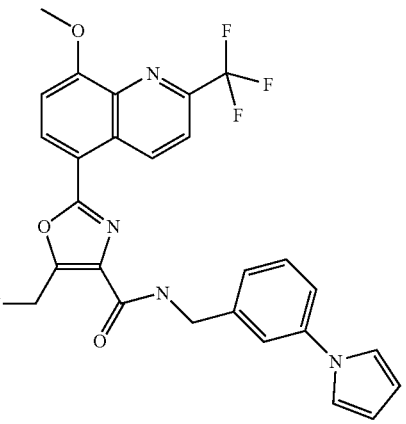 | 522 |

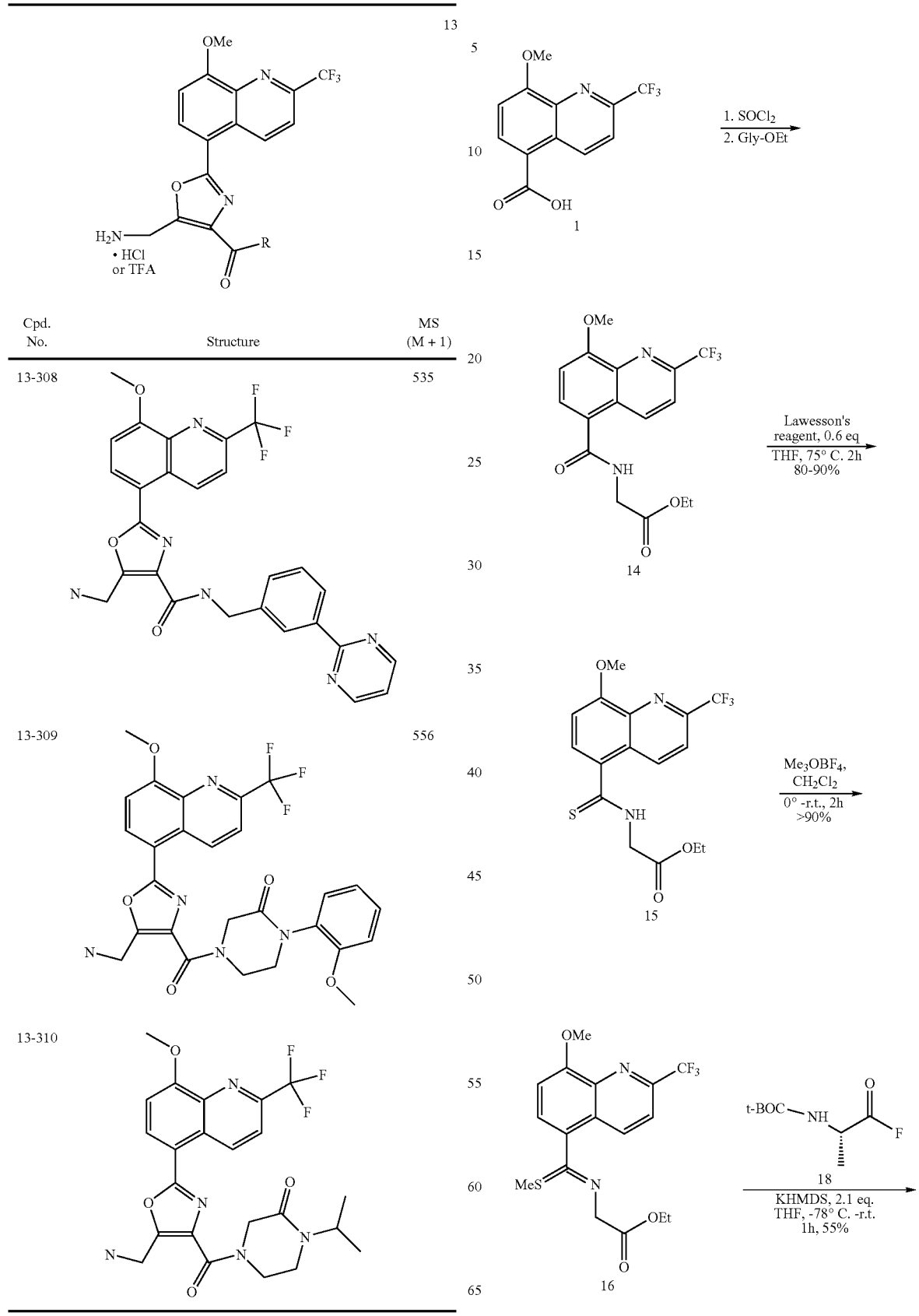

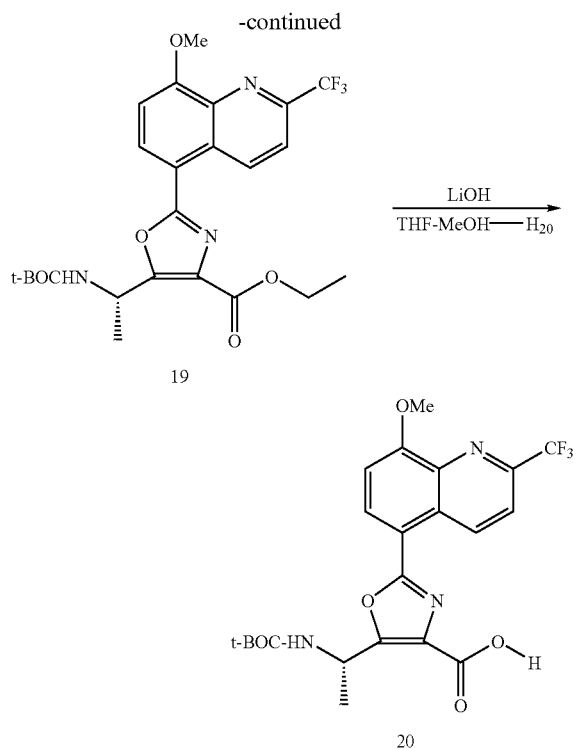

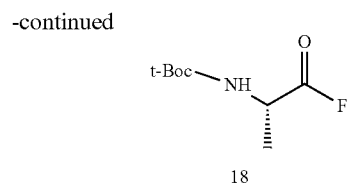

A neat liquid of cyanuric fluoride (3.4 ml, 40 mmol) was added dropwise to a cooled solution of N-[(1,1-dimethyl-ethoxy)carbonyl]-L-alanine (compound 17) (3.90 g, 20 mmol) in pyridine (1.78 ml, 22 mmol) and dry $CH_2Cl_2$ (50 ml) at $-40°$ C. The reaction was kept at $-30°$ C. to $-10°$ C. for 2 h. After 2 h, crushed ice and $CH_2Cl_2$ (100 ml) were added. After stirring for 5 min, the mixture was filtered twice, first with a coarse, then with a medium glass filter funnel. The clear solution was separated and the organic phase was washed with $H_2O$, dried ($Na_2SO_4$), filtered and concentrated at RT to give compound 18 as a white solid (3.59 g, 18.7 mmol) with a 94% yield.

Step 5: Compound 18 (2.87 g, 15 mmol) was added to a solution of compound 16 (5.0 g, 12.5 mmol) in dry THF (60 ml). The reaction mixture was cooled to $-78°$ C. and KHMDS (0.5 M in toluene) (52.5 ml, 26.25 mmol) was added dropwise over 40 min. During the addition of the first equivalent of base, the reaction mixture turned a deep blue color, which disappeared immediately. A deep brown color was formed when the second equivalent of base was added. The reaction solution was kept at $-78°$ C. for 1 h then gradually warmed to RT. After completion of the reaction (checked by TLC), ice-cold 0.5 M HCl solution (70 ml) was added. The organic layer was separated and the aqueous layer was extracted with EtOAc (70 ml). The combined organic layer were washed with $NaHCO_3$ solution and brine, dried ($Na_2SO_4$), filtered and concentrated to give a crude product which was purified by silica gel chromatograph to yield compound 19 as a solid (3.5 g, 6.88 mmol, yield 55%). Alternative method for the preparation of compound 19:

Step 4b:

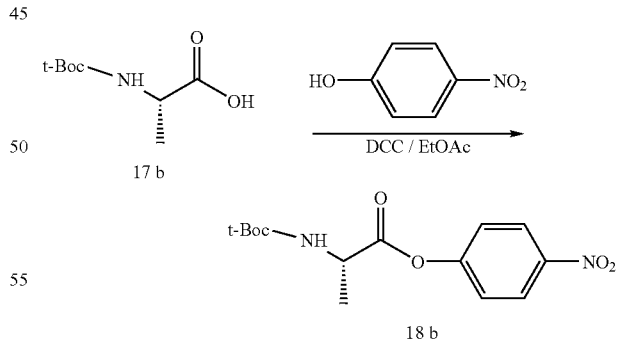

Step 1: Glycine ethyl ester hydrochloride (14 g, 100 mmol) was mixed with TEA (29 ml, 200 mmol) in dry $CH_2Cl_2$ and cooled in an ice-water bath. Compound 2 (80 mmol) (see Example 1) in dry $CH_2Cl_2$ (150 ml) was transferred by cannulation into the above cooled solution. The resulting mixture was allowed to warm to RT slowly. After 2 h, reaction was complete and water (300 ml) was added to dissolve the TEA salt. The organic layer was separated, washed with 5% HCl solution, then water, dried ($Na_2SO_4$), filtered and concentrated to give a crude solid, Compound 14, which was used in the next step without further purification.

Step 2: Compound 14 (7.2 g, 20 mmol) was mixed with Lawesson's reagent (5.5 g, 13.6 mmol) in anhydrous THF (100 ml) and heated to 78° C. for 40 min. After cooling to RT, THF was removed and product was purified by silica chromatography, eluting with 100% $CH_2Cl_2$ to 5% EtOAc in $CH_2Cl_2$, to give compound 15 as a yellow product.

Step 3: Compound 15 (3.9 g, 10 mmol) was dissolved in dry $CH_2Cl_2$ (40 ml) and cooled to $-78°$ C. Trimethyloxonium tetrafluoroborate (1.6 g, 11 mmol) was added in one portion. The resulting mixture was then stirred in an ice-water bath for 2 h. $NaHCO_3$ solution was added to quench the reaction. The organic layer was separated, washed with $H_2O$, dried ($Na_2SO_4$), and evaporated to give compound 16 as a crude solid which was used in the next reaction without purification.

Step 4a:

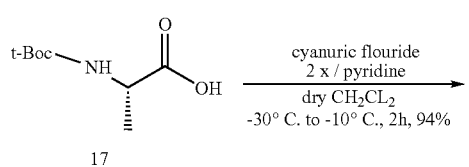

A mixture of BOC-L-alanine (17b) (2.9 g, 15.4 mmol), p-nitrophenol (3.3 g, 15.4 mmol) and DCC (3.3 g, 16.2 mmol) in EtOAc (60 ml) was stirred at RT for 2 h. A white precipitate was formed; the solid was filtered off and the filtrate was evaporated. The crude material was purified on a Biotage silica column, eluting with 20% hexane in $CH_2Cl_2$ to give compound 18b (2.8 g, 9 mmol, 58.4% yield) as a yellow solid. LCMS $C_{14}H_{18}N_2O_6$ $[M+1]^+$ 311.1.

Step 5b: By a method analogous to that described in Example 5, Step 5, using compound 18b in place of compound 18, compound 19 was prepared.

Step 6: At 0° C., LiOH solution (150 mg, 6 mmol, in 15 ml of H$_2$O) was added to a solution of compound 19 (1.02 g, 2 mmol) in THF (37 ml). After 1 h at 0° C., the reaction was gradually warmed to RT and stirred at RT overnight. After the reaction was complete, EtOAc (50 ml) and H$_2$O (5 ml) were added, followed by the addition of 1 N HCl to acidify the mixture. The organic phase was separated, dried (Na$_2$SO$_4$), filtered and concentrated to give the title compound 20 as a white solid (0.94 g, 1.95 mmol, 98% yield). MS: C$_{22}$H$_{22}$F$_3$N$_3$O$_6$ [M+1]$^+$482.1.

EXAMPLE 6

Step 1: A mixture of 4-chlorobenzaldehyde (21) (0.79 g, 5.45 mmol), 2-hydroxyethyl amine (22) (0.34 ml, 5.45 mmol) and Na$_2$SO$_4$ (1.44 g, 10.9 mmol) in dichloroethane (40 ml) was stirred at RT for 40 min. To this mixture, NaBH(OAc)$_3$ (3.12 g, 14.72 mmol) and AcOH (0.82 ml, 13.67 mmol) were added. After stirring at RT overnight, the reaction was quenched with saturated NaHCO$_3$ solution. The mixture was diluted with brine (200 ml) and extracted with CH$_2$Cl$_2$ (100 ml, 3×), combined and washed with brine (100 ml, 2×), dried (MgSO$_4$), filtered and evaporated to give crude compound 23 as an oil. The oil was purified with flash grade silica gel (100 g), eluting with 5% (1:9) (NH$_4$OH/CH$_3$OH)/95% CH$_2$Cl$_2$ to yield compound 23 (0.3 g, 1.62 mmol, 30% yield).

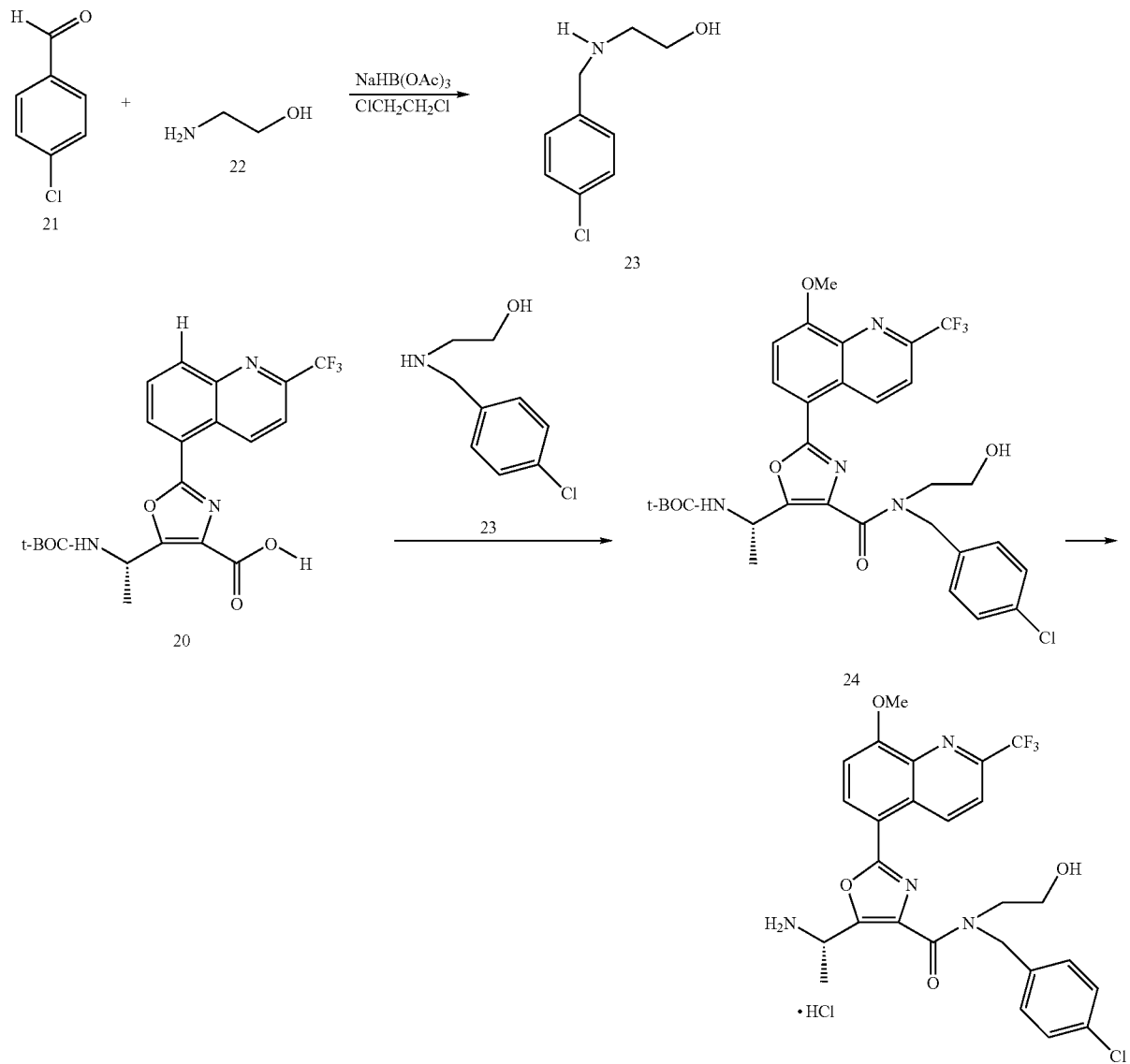

Step 2: A mixture of compound 20 (0.241 g, 0.5 mmol), compound 23 (92.8 mg, 0.5 mmol), HATU (285 mg, 0.75 mmol) and DIPEA (0.131 ml, 0.75 mmol) in dry DMF (3.0 ml) was stirred at RT for 4 h. After the reaction was complete, water (3 ml) was added to quench the reaction and the mixture was stirred for 10 min. Solid was collected, rinsed with water, and redissolved in $CH_2Cl_2$ (10 ml), dried ($Na_2SO_4$), filtered and evaporated. Product was purified by flash grade silica gel (100 g), eluting with 4.5% (1:9) ($NH_4OH/CH_3OH$)/95% $CH_2Cl_2$ to give pure compound 24 (0.18 g, 0.28 mmol, 56% yield) as a solid.

4 N HCl-dioxane solution (0.8 ml, 3.2 mmol) and $CH_3OH$ (1 ml) were added to a solution of compound 24 (0.18 g, 0.33 mmol) in $CH_2Cl_2$ (2 ml). The mixture was stirred at RT overnight. Solvents were evaporated and product was triturated with $CH_2Cl_2$, filtered and dried under high vacuum to give title compound 25 as a HCl salt. LCMS: $C_{26}H_{24}F_3N_4O_4Cl$. HCl $[M+1]^+$549.1

EXAMPLE 7

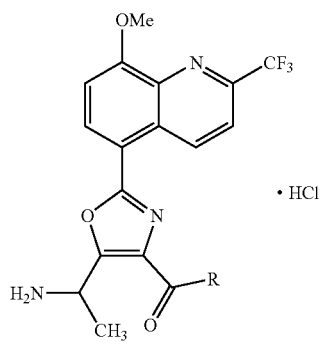

26

By employing methods analogous to those described in Example 6, Step 2, the following compounds were prepared using an appropriate aromatic or heteroaromatic amine coupled with compound 20 either by HATU or DEC (Example 4). The data for compounds of formula 26 are as follows:

| Cpd. No. | Structure | MS (M + 1) |
|---|---|---|
| 26-1 | 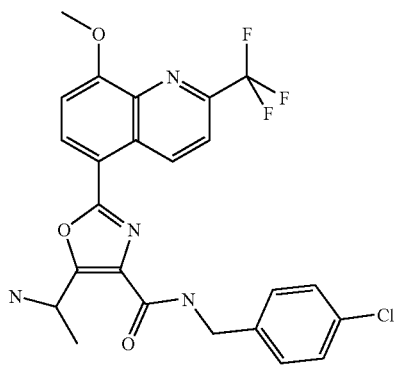 | 505 |

| Cpd. No. | Structure | MS (M + 1) |
|---|---|---|
| 26-2 | 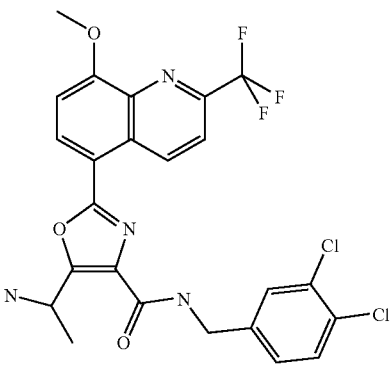 | 539 |
| 26-3 | 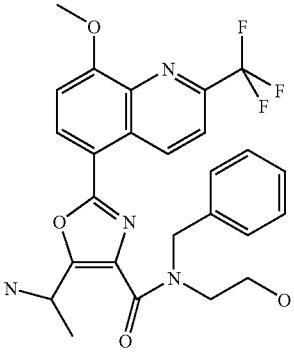 | 515 |
| 26-4 | 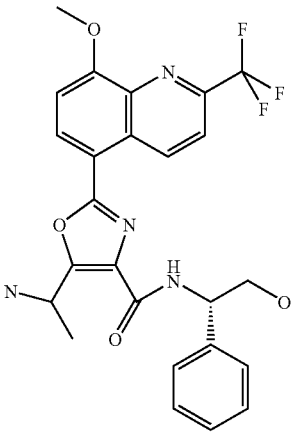 | 501 |

| Cpd. No. | Structure | MS (M + 1) |
|---|---|---|
| 26-5 | 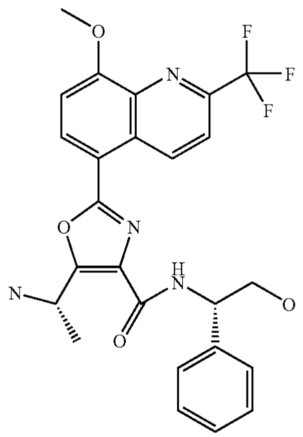 | 501 |
| 26-6 | 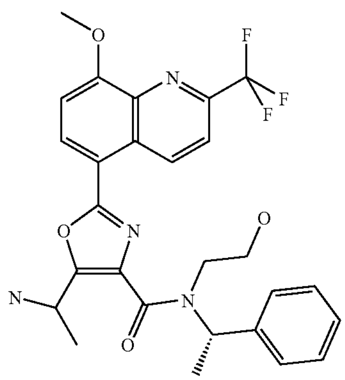 | 529 |
| 26-7 | 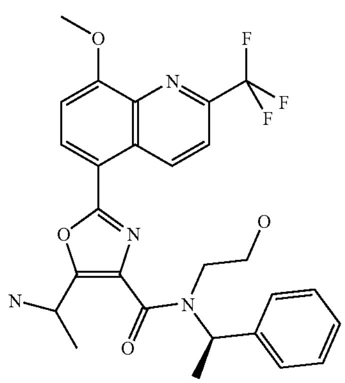 | 529 |
| 26-8 | 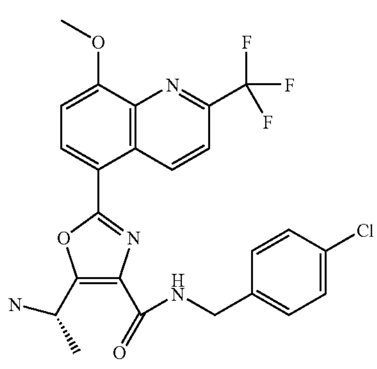 | 505 |

| Cpd. No. | Structure | MS (M + 1) |
|---|---|---|
| 26-9 | 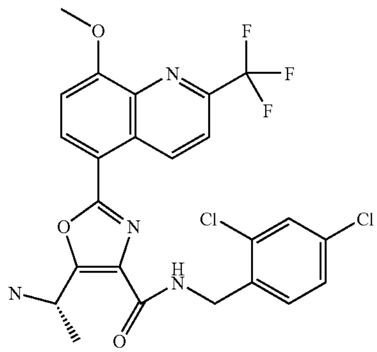 | 539 |
| 26-10 | 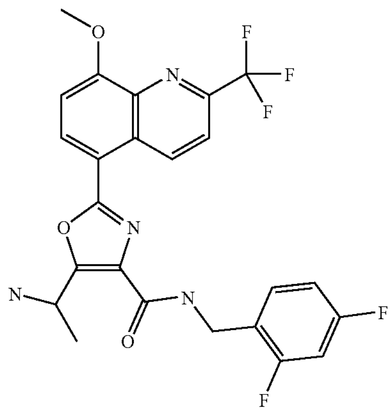 | 507 |
| 26-11 | 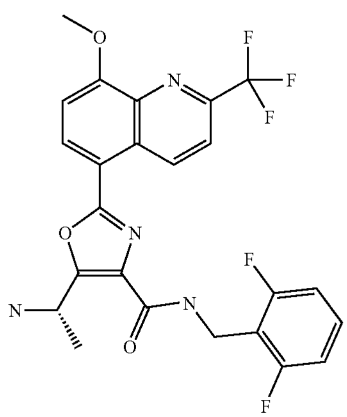 | 507 |
| 26-12 | 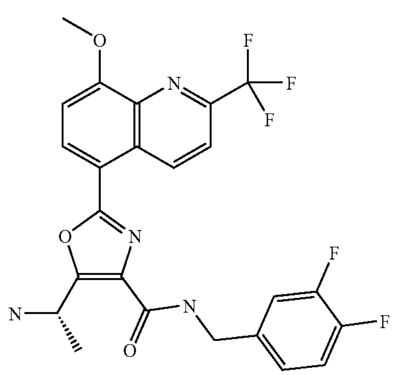 | 507 |

| Cpd. No. | Structure | MS (M + 1) |
|---|---|---|
| 26-13 | 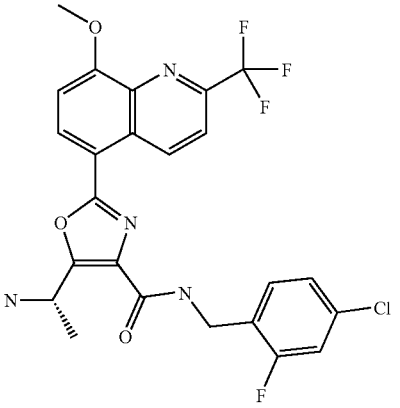 | 523 |
| 26-14 | 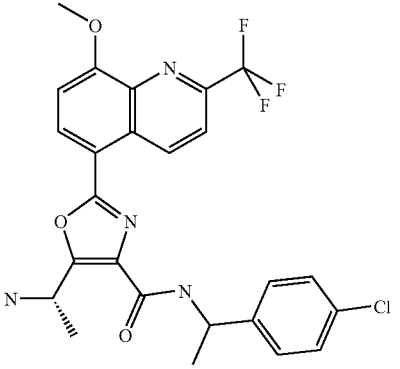 | 519 |
| 26-15 | 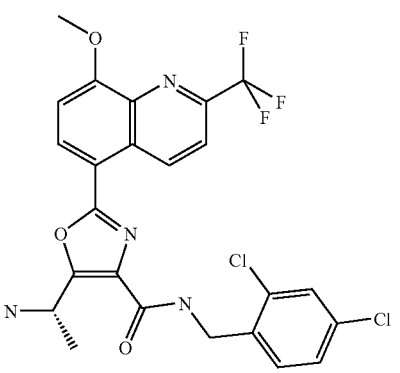 | 540 |
| 26-16 | 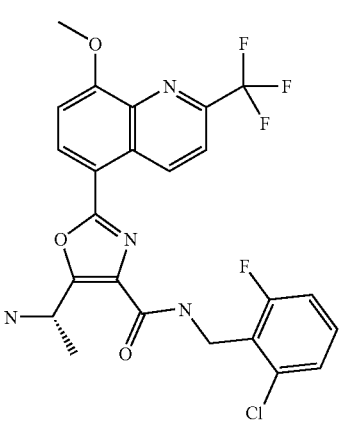 | 523 |

| Cpd. No. | Structure | MS (M + 1) |
|---|---|---|
| 26-17 | 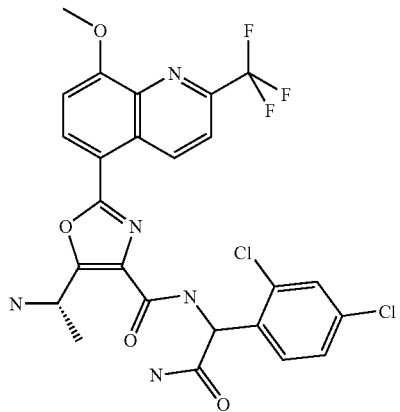 | 583 |
| 26-18 | 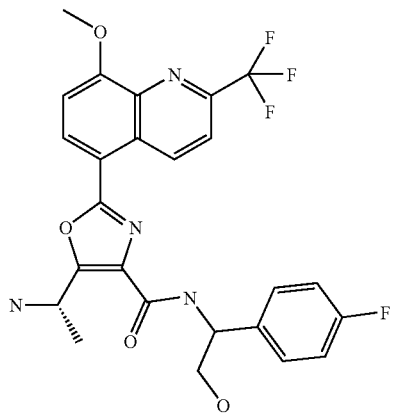 | 519 |
| 26-19 | 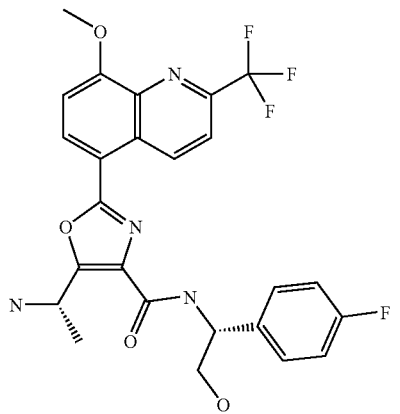 | 519 |

-continued
| Cpd. No. | Structure | MS (M + 1) |
|---|---|---|
| 26-20 | 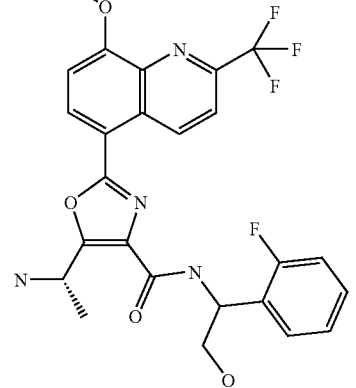 | 519 |
| 26-21 | 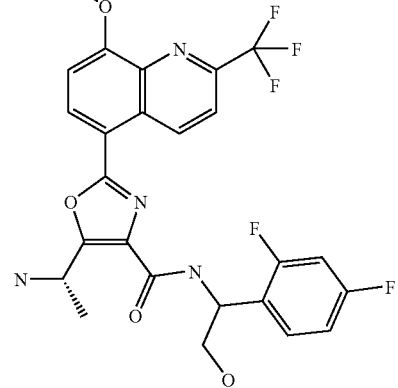 | 537 |
| 26-22 | 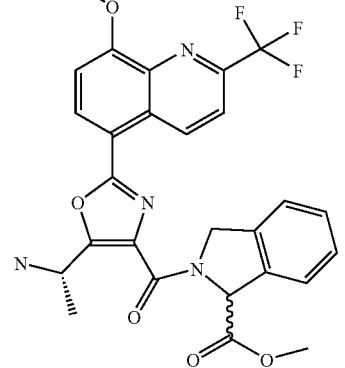 | 541 |

-continued

| Cpd. No. | Structure | MS (M + 1) |
|---|---|---|
| 26-23 | 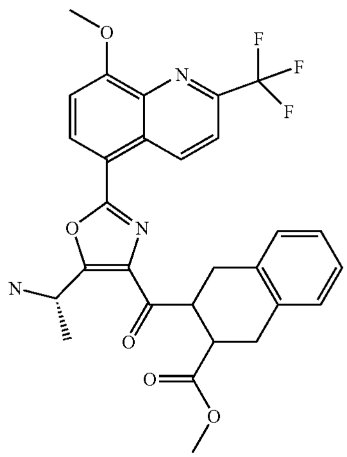 | 555 |
| 26-24 | 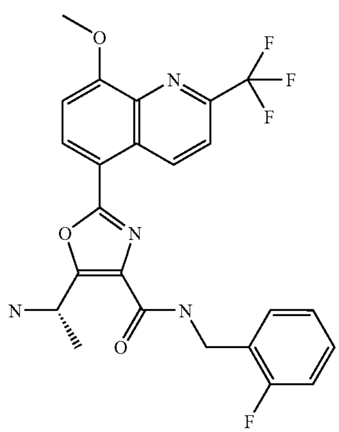 | 489 |
| 26-25 | 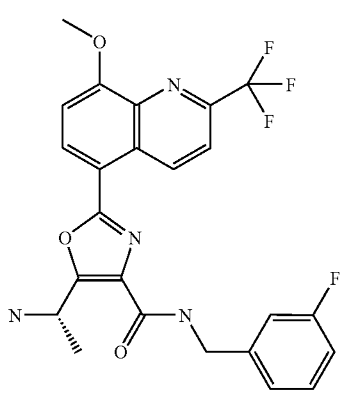 | 489 |

| Cpd. No. | Structure | MS (M + 1) |
|---|---|---|
| 26-26 | 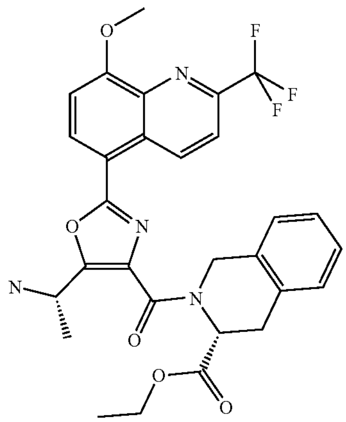 | 569 |
| 26-27 | 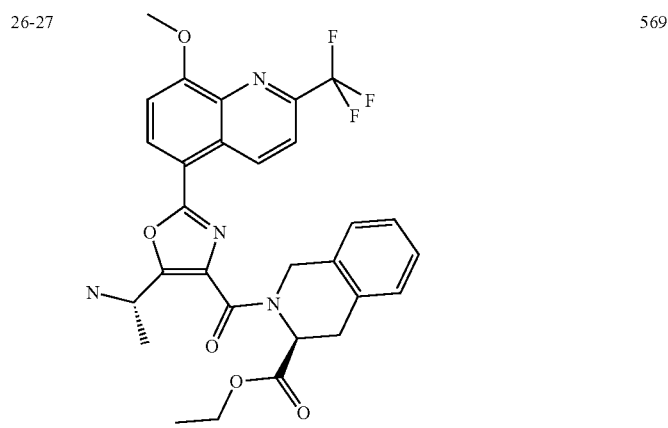 | 569 |
| 26-28 | 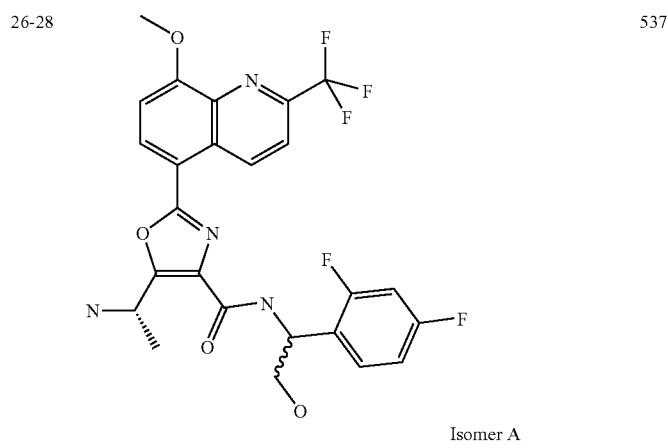<br>Isomer A | 537 |

| Cpd. No. | Structure | MS (M + 1) |
|---|---|---|
| 26-29 | Isomer B | 537 |
| 26-30 | 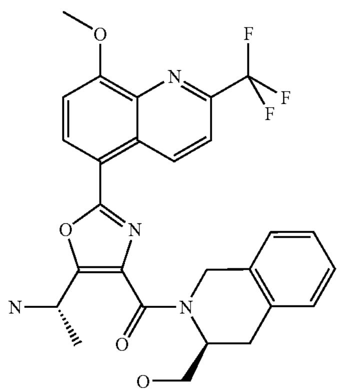 | 527 |
| 26-31 | 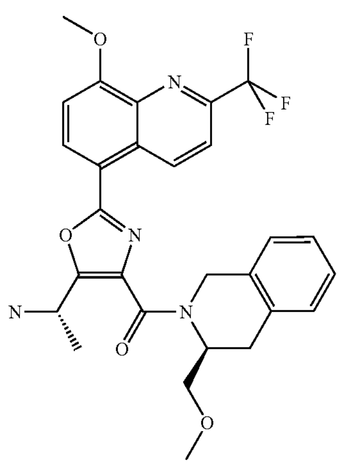 | 541 |

-continued
| Cpd. No. | Structure | MS (M + 1) |
|---|---|---|
| 26-32 | 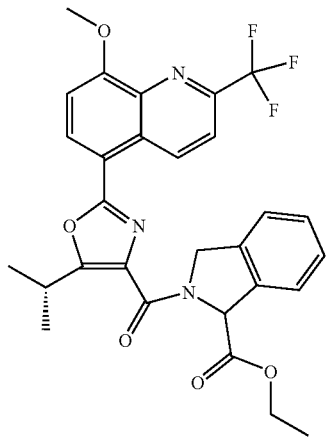 | 555 |
| 26-33 | 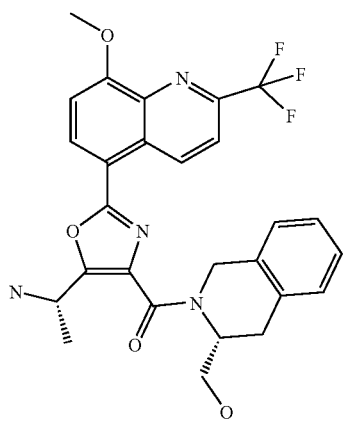 | 527 |
| 26-34 | 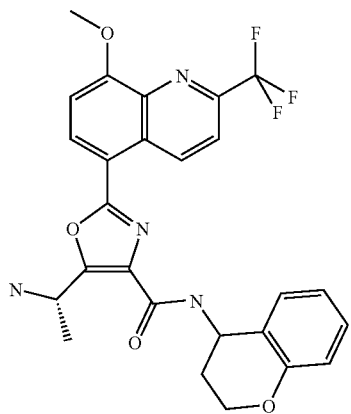 | 513 |

-continued

| Cpd. No. | Structure | MS (M + 1) |
|---|---|---|
| 26-35 | 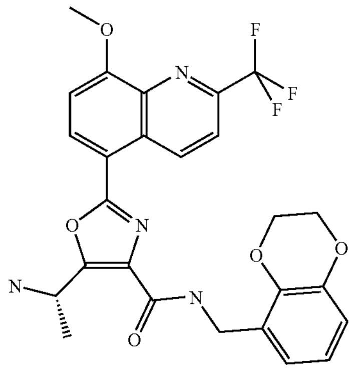 | 529 |
| 26-36 | 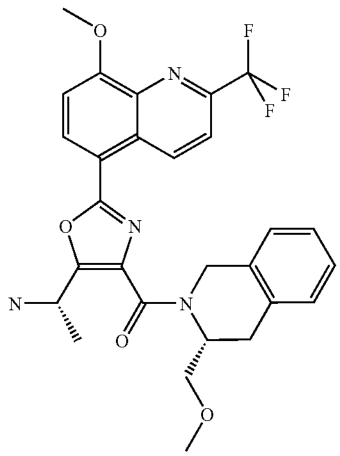 | 541 |
| 26-37 | 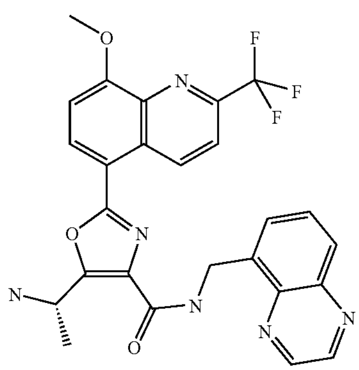 | 523 |
| 26-38 | 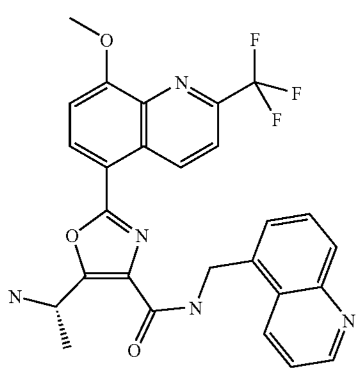 | 522 |

| Cpd. No. | Structure | MS (M + 1) |
|---|---|---|
| 26-39 | 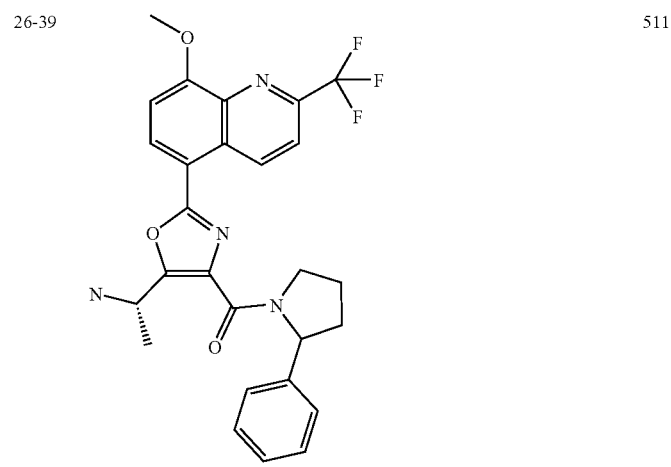 | 511 |
| 26-40 | 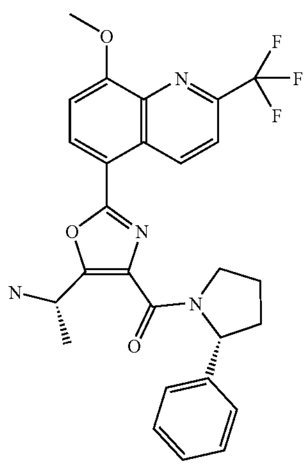 | 511 |
| 26-41 | 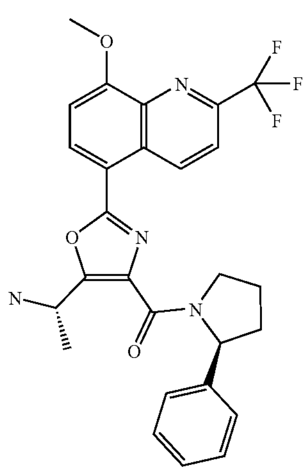 | 511 |

| Cpd. No. | Structure | MS (M + 1) |
|---|---|---|
| 26-42 | 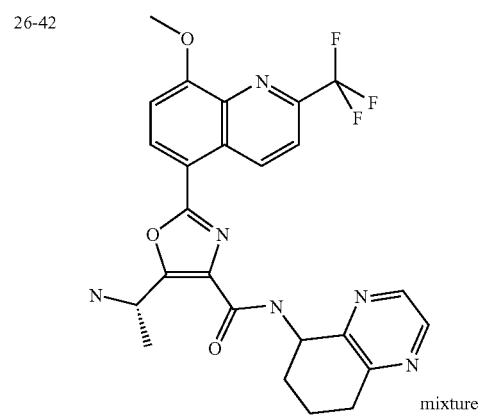 mixture | 513 |
| 26-43 | 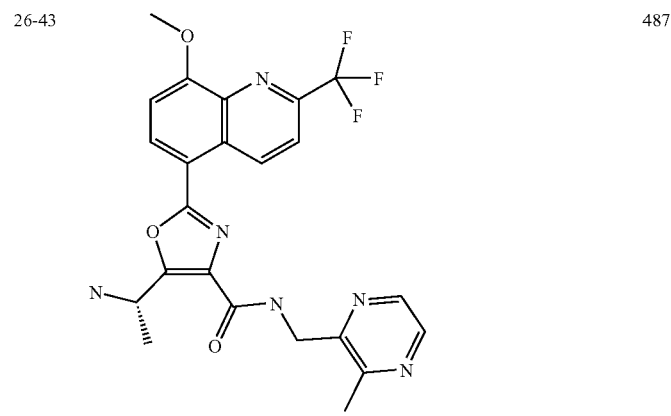 | 487 |
| 26-44 | 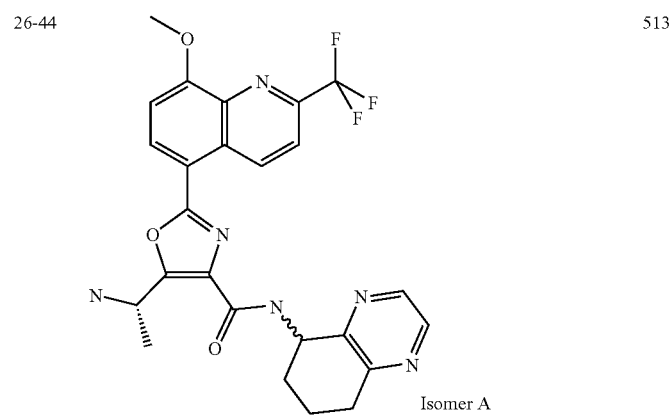 Isomer A | 513 |

-continued

| Cpd. No. | Structure | MS (M + 1) |
|---|---|---|
| 26-45 | isomer B | 513 |
| 26-46 | 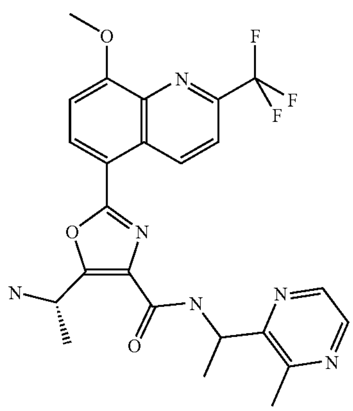 | 500 |
| 26-47 | 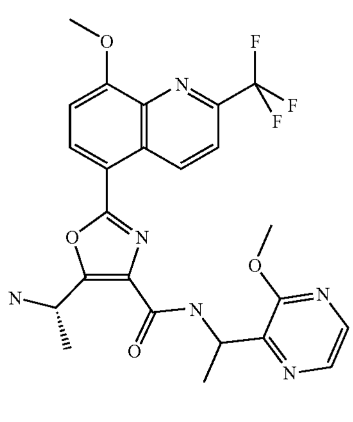 | 517 |

| Cpd. No. | Structure | MS (M + 1) |
|---|---|---|
| 26-48 | 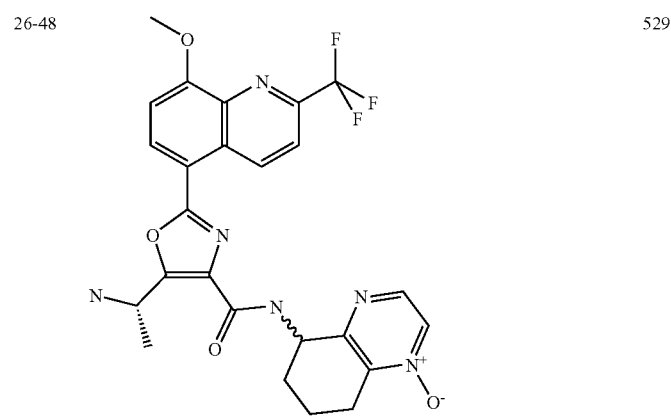 | 529 |
| 26-49 | 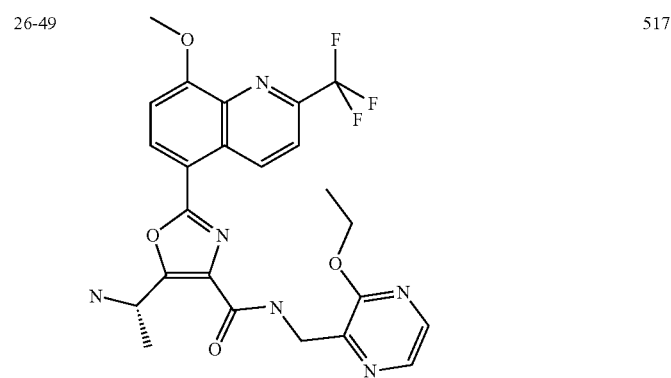 | 517 |
| 26-50 | 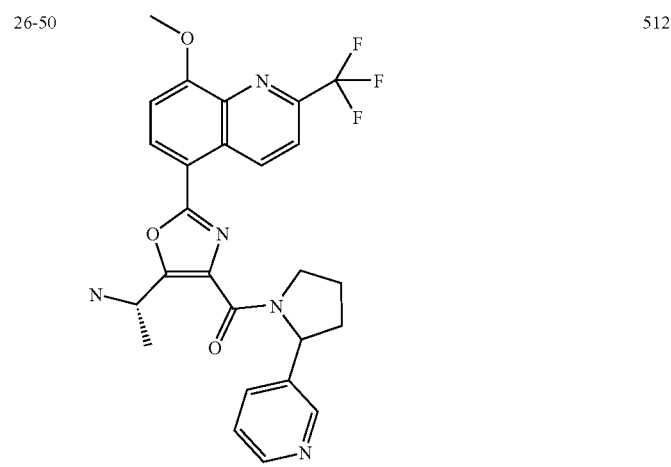 | 512 |

-continued

| Cpd. No. | Structure | MS (M + 1) |
|---|---|---|
| 26-51 | 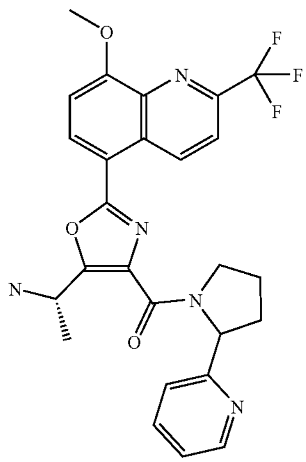 | 512 |
| 26-52 | 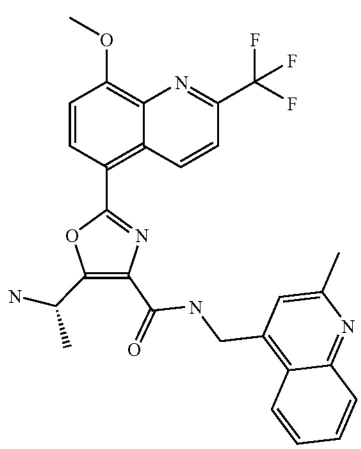 | 536 |
| 26-53 | 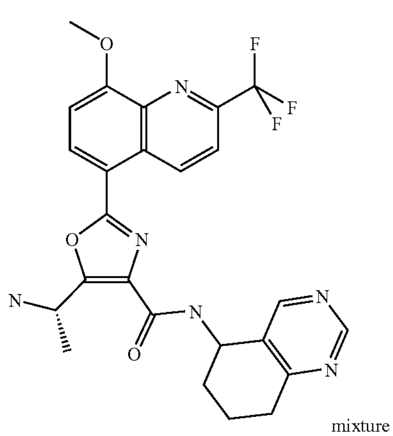 | 513 |
| | mixture | |

-continued

| Cpd. No. | Structure | MS (M + 1) |
|---|---|---|
| 26-54 | isomer A | 513 |
| 26-55 | isomer B | 513 |
| 26-56 | 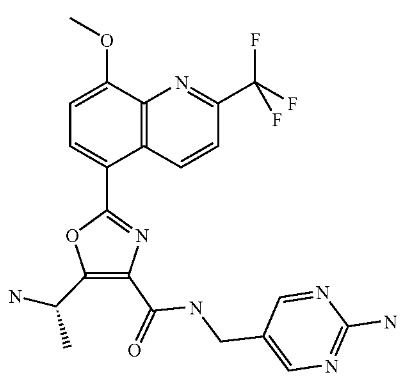 | 488 |

-continued

| Cpd. No. | Structure | MS (M + 1) |
|---|---|---|
| 26-57 | 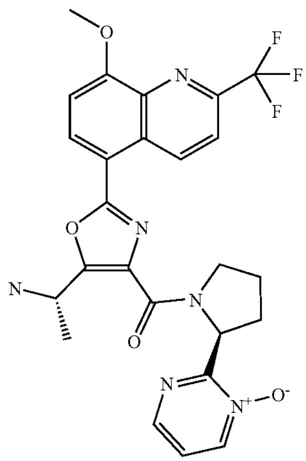 | 529 |
| 26-58 | 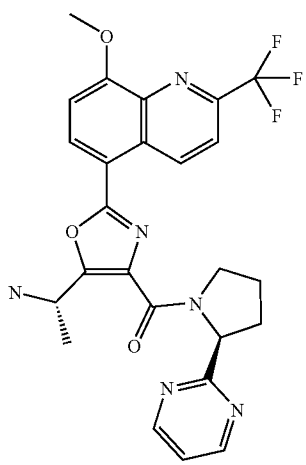 | 513 |
| 26-59 | 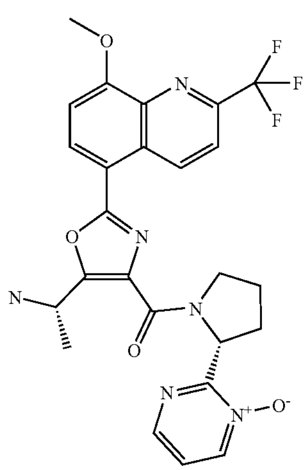 | 529 |

| Cpd. No. | Structure | MS (M + 1) |
|---|---|---|
| 26-60 | 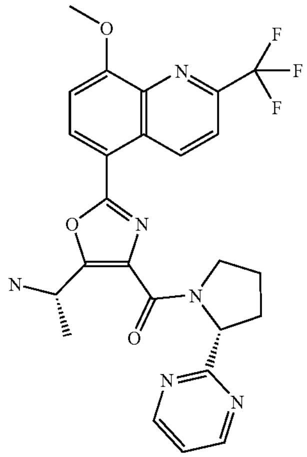 | 513 |
| 26-61 | 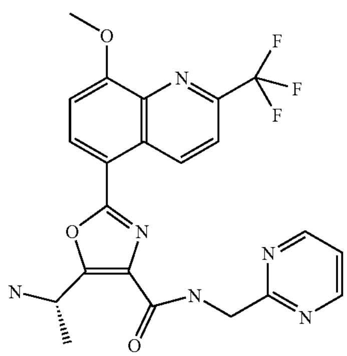 | 473 |
| 26-62 | 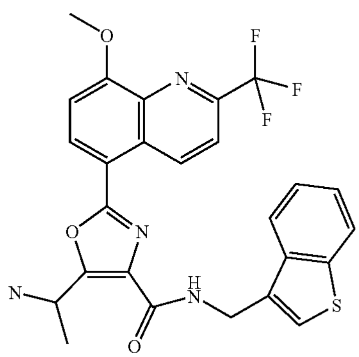 | 527 |
| 26-63 | 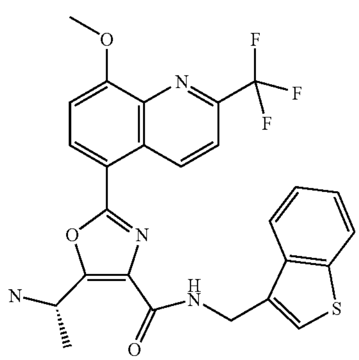 | 527 |

| Cpd. No. | Structure | MS (M + 1) |
|---|---|---|
| 26-64 | 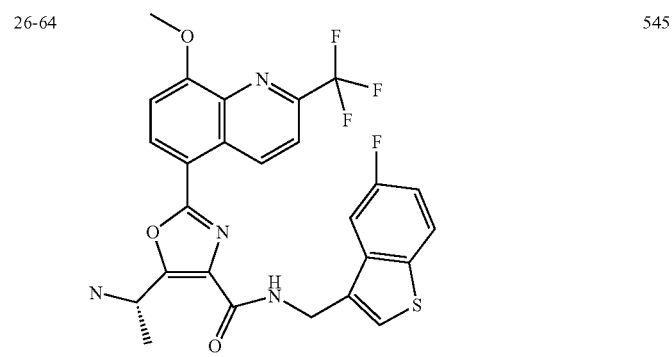 | 545 |
| 26-65 | 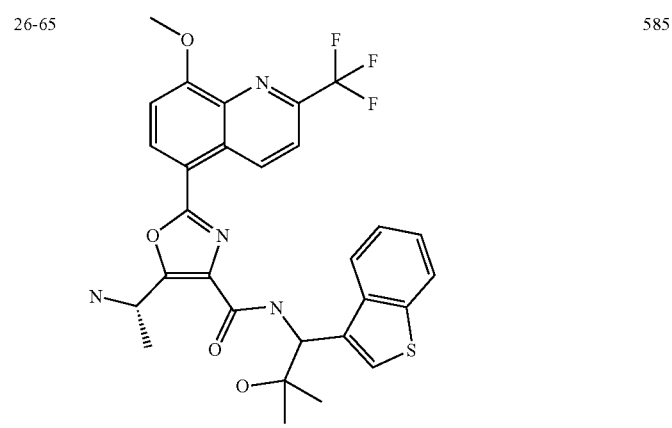 | 585 |
| 26-66 | 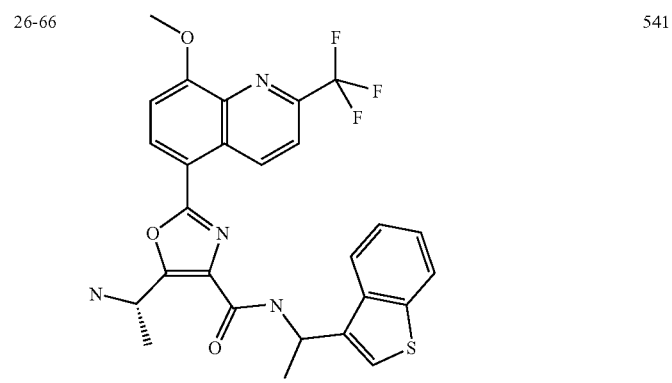 | 541 |

-continued
| Cpd. No. | Structure | MS (M + 1) |
|---|---|---|
| 26-67 | 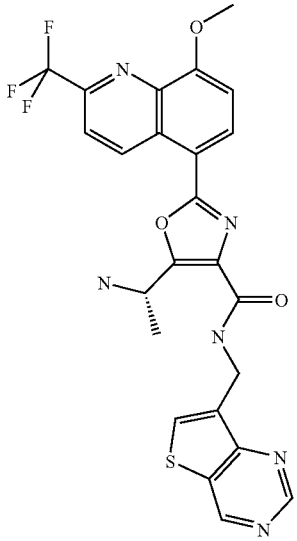 | 529 |
| 26-68 | 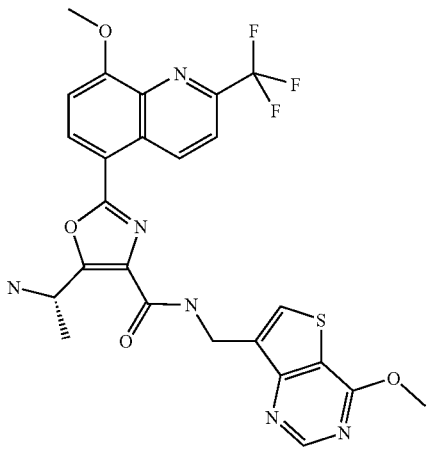 | 559 |
| 26-69 | 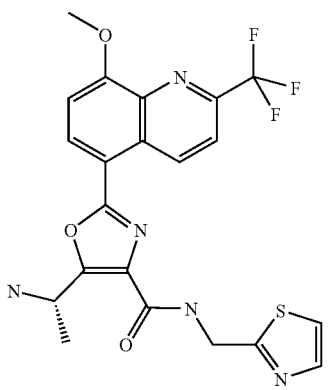 | 478 |

| Cpd. No. | Structure | MS (M + 1) |
|---|---|---|
| 26-70 | 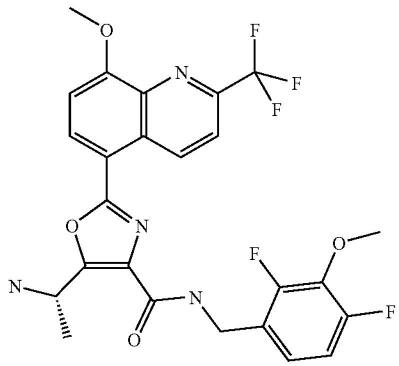 | 537 |
| 26-71 | 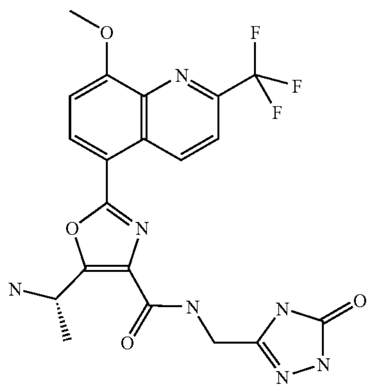 | 478 |
| 26-72 | 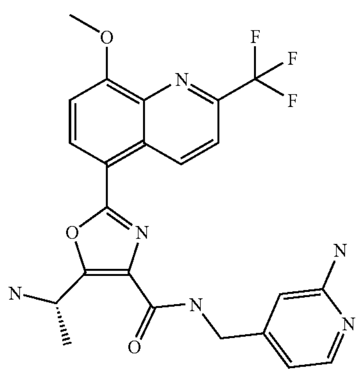 | 487 |
| 26-73 | 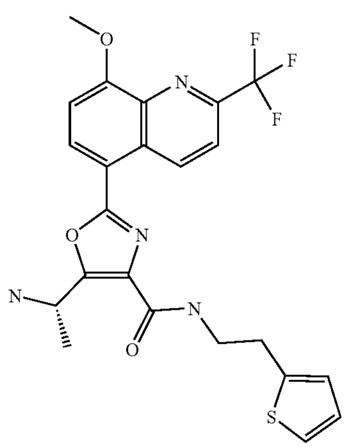 | 491 |

-continued
| Cpd. No. | Structure | MS (M + 1) |
|---|---|---|
| 26-74 | 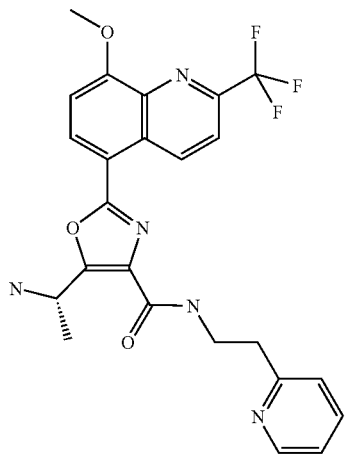 | 486 |
| 26-75 | 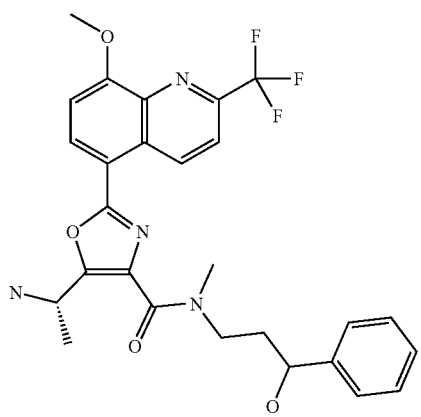 | 529 |
| 26-76 | 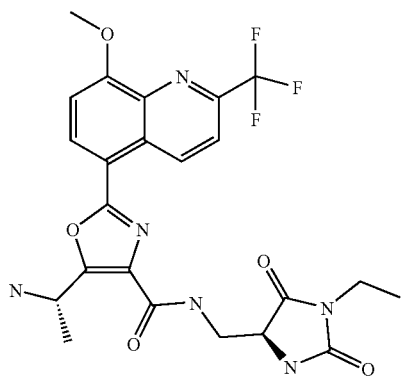 | 521 |

-continued
| Cpd. No. | Structure | MS (M + 1) |
|---|---|---|
| 26-77 | 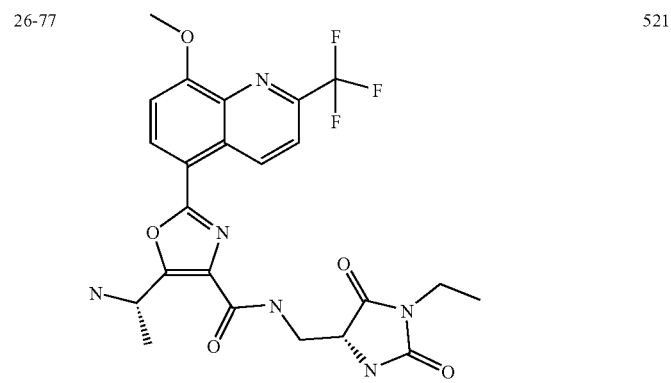 | 521 |
| 26-78 | 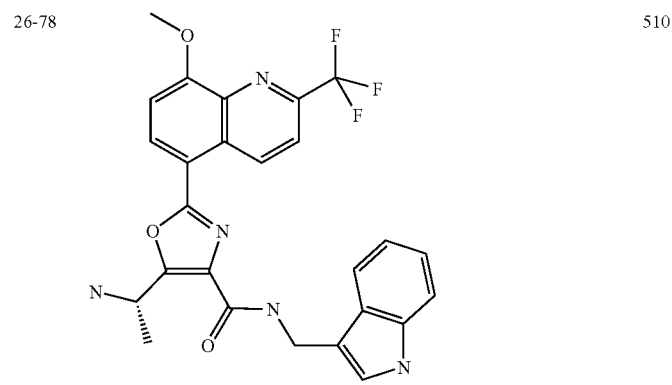 | 510 |
| 26-79 | 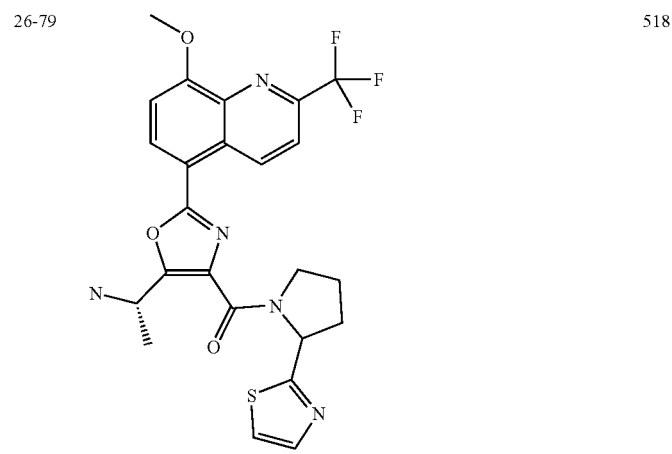 | 518 |

-continued

| Cpd. No. | Structure | MS (M + 1) |
|---|---|---|
| 26-80 | 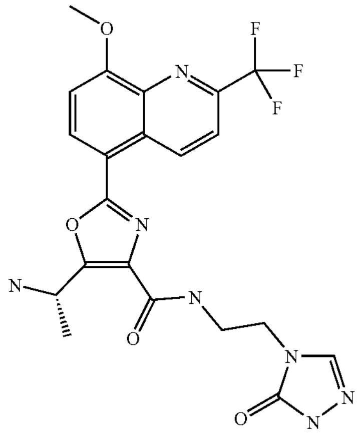 | 492 |
| 26-81 | 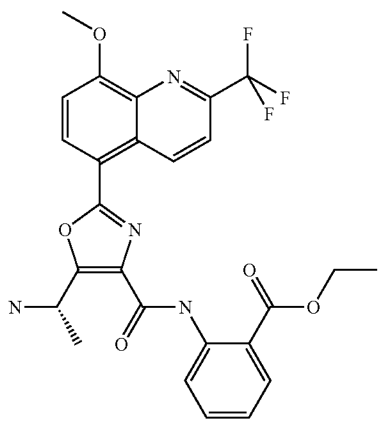 | 529 |
| 26-82 | 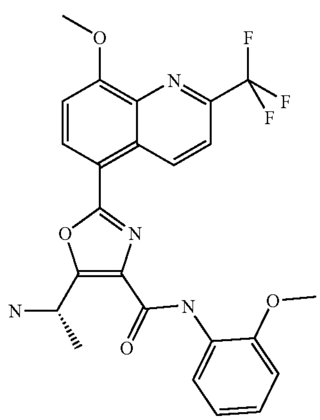 | 487 |

|Cpd. No.|Structure|MS (M + 1)|
|---|---|---|
|26-83|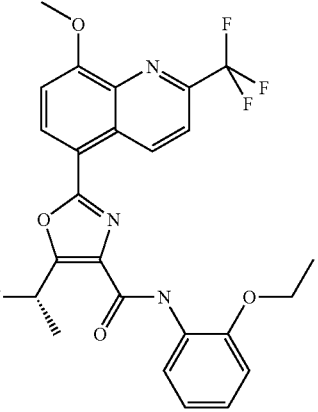|501|
|26-84|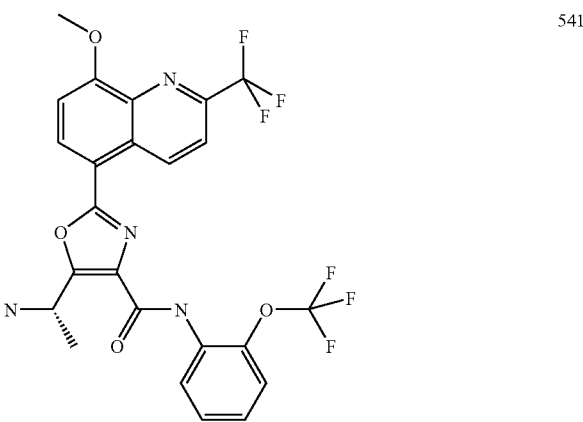|541|
|26-85|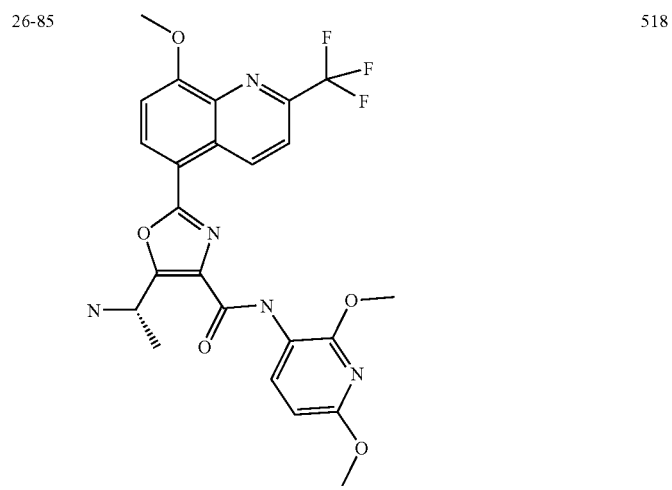|518|

-continued
| Cpd. No. | Structure | MS (M + 1) |
|---|---|---|
| 26-86 | 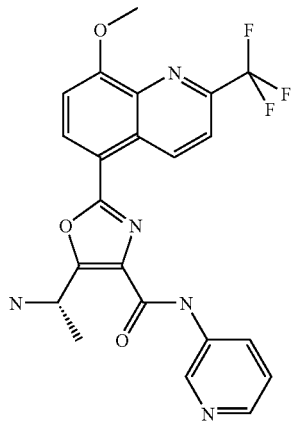 | 458 |
| 26-87 | 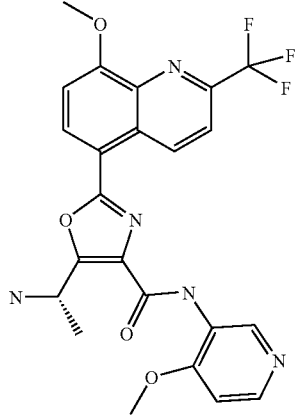 | 488 |
| 26-88 | 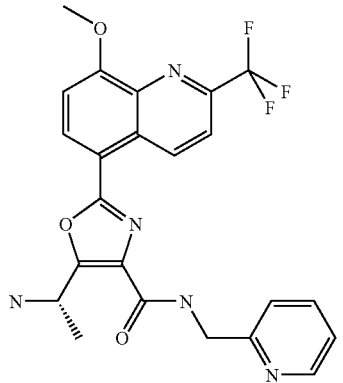 | 472 |

-continued
| Cpd. No. | Structure | MS (M + 1) |
|---|---|---|
| 26-89 | 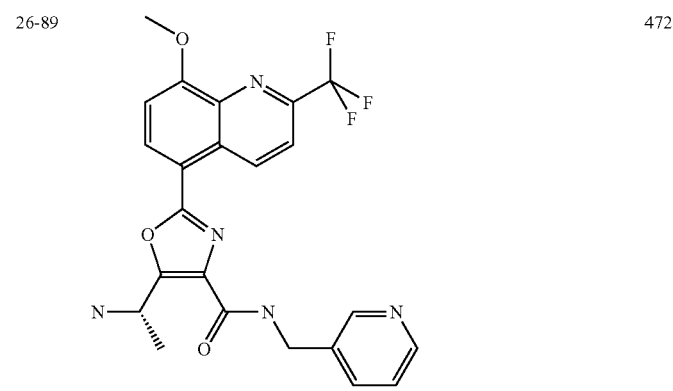 | 472 |
| 26-90 | 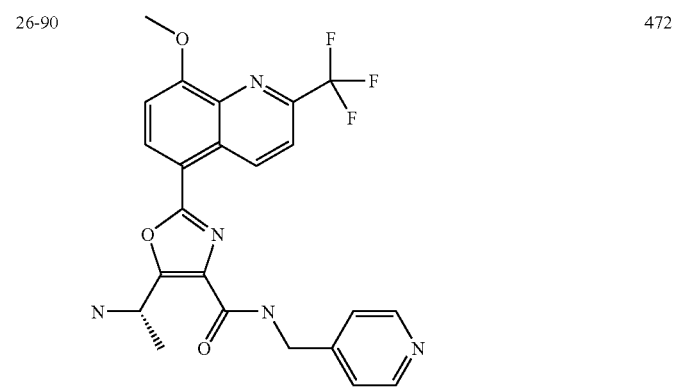 | 472 |
| 26-91 | 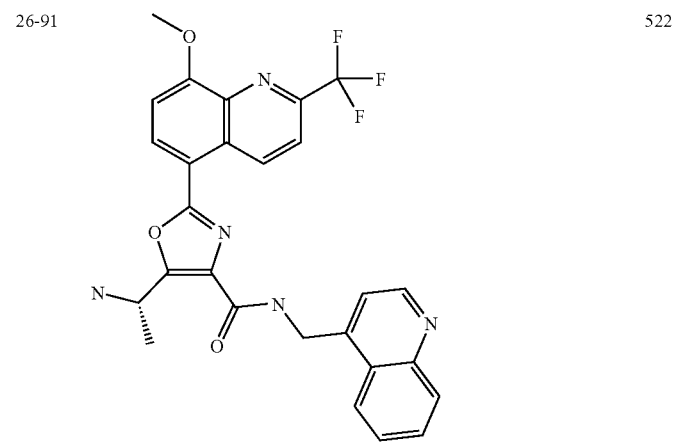 | 522 |

-continued

| Cpd. No. | Structure | MS (M + 1) |
|---|---|---|
| 26-92 | 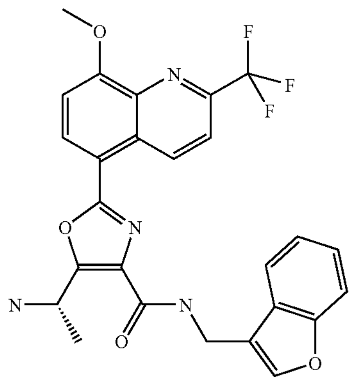 | 511 |
| 26-93 | 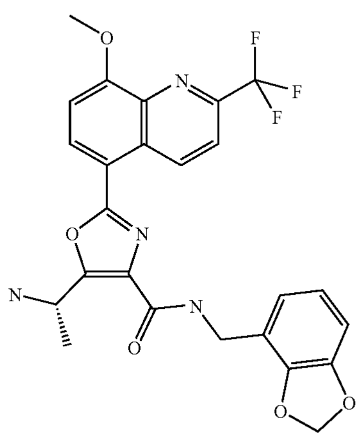 | 515 |
| 26-94 | 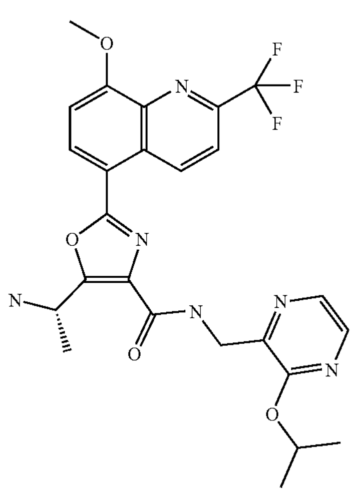 | 514 |

-continued

| Cpd. No. | Structure | MS (M + 1) |
|---|---|---|
| 26-95 | 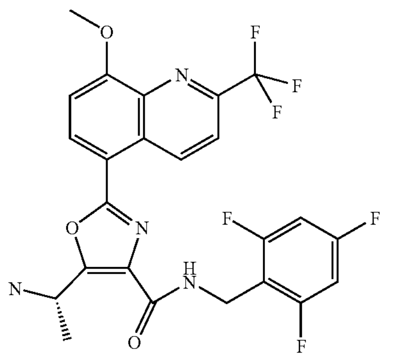 | 525 |
| 26-96 | 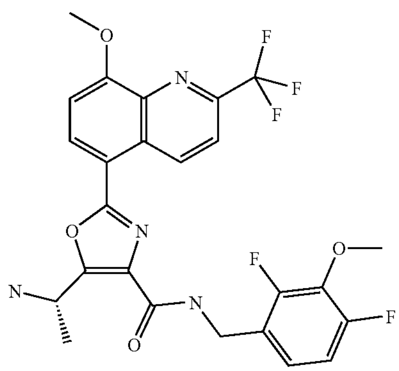 | 537 |
| 26-97 | 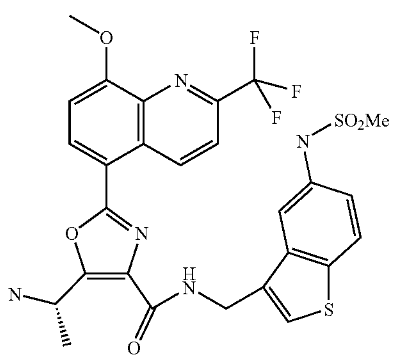 | 620 |
| 26-98 | 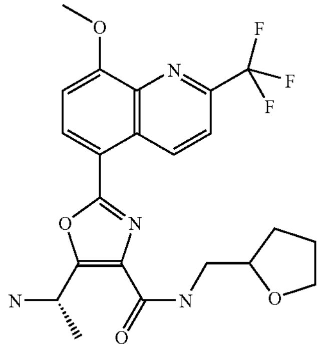 | 465 |

| Cpd. No. | Structure | MS (M + 1) |
|---|---|---|
| 26-99 | 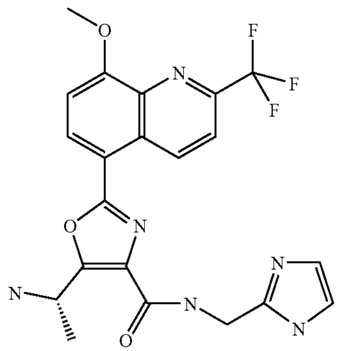 | 461 |
| 26-100 | 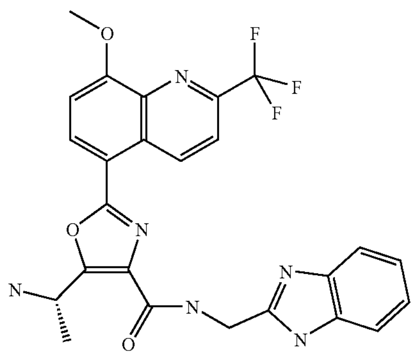 | 511 |
| 26-101 | 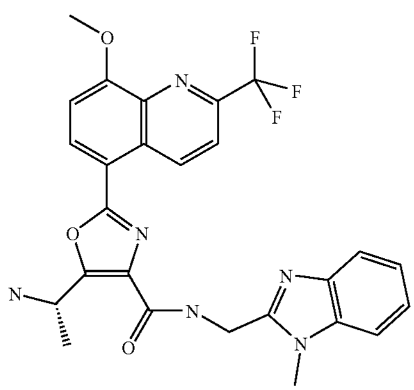 | 524 |
| 26-102 | 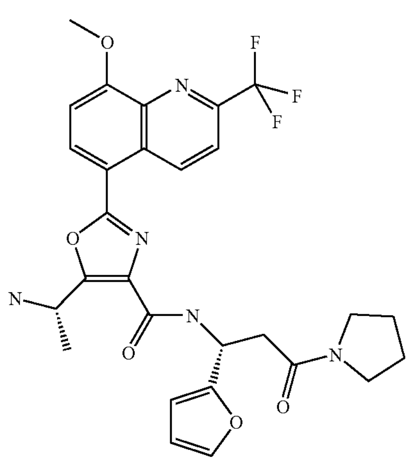 | 572 |

-continued

| Cpd. No. | Structure | MS (M + 1) |
|---|---|---|
| 26-103 | 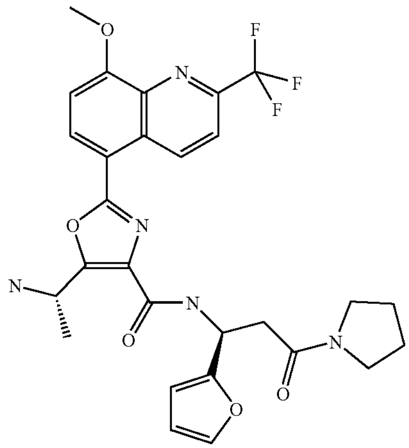 | 572 |
| 26-104 | 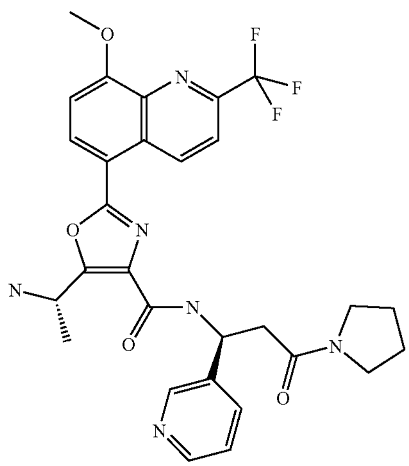 | 583 |
| 26-105 | 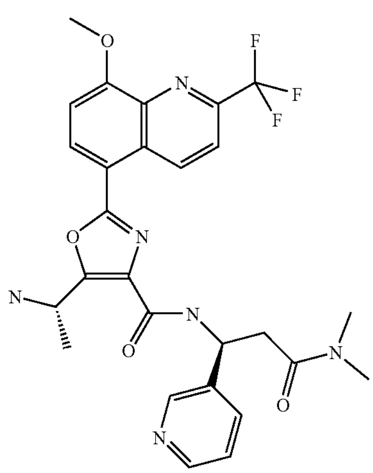 | 557 |

-continued
| Cpd. No. | Structure | MS (M + 1) |
|---|---|---|
| 26-106 | 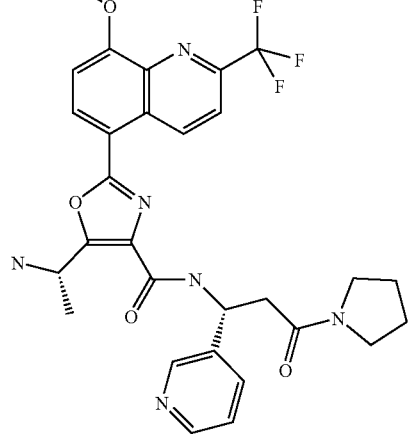 | 583 |
| 26-107 | 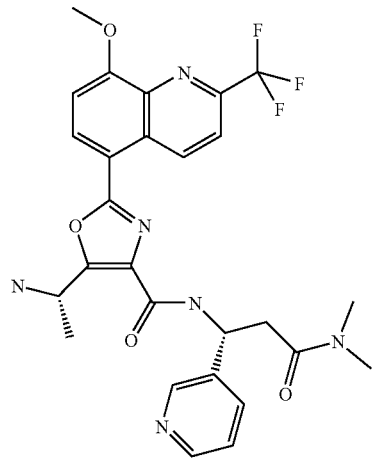 | 557 |
| 26-108 | 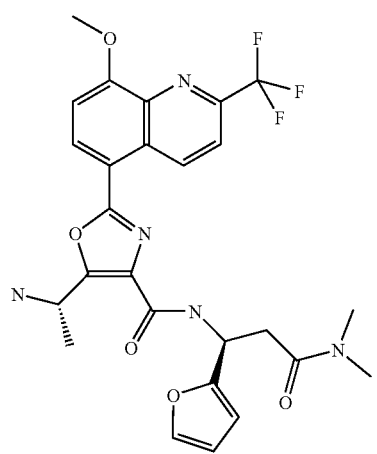 | 546 |

| Cpd. No. | Structure | MS (M + 1) |
|---|---|---|
| 26-109 | 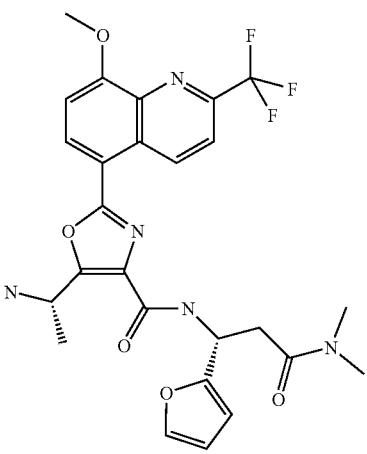 | 546 |
| 26-110 | 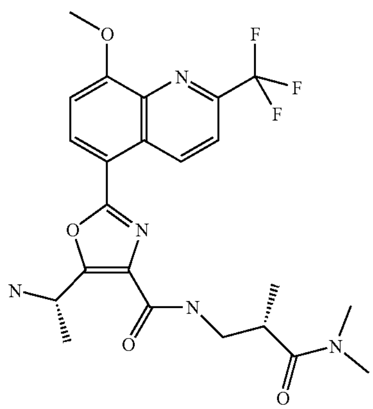 | 494 |
| 26-111 | 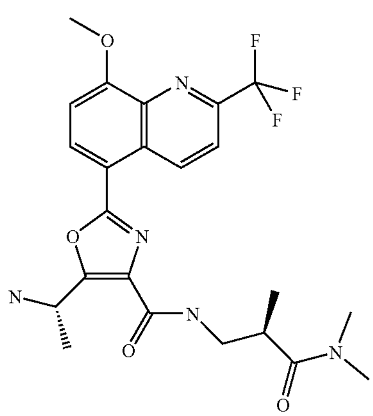 | 494 |

-continued

| Cpd. No. | Structure | MS (M + 1) |
|---|---|---|
| 26-112 | 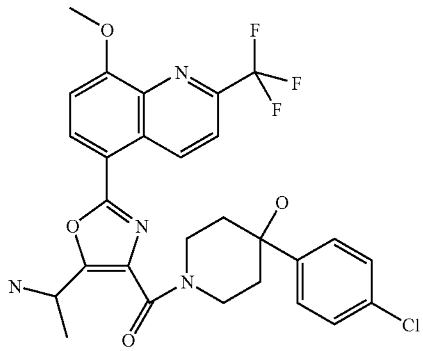 | 575 |
| 26-113 | 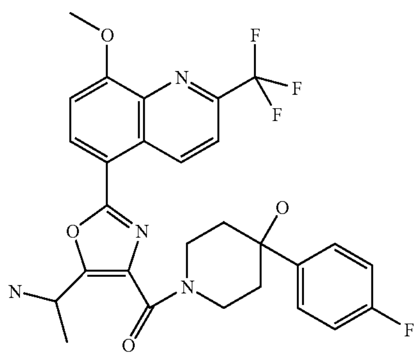 | 559 |
| 26-114 | 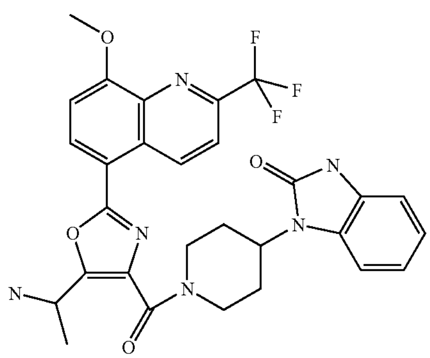 | 581 |
| 26-115 | 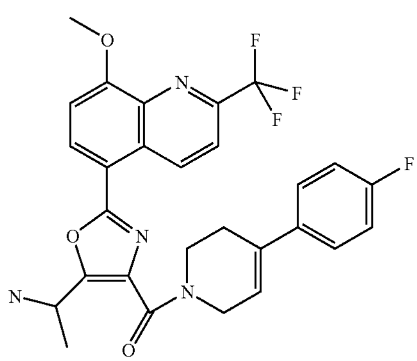 | 541 |

-continued
| Cpd. No. | Structure | MS (M + 1) |
|---|---|---|
| 26-116 | 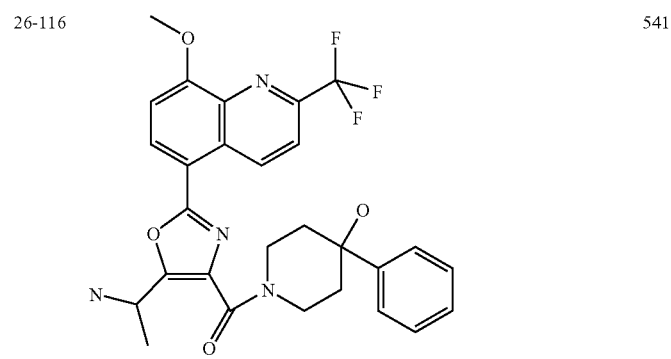 | 541 |
| 26-117 | 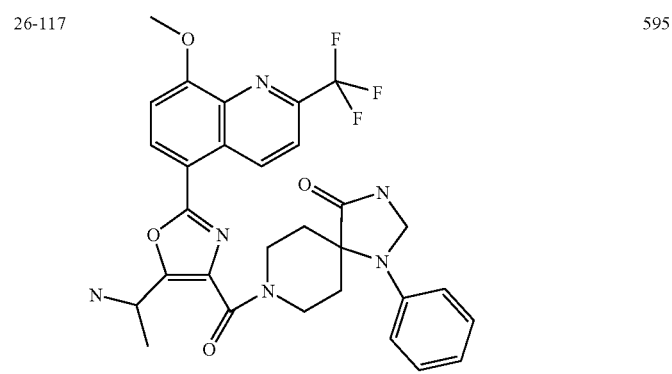 | 595 |
| 26-118 | 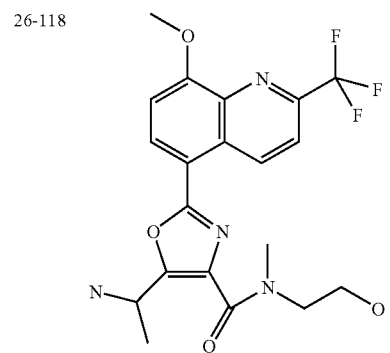 | |
| 26-119 | 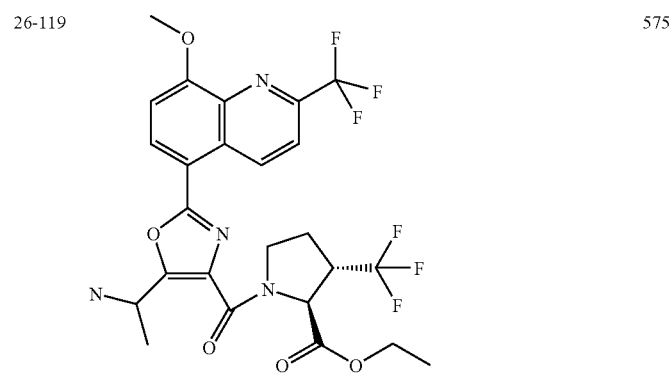 | 575 |

| Cpd. No. | Structure | MS (M + 1) |
|---|---|---|
| 26-120 | 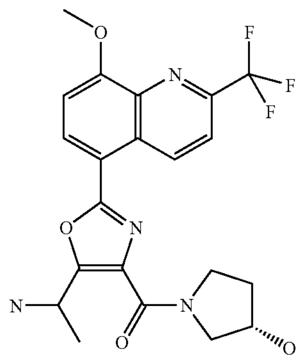 | 451 |
| 26-121 | 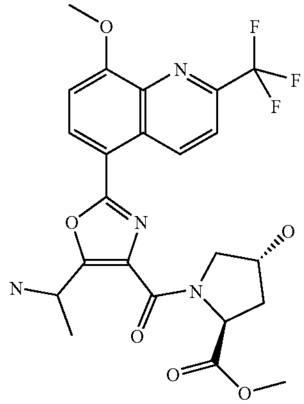 | 509 |
| 26-122 | 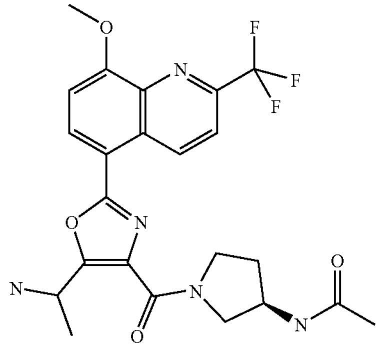 | 492 |
| 26-123 | 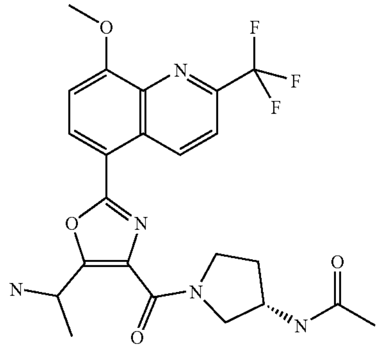 | 492 |

| Cpd. No. | Structure | MS (M + 1) |
|---|---|---|
| 26-124 | 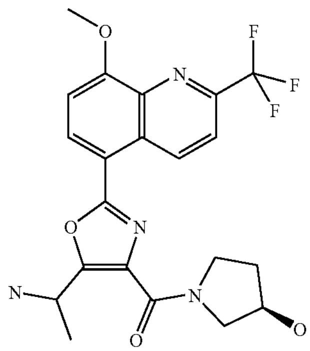 | 451 |
| 26-125 | 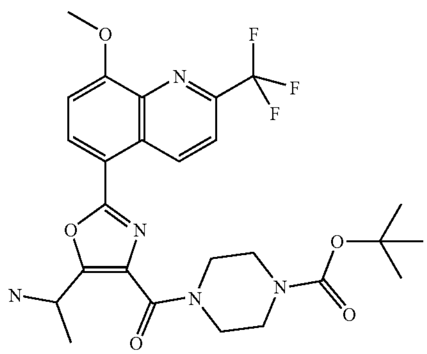 | 550 |
| 26-126 | 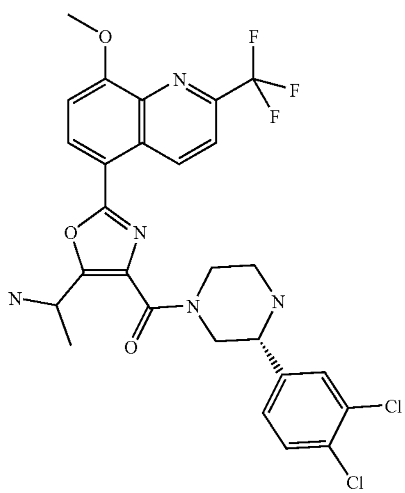 | 594 |
| 26-127 | 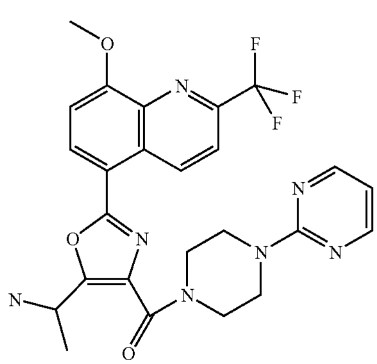 | 528 |

| Cpd. No. | Structure | MS (M + 1) |
|---|---|---|
| 26-128 | 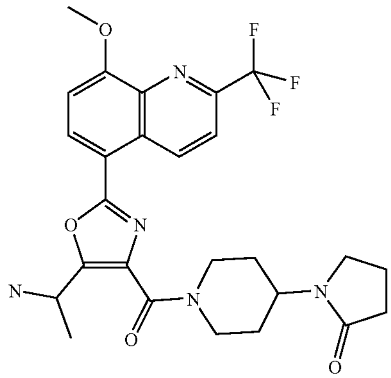 | 523 |
| 26-129 | 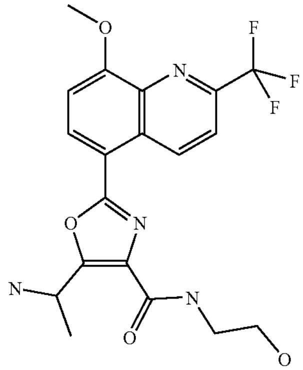 | 425 |
| 26-130 | 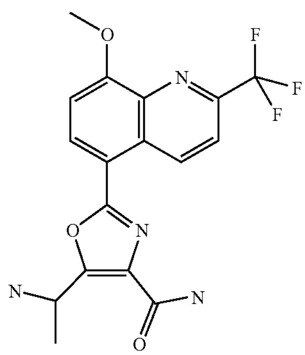 | 381 |
| 26-131 | 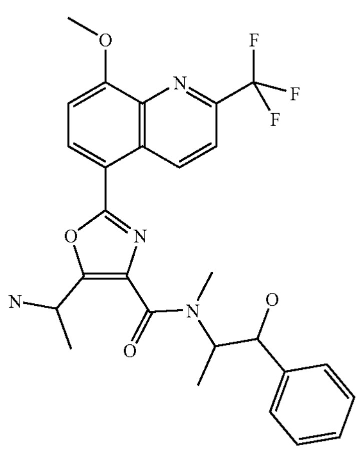 | 529 |

-continued

| Cpd. No. | Structure | MS (M + 1) |
|---|---|---|
| 26-132 | 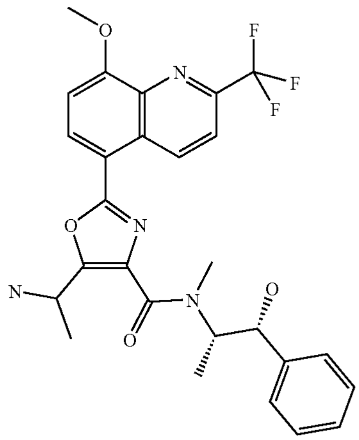 | 529 |
| 26-133 | 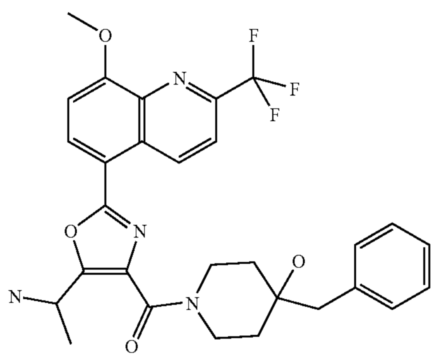 | 555 |
| 26-134 | 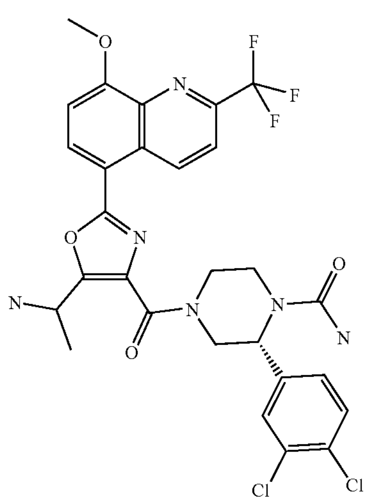 | 637 |

| Cpd. No. | Structure | MS (M + 1) |
|---|---|---|
| 26-135 | 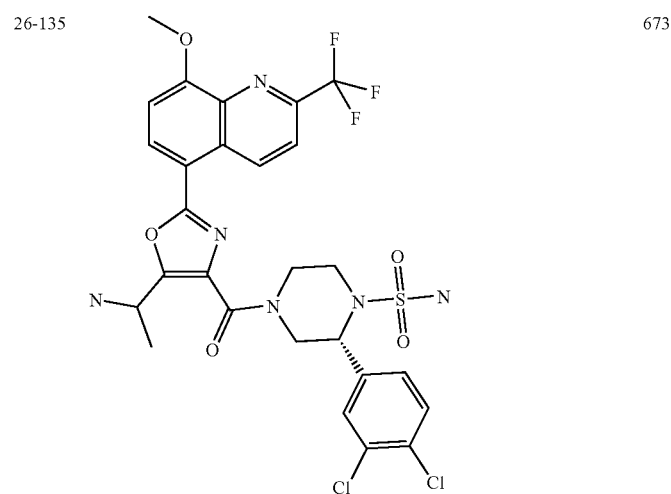 | 673 |
| 26-136 | 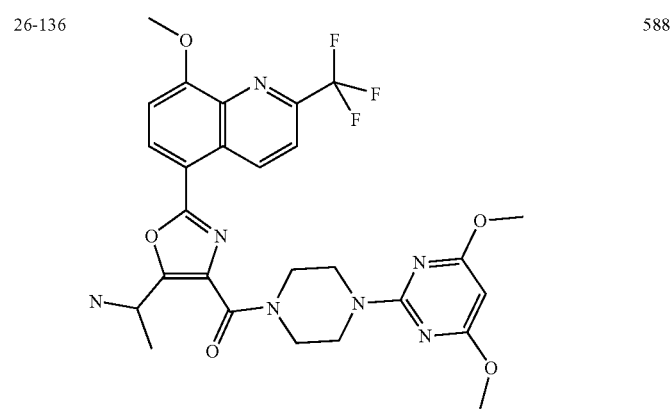 | 588 |
| 26-137 | 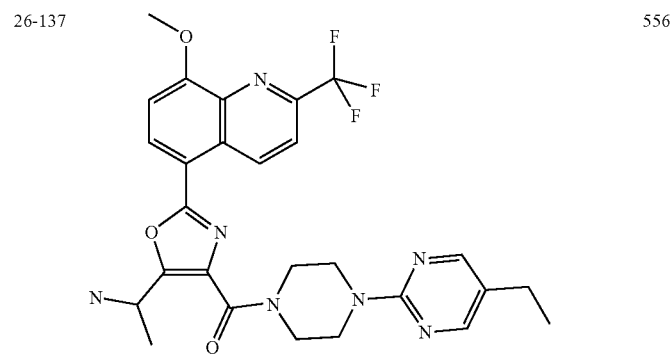 | 556 |

| Cpd. No. | Structure | MS (M + 1) |
|---|---|---|
| 26-138 | 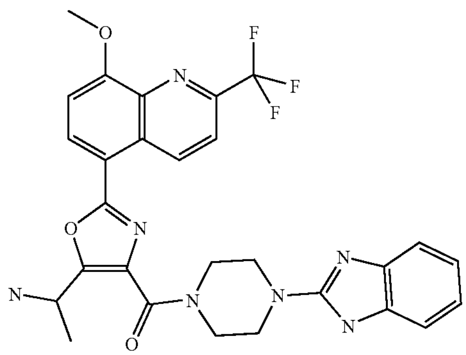 | 566 |
| 26-139 | 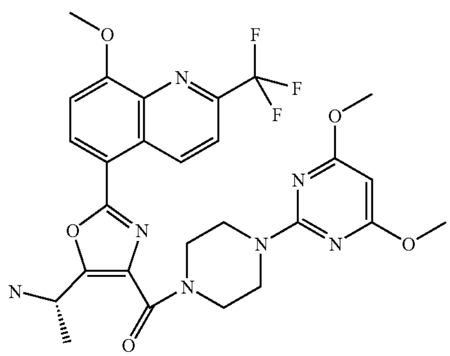 | 588 |
| 26-140 | 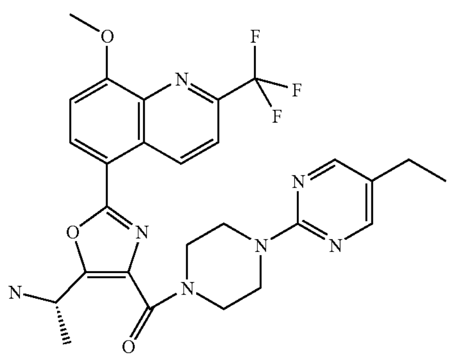 | 556 |
| 26-141 | 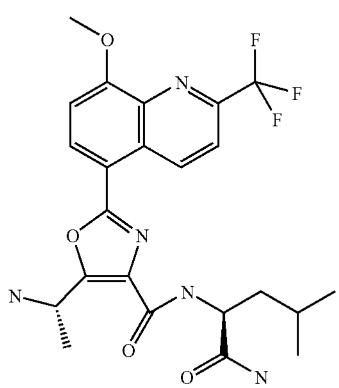 | 494 |

-continued

| Cpd. No. | Structure | MS (M + 1) |
|---|---|---|
| 26-142 | 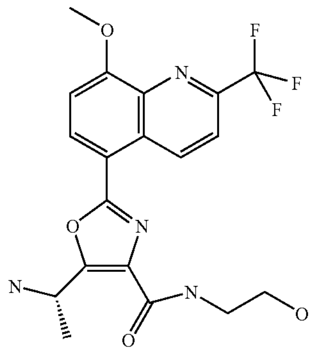 | 425 |
| 26-143 | 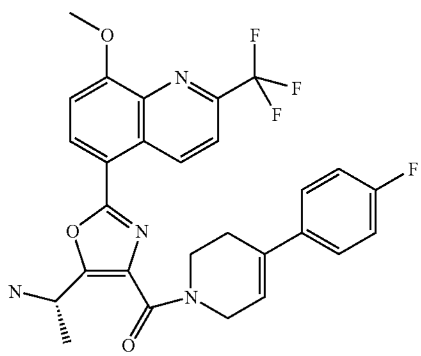 | 541 |
| 26-144 | 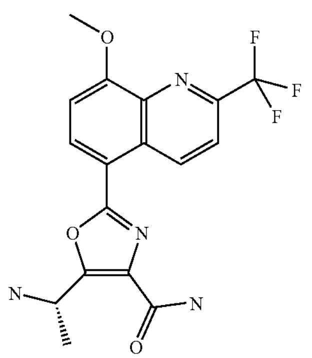 | 381 |
| 26-145 | 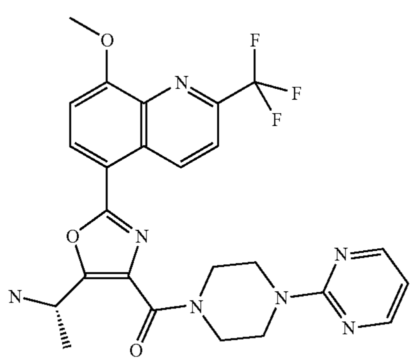 | 528 |

| Cpd. No. | Structure | MS (M + 1) |
|---|---|---|
| 26-146 | 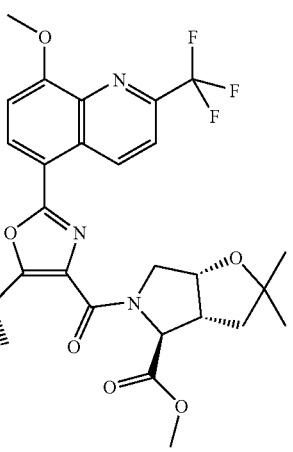 | 563 |
| 26-147 | 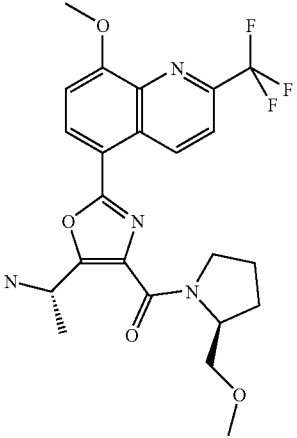 | 479 |
| 26-148 | 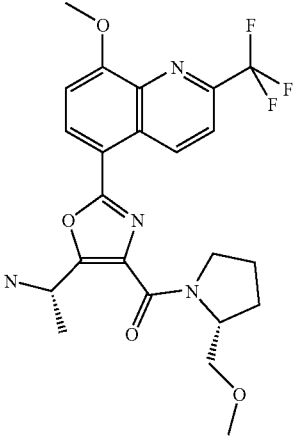 | 479 |

-continued

| Cpd. No. | Structure | MS (M + 1) |
|---|---|---|
| 26-149 | 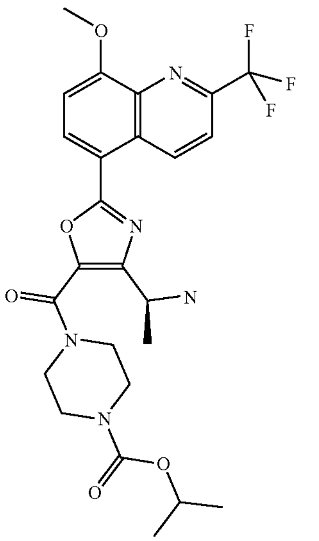 | 536 |
| 26-150 | 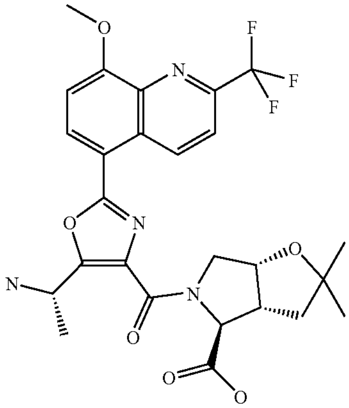 | 549 |
| 26-151 | 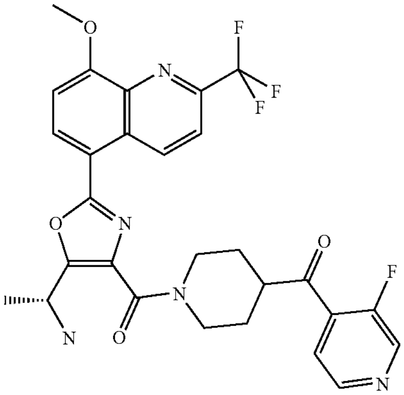 | 572 |

| Cpd. No. | Structure | MS (M + 1) |
|---|---|---|
| 26-152 | 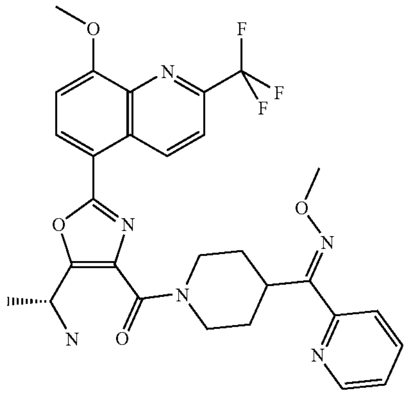 | 583 |
| 26-153 | 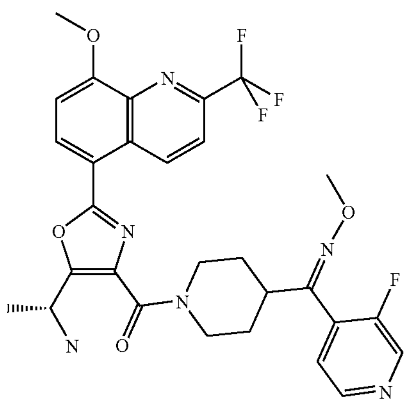 | 601 |
| 26-154 | 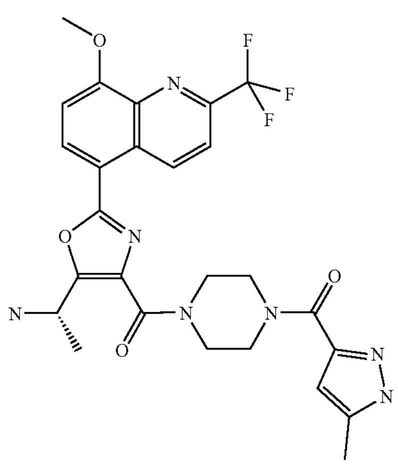 | 558 |

-continued

| Cpd. No. | Structure | MS (M + 1) |
|---|---|---|
| 26-155 | 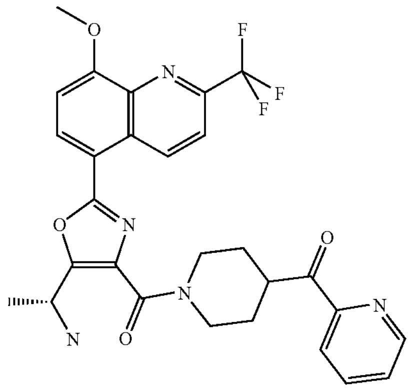 | 554 |
| 26-156 | 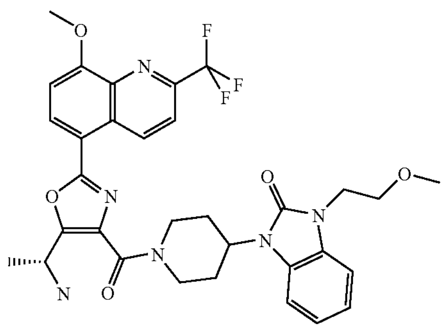 | 639 |
| 26-157 | 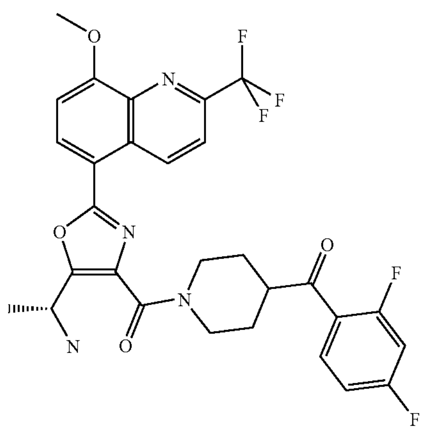 | 589 |
| 26-158 | 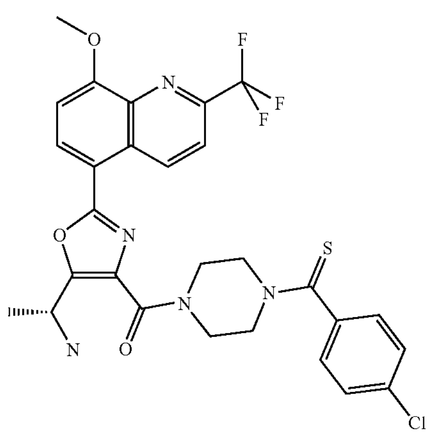 | 604 |

-continued
| Cpd. No. | Structure | MS (M + 1) |
|---|---|---|
| 26-159 | 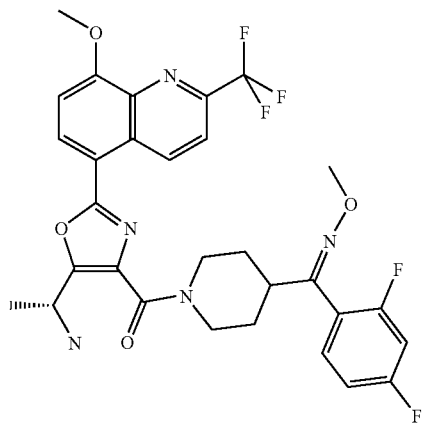 | 618 |
| 26-160 | 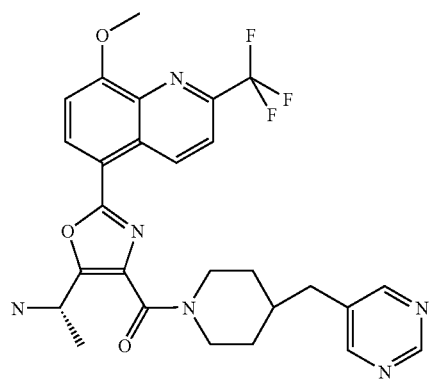 | 541 |
| 26-161 | 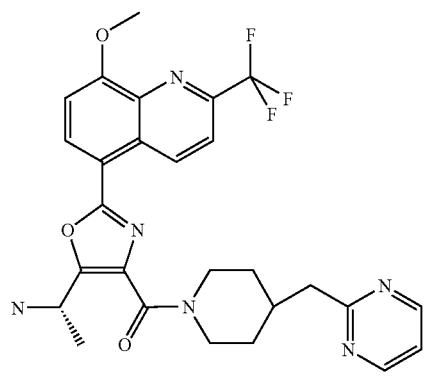 | 541 |

| Cpd. No. | Structure | MS (M + 1) |
|---|---|---|
| 26-162 | 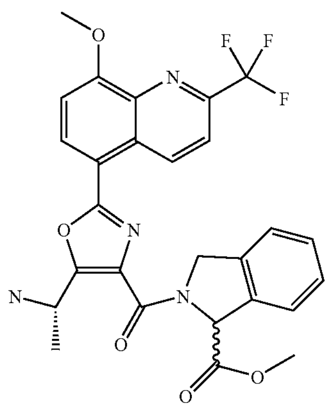 | 541 |
| 26-163 | 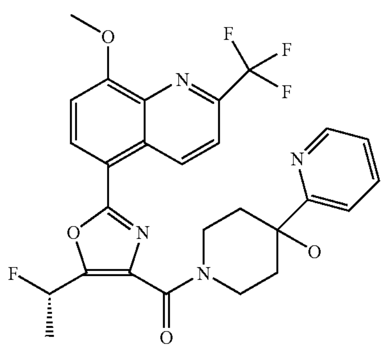 | 542 |
| 26-164 | 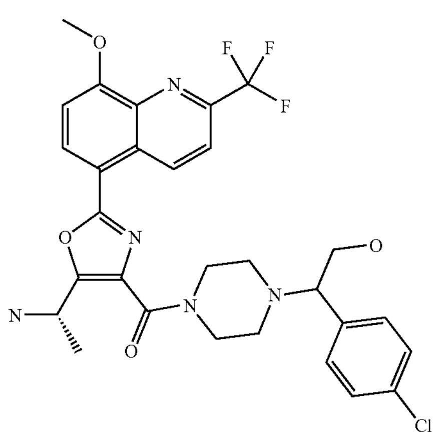 | 604 |
| 26-165 | 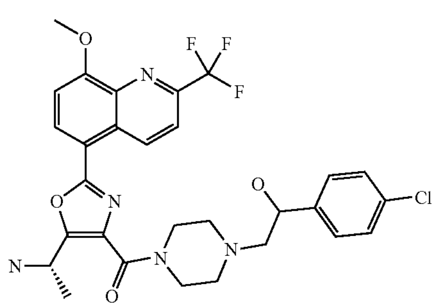 | 604 |

-continued

| Cpd. No. | Structure | MS (M + 1) |
|---|---|---|
| 26-166 | 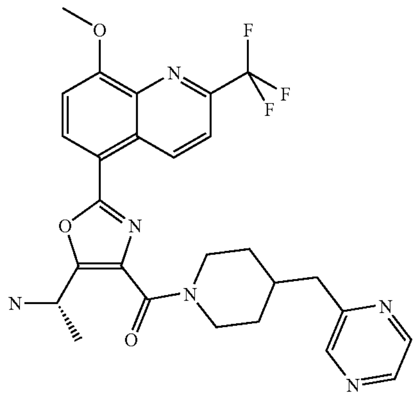 | 541 |
| 26-167 | 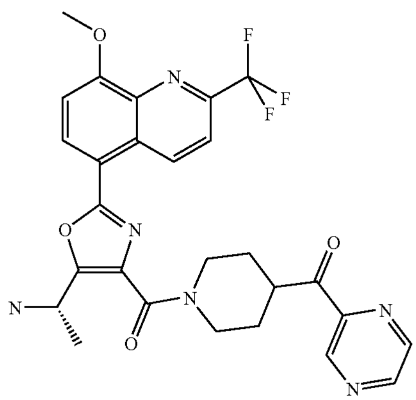 | 555 |
| 26-168 | 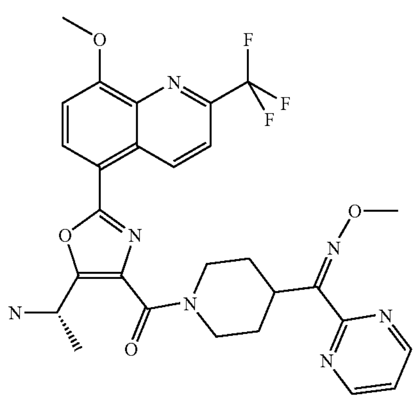 | 584 |

-continued
| Cpd. No. | Structure | MS (M + 1) |
|---|---|---|
| 26-169 | 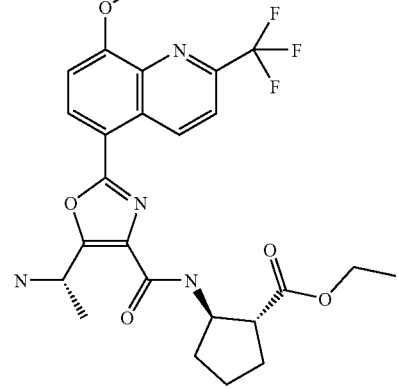 | 521 |
| 26-170 | 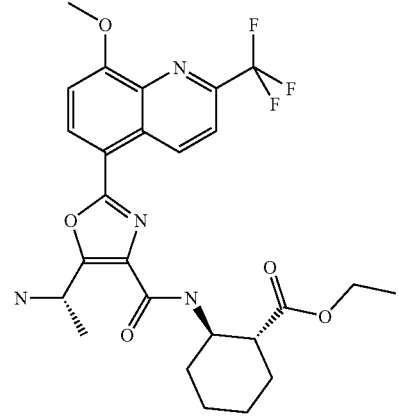 | 535 |
| 26-171 | 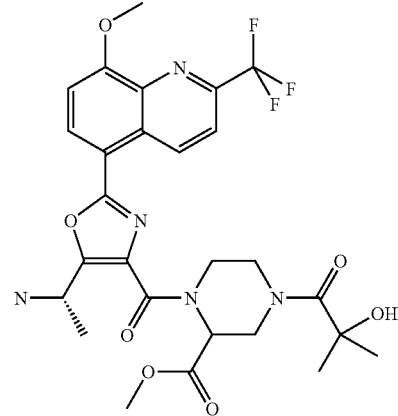 | 594 |

| Cpd. No. | Structure | MS (M + 1) |
|---|---|---|
| 26-172 | 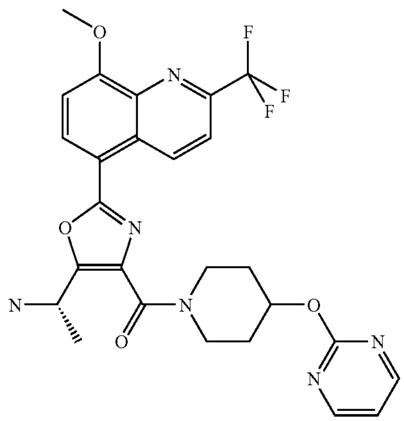 | 543 |
| 26-173 | 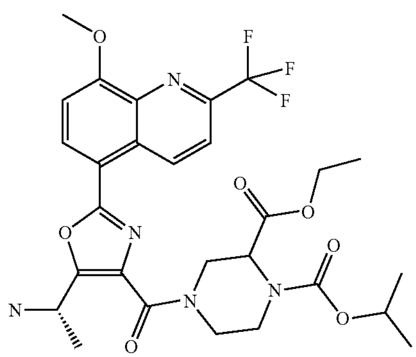 | 608 |
| 26-174 | 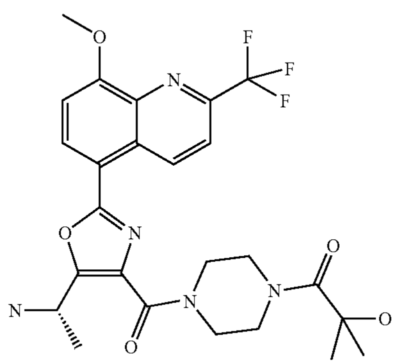 | 536 |
| 26-175 | 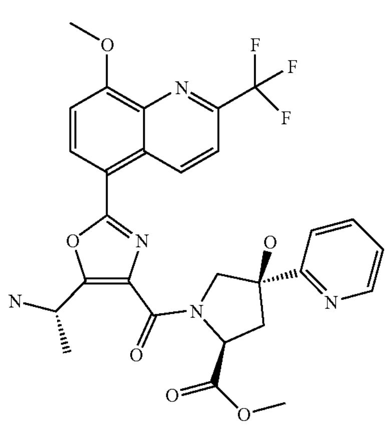 | 586 |

| Cpd. No. | Structure | MS (M + 1) |
|---|---|---|
| 26-176 | 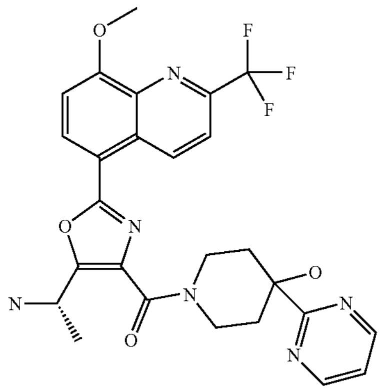 | 543 |
| 26-177 | 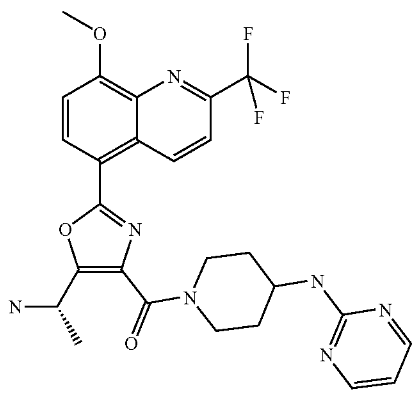 | 542 |
| 26-178 | 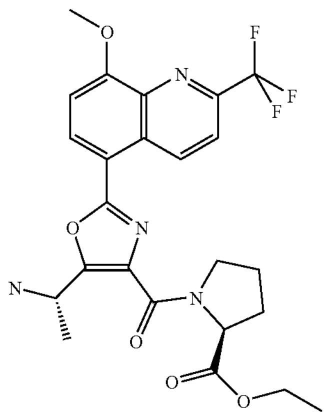 | 507 |

| Cpd. No. | Structure | MS (M + 1) |
|---|---|---|
| 26-179 | 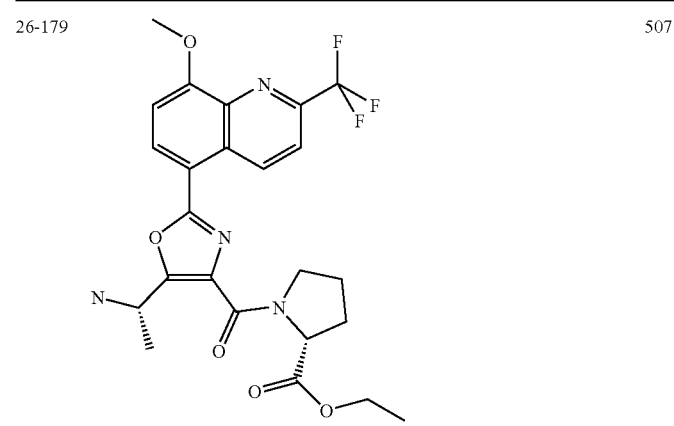 | 507 |
| 26-180 | 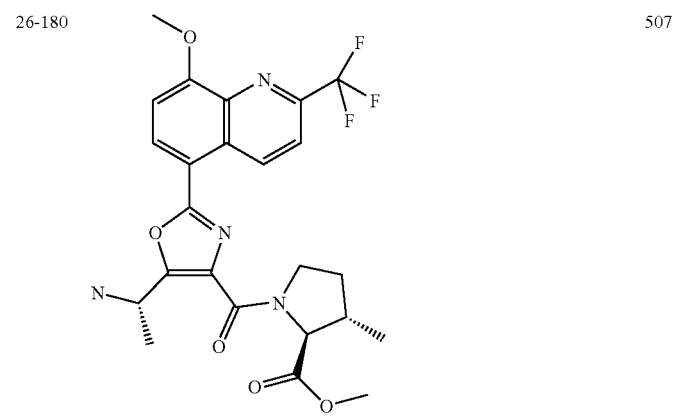 | 507 |
| 26-181 | 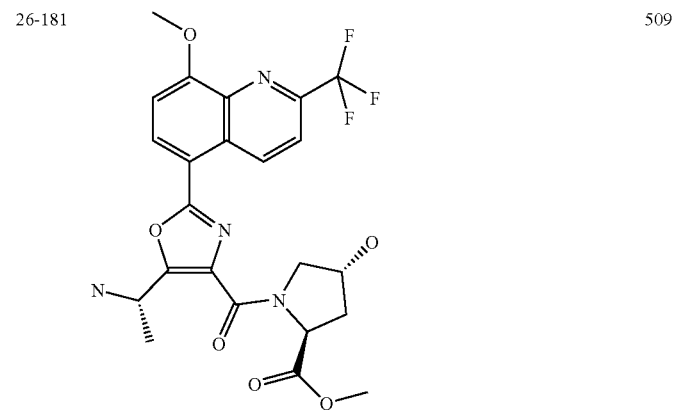 | 509 |

| Cpd. No. | Structure | MS (M + 1) |
|---|---|---|
| 26-182 | 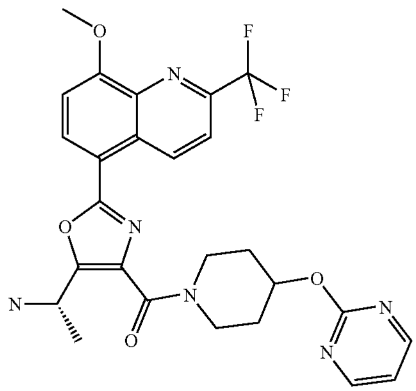 | 543 |
| 26-183 | 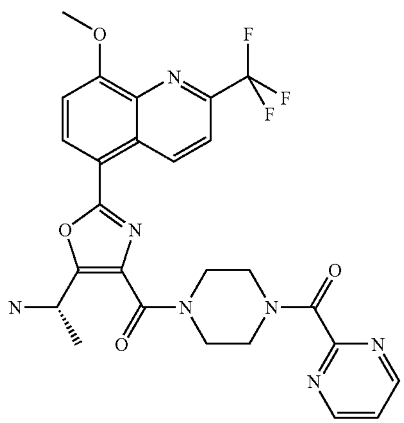 | 556 |
| 26-184 | 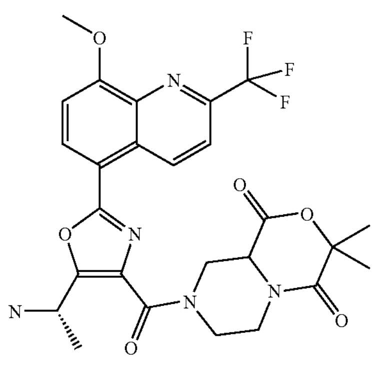 | 562 |
| 26-185 | 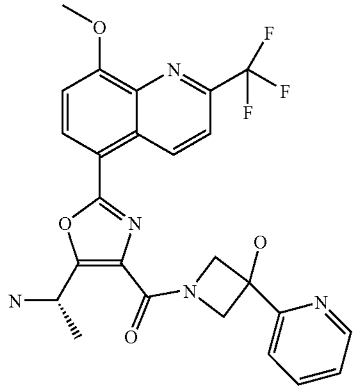 | 514 |

| Cpd. No. | Structure | MS (M + 1) |
|---|---|---|
| 26-186 | 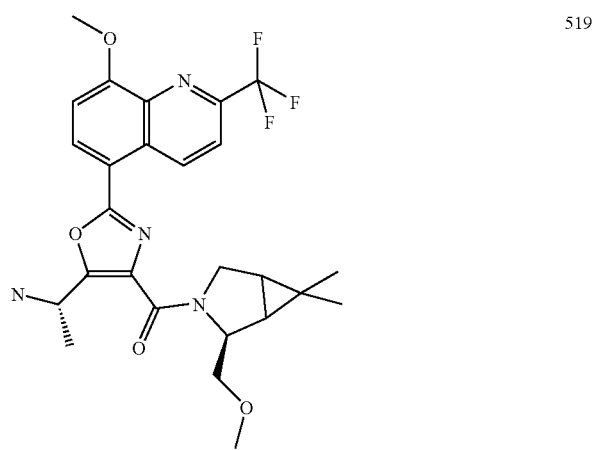 | 589 |
| 26-187 | 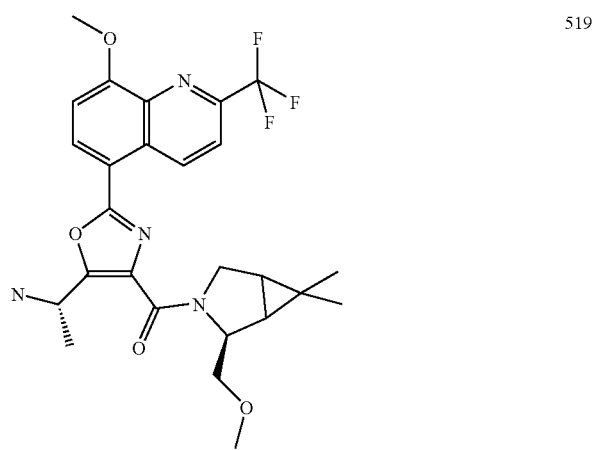 | 519 |
| 26-188 | 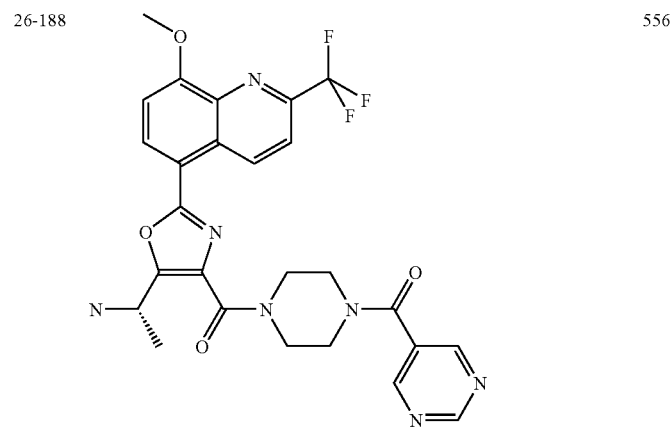 | 556 |

-continued
| Cpd. No. | Structure | MS (M + 1) |
|---|---|---|
| 26-189 | 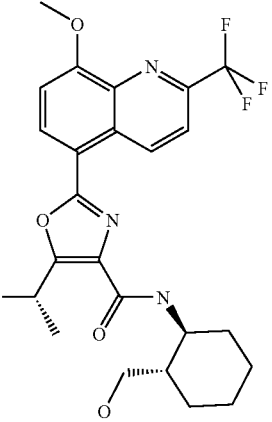 | 493 |
| 26-190 | 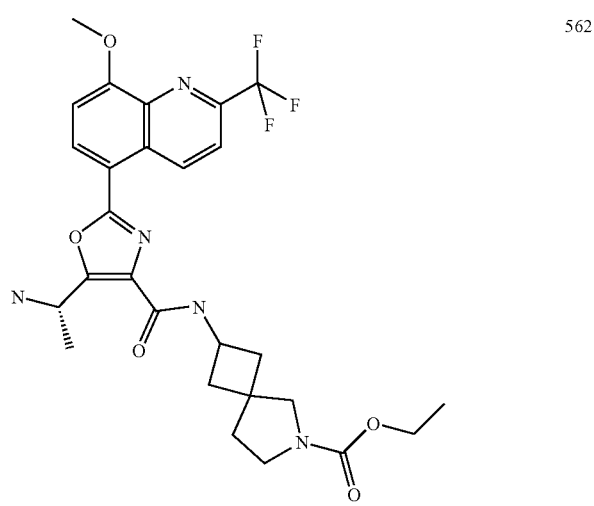 | 562 |
| 26-191 | 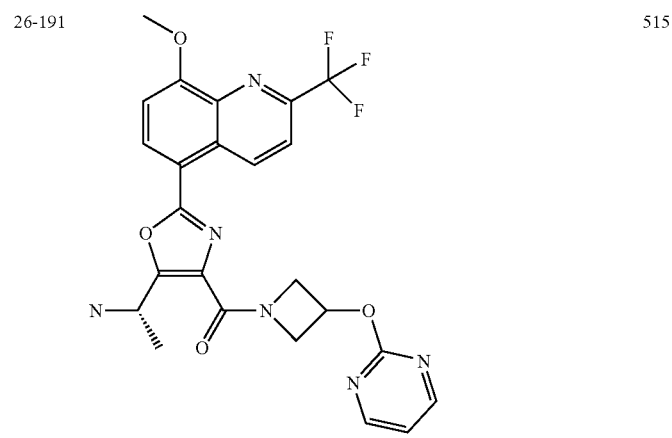 | 515 |

| Cpd. No. | Structure | MS (M + 1) |
|---|---|---|
| 26-192 | 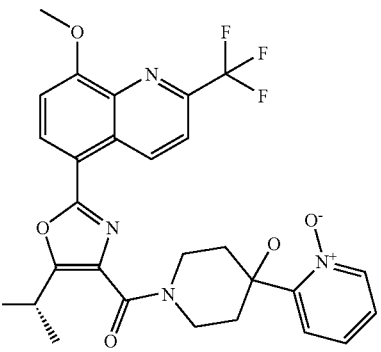 | 558 |
| 26-193 | 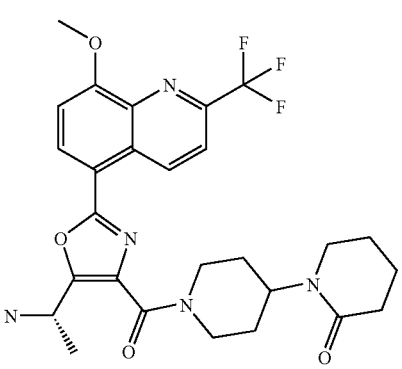 | 546 |
| 26-194 | 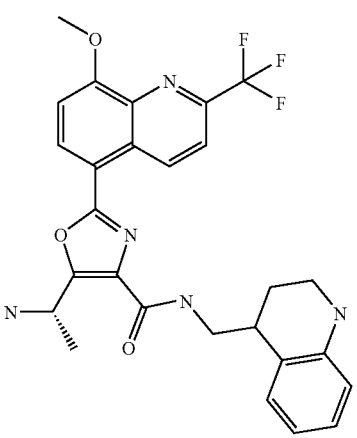 | 526 |
| 26-195 | 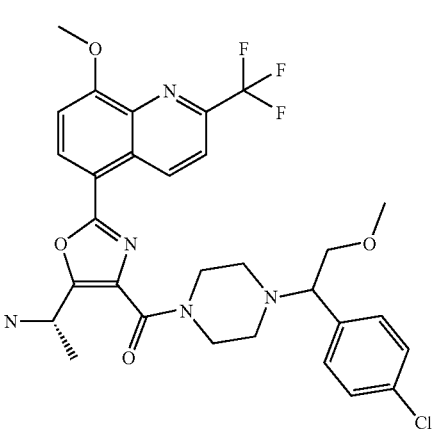 | 618 |

| Cpd. No. | Structure | MS (M + 1) |
|---|---|---|
| 26-196 | 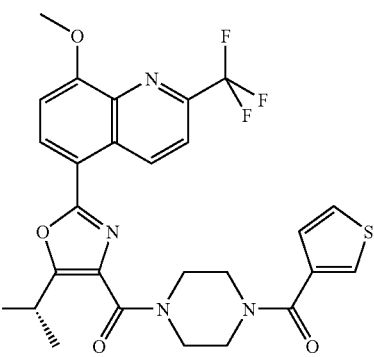 | 560 |
| 26-197 | 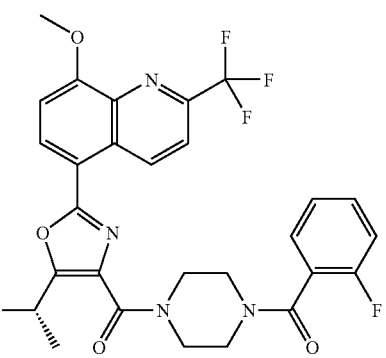 | 572 |
| 26-198 | 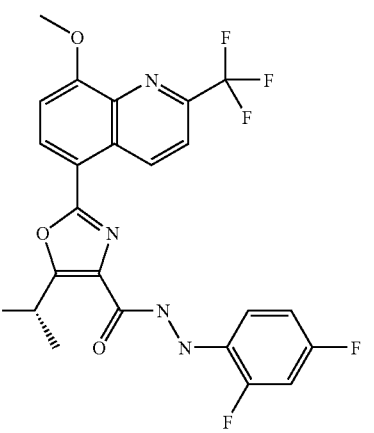 | 508 |
| 26-199 | 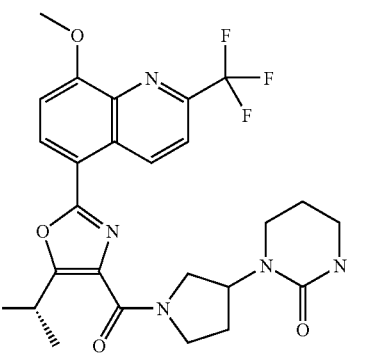 | 533 |

| Cpd. No. | Structure | MS (M + 1) |
|---|---|---|
| 26-200 | 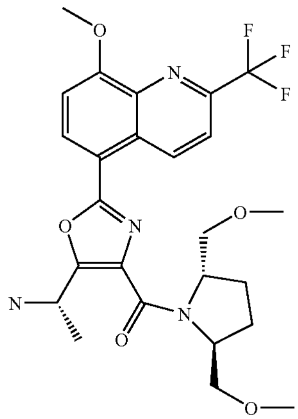 | 523 |
| 26-201 | 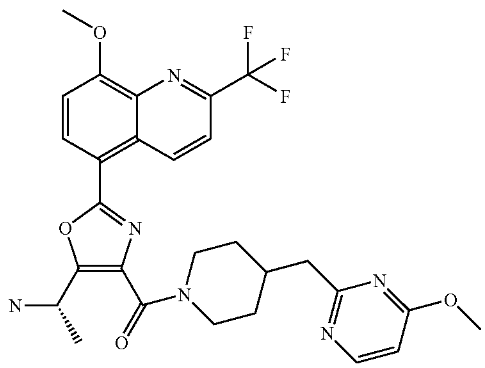 | 571 |
| 26-202 | 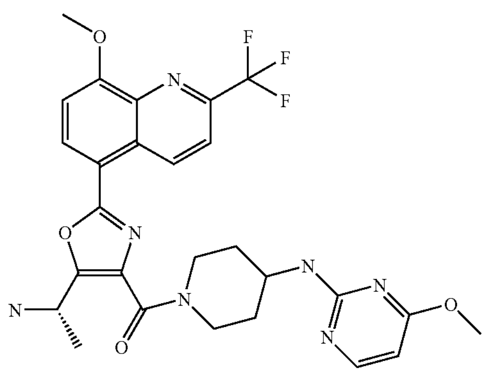 | 572 |
| 26-203 | 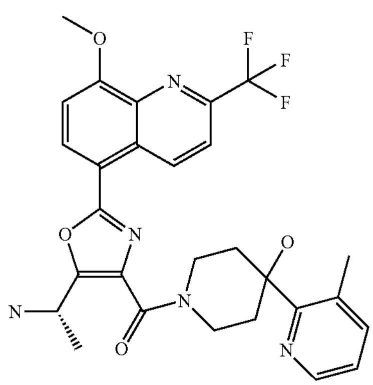 | 556 |

-continued

| Cpd. No. | Structure | MS (M + 1) |
|---|---|---|
| 26-204 | 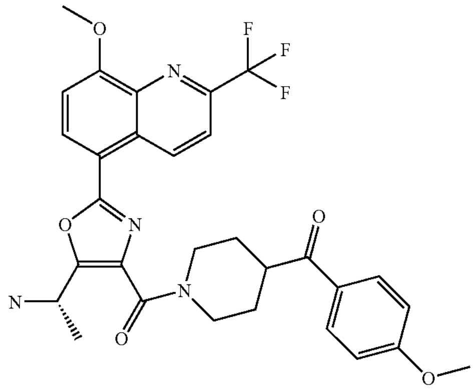 | 583 |
| 26-205 | 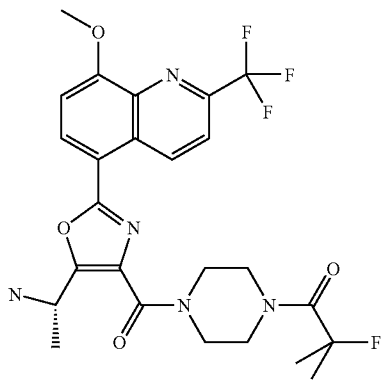 | 538 |
| 26-206 | 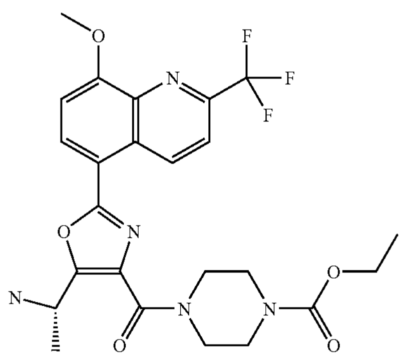 | 522 |
| 26-207 | 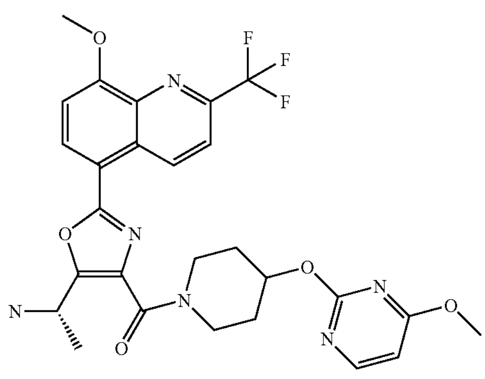 | 573 |

| Cpd. No. | Structure | MS (M + 1) |
|---|---|---|
| 26-208 | 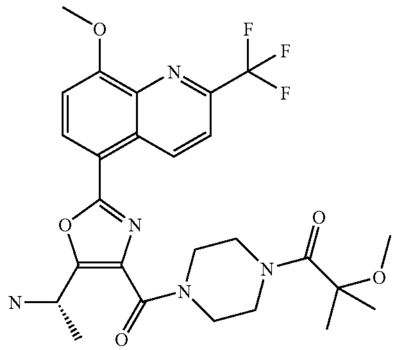 | 550 |
| 26-209 | 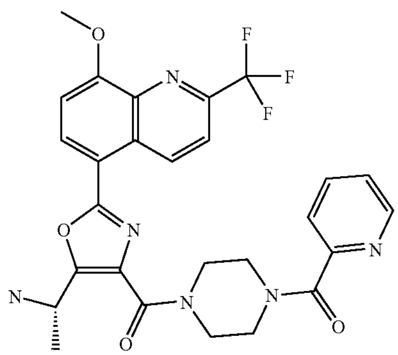 | 555 |
| 26-210 | 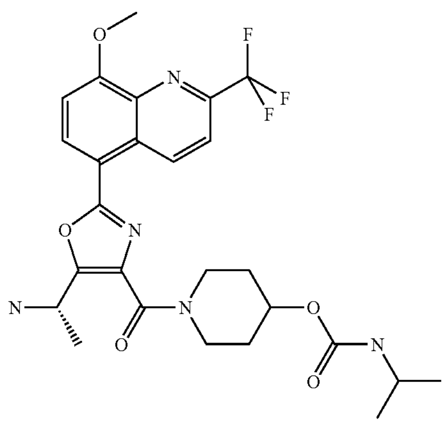 | 550 |
| 26-211 | 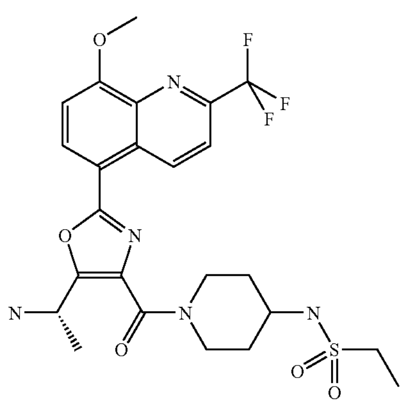 | 556 |

-continued

| Cpd. No. | Structure | MS (M + 1) |
|---|---|---|
| 26-212 | 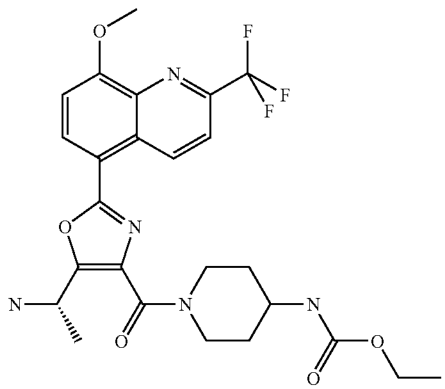 | 536 |
| 26-213 | 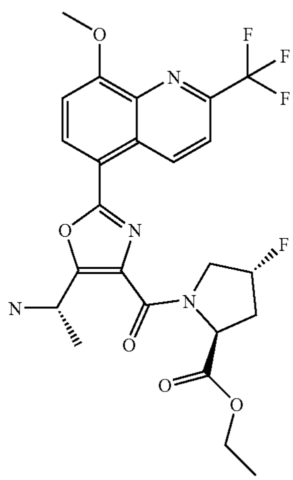 | 525 |
| 26-214 | 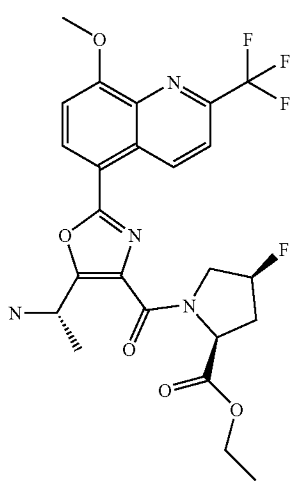 | 525 |

-continued
| Cpd. No. | Structure | MS (M + 1) |
|---|---|---|
| 26-215 | 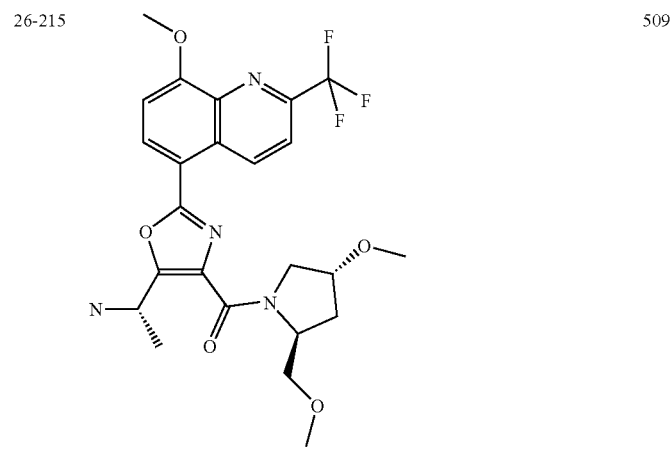 | 509 |
| 26-216 | 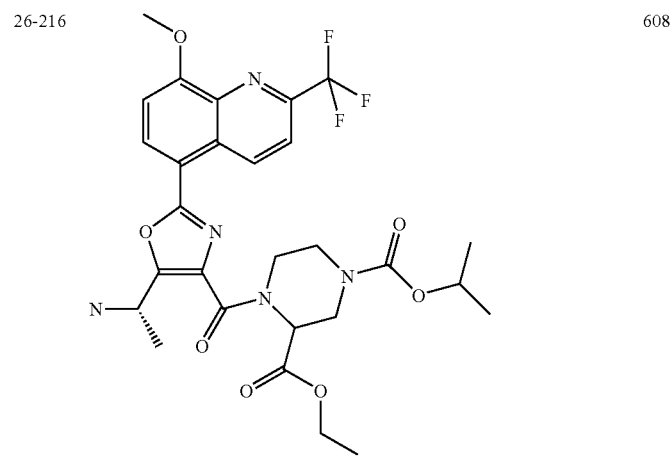 | 608 |
| 26-217 | 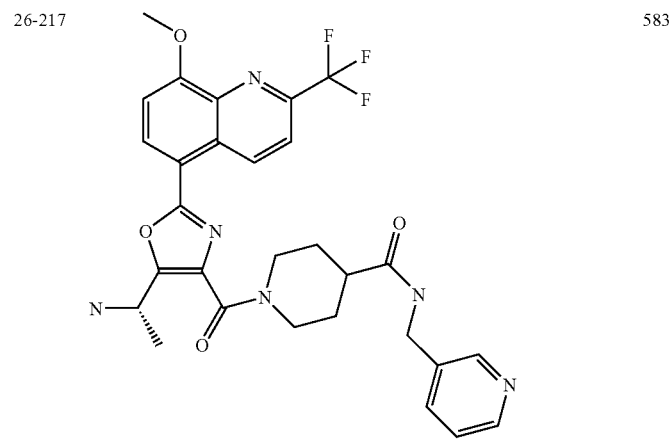 | 583 |

-continued

| Cpd. No. | Structure | MS (M + 1) |
|---|---|---|
| 26-218 | 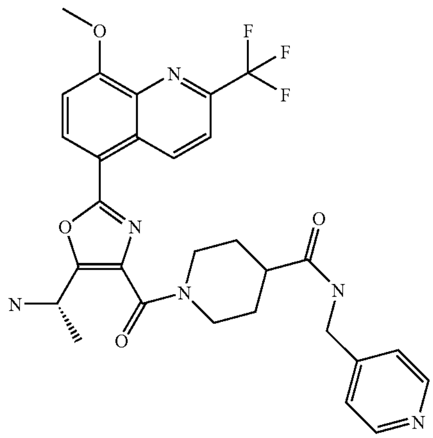 | 583 |
| 26-219 | 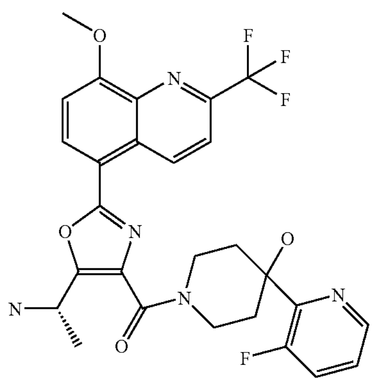 | 560 |
| 26-220 | 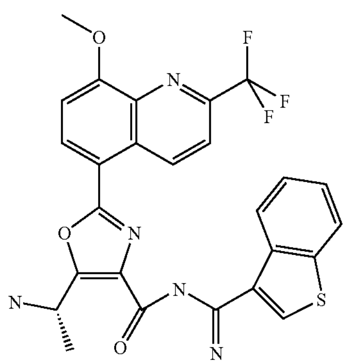 | 540 |
| 26-221 | 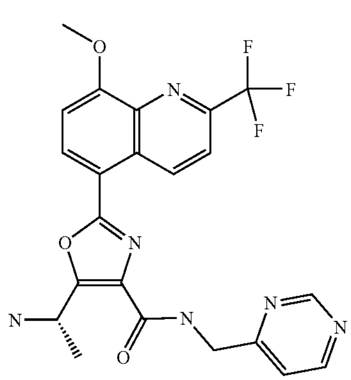 | 473 |

-continued
| Cpd. No. | Structure | MS (M + 1) |
|---|---|---|
| 26-222 | 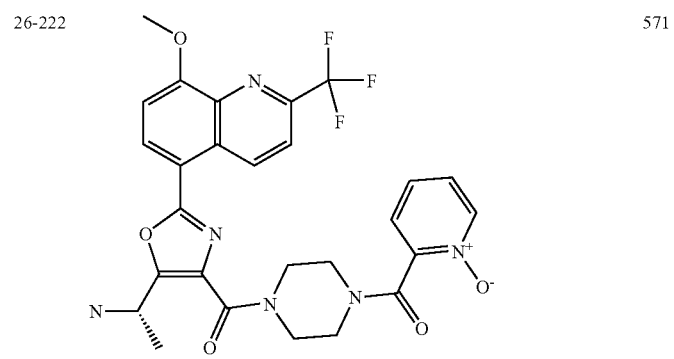 | 571 |
| 26-223 | 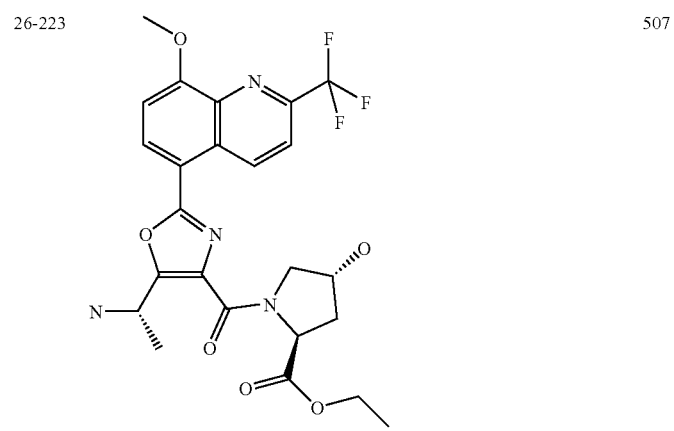 | 507 |
| 26-224 | 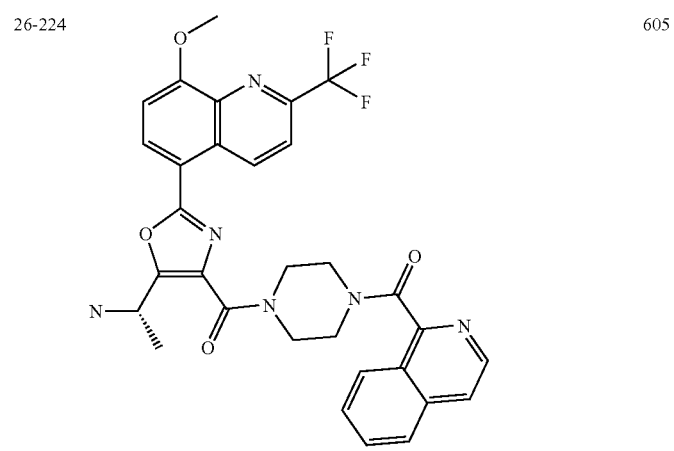 | 605 |

-continued

| Cpd. No. | Structure | MS (M + 1) |
|---|---|---|
| 26-226 | 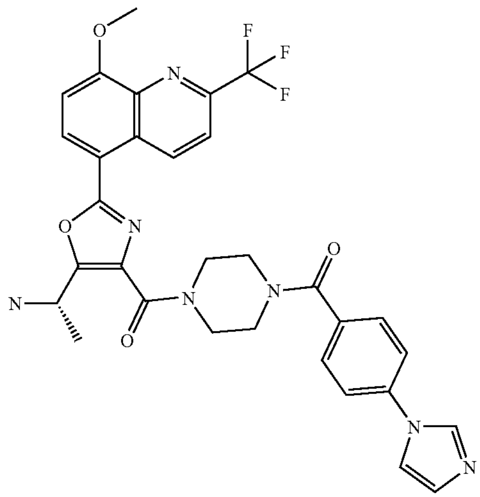 | 620 |
| 26-227 | 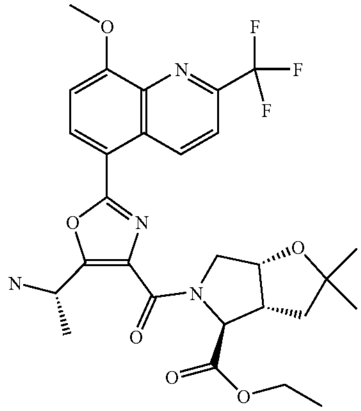 | 577 |
| 26-228 | 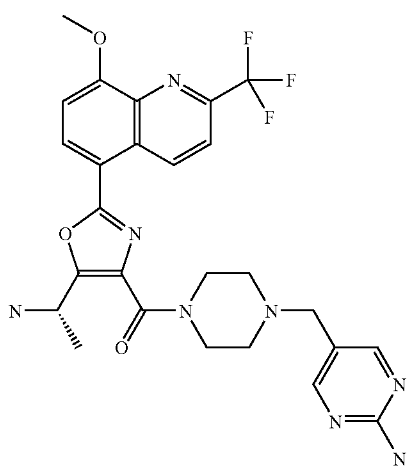 | 557 |

-continued

| Cpd. No. | Structure | MS (M + 1) |
|---|---|---|
| 26-229 | 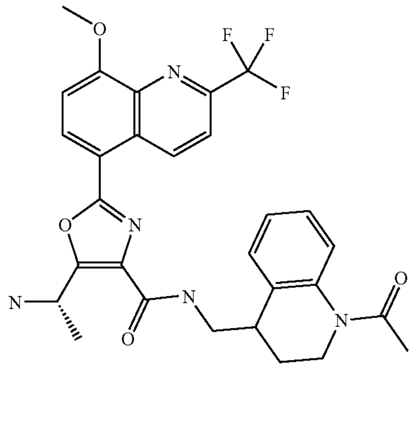 | 568 |
| 26-230 | 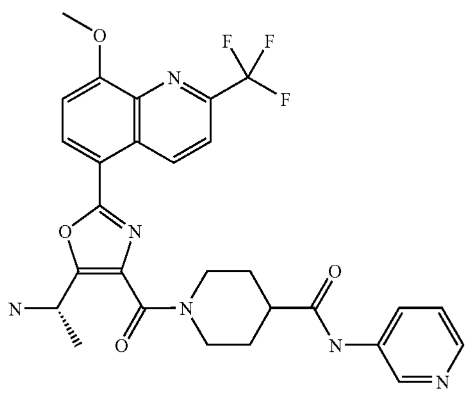 | 569 |
| 26-231 | 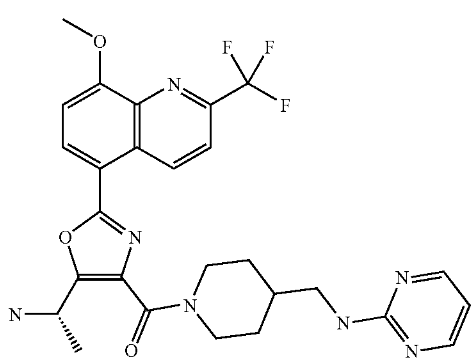 | 556 |

| Cpd. No. | Structure | MS (M + 1) |
|---|---|---|
| 26-232 | 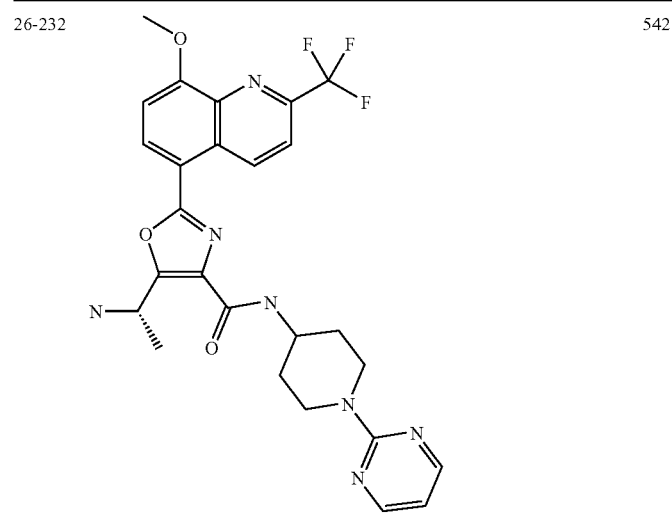 | 542 |
| 26-234 | 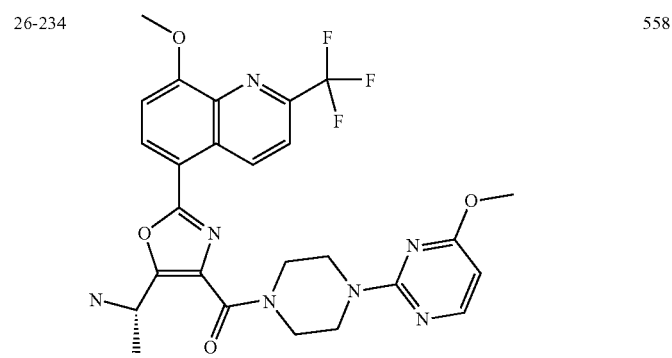 | 558 |
| 26-235 | 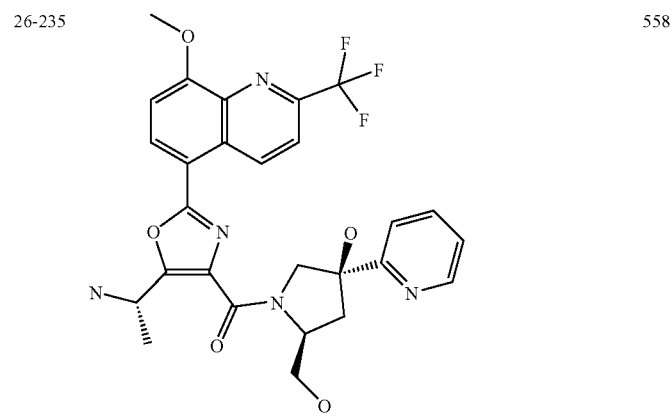 | 558 |

-continued
| Cpd. No. | Structure | MS (M + 1) |
|---|---|---|
| 26-236 | 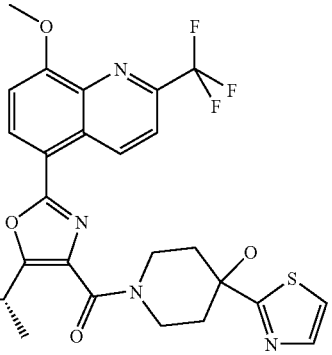 | 548 |
| 26-237 | 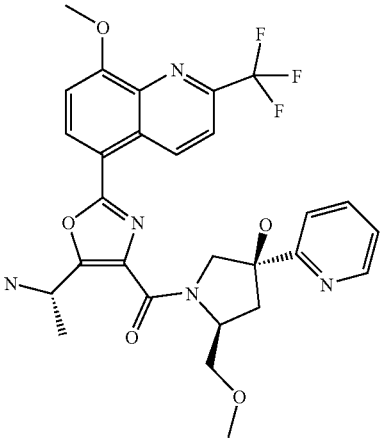 | 572 |
| 26-238 | 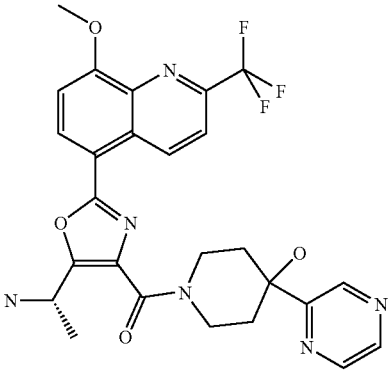 | 543 |

| Cpd. No. | Structure | MS (M + 1) |
|---|---|---|
| 26-239 | 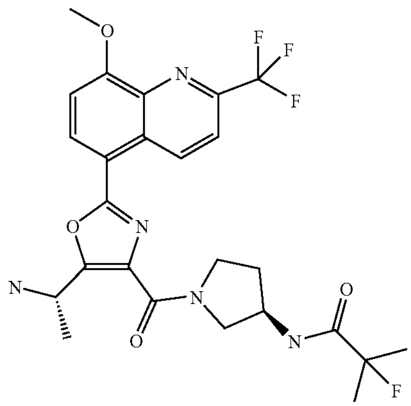 | 538 |
| 26-240 | 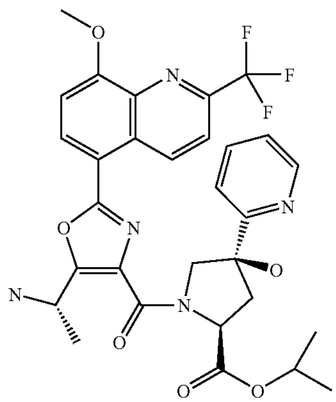 | 614 |
| 26-241 | 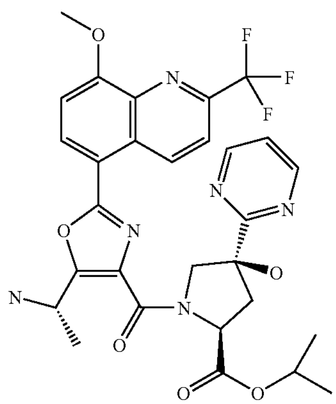 | 615 |
| 26-242 | 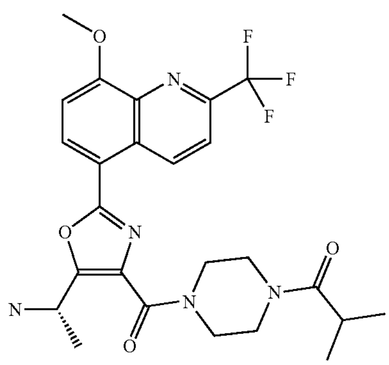 | 520 |

-continued

| Cpd. No. | Structure | MS (M + 1) |
|---|---|---|
| 26-243 | 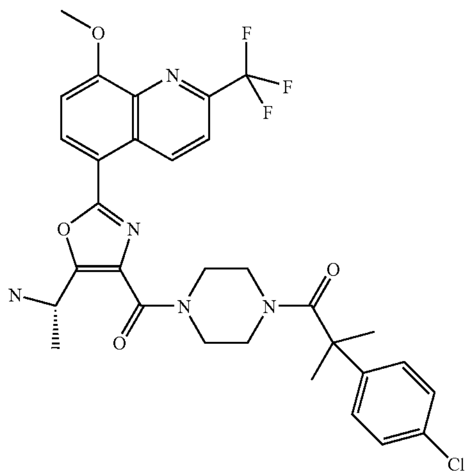 | 630 |
| 26-244 | 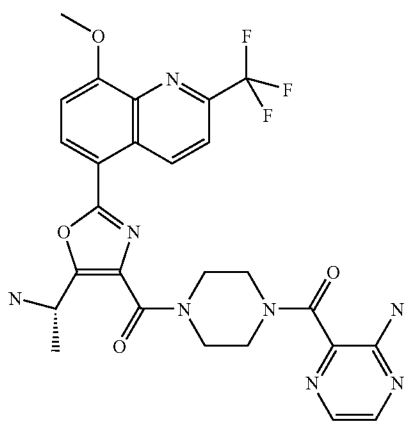 | 571 |
| 26-245 | 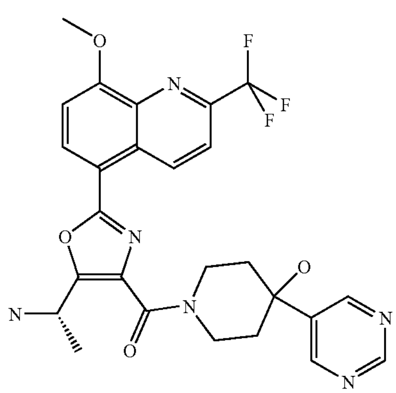 | 543 |

| Cpd. No. | Structure | MS (M + 1) |
|---|---|---|
| 26-246 | 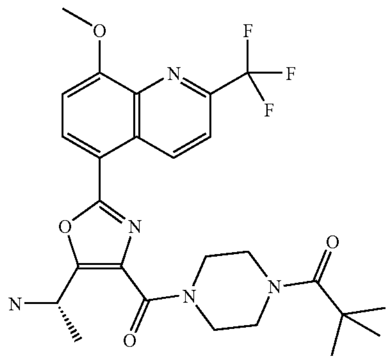 | 534 |
| 26-247 | 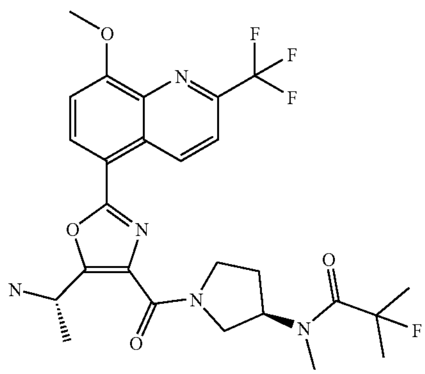 | 552 |
| 26-248 | 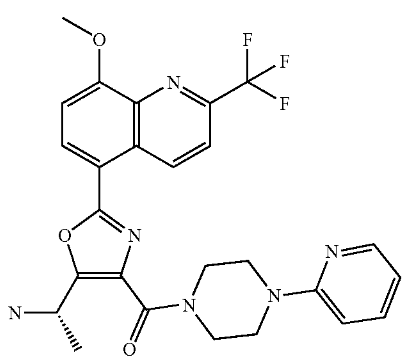 | 527 |
| 26-249 | 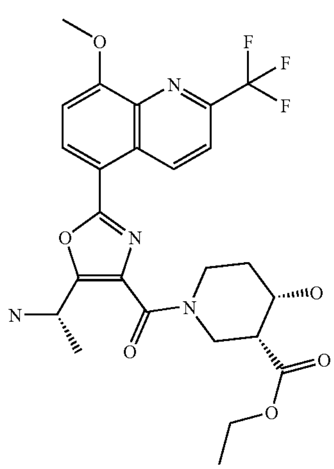 | 537 |

-continued

| Cpd. No. | Structure | MS (M + 1) |
|---|---|---|
| 26-250 | 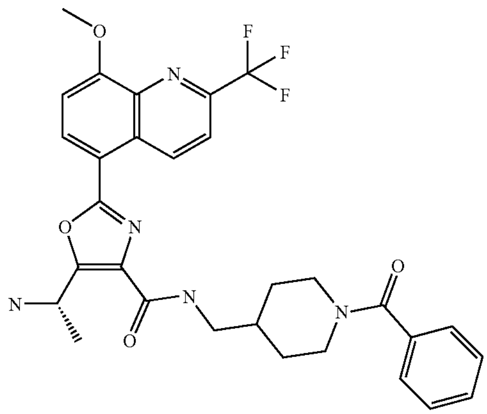 | 582 |
| 26-251 | 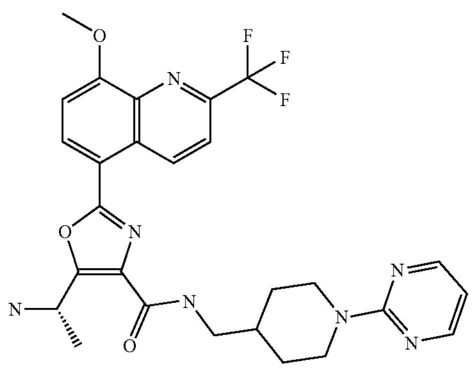 | 556 |
| 26-252 | 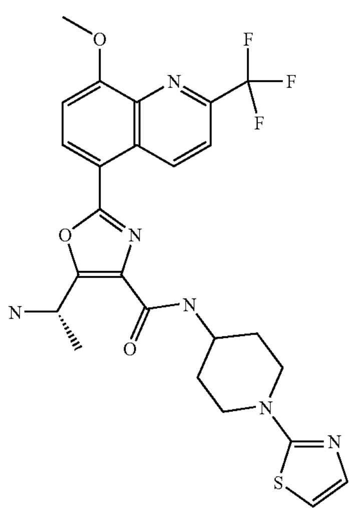 | 547 |

-continued
| Cpd. No. | Structure | MS (M + 1) |
|---|---|---|
| 26-253 | 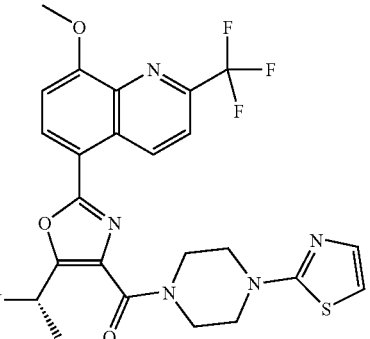 | 533 |
| 26-254 | 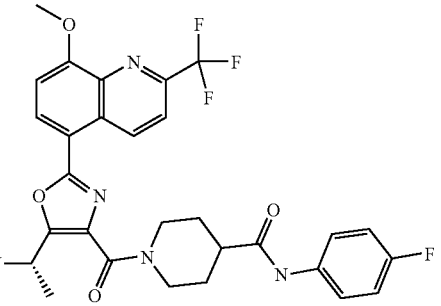 | 586 |
| 26-255 | 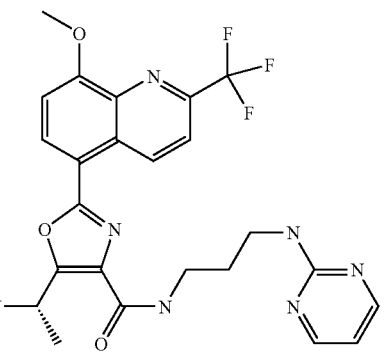 | 516 |
| 26-256 | 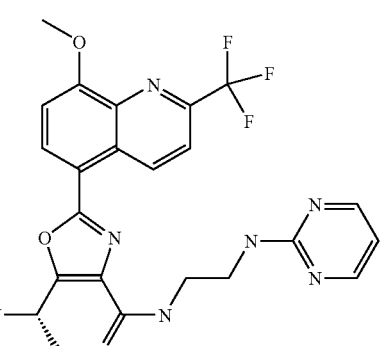 | 502 |

-continued

| Cpd. No. | Structure | MS (M + 1) |
|---|---|---|
| 26-257 | 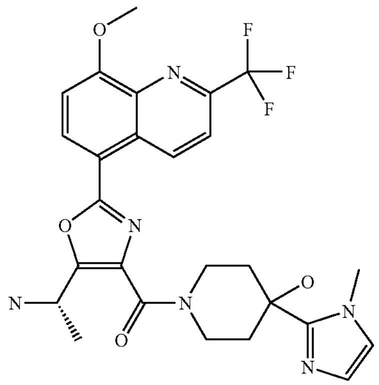 | 545 |
| 26-258 | 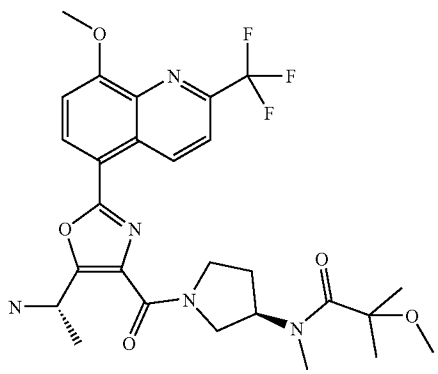 | 564 |
| 26-259 | 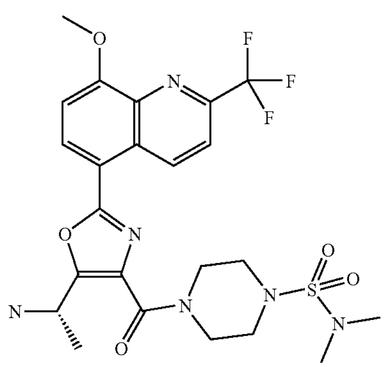 | 557 |

| Cpd. No. | Structure | MS (M + 1) |
|---|---|---|
| 26-260 | 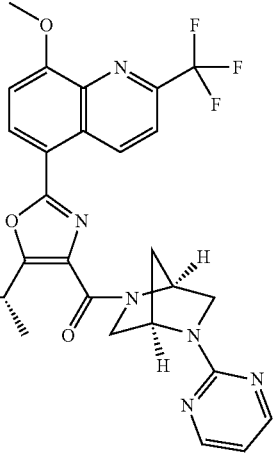 | 540 |
| 26-261 | 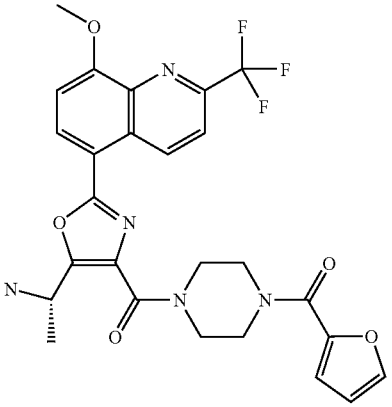 | 544 |
| 26-262 | 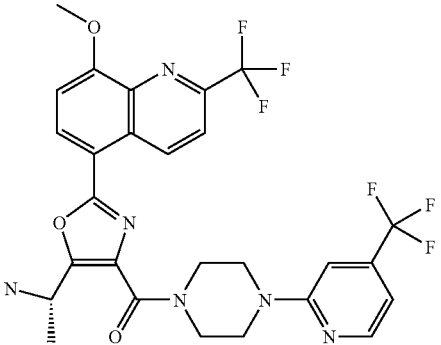 | 595 |
| 26-263 | 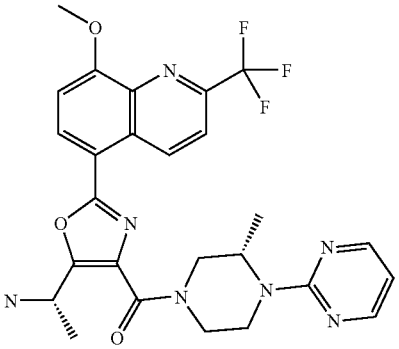 | 542 |

-continued
| Cpd. No. | Structure | MS (M + 1) |
|---|---|---|
| 26-264 | 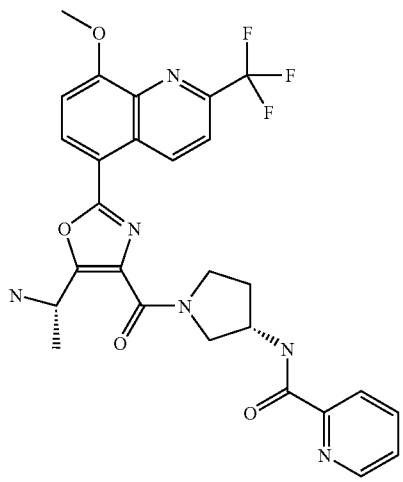 | 555 |
| 26-265 | 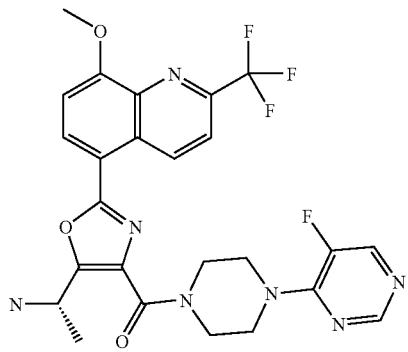 | 546 |
| 26-266 | 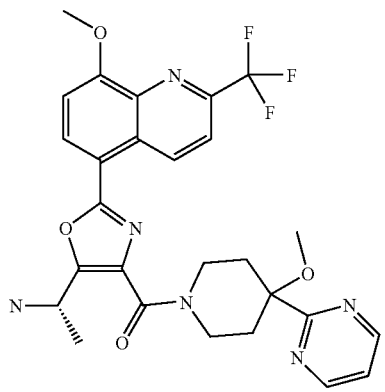 | 557 |

-continued

| Cpd. No. | Structure | MS (M + 1) |
|---|---|---|
| 26-267 | 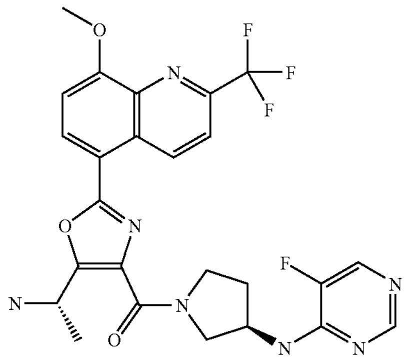 | 546 |
| 26-268 | 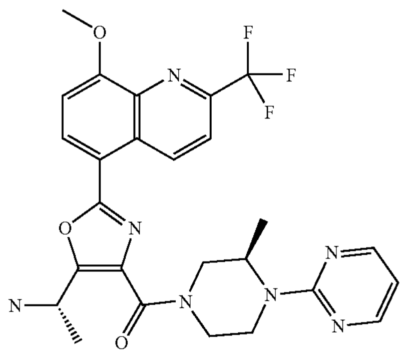 | 542 |
| 26-269 | 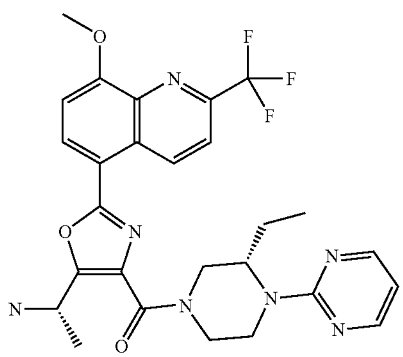 | 556 |
| 26-270 | 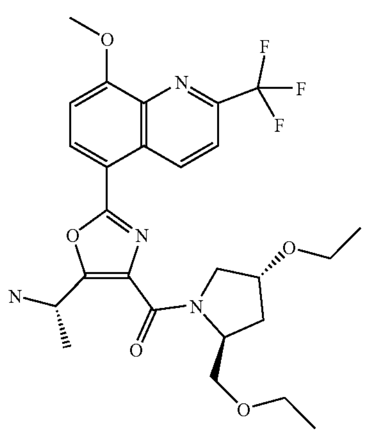 | 537 |

| Cpd. No. | Structure | MS (M + 1) |
|---|---|---|
| 26-271 | 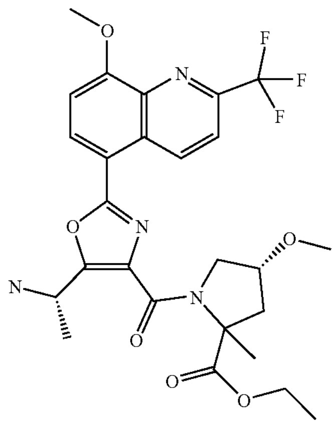 | 551 |
| 26-272 | 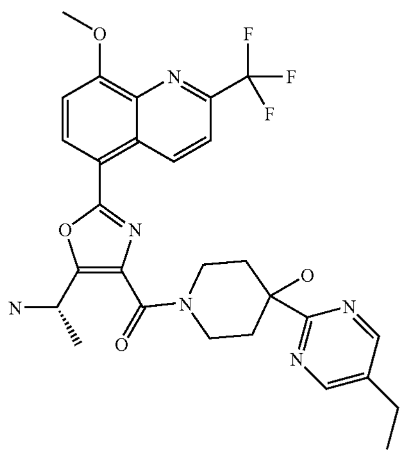 | 571 |
| 26-273 | 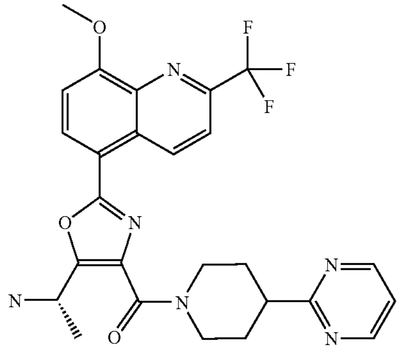 | 527 |

-continued
| Cpd. No. | Structure | MS (M + 1) |
|---|---|---|
| 26-274 | 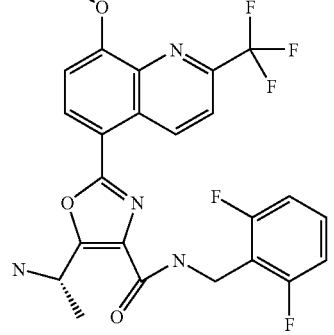 | 439 |
| 26-275 | 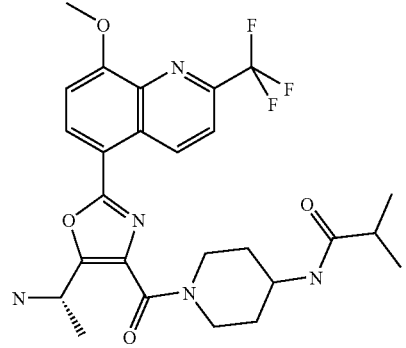 | 552 |
| 26-276 | 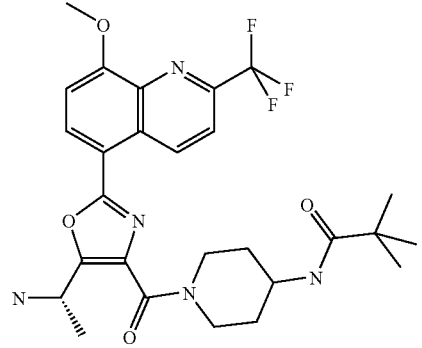 | 548 |
| 26-277 | 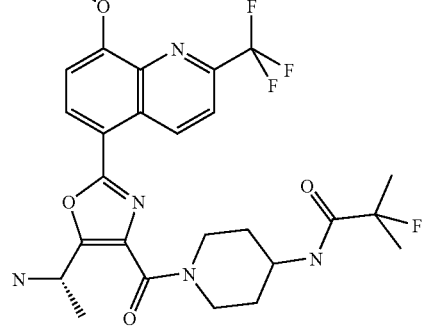 | 552 |

-continued

| Cpd. No. | Structure | MS (M + 1) |
|---|---|---|
| 26-278 | 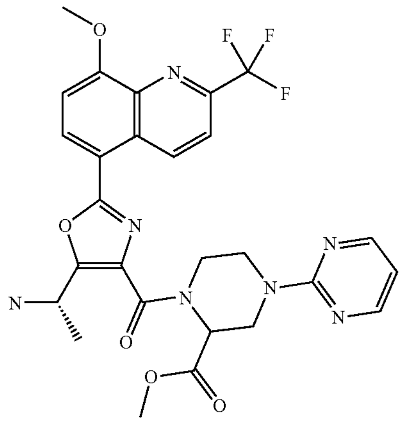 | 586 |
| 26-279 | 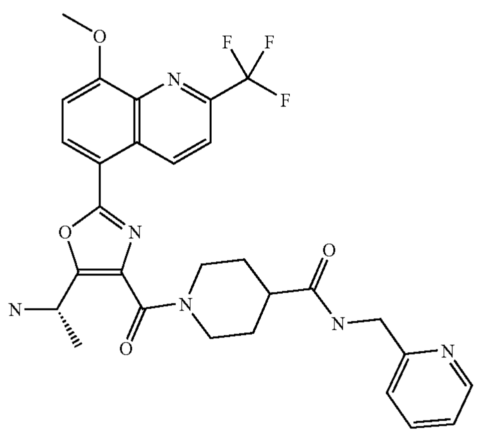 | 583 |
| 26-280 | 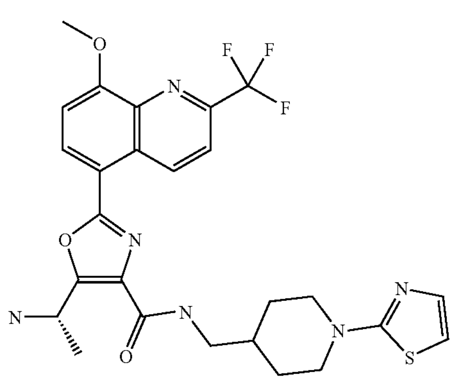 | 561 |

-continued

| Cpd. No. | Structure | MS (M + 1) |
|---|---|---|
| 26-281 | 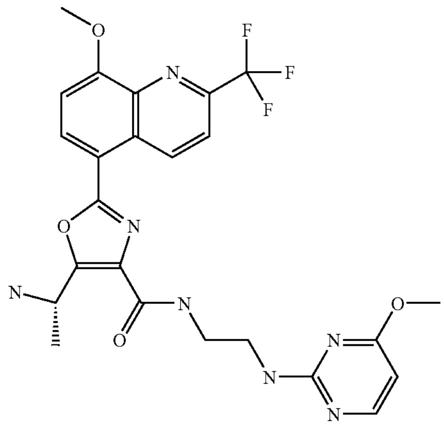 | 532 |
| 26-282 | 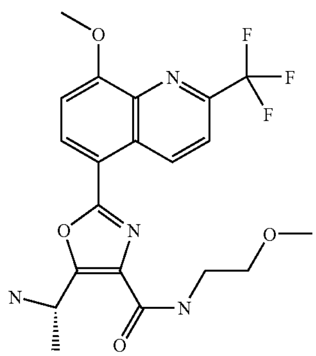 | 439 |
| 26-283 | 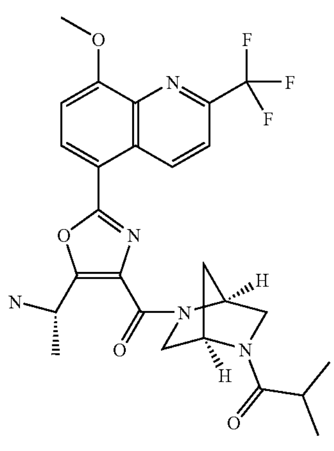 | 532 |

| Cpd. No. | Structure | MS (M + 1) |
|---|---|---|
| 26-264 | 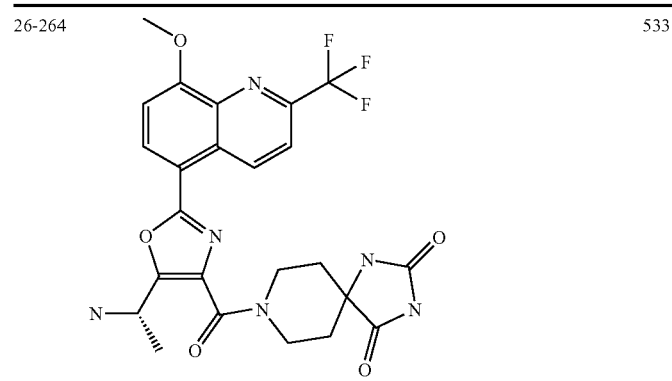 | 533 |
| 26-285 | 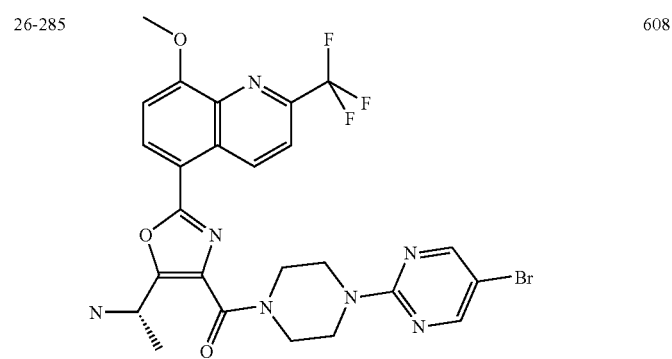 | 608 |
| 26-286 | 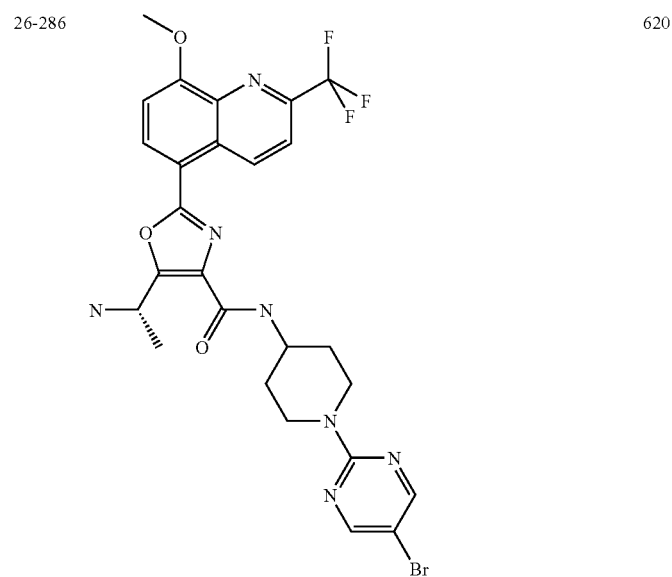 | 620 |

| Cpd. No. | Structure | MS (M + 1) |
|---|---|---|
| 26-287 | 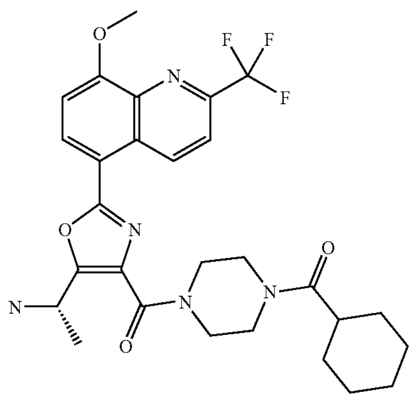 | 560 |
| 26-288 | 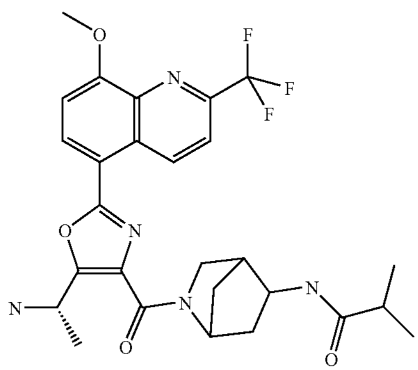 | 546 |
| 26-289 | 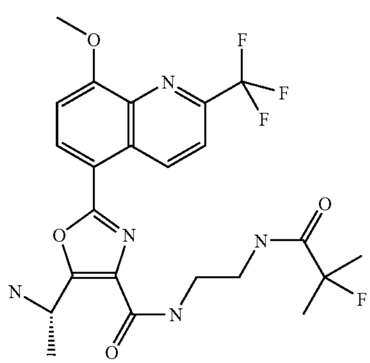 | 512 |
| 26-290 | 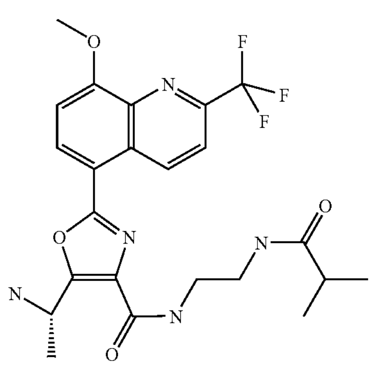 | 494 |

| Cpd. No. | Structure | MS (M + 1) |
|---|---|---|
| 26-291 | 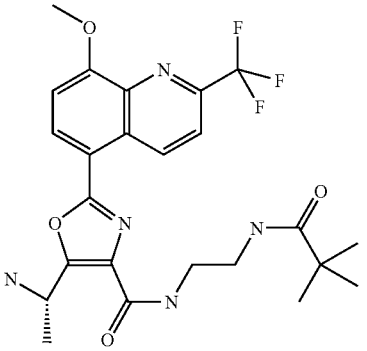 | 508 |
| 26-292 | 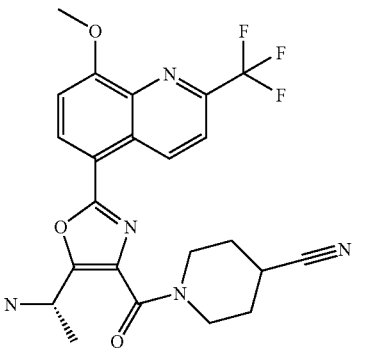 | 474 |
| 26-293 | 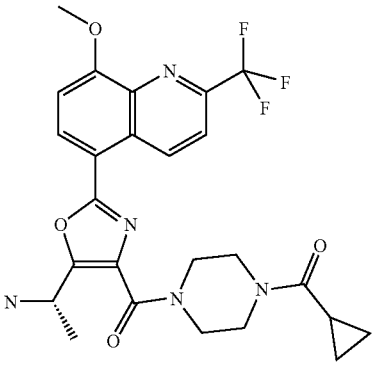 | 518 |
| 26-294 | 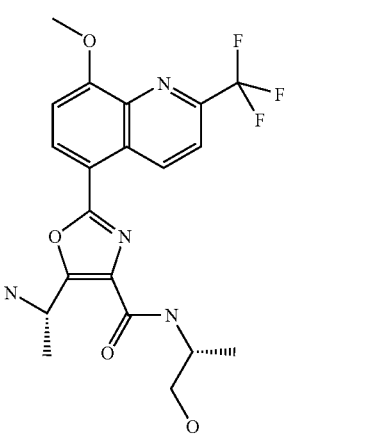 | 439 |

-continued

| Cpd. No. | Structure | MS (M + 1) |
|---|---|---|
| 26-295 | 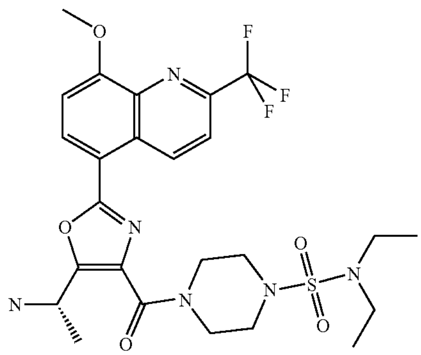 | 585 |
| 26-296 | 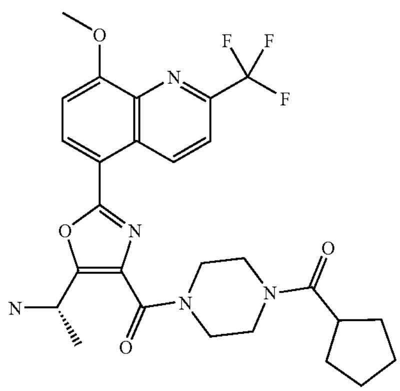 | 546 |
| 26-297 | 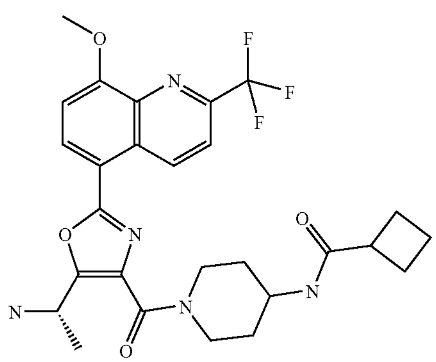 | 546 |
| 26-298 | 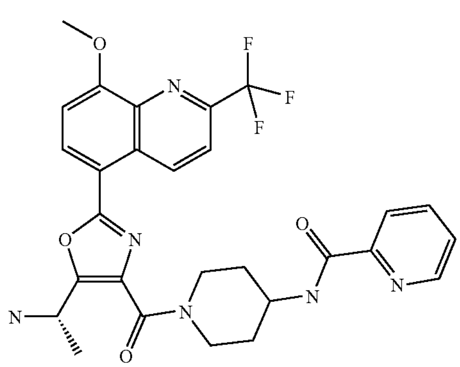 | 569 |

-continued

| Cpd. No. | Structure | MS (M + 1) |
|---|---|---|
| 26-299 | 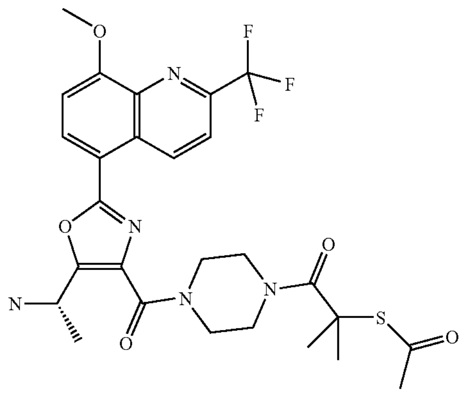 | 594 |
| 26-300 | 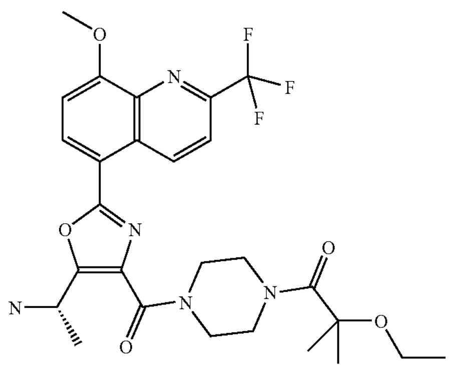 | 564 |
| 26-301 | 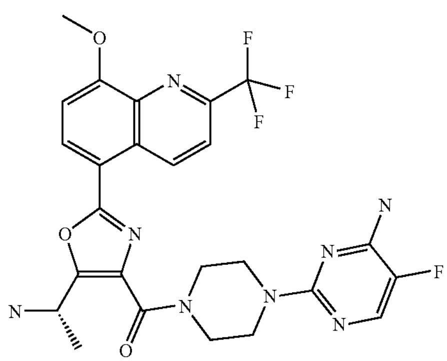 | 561 |
| 26-302 | 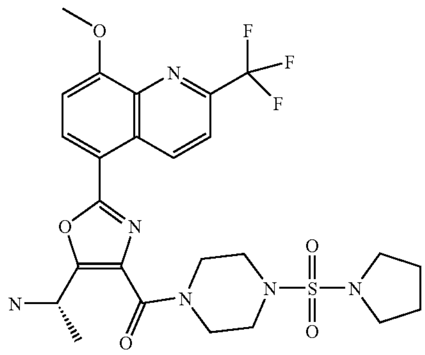 | 583 |

-continued

| Cpd. No. | Structure | MS (M + 1) |
|---|---|---|
| 26-303 | 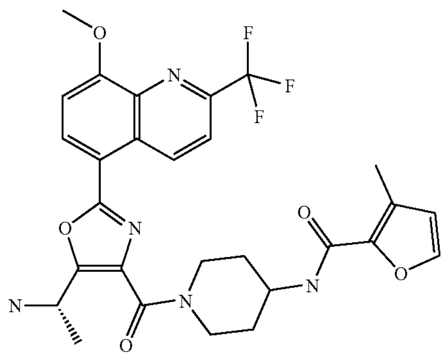 | 572 |
| 26-304 | 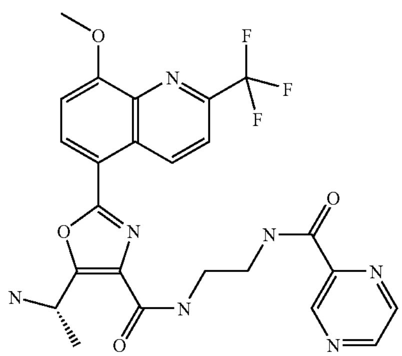 | 530 |
| 26-305 | 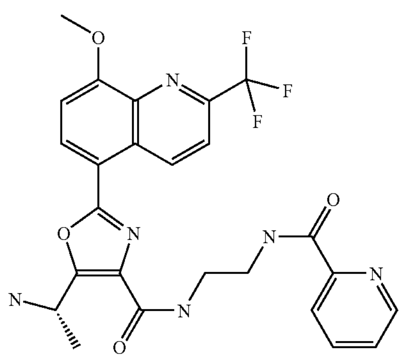 | 529 |
| 26-306 | 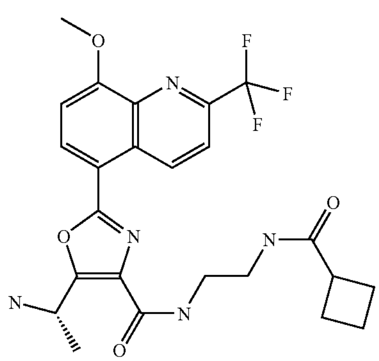 | 506 |

-continued

| Cpd. No. | Structure | MS (M + 1) |
|---|---|---|
| 26-307 | 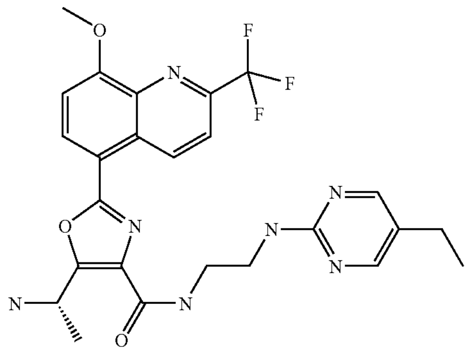 | 530 |
| 26-308 | 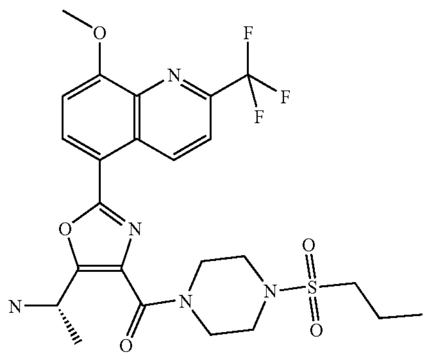 | 556 |
| 26-309 | 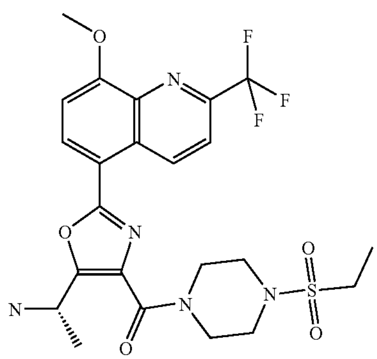 | 542 |
| 26-310 | 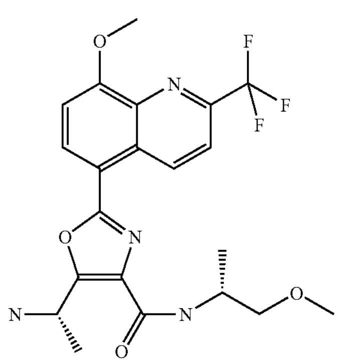 | 453 |

-continued

| Cpd. No. | Structure | MS (M + 1) |
|---|---|---|
| 26-311 | 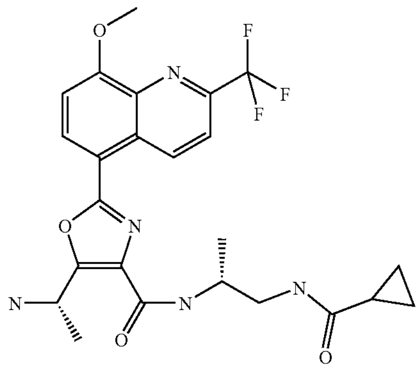 | 506 |
| 26-312 | 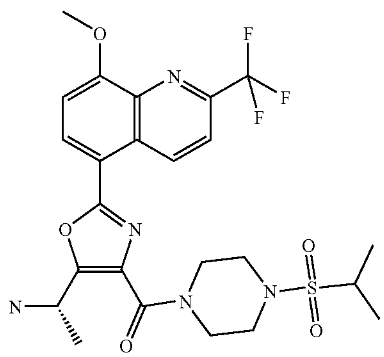 | 556 |
| 26-313 | 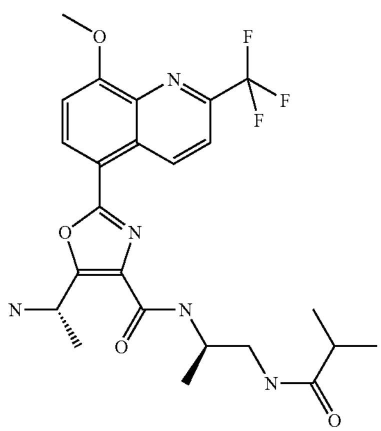 | 508 |
| 26-314 | 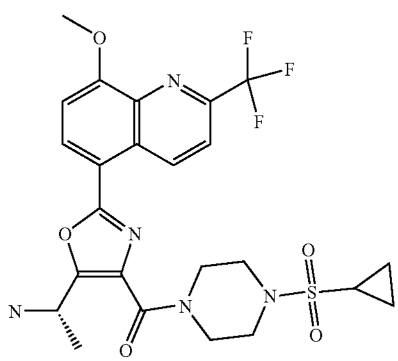 | 554 |

-continued

| Cpd. No. | Structure | MS (M + 1) |
|---|---|---|
| 26-315 | 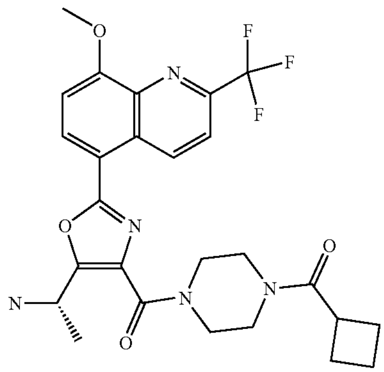 | 532 |
| 26-316 | 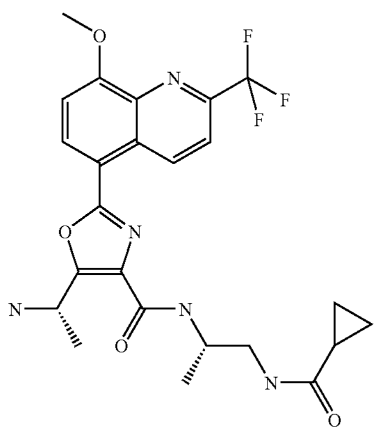 | 506 |
| 26-317 | 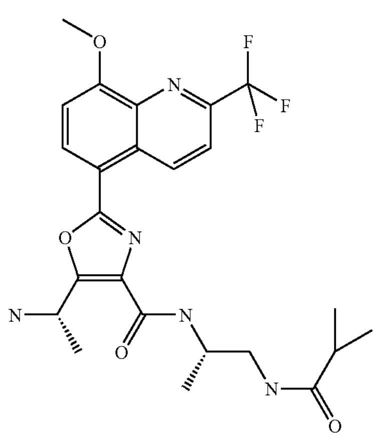 | 507 |

| Cpd. No. | Structure | MS (M + 1) |
|---|---|---|
| 26-318 | 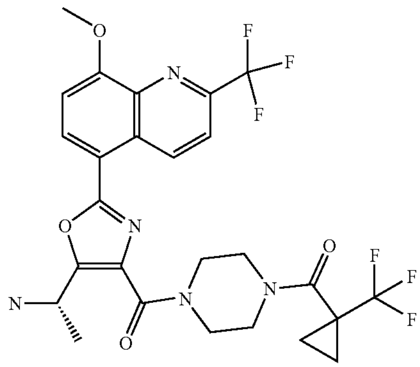 | 586 |
| 26-319 | 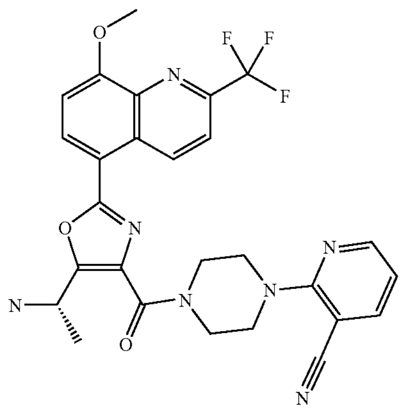 | 552 |
| 26-320 | 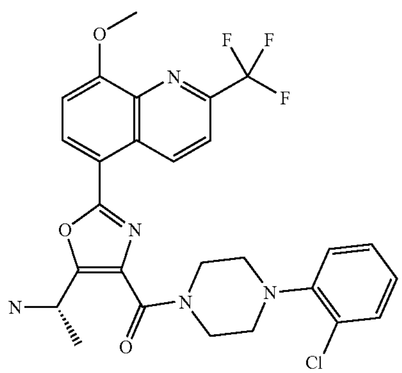 | 560 |
| 26-321 | 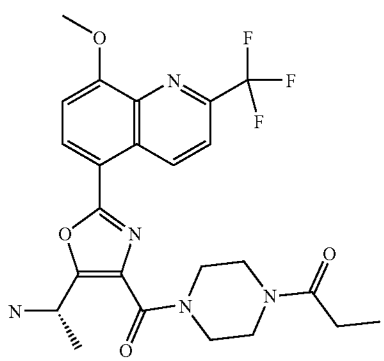 | 506 |

| Cpd. No. | Structure | MS (M + 1) |
|---|---|---|
| 26-322 | 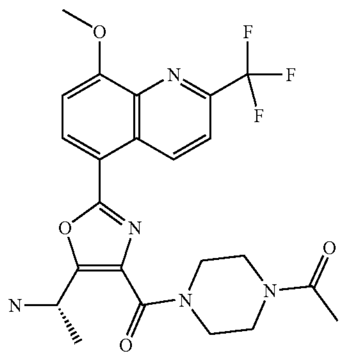 | 492 |
| 26-323 | 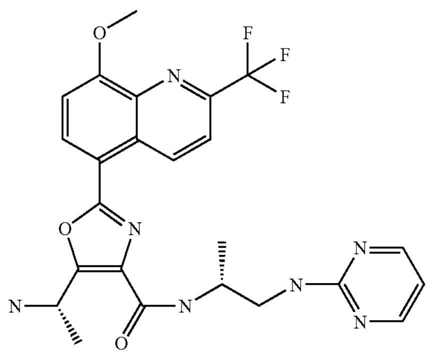 | 516 |
| 26-324 | 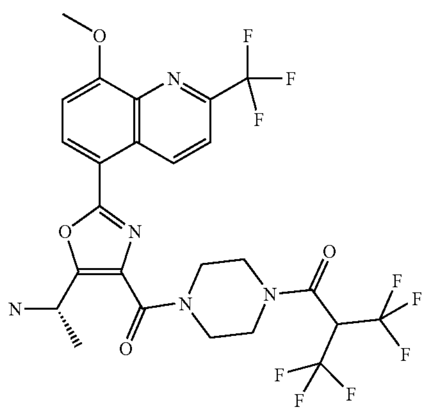 | 642 |
| 26-325 | 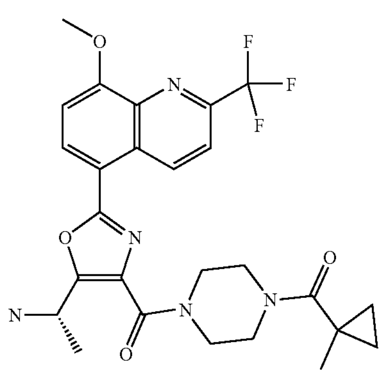 | 532 |

| Cpd. No. | Structure | MS (M + 1) |
|---|---|---|
| 26-326 | 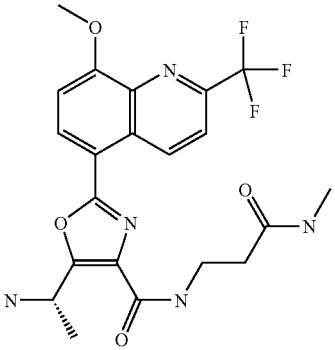 | 466 |
| 26-327 | 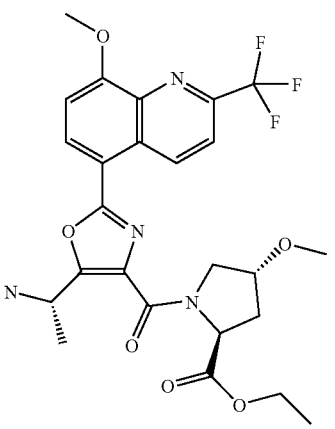 | 537 |
| 26-328 | 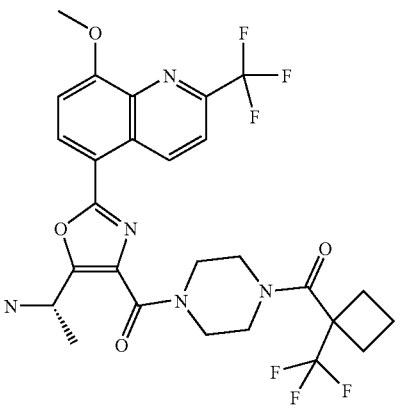 | 600 |
| 26-329 | 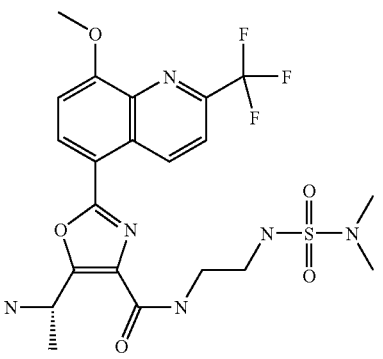 | 531 |

-continued

| Cpd. No. | Structure | MS (M + 1) |
|---|---|---|
| 26-330 | 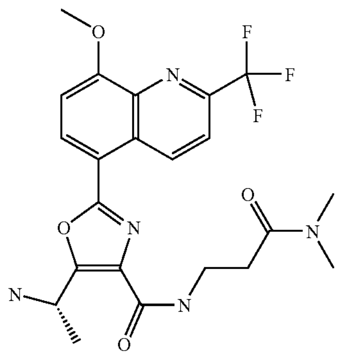 | 480 |
| 26-331 | 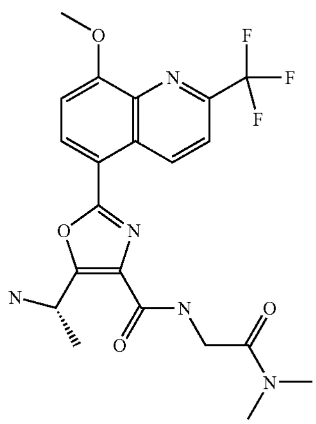 | 466 |
| 26-332 | 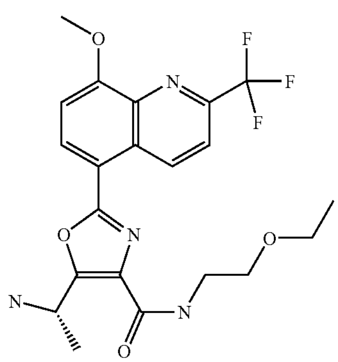 | 453 |
| 26-333 | 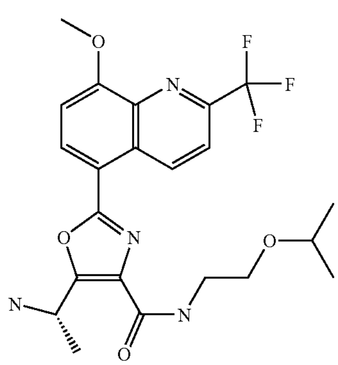 | 466 |

| Cpd. No. | Structure | MS (M + 1) |
|---|---|---|
| 26-334 | 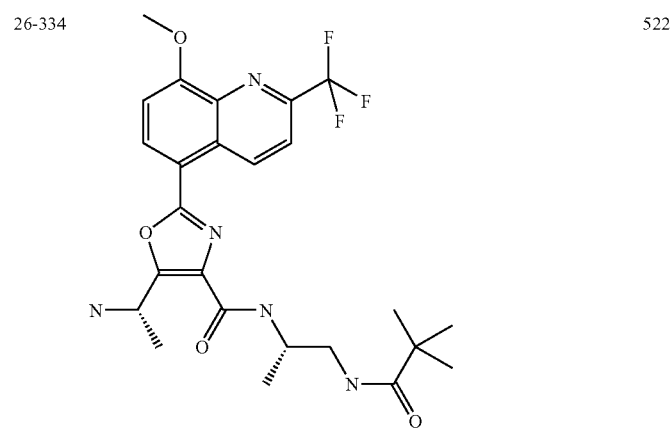 | 522 |
| 26-335 | 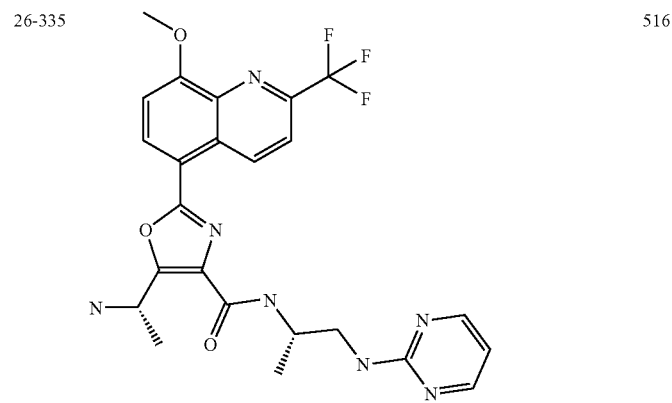 | 516 |
| 26-336 | 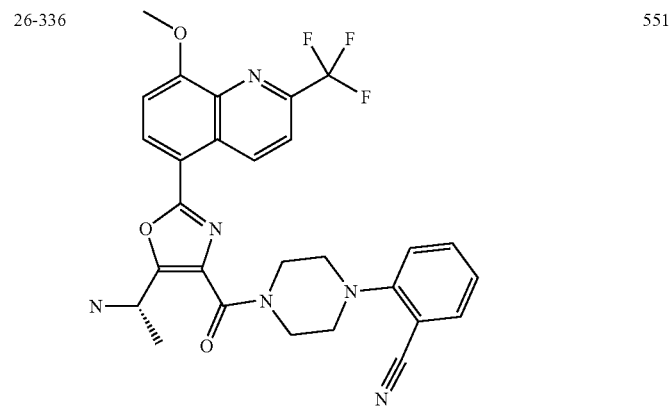 | 551 |

| Cpd. No. | Structure | MS (M + 1) |
|---|---|---|
| 26-337 | 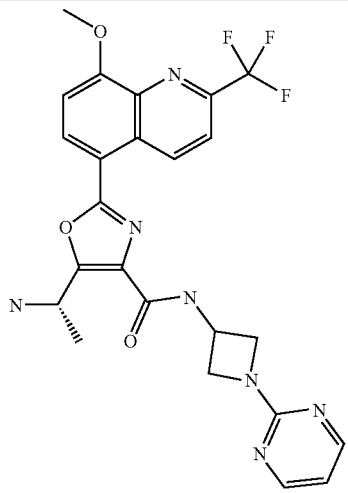 | 514 |
| 26-338 | 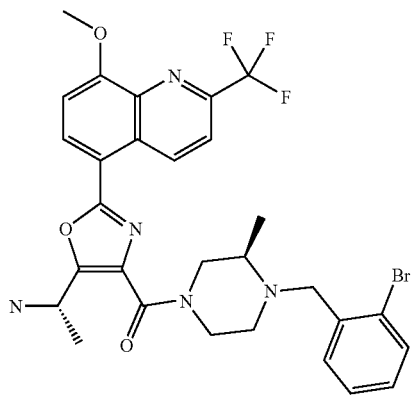 | 632 |
| 26-339 | 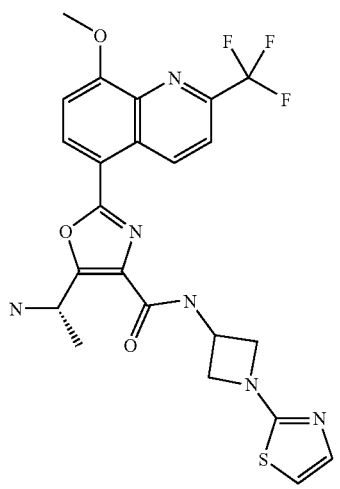 | 519 |

| Cpd. No. | Structure | MS (M + 1) |
|---|---|---|
| 26-340 | 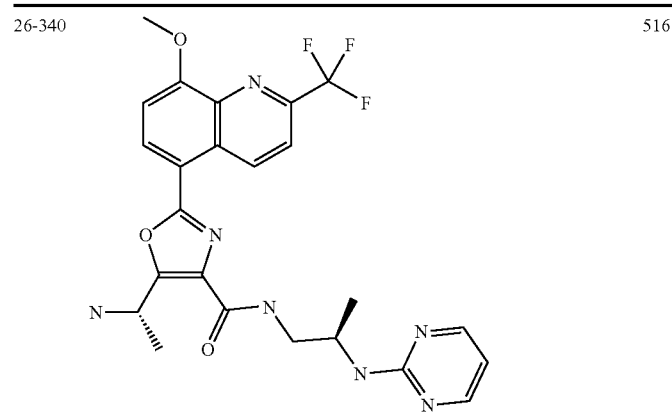 | 516 |
| 26-341 | 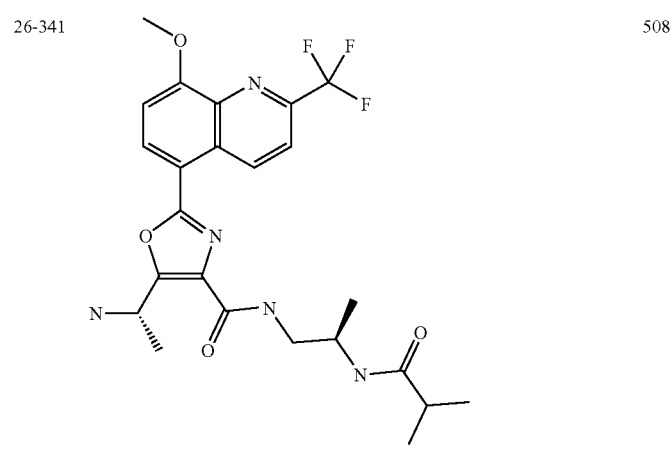 | 508 |
| 26-342 | 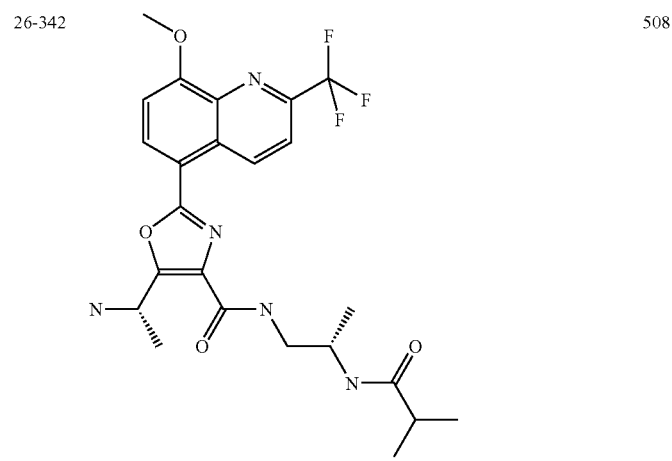 | 508 |

| Cpd. No. | Structure | MS (M + 1) |
|---|---|---|
| 26-343 | 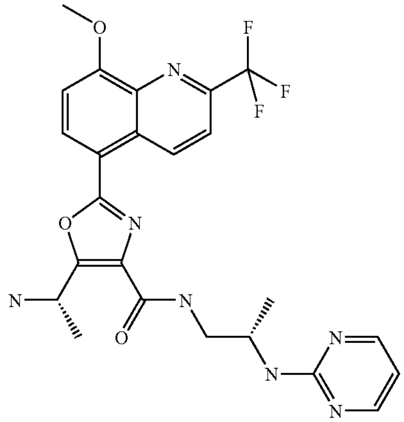 | 516 |
| 26-344 | 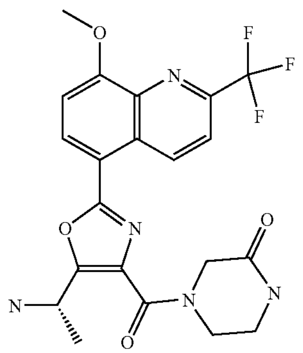 | 496 (M + ! + H) |
| 26-345 | 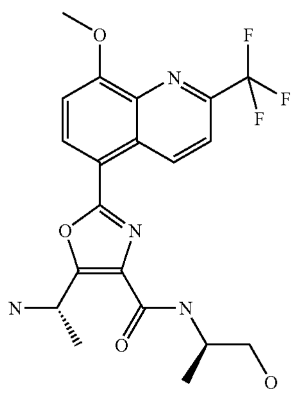 | 439 |
| 26-346 | 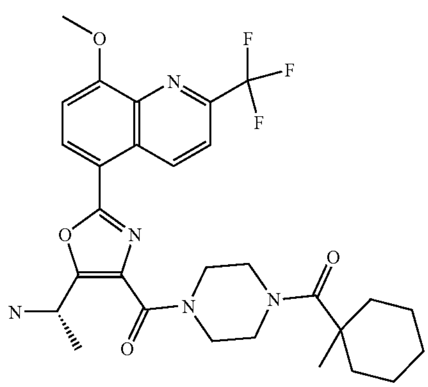 | 574 |

| Cpd. No. | Structure | MS (M + 1) |
|---|---|---|
| 26-347 | 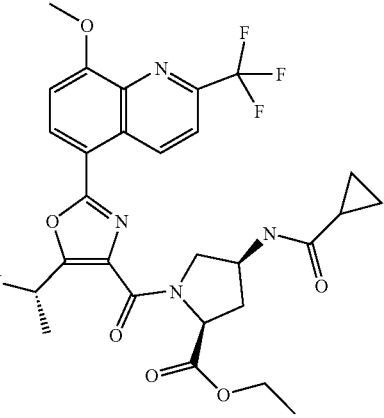 | 590 |
| 26-348 | 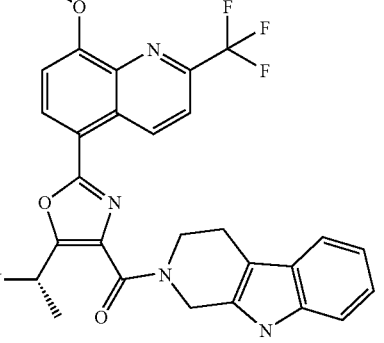 | 536 |
| 26-349 | 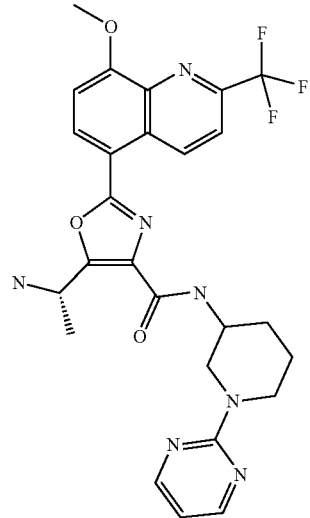 | 542 |

| Cpd. No. | Structure | MS (M + 1) |
|---|---|---|
| 26-350 | 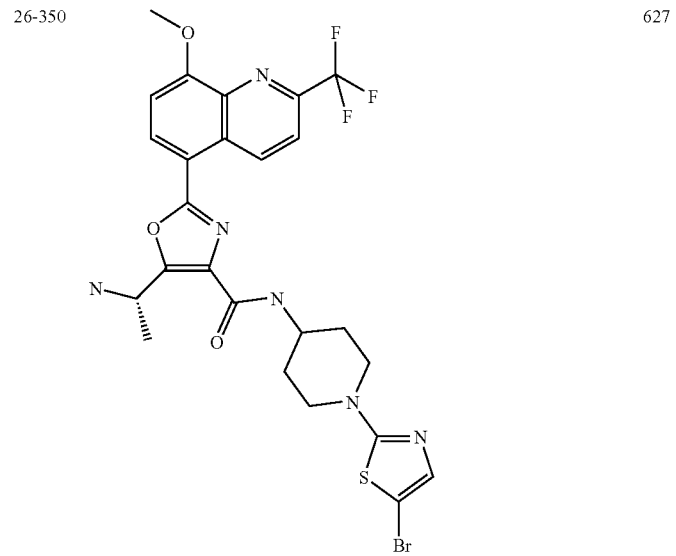 | 627 |
| 26-351 | 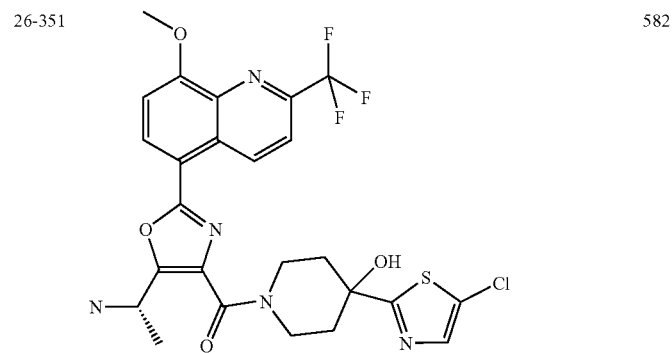 | 582 |
| 26-352 | 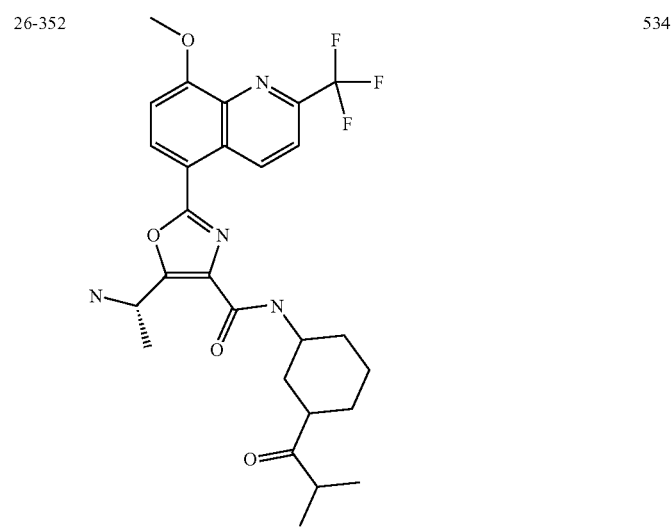 | 534 |

-continued
| Cpd. No. | Structure | MS (M + 1) |
|---|---|---|
| 26-353 | 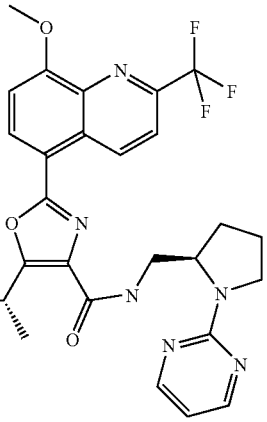 | 542 |
| 26-354 | 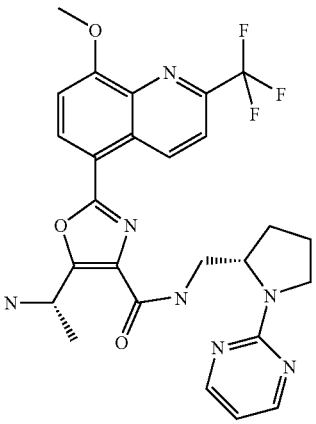 | 542 |
| 26-355 | 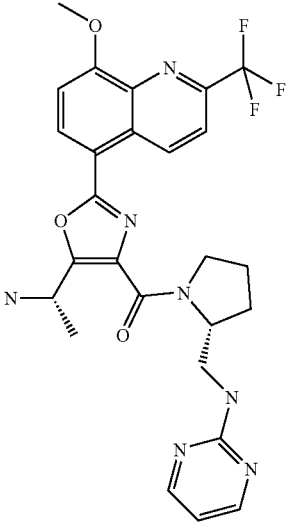 | 542 |

-continued
| Cpd. No. | Structure | MS (M + 1) |
|---|---|---|
| 26-356 | 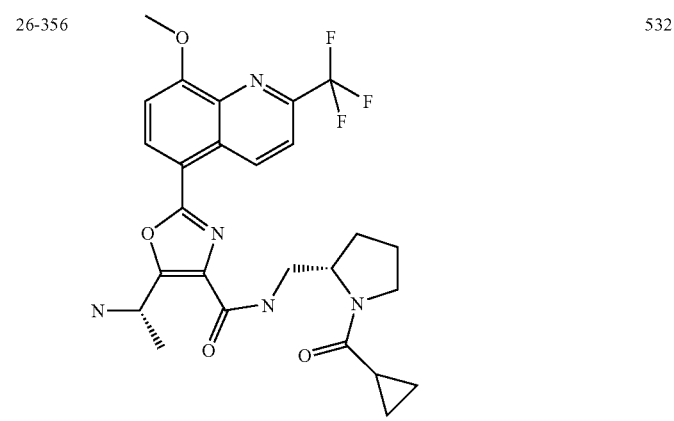 | 532 |
| 26-357 | 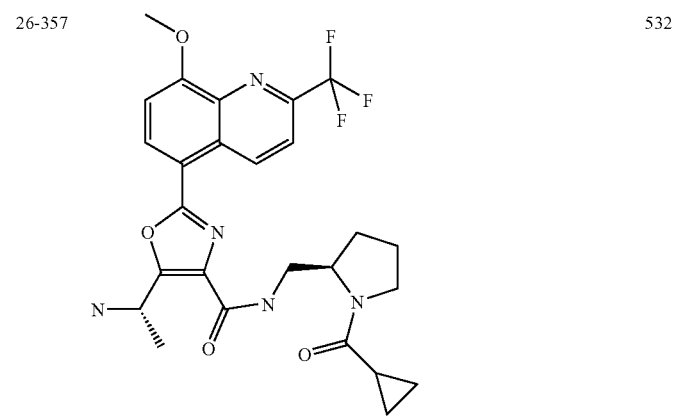 | 532 |
| 26-358 | 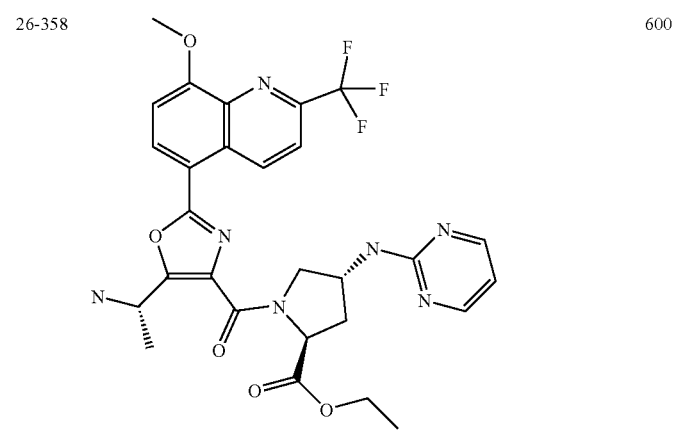 | 600 |

| Cpd. No. | Structure | MS (M + 1) |
|---|---|---|
| 26-359 | 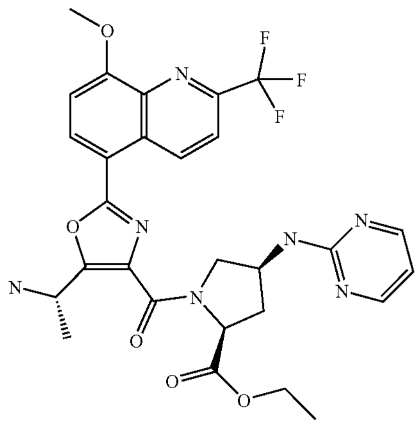 | 600 |
| 26-360 | 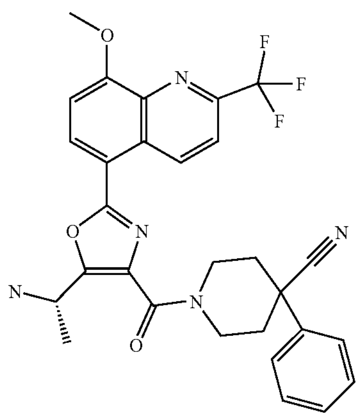 | 550 |
| 26-361 | 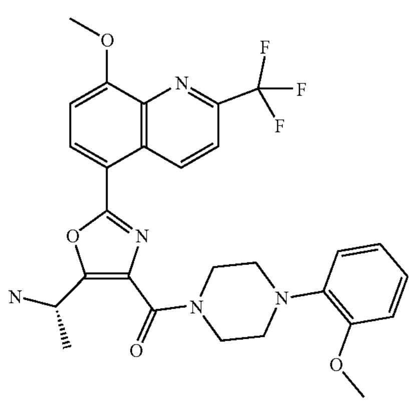 | 556 |

-continued
| Cpd. No. | Structure | MS (M + 1) |
|---|---|---|
| 26-362 | 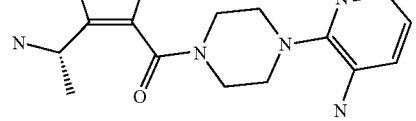 | 542 |
| 26-363 | 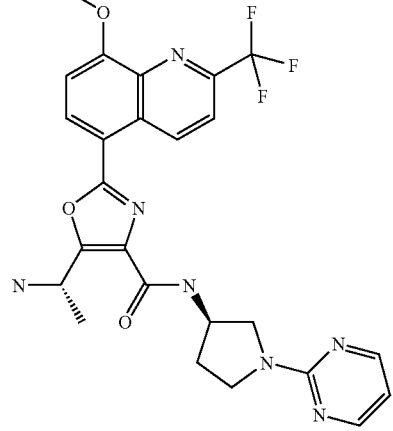 | 528 |
| 26-364 | 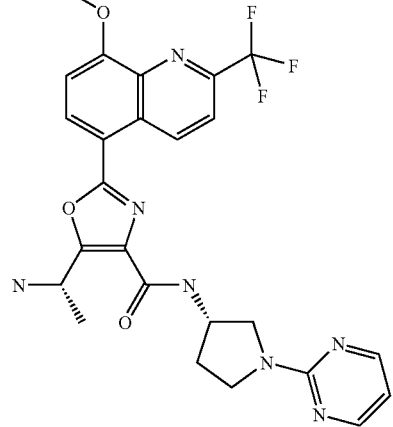 | 528 |

|Cpd. No.|Structure|MS (M + 1)|
|---|---|---|
|26-365|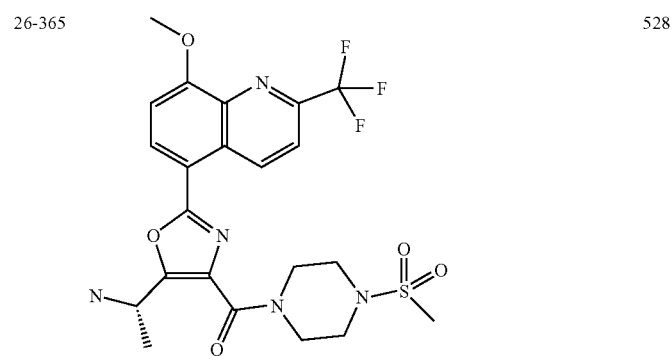|528|
|26-366|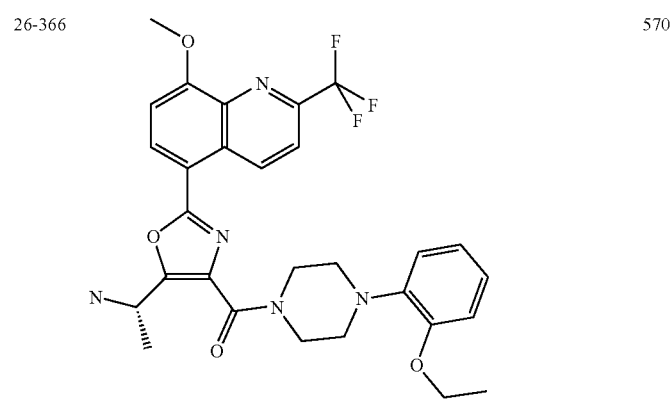|570|
|26-367|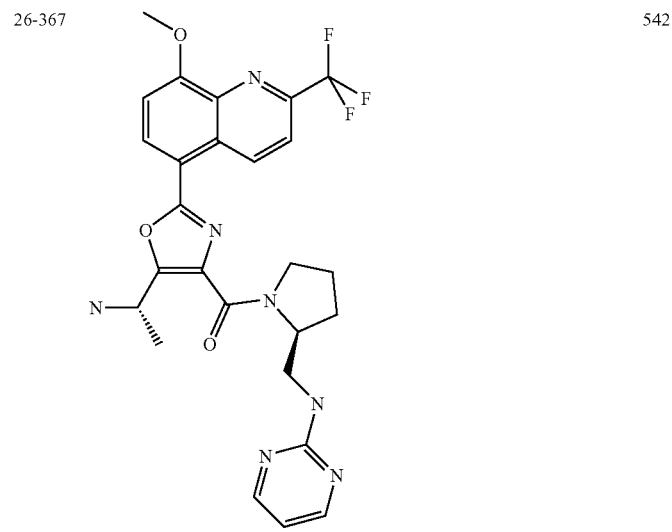|542|

-continued

| Cpd. No. | Structure | MS (M + 1) |
|---|---|---|
| 26-368 | 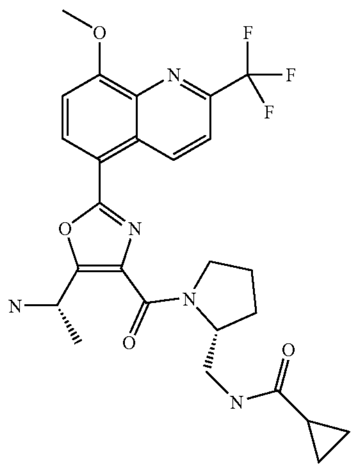 | 532 |
| 26-369 | 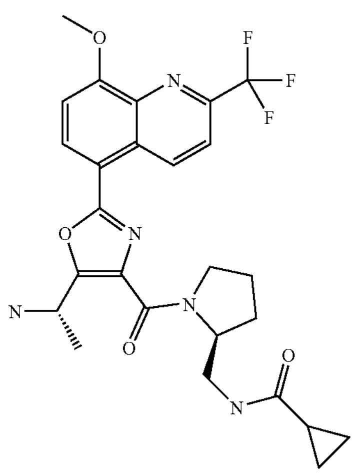 | 532 |
| 26-370 | 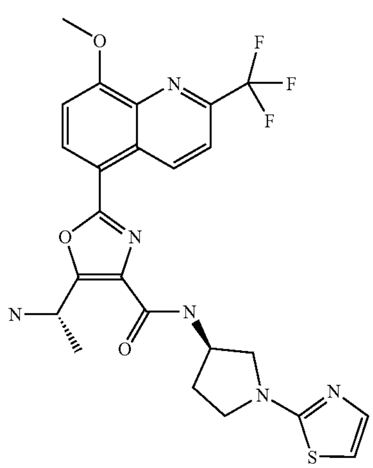 | 533 |

-continued
| Cpd. No. | Structure | MS (M + 1) |
|---|---|---|
| 26-371 | 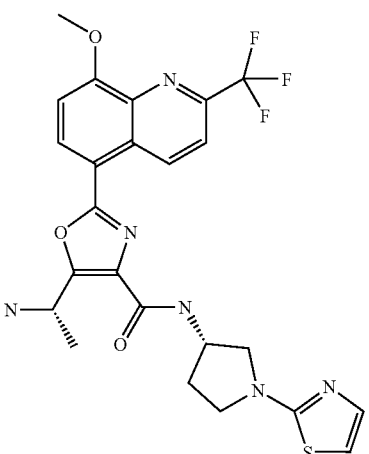 | 533 |
| 26-372 | 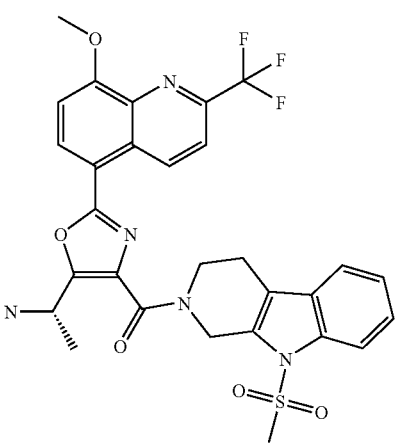 | 614 |
| 26-373 | 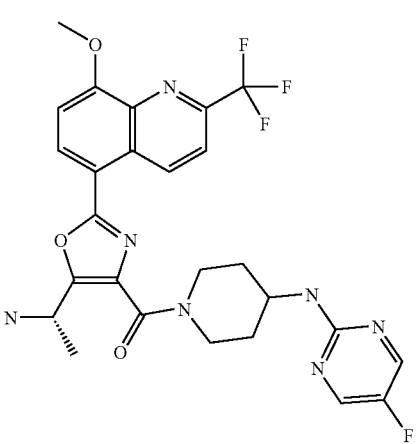 | 560 |

| Cpd. No. | Structure | MS (M + 1) |
|---|---|---|
| 26-374 | 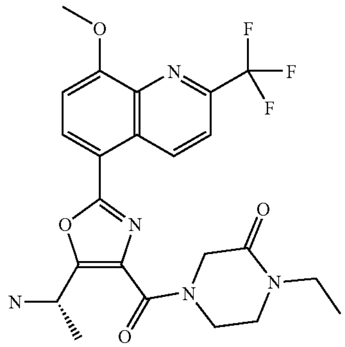 | 492 |
| 26-375 | 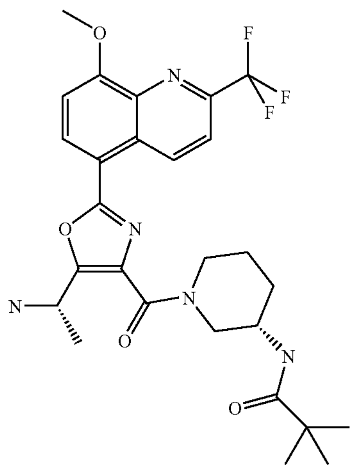 | 548 |
| 26-376 | 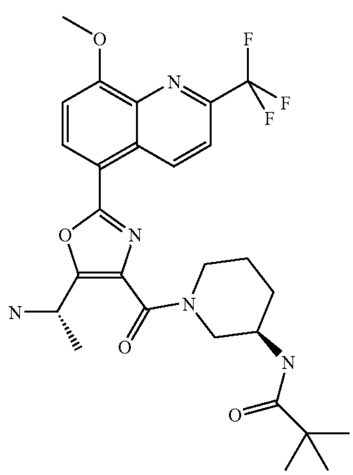 | 548 |

| Cpd. No. | Structure | MS (M + 1) |
|---|---|---|
| 26-377 | 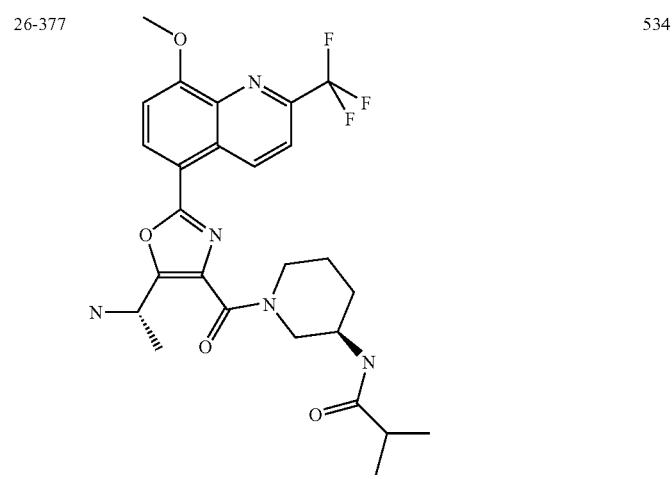 | 534 |
| 26-378 | 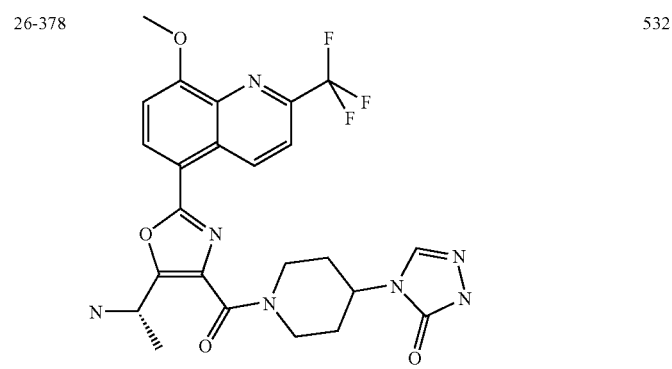 | 532 |
| 26-379 | 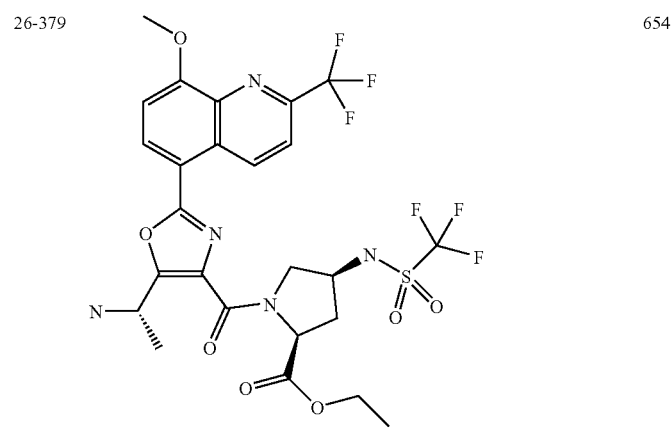 | 654 |

-continued
| Cpd. No. | Structure | MS (M + 1) |
|---|---|---|
| 26-380 | 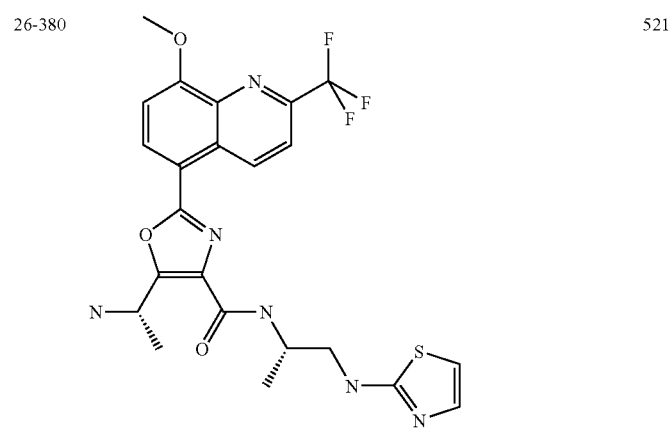 | 521 |
| 26-381 | 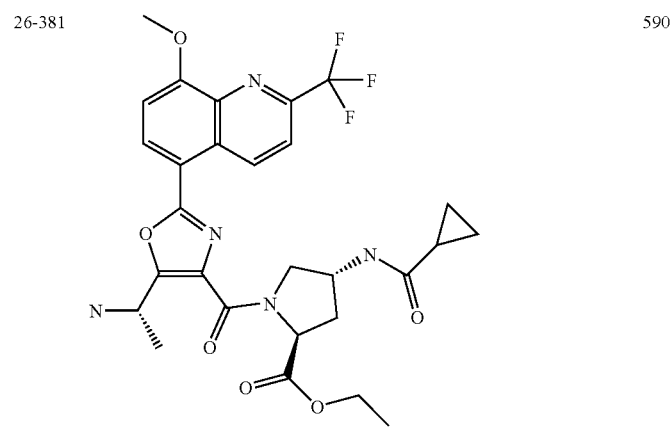 | 590 |
| 26-382 | 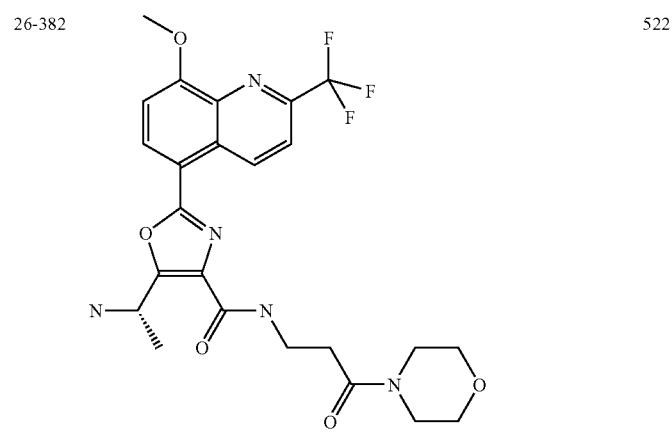 | 522 |

| Cpd. No. | Structure | MS (M + 1) |
|---|---|---|
| 26-383 | 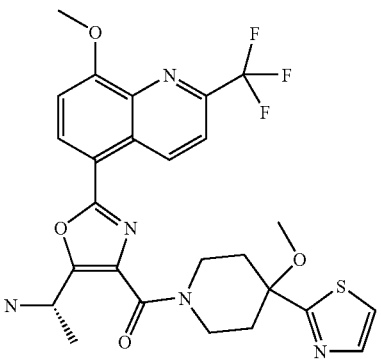 | 562 |
| 26-384 | 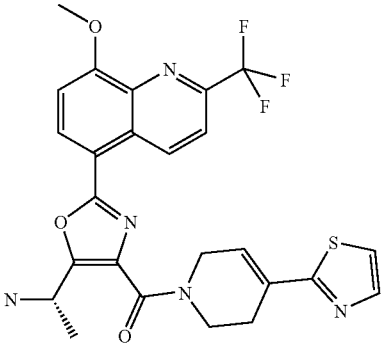 | 530 |
| 26-385 | 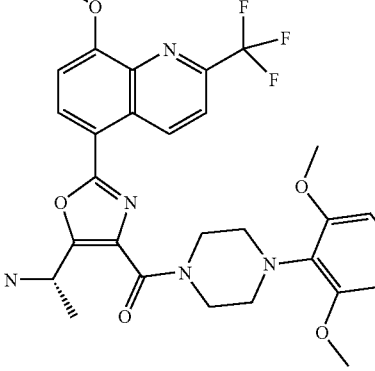 | 586 |
| 26-386 | 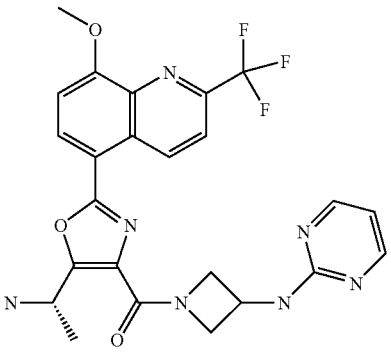 | 514 |

-continued

| Cpd. No. | Structure | MS (M + 1) |
|---|---|---|
| 26-387 | 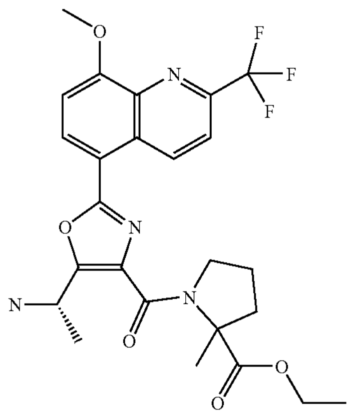 | 521 |
| 26-388 | 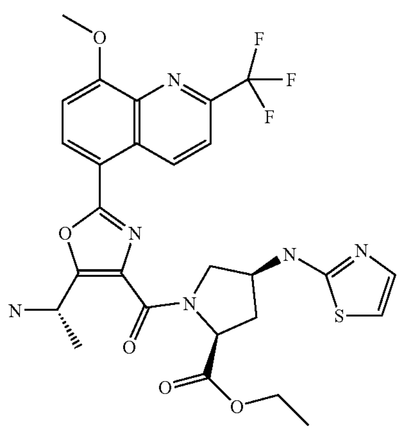 | 605 |
| 26-389 | 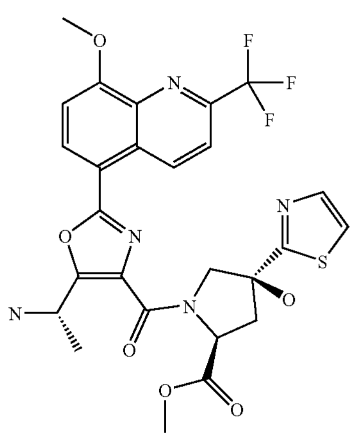 | 592 |

-continued

| Cpd. No. | Structure | MS (M + 1) |
|---|---|---|
| 26-390 | 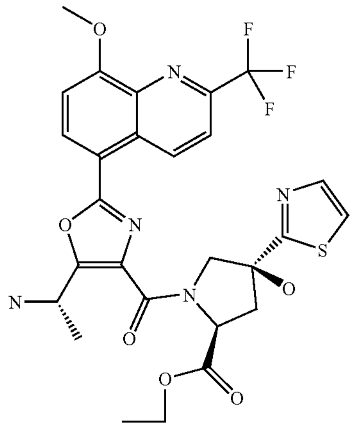 | 606 |
| 26-391 | 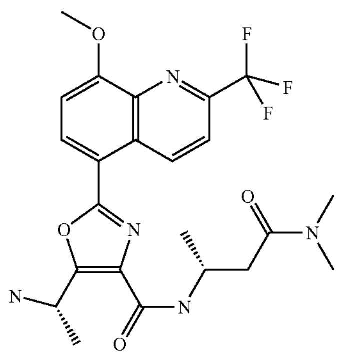 | 494 |
| 26-392 | 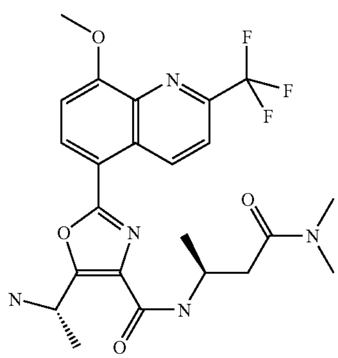 | 494 |
| 26-393 | 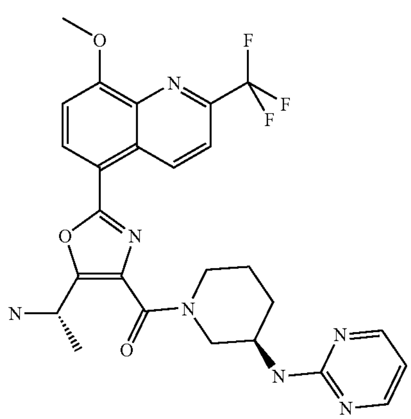 | 542 |

| Cpd. No. | Structure | MS (M + 1) |
|---|---|---|
| 26-394 | 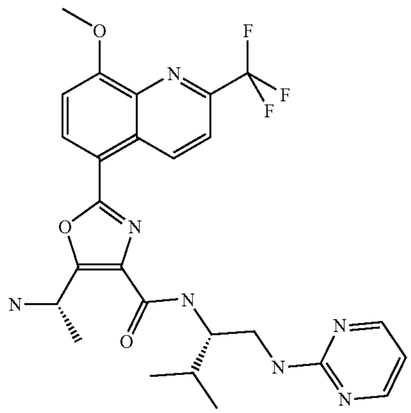 | 544 |
| 26-395 | 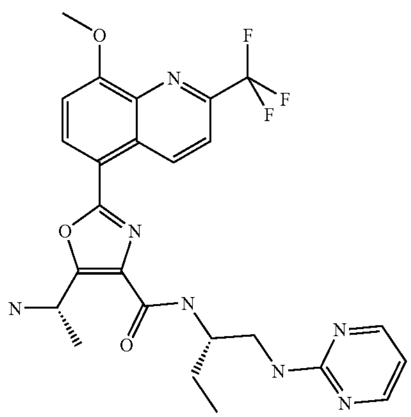 | 530 |
| 26-396 | 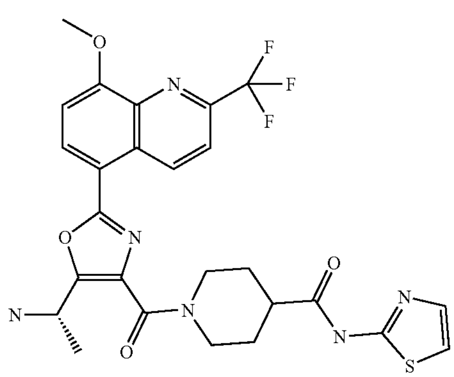 | 575 |

| Cpd. No. | Structure | MS (M + 1) |
|---|---|---|
| 26-397 | 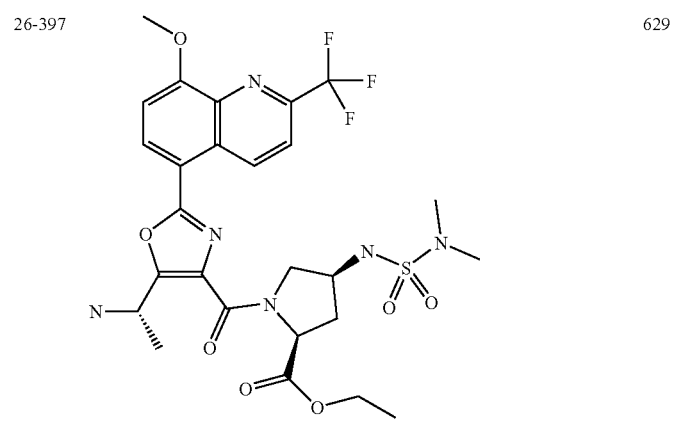 | 629 |
| 26-398 | 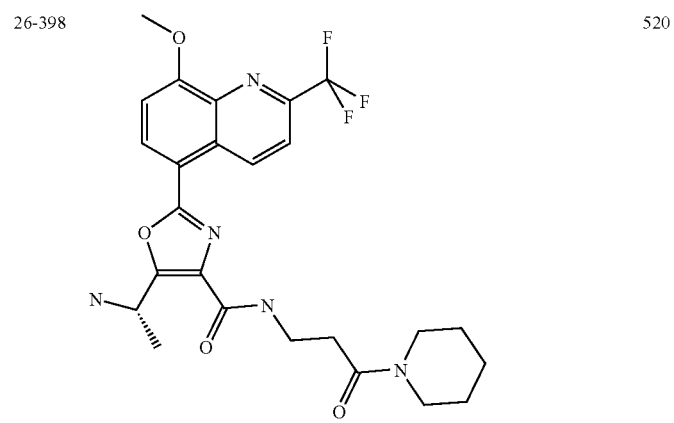 | 520 |
| 26-399 | 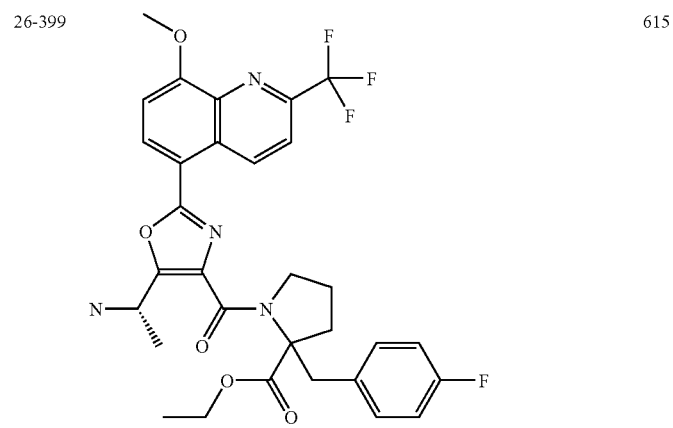 | 615 |

-continued

| Cpd. No. | Structure | MS (M + 1) |
|---|---|---|
| 26-400 | 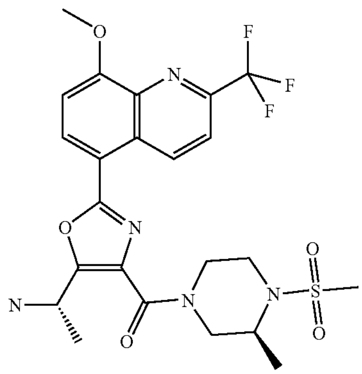 | 542 |
| 26-401 | 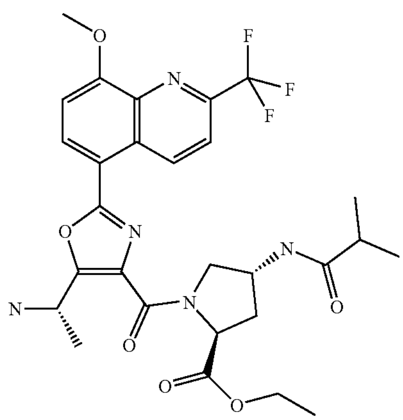 | 592 |
| 26-402 | 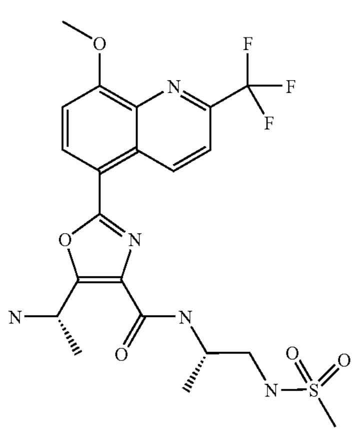 | 516 |

-continued

| Cpd. No. | Structure | MS (M + 1) |
|---|---|---|
| 26-403 | 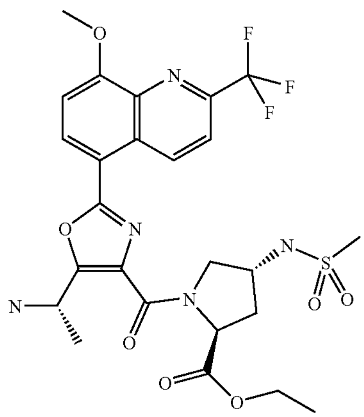 | 600 |
| 26-404 | 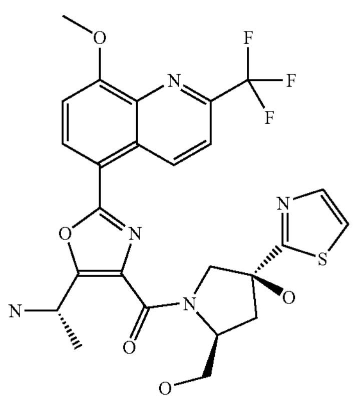 | 564 |
| 26-405 | 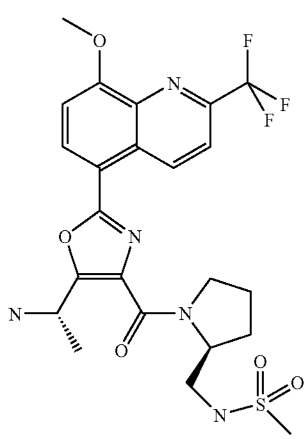 | 542 |

-continued

| Cpd. No. | Structure | MS (M + 1) |
|---|---|---|
| 26-406 | 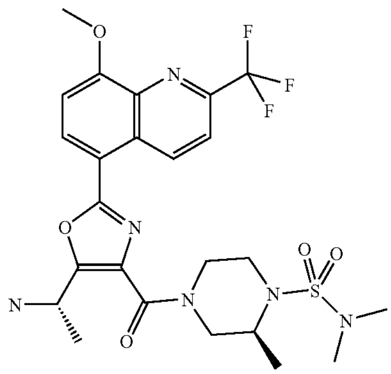 | 571 |
| 26-407 | 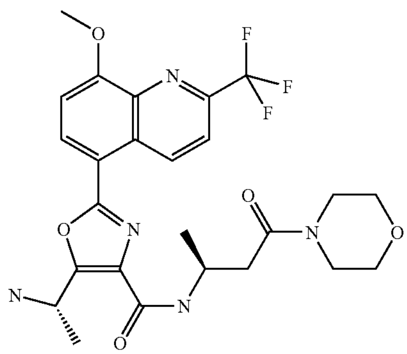 | 536 |
| 26-408 | 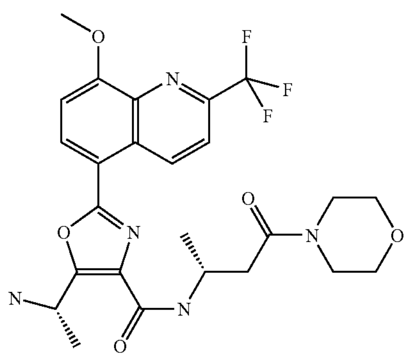 | 536 |
| 26-409 | 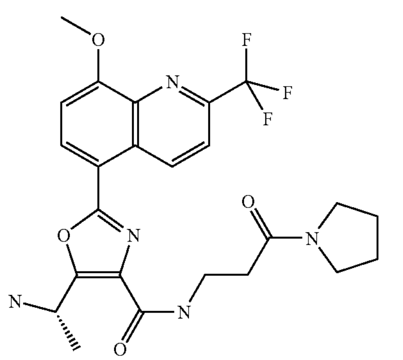 | 506 |

-continued
| Cpd. No. | Structure | MS (M + 1) |
|---|---|---|
| 26-410 | 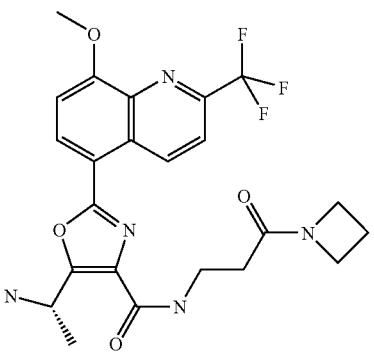 | 492 |
| 26-411 | 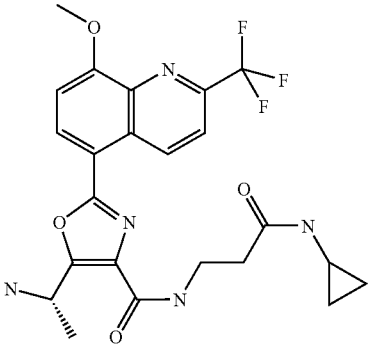 | 492 |
| 26-412 | 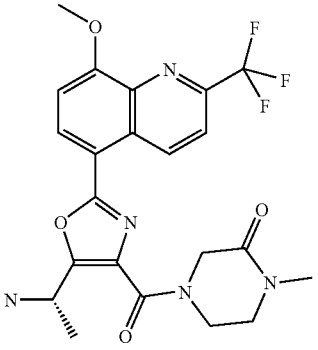 | 478 |
| 26-413 | 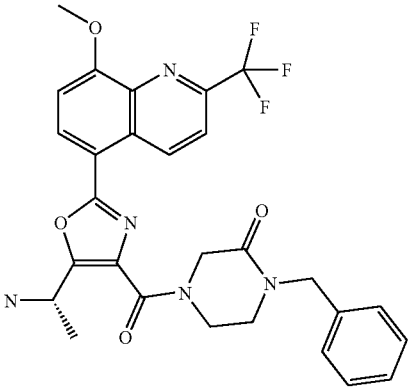 | 554 |

-continued
| Cpd. No. | Structure | MS (M + 1) |
|---|---|---|
| 26-414 | 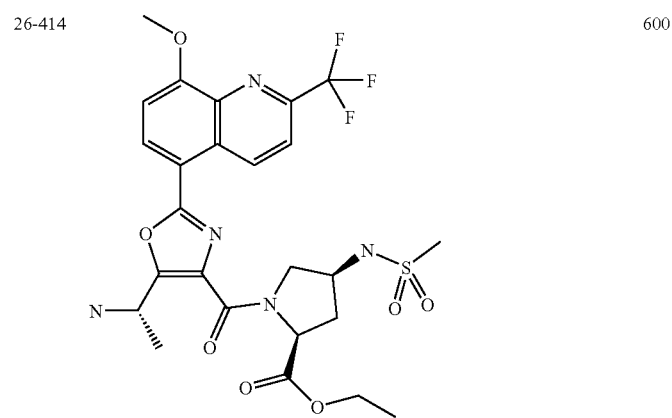 | 600 |
| 26-415 | 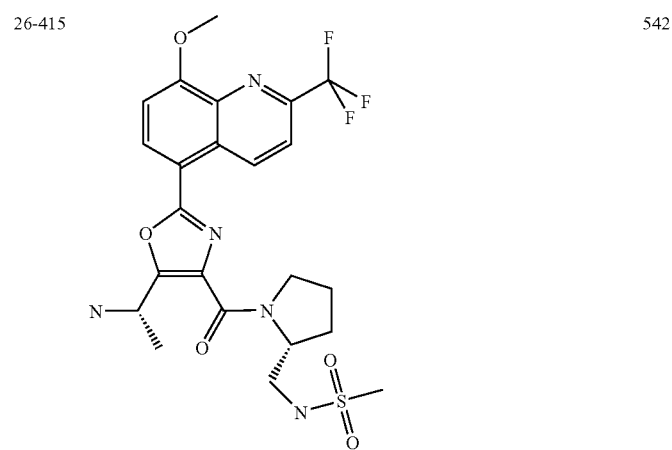 | 542 |
| 26-416 | 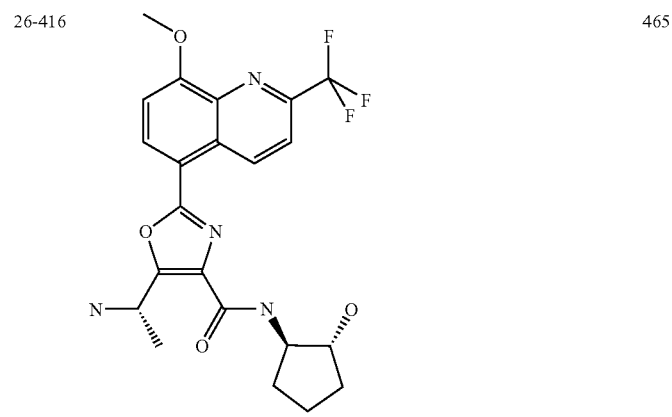 | 465 |

-continued
| Cpd. No. | Structure | MS (M + 1) |
|---|---|---|
| 26-417 | 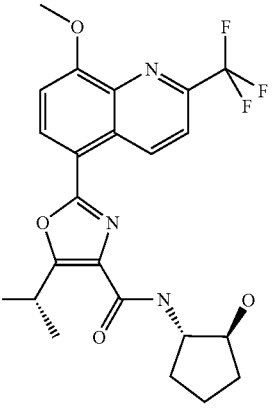 | 465 |
| 26-418 | 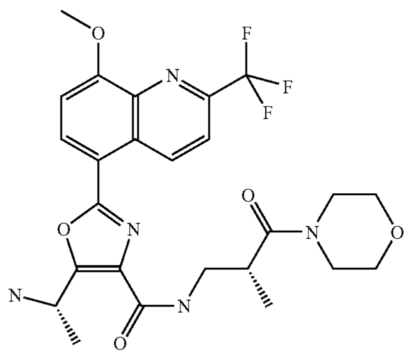 | 536 |
| 26-419 | 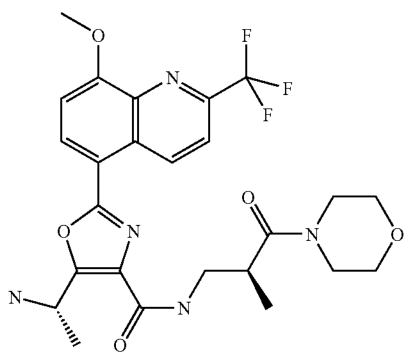 | 536 |
| 26-420 | 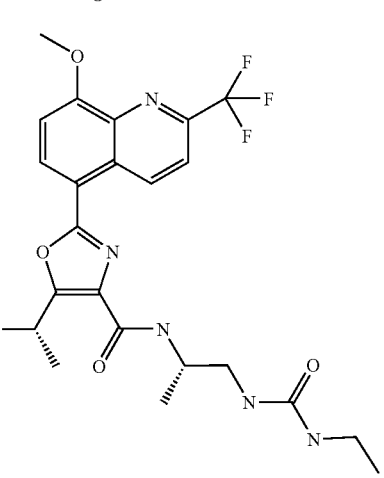 | 509 |

| Cpd. No. | Structure | MS (M + 1) |
|---|---|---|
| 26-421 | 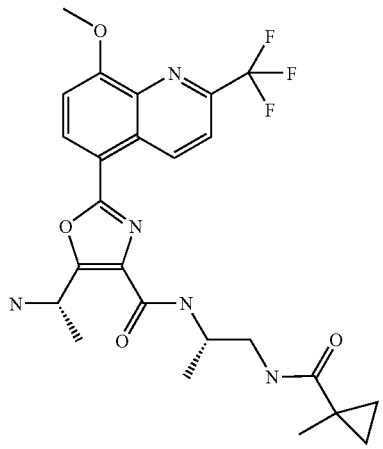 | 520 |
| 26-422 | 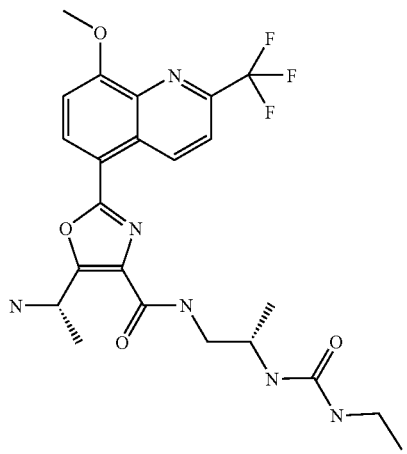 | 509 |
| 26-423 | 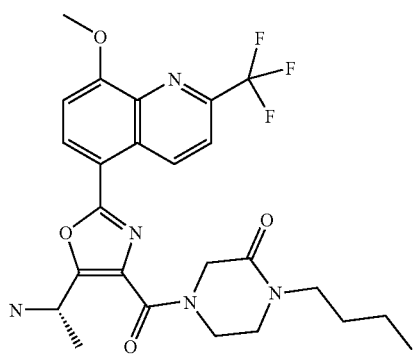 | 520 |

-continued

| Cpd. No. | Structure | MS (M + 1) |
|---|---|---|
| 26-424 | 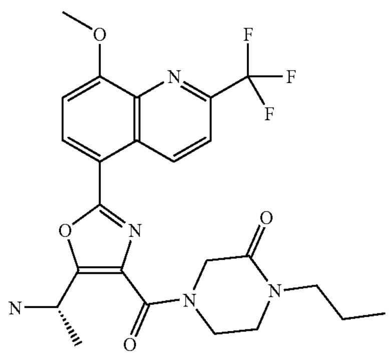 | 506 |
| 26-425 | 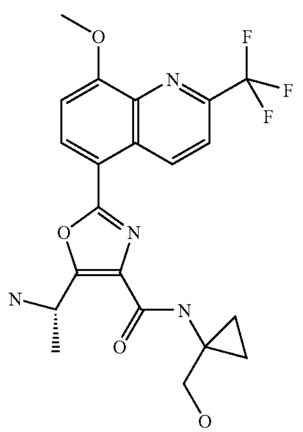 | 451 |
| 26-426 | 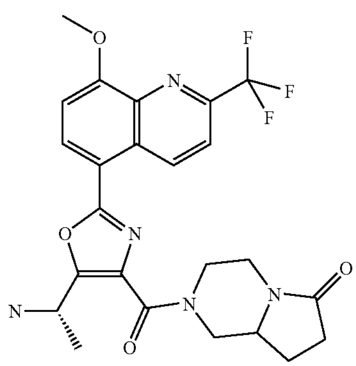 | 504 |
| 26-427 | 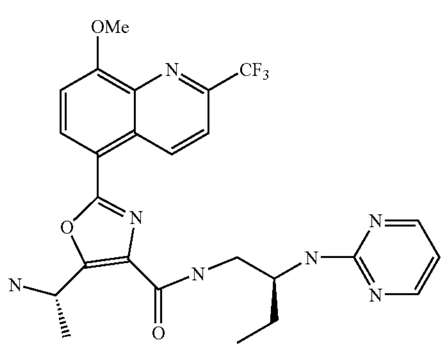 | 530 |

-continued

| Cpd. No. | Structure | MS (M + 1) |
|---|---|---|
| 26-428 | 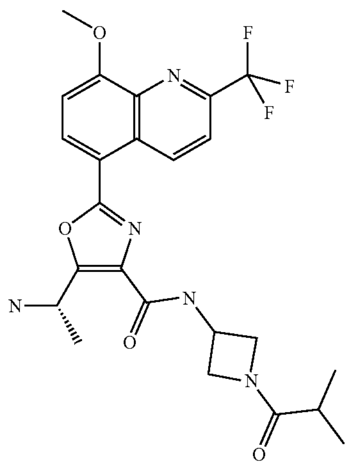 | 506 |
| 26-429 | 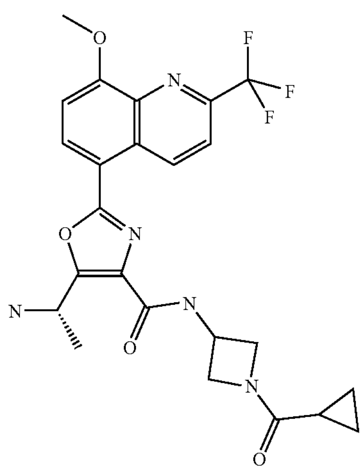 | 504 |
| 26-430 | 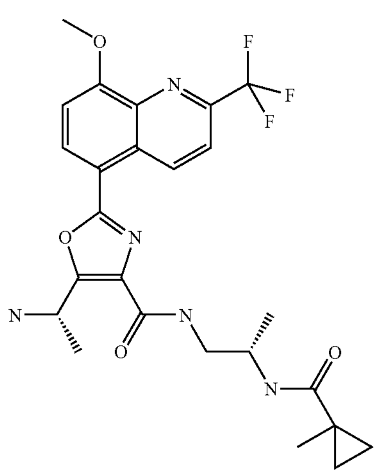 | 520 |

-continued
| Cpd. No. | Structure | MS (M + 1) |
|---|---|---|
| 26-431 | 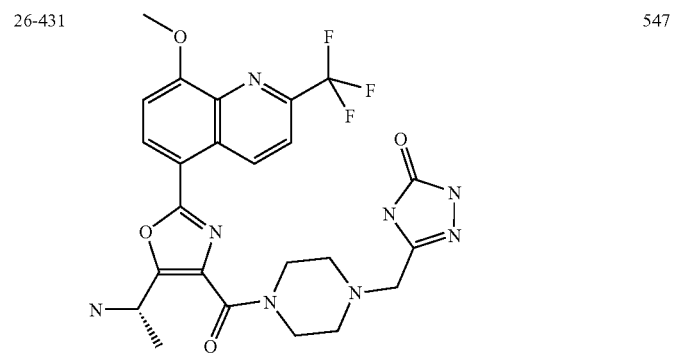 | 547 |
| 26-432 | 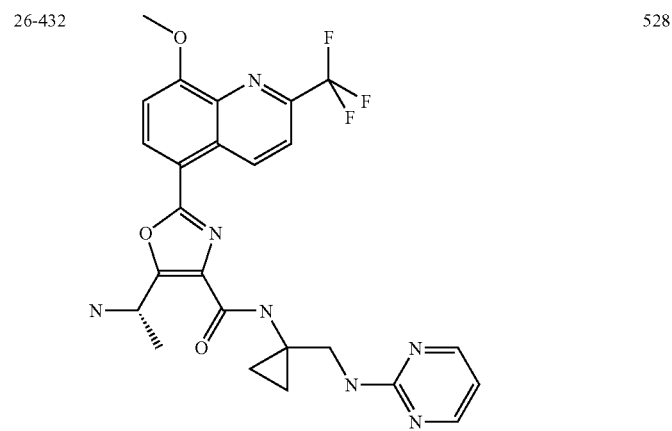 | 528 |
| 26-433 | 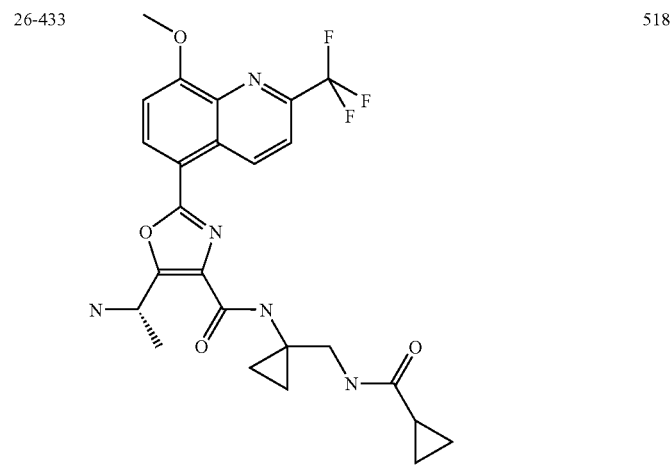 | 518 |

| Cpd. No. | Structure | MS (M + 1) |
|---|---|---|
| 26-434 | 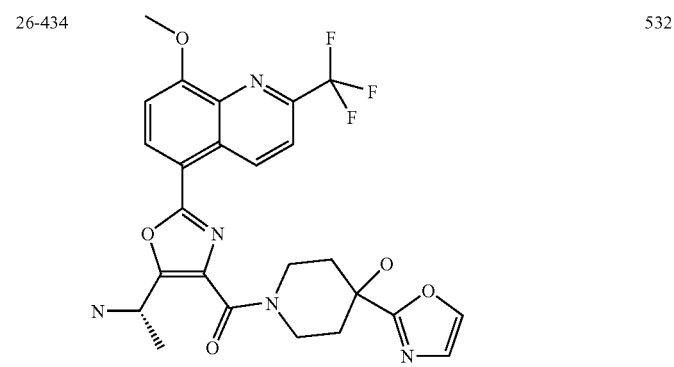 | 532 |
| 26-435 | 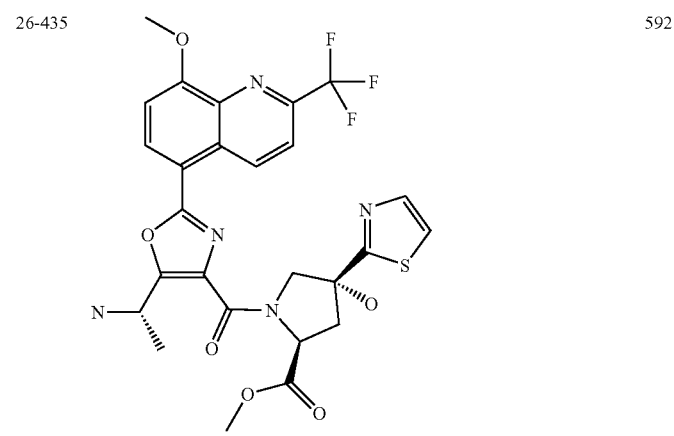 | 592 |
| 26-436 | 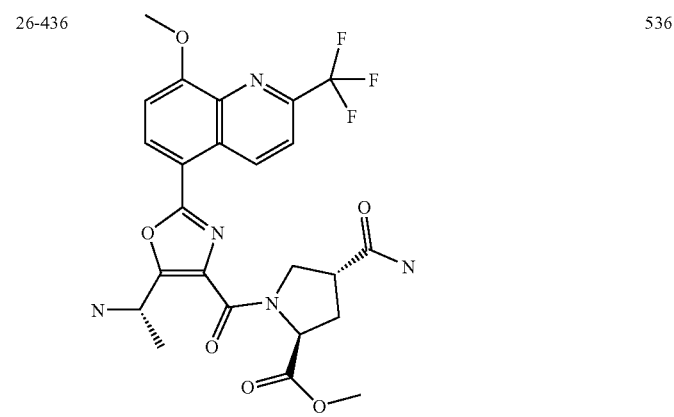 | 536 |

-continued

| Cpd. No. | Structure | MS (M + 1) |
|---|---|---|
| 26-437 | 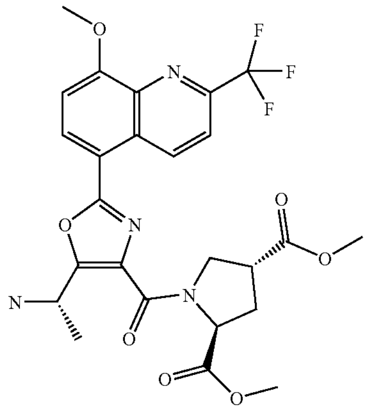 | 551 |
| 26-438 | 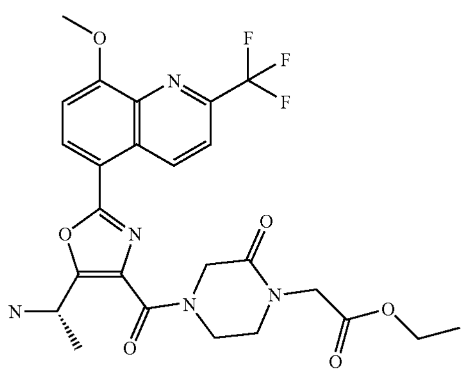 | 550 |
| 26-439 | 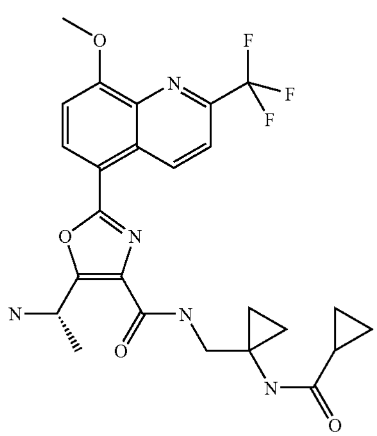 | 518 |

| Cpd. No. | Structure | MS (M + 1) |
|---|---|---|
| 26-440 | 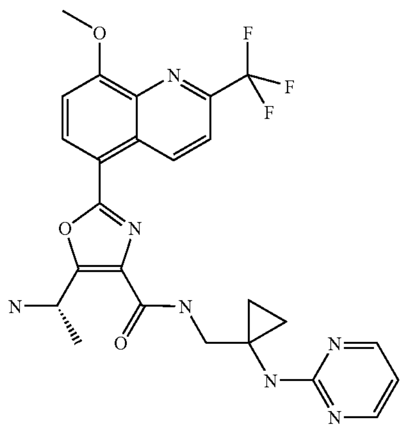 | 528 |
| 26-441 | 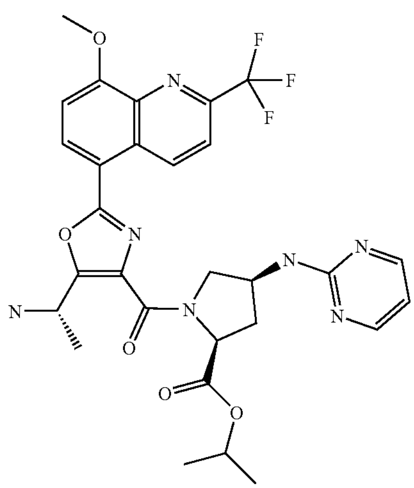 | 614 |
| 26-442 | 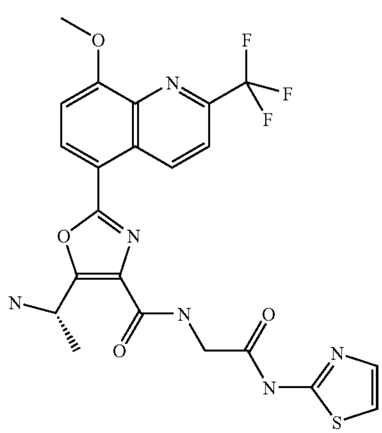 | 521 |

-continued

| Cpd. No. | Structure | MS (M + 1) |
|---|---|---|
| 26-443 | 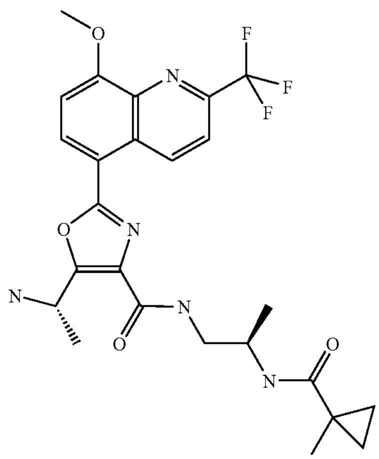 | 520 |
| 2-444 | 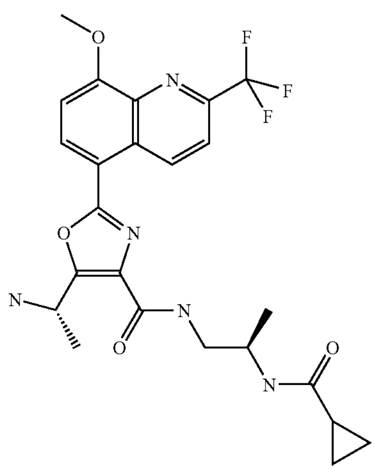 | 506 |
| 26-445 | 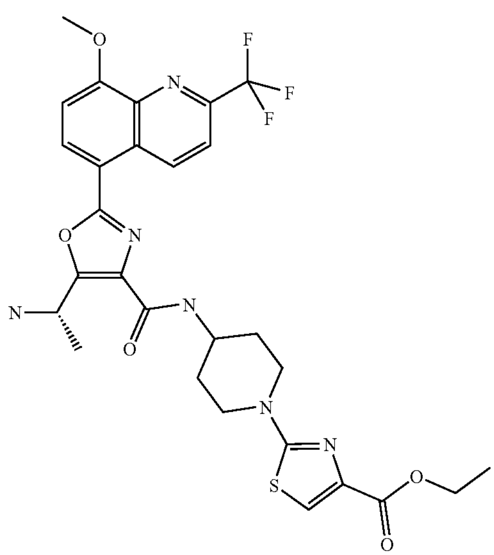 | 619 |

| Cpd. No. | Structure | MS (M + 1) |
|---|---|---|
| 26-446 | 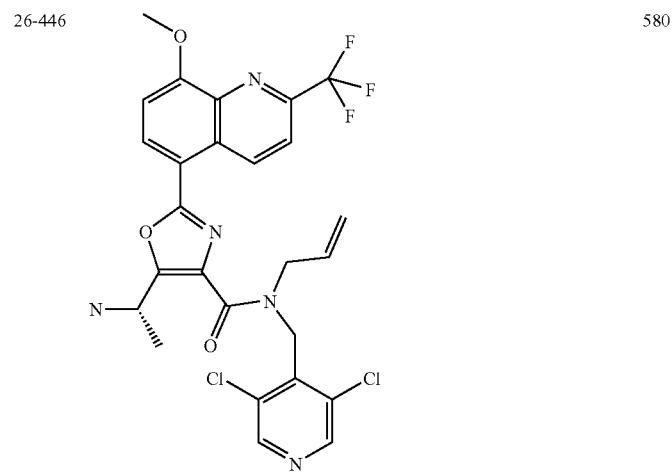 | 580 |
| 26-447 | 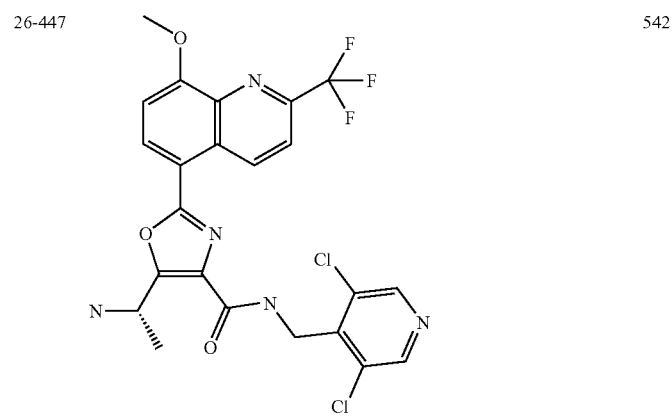 | 542 |
| 26-448 | 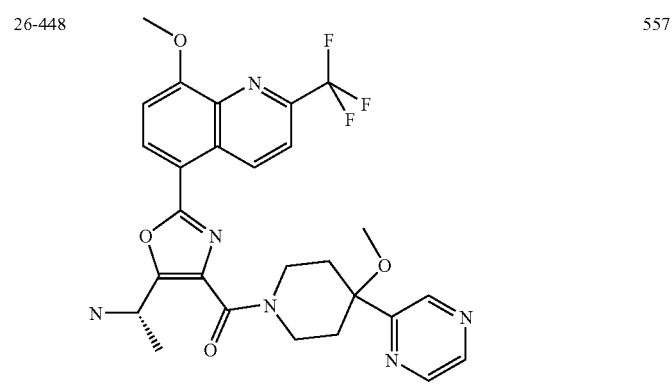 | 557 |

-continued

| Cpd. No. | Structure | MS (M + 1) |
|---|---|---|
| 26-449 | 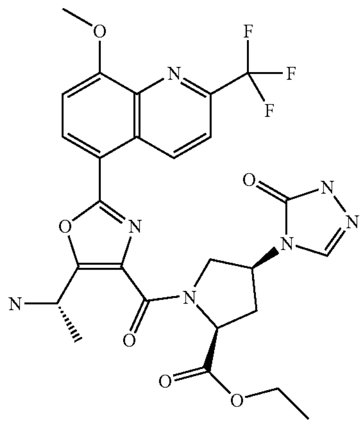 | 590 |
| 26-450 | 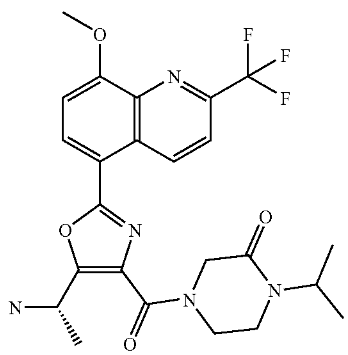 | 506 |
| 26-451 | 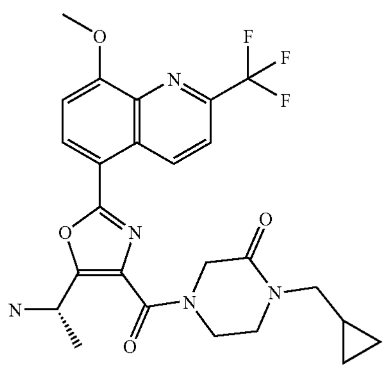 | 518 |
| 26-452 | 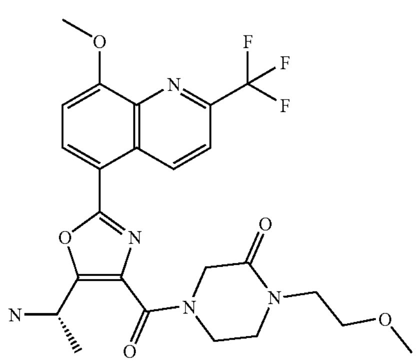 | 522 |

-continued
| Cpd. No. | Structure | MS (M + 1) |
|---|---|---|
| 26-453 | 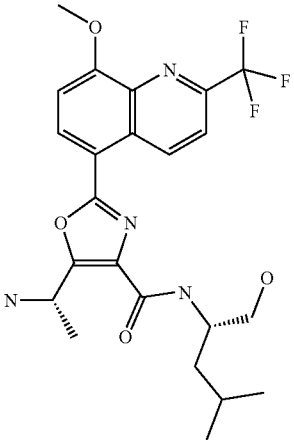 | 481 |
| 26-454 | 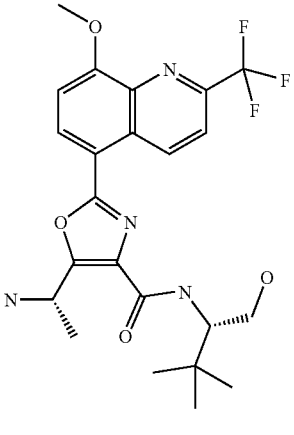 | 481 |
| 26-455 | 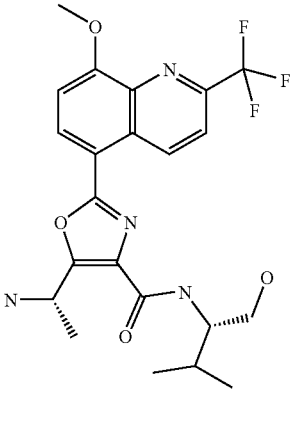 | 467 |

-continued

| Cpd. No. | Structure | MS (M + 1) |
|---|---|---|
| 26-456 | 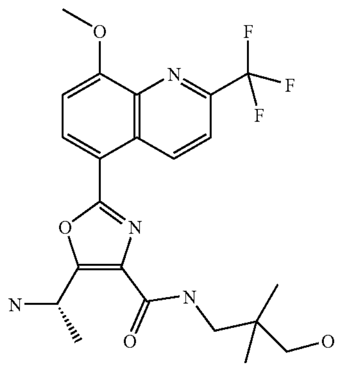 | 467 |
| 26-457 | 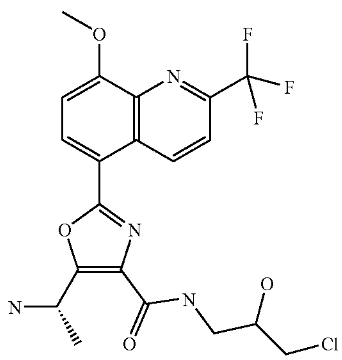 | 473 |
| 26-458 | 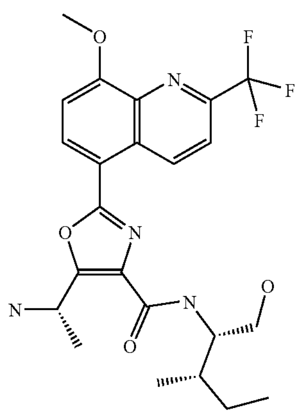 | 481 |
| 26-459 | 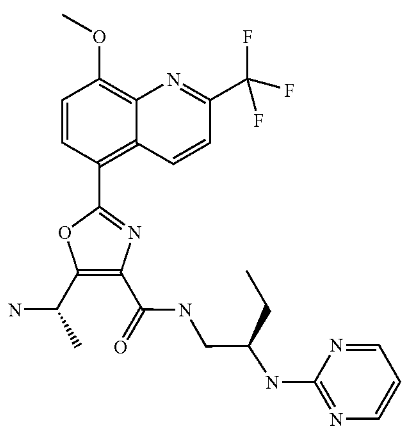 | 530 |

| Cpd. No. | Structure | MS (M + 1) |
|---|---|---|
| 26-460 | 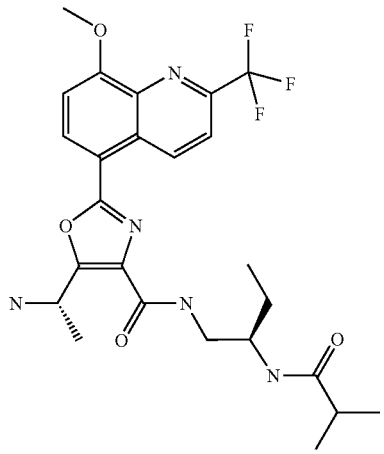 | 522 |
| 26-461 | 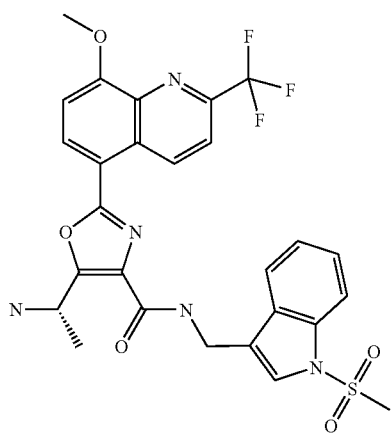 | 588 |
| 26-462 | 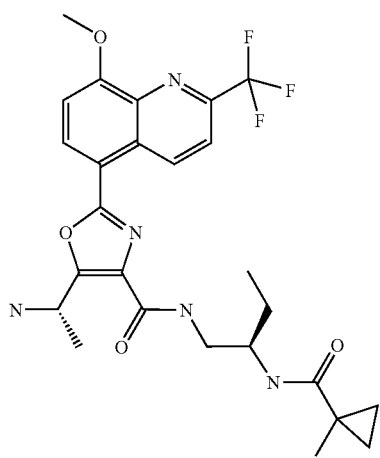 | 534 |

-continued

| Cpd. No. | Structure | MS (M + 1) |
|---|---|---|
| 26-463 | 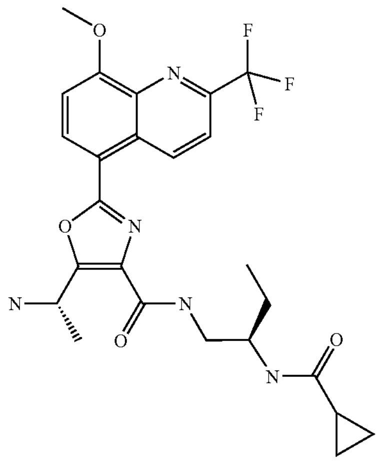 | 520 |
| 26-464 | 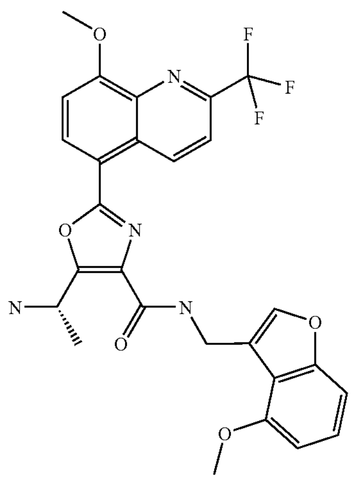 | 541 |
| 26-465 | 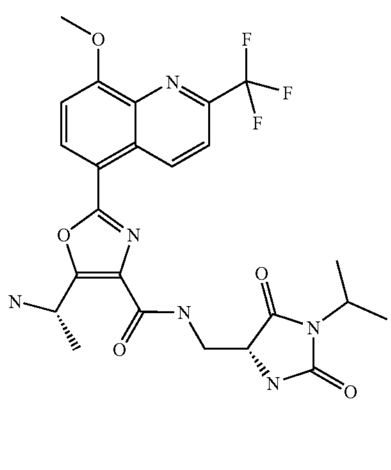 | 535 |

-continued

| Cpd. No. | Structure | MS (M + 1) |
|---|---|---|
| 26-466 | 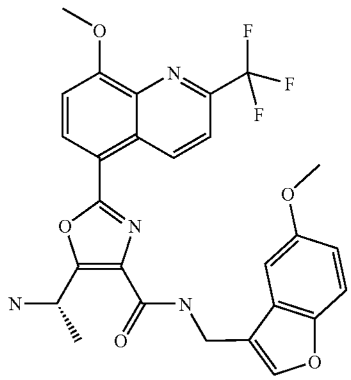 | 541 |
| 26-467 | 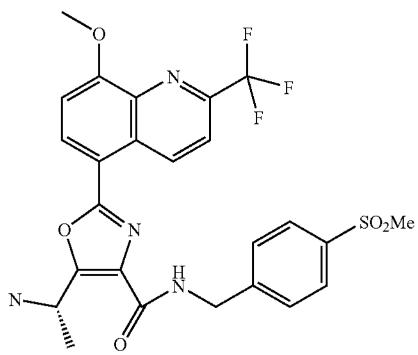 | 549 |
| 26-468 | 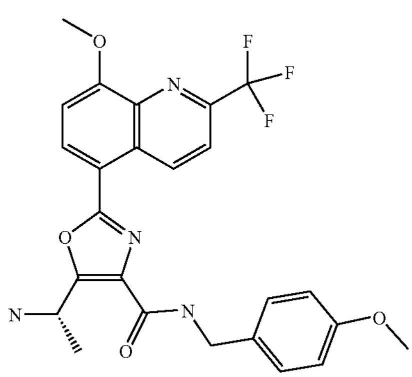 | 501 |

-continued

| Cpd. No. | Structure | MS (M + 1) |
|---|---|---|
| 26-469 | 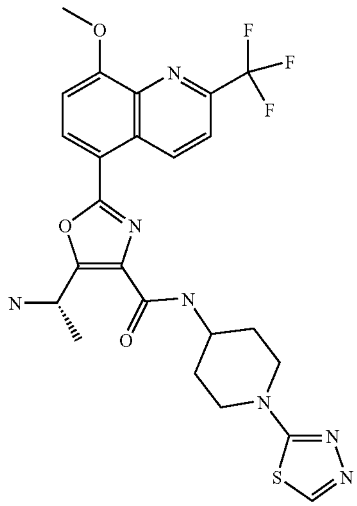 | 548 |
| 26-470 | 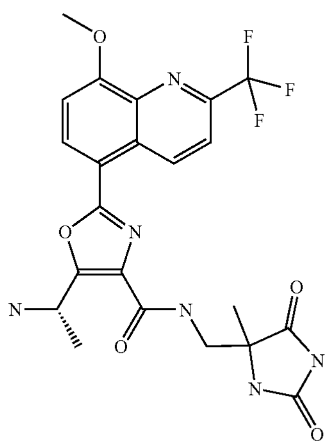 | 507 |
| 26-471 | 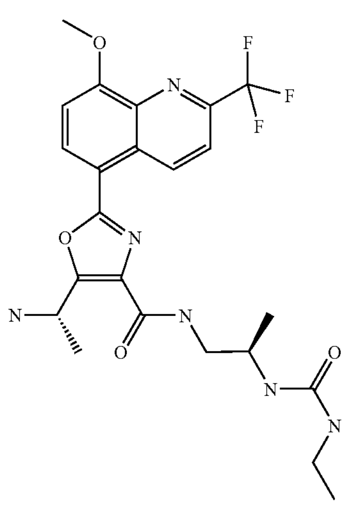 | 509 |

| Cpd. No. | Structure | MS (M + 1) |
|---|---|---|
| 26-472 | 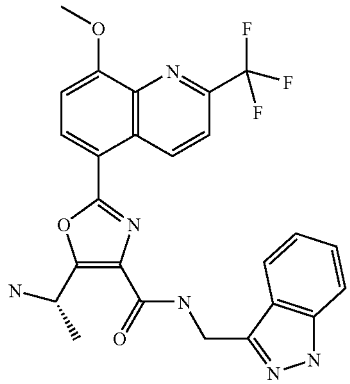 | 511 |
| 26-473 | 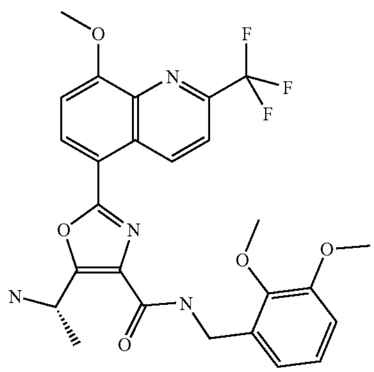 | 531 |
| 26-474 | 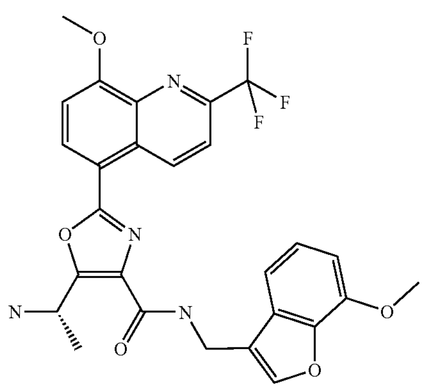 | 557 |
| 26-475 | 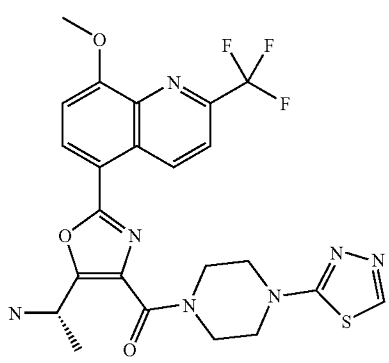 | 534 |

| Cpd. No. | Structure | MS (M + 1) |
|---|---|---|
| 26-476 | 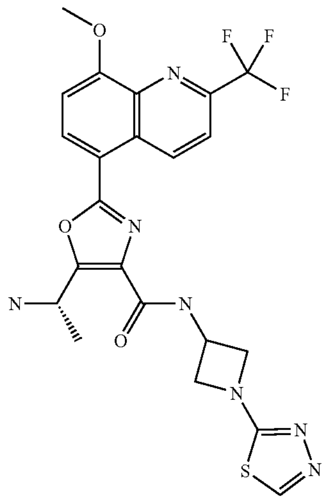 | 520 |
| 26-477 | 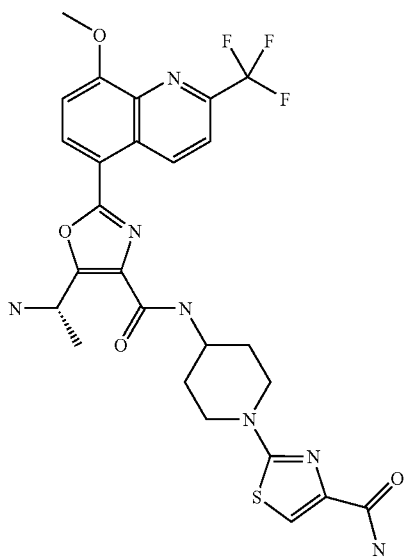 | 590 |
| 26-478 | 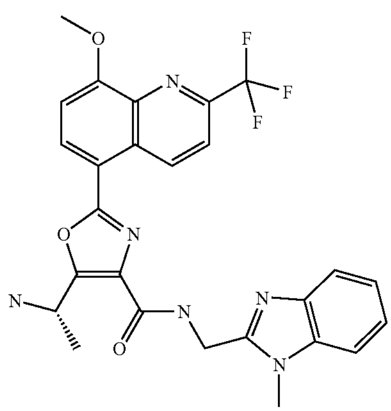 | 525 |

-continued

| Cpd. No. | Structure | MS (M + 1) |
|---|---|---|
| 26-479 | 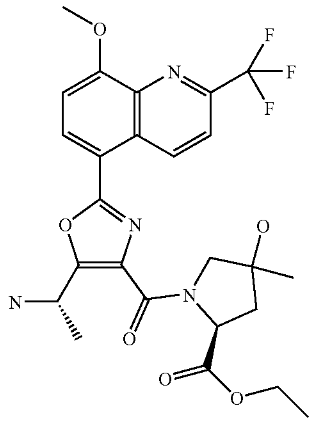 | 537 |
| 26-480 | 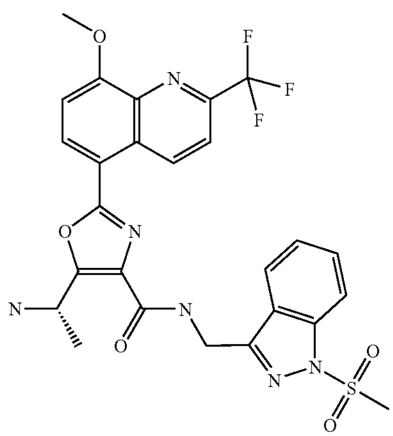 | 589 |
| 26-481 | 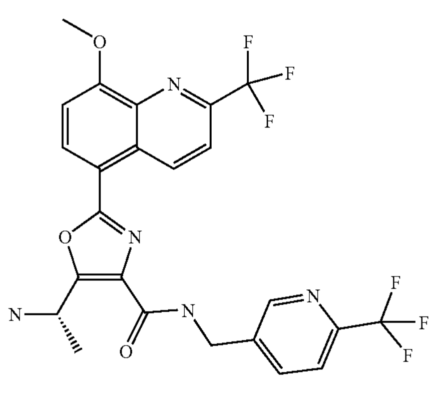 | 540 |

| Cpd. No. | Structure | MS (M + 1) |
|---|---|---|
| 26-482 | 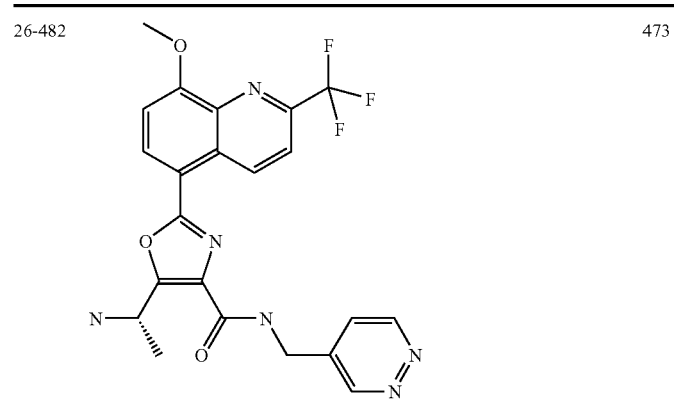 | 473 |
| 26-483 | 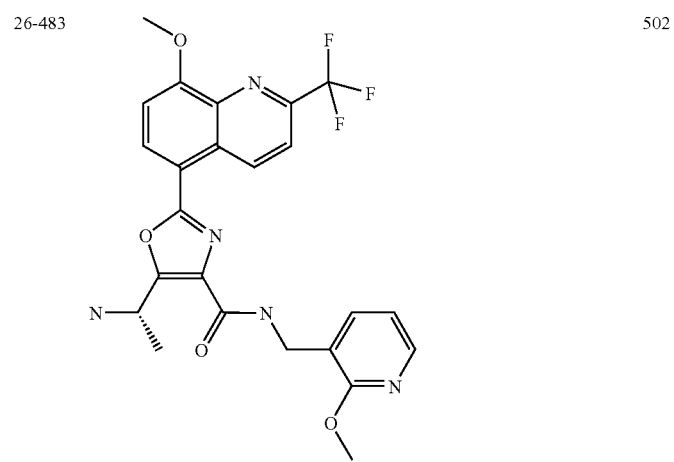 | 502 |
| 26-484 | 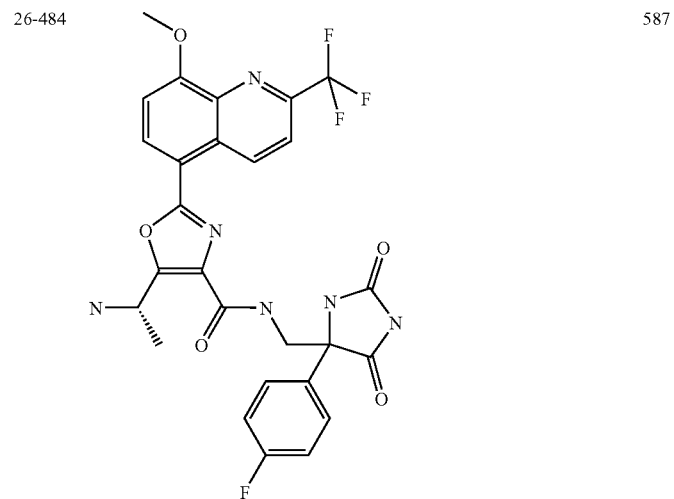 | 587 |

-continued

| Cpd. No. | Structure | MS (M + 1) |
|---|---|---|
| 26-485 | 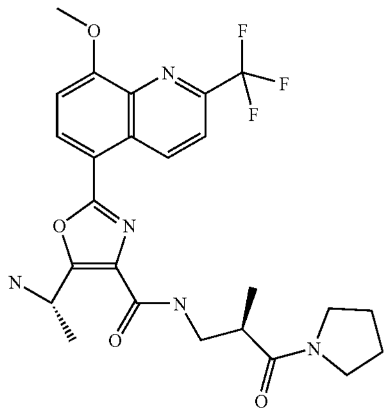 | 520 |
| 26-486 | 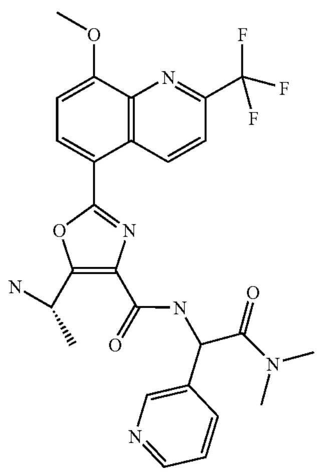 | 543 |
| 26-487 | 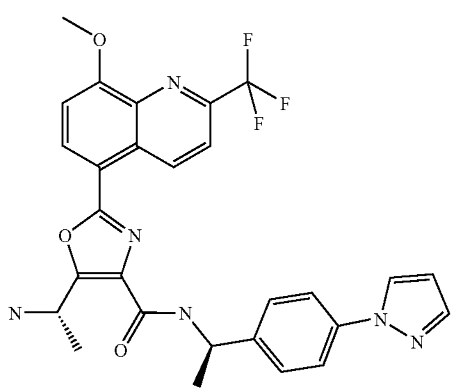 | 551 |

| Cpd. No. | Structure | MS (M + 1) |
|---|---|---|
| 26-488 | 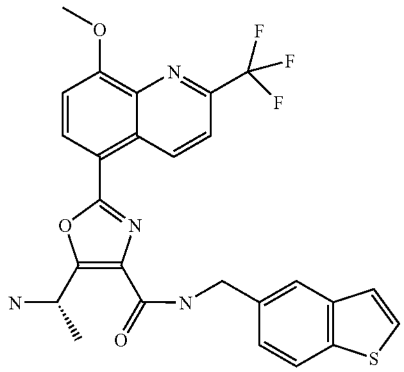 | 527 |
| 26-489 | 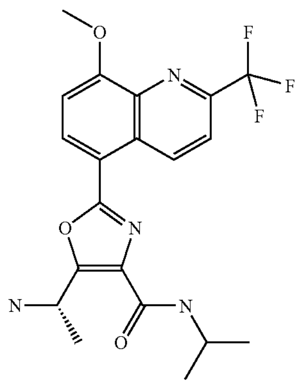 | 423 |
| 26-490 | 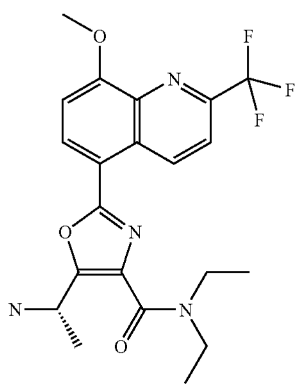 | 437 |
| 26-491 | 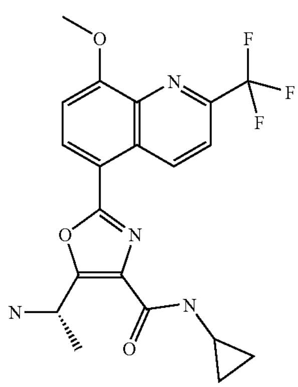 | 421 |

-continued

| Cpd. No. | Structure | MS (M + 1) |
|---|---|---|
| 26-492 | 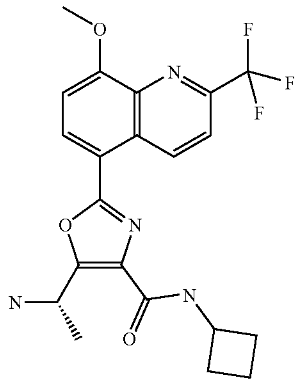 | 435 |
| 26-493 | 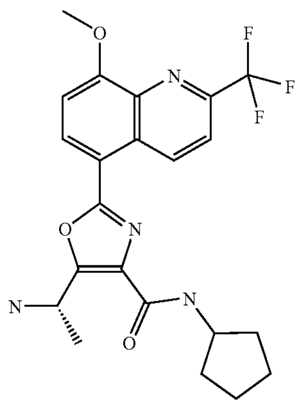 | 449 |
| 26-494 | 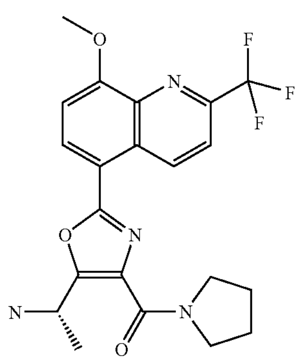 | 435 |

-continued
| Cpd. No. | Structure | MS (M + 1) |
|---|---|---|
| 26-495 | 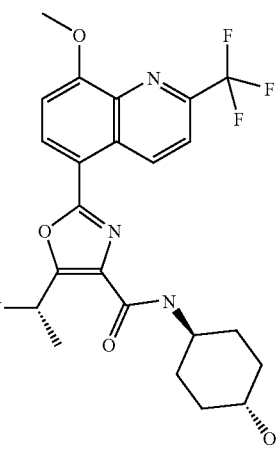 | 479 |
| 26-496 | 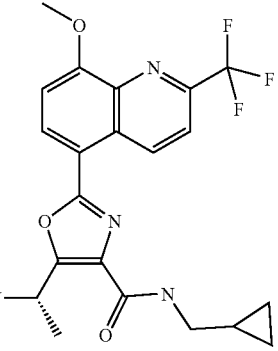 | 435 |
| 26-497 | 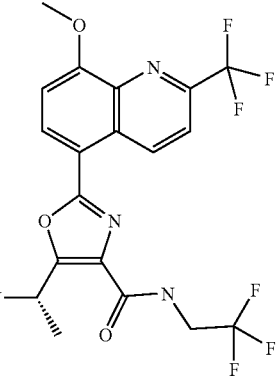 | 463 |

-continued
| Cpd. No. | Structure | MS (M + 1) |
|---|---|---|
| 26-498 | 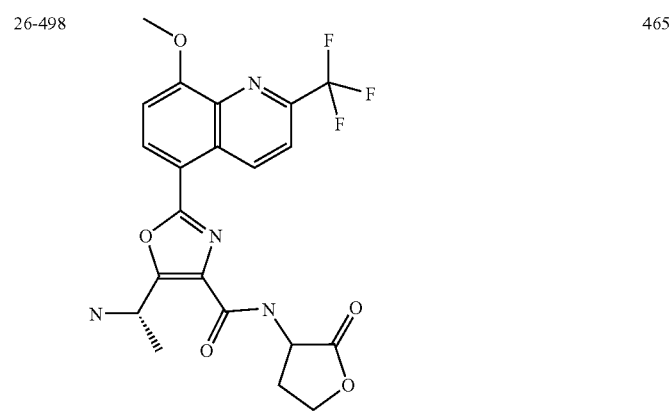 | 465 |
| 26-499 | 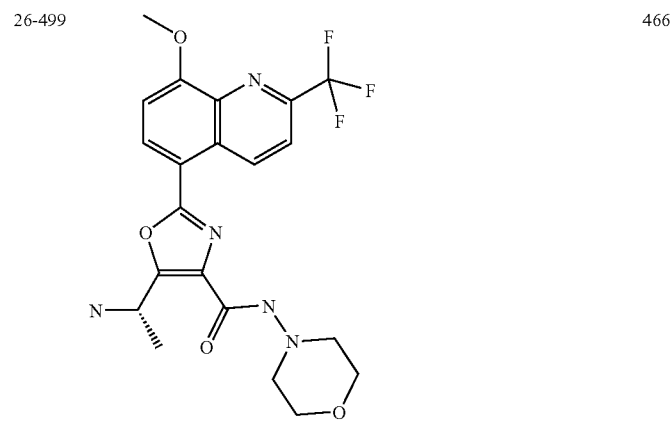 | 466 |
| 26-500 | 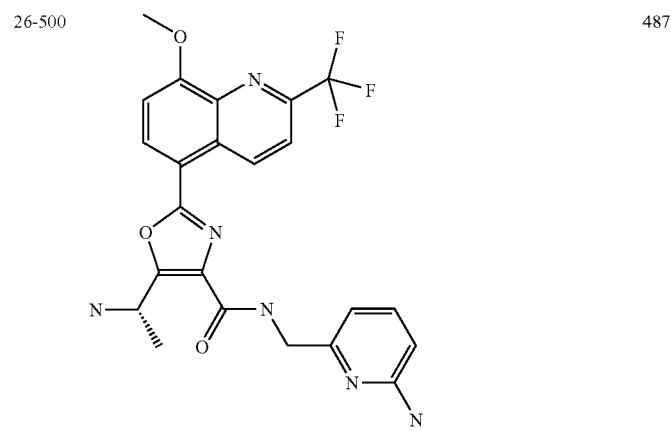 | 487 |

-continued
| Cpd. No. | Structure | MS (M + 1) |
|---|---|---|
| 26-501 | 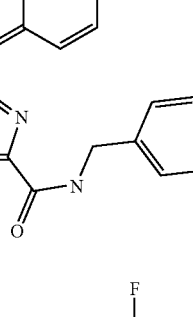 | 511 |
| 26-502 | 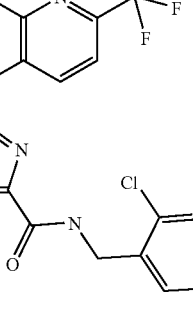 | 541, 543 |
| 26-503 | 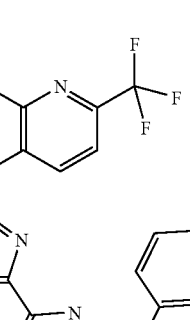 | 531 |
| 26-504 | 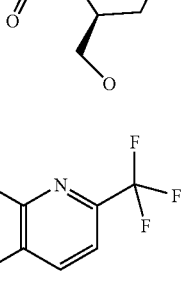 | 492 |

-continued

| Cpd. No. | Structure | MS (M + 1) |
|---|---|---|
| 26-505 | 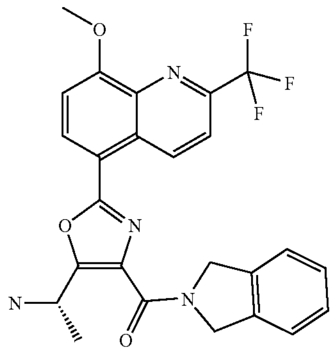 | 483 |
| 26-506 | 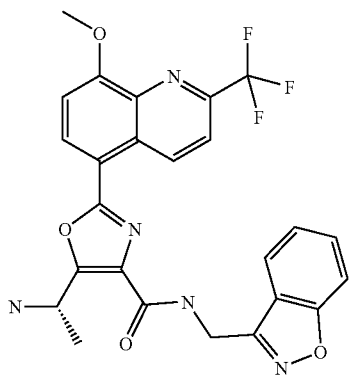 | 512 |
| 26-507 | 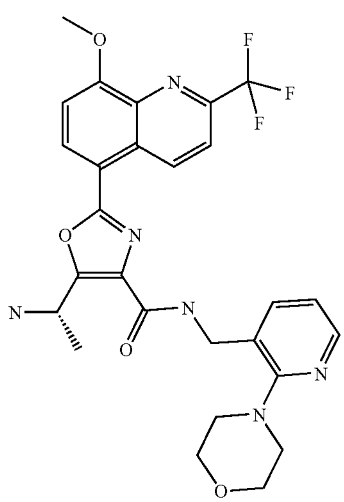 | 557 |

-continued
| Cpd. No. | Structure | MS (M + 1) |
|---|---|---|
| 26-508 | 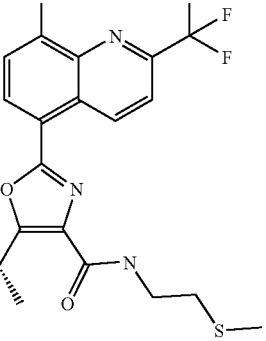 | 455 |
| 26-509 | 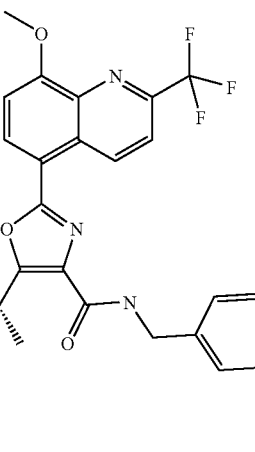 | 549 |
| 26-510 | 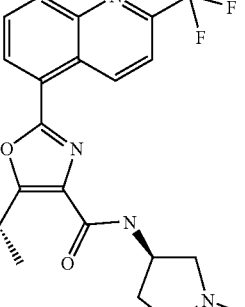 | 518 |

| Cpd. No. | Structure | MS (M + 1) |
|---|---|---|
| 26-511 | 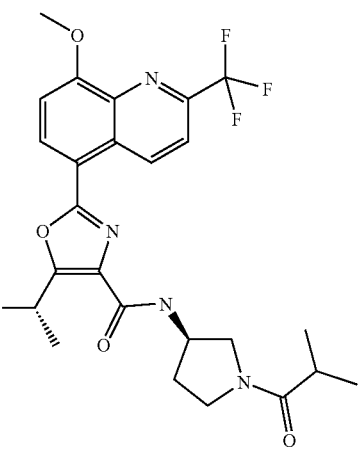 | 520 |
| 26-512 | 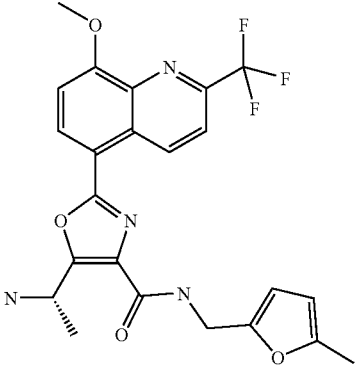 | 475 |
| 26-513 | 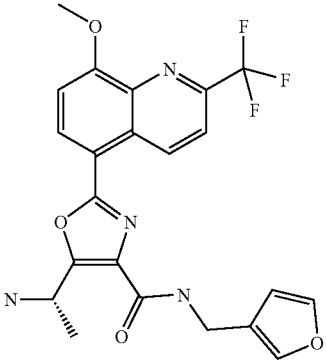 | 461 |

| Cpd. No. | Structure | MS (M + 1) |
|---|---|---|
| 26-514 | 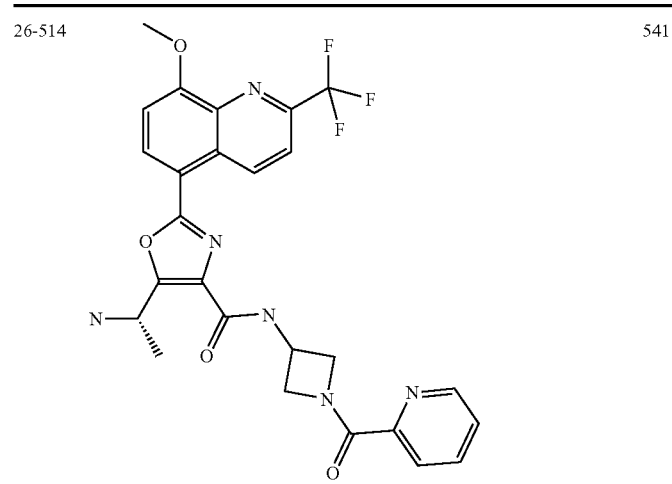 | 541 |
| 26-515 | 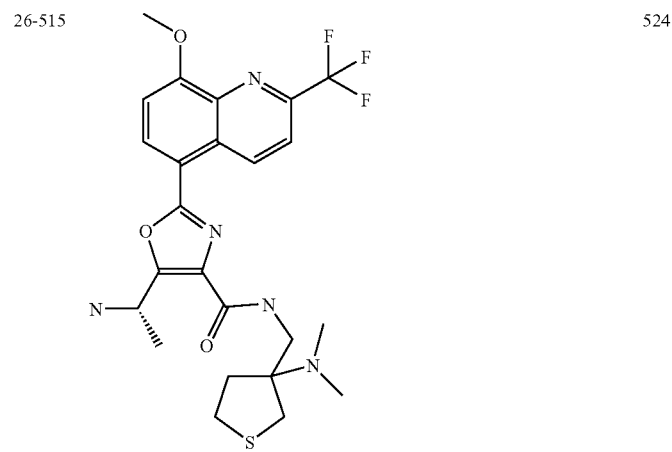 | 524 |
| 26-516 | 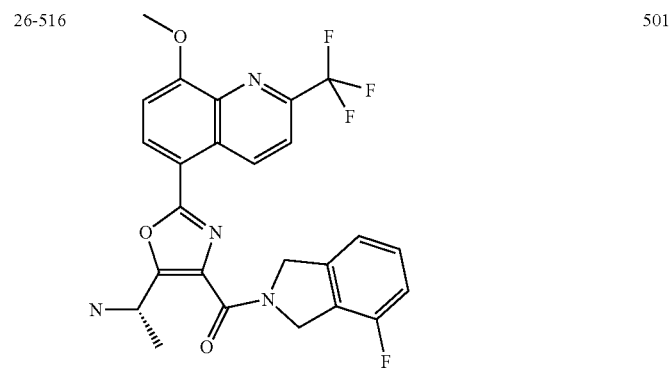 | 501 |

-continued
| Cpd. No. | Structure | MS (M + 1) |
|---|---|---|
| 26-517 | 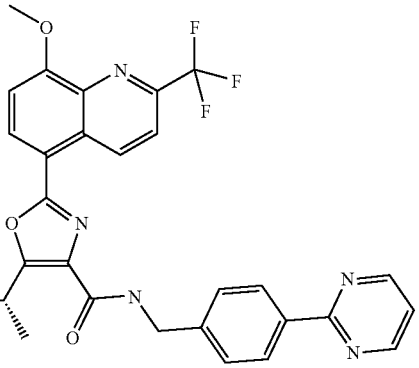 | 549 |
| 26-518 | 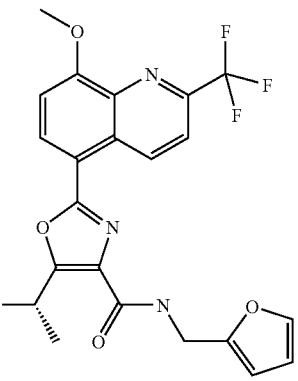 | 461 |
| 26-519 | 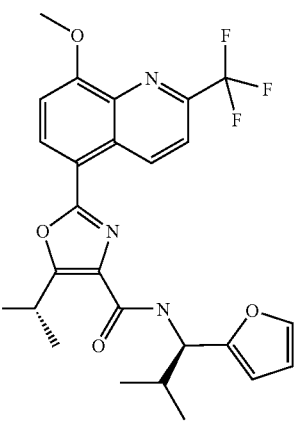 | 503 |

| Cpd. No. | Structure | MS (M + 1) |
|---|---|---|
| 26-520 | 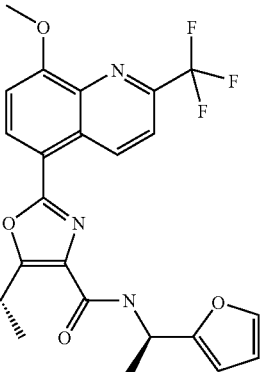 | 517 |
| 26-521 | 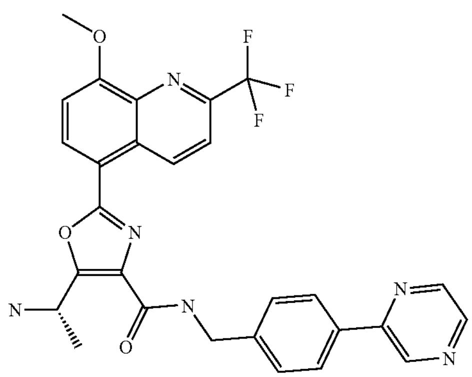 | 549 |
| 26-522 | 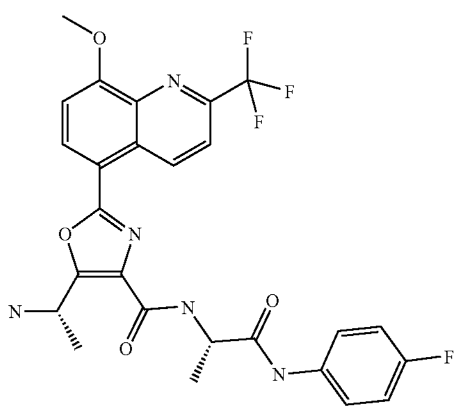 | 546 |

| Cpd. No. | Structure | MS (M + 1) |
|---|---|---|
| 26-523 | 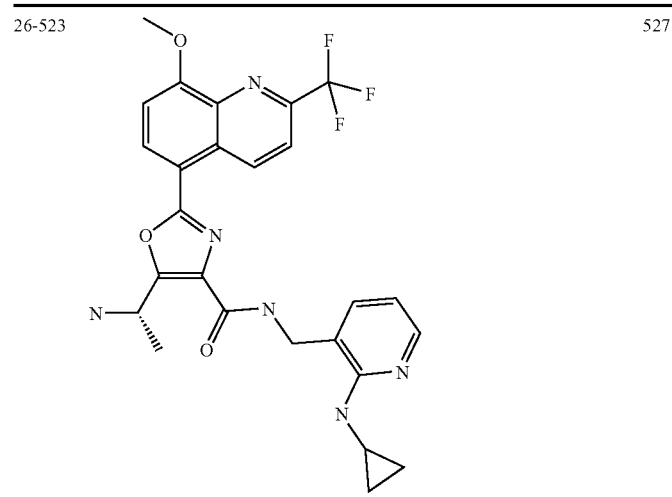 | 527 |
| 26-524 | 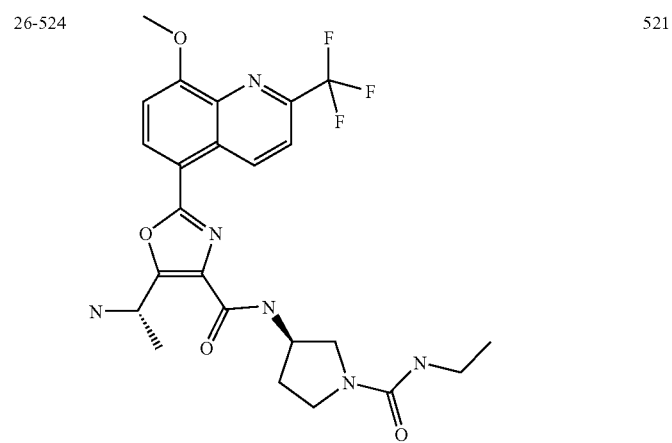 | 521 |
| 26-525 | 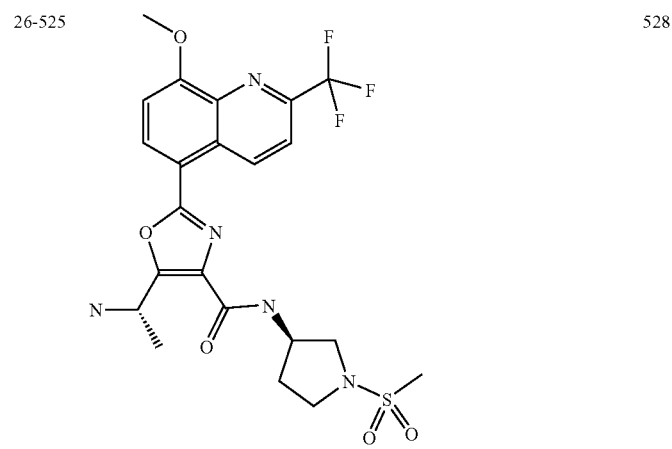 | 528 |

| Cpd. No. | Structure | MS (M + 1) |
|---|---|---|
| 26-526 | 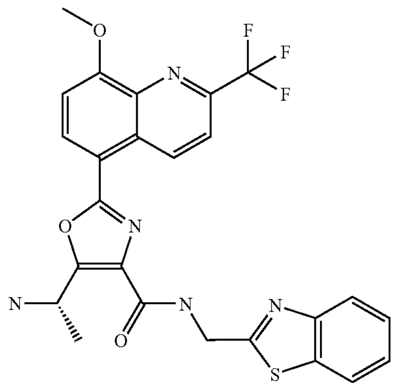 | 528 |
| 26-527 | 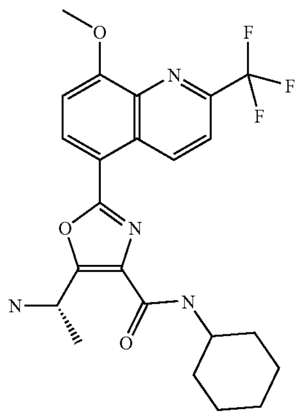 | 463 |
| 26-528 | 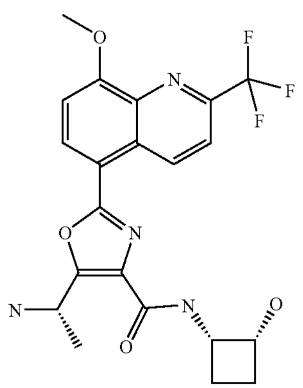 | 451 |
| 26-529 | 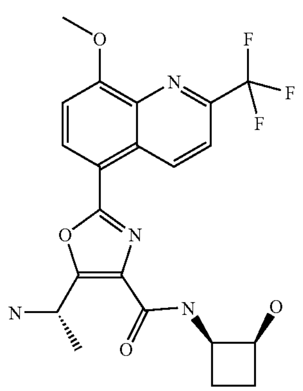 | 451 |

| Cpd. No. | Structure | MS (M + 1) |
|---|---|---|
| 26-530 | 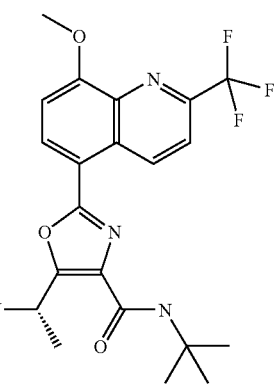 | 437 |
| 26-531 | 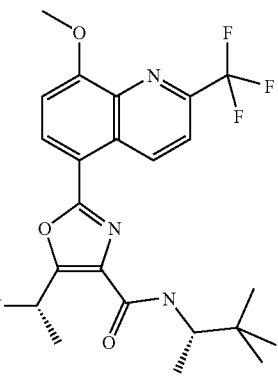 | 465 |
| 26-532 | 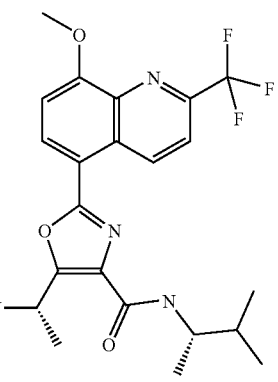 | 451 |
| 26-533 | 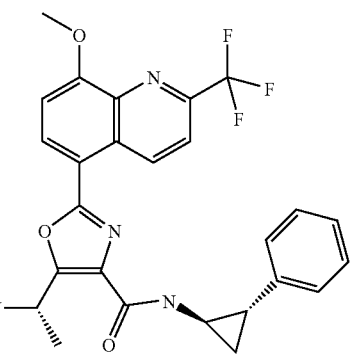 | 497 |

| Cpd. No. | Structure | MS (M + 1) |
|---|---|---|
| 26-534 | 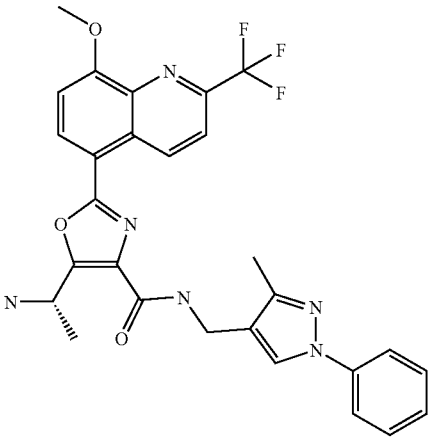 | 552 |
| 26-535 | 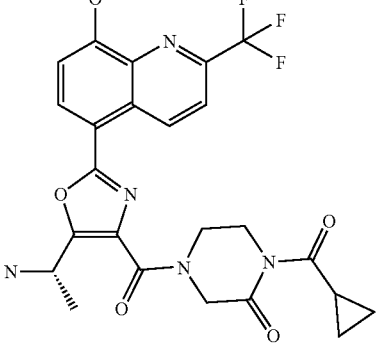 | 532 |
| 26-536 | 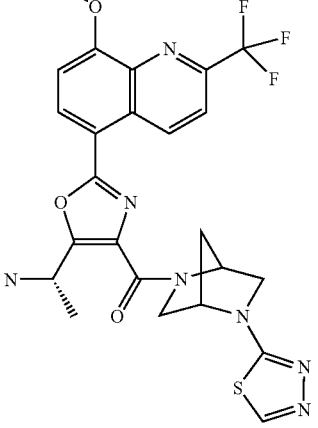 | 546 |

-continued
| Cpd. No. | Structure | MS (M + 1) |
|---|---|---|
| 26-537 | 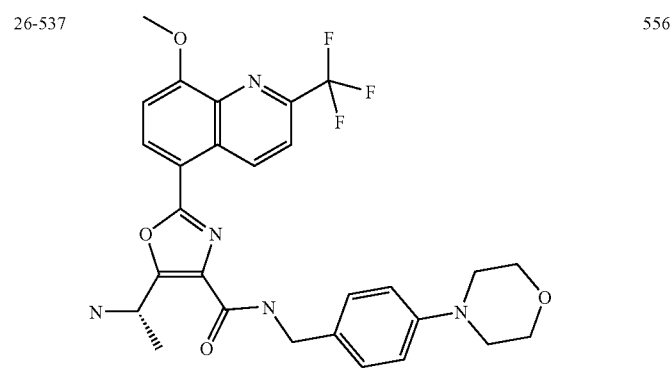 | 556 |
| 26-538 | 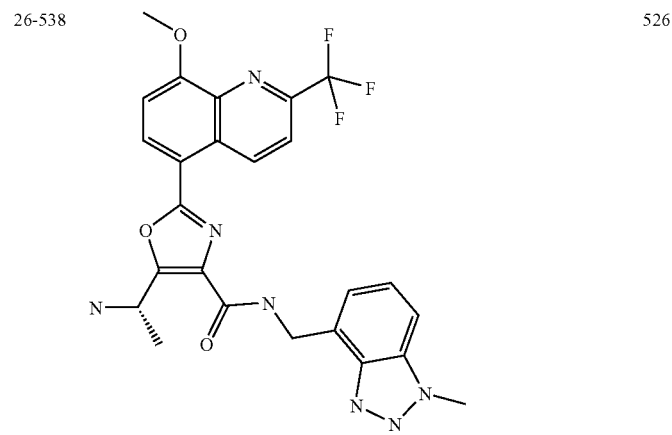 | 526 |
| 26-539 | 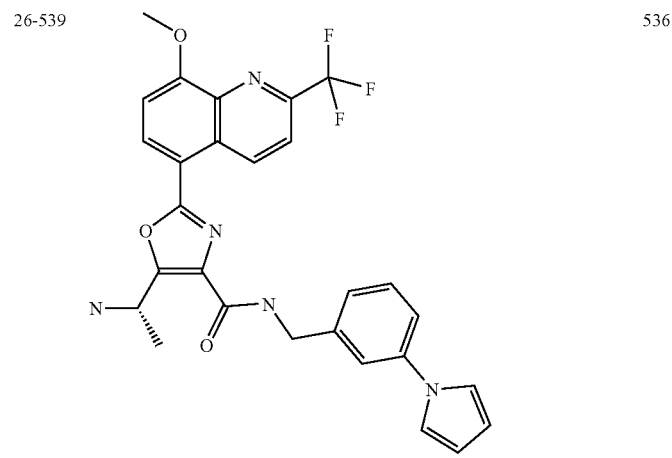 | 536 |

-continued

| Cpd. No. | Structure | MS (M + 1) |
|---|---|---|
| 26-540 | 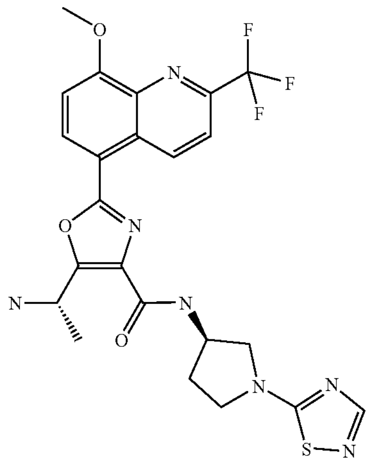 | 534 |
| 26-541 | 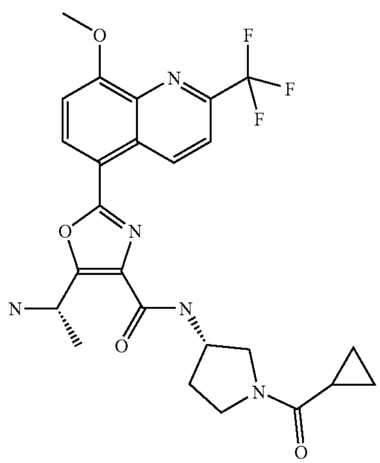 | 518 |
| 26-542 | 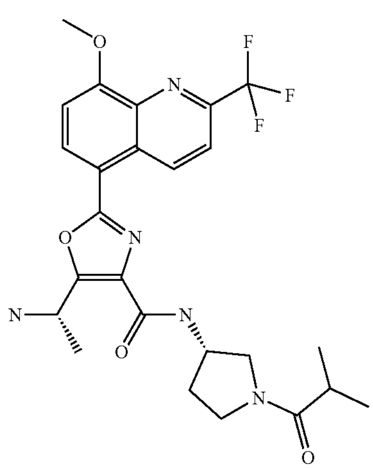 | 520 |

| Cpd. No. | Structure | MS (M + 1) |
|---|---|---|
| 26-543 | 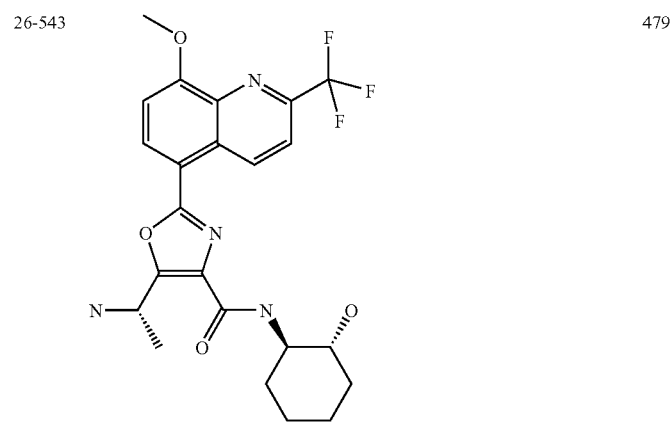 | 479 |
| 26-544 | 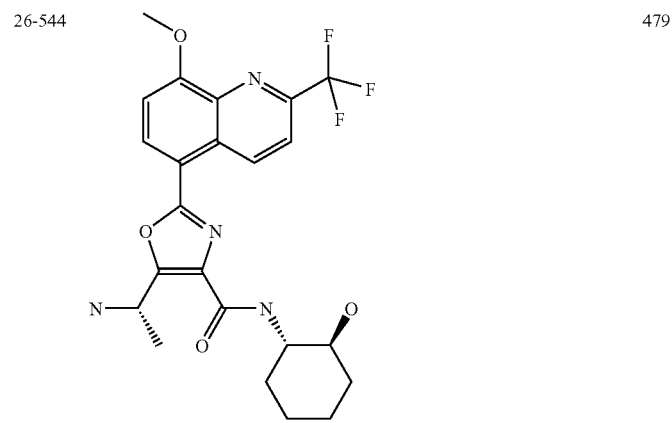 | 479 |
| 26-545 | 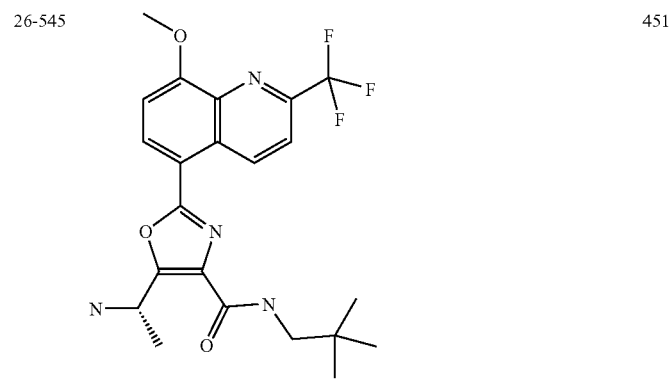 | 451 |

| Cpd. No. | Structure | MS (M + 1) |
|---|---|---|
| 26-546 | 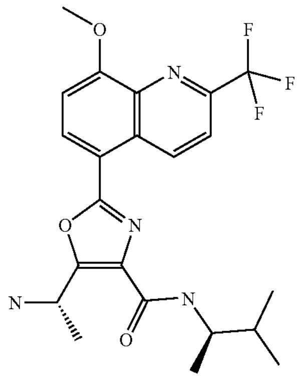 | 451 |
| 26-547 | 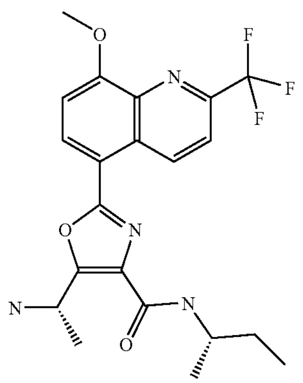 | 437 |
| 26-548 | 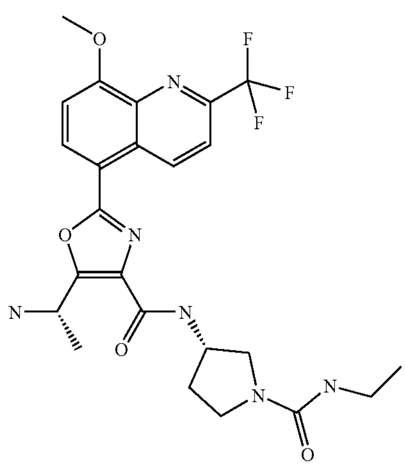 | 521 |

| Cpd. No. | Structure | MS (M + 1) |
|---|---|---|
| 26-549 | 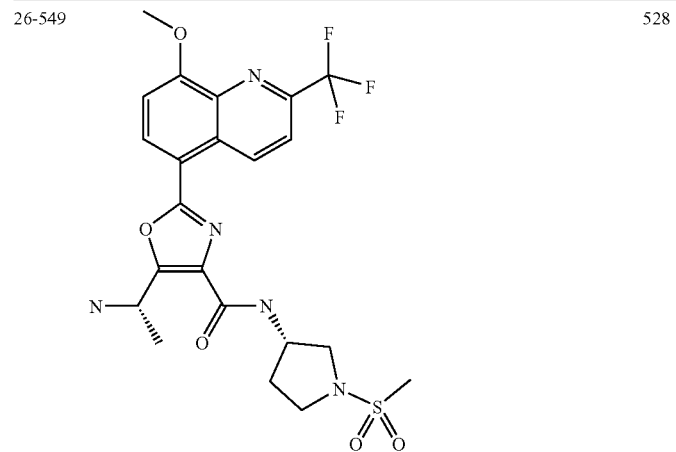 | 528 |
| 26-550 | 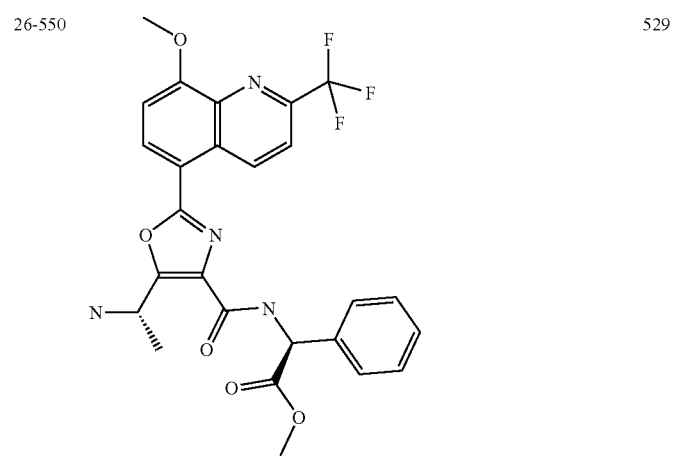 | 529 |
| 26-551 | 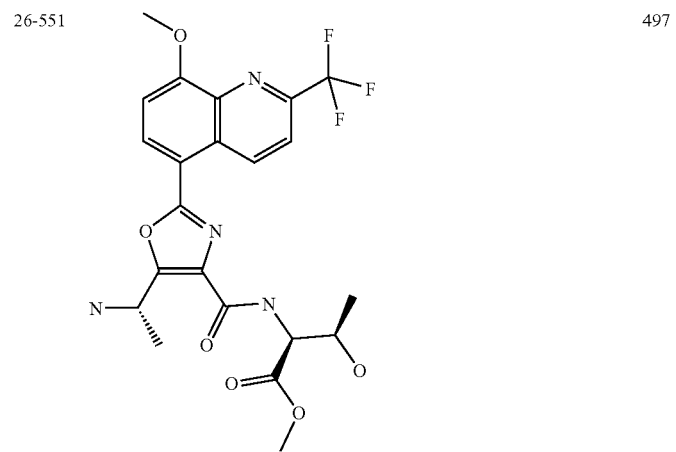 | 497 |

-continued

| Cpd. No. | Structure | MS (M + 1) |
|---|---|---|
| 26-552 | 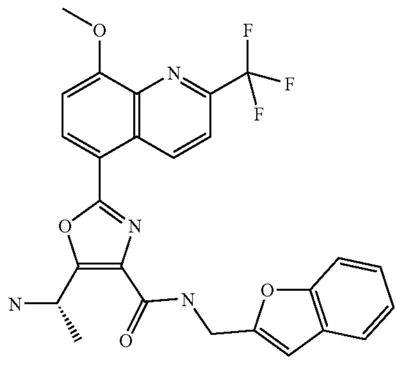 | 511 |
| 26-553 | 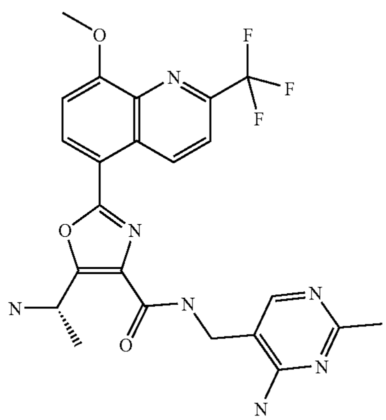 | 502 |
| 26-554 | 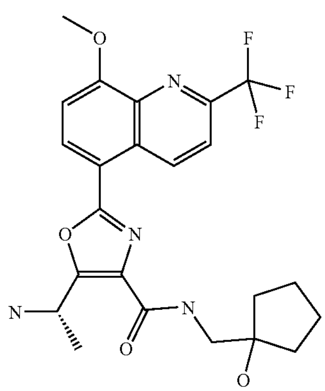 | 479 |
| 26-555 | 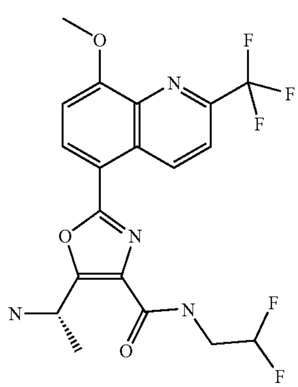 | 445 |

-continued
| Cpd. No. | Structure | MS (M + 1) |
|---|---|---|
| 26-556 | 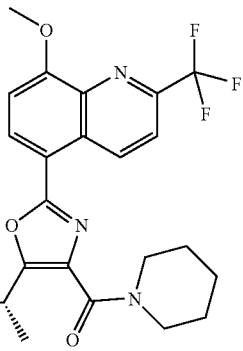 | 449 |
| 26-557 | 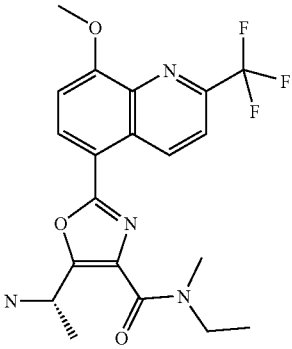 | 423 |
| 26-558 | 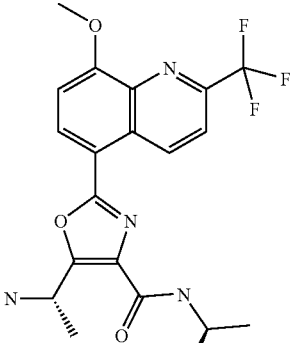 | 437 |
| 26-559 | 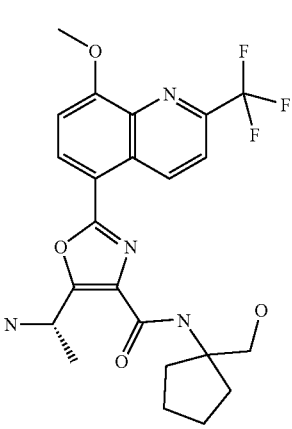 | 479 |

| Cpd. No. | Structure | MS (M + 1) |
|---|---|---|
| 26-560 | 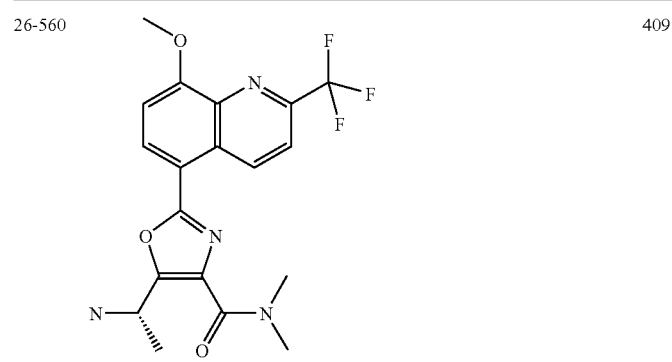 | 409 |
| 26-561 | 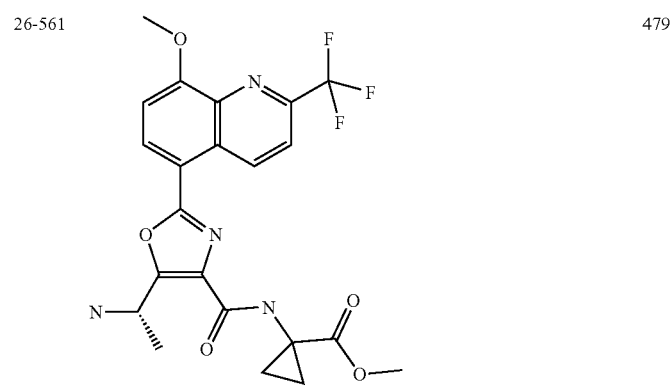 | 479 |
| 26-562 | 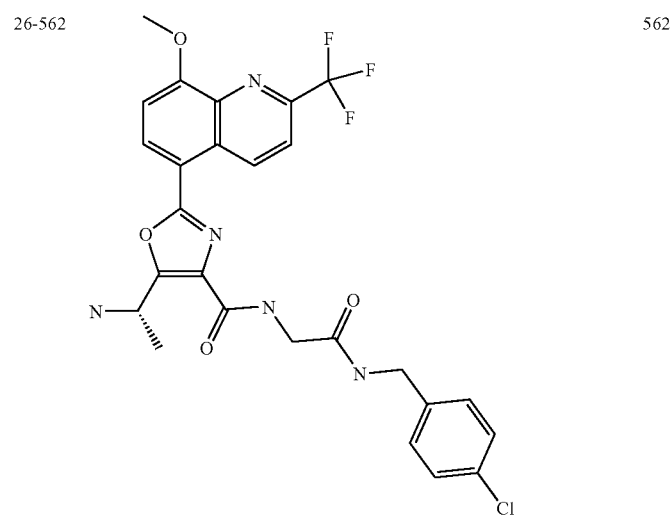 | 562 |

| Cpd. No. | Structure | MS (M + 1) |
|---|---|---|
| 26-563 | 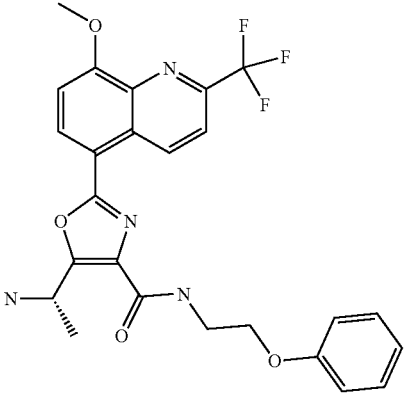 | 501 |
| 26-564 | 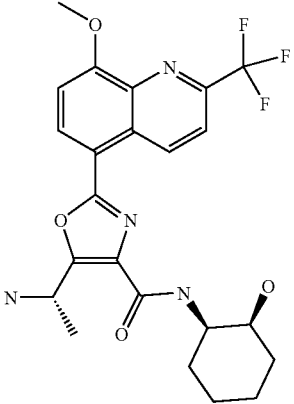 | 479 |
| 26-565 | 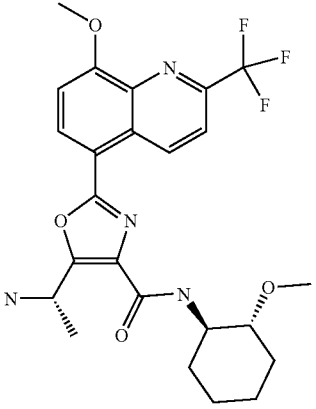 | 493 |

-continued

| Cpd. No. | Structure | MS (M + 1) |
|---|---|---|
| 26-566 | 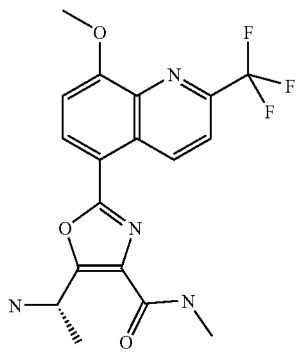 | 395 |
| 26-567 | 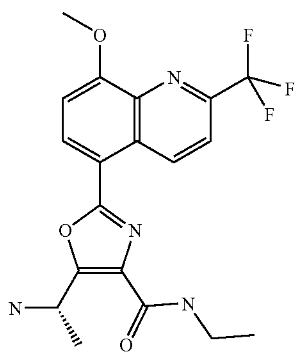 | 409 |
| 26-568 | 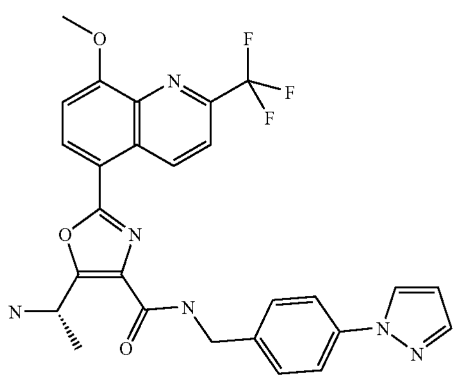 | 537 |
| 26-569 | 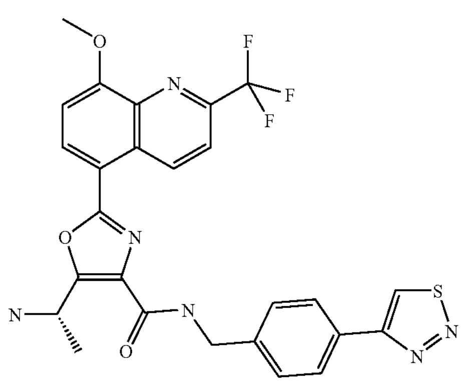 | 555 |

-continued
| Cpd. No. | Structure | MS (M + 1) |
|---|---|---|
| 26-570 | 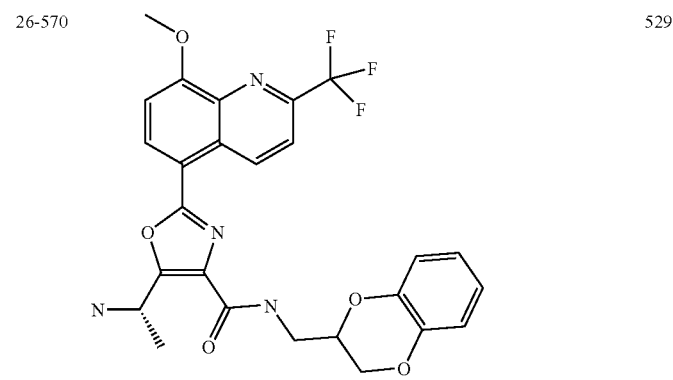 | 529 |
| 26-571 | 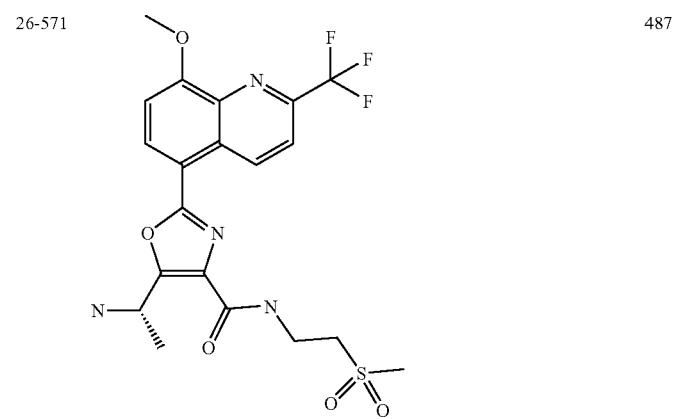 | 487 |
| 26-572 | 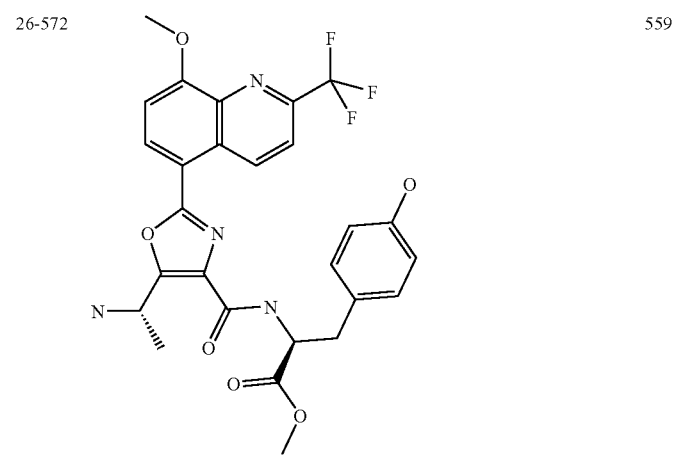 | 559 |

-continued

| Cpd. No. | Structure | MS (M + 1) |
|---|---|---|
| 26-573 | 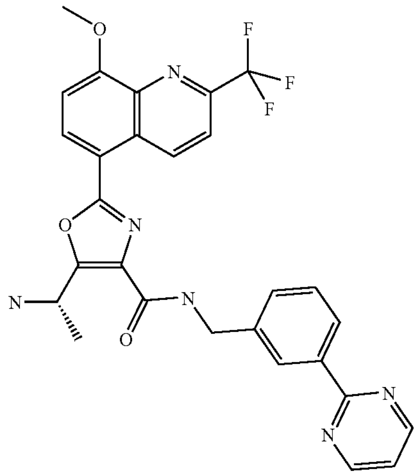 | 549 |
| 26-574 | 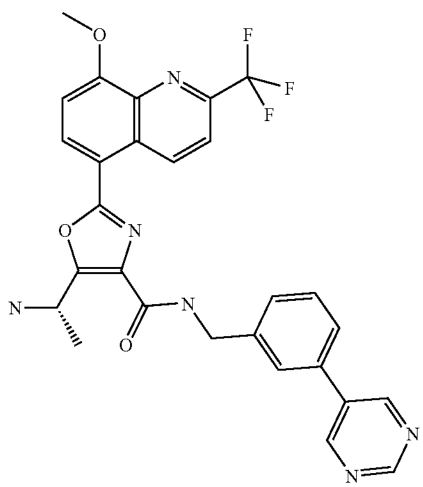 | 549 |
| 26-575 | 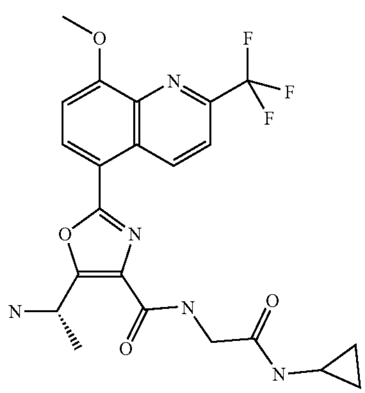 | 478 |

-continued

| Cpd. No. | Structure | MS (M + 1) |
|---|---|---|
| 26-576 | 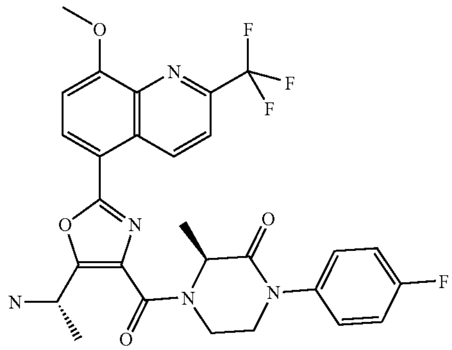 | 572 |
| 26-577 | 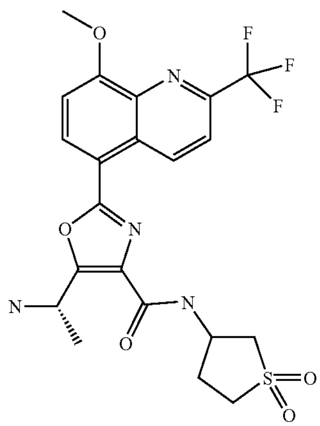 | 499 |
| 26-578 | 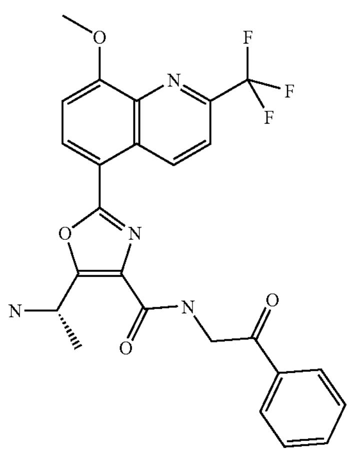 | 499 |

-continued
| Cpd. No. | Structure | MS (M + 1) |
|---|---|---|
| 26-579 | 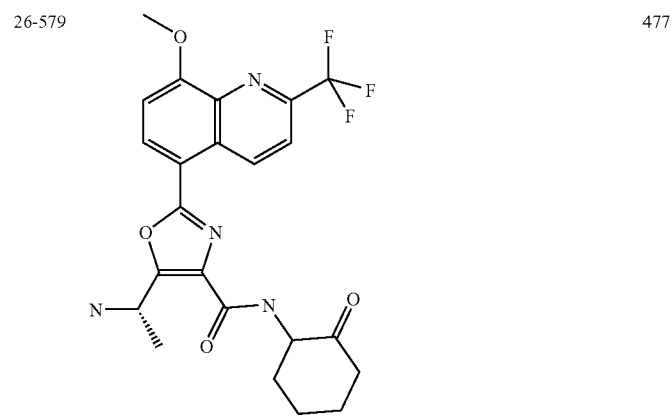 | 477 |
| 26-580 | 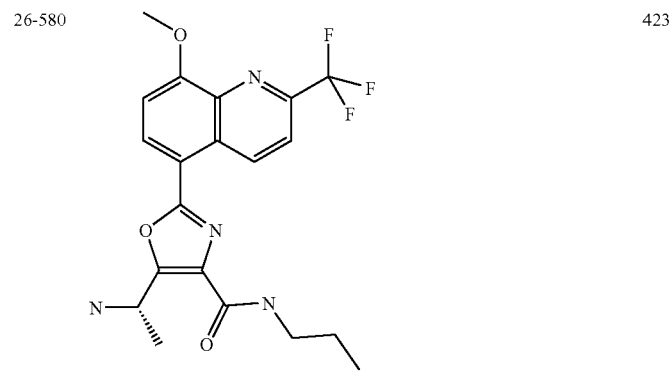 | 423 |
| 26-581 | 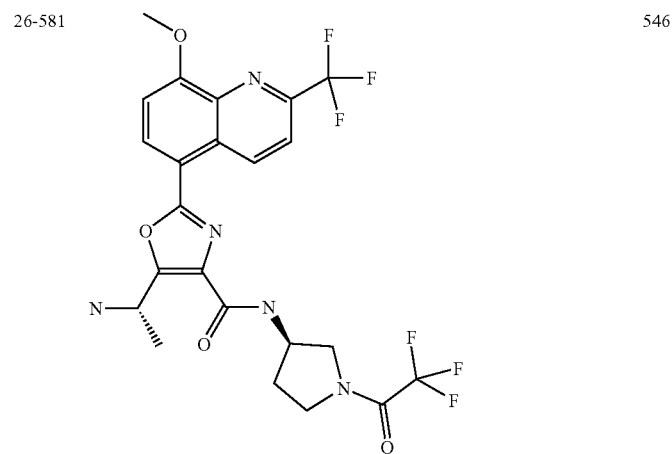 | 546 |

-continued

| Cpd. No. | Structure | MS (M + 1) |
|---|---|---|
| 26-582 | 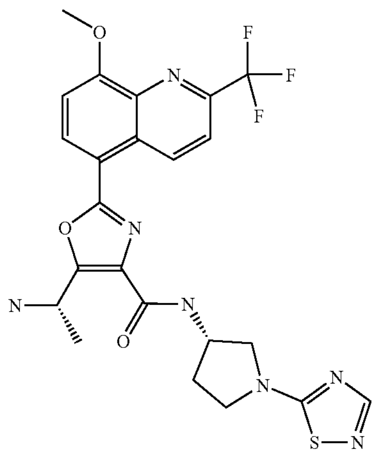 | 534 |
| 26-583 | 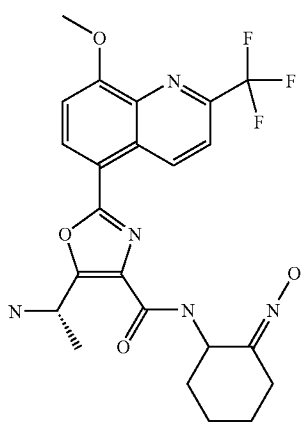 | 492 |
| 26-584 | 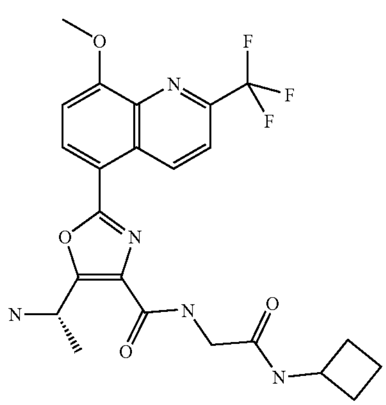 | 492 |

-continued

| Cpd. No. | Structure | MS (M + 1) |
|---|---|---|
| 26-585 | 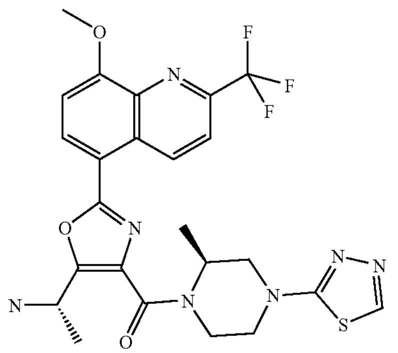 | 548 |
| 26-586 | 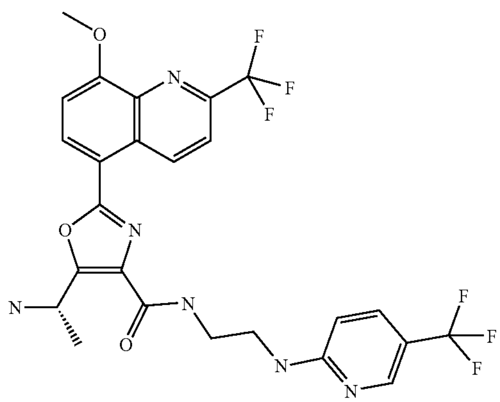 | 569 |
| 26-587 | 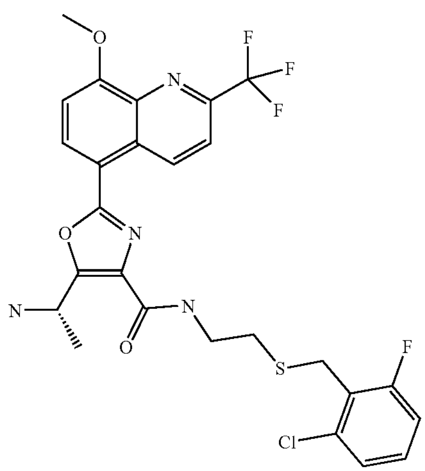 | 583 |
| 26-588 | 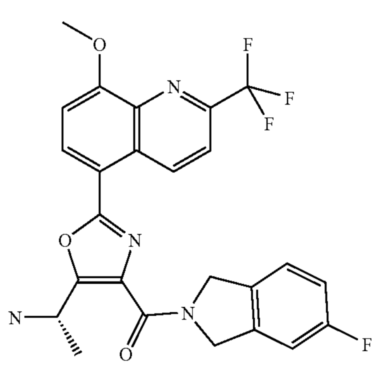 | 501 |

-continued
| Cpd. No. | Structure | MS (M + 1) |
|---|---|---|
| 26-589 | 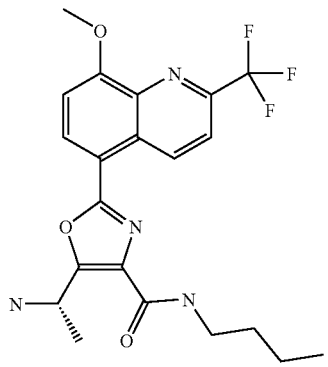 | 437 |
| 26-590 | 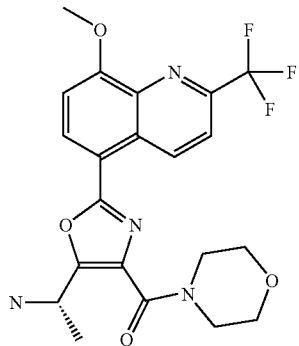 | 451 |
| 26-591 | 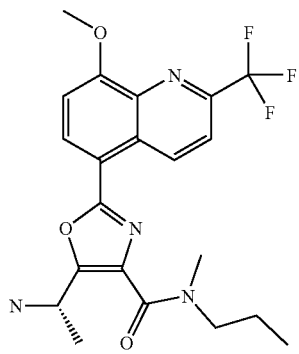 | 437 |
| 26-592 | 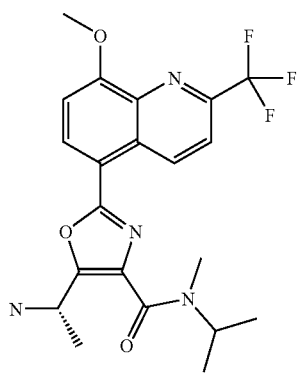 | 437 |

-continued

| Cpd. No. | Structure | MS (M + 1) |
|---|---|---|
| 26-593 | 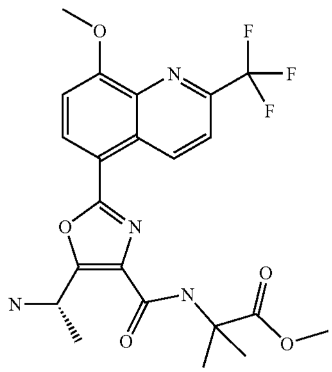 | 481 |
| 26-594 | 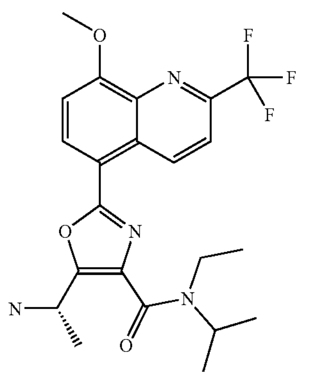 | 451 |
| 26-595 | 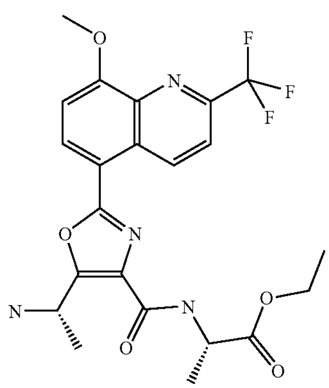 | 481 |
| 26-596 | 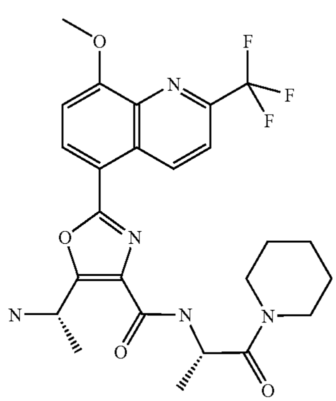 | 520 |

-continued
| Cpd. No. | Structure | MS (M + 1) |
|---|---|---|
| 26-597 | 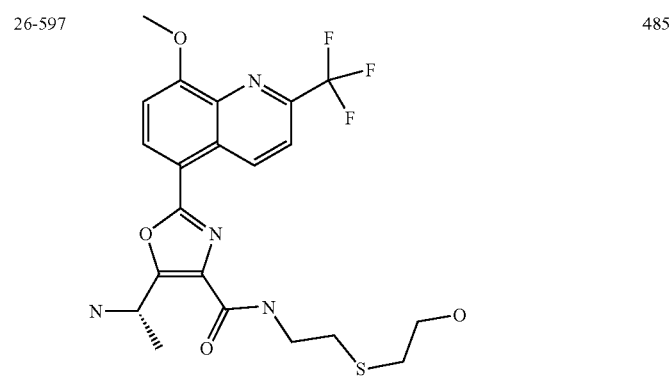 | 485 |
| 26-598 | 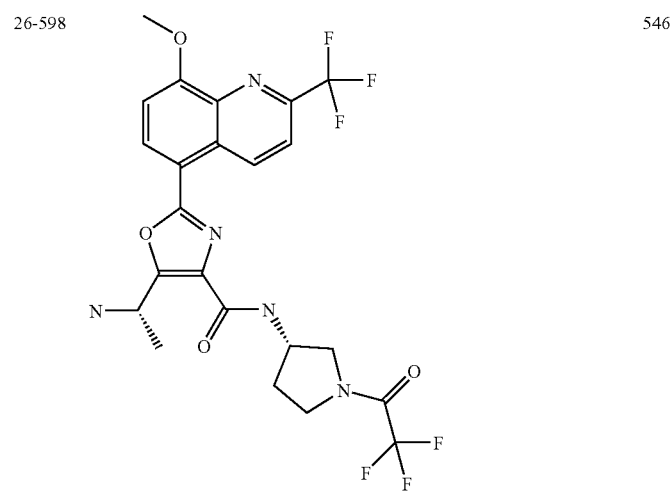 | 546 |
| 26-599 | 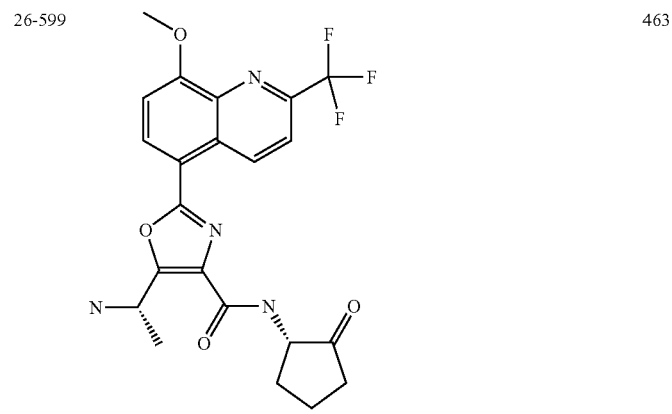 | 463 |

-continued
| Cpd. No. | Structure | MS (M + 1) |
|---|---|---|
| 26-600 | 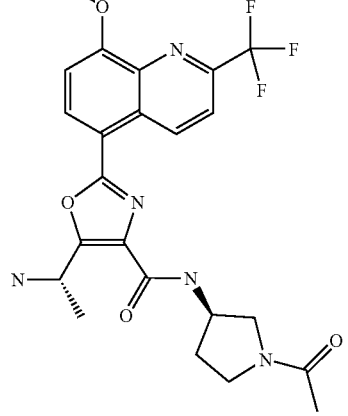 | 492 |
| 26-601 | 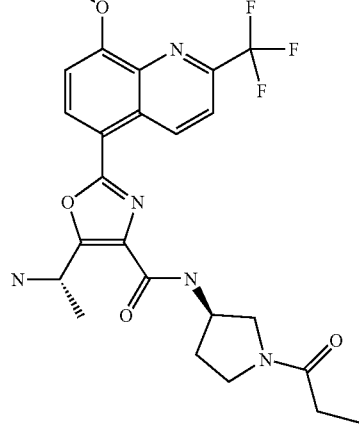 | 506 |
| 26-602 | 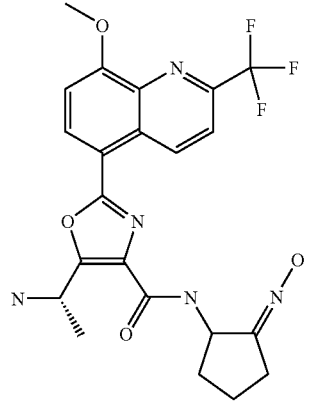 | 478 |

-continued
| Cpd. No. | Structure | MS (M + 1) |
|---|---|---|
| 26-603 | 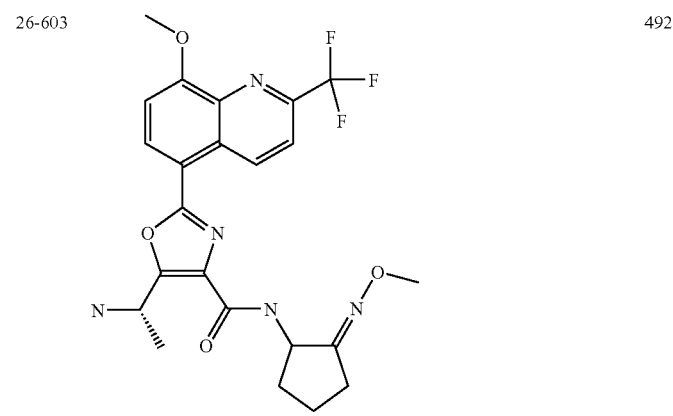 | 492 |
| 26-604 | 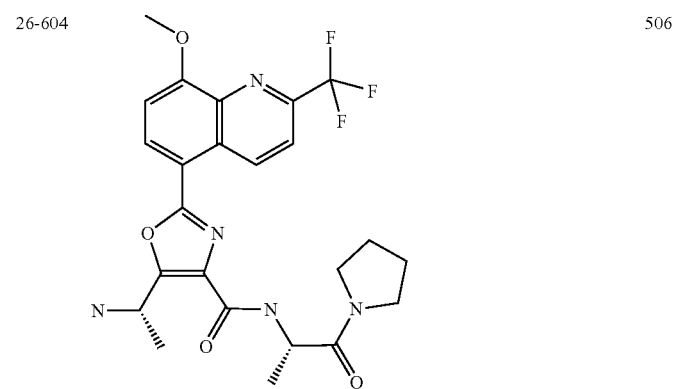 | 506 |
| 26-605 | 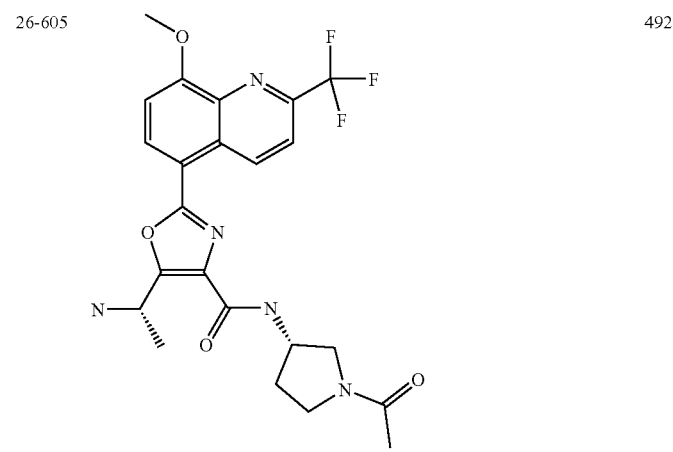 | 492 |

-continued

| Cpd. No. | Structure | MS (M + 1) |
|---|---|---|
| 26-606 | 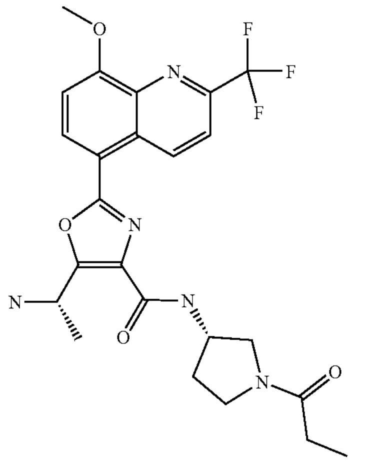 | 506 |
| 26-607 | 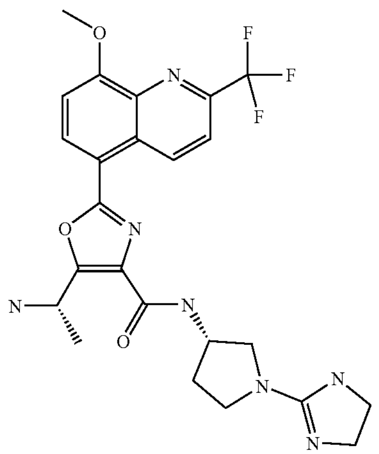 | 518 |
| 26-608 | 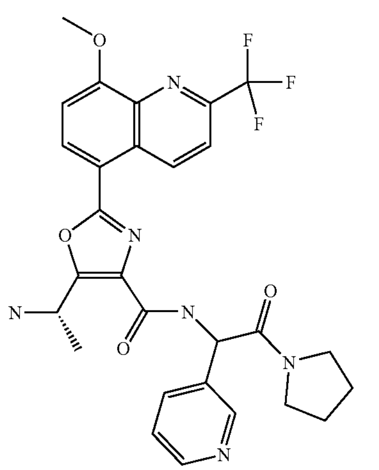 | 569 |

-continued
| Cpd. No. | Structure | MS (M + 1) |
|---|---|---|
| 26-609 | 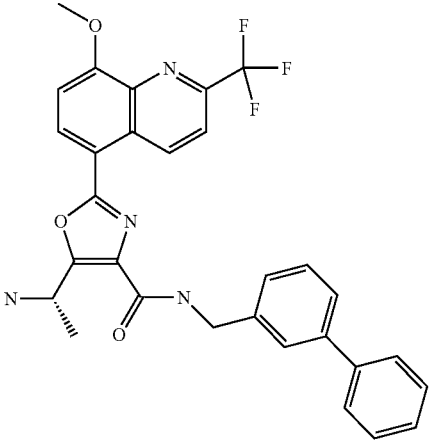 | 547 |
| 26-610 | 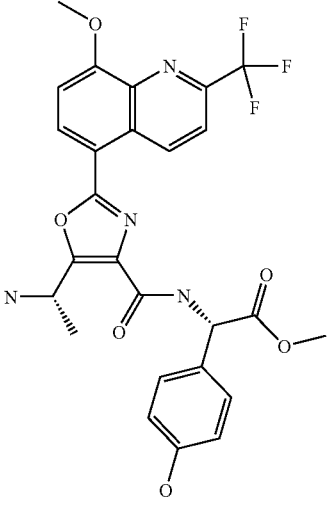 | 545 |
| 26-611 | 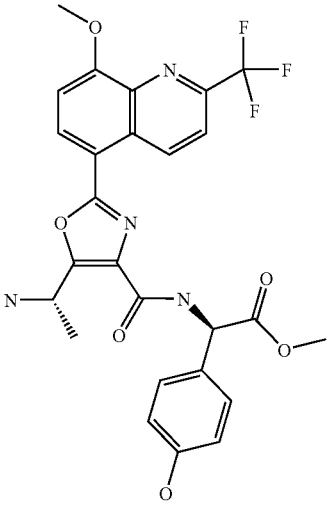 | 545 |

-continued

| Cpd. No. | Structure | MS (M + 1) |
|---|---|---|
| 26-612 | 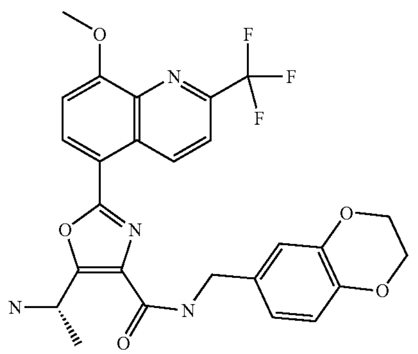 | 529 |
| 26-613 | 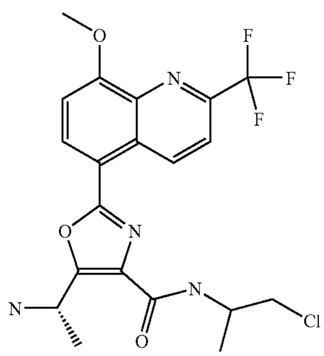 | 457 |
| 26-614 | 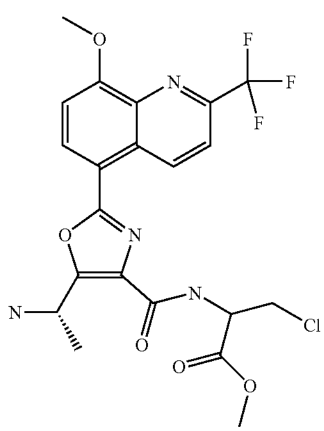 | 501 |
| 26-615 | 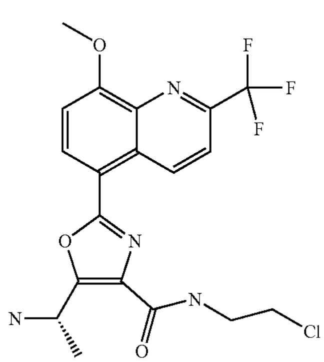 | 443 |

-continued

| Cpd. No. | Structure | MS (M + 1) |
|---|---|---|
| 26-616 | 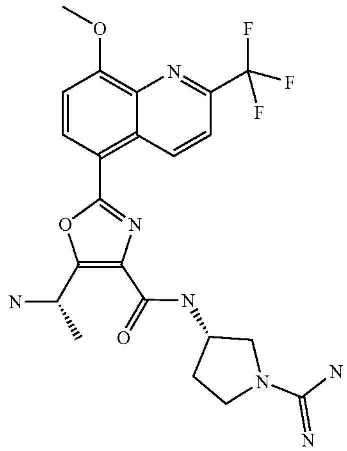 | 492 |
| 26-617 | 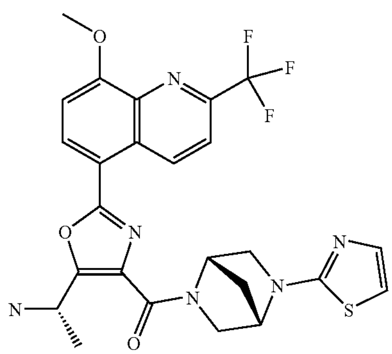 | 545 |
| 26-618 | 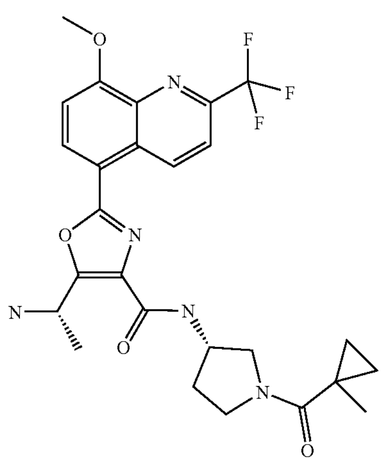 | 532 |

| Cpd. No. | Structure | MS (M + 1) |
|---|---|---|
| 26-619 | 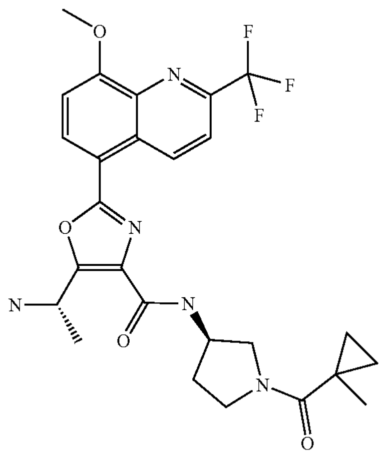 | 532 |
| 26-620 | 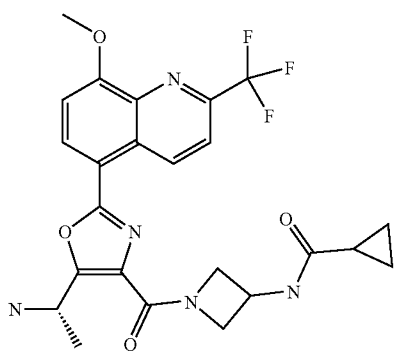 | 504 |
| 26-621 | 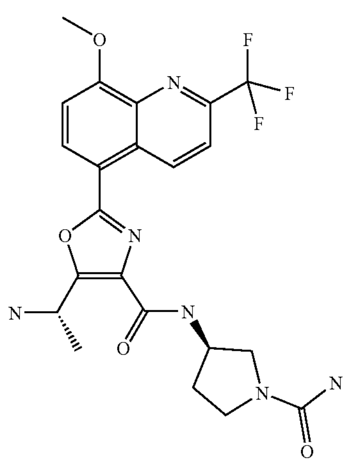 | 492 |

| Cpd. No. | Structure | MS (M + 1) |
|---|---|---|
| 26-622 | 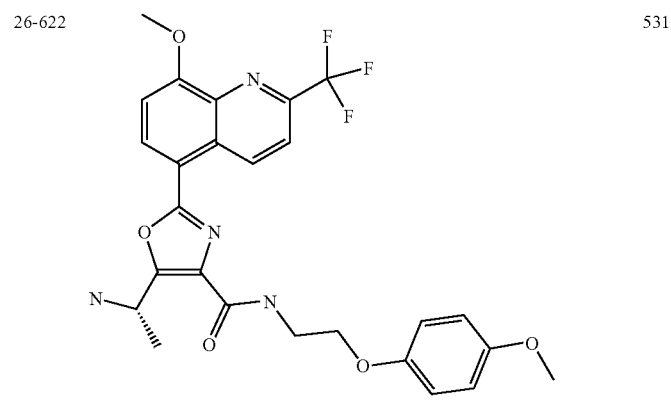 | 531 |
| 26-623 | 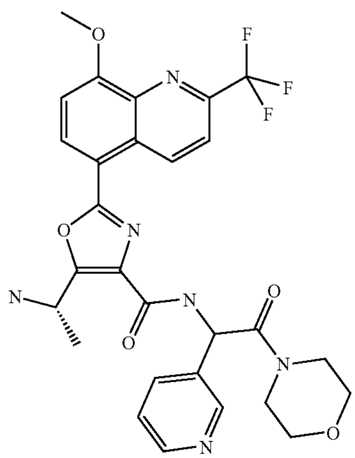 | 585 |
| 26-624 | 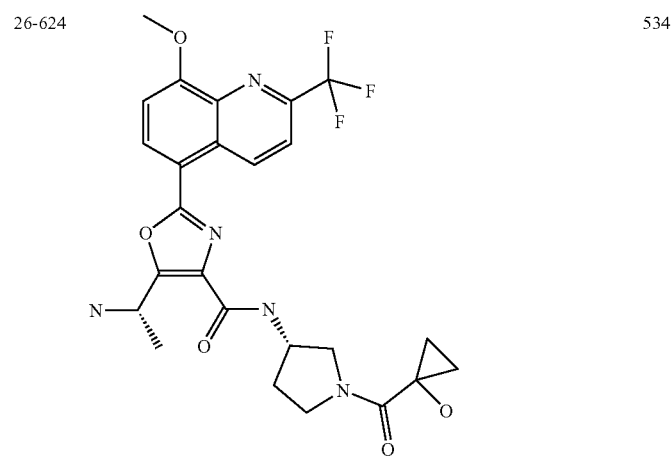 | 534 |

| Cpd. No. | Structure | MS (M + 1) |
|---|---|---|
| 26-625 | 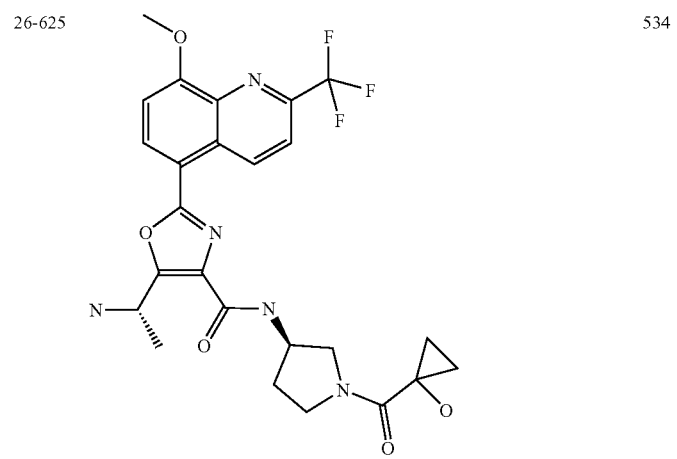 | 534 |
| 26-626 | 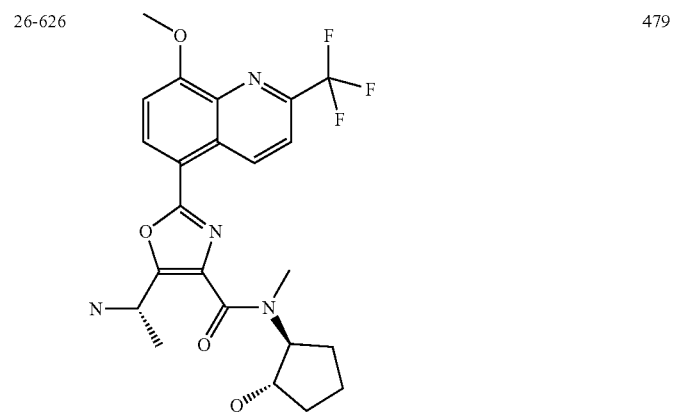 | 479 |
| 26-627 | 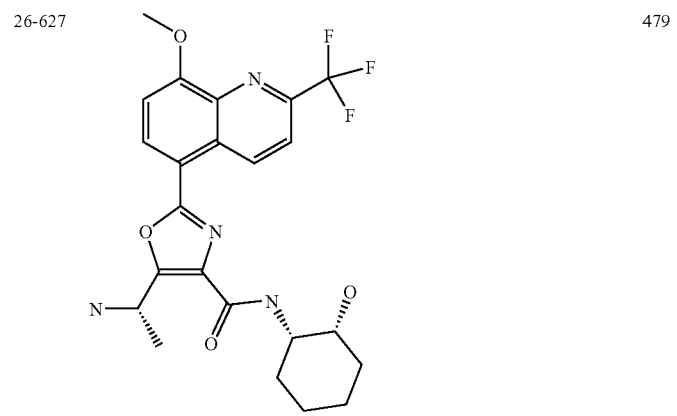 | 479 |

| Cpd. No. | Structure | MS (M + 1) |
|---|---|---|
| 26-628 | 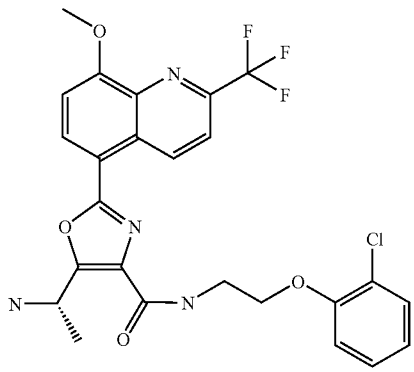 | 535 |
| 26-629 | 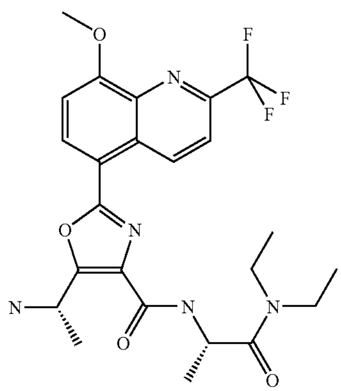 | 508 |
| 26-630 | 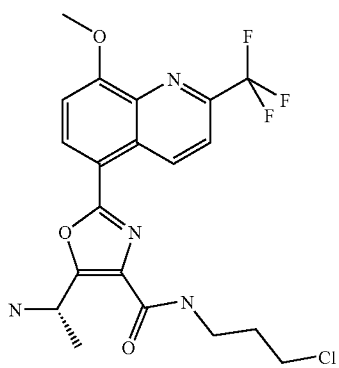 | 457 |
| 26-631 | 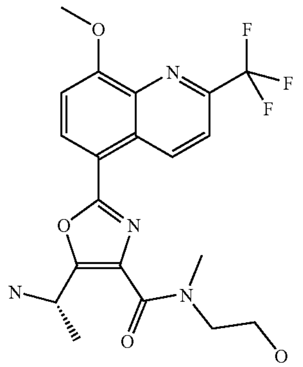 | 439 |

-continued

| Cpd. No. | Structure | MS (M + 1) |
|---|---|---|
| 26-632 | 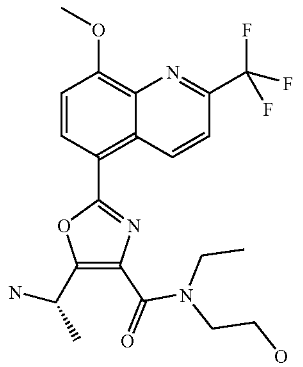 | 453 |
| 26-633 | 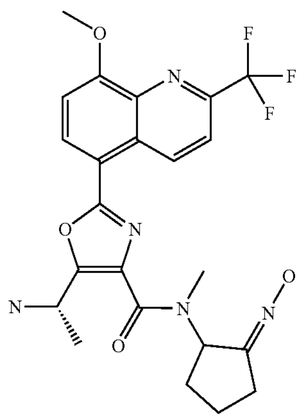 | 492 |
| 26-634 | 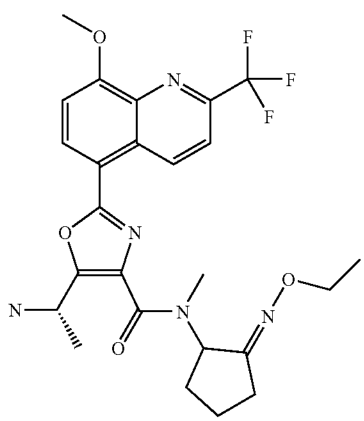 | 520 |
| 26-635 | 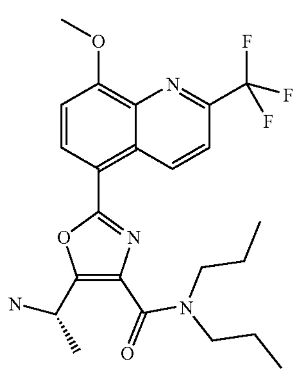 | 465 |

| Cpd. No. | Structure | MS (M + 1) |
|---|---|---|
| 26-636 | 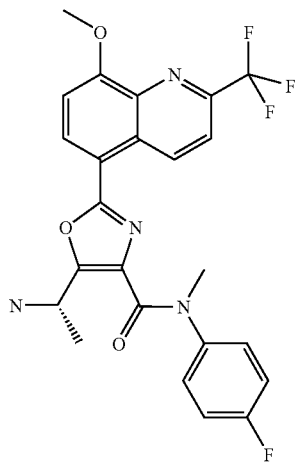 | 489 |
| 26-637 | 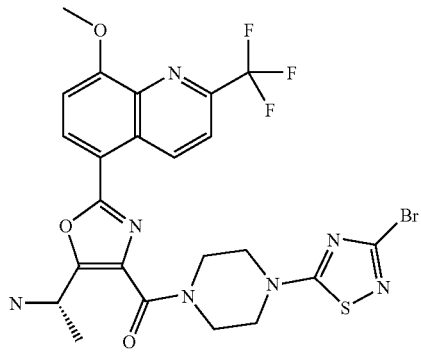 | 613 |
| 26-638 | 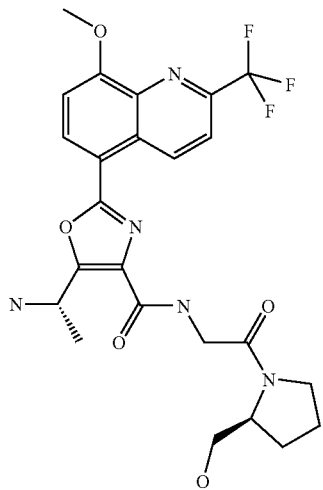 | 522 |

-continued
| Cpd. No. | Structure | MS (M + 1) |
|---|---|---|
| 26-639 | 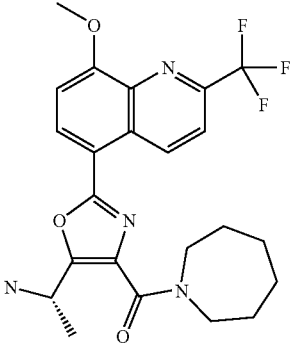 | 463 |
| 26-640 | 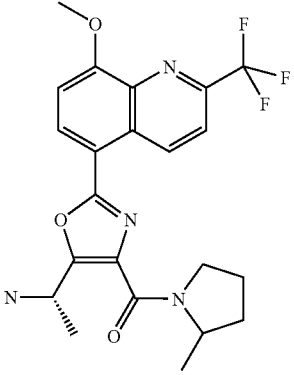 | 449 |
| 26-641 | 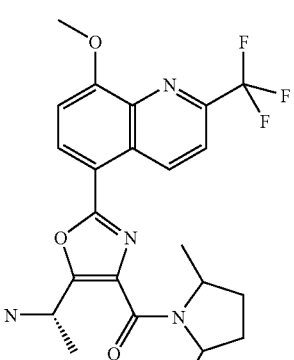 | 463 |

| Cpd. No. | Structure | MS (M + 1) |
|---|---|---|
| 26-642 | 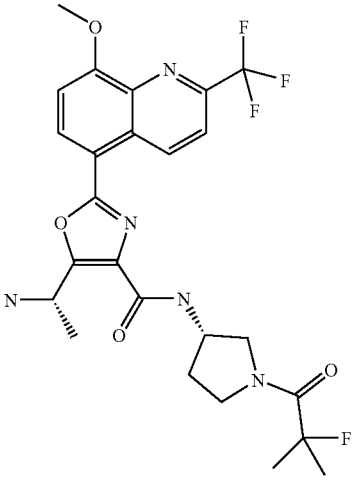 | 538 |
| 26-643 | 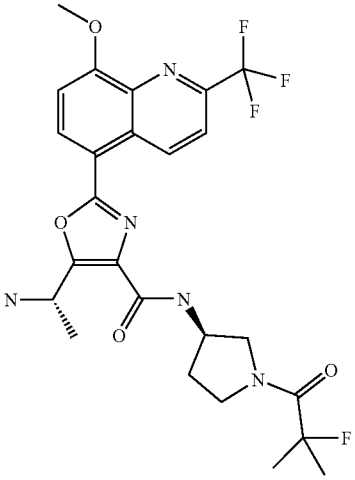 | 538 |
| 26-644 | 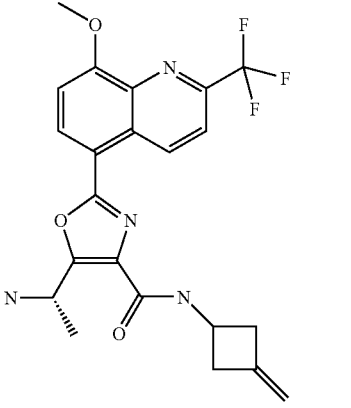 | 447 |

| Cpd. No. | Structure | MS (M + 1) |
| --- | --- | --- |
| 26-645 | 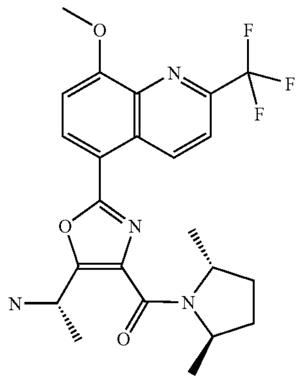 | 463 |
| 26-646 | 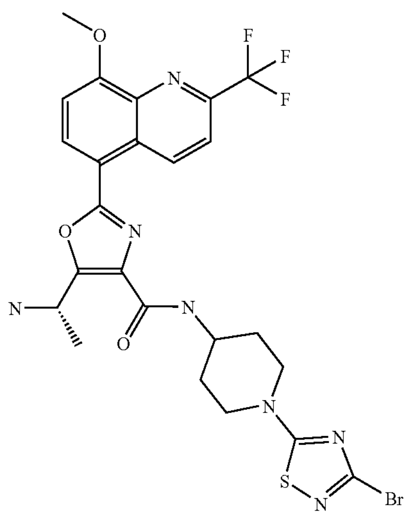 | 627 |
| 26-647 | 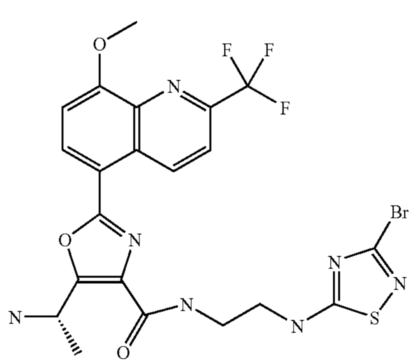 | 588 |

-continued

| Cpd. No. | Structure | MS (M + 1) |
|---|---|---|
| 26-648 | 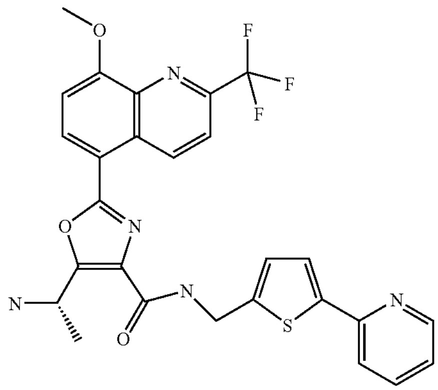 | 554 |
| 26-649 | 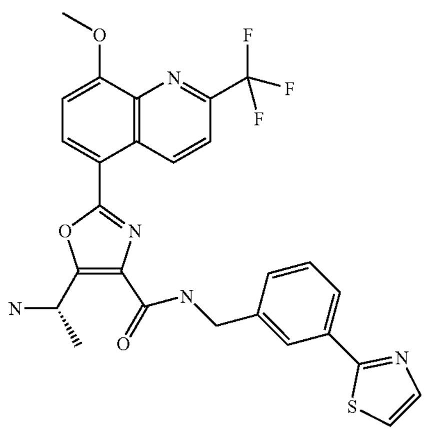 | 554 |
| 26-650 | 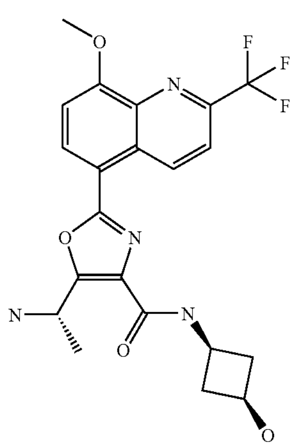 | 451 |

-continued

| Cpd. No. | Structure | MS (M + 1) |
|---|---|---|
| 26-651 | 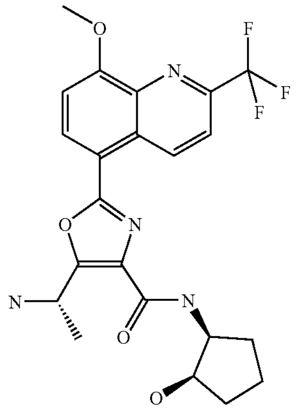 | 465 |
| 26-652 | 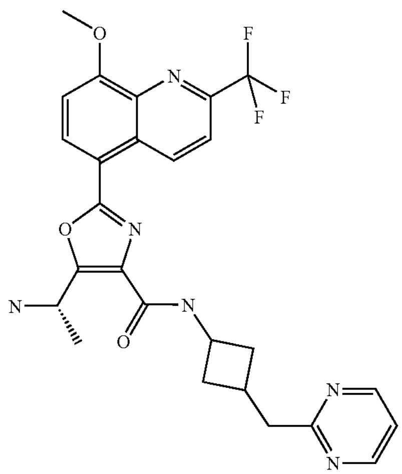 | 527 |
| 26-653 | 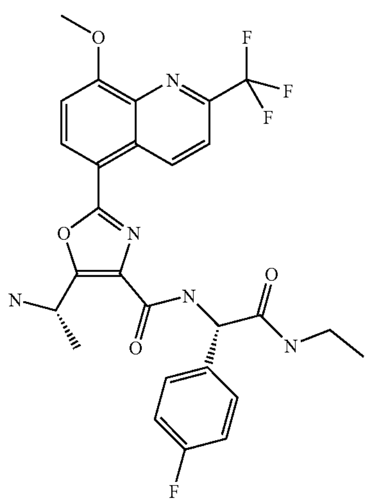 | 560 |

-continued

| Cpd. No. | Structure | MS (M + 1) |
|---|---|---|
| 26-654 | 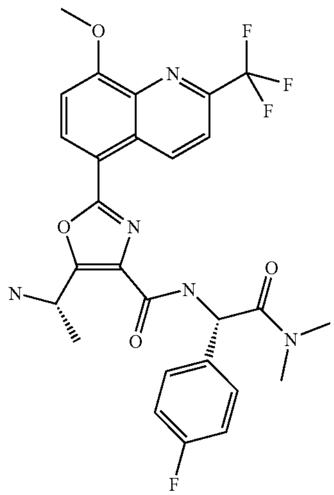 | 560 |
| 26-655 | 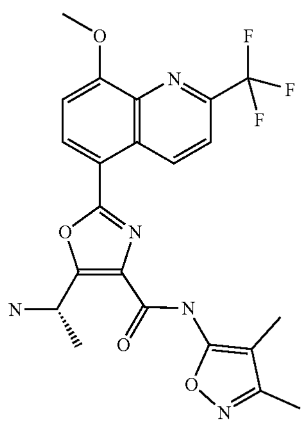 | 476 |
| 26-656 | 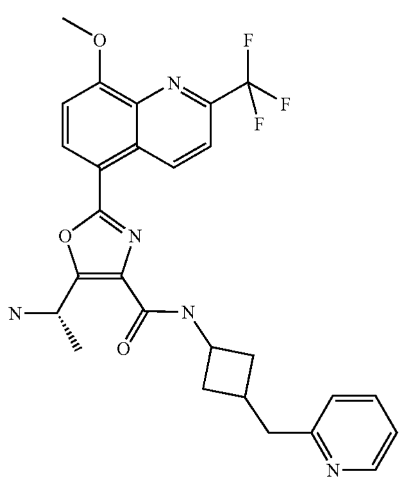 | 526 |

-continued
| Cpd. No. | Structure | MS (M + 1) |
|---|---|---|
| 26-657 | 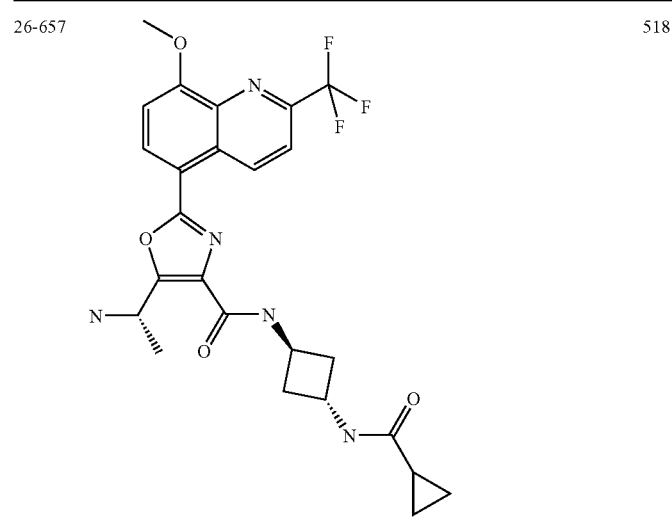 | 518 |
| 26-658 | 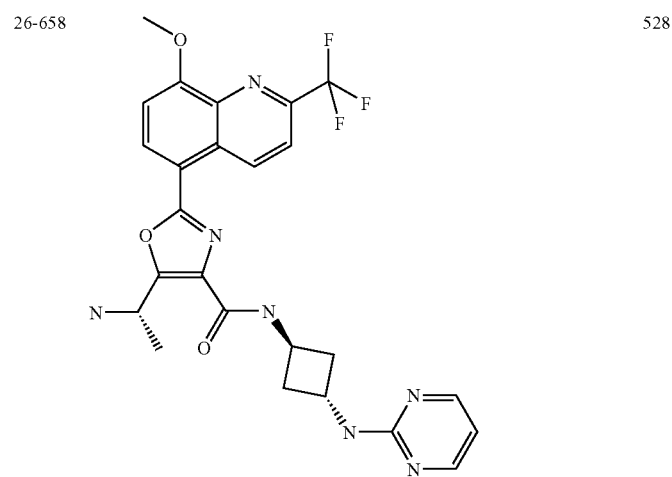 | 528 |
| 26-659 | 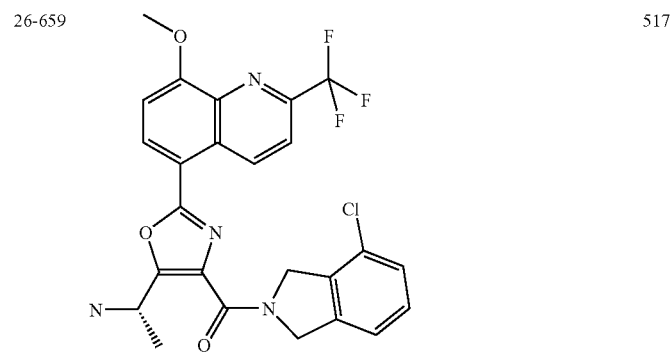 | 517 |

-continued

| Cpd. No. | Structure | MS (M + 1) |
|---|---|---|
| 26-660 | 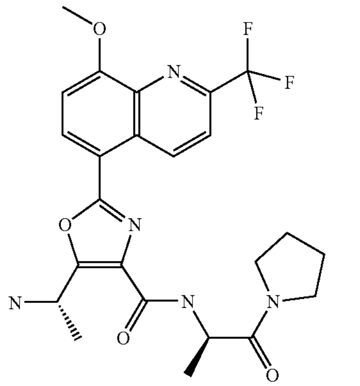 | 506 |
| 26-661 | 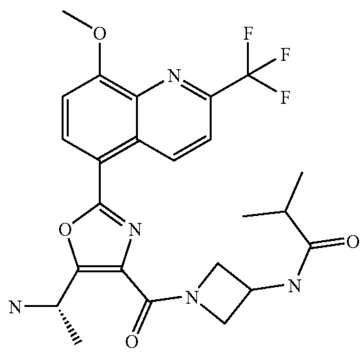 | 506 |
| 26-662 | 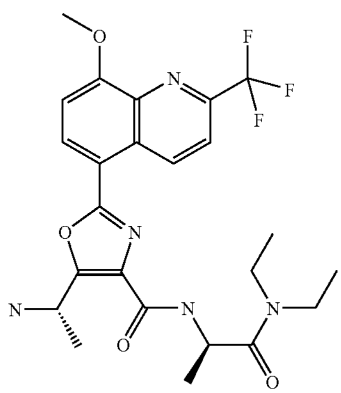 | 508 |
| 26-663 | 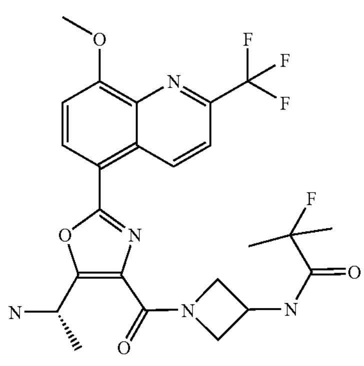 | 524 |

| Cpd. No. | Structure | MS (M + 1) |
|---|---|---|
| 26-664 | 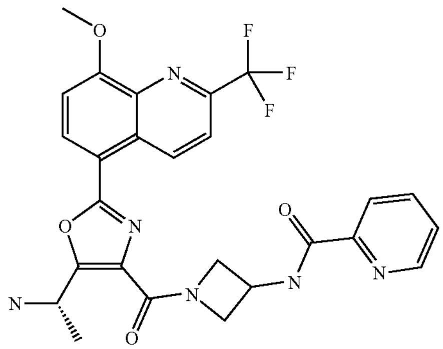 | 541 |
| 26-665 | 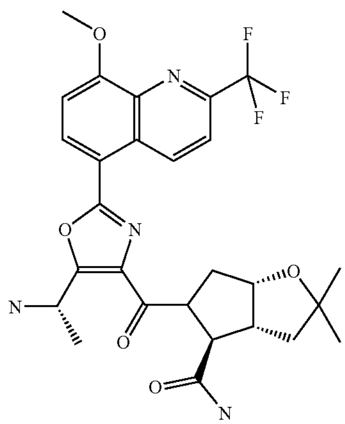 | 548 |
| 26-666 | 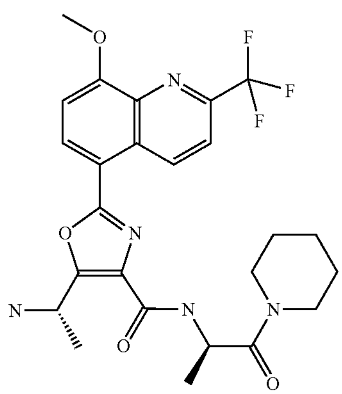 | 520 |
| 26-667 | 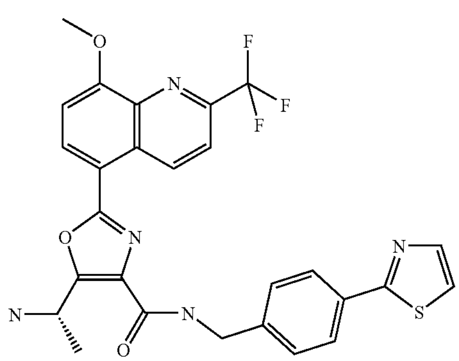 | 554 |

-continued
| Cpd. No. | Structure | MS (M + 1) |
|---|---|---|
| 26-668 | 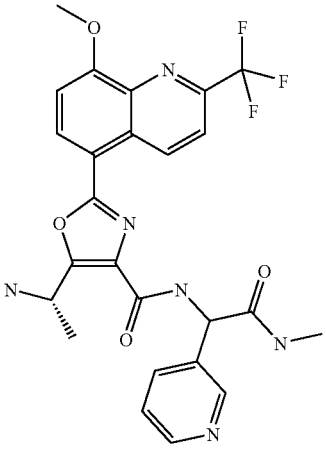 | 529 |
| 26-669 | 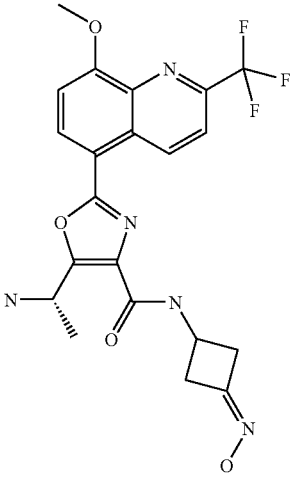 | 464 |
| 26-670 | 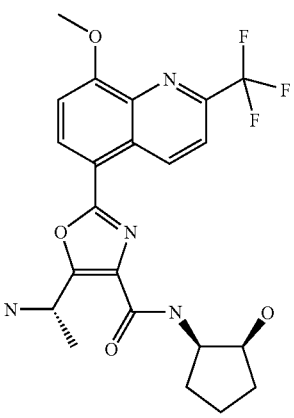 | 465 |

| Cpd. No. | Structure | MS (M + 1) |
|---|---|---|
| 26-671 | 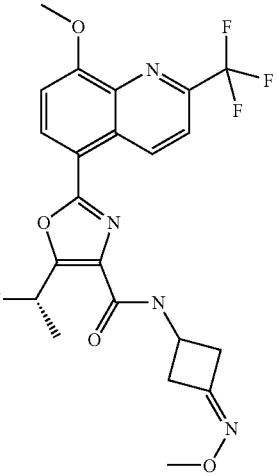 | 478 |
| 26-672 | 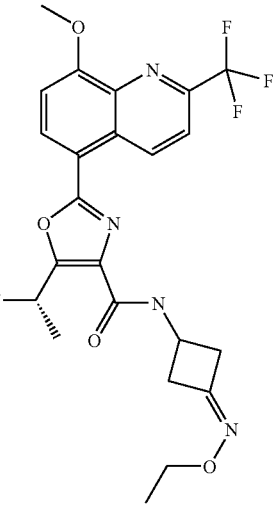 | 492 |
| 26-673 | 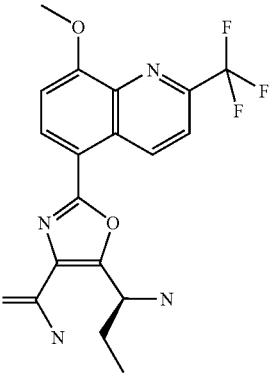 | 395 |

| Cpd. No. | Structure | MS (M + 1) |
|---|---|---|
| 26-674 | 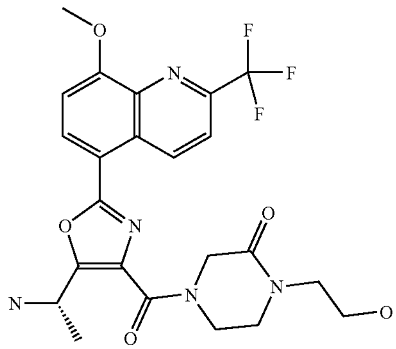 | 508 |
| 26-675 | 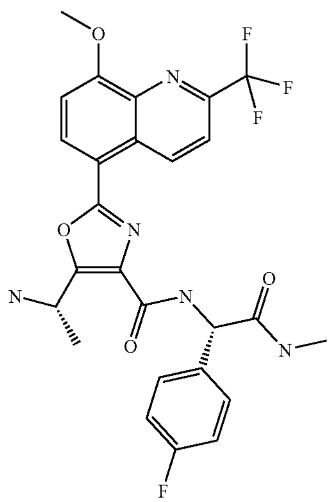 | 546 |
| 26-676 | 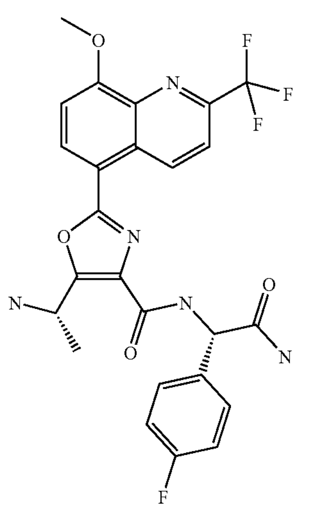 | 532 |

|Cpd. No.|Structure|MS (M + 1)|
|---|---|---|
|26-677|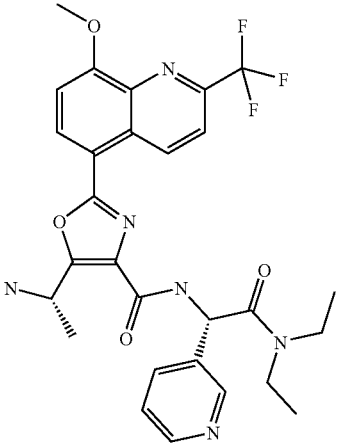|571|
|26-678|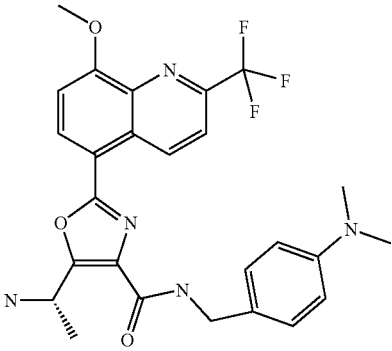|514|
|26-679|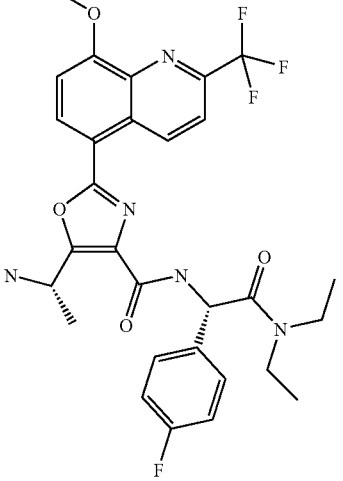|588|

| Cpd. No. | Structure | MS (M + 1) |
|---|---|---|
| 26-680 | 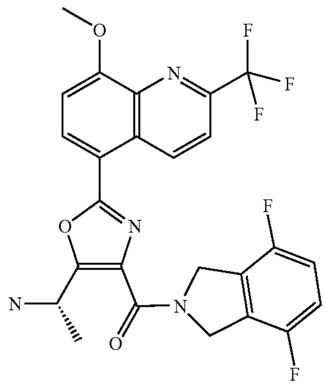 | 519 |
| 26-681 | 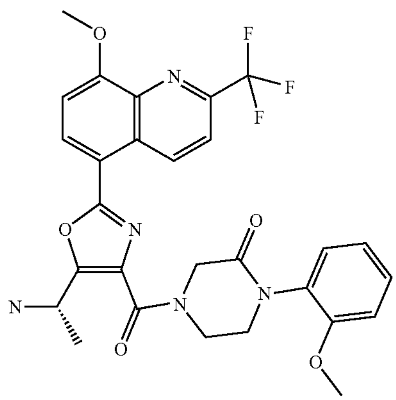 | 570 |
| 26-682 | 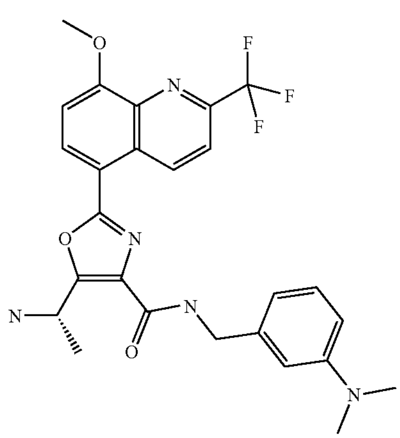 | 514 |

-continued

| Cpd. No. | Structure | MS (M + 1) |
|---|---|---|
| 26-683 | 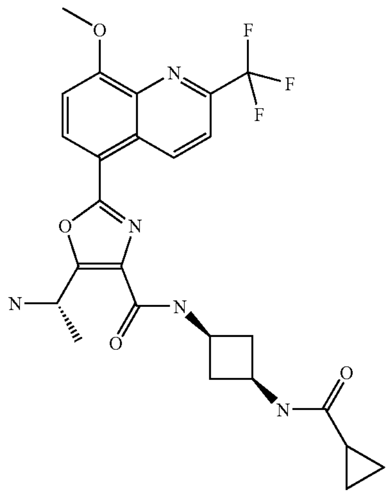 | 518 |
| 26-684 | 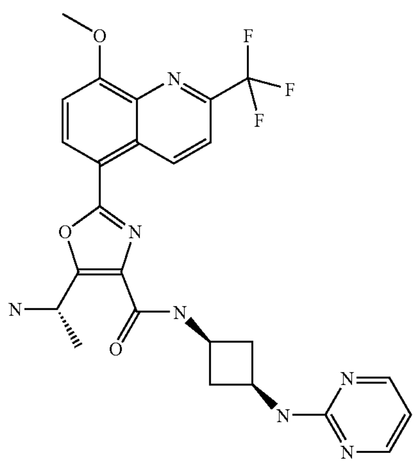 | 528 |
| 26-685 | 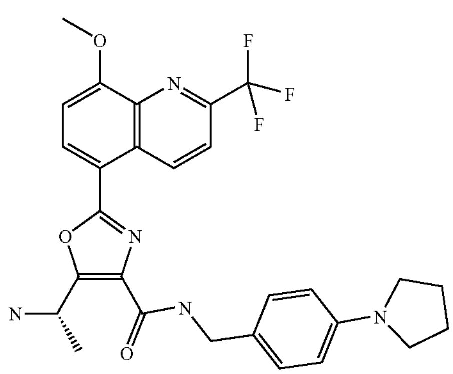 | 540 |

-continued
| Cpd. No. | Structure | MS (M + 1) |
|---|---|---|
| 26-686 | 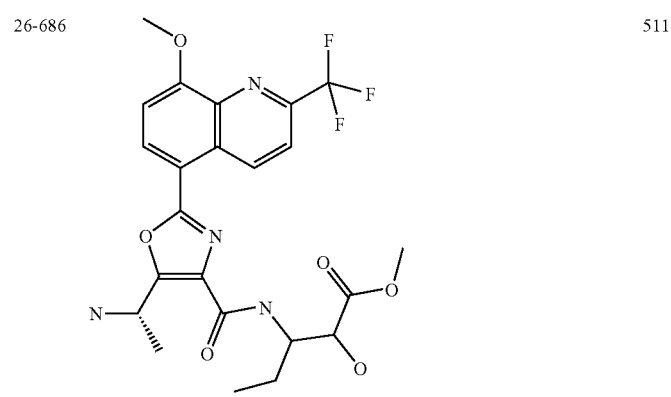 | 511 |
| 26-687 | 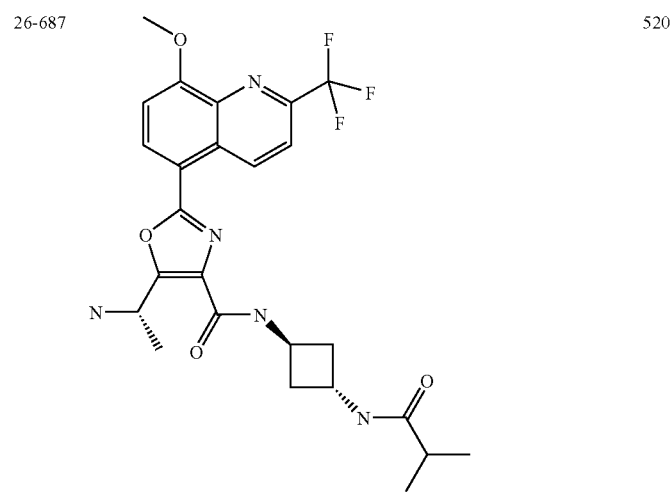 | 520 |
| 26-688 | 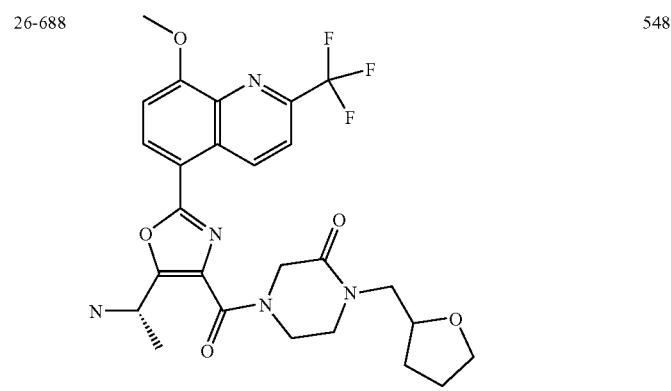 | 548 |

| Cpd. No. | Structure | MS (M + 1) |
|---|---|---|
| 26-689 | 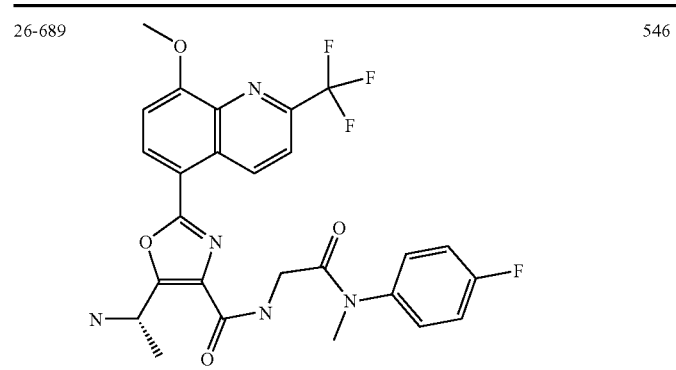 | 546 |
| 26-690 | 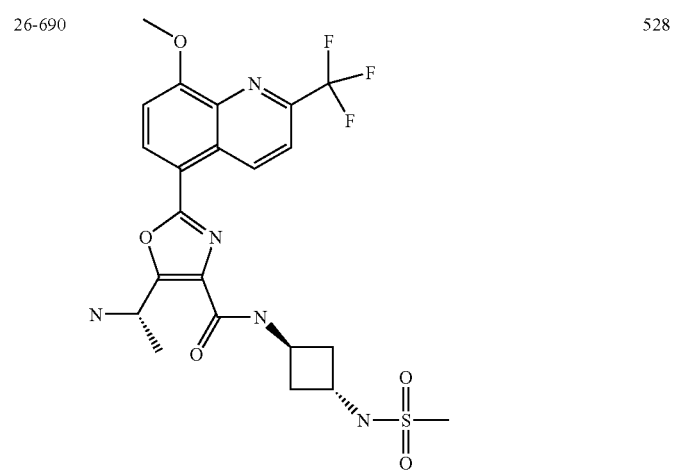 | 528 |
| 26-691 | 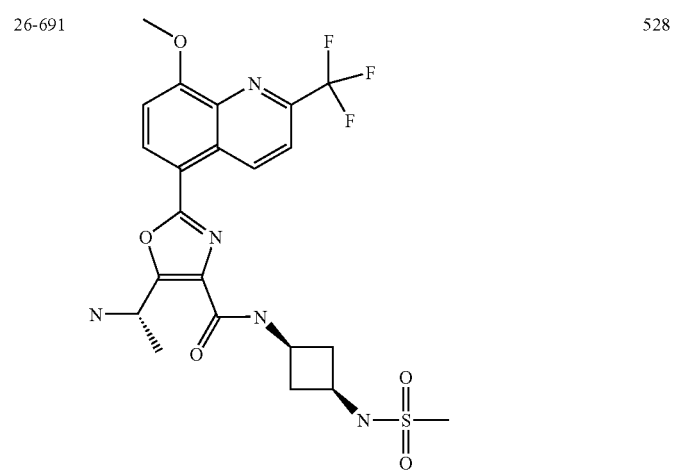 | 528 |

-continued
| Cpd. No. | Structure | MS (M + 1) |
|---|---|---|
| 26-692 | 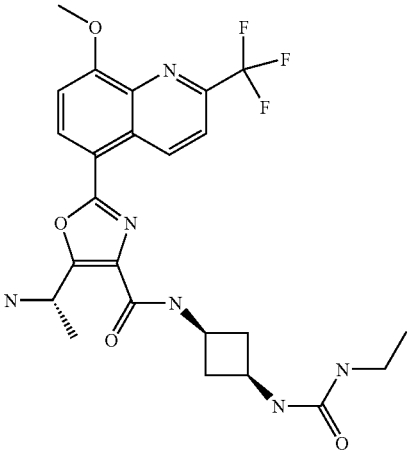 | 521 |
| 26-693 | 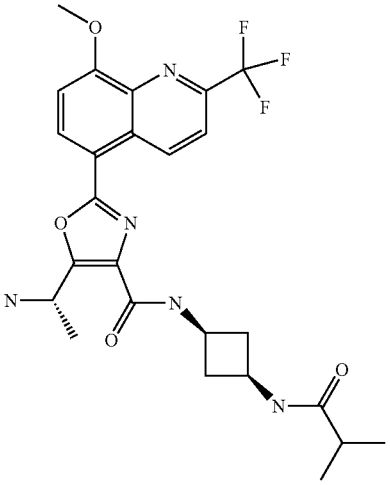 | 520 |
| 26-694 | 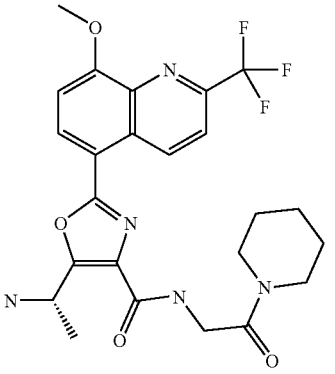 | 506 |

| Cpd. No. | Structure | MS (M + 1) |
|---|---|---|
| 26-695 | 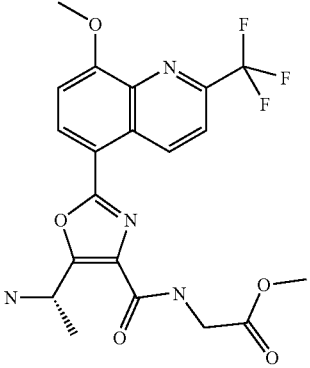 | 453 |
| 26-696 | 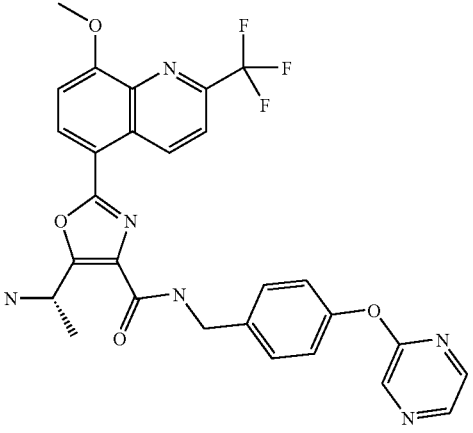 | 565 |
| 26-697 | 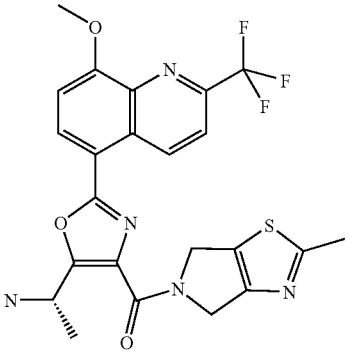 | 504 |
| 26-698 | 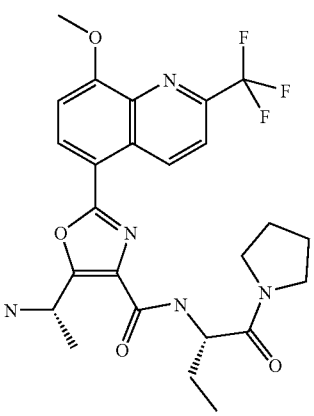 | 520 |

| Cpd. No. | Structure | MS (M + 1) |
|---|---|---|
| 26-699 | 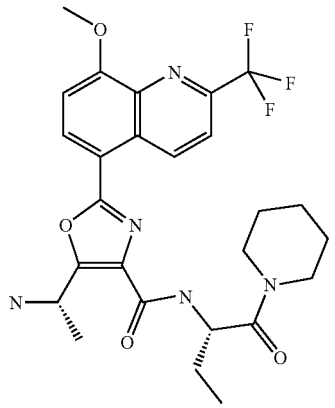 | 534 |
| 26-700 | 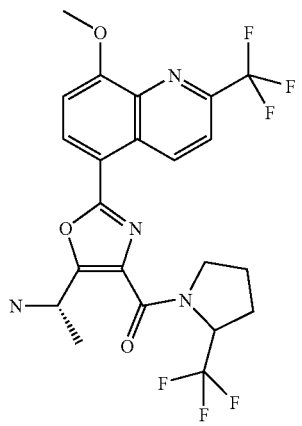 | 503 |
| 26-701 | 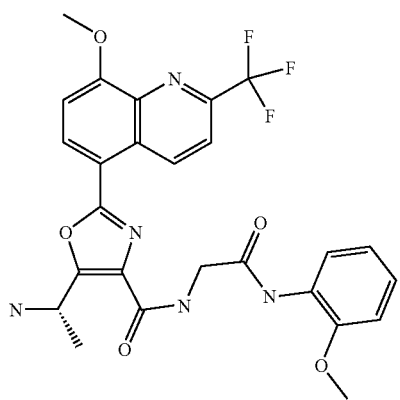 | 544 |

-continued
| Cpd. No. | Structure | MS (M + 1) |
|---|---|---|
| 26-702 | 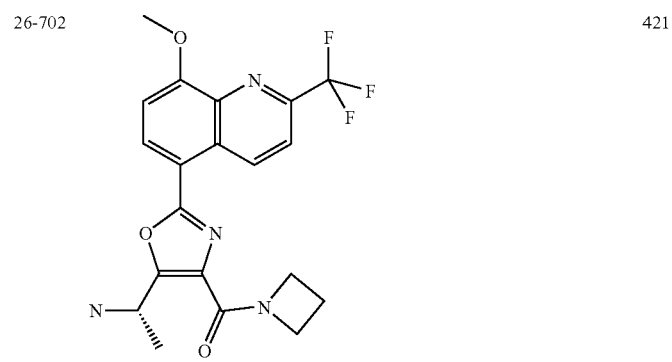 | 421 |
| 26-703 | 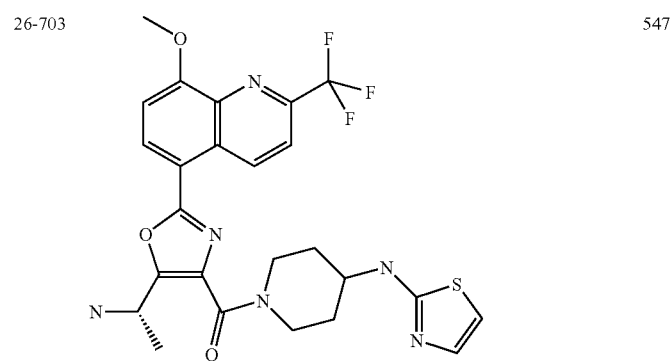 | 547 |
| 26-704 | 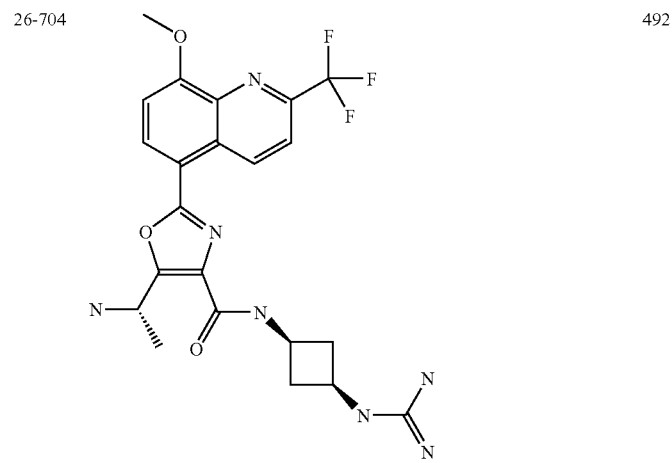 | 492 |

-continued
| Cpd. No. | Structure | MS (M + 1) |
|---|---|---|
| 26-705 | 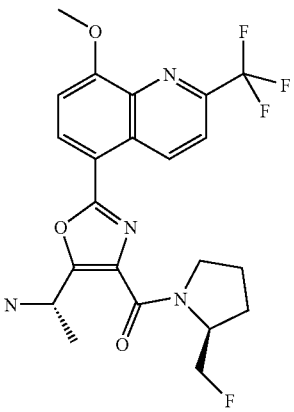 | 467 |
| 26-706 | 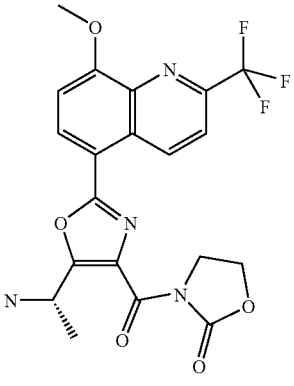 | 451 |
| 26-707 | 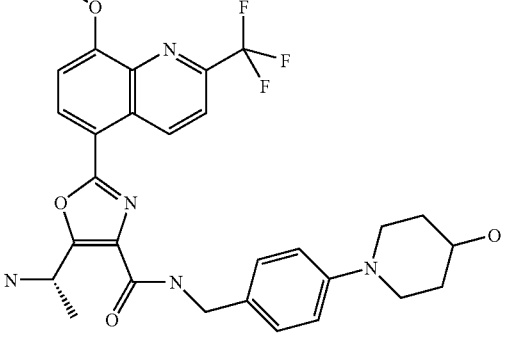 | 570 |
| 26-708 | 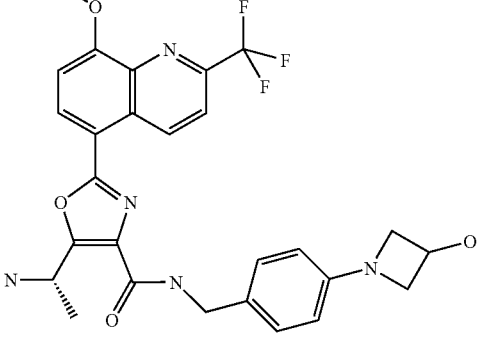 | 542 |

| Cpd. No. | Structure | MS (M + 1) |
|---|---|---|
| 26-709 | 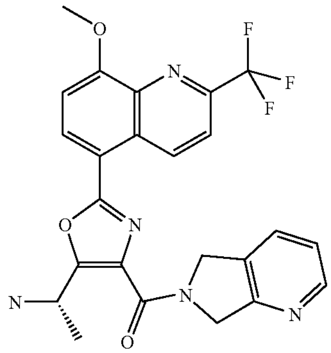 | 484 |
| 26-710 | 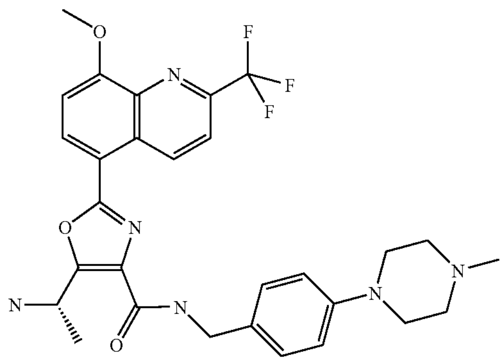 | 569 |
| 26-711 | 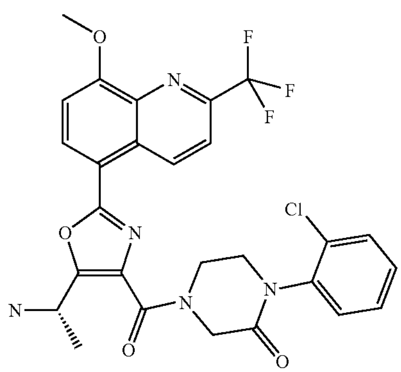 | 574 |
| 26-712 | 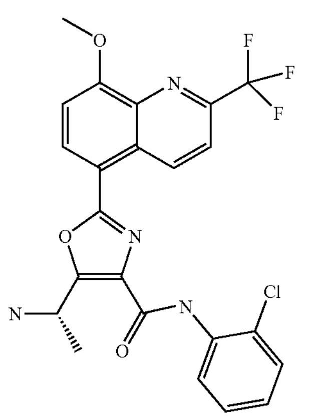 | 491 |

-continued
| Cpd. No. | Structure | MS (M + 1) |
|---|---|---|
| 26-713 | 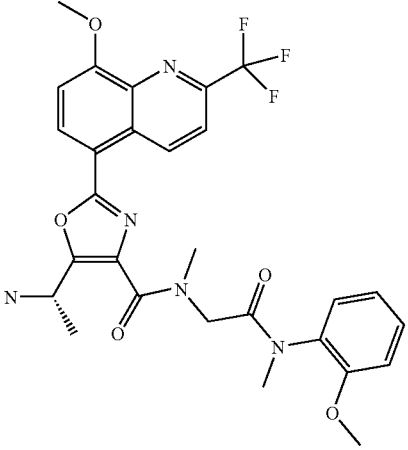 | 572 |
| 26-714 | 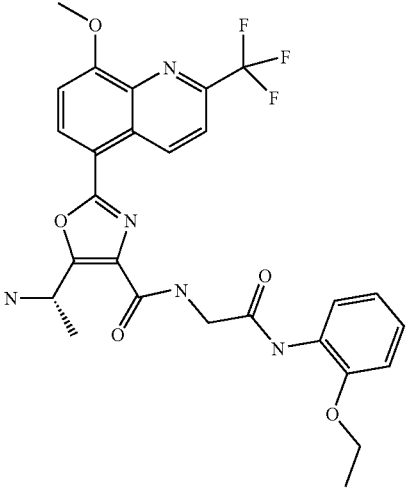 | 558 |
| 26-715 | 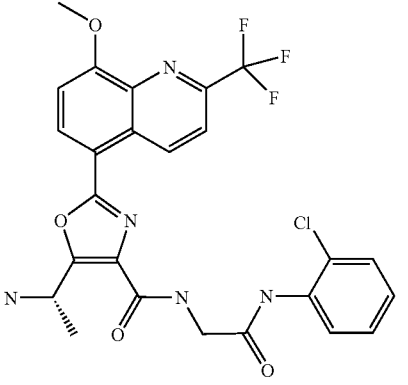 | 548 |

-continued

| Cpd. No. | Structure | MS (M + 1) |
|---|---|---|
| 26-716 | 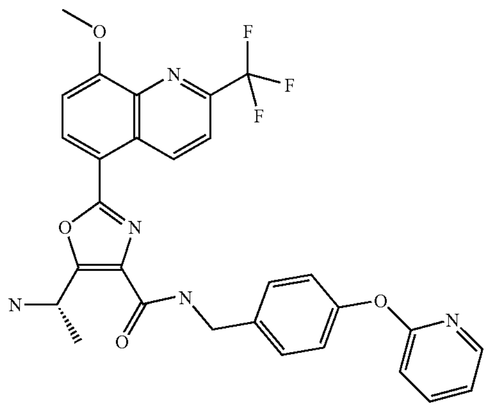 | 564 |
| 26-717 | 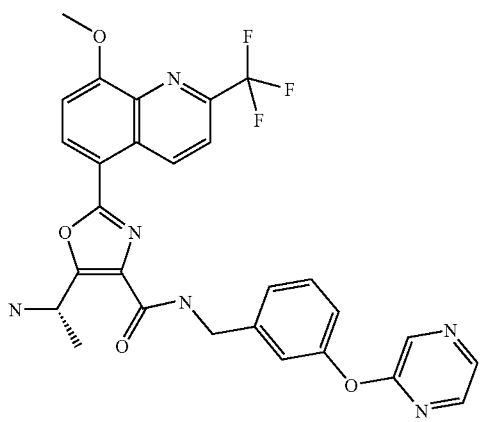 | 565 |
| 26-718 | 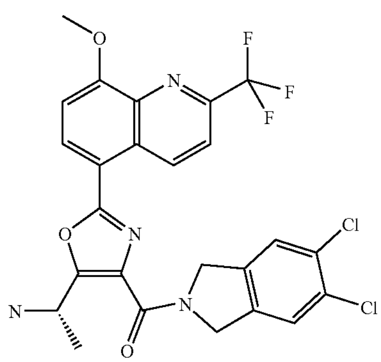 | 551 |
| 26-719 | 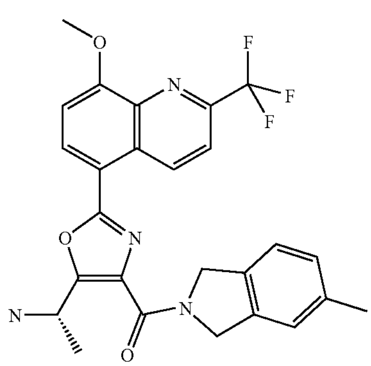 | 497 |

| Cpd. No. | Structure | MS (M + 1) |
|---|---|---|
| 26-720 | 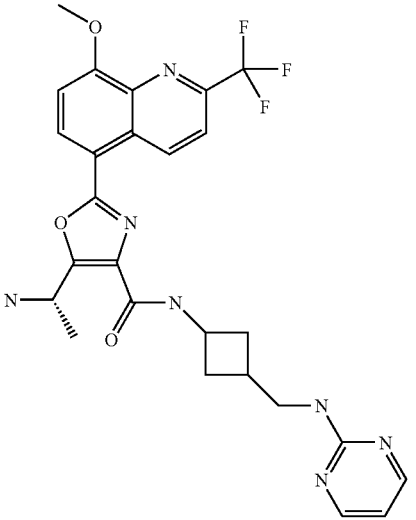 | 542 |
| 26-721 | 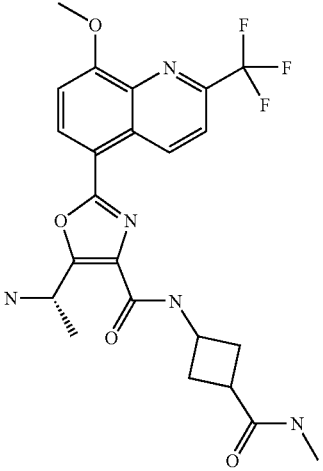 | 492 |
| 26-722 | 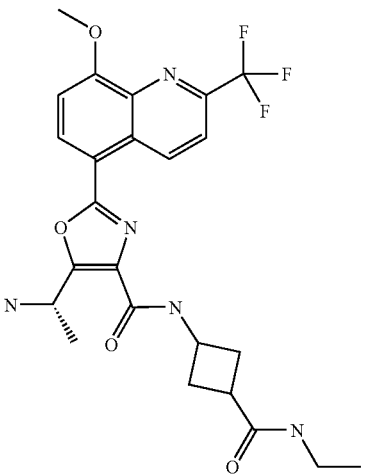 | 506 |

| Cpd. No. | Structure | MS (M + 1) |
|---|---|---|
| 26-723 | 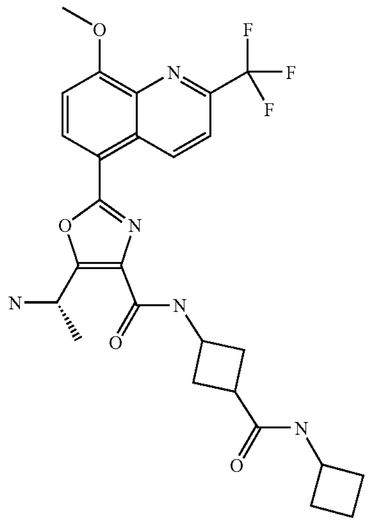 | 532 |
| 26-724 | 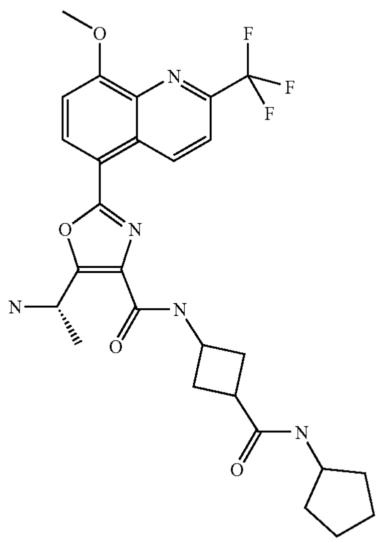 | 546 |
| 26-725 | 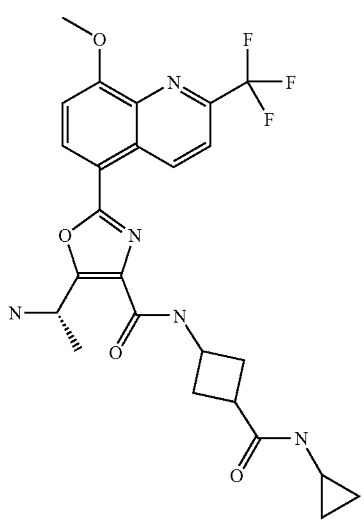 | 518 |

| Cpd. No. | Structure | MS (M + 1) |
|---|---|---|
| 26-726 | 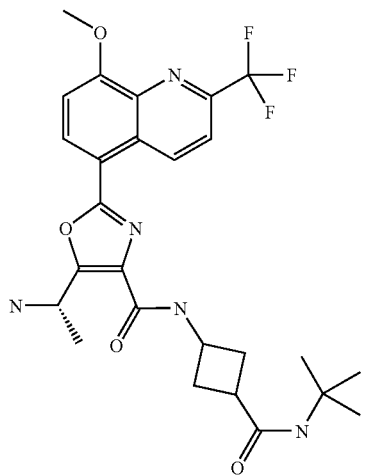 | 534 |
| 26-727 | 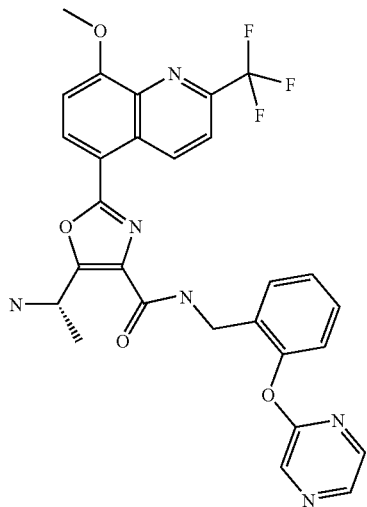 | 565 |
| 26-728 | 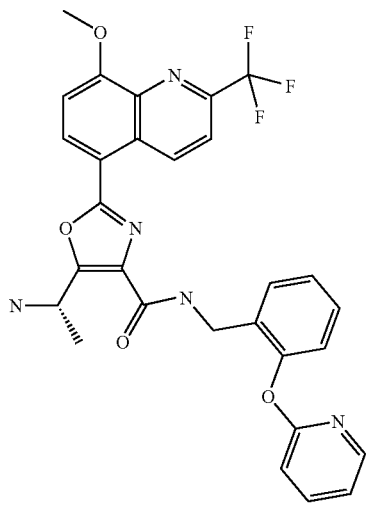 | 564 |

| Cpd. No. | Structure | MS (M + 1) |
|---|---|---|
| 26-729 | 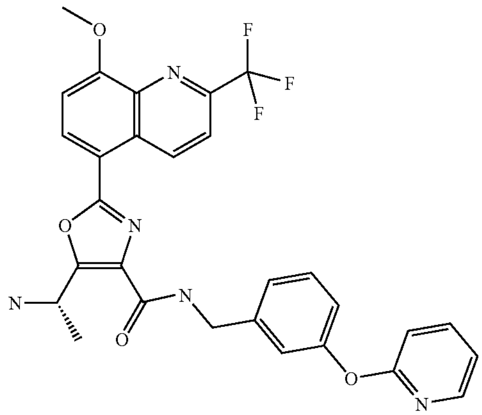 | 564 |
| 26-730 | 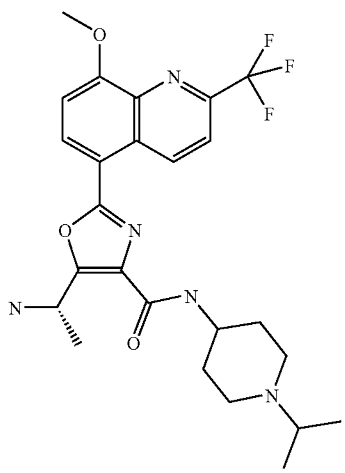 | 506 |
| 26-731 | 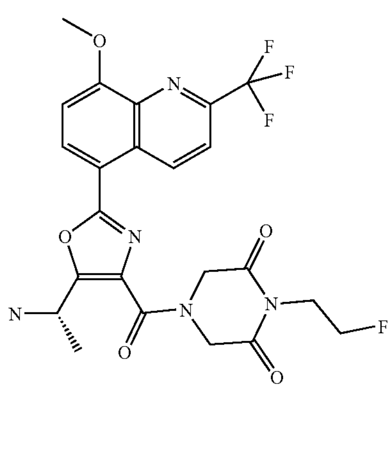 | 532 M + Na |

| Cpd. No. | Structure | MS (M + 1) |
|---|---|---|
| 26-732 | 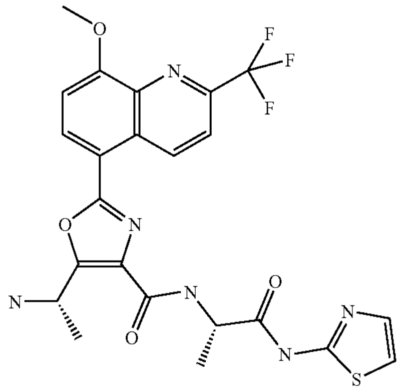 | 535 |
| 26-733 | 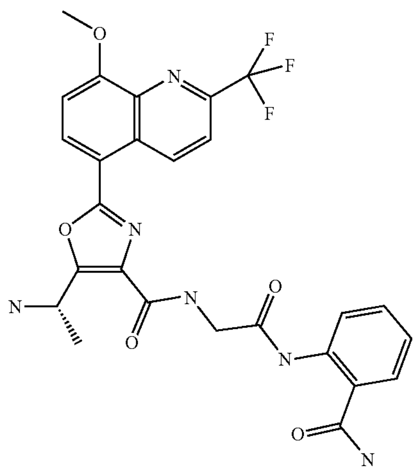 | 557 |
| 26-734 | 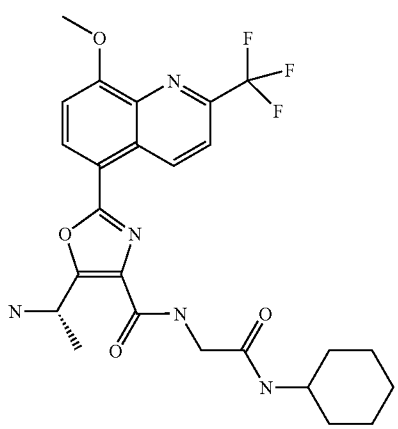 | 520 |

-continued

| Cpd. No. | Structure | MS (M + 1) |
|---|---|---|
| 26-735 | 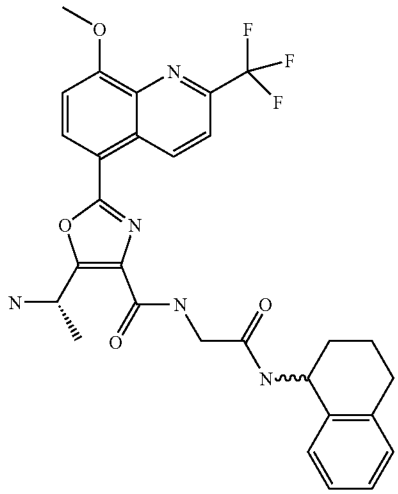 | 568 |
| 26-736 | 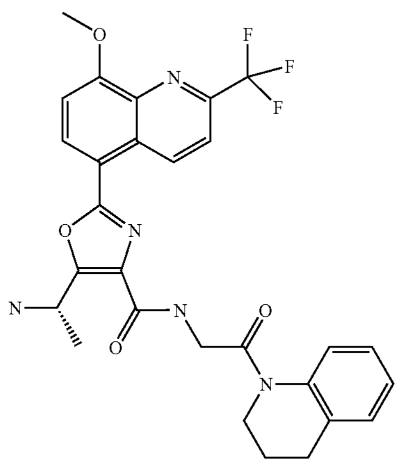 | 554 |
| 26-737 | 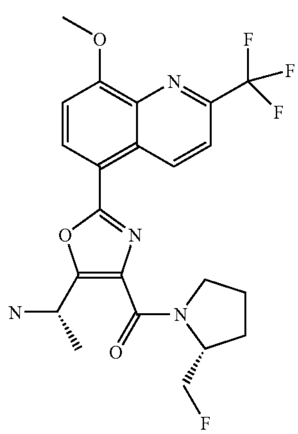 | 467 |

-continued

| Cpd. No. | Structure | MS (M + 1) |
|---|---|---|
| 26-738 | 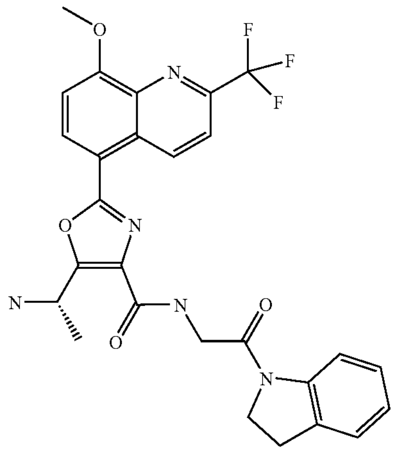 | 540 |
| 26-739 | 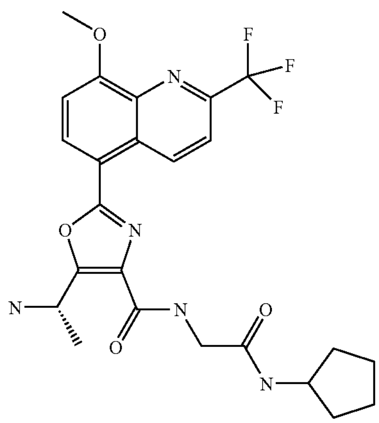 | 506 |
| 26-740 | 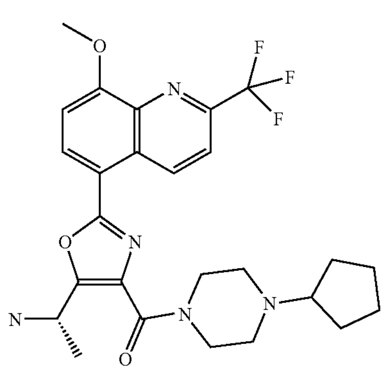 | 518 |

| Cpd. No. | Structure | MS (M + 1) |
|---|---|---|
| 26-741 | 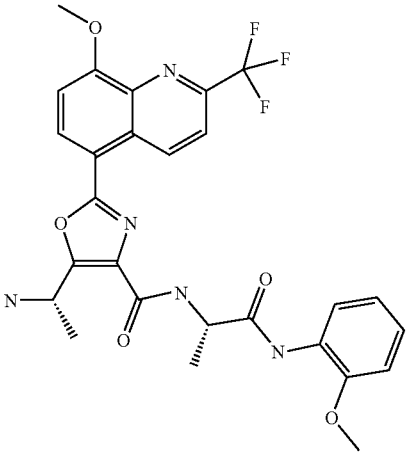 | 558 |
| 26-742 | 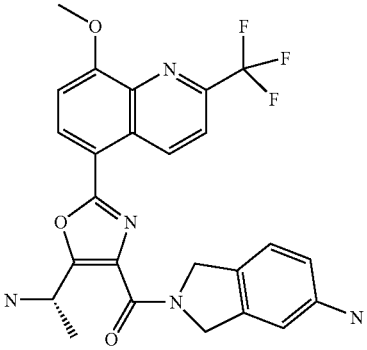 | 498 |
| 26-743 | 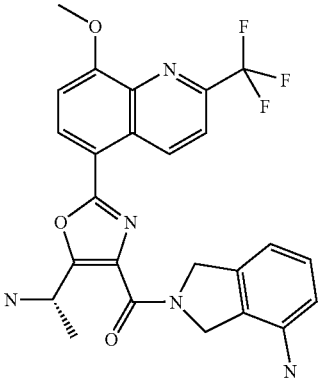 | 498 |

| Cpd. No. | Structure | MS (M + 1) |
|---|---|---|
| 26-744 | 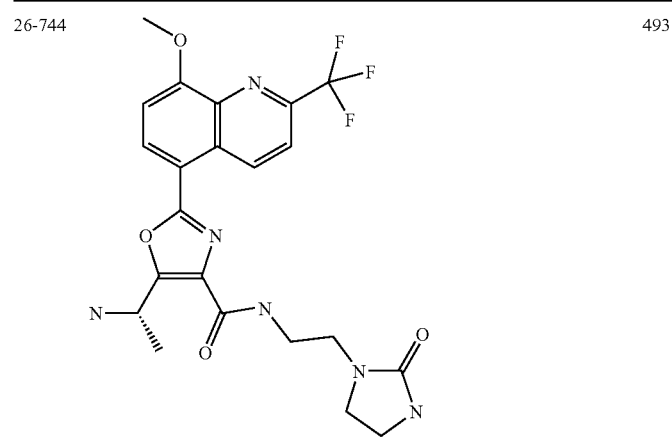 | 493 |
| 26-745 | 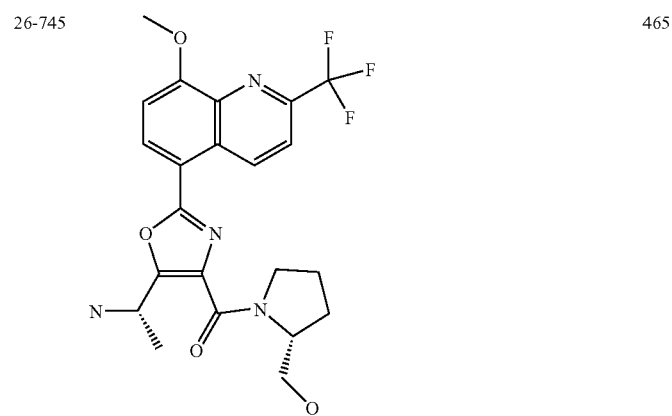 | 465 |
| 26-746 | 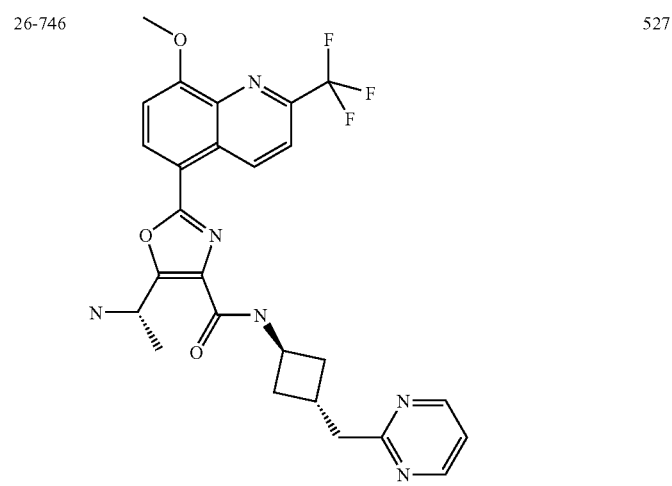 | 527 |

| Cpd. No. | Structure | MS (M + 1) |
|---|---|---|
| 26-747 | 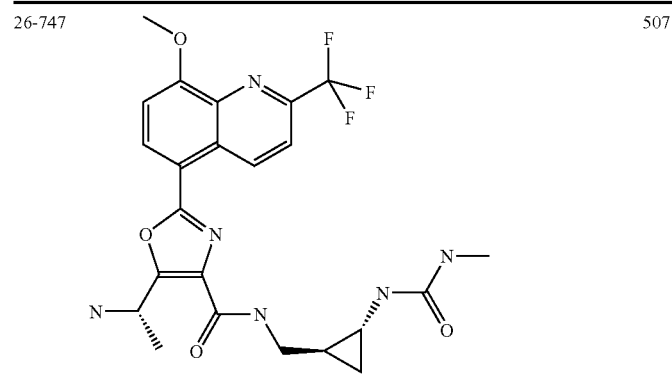 | 507 |
| 26-748 | 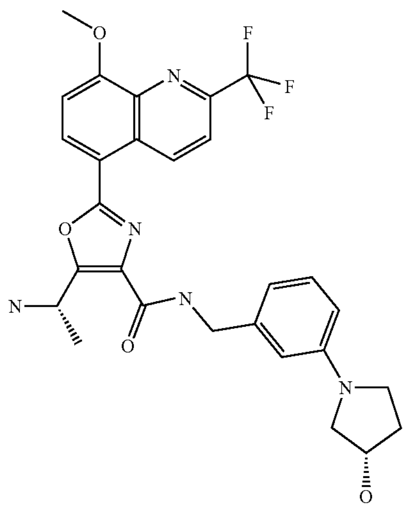 | 556 |
| 26-749 | 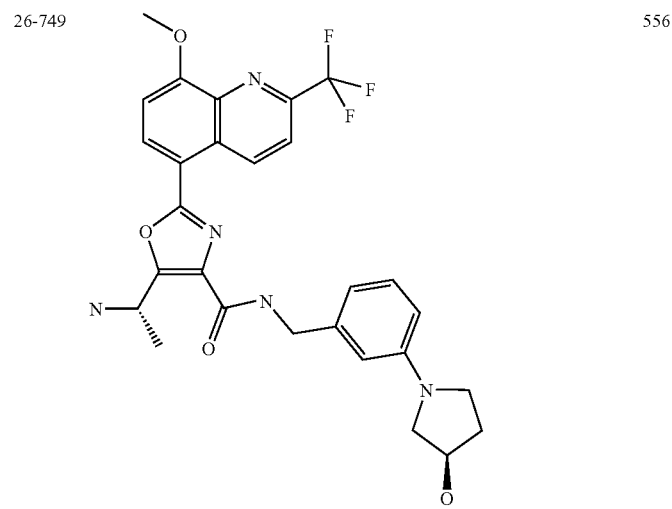 | 556 |

-continued
| Cpd. No. | Structure | MS (M + 1) |
|---|---|---|
| 26-750 | 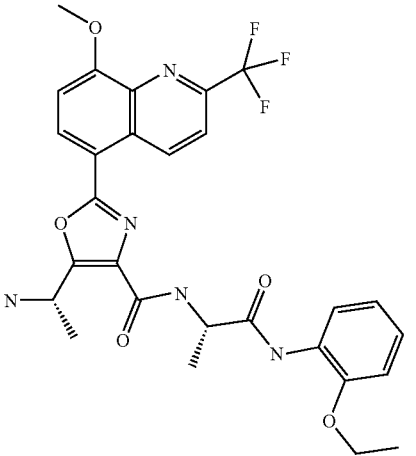 | 572 |
| 26-751 | 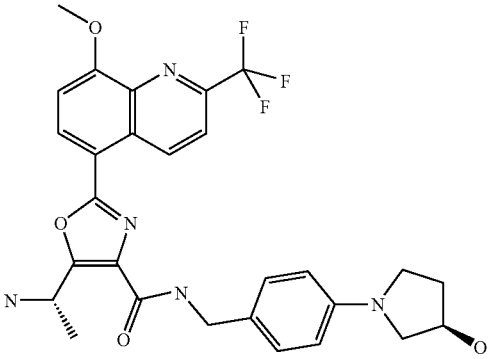 | 556 |
| 26-752 | 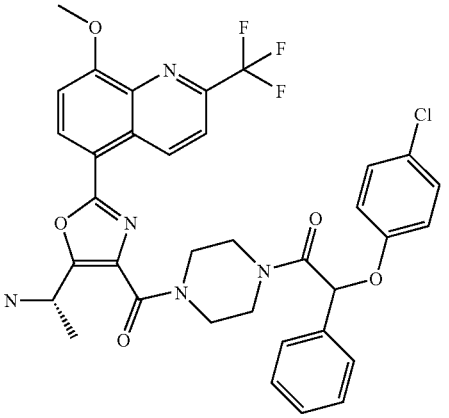 | 695 |

|Cpd. No.|Structure|MS (M + 1)|
|---|---|---|
| 26-753 | 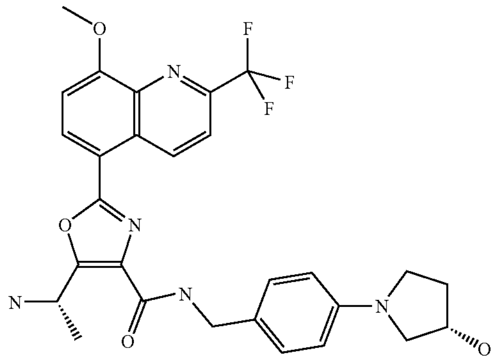 | 556 |
| 26-754 | 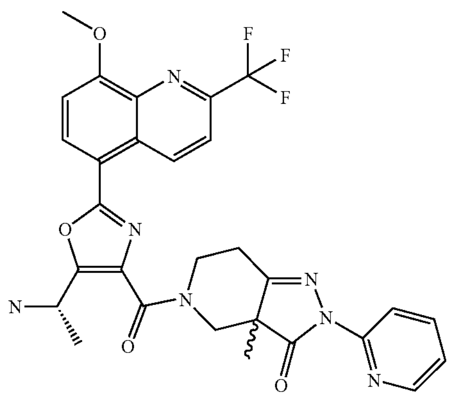 | 594 |
| 26-755 | 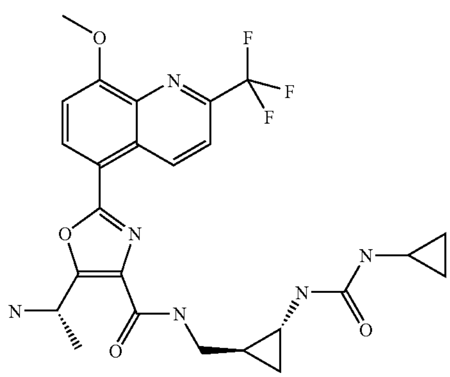 | 533 |
| 26-756 | 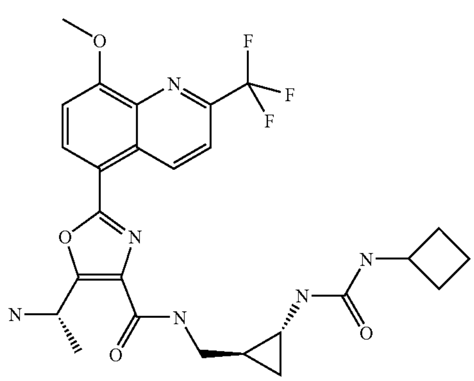 | 547 |

-continued
| Cpd. No. | Structure | MS (M + 1) |
|---|---|---|
| 26-757 | 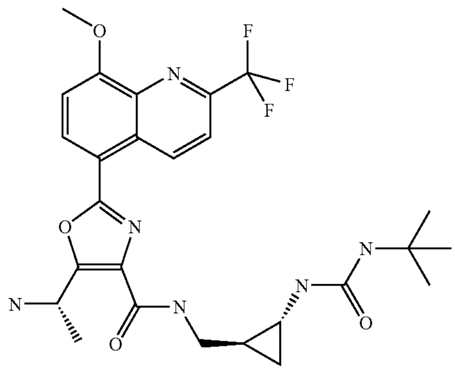 | 549 |
| 26-758 | 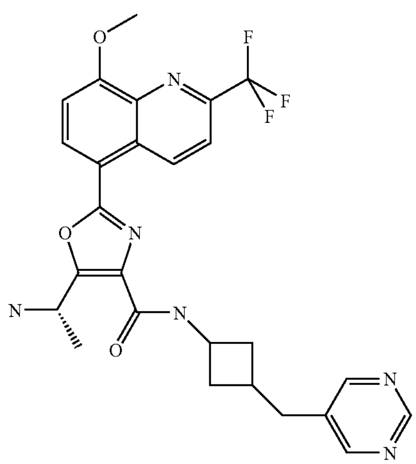 | 527 |
| 26-759 | 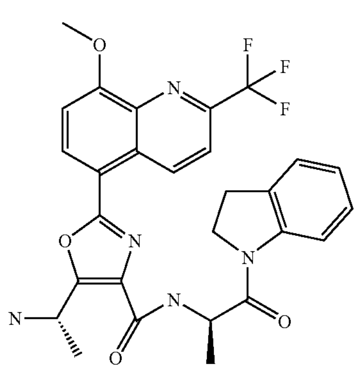 | 554 |
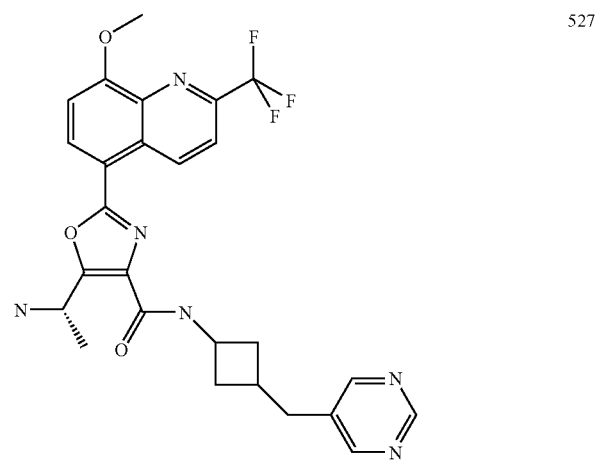

| Cpd. No. | Structure | MS (M + 1) |
|---|---|---|
| 26-760 | 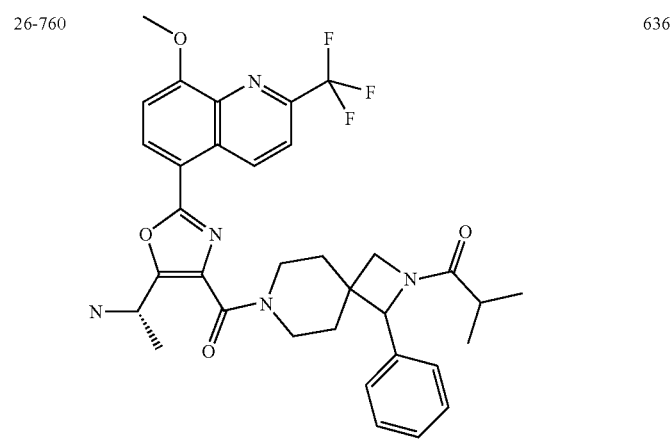 | 636 |
| 26-761 | 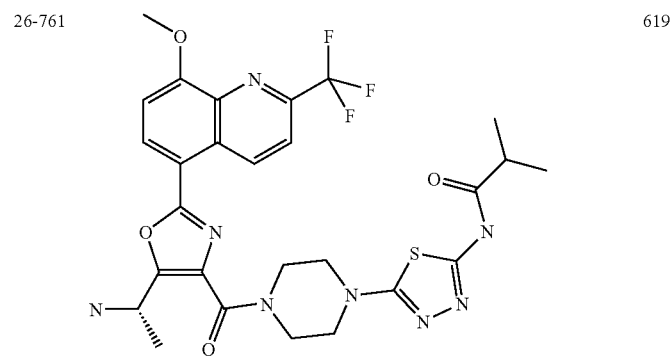 | 619 |
| 26-762 | 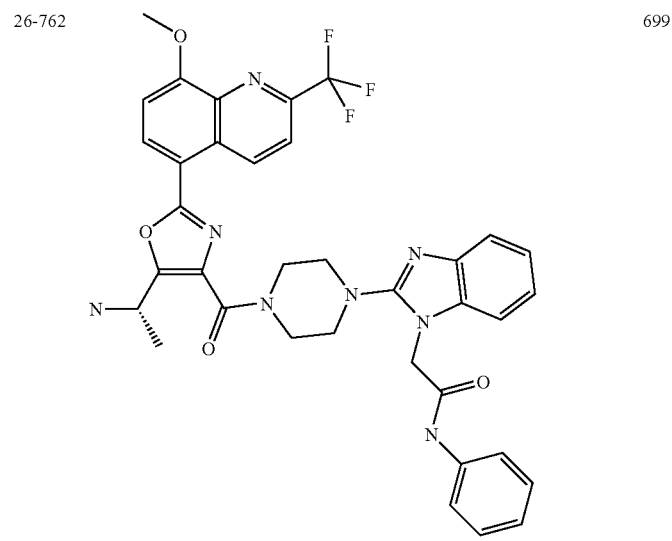 | 699 |

-continued

| Cpd. No. | Structure | MS (M + 1) |
|---|---|---|
| 26-763 | 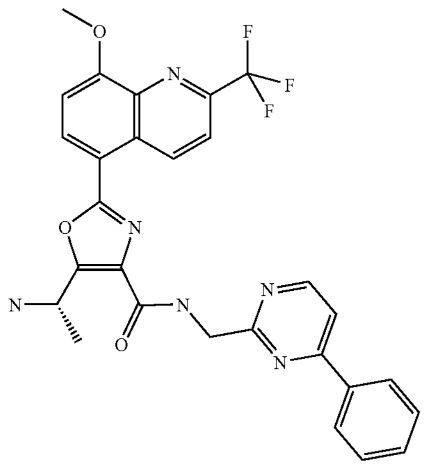 | 549 |
| 26-764 | 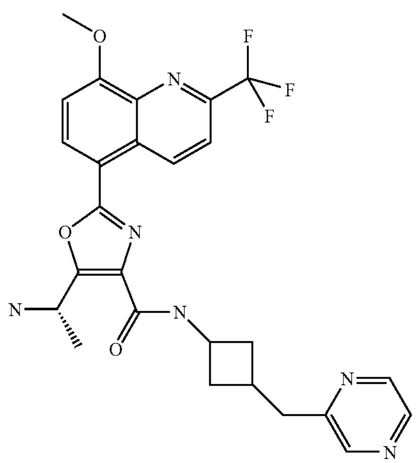 | 527 |
| 26-765 | 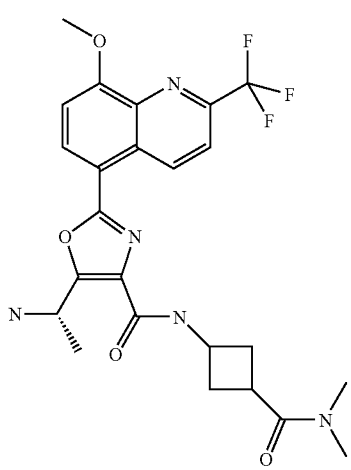 | 506 |

-continued

| Cpd. No. | Structure | MS (M + 1) |
|---|---|---|
| 26-766 | 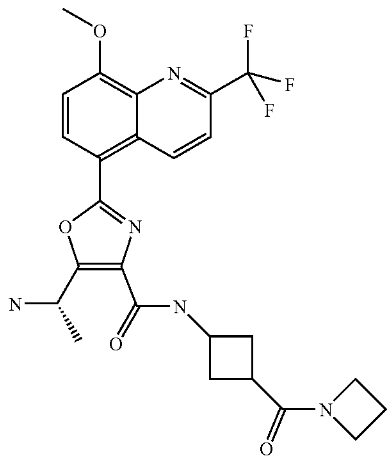 | 518 |
| 26-767 | 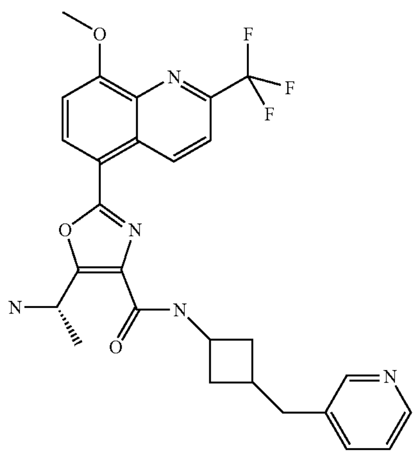 | 526 |
| 26-768 | 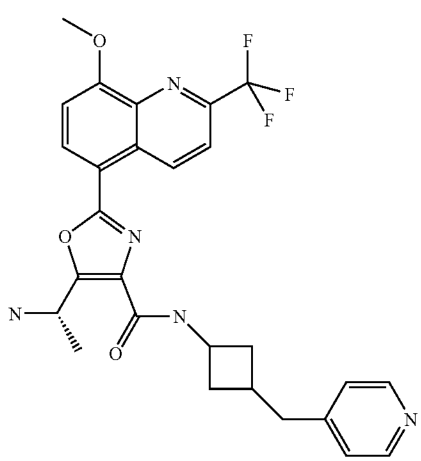 | 526 |

-continued
| Cpd. No. | Structure | MS (M + 1) |
|---|---|---|
| 26-769 | 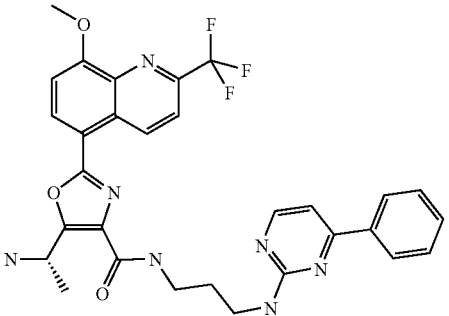 | 592 |
| 26-770 | 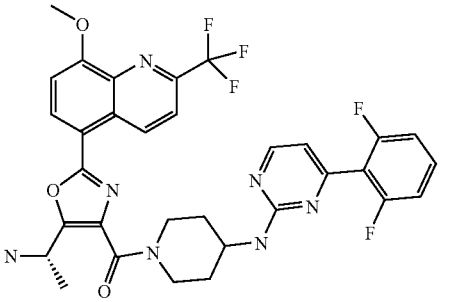 | 654 |
| 26-771 | 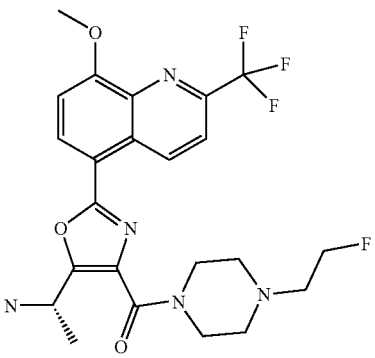 | 496 |
| 26-772 | 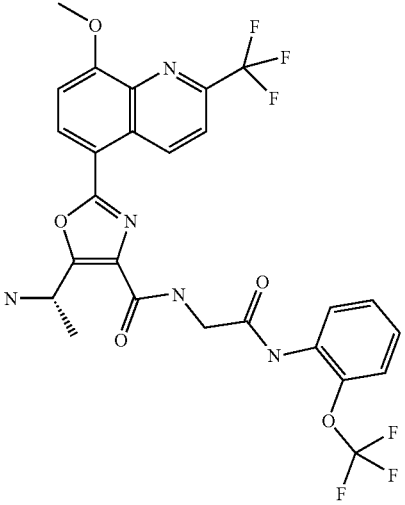 | 598 |

-continued

| Cpd. No. | Structure | MS (M + 1) |
|---|---|---|
| 26-773 | 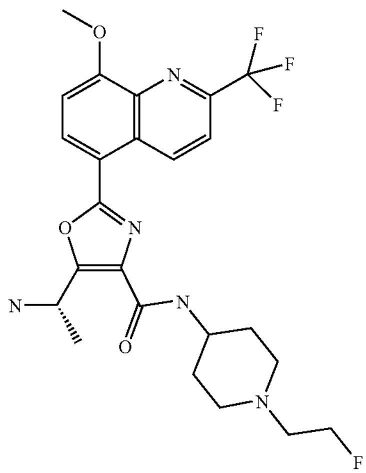 | 510 |
| 26-774 | 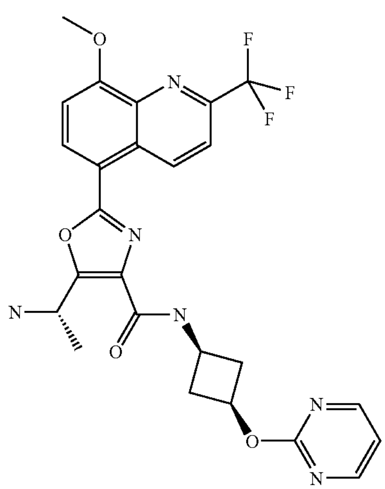 | 529 |
| 26-775 | 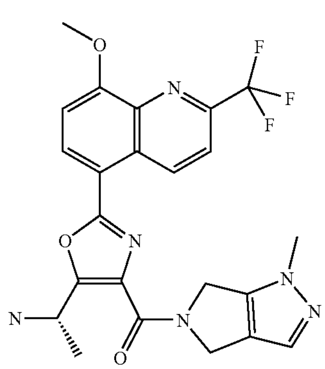 | 487 |

-continued

| Cpd. No. | Structure | MS (M + 1) |
|---|---|---|
| 26-776 | 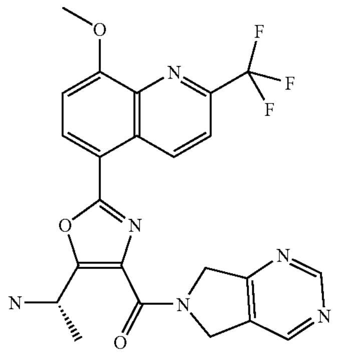 | 485 |
| 26-777 | 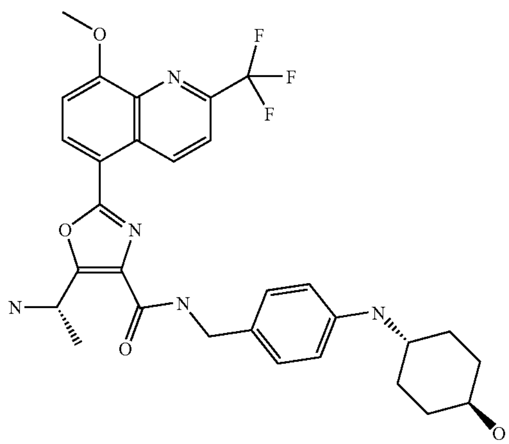 | 584 |
| 26-778 | 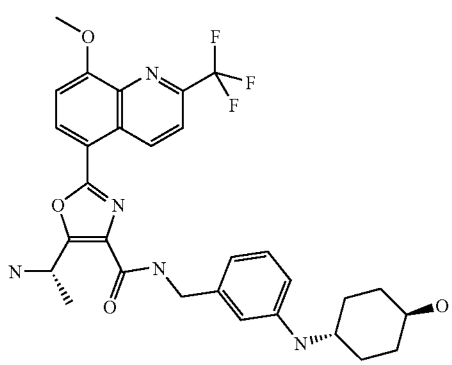 | 584 |

| Cpd. No. | Structure | MS (M + 1) |
|---|---|---|
| 26-779 | 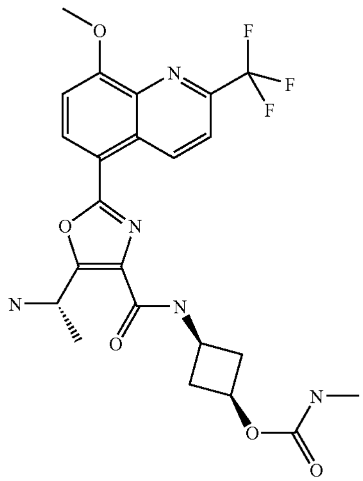 | 508 |
| 26-780 | 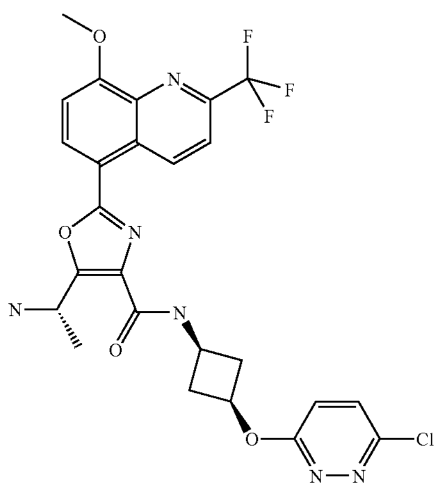 | 563 |
| 26-781 | 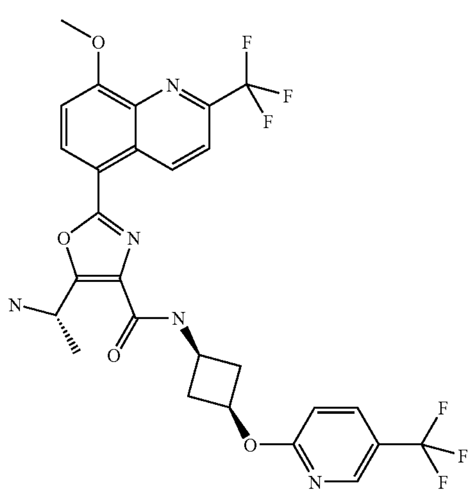 | 596 |

-continued

| Cpd. No. | Structure | MS (M + 1) |
|---|---|---|
| 26-782 | 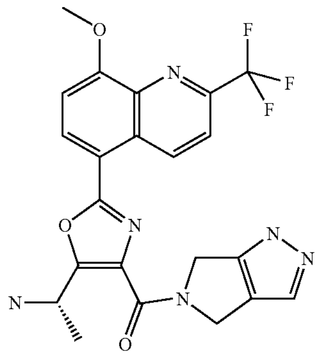 | 473 |
| 26-783 | 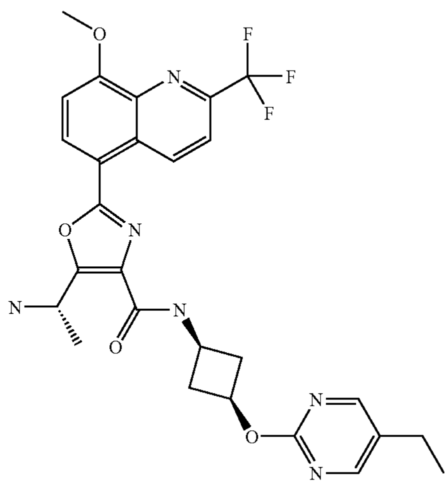 | 557 |
| 26-784 | 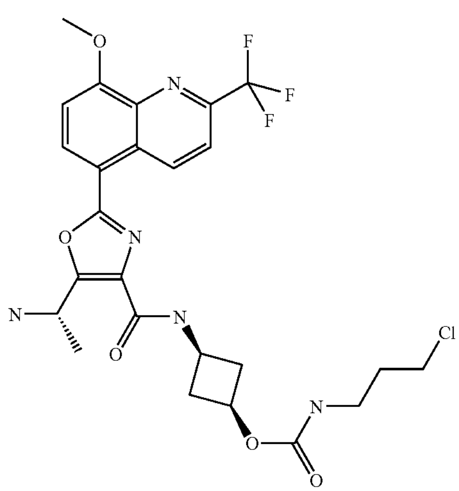 | 570 |

-continued

| Cpd. No. | Structure | MS (M + 1) |
|---|---|---|
| 26-785 | 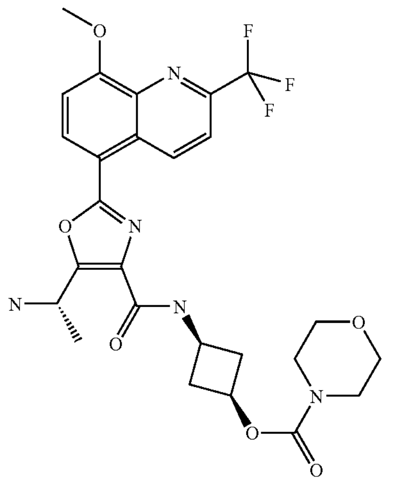 | 564 |
| 26-786 | 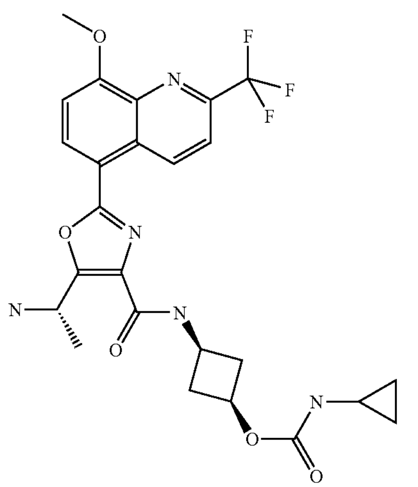 | 534 |
| 26-787 | 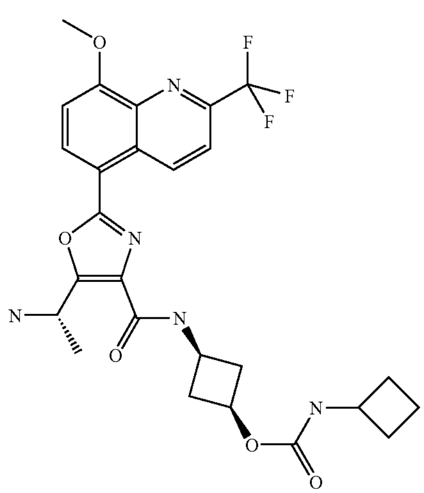 | 548 |

-continued
| Cpd. No. | Structure | MS (M + 1) |
|---|---|---|
| 26-788 | 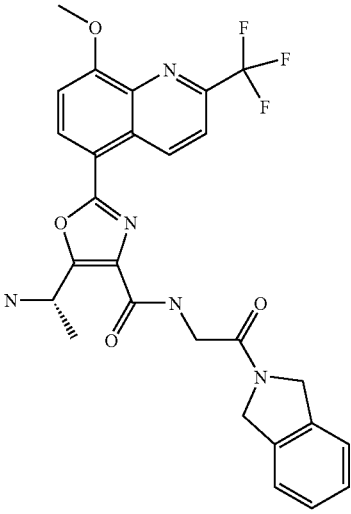 | 540 |
| 26-789 | 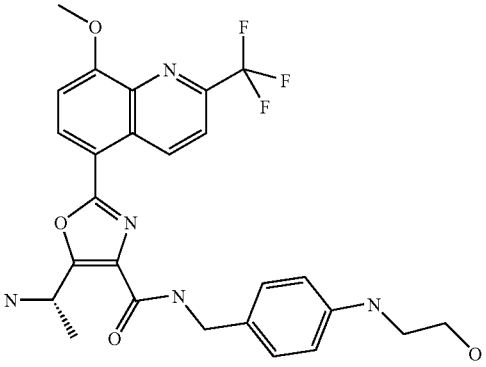 | 530 |
| 26-790 | 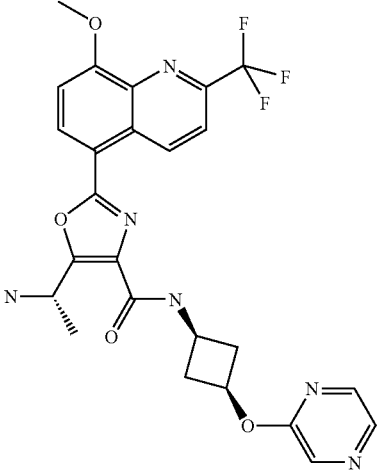 | 529 |

-continued

| Cpd. No. | Structure | MS (M + 1) |
|---|---|---|
| 26-791 | 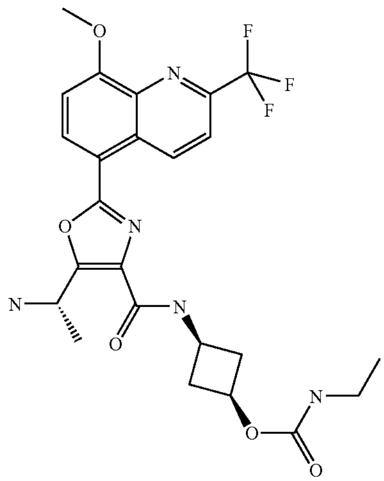 | 522 |
| 26-792 | 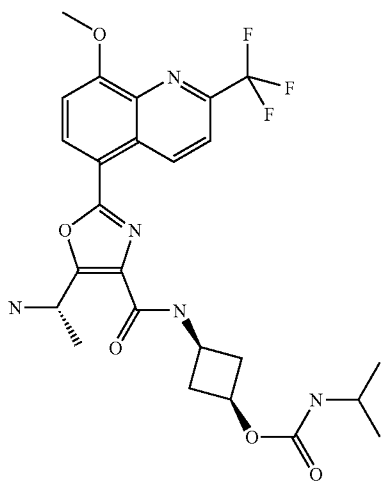 | 536 |
| 26-793 | 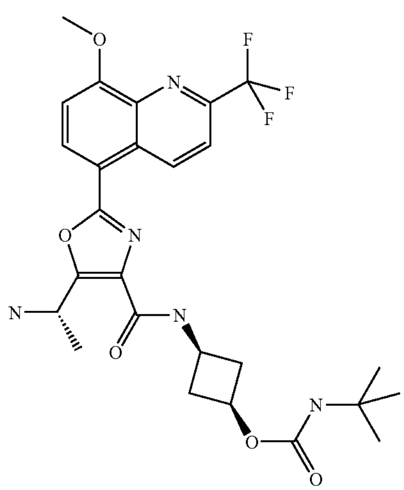 | 550 |

-continued

| Cpd. No. | Structure | MS (M + 1) |
|---|---|---|
| 26-794 | 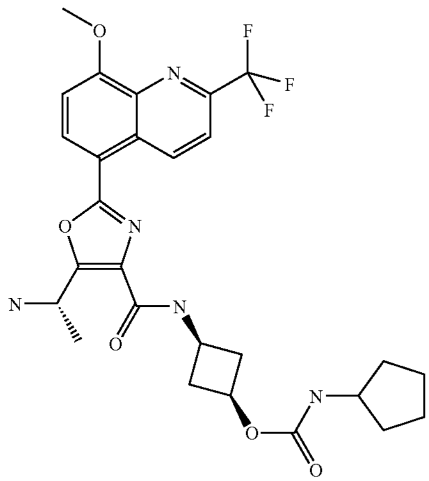 | 562 |
| 26-795 | 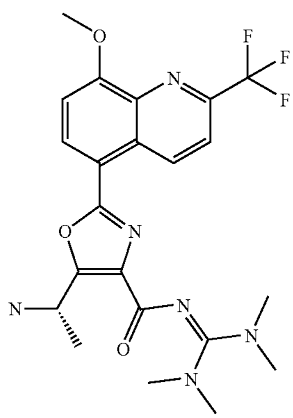 | 479 |
| 26-796 | 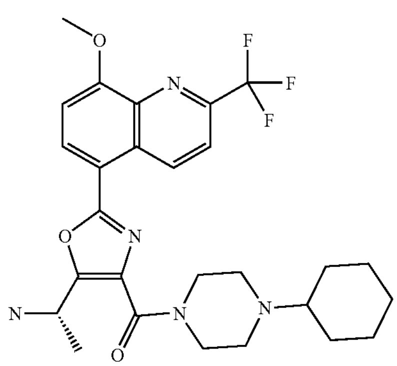 | 532 |

-continued
| Cpd. No. | Structure | MS (M + 1) |
|---|---|---|
| 26-797 | 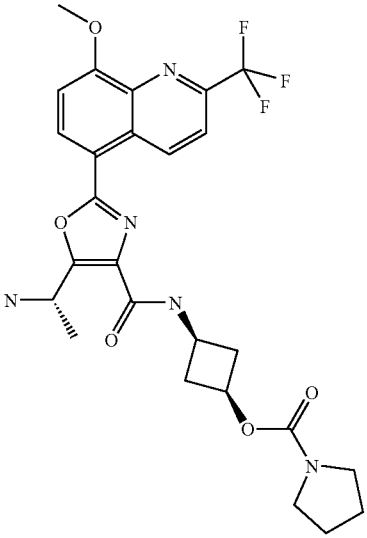 | 548 |
| 26-798 | 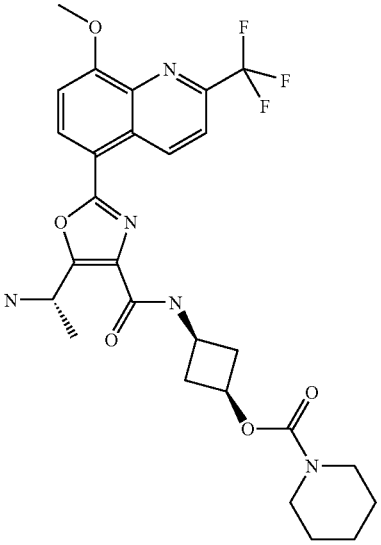 | 562 |
| 26-799 | 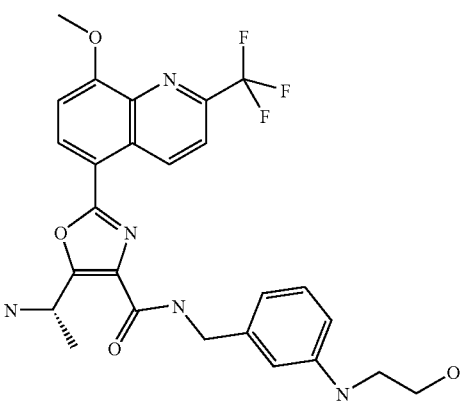 | 530 |

-continued

| Cpd. No. | Structure | MS (M + 1) |
| --- | --- | --- |
| 26-800 | 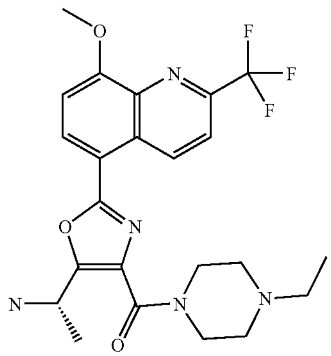 | 478 |
| 26-801 | 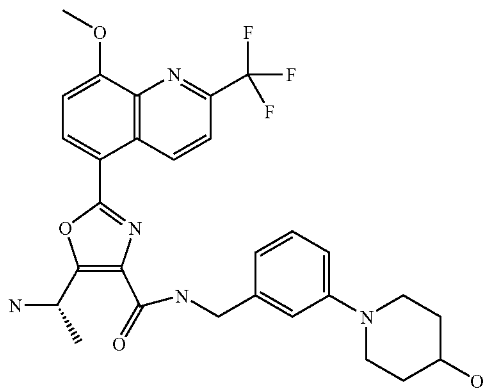 | 570 |
| 26-802 | 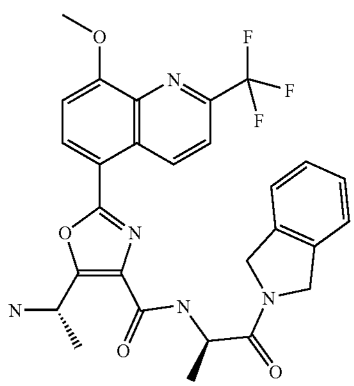 | 554 |
| 26-803 | 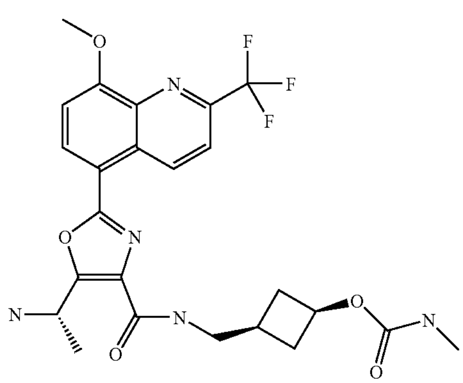 | 522 |

-continued
| Cpd. No. | Structure | MS (M + 1) |
|---|---|---|
| 26-804 | 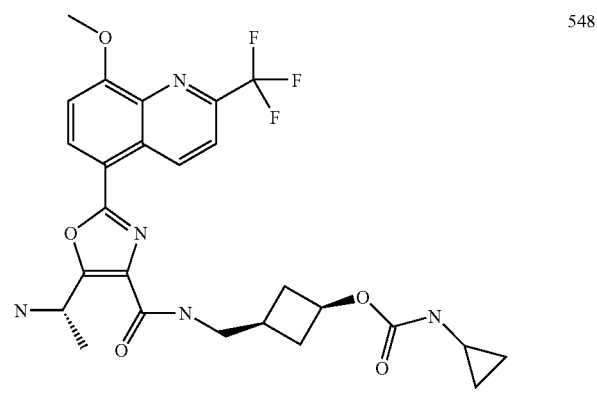 | 536 |
| 26-805 | 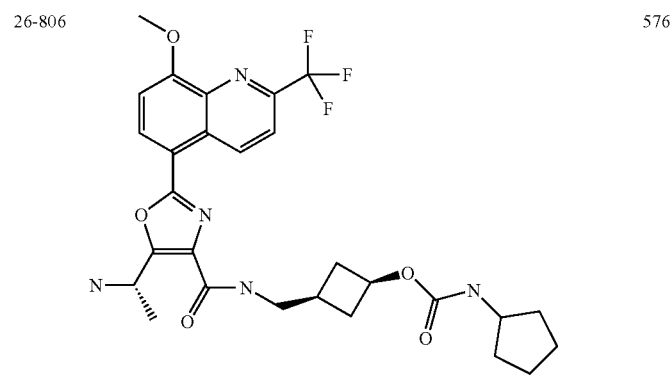 | 548 |
| 26-806 | 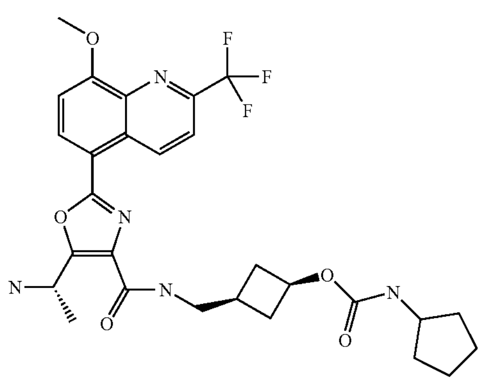 | 576 |

| Cpd. No. | Structure | MS (M + 1) |
|---|---|---|
| 26-807 | 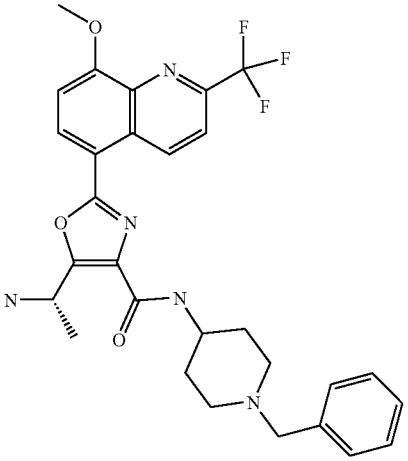 | 554 |
| 26-808 | 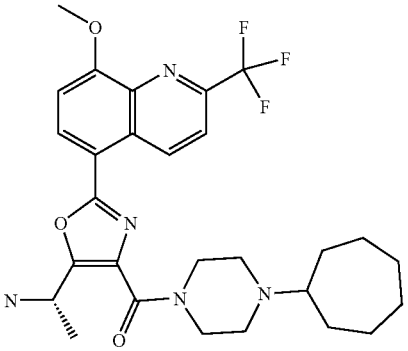 | 546 |
| 26-809 | 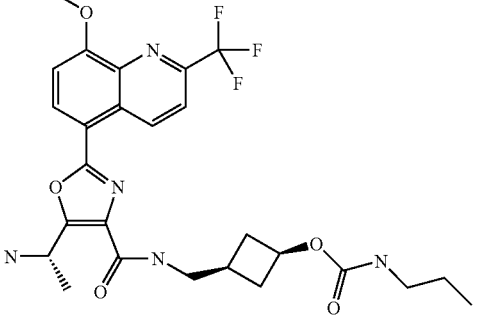 | 550 |
| 26-810 | 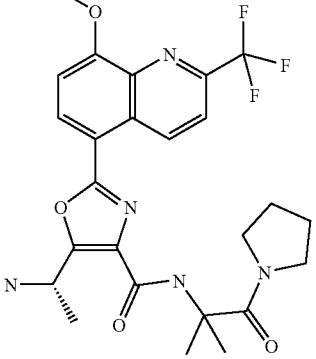 | 520 |

-continued

| Cpd. No. | Structure | MS (M + 1) |
|---|---|---|
| 26-811 | 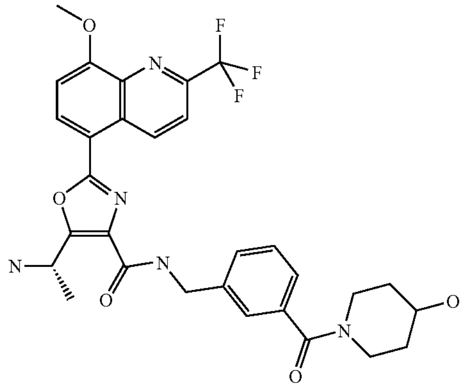 | 598 |
| 26-812 | 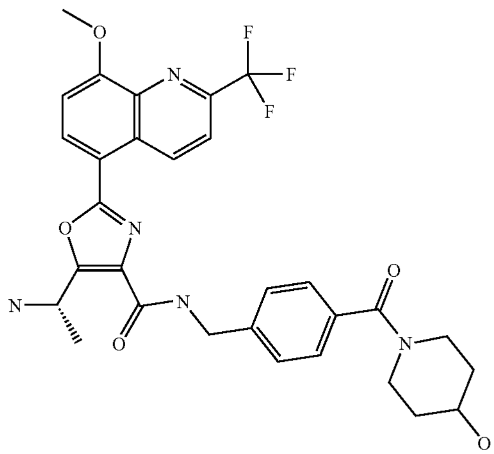 | 598 |
| 26-813 | 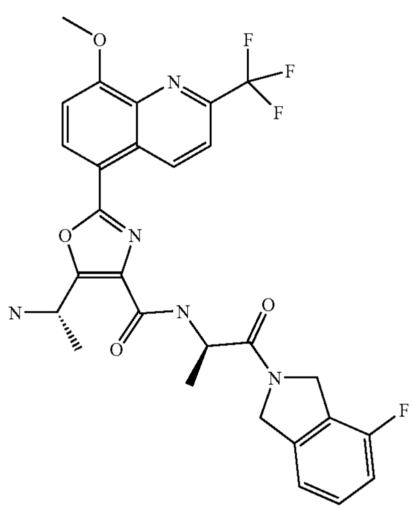 | 572 |

-continued

| Cpd. No. | Structure | MS (M + 1) |
|---|---|---|
| 26-814 | 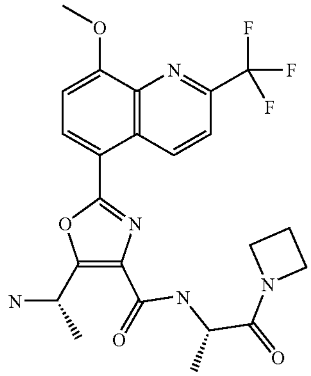 | 492 |
| 26-815 | 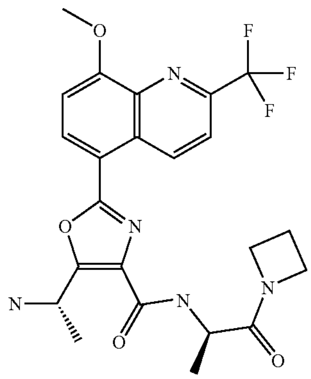 | 492 |
| 26-816 | 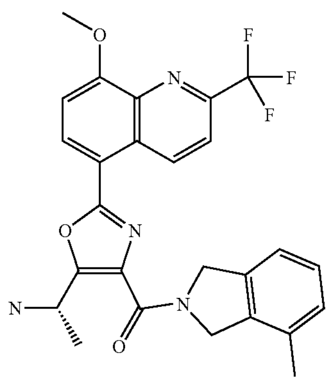 | 497 |
| 26-817 | 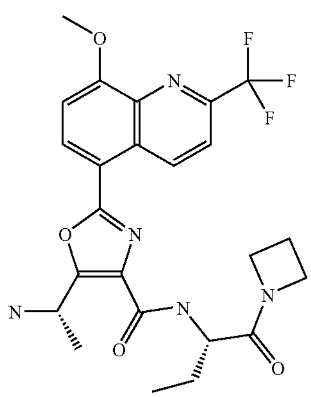 | 506 |

-continued
| Cpd. No. | Structure | MS (M + 1) |
|---|---|---|
| 26-818 | 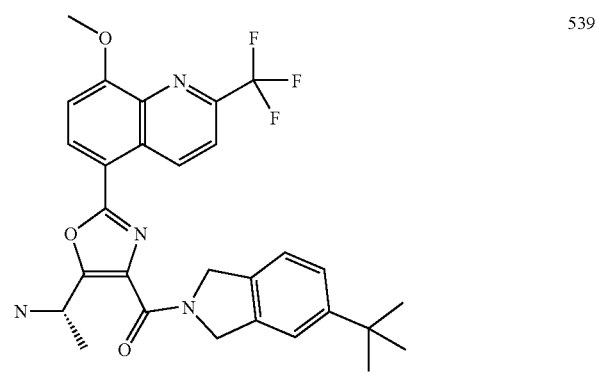 | 489 |
| 26-819 | 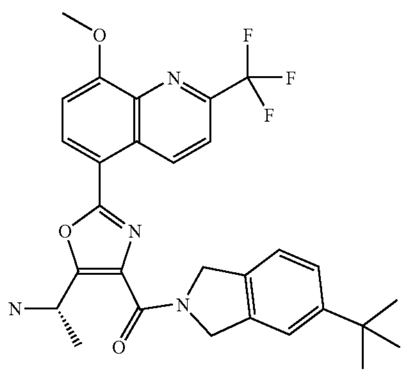 | 539 |
| 26-820 | 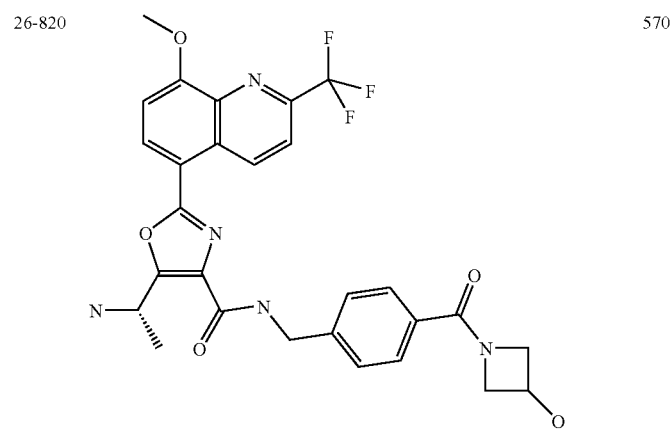 | 570 |

| Cpd. No. | Structure | MS (M + 1) |
|---|---|---|
| 26-821 | 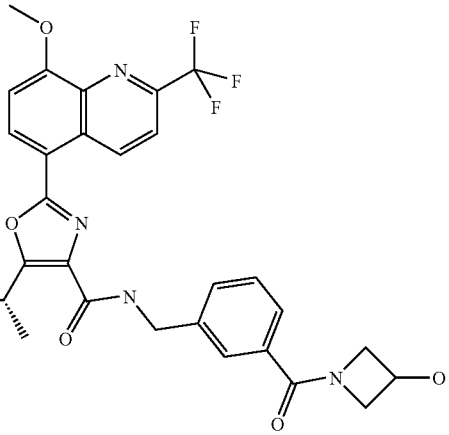 | 570 |
| 26-822 | 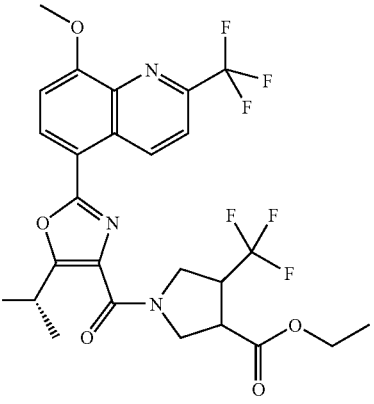 | 575 |
| 26-823 | 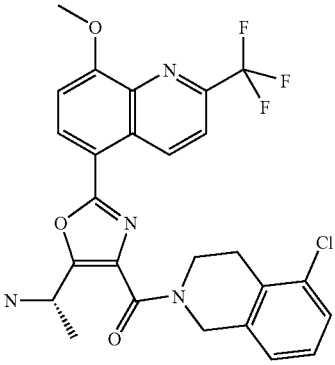 | 531 |

-continued

| Cpd. No. | Structure | MS (M + 1) |
|---|---|---|
| 26-824 | 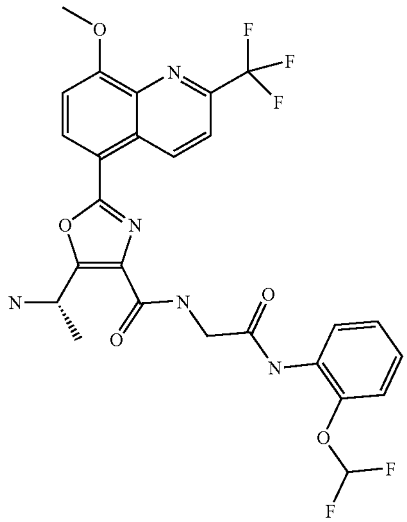 | 580 |
| 26-825 | 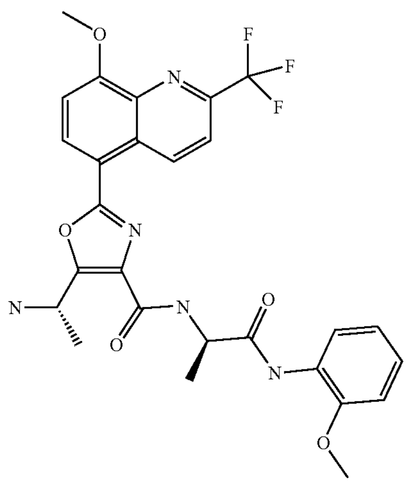 | 558 |
| 26-826 | 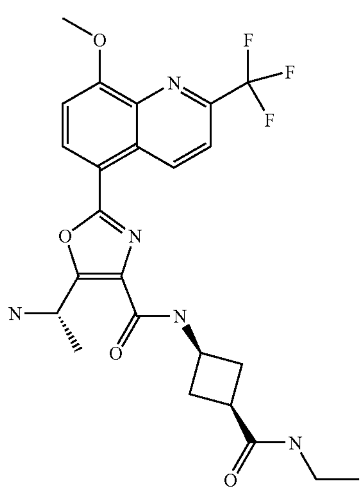 | 506 |

-continued

| Cpd. No. | Structure | MS (M + 1) |
|---|---|---|
| 26-827 | 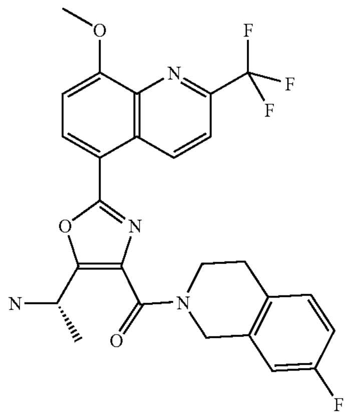 | 515 |
| 26-828 | 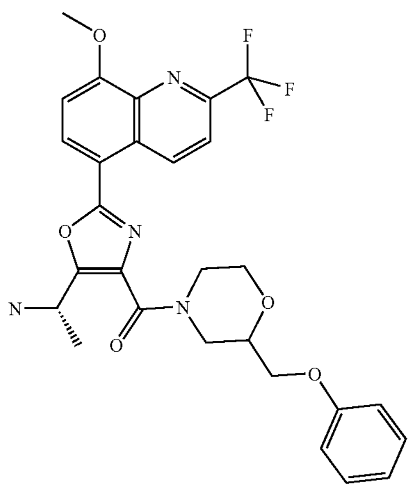 | 557 |
| 26-829 | 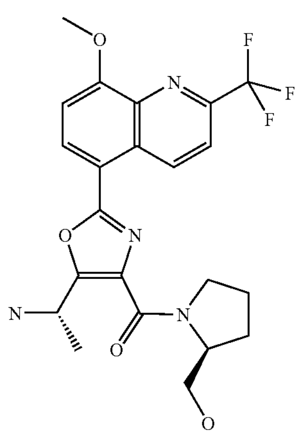 | 465 |

-continued

| Cpd. No. | Structure | MS (M + 1) |
|---|---|---|
| 26-830 | 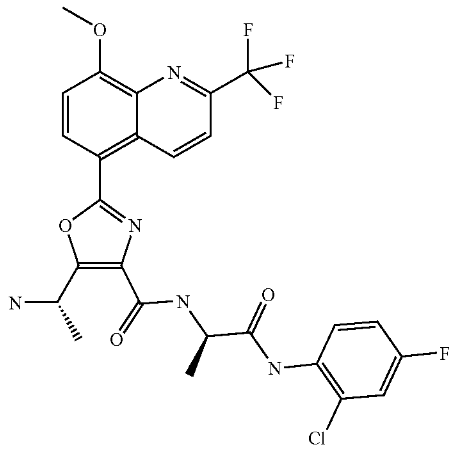 | 566 |
| 26-831 | 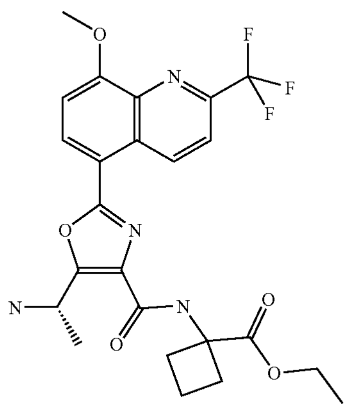 | 507 |
| 26-832 | 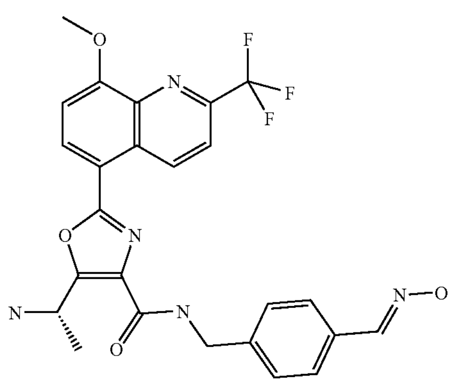 | 514 |

| Cpd. No. | Structure | MS (M + 1) |
|---|---|---|
| 26-833 | 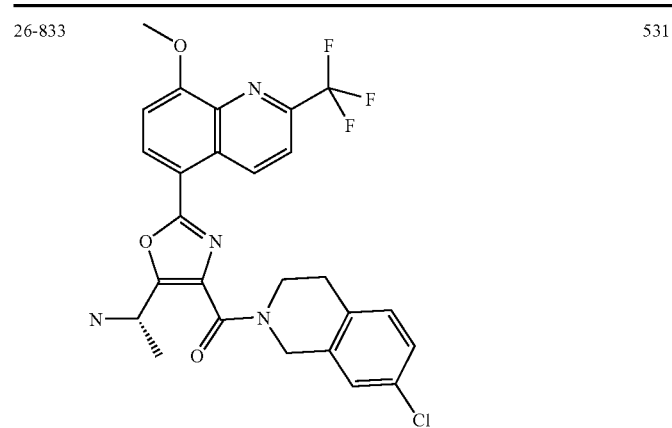 | 531 |
| 26-834 | 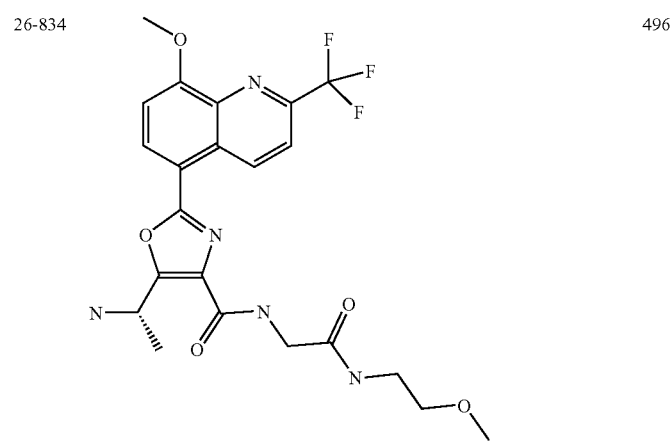 | 496 |
| 26-835 | 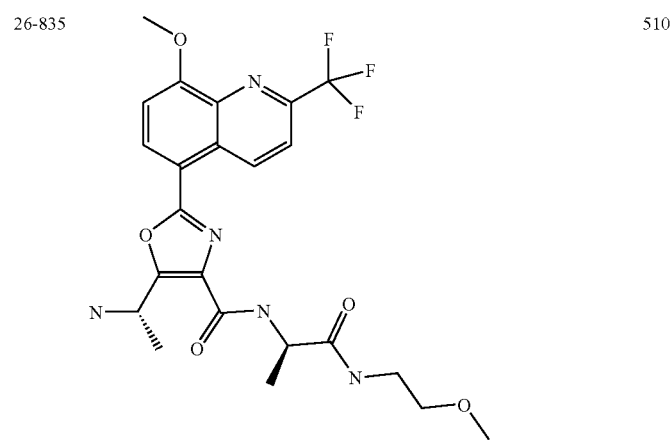 | 510 |

| Cpd. No. | Structure | MS (M + 1) |
|---|---|---|
| 26-836 | 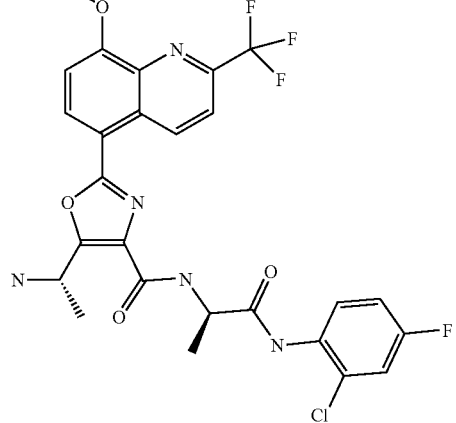 | 580 |
| 26-837 | 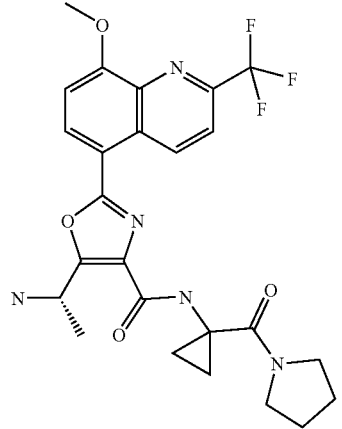 | 518 |
| 26-838 | 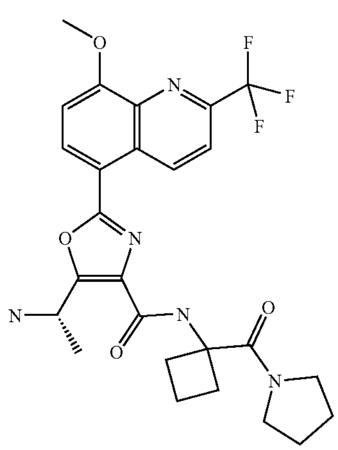 | 532 |

| Cpd. No. | Structure | MS (M + 1) |
|---|---|---|
| 26-839 | 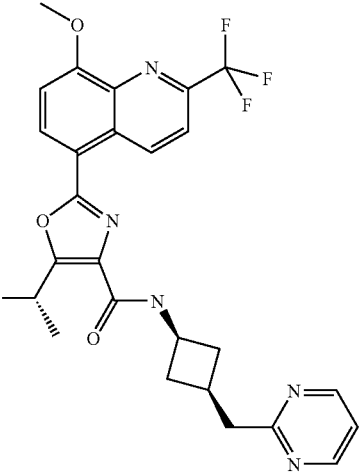 | 527 |
| 26-840 | 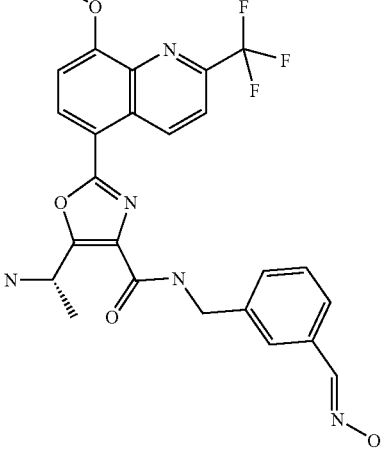 | 514 |
| 26-841 | 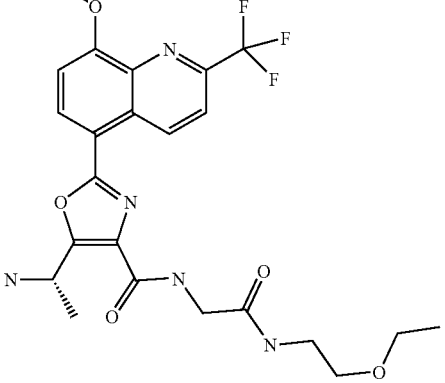 | 510 |

-continued

| Cpd. No. | Structure | MS (M + 1) |
|---|---|---|
| 26-842 | 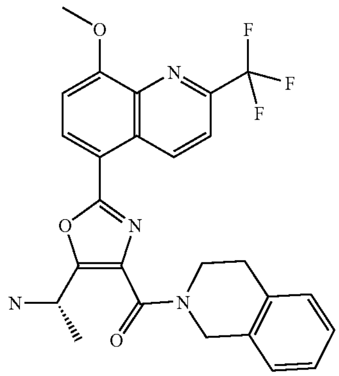 | 497 |
| 26-843 | 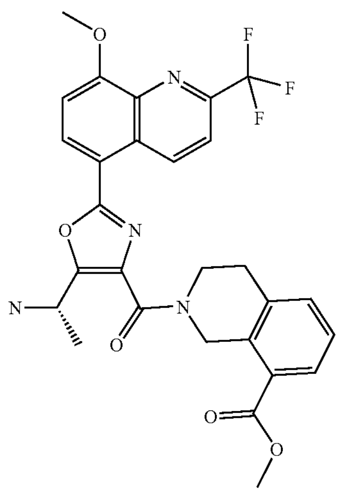 | 555 |
| 26-844 | 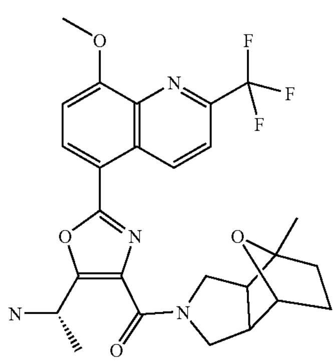 | 517 |

| Cpd. No. | Structure | MS (M + 1) |
|---|---|---|
| 26-845 | 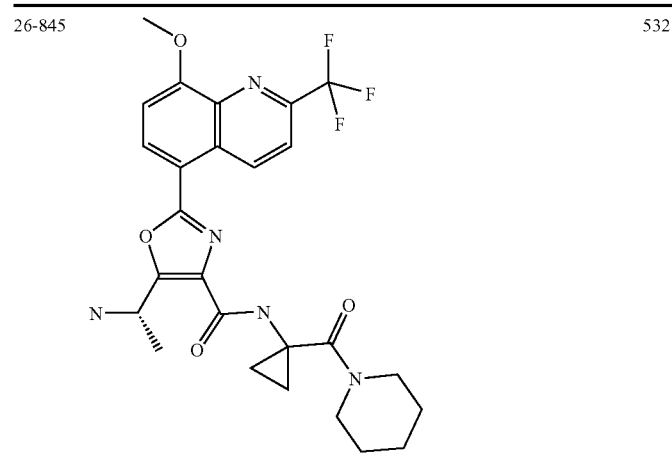 | 532 |
| 26-846 | 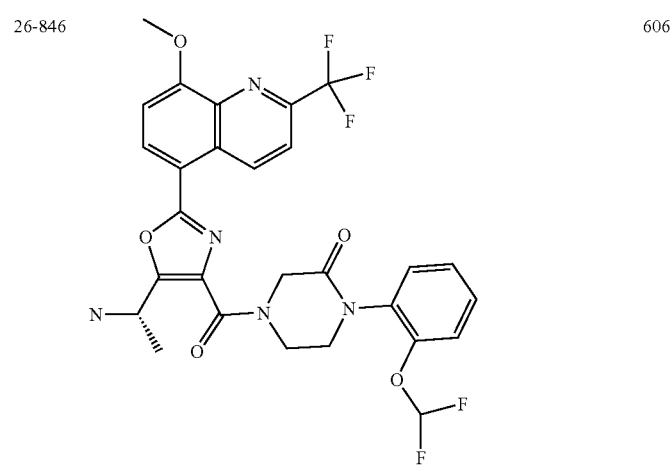 | 606 |
| 26-847 | 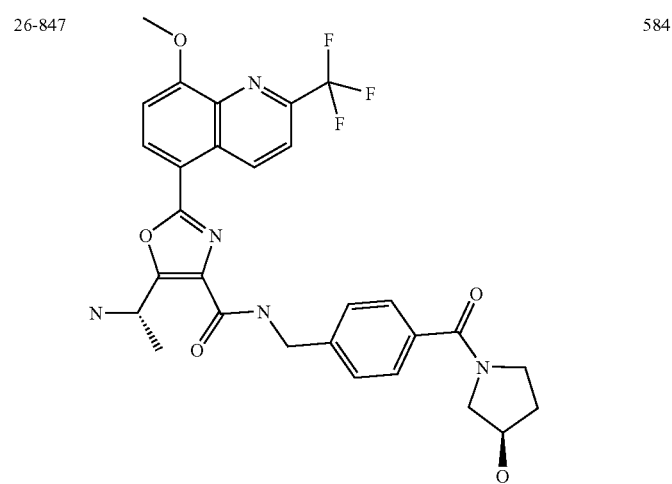 | 584 |

-continued

| Cpd. No. | Structure | MS (M + 1) |
|---|---|---|
| 26-848 | 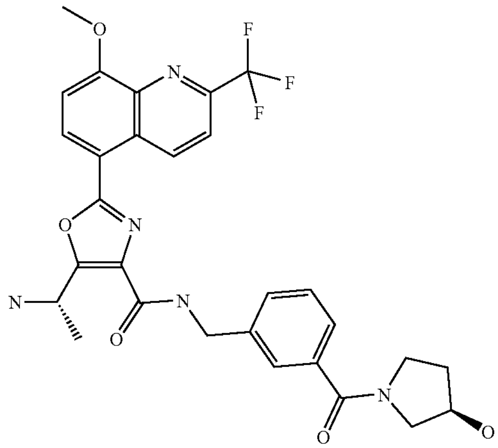 | 584 |
| 26-849 | 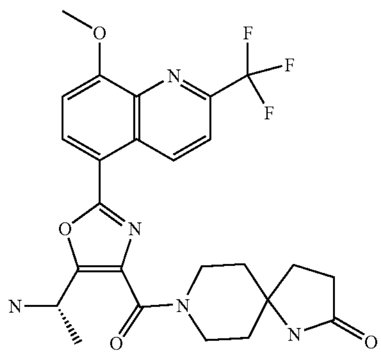 | 518 |
| 26-850 | 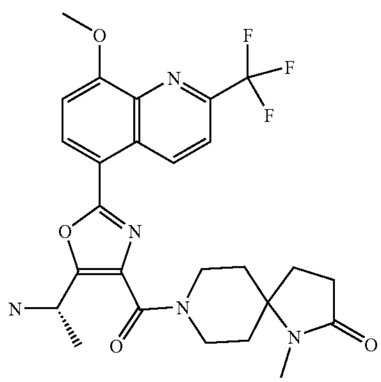 | 532 |
| 26-851 | 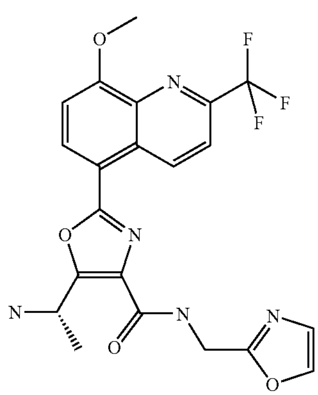 | 462 |

-continued
| Cpd. No. | Structure | MS (M + 1) |
|---|---|---|
| 26-852 | 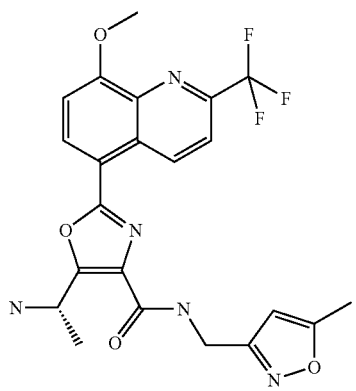 | 476 |
| 26-853 | 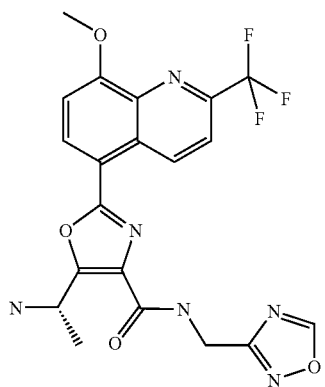 | 463 |
| 26-854 | 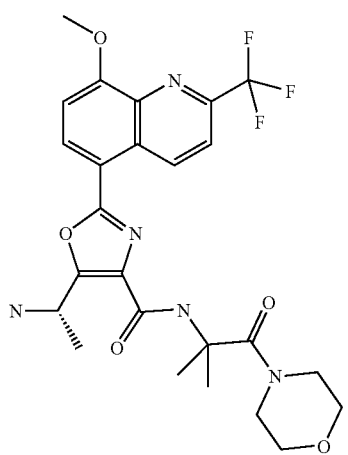 | 536 |

-continued

| Cpd. No. | Structure | MS (M + 1) |
|---|---|---|
| 26-855 | 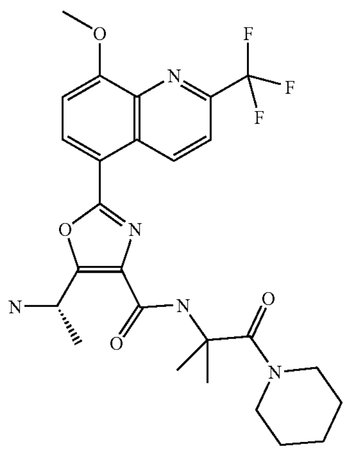 | 534 |
| 26-856 | 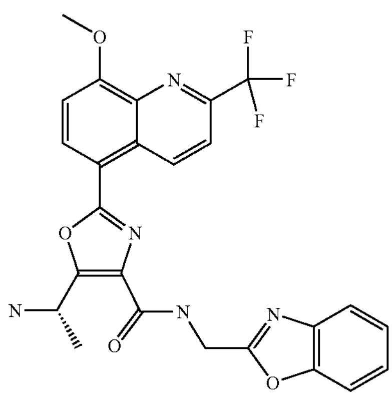 | 512 |
| 26-857 | 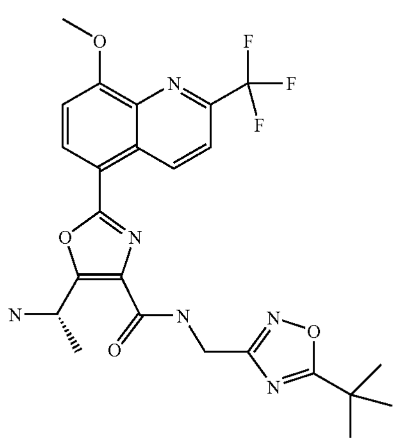 | 519 |

| Cpd. No. | Structure | MS (M + 1) |
|---|---|---|
| 26-858 | 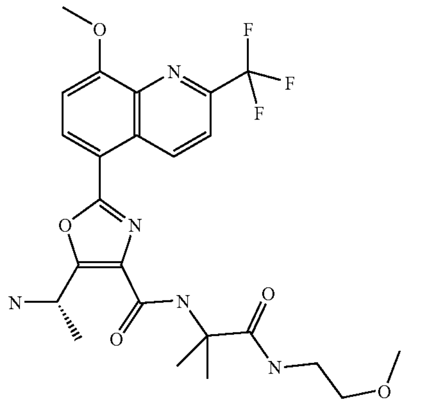 | 524 |
| 26-859 | 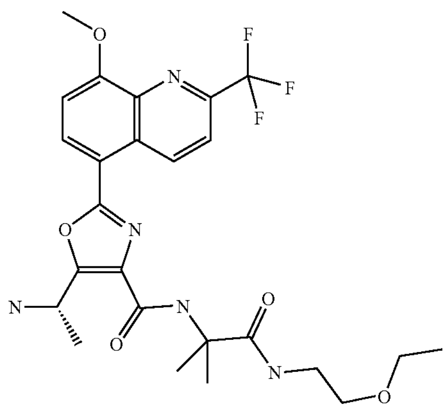 | 538 |
| 26-860 | 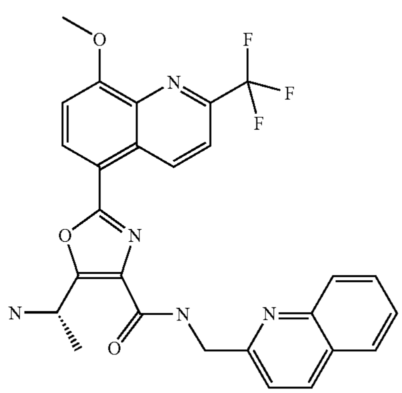 | 522 |

| Cpd. No. | Structure | MS (M + 1) |
|---|---|---|
| 26-861 | 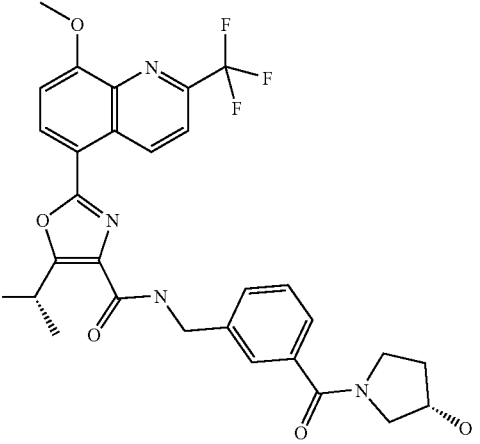 | 584 |
| 26-862 | 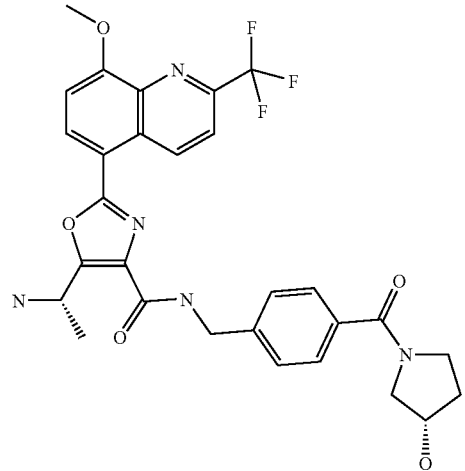 | 584 |
| 26-863 | 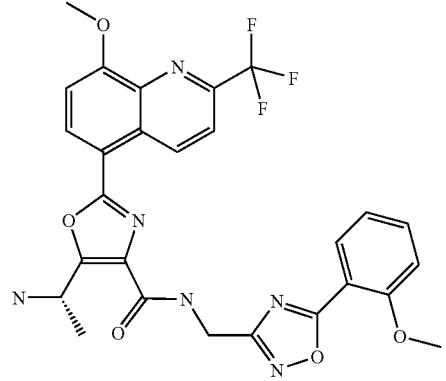 | 569 |

| Cpd. No. | Structure | MS (M + 1) |
|---|---|---|
| 26-864 | 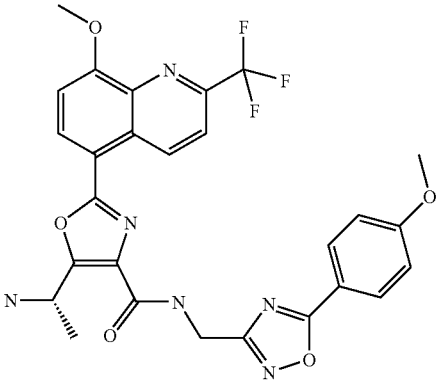 | 569 |
| 26-865 | 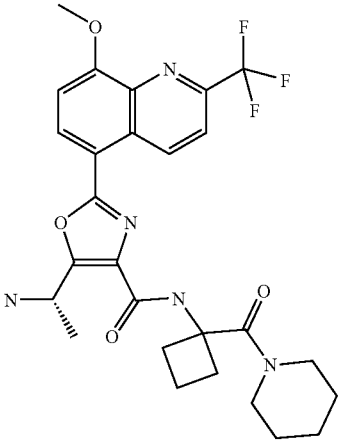 | 546 |
| 26-866 | 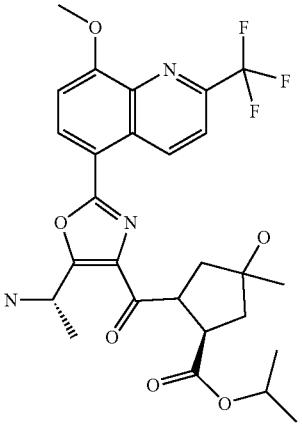 | 551 |

| Cpd. No. | Structure | MS (M + 1) |
|---|---|---|
| 26-867 | 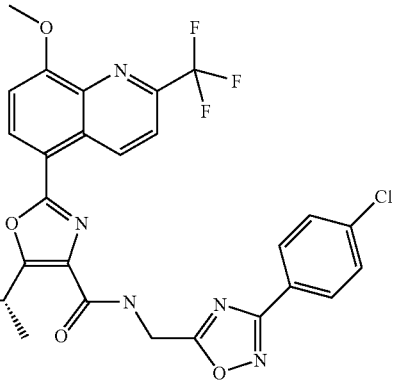 | 573 |
| 26-868 | 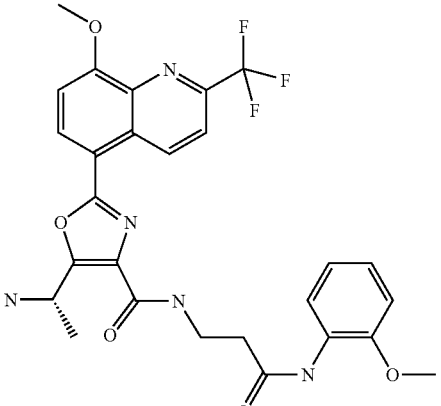 | 558 |
| 26-869 | 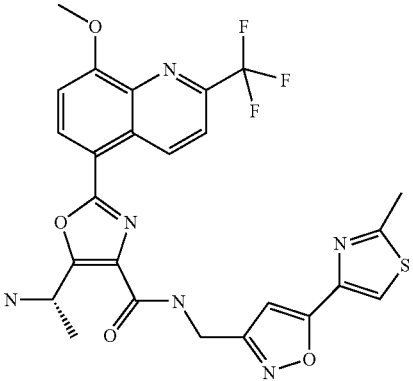 | 559 |

-continued
| Cpd. No. | Structure | MS (M + 1) |
|---|---|---|
| 26-870 | 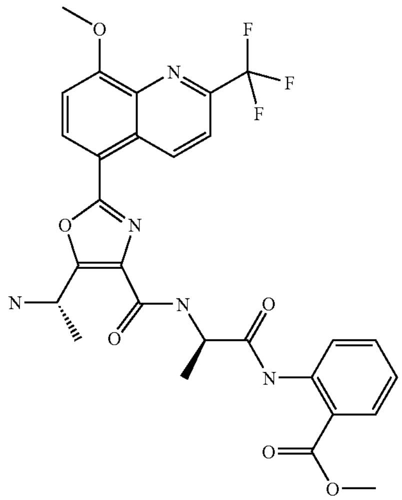 | 586 |
| 26-871 | 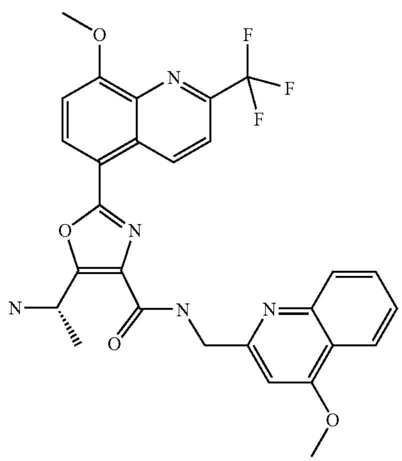 | 552 |
| 26-872 | 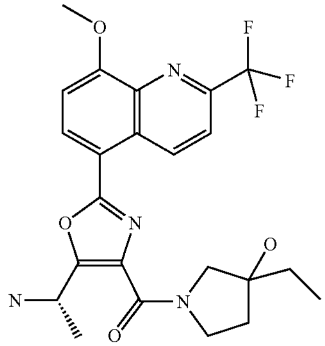 | 479 |
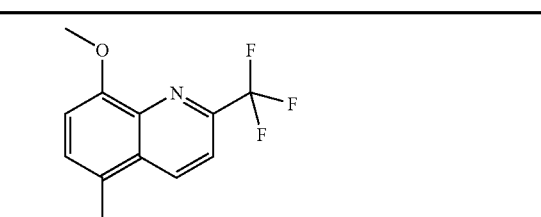

| Cpd. No. | Structure | MS (M + 1) |
|---|---|---|
| 26-873 | 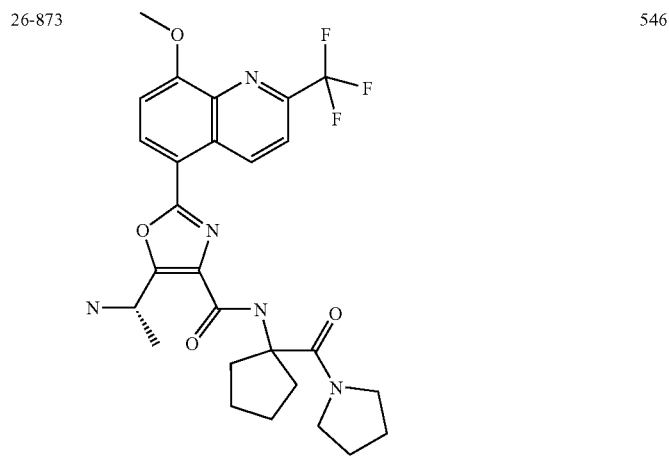 | 546 |
| 26-874 | 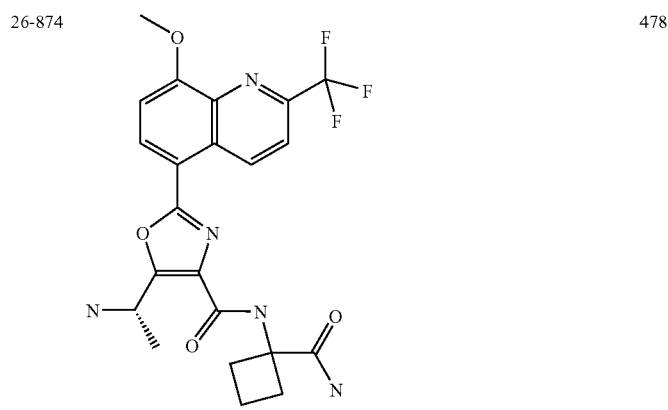 | 478 |
| 26-875 | 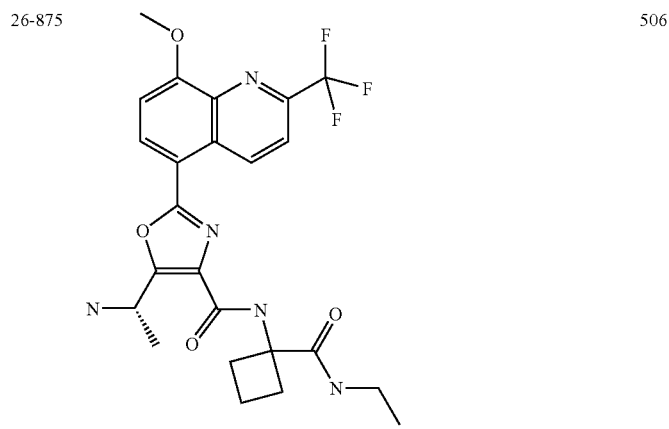 | 506 |

-continued
| Cpd. No. | Structure | MS (M + 1) |
|---|---|---|
| 26-876 | 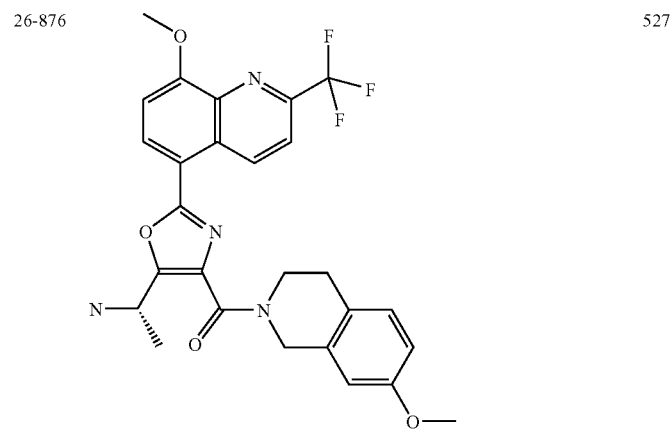 | 527 |
| 26-877 | 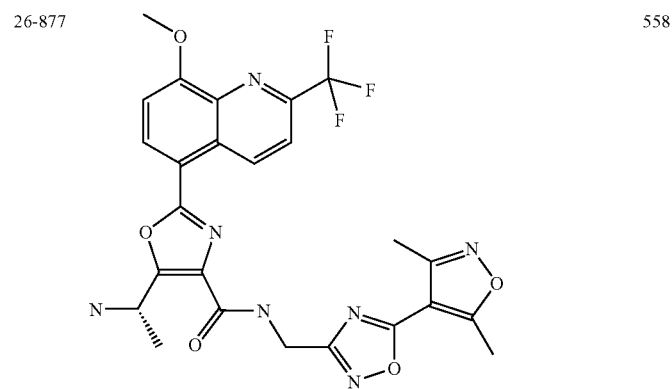 | 558 |
| 26-878 | 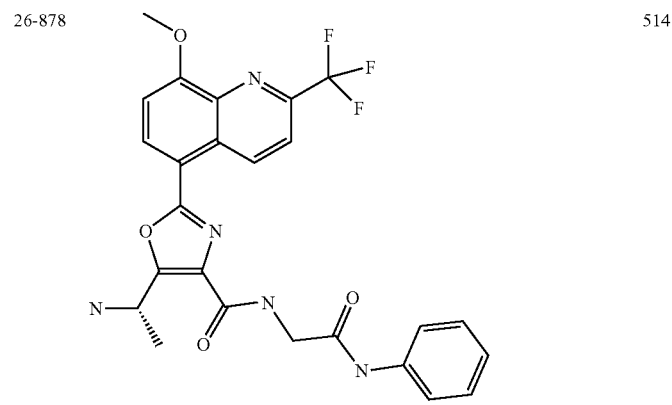 | 514 |

-continued
| Cpd. No. | Structure | MS (M + 1) |
|---|---|---|
| 26-879 | 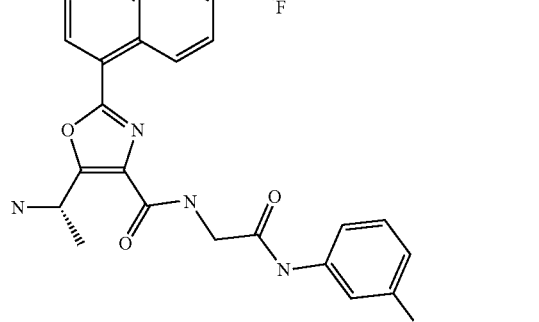 | 544 |
| 26-880 | 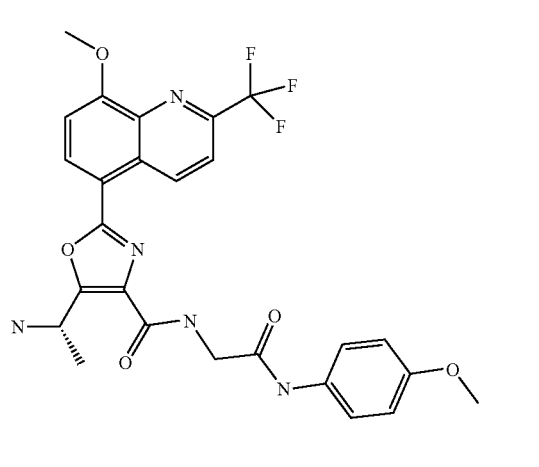 | 544 |
| 26-881 | 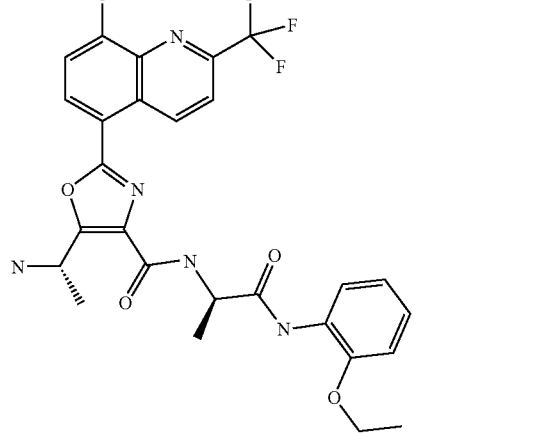 | 572 |

-continued

| Cpd. No. | Structure | MS (M + 1) |
|---|---|---|
| 26-882 | 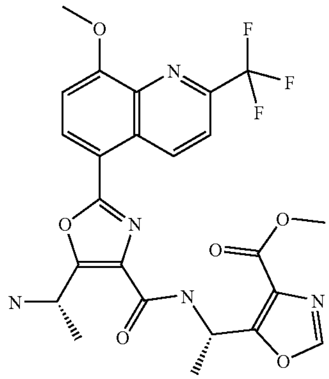 | 534 |
| 26-883 | 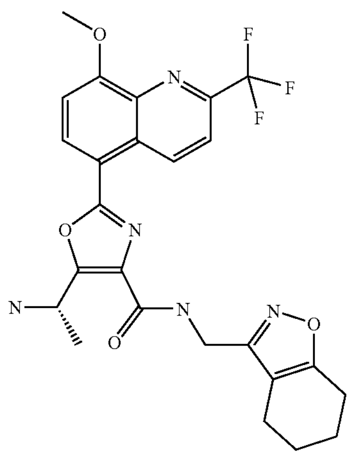 | 516 |
| 26-884 | 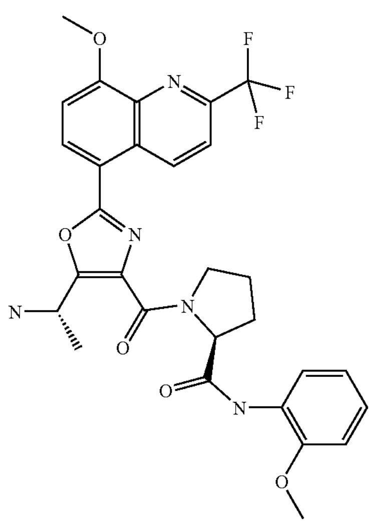 | 584 |

| Cpd. No. | Structure | MS (M + 1) |
|---|---|---|
| 26-885 | 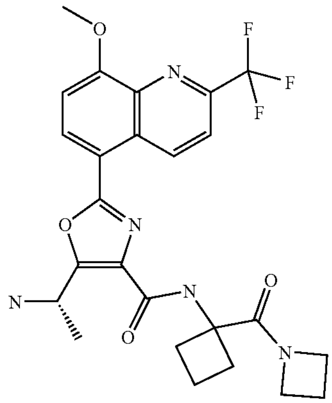 | 518 |
| 26-886 | 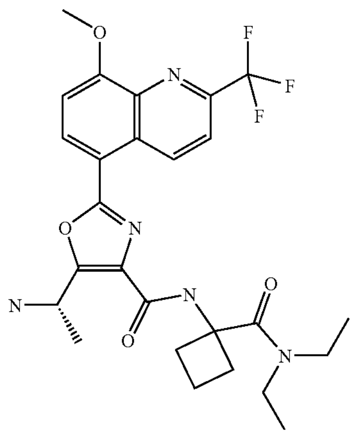 | 534 |
| 26-887 | 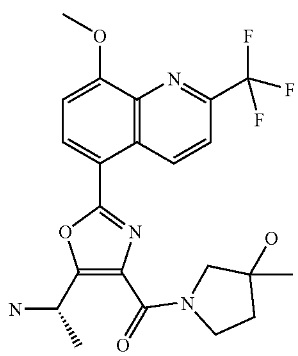 | 465 |
| 26-888 | 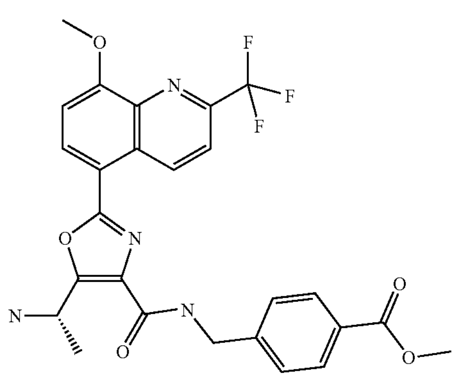 | 529 |

-continued

| Cpd. No. | Structure | MS (M + 1) |
|---|---|---|
| 26-889 | 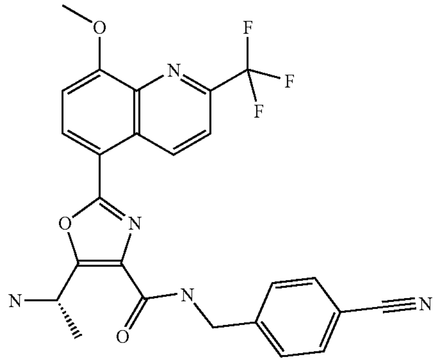 | 496 |
| 26-890 | 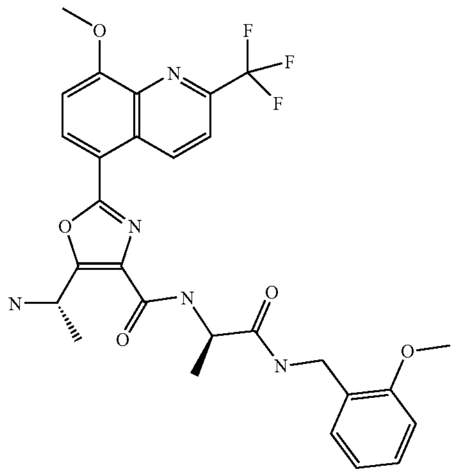 | 572 |
| 26-891 | 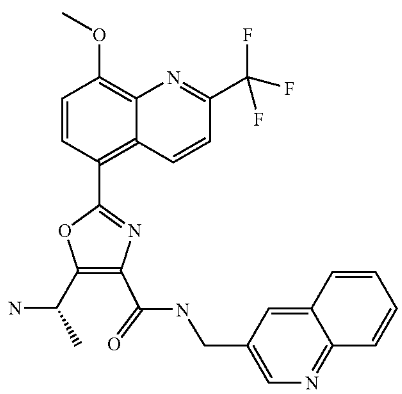 | 522 |
| 26-892 | 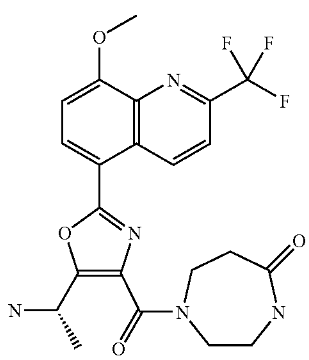 | 478 |

-continued

| Cpd. No. | Structure | MS (M + 1) |
|---|---|---|
| 26-893 | 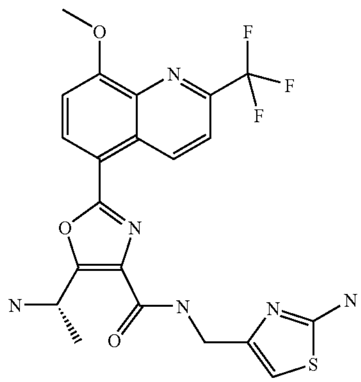 | 493 |
| 26-894 | 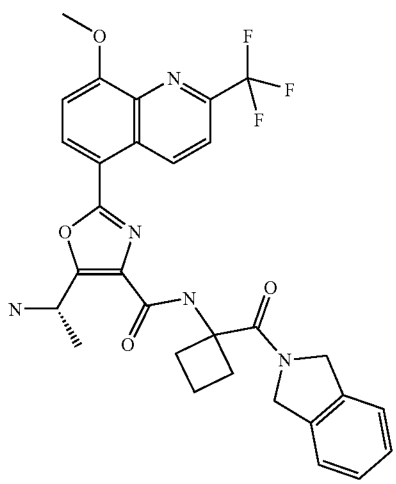 | 580 |
| 26-895 | 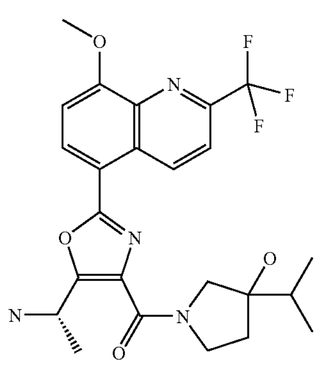 | 493 |

| Cpd. No. | Structure | MS (M + 1) |
|---|---|---|
| 26-896 | 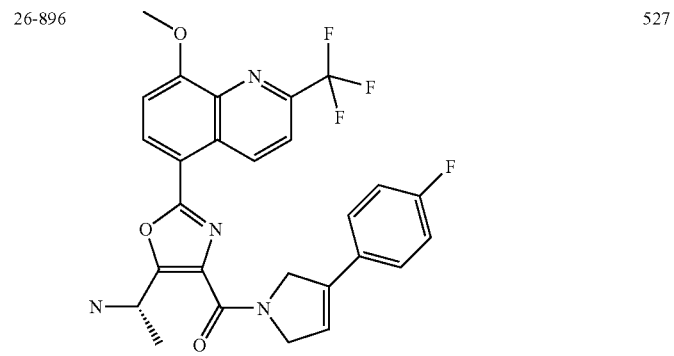 | 527 |
| 26-897 | 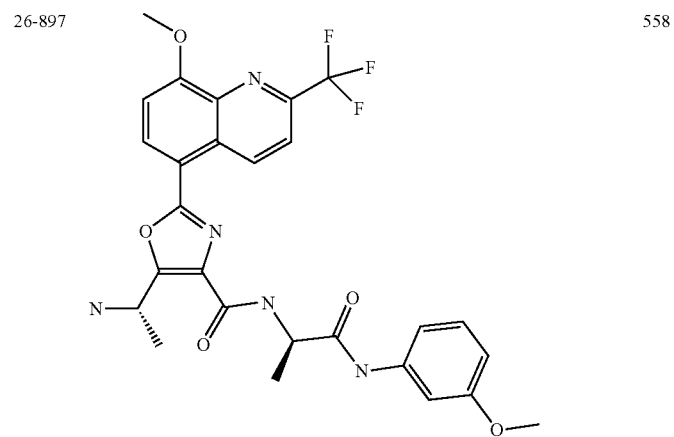 | 558 |
| 26-898 | 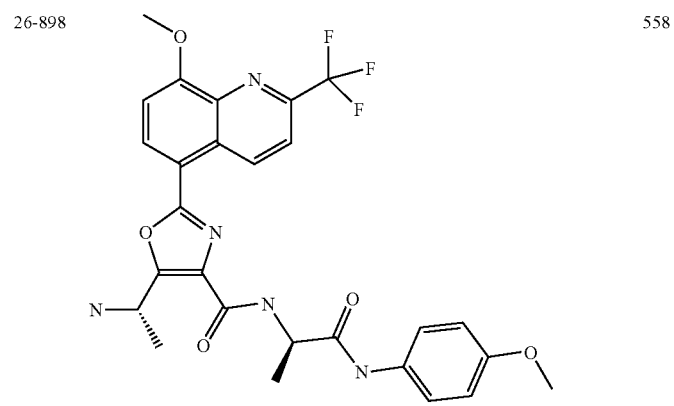 | 558 |

-continued

| Cpd. No. | Structure | MS (M + 1) |
|---|---|---|
| 26-899 | 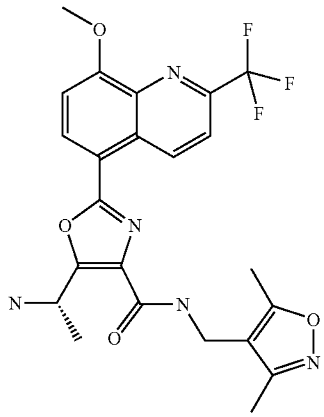 | 490 |
| 26-890 | 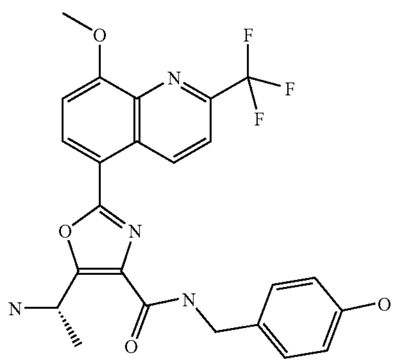 | 487 |
| 26-891 | 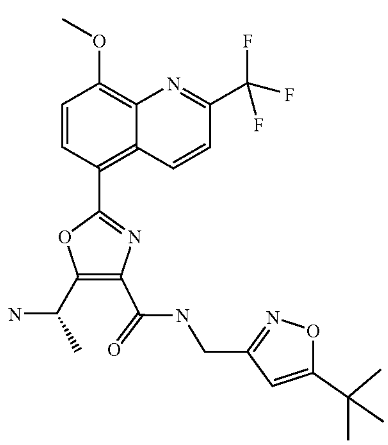 | 518 |

-continued
| Cpd. No. | Structure | MS (M + 1) |
|---|---|---|
| 26-892 | 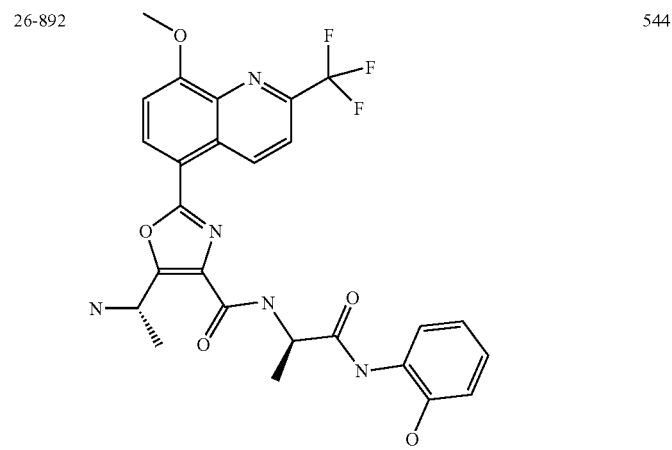 | 544 |
| 26-893 | 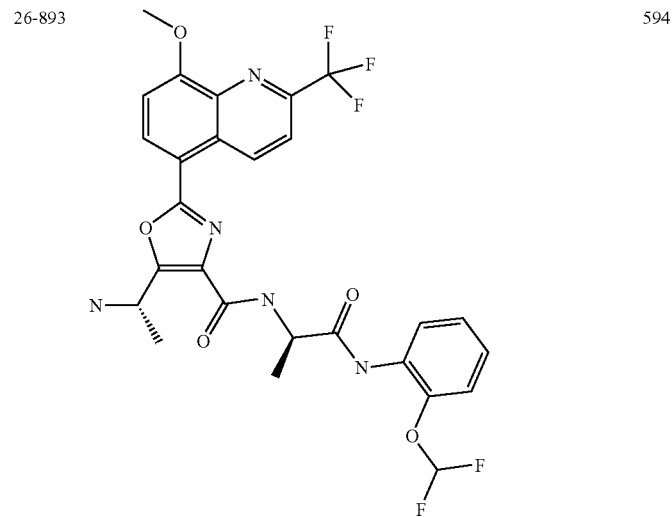 | 594 |
| 26-894 | 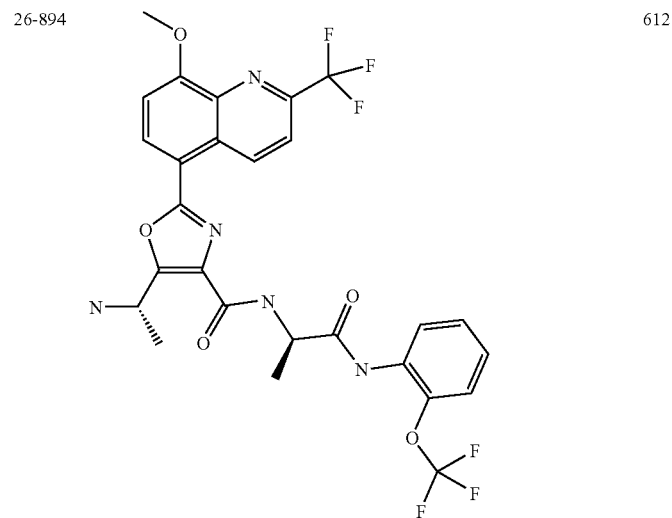 | 612 |

-continued
| Cpd. No. | Structure | MS (M + 1) |
|---|---|---|
| 26-895 | 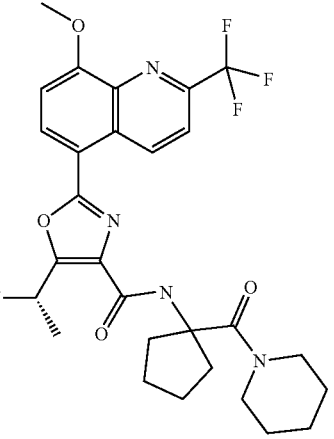 | 560 |
| 26-896 | 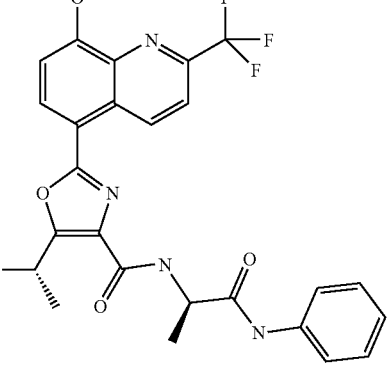 | 528 |
| 26-897 | 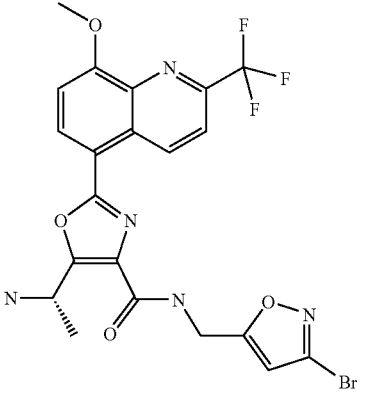 | 540 |

| Cpd. No. | Structure | MS (M + 1) |
|---|---|---|
| 26-898 | 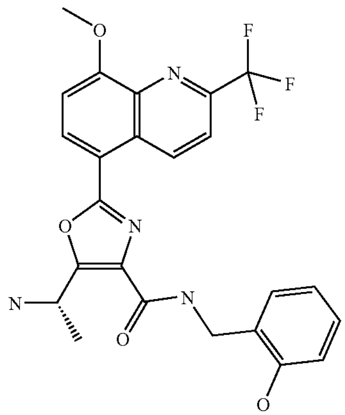 | 487 |
| 26-899 | 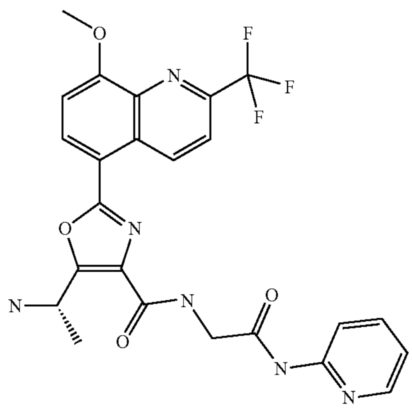 | 515 |
| 26-900 | 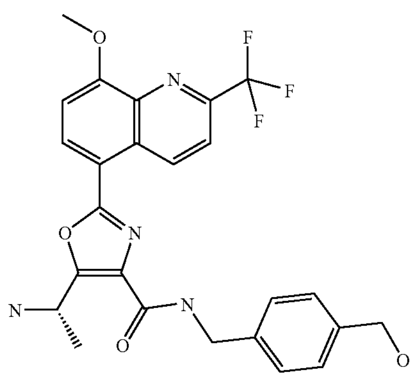 | 501 |
| 26-901 | 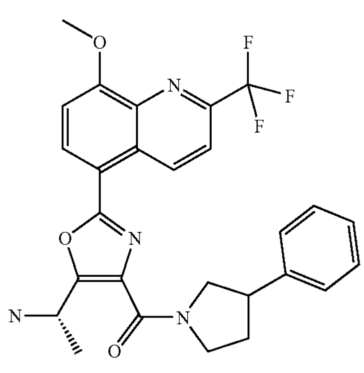 | 511 |

| Cpd. No. | Structure | MS (M + 1) |
|---|---|---|
| 26-902 | 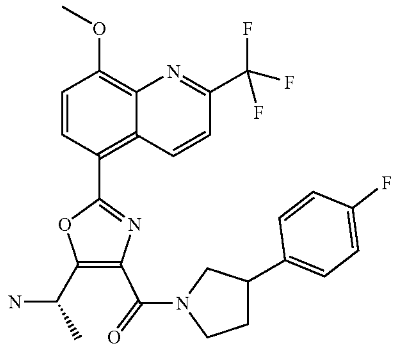 | 529 |
| 26-903 | 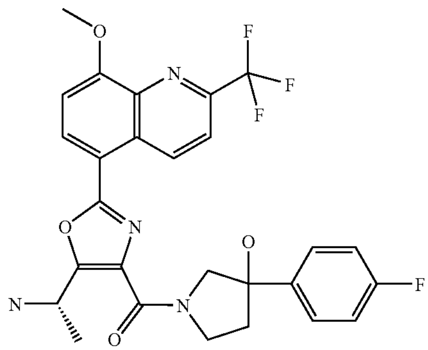 | 545 |
| 26-904 | 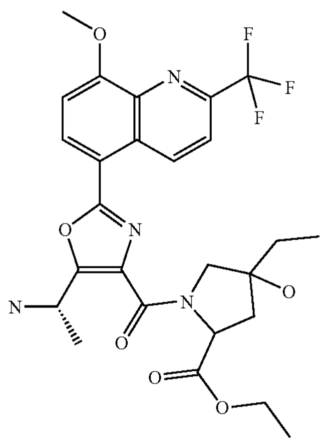 | 551 |
| 26-905 | 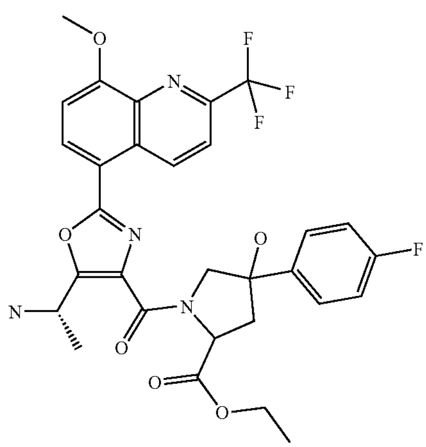 | 617 |

US 7,511,062 B2
-continued
| Cpd. No. | Structure | MS (M + 1) |
|---|---|---|
| 26-906 | 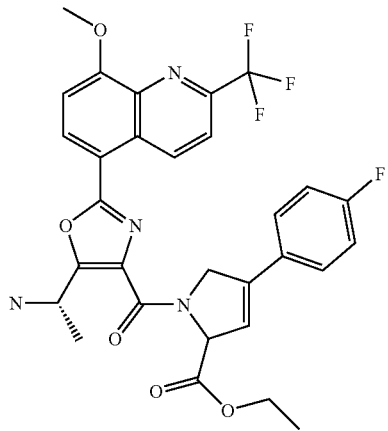 | 599 |
| 26-907 | 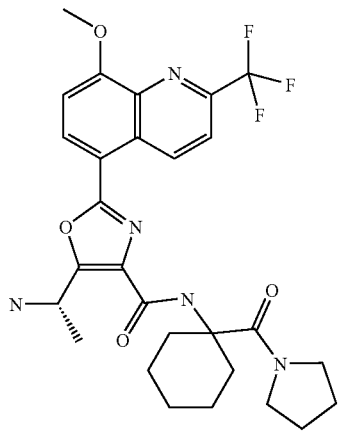 | 560 |
| 26-908 | 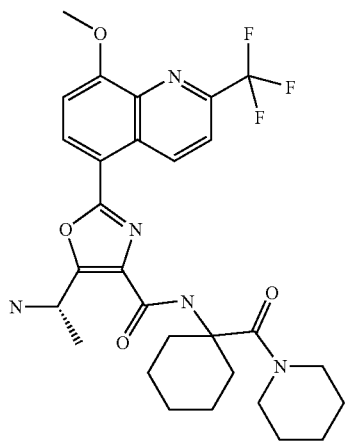 | 574 |

| Cpd. No. | Structure | MS (M + 1) |
|---|---|---|
| 26-909 | 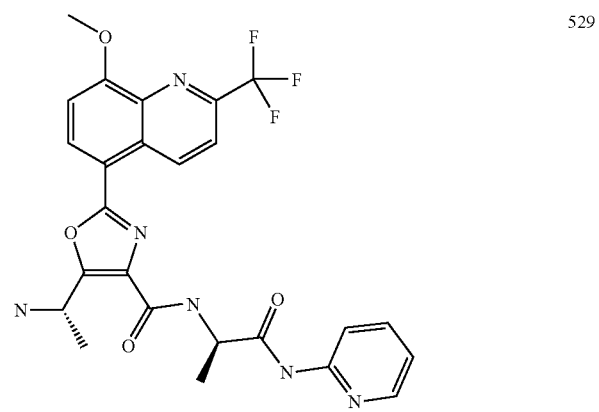 | 501 |
| 26-910 | 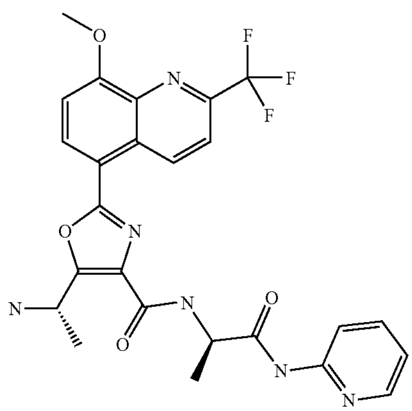 | 529 |
| 26-911 | 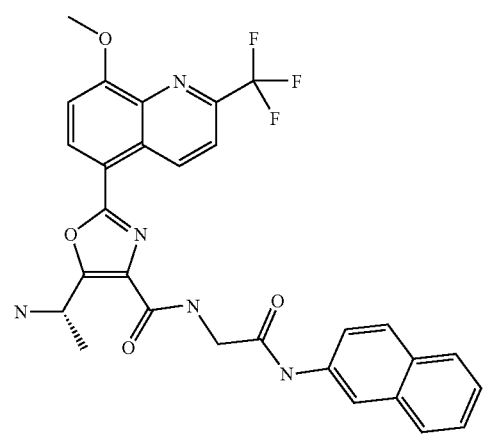 | 564 |

| Cpd. No. | Structure | MS (M + 1) |
|---|---|---|
| 26-912 | 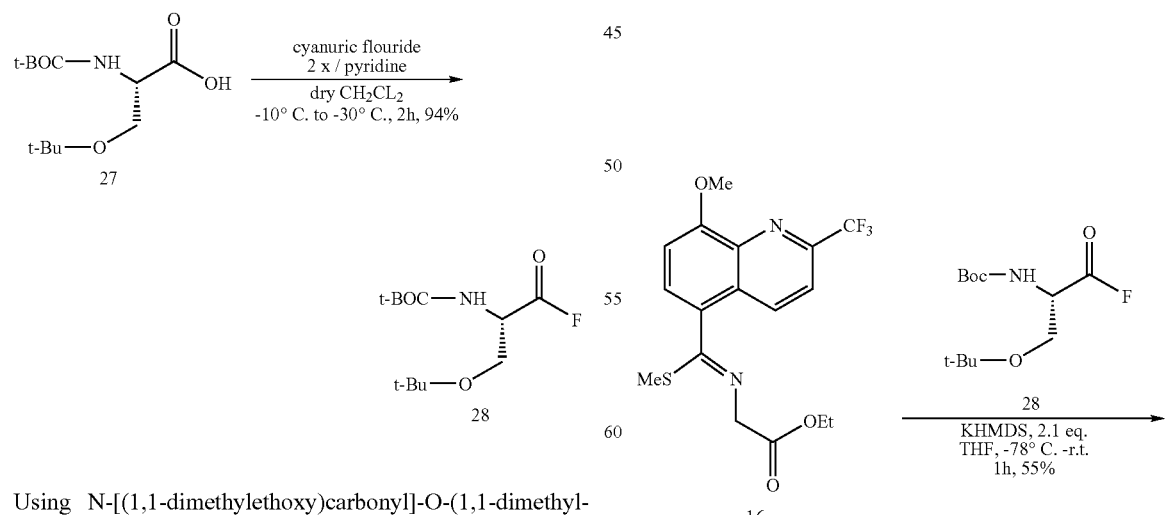 | 578 |
| 26-913 | 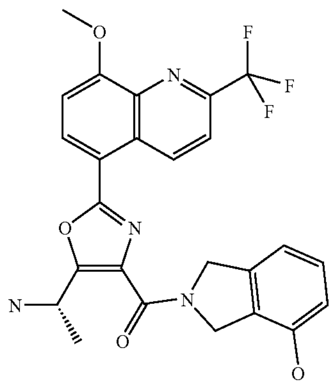 | 499 |
EXAMPLE 8
Step 1:
Step 2:
Using N-[(1,1-dimethylethoxy)carbonyl]-O-(1,1-dimethylethyl)-L-serine (compound 27) as starting material, [1(S)-[(1,1-dimethylethoxy)methyl]-2-fluoro-2-oxoethyl] carbamic acid, 1,1-dimethylethyl ester (compound 28) was prepared by a method analogous to that in Example 5, step 4.

-continued

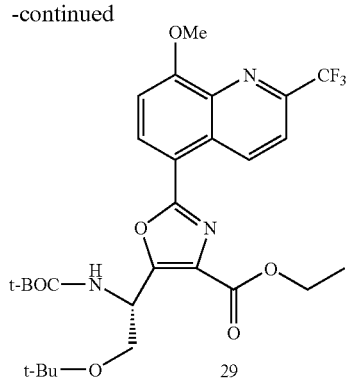

0.5 M KHMDS in toluene (92.5 ml, 46.25 mmol) was added slowly via a syringe to a mixture of compound 16 (8.5 g, 22 mmol) and compound 28 (6.8 g, 25.8 mmol) in dry THF (90 ml) at −78° C. The mixture was slowly warmed to RT, then stirred at RT for 1 h. After the reaction was complete, it was quenched with 1 N HCl (80 ml)(cooled with ice-water bath), diluted with saturated NH$_4$Cl solution (100 ml), extracted with EtOAc (200 ml×2), dried (Na$_2$SO$_4$), filtered and evaporated. Crude material was purified on Biotage with CH$_2$Cl$_2$ (4 L) and 5% EtOAc/CH$_2$Cl$_2$ (4 L) to give compound 29 as a light yellow solid (6.5 g, 11.8 mmol, 52%). MS C$_{28}$H$_{34}$F$_3$N$_3$O$_7$ [M+1]$^+$582.1.

EXAMPLE 9

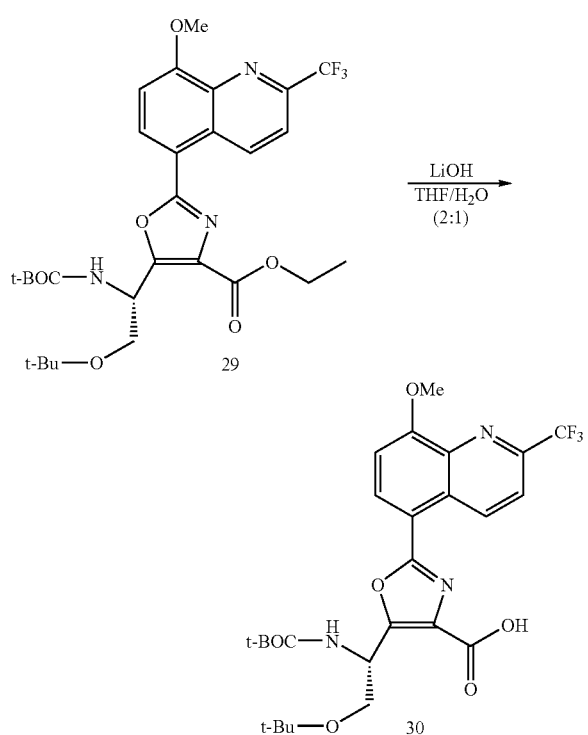

Compound 29 (13.5 g, 23.24 mmol) was treated with THF: H$_2$O (2:1) (200 ml) and LiOH.H$_2$O (0.95 g, 39.6 mmol) (dissolved in 10 ml of H$_2$O). After stirring at RT for 2 h, the suspension was not dissolved. Additional THF:H$_2$O (2:1) (100 ml) and LiOH.H$_2$O (0.95 g, 39.6 mmol) was added. It was stirred at RT overnight. After completion, the reaction was neutralized with 1 N HCl. The mixture was extracted with CH$_2$Cl$_2$ (100 ml×3), combined, washed with brine (100 ml), dried (Na$_2$SO$_4$), filtered and evaporated to give the title compound 30 as a yellow solid (11.8 g, 21.3 mmol, 92%). LCMS: C$_{26}$H$_3$F$_3$N$_3$O$_7$ [M+1]$^+$554.1.

EXAMPLE 10

Step 1:

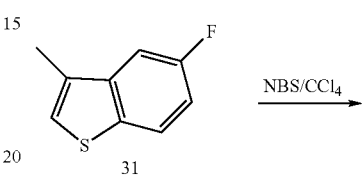

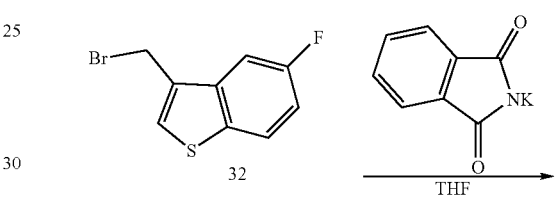

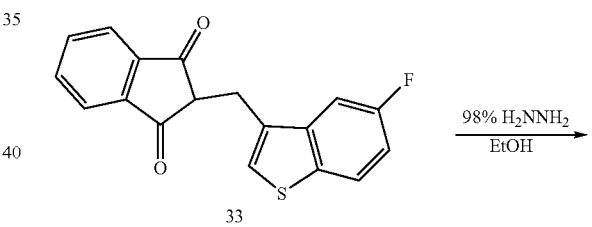

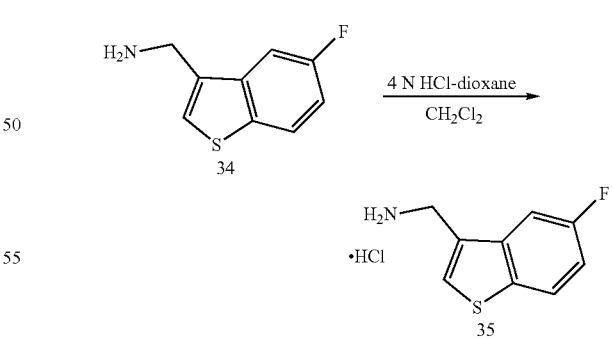

By a method analogous to Example 2, using 5-fluoro-3-methyl-benzo[B]-thiophene (31) as starting material, compound 33 was obtained. It was treated with 10 equivalents of 98% hydrazine in absolute EtOH and CH$_2$Cl$_2$ (1:1) to give compound 34, which was purified by treatment with a slight excess of 4 N HCl/dioxane solution to give compound 35 as a HCl salt. FABMS: C$_9$H$_8$FNS. HCl [M+1]$^+$182.0

Step 2:

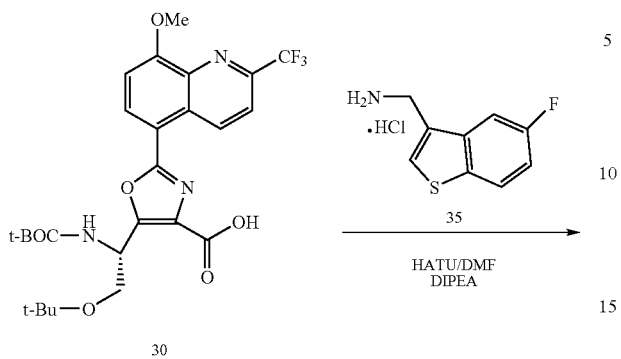

30

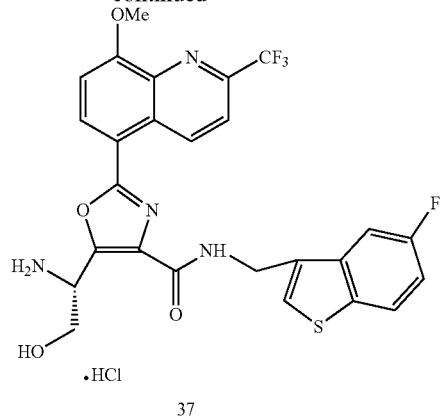

37

The protecting groups on compound 36 were removed by treatment with HCl-dioxane/CH$_2$Cl$_2$ or CF$_3$COOH. The title compound 37 was obtained directly as a HCl salt or as a TFA salt depending on the acid treatment. The TFA salt was neutralized with NH$_4$OH and converted to HCl salt with 1.0 equivalent of HCl. HRMS C$_{26}$H$_{20}$F$_4$N$_4$O$_4$S. HCl calculated [M+1]$^+$561.1220, Found 561.1230.

EXAMPLE 11

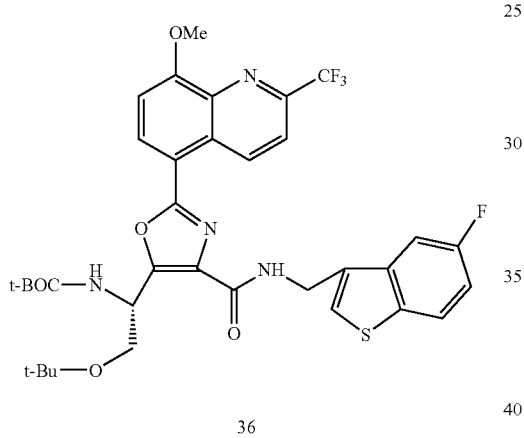

36

By methods analogous to those described in Example 3, using compound 35 as a starting material, compound 36 was obtained.

Step 3:

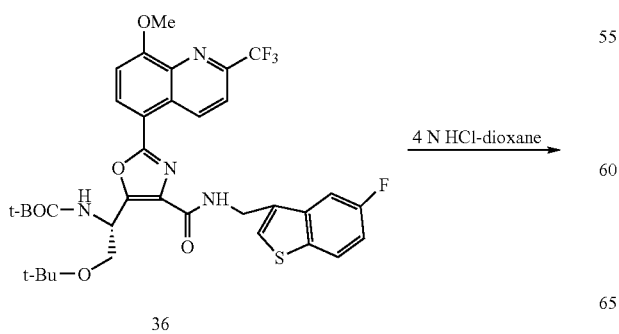

36

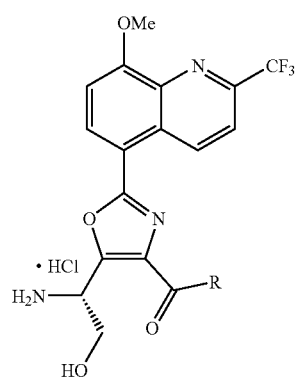

38

By employing analogous methods to those described in Example 10, the following compounds were obtained as HCl salts using compound 30 coupled with the appropriate primary or secondary amine, followed by removal of the protecting group as described for Example 10, step 3.

| Cpd. No. | Structure | MS (M+1) |
|---|---|---|
| 38-1 | 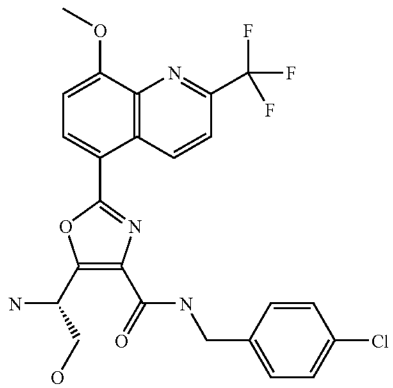 | 521 |
| 38-2 | 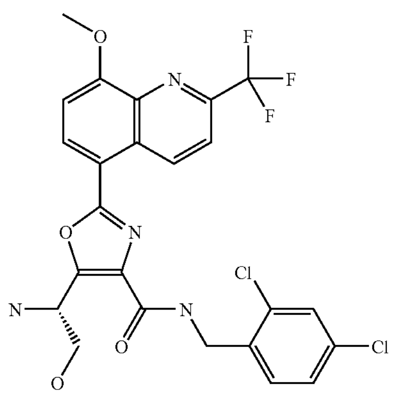 | 557 |
| 38-3 | 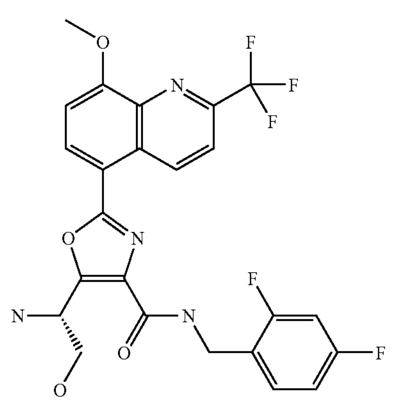 | 523 |
| 38-4 | | 539 |
| 38-5 | | 523 |
| 38-6 | | 523 |

| Cpd. No. | Structure | MS (M + 1) |
|---|---|---|
| 38-7 | 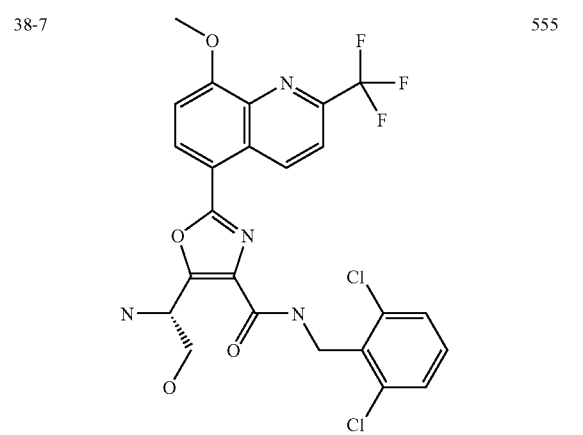 | 555 |
| 38-8 | 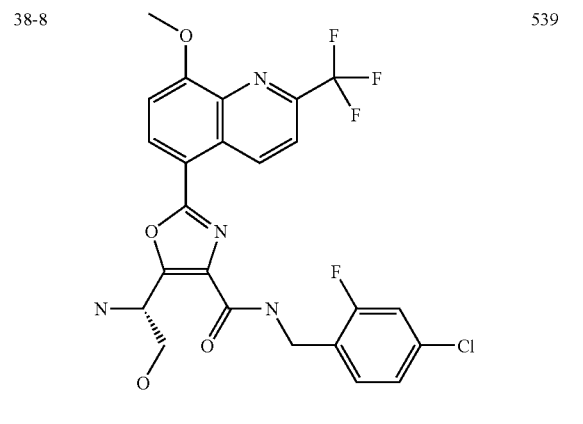 | 539 |
| 38-9 | 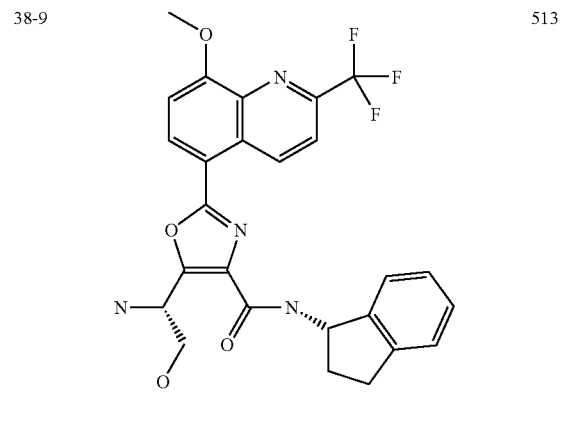 | 513 |
| Cpd. No. | Structure | MS (M + 1) |
|---|---|---|
| 38-10 | 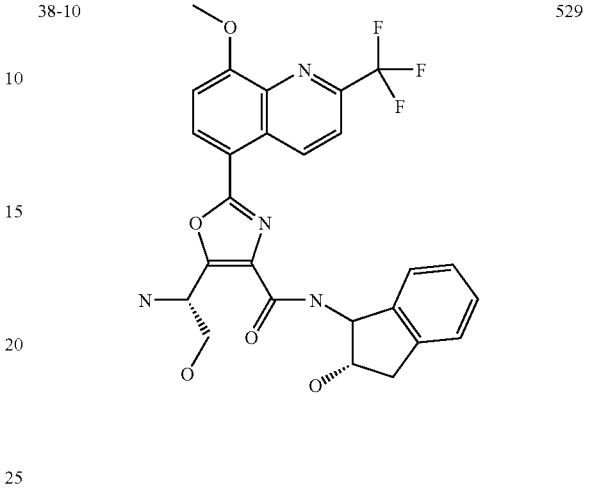 | 529 |
| 38-11 | 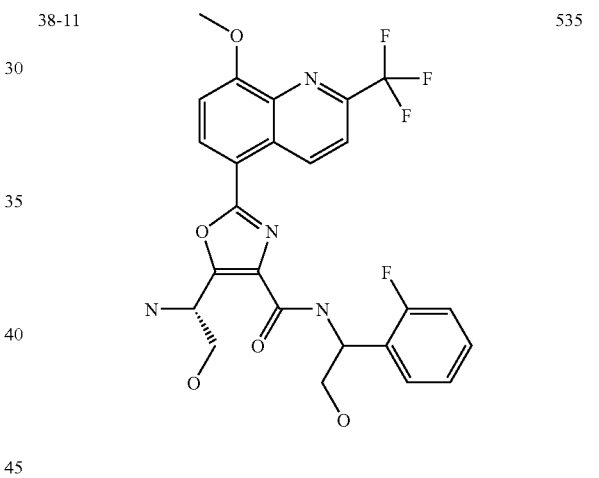 | 535 |
| 38-12 | 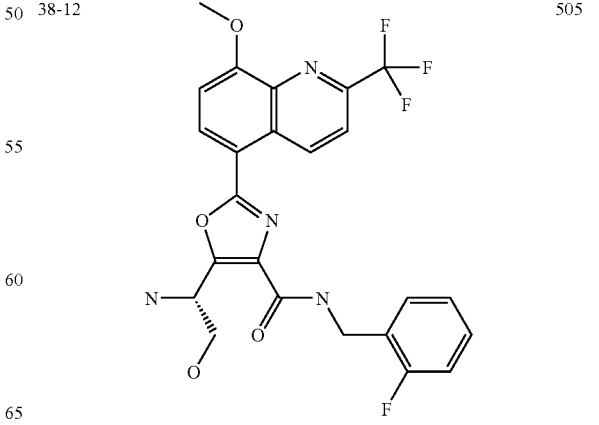 | 505 |

-continued
| Cpd. No. | Structure | MS (M + 1) |
|---|---|---|
| 38-13 | 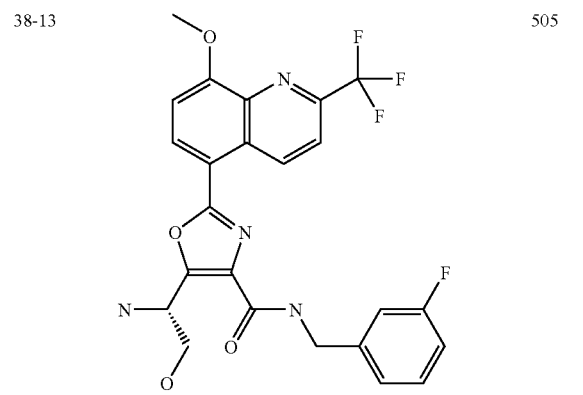 | 505 |
| 38-14 | 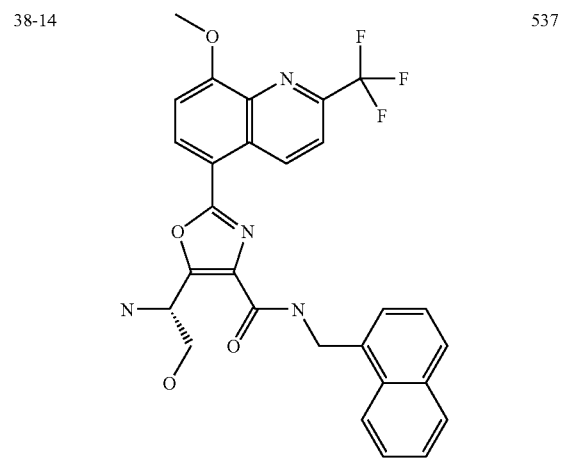 | 537 |
| 38-15 | 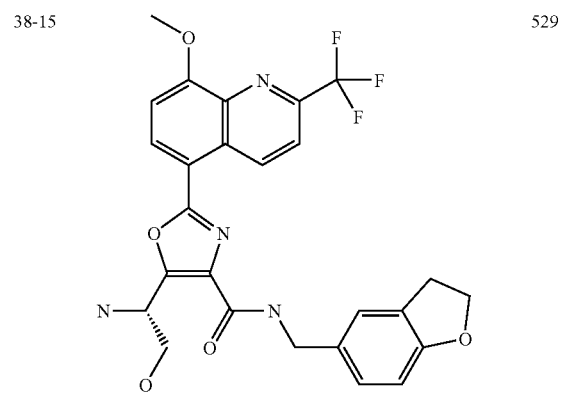 | 529 |
-continued
| Cpd. No. | Structure | MS (M + 1) |
|---|---|---|
| 38-16 | 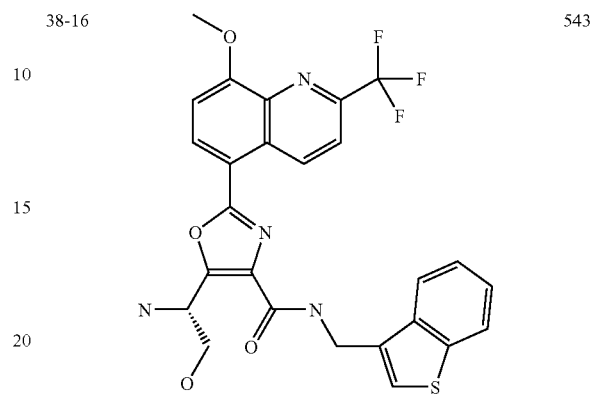 | 543 |
| 38-17 | 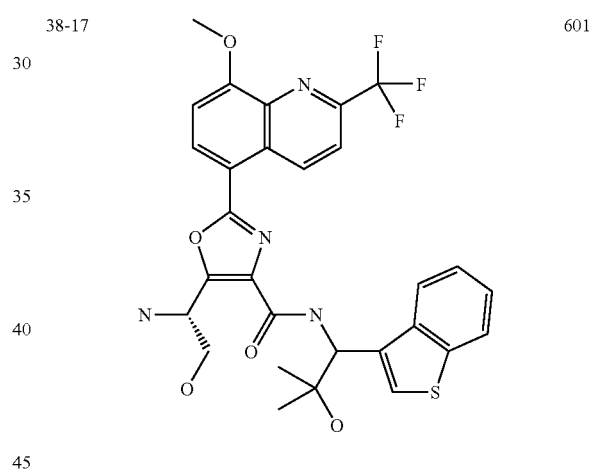 | 601 |
| 38-18 | 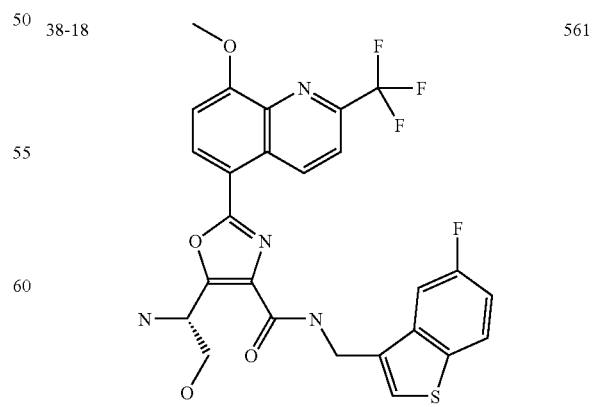 | 561 |

729
-continued
| Cpd. No. | Structure | MS (M + 1) |
|---|---|---|
| 38-19 | 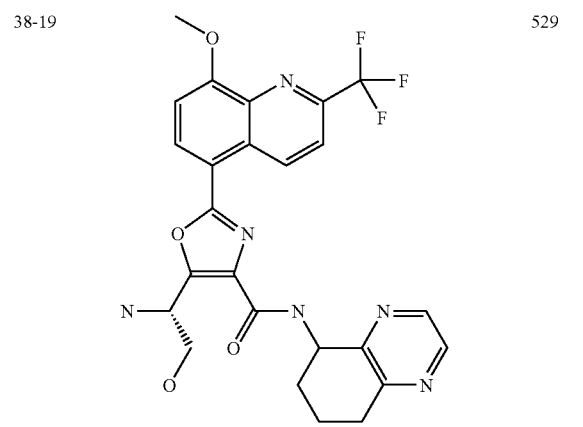 | 529 |
| 38-20 | 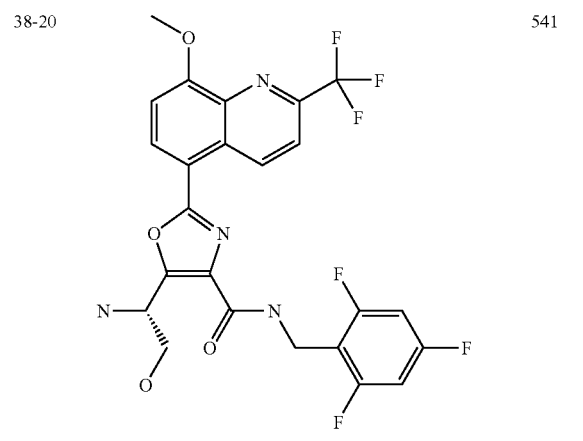 | 541 |
| 38-21 | 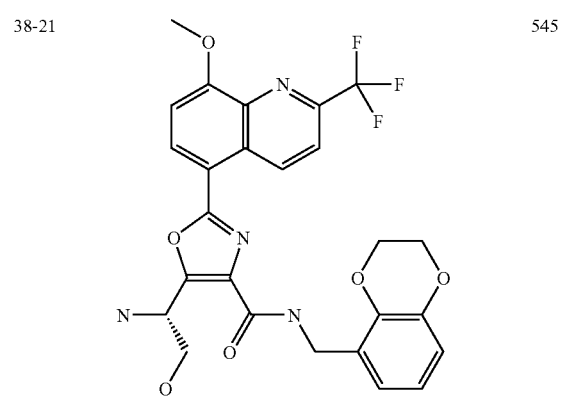 | 545 |
730
-continued
| Cpd. No. | Structure | MS (M + 1) |
|---|---|---|
| 38-22 | 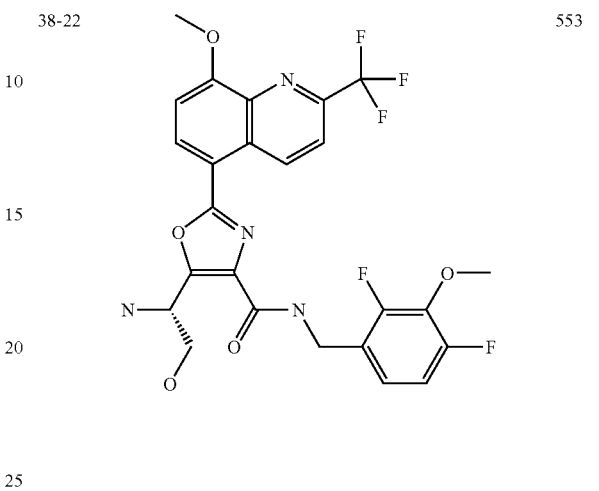 | 553 |
| 38-23 | 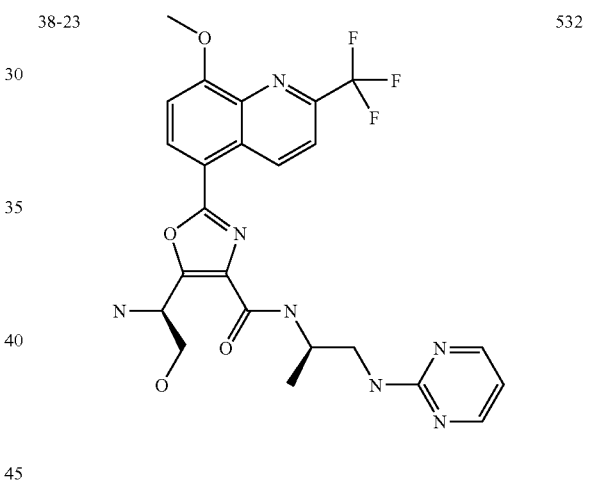 | 532 |
| 38-24 | 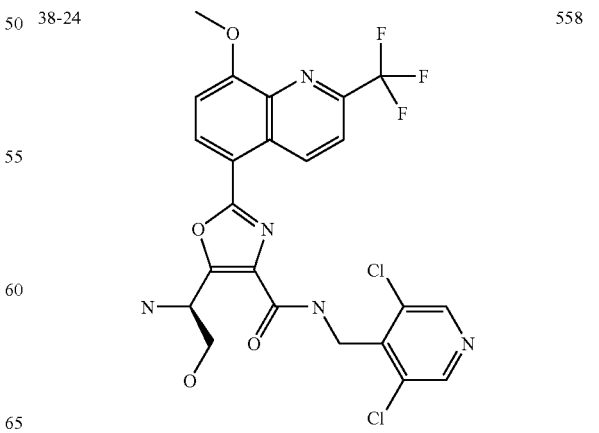 | 558 |

-continued
| Cpd. No. | Structure | MS (M + 1) |
|---|---|---|
| 38-25 | 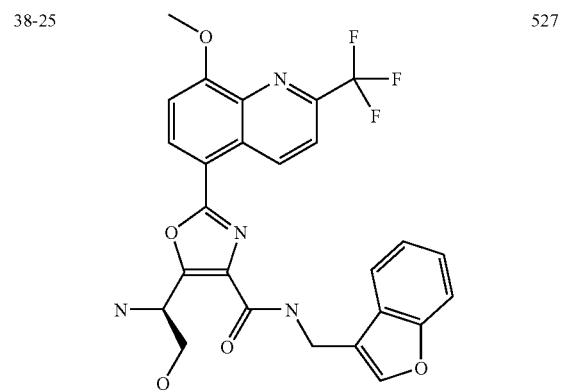 | 527 |
| 38-26 | 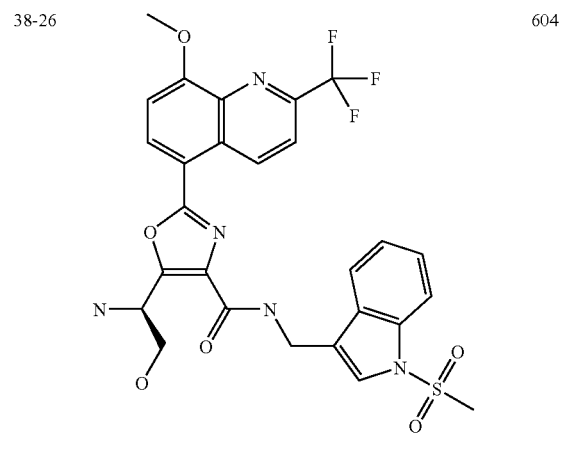 | 604 |
| 38-27 | 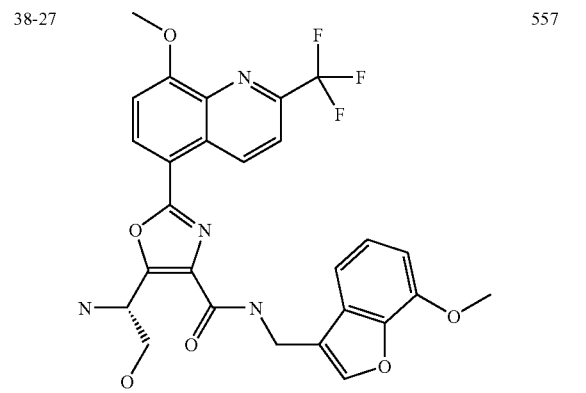 | 557 |
-continued
| Cpd. No. | Structure | MS (M + 1) |
|---|---|---|
| 38-28 | 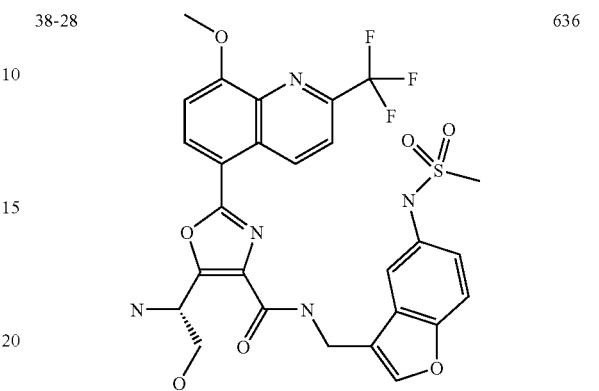 | 636 |
| 38-29 | 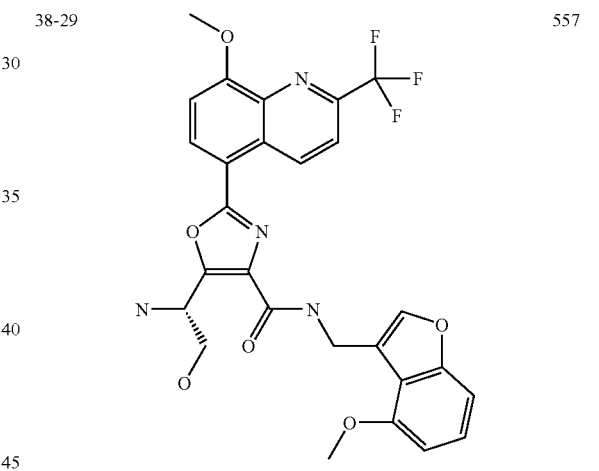 | 557 |
| 38-30 | 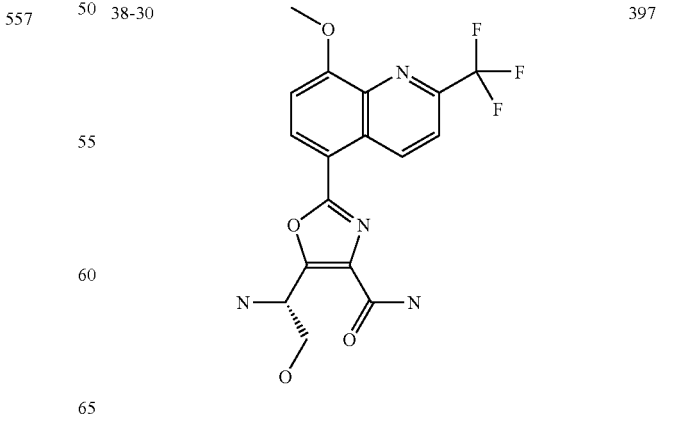 | 397 |

| Cpd. No. | Structure | MS (M + 1) |
|---|---|---|
| 38-31 | 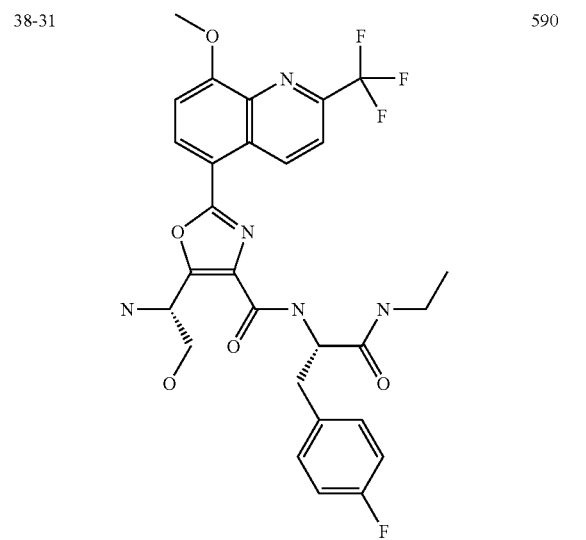 | 590 |
| 38-32 | 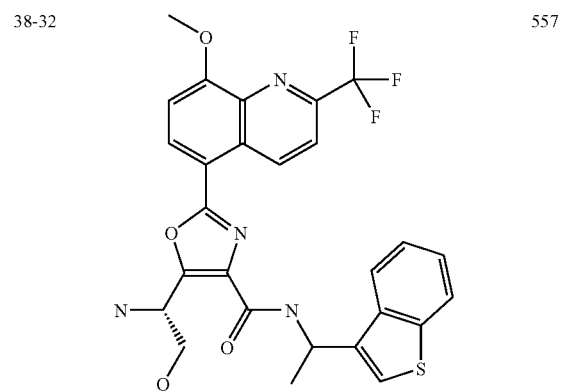 | 557 |
| 38-33 | 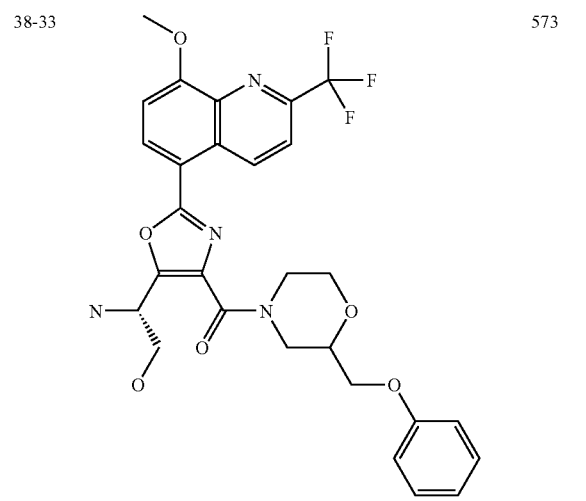 | 573 |
| Cpd. No. | Structure | MS (M + 1) |
|---|---|---|
| 38-34 | 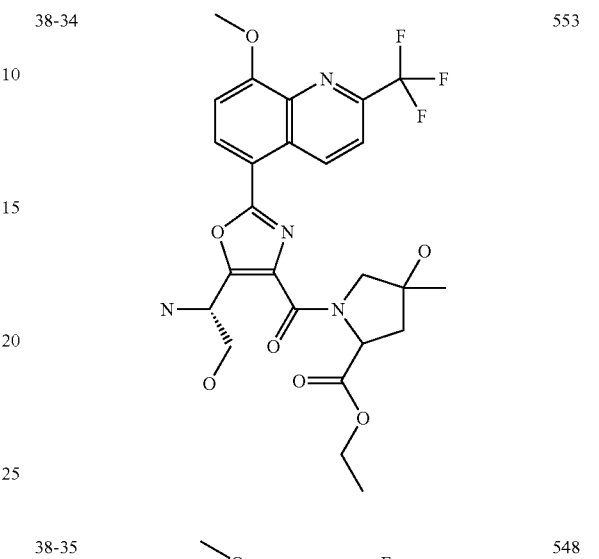 | 553 |
| 38-35 | 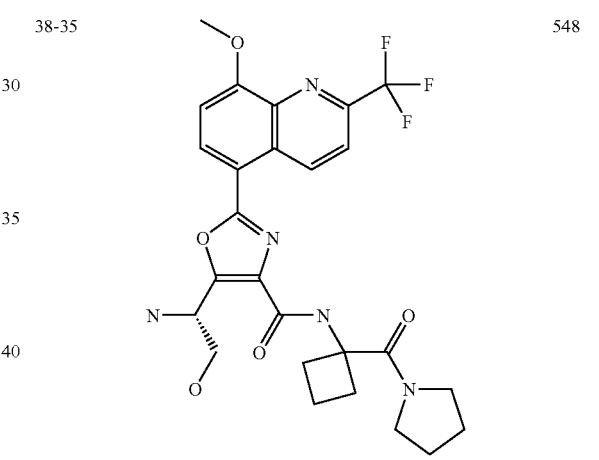 | 548 |
| 38-36 | 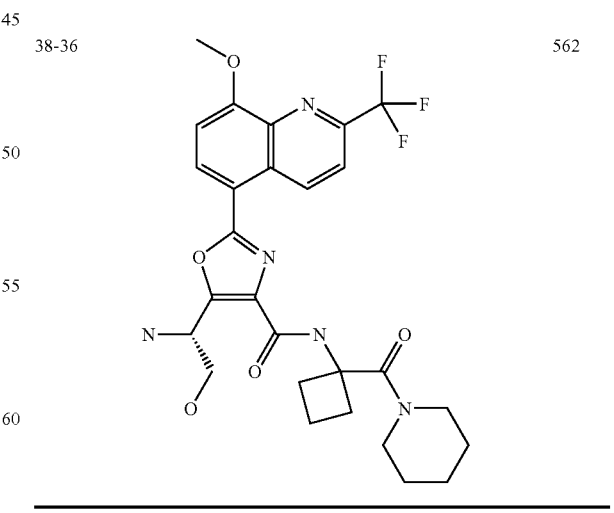 | 562 |

EXAMPLE 12

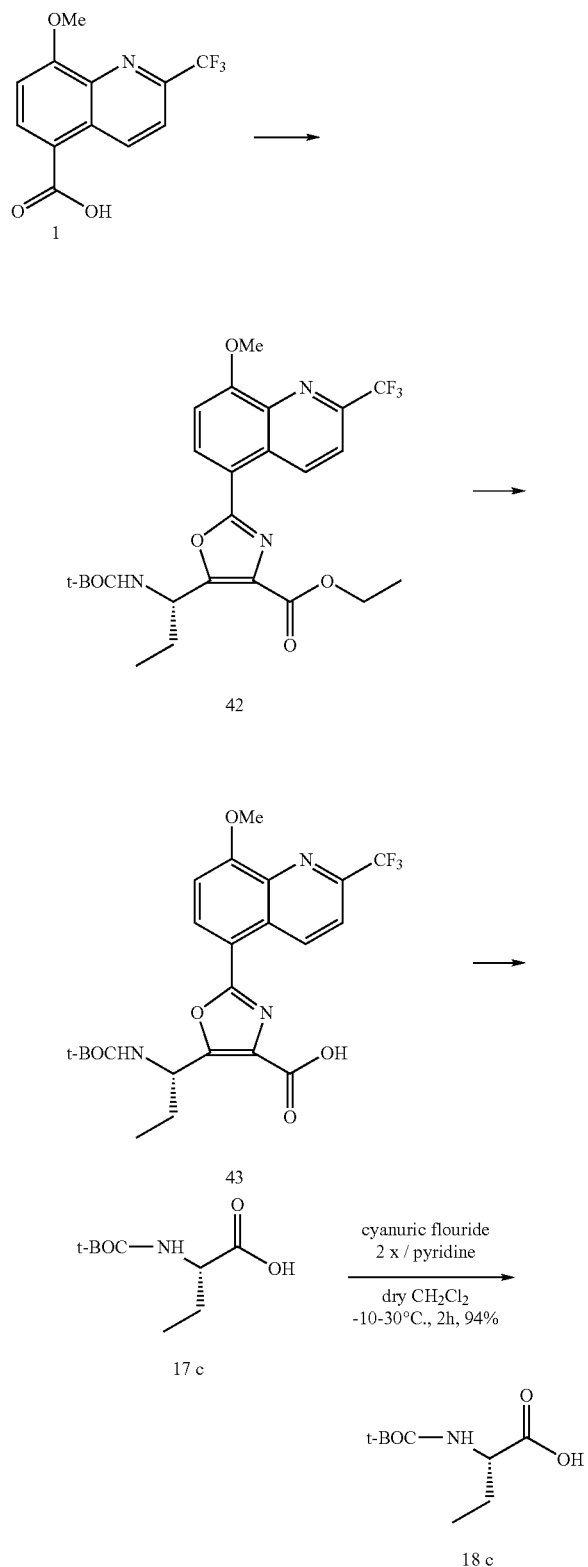

By employing methods analogous to those described for Example 5, using compound 18c in place of compound 18, compound 42 was obtained, which was treated with LiOH.H₂O to give the title compound 43.

EXAMPLE 13

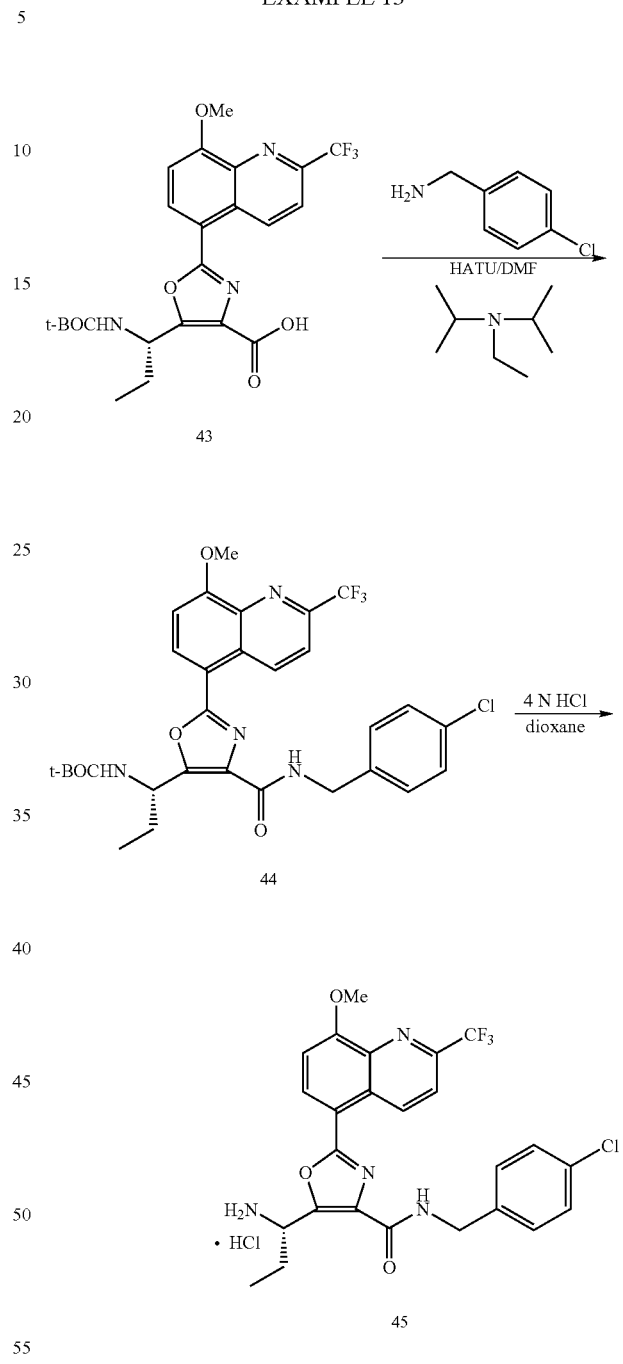

By employing methods analogous to those described in Example 6, using compound 43 in place of compound 20 and 4-chlorobenzylamine in place of compound 23 in the coupling reaction, compound 44 was obtained. After removal of the t-BOC group of compound 44 with HCl, the title compound 45 was obtained as a HCl salt. MS: $C_{25}H_{22}ClF_3N_4O_3 \cdot HCl$ [M+1]⁺519.1.

Using a procedure similar to that described for compound 45, the following compounds were prepared:

| Cpd. No. | Structure | MS (M+1) |
|---|---|---|
| 45-1 | 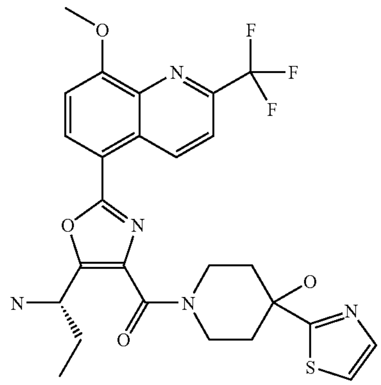 | 562 |
| 45-2 | 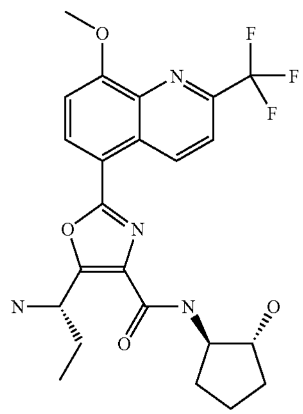 | 479 |
| 45-3 | 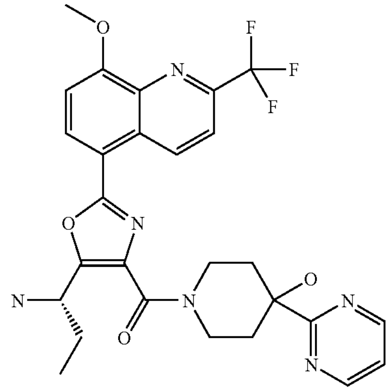 | 557 |
| 45-4 | 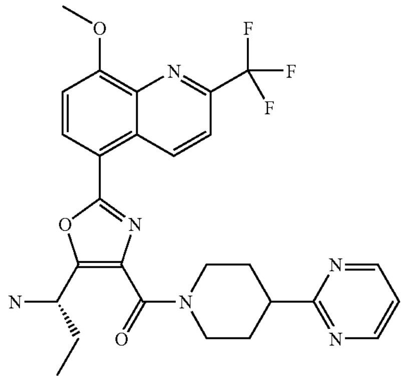 | 541 |
| 45-5 | | 576 |
| 45-6 | | 569 |
| 45-7 | | 506 |

| Cpd. No. | Structure | MS (M + 1) |
|---|---|---|
| 45-8 | | 479 |
| 45-9 | | 449 |
| 45-10 | | 435 |
| Cpd. No. | Structure | MS (M + 1) |
|---|---|---|
| 45-11 | | 506 |
EXAMPLE 14
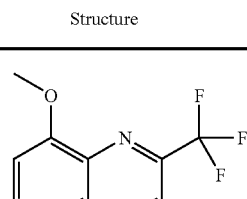

By employing methods analogous to those described in Example 6, using compound 43 in place of compound 20 and compound 9 in place of compound 23 compound 46 was obtained. After removal of the t-BOC group of compound 46 with HCl, the title compound 47 was obtained as a HCl salt. MS $C_{27}H_{23}F_3N_4O_3S \cdot HCl$ [M+1]$^+$541.1.

EXAMPLE 15

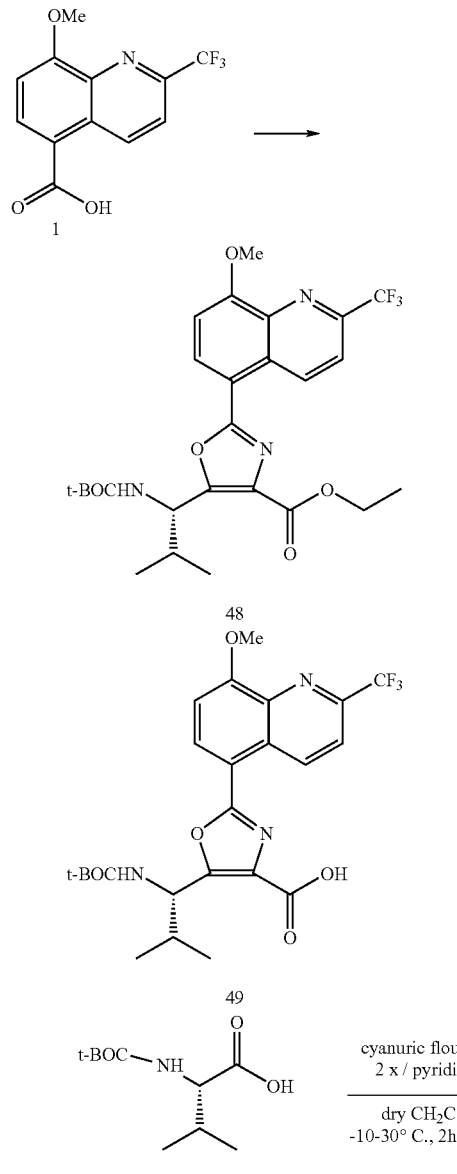

compound 48 was obtained, which was treated with LiOH·H$_2$O to obtain the title compound 49.

EXAMPLE 16

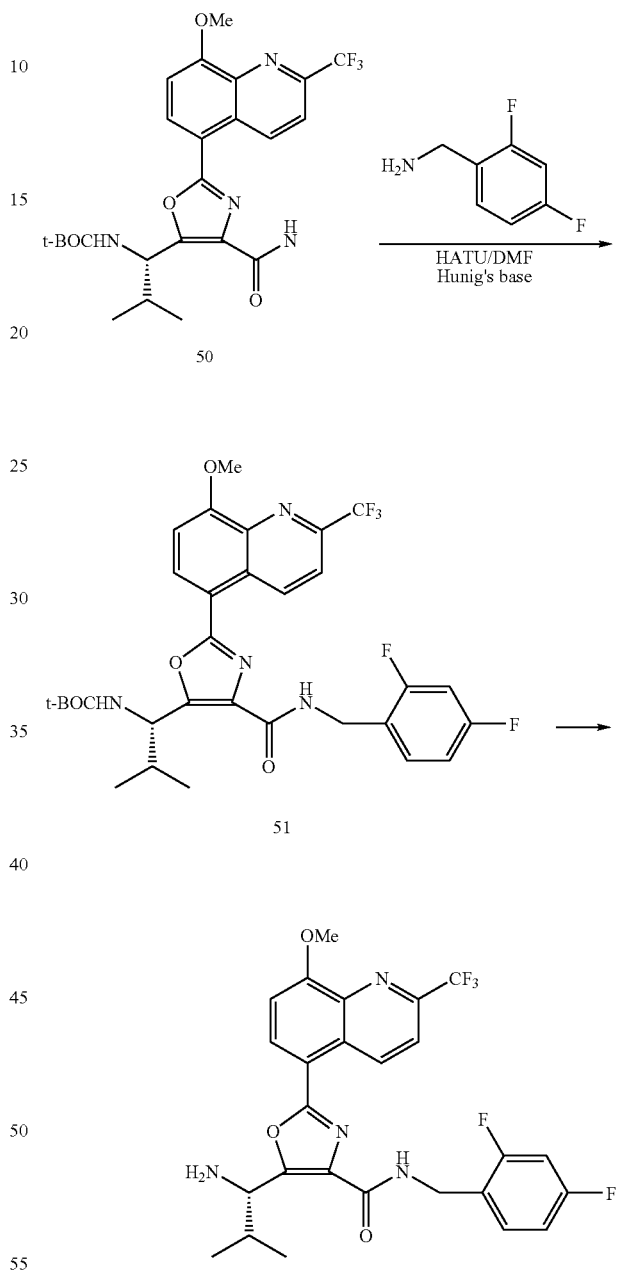

By employing methods analogous to those described in Example 6, using compound 50 in place of compound 20 and 2,4-diflurobenzylamine in place compound 23, compound 51 was obtained. After removal of the t-BOC group of compound 51 with HCl, the title compound 52 was obtained as a HCl salt. MS: $C_{26}H_{23}F_5N_4O_3 \cdot HCl$ [M+1]$^+$535.

Using similar procedures and the appropriate staring materials, the following compounds were also prepared:

By employing methods analogous to those described in Example 5, using compound 18d in place of compound 18,

744

EXAMPLE 17

| Cpd. No. | Structure | MS (M + 1) |
|---|---|---|
| 47-1 | 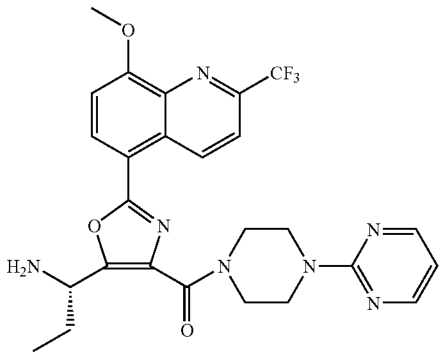 | 542 |
| 47-2 | 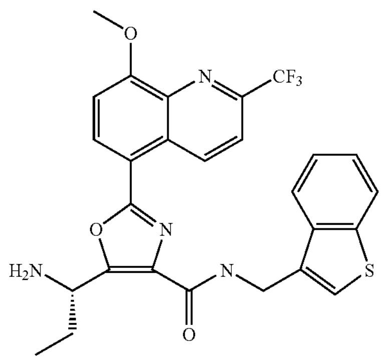 | 541 |
| 47-3 | 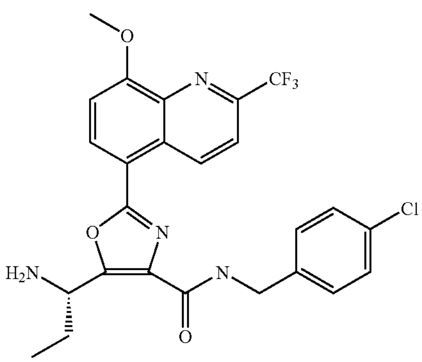 | 519 |
| 52-1 | 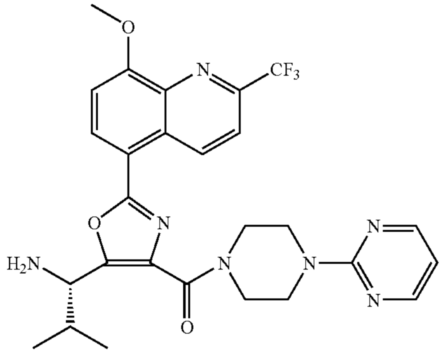 | 556 |

By employing methods analogous to those described in Example 5, using compound 18e in place of compound 18, compound 53 was obtained, which was treated with LiOH.H₂O to yield the title compound 54.

EXAMPLE 18

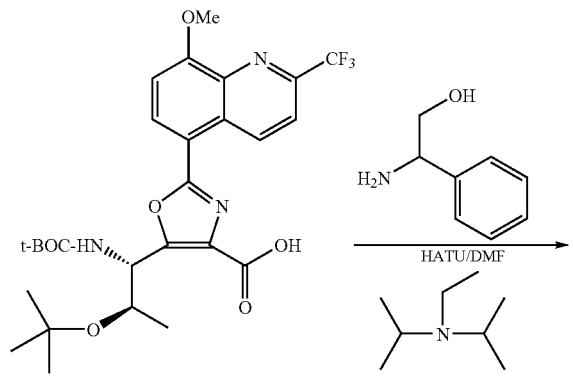

55

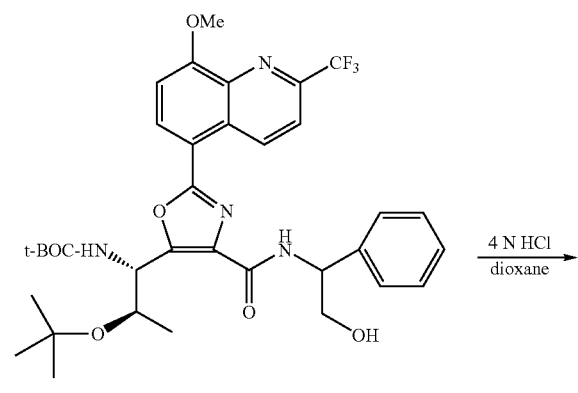

56

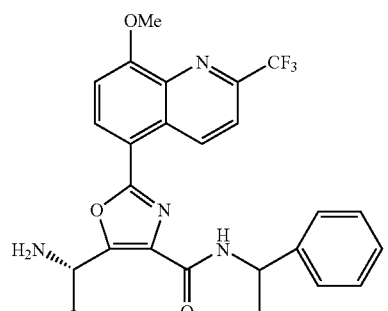

57

By employing methods analogous to those described in Example 10, using compound 55 in place of compound 30 and 1-amino-2-hydroxyethyl benzene in place of compound 35, compound 56 was obtained. After purification and removal of the t-BOC group of compound 56 with HCl, compound 57 was obtained as a HCl salt. MS: $C_{26}H_{25}F_3N_4O_5$. HCl $[M+1]^+$567.1.

EXAMPLE 19

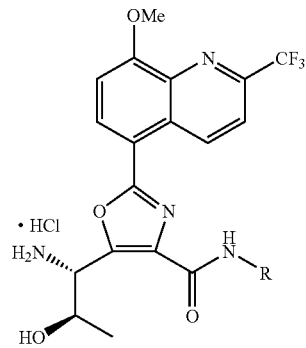

58

Using the appropriate aromatic or heteroaromatic amine reagent coupled with compound 55 according to the procedure described for Example 10, steps 2 and 3, the desired compound 58 was obtained as a hydrochloride salt.

| Cpd. No. | Structure | MS (M + 1) |
|---|---|---|
| 58-1 | 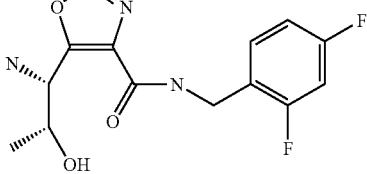 | 537 |
| 58-2 | 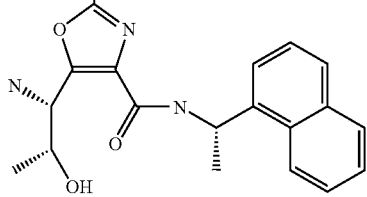 | 564 |

-continued

| Cpd. No. | Structure | MS (M + 1) |
|---|---|---|
| 58-3 | 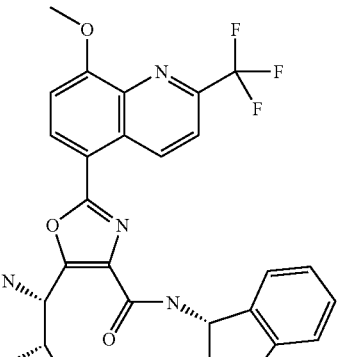 | 543 |

EXAMPLE 20

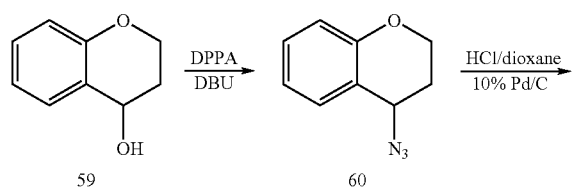

Step 1: DBU (1.7 g, 11 mmol) was added to a mixture of 4-chromanol (59) (1.5 g, 10 mmol) and diphenyl-phosphoryl azide (DPPA) (3.0 g, 11 mmol) in $CH_2Cl_2$ (10 ml) at RT. The mixture immediately turned brown (a water bath was used to cool the reaction temperature). The solution was stirred at RT overnight. After completion of the reaction, the reaction mixture was diluted with ether/EtOAc (1:1) (100 ml) and washed with saturated $NaHCO_3$, 5% HCl and brine. The organic layer was dried ($Na_2CO_3$), filtered and concentrated to give a residue which was purified by column chromatography, eluting with 30% $CH_2Cl_2$/hexane to give compound 60 (1.45 g, 0.83 mmol) with a 83% of yield.

Step 2: 4 N HCl/dioxane (2 ml) and 10% Pd/C (0.5 g) were added to a solution of compound 60 (1.3 g, 7.4 mmol) in MeOH (50 ml). The mixture was stirred under a $H_2$ balloon at RT for 46 h. After the reaction was complete, the solid was filtered off. The filtrate was concentrated and to obtain the desired amine (61) as a light yellow HCl salt. LCMS $C_9H_{11}NO$. HCl $[M+1]^+149.0$.

EXAMPLE 21

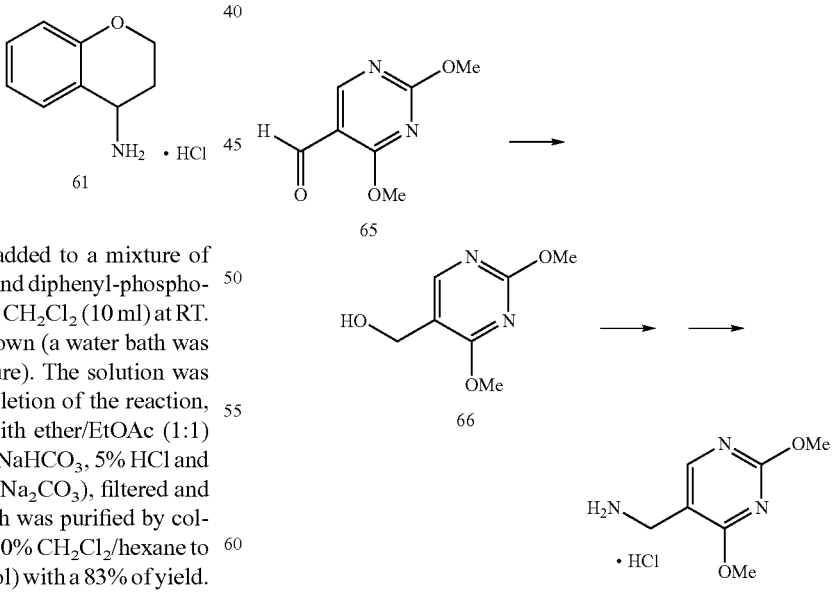

By employing methods analogous to those described for Example 20, replacing compound 59 with 62 and 60 with 63, the title compound 64 was obtained as an amine HCl salt. LCMS $C_9H_{11}O_2N$. HCl $[M+1]^+166.0$

EXAMPLE 22

$NaBH_4$ (0.7 g, 18.5 mmol) at RT was added to a solution of compound 65 (0.6 g, 3.57 mmol) in MeOH (20 ml) cooled with a water bath. After 10 min, solvent was removed. The residue was treated with 5% NaHCO$_3$ and the product was extracted with CH$_2$Cl$_2$, then with EtOAc. The combined organic solution was washed with brine, dried (Na$_2$SO$_4$), filtered and concentrated to give compound 66 as a white solid. Using a method similar to Example 27, the title compound 67 was obtained as a HCl salt. LCMS C$_7$H$_{11}$N$_3$O$_2$.HCl [M+1]$^+$170.0

EXAMPLE 23

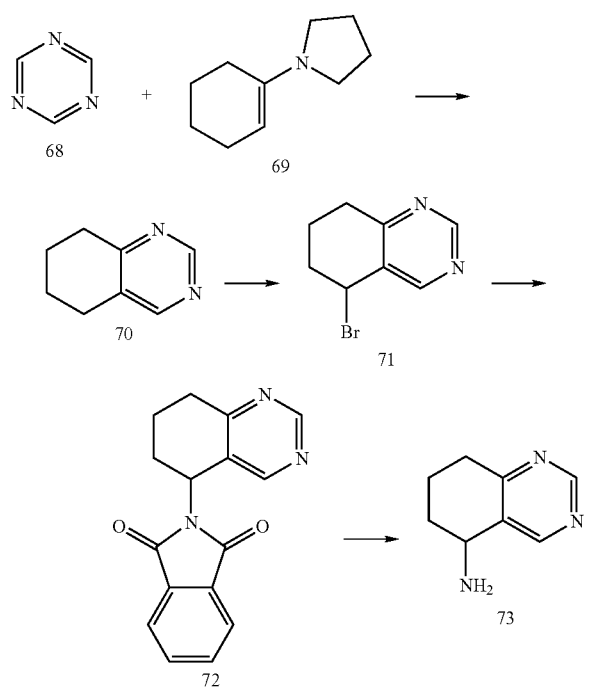

Solid 1,3,5-triazine (2.4 g, 30 mmol) (68) was mixed with 1-(pyrrolidino)-1-cyclohexene (69) in a pressure tube (15 ml) and heated at 93° C. (bath temperature) with stirring for 22 h. After completion of the reaction, the reaction mixture was concentrated and dissolved in CH$_2$Cl$_2$, washed with saturated NaHCO$_3$ solution, dried (Na$_2$SO$_4$), then purified by column chromatography to give compound 70 as a solid.

The title compound 73 was prepared according to the procedure described for Example 2, and step 2 of Example 3.

EXAMPLE 24

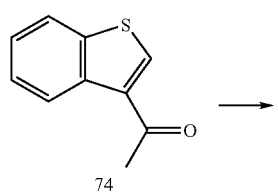

-continued

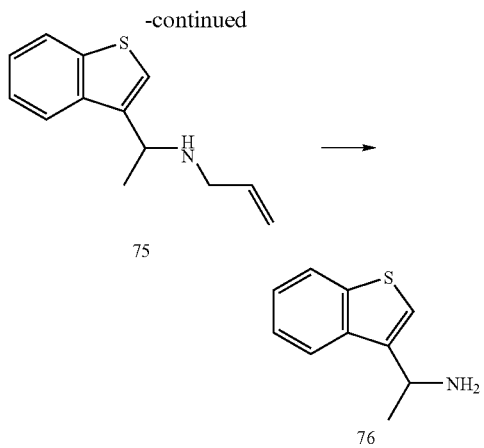

A mixture containing 3-acetylthianaphthene (74) (0.5 g, 2.8 mmol), allylamine (0.42 g, 5.6 mmol), NaBH(OAc)$_3$ (1.2 g, 5.6 mmol), and HOAc (0.15 ml) in dichloroethane (15 ml) was stirred at RT overnight. After completion, the reaction mixture was quenched with NaHCO$_3$ and extracted with CH$_2$Cl$_2$. The organic solvent was dried (Na$_2$SO$_4$), filtered and evaporated. The crude material was purified by column chromatography to give compound 75 (0.43 g) as an oil.

N,N-dimethylbarbituric acid (0.65 g, 4.14 mmol) and tetrakis-(triphenyl-phosphine)palladium (16 mg, 0.0138 mmol) were added to a solution of compound 75 (0.3 g, 1.38 mmol) in CH$_2$Cl$_2$ (30 ml). The mixture was stirred at 40° C. for 2 h, then at RT overnight. After completion of the reaction, the mixture was diluted with CH$_2$Cl$_2$ and washed with saturated Na$_2$CO$_3$ solution. The organic layer was separated and the aqueous layer was re-extracted with CH$_2$Cl$_2$. The organic fractions were combined and concentrated. The crude material was purified by silica gel chromatography to give the title compound 76 as an oil.

EXAMPLE 25

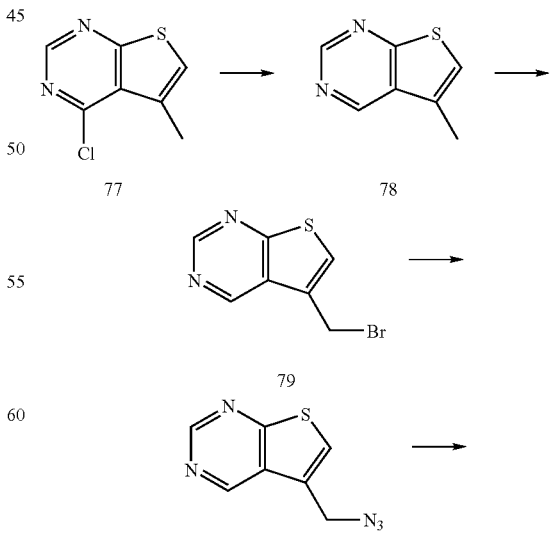

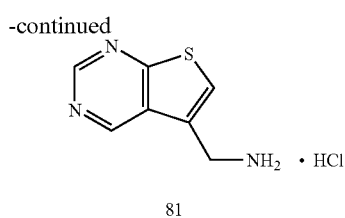

81

Step 1: MgO (0.4 g, 10 mmol) and 10% Pd/C (0.5 g) were added to a solution of compound 77 (1.0 g, 5.4 mmol) in EtOH:MeOH (1:1) (100 ml). The mixture was stirred at RT overnight. After completion of the reaction, MgO and Pd/C were filtered off and the filtrate was concentrated to dryness. The residue was dissolved in EtOAc and washed with water, dried ($Na_2SO_4$), filtered and evaporated to give a solid compound 78.

Step 2: Using the procedure described in Example 2, Step 1, the bromo derivative 79 was obtained. The crude material was used in the next reaction without purification.

Step 3: Sodium azide was mixed with DMSO and stirred at RT until all solid was dissolved. Compound 78 was added at RT, and after stirring at RT for 1 h, ice-water was added. The product was extracted with EtOAc:ether (1:1). The combined organic layers were washed with water, dried ($Na_2SO_4$), filtered and evaporated to obtain the azido derivative 80, as an oil.

Step 4: By employing methods analogous to Example 20, Step 2, the azido derivative 80 was converted to the title compound 81 as a hydrochloride salt.

EXAMPLE 26

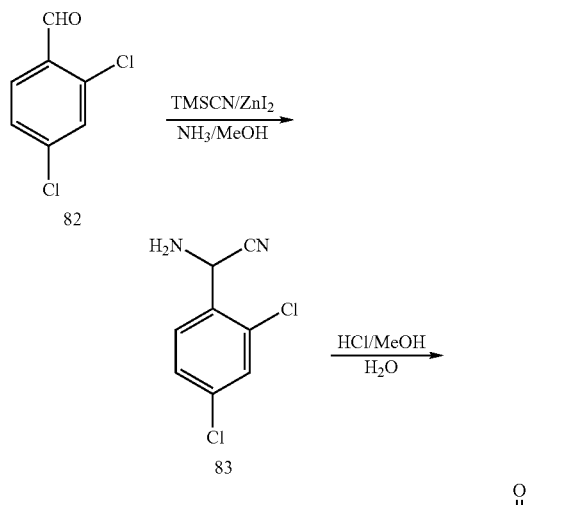

Step 1: $ZnI_2$ (0.64 g, 2 mmol) was added in one portion at RT under $N_2$ to a mixture of 2,4-dichlorobenzaldehyde (82) (3.5 g, 20 mmol) and TMSCN (2.6 g, 26 mmol). After 15 min, 7 N $NH_3$ solution in MeOH (20 ml) was added and the mixture was stirred at 40° C. for 2 h. Solvents were evaporated and the residue was re-dissolved in $Et_2O$, washed with water, dried ($MgSO_4$) and filtered. HCl gas was bubbled through the filtrate to give an off-white solid of compound 83 (3.5 g, 74%). MS: $C_8H_6N_2Cl_2$, $[M+1]^+202$.

Step 2: A stream of HCl gas was bubbled through a solution of compound 83 (3.5 g, 14.8 mmol) in MeOH (85 ml) for 4 h. Water (2 ml) was added and the reaction mixture was concentrated to provide an off-white solid of compound 84 (3.4 g, 90%) as a HCl salt. MS: $C_8H_8N_2OCl_2$, $[M+1]^+219$

EXAMPLE 27

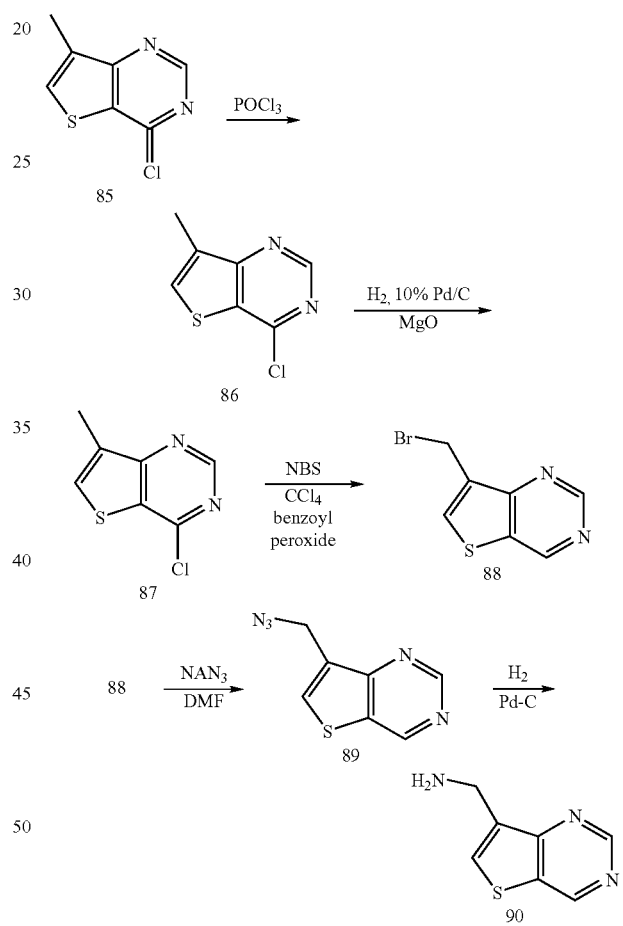

Step 1: Compound 85 (2.4 g, 14.4 mmol) was suspended in phosphorus oxychloride (30 ml) and heated to reflux for 15 h. The reaction mixture was cooled to RT, and saturated (aq) $NaHCO_3$ (250 ml) was added carefully with vigorous stirring at 0° C., followed by the addition of $Et_2O$ (150 ml). The aqueous layer was separated and extracted with $Et_2O$. The organic layers were combined, washed with brine, filtered and concentrated to give compound 86 as a yellow oil (2.14 g, 81%). MS: $C_7H_5ClN_2S$ [M+1] 185; [M+2], 186

Step 2: Compound 87 was obtained as a white solid (93% yield) according to the procedure described for the Example 25, Step 1. MS: $C_7H_6N_2S$ $[M+1]^+151$.

Step 3: Compound 88 [MS: $C_7H_5BrN_2S$ [M+1]+$Br^{79}$ 229, $Br^{81}$ 231] was synthesized from compound 88 according to the method described in Example 2, Step 1. The bromoderivative 88 was converted to its azido-derivative-89 [MS: $C_7H_5N_5S$ [M+1]+192] according to the procedure described for Example 25, Step 3. The title compound 90 was obtained as a HCl salt by hydrogenation of compound 89 according to the procedure described for Example 20. MS: $C_7H_7N_3S$ [M+1]$^+$166.

EXAMPLE 28

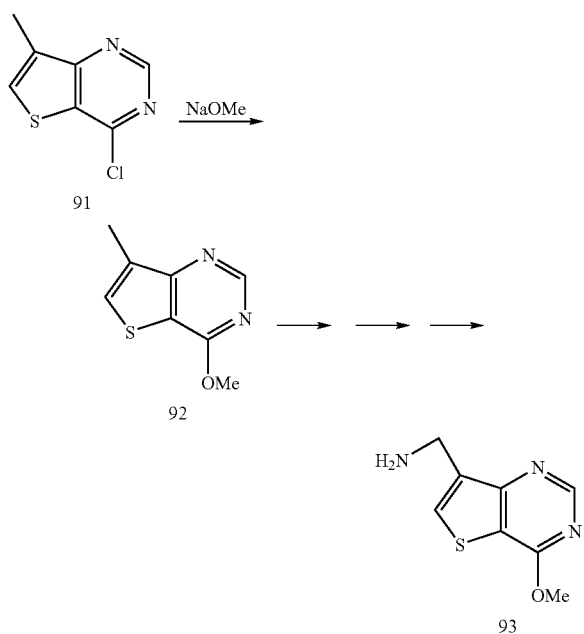

Step 1: Compound 91 (1.47 g, 7.99 mmol) was treated with a solution of 0.5 M NaOMe in MeOH (32 ml) under $N_2$. The suspension was stirred at RT overnight. The solvent was removed and the resultant residue partitioned between EtOAc (75 ml) and water (75 ml). The aqueous layer was separated and extracted with EtOAc. The organic extracts were combined, dried (MgSO$_4$), filtered and concentrated in vacuo to give 1.41 g (98%) of white solid, compound 92. MS: $C_8H_8N_2OS$ [M+1]$^+$181.

Step 2: The title compound 93 was obtained from compound 92 using methods similar to those described for Example 27, Step 3. MS: $C_8H_9N_3SO$ [M+1]$^+$196.

EXAMPLE 29

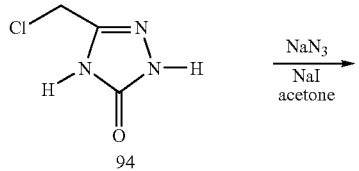

-continued

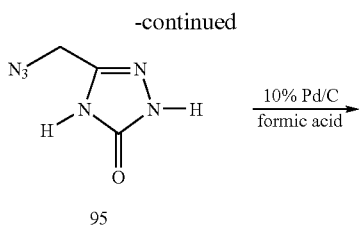

Compound 94 was prepared according to the literature (Tetrahedron Letters 41, 8661-8664, (2000)). Compound 94 (3.0 g, 22.5 mmol) was mixed with NaI (3.37 g, 22.5 mmol) and NaN$_3$ (1.9 g, 29 mmol) in CH$_2$Cl$_2$/acetone (1:1, 250 ml) and refluxed for 36 h. After completion of the reaction, the reaction mixture was filtered and the filtrate concentrated to dryness. Crude compound 95 was purified on Biotage system, eluting with 2% MeOH in CH$_2$Cl$_2$, to obtain pure compound 95 as a white solid. Compound 95 (2.46 g, 17.6 mmol) was dissolved in MeOH (100 ml) and formic acid (0.81 ml, 17.6 mmol), and 10% Pd/C (490 mg) was added. The mixture was stirred at RT under a H$_2$ balloon overnight. The solids were filtered off and the filtrate was evaporated to give the title compound, 96, as a formic acid salt. MS: $C_3H_6N_4O$ [M+1]$^+$ 115.

EXAMPLE 30

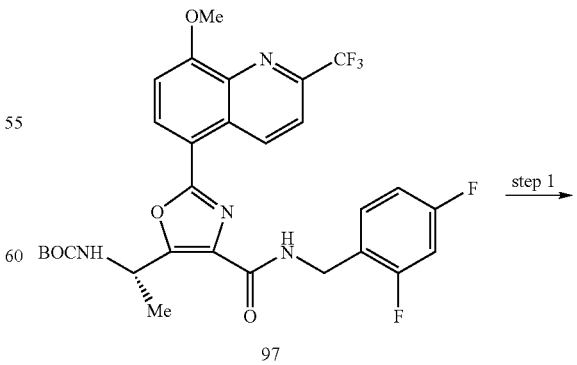

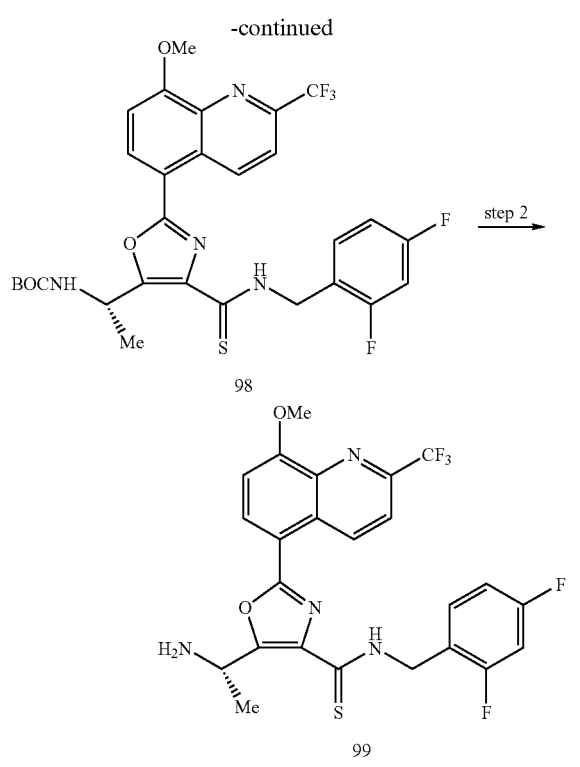

Step 1: To a solution of compound 97 (280 mg, 0.462 mmol) dissolved in THF (10 ml) was added Lawesson reagent (467 mg, 1.15 mmol). The reaction mixture was heated at reflux for 24 h then cooled to RT. The solvent was evaporated. Purification by silica gel chromatography (eluant: 1%-3% EtOAc—$CH_2Cl_2$) gave 166 mg (0.267 mmol, 58%) of the product 98 as a yellow foam. MS (M+1): m/e 623.

Step 2: To a solution of compound 98 (273 mg, 0.438 mmol) dissolved in $CH_2Cl_2$ (4 ml) was added TFA (1 ml). The reaction mixture was stirred at RT for 4 h. The solvent was evaporated, and the crude product was dissolved in 10 ml of 1:1 $CH_2Cl_2$: MeOH and diethylaminomethylpolystyrene resin (0.50 g, from Fluka) was added. The resulting mixture was stirred for 15 min, filtered, and the resin was washed with MeOH. The filtrate was evaporated. Purification by silica gel chromatography (eluant: 2%-3% MeOH—$CH_2Cl_2$) gave 169 mg (0.323 mmol, 74%) of the product 99 as a yellow foam. MS (M+1): m/e 523.

EXAMPLE 31

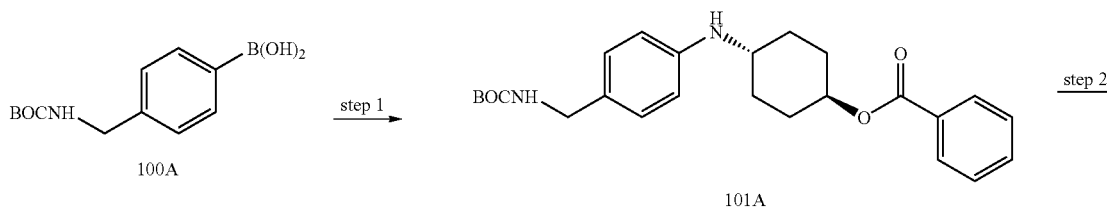

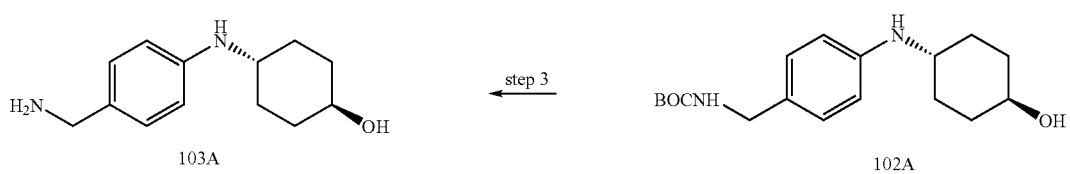

Step 3: To a solution of trans-4-benzoyl-cyclohexylamine (2.06 g, 9.4 mmol) dissolved in dry CH$_2$Cl$_2$ (50 ml) was added 3A sieves (3 g), Et$_3$N (2.38 g, 3.3 ml, 23.5 mmol), [4-(N-BOC-aminomethyl)phenyl]boronic acid 100A (3.00 g, 11.9 mmol), and copper acetate (2.16 g, 11.9 mmol). The reaction mixture was stirred at RT for 24 h. 2 N aqueous NH$_4$OH (50 ml) was added, and the reaction mixture was filtered to remove the sieves which were washed with additional CH$_2$Cl$_2$ and 2 N aqueous NH$_4$OH. The layers of the filtrate were separated, and the aqueous layer was extracted width CH$_2$Cl$_2$. The combined organic extract was dried (MgSO$_4$), filtered, and concentrated. Purification by silica gel chromatography (eluant: 5%-10% EtOAc—CH$_2$Cl$_2$) gave 0.73 g (1.72 mmol, 18%) of the product 101A as a yellow foam. MS (M+1): m/e 425.

The following intermediates were synthesized by using a similar procedure:

| Number | Compound | MS (M + 1) |
|---|---|---|
| 101B | | 277 |
| 101C | | 371 |
| 101D | | 349 |
| 101E | | 321 |
| 101F | | 335 |
| 101G | | 335 |
| 101H | | 425 |

-continued

| Number | Compound | MS (M + 1) |
|---|---|---|
| 101I | 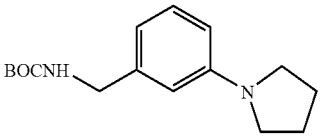 | 277 |
| 101J | 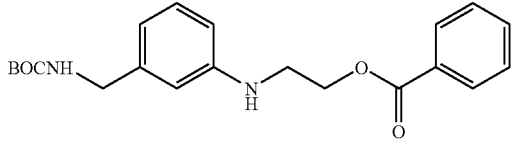 | 371 |
| 101K | 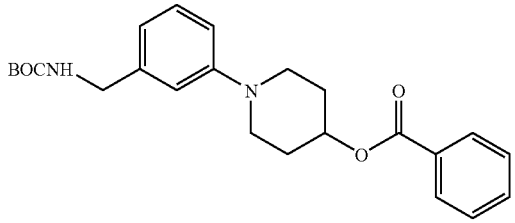 | 411 |
| 101L | 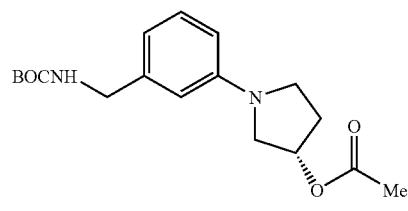 | 335 |
| 101M | 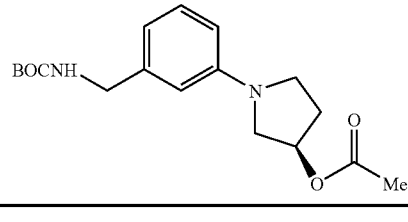 | 335 |

Step 2: To a solution of compound 101A (0.72 g, 1.70 mmol) dissolved in THF (6 ml) MeOH (6 ml), and water (3 ml) was added LiOH (0.36 g, 8.48 mmol). The reaction mixture was stirred at RT for 4 h. The solvent was evaporated, saturated NH$_4$Cl (25 ml) was added, and the aqueous solution was extracted with CH$_2$Cl$_2$. The combined organic extract was dried (MgSO$_4$), filtered, and concentrated. Purification by silica gel chromatography (eluant: 3%-5% MeOH—CH$_2$Cl$_2$) gave 0.48 g (1.50 mmol, 89%) of the product 102A as a white foam. MS (M+1): m/e 321.

The following intermediates were synthesized by using a similar procedure:

| Number | Compound | MS (M + 1) |
|---|---|---|
| 102B | 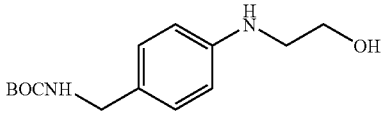 | 267 |
| 102C | 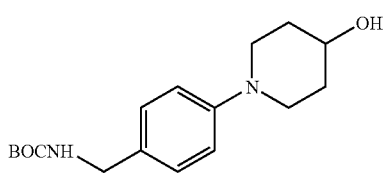 | 307 |
| 102D | 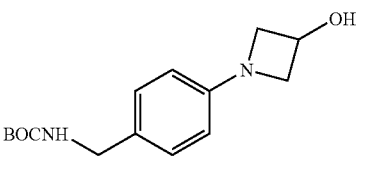 | 279 |

| Number | Compound | MS (M + 1) |
|---|---|---|
| 102E | [structure: BOCNH-CH2-phenyl-N-pyrrolidine-OH] | 293 |
| 102F | [structure: BOCNH-CH2-phenyl-N-pyrrolidine-OH] | 293 |
| 102G | [structure: BOCNH-CH2-phenyl-NH-cyclohexyl-OH] | 321 |
| 102H | [structure: BOCNH-CH2-phenyl-NH-CH2CH2-OH] | 267 |
| 102I | [structure: BOCNH-CH2-phenyl-N-piperidine-OH] | 307 |
| 102J | [structure: BOCNH-CH2-phenyl-N-pyrrolidine-OH] | 293 |
| 102K | [structure: BOCNH-CH2-phenyl-N-pyrrolidine-OH] | 293 |

Step 3: To a solution of compound 102A (475 mg, 1.48 mmol) dissolved in 1:1 CH$_2$Cl$_2$:MeOH (10 ml) was added 4 N HCl in dioxane (3.0 ml, 11.9 mmol). The reaction mixture was stirred at RT for 3 h. The solvent was evaporated to give 429 mg (1.46 mmol, 99%) of the product 103A as a white solid. MS (M+1): m/e 221.

To a solution of compound 102D (0.73 g, 2.62 mmol) suspended in CH$_2$Cl$_2$ (18 ml) was added TFA (3 ml). The reaction mixture was stirred at RT for 3 h. The solvent was evaporated, and the TFA salt of the product was dissolved in MeOH (20 ml). Diethylaminomethylpolystrene resin (4 g, Fluka) was added and stirred at RT for 20 min. The resin was removed by filtration and washed with MeOH. The filtrate was concentrated to give 0.47 g (2.62 mmol, 100%) of the product 103B as a yellow solid. MS (M+1-OH): m/e 162.

The following intermediates were synthesized by using a similar procedure:

| Number | Compound | MS (M + 1) |
|---|---|---|
| 103C | [structure: H$_2$N-CH$_2$-phenyl-NH-CH2CH2-OH] | 150 (M + 1-OH) |
| 103D | [structure: H$_2$N-CH$_2$-phenyl-N-piperidine-OH] | 207 |
| 103E | [structure: H$_2$N-CH$_2$-phenyl-N-pyrrolidine-OH] | 176 M + 1-OH |
| 103F | [structure: H$_2$N-CH$_2$-phenyl-N-pyrrolidine-OH] | 176 M + 1-OH |
| 103G | [structure: H$_2$N-CH$_2$-phenyl-NH-cyclohexyl-OH] | 221 |
| 103H | [structure: H$_2$N-CH$_2$-phenyl-NH-CH2CH2-OH] | 167 |
| 103I | [structure: H$_2$N-CH$_2$-phenyl-N-piperidine-OH] | 207 |
| 103J | [structure: H$_2$N-CH$_2$-phenyl-N-pyrrolidine-OH] | 193 |

763

-continued

| Number | Compound | MS (M + 1) |
|---|---|---|
| 103K | 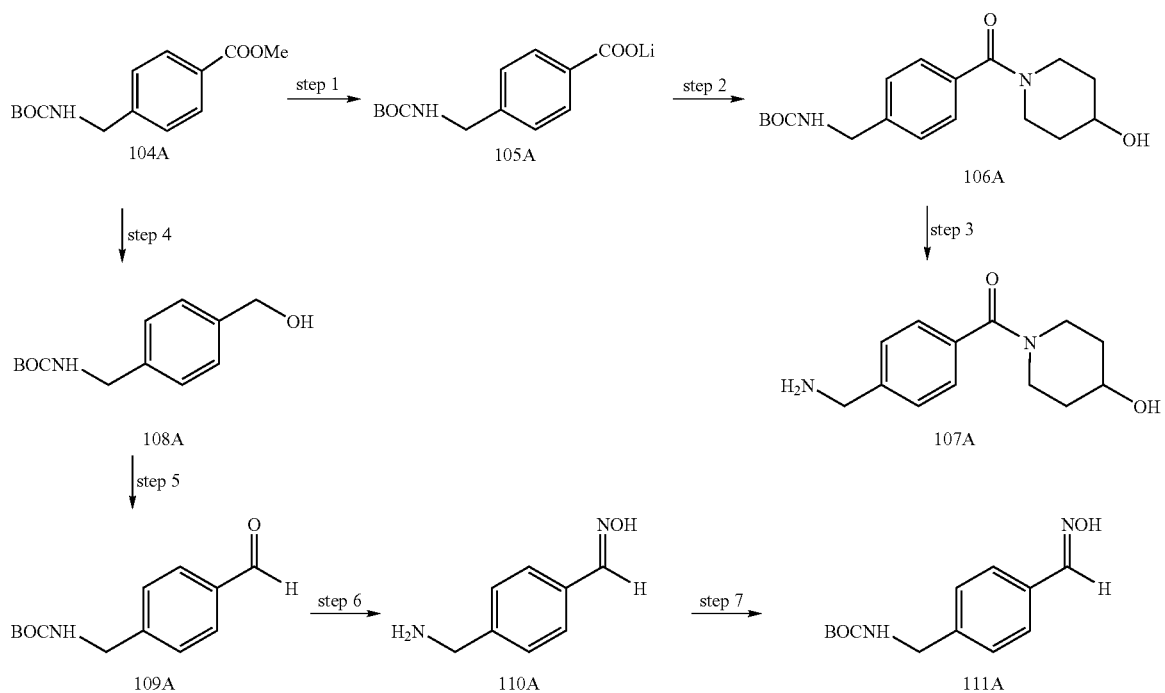 | 193 |

EXAMPLE 32

764

The following intermediates were synthesized by using a similar procedure:

| Number | Compound | MS (M + 1) |
|---|---|---|
| 106B | | 307 |

Step 1: To a solution of methyl 4-(BOC-aminomethyl)-benzoate 104A (4.15 g, 15.6 mmol) dissolved in THF (20 ml), MeOH (20 ml), and water (10 ml) was added LiOH (0.72 g, 17.2 mmol). The reaction mixture was stirred at RT for 24 h. The solvent was evaporated to give 4.02 g (15.6 mmol, 100%) of the product 105A as a white solid. MS (M+2-tBu for acid COOH): m/e 196.

Step 2: To a solution of 4-hydroxypiperidine (0.41 g, 4.08 mmol) dissolved in dry DMF (20 ml) was added 3A sieves (1.0 g) and the mixture was stirred at RT for 15 min. HOBT (0.55 g, 4.08 mmol), EDCI (0.78 g, 4.08 mmol), compound 105A (0.70 g, 2.72 mmol), and Et$_3$N (0.55 g, 0.76 ml, 5.44 mmol) were then added. The reaction mixture was stirred at RT for 20 h. The solvent was evaporated, 0.2 N NaOH (40 ml) was added, and the aqueous solution was extracted with CH$_2$Cl$_2$. The combined organic extract was dried (MgSO$_4$), filtered, and concentrated. Purification by silica gel chromatography (eluant: 5%-10% MeOH—CH$_2$Cl$_2$) gave 0.78 g (2.33 mmol, 86%) of the product 106A as a white foam. MS (M+1): m/e 335.

-continued

| Number | Compound | MS (M + 1) |
|---|---|---|
| 106C | | 321 |

-continued

| Number | Compound | MS (M + 1) |
|---|---|---|
| 106D | | 321 |
| 106E | | 335 |
| 106F | | 307 |
| 106G | | 321 |
| 106H | | 321 |
| 106I | | 266 |
| 106J | | 308 |
| 106K | | 306 |

-continued

| Number | Compound | MS (M + 1) |
|---|---|---|
| 106L | | 322 |

Step 3: Using the procedure of step 3 from Example 31, the following intermediates were synthesized:

| Number | Compound | MS (M + 1) |
|---|---|---|
| 107A | | 235 |
| 107B | | 207 |
| 107C | | 221 |
| 107D | | 221 |
| 107E | | 235 |
| 107F | | 207 |

-continued

| Number | Compound | MS (M + 1) |
|---|---|---|
| 107G | H₂N-[benzene-CH₂NH₂ meta]-C(=O)-N(pyrrolidine-3-OH, stereo) | 221 |
| 107H | H₂N-[benzene-CH₂NH₂ meta]-C(=O)-N(pyrrolidine-3-OH, opposite stereo) | 221 |
| 107I | H₂N-CH(3-pyridyl)-C(=O)-NHMe | 166 |
| 107J | H₂N-CH(3-pyridyl)-C(=O)-NEt₂ | 208 |
| 107K | H₂N-CH(3-pyridyl)-C(=O)-N(pyrrolidine) | 206 |
| 107L | H₂N-CH(3-pyridyl)-C(=O)-N(morpholine) | 222 |

Step 4: To a solution of compound 104A (2.47 g, 9.31 mmol) dissolved in Et₂O (50 ml) was added LiBH₄ (0.81 g, 37.2 mmol) then MeOH (1.19 g, 1.5 ml, 37.2 mmol). The reaction mixture was heated at reflux for 5 h and then cooled to RT. The solvent was evaporated. Water (50 ml) was added, and the aqueous solution was extracted with CH₂Cl₂. The combined organic extract was dried (MgSO₄), filtered, and concentrated. Purification by silica gel chromatography (eluant: 5%-8% MeOH —CH₂Cl₂) gave 2.15 g (9.06 mmol, 97%) of the product 108A as a white solid. MS (M+1): m/e 238.

The following intermediate was synthesized by using a similar procedure:

| Number | Compound | MS (M + 1) |
|---|---|---|
| 108B | BOCNH-CH₂-[benzene meta]-CH₂-OH | 182 M + 2-tBu |

Step 5: To a solution of oxalyl chloride (1.43 g, 0.98 ml, 11.3 mmol) dissolved in dry CH₂Cl₂ (20 ml) and cooled to −78° C. under a N₂ atmosphere was added DMSO (1.76 g, 1.6 ml, 22.5 mmol) dissolved in CH₂Cl₂ (5 ml) dropwise via addition funnel. The reaction mixture was stirred at −78° C. for 15 min then compound 108A (2.14 g, 9.02 mmol) dissolved in CH₂Cl₂ (25 ml) was added dropwise via addition funnel. The reaction mixture was stirred at −78° C. for 60 min, then Et₃N (2.74 g, 3.8 ml, 27.0 mmol) was added. The reaction mixture was stirred at −78° C. for 20 min, then warmed to RT. Water (75 ml) was added, and the aqueous solution was extracted with CH₂Cl₂. The combined organic extract was dried (MgSO₄), filtered, and concentrated. Purification by silica gel chromatography (eluant: 2%-3% MeOH —CH₂Cl₂) gave 2.12 g (9.02 mmol, 100%) of the product 109A as a white solid. MS (M+1): m/e 236.

The following intermediate was synthesized by using a similar procedure:

| Number | Compound | MS (M + 1) |
|---|---|---|
| 109B | BOCNH-CH₂-[benzene meta]-CHO | 180 M + 2-tBu |

Step 6: To a solution of compound 109A (0.50 g, 2.12 mmol) dissolved in 10% water by volume in EtOH (20 ml) was added sodium acetate (1.05 g, 12.7 mmol) and hydroxylamine hydrochloride (0.59 g, 8.50 mmol). The reaction mixture was heated at reflux for 4 h and then cooled to RT. The solvent was evaporated. Water (30 ml) was added, and the aqueous solution was extracted with CH₂Cl₂. The combined organic extract was dried (MgSO₄), filtered, and concentrated to give 0.53 g (2.12 mmol, 100%) of the product 110A as a white solid. MS (M+1): m/e 251.

The following intermediate was synthesized by using a similar procedure:

| Number | Compound | MS (M + 1) |
|---|---|---|
| 110B | BOCNH-CH₂-[benzene meta]-CH=NOH | 195 M + 2-tBu |

Step 7: Using the procedure of step 3 from Example 31, the following intermediates were synthesized:

| Number | Compound | MS (M + 1) |
|---|---|---|
| 111A | H₂N—⟨benzene⟩—CH=NOH | 151 |
| 111B | H₂N—⟨benzene⟩—CH=NOH | 151 |

EXAMPLE 33

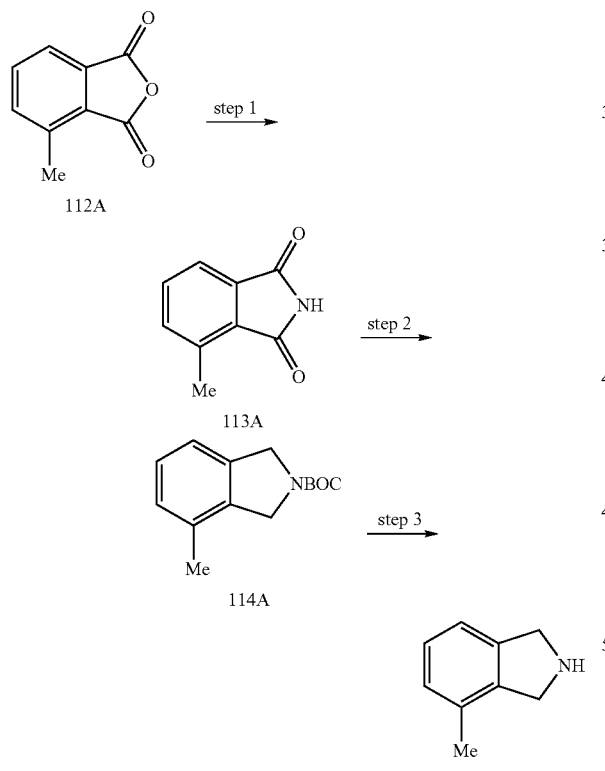

| Number | Compound | MS (M + 1) |
|---|---|---|
| 113B | tBu-substituted isoindoline-1,3-dione | 204 |
| 113C | OH-substituted isoindoline-1,3-dione | 164 |
| 113D | F-substituted isoindoline-1,3-dione | 165 for M+ |
| 113E | difluoro isoindoline-1,3-dione | 184 |

Step 2: To compound 113A (4.80 g, 29.8 mmol) was added 1 M borane in THF (104 ml, 0.104 mol) under a N₂ atmosphere. The reaction mixture was heated at reflux for 16 h and then cooled to 0° C. EtOH (80 ml) and K₂CO₃ (9.20 g, 66 mmol) were added carefully. The resulting mixture was heated at reflux for 16 h and then cooled to RT. (tBOC)₂O (10.00 g, 45.8 mmol) was added, and the reaction mixture was stirred at RT for 3 h. The solvent was evaporated. Water (200 ml) was added, and the aqueous solution was extracted with CH₂Cl₂. The combined organic extract was dried (MgSO₄), filtered, and concentrated. Purification by silica gel chromatography (eluant: 5% EtOAc—CH₂Cl₂) gave 4.50 g (19.3 mmol, 64%) of the product 114A as a beige foam. MS (M+2-tBu): m/e 178.

The following intermediates were synthesized by using a similar procedure:

| Number | Compound | MS (M + 1) |
|---|---|---|
| 114B | tBu-isoindoline-NBOC | 220 M + 2-tBu |
| 114C | OH-isoindoline-NBOC | 180 M + 2-tBu |

Step 1: 3-Methylphthalic anhydride 112A (5.00 g, 30.8 mmol) and urea (1.85 g, 30.8 mmol) were combined and heated at 320-350° C. with stirring for 5 min, then cooled to RT. The brown solid was triturated with water and filtered. The solid was washed with water and dried to give 4.80 g (29.8 mmol, 97%) of the product 113A as a pink solid. MS (M+1): m/e 162.

The following intermediates were synthesized by using a similar procedure:

-continued
| Number | Compound | MS (M + 1) |
|---|---|---|
| 114D | 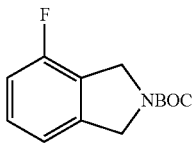 | 182 M + 2-tBu |
| 114E | 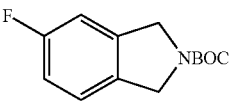 | 182 M + 2-tBu |
| 114F | 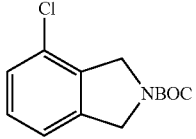 | 198 M + 2-tBu |
| 114G | 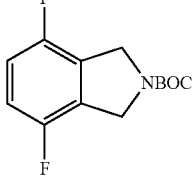 | 200 M + 2-tBu |
| 114H | 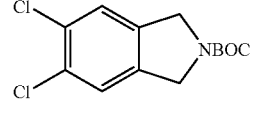 | 232 M + 2-tBu |
| 114I | 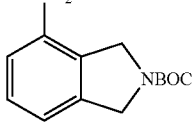 | 235 |
| 114J | 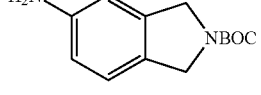 | 235 |
Step 3: Using the procedure of step 3 from Example 31, the following intermediates were synthesized:
| Number | Compound | MS (M + 1) |
|---|---|---|
| 115A | 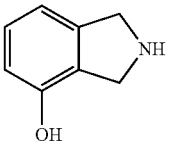 | 134 |
| 115B | 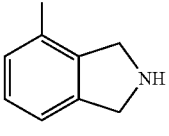 | 176 |
-continued
| Number | Compound | MS (M + 1) |
|---|---|---|
| 115C | 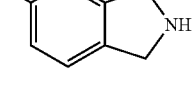 | 136 |
| 115D | 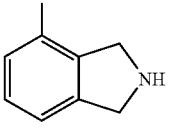 | 138 |
| 115E | 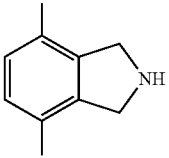 | 138 |
| 115F | 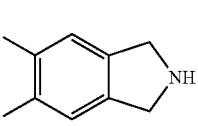 | 154 |
| 115G | 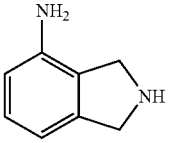 | 156 |
| 115H | 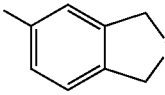 | 188 |
| 115I | 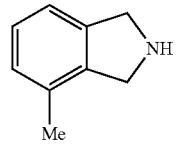 | 135 |
| 115J | 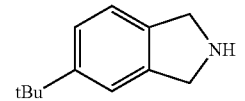 | 135 |
EXAMPLE 34
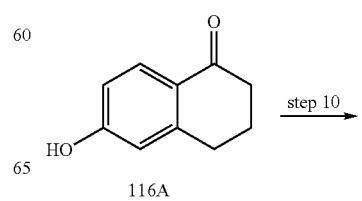
116A -continued

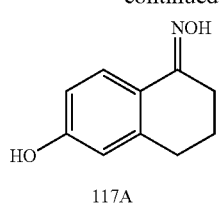

117A step 13 →

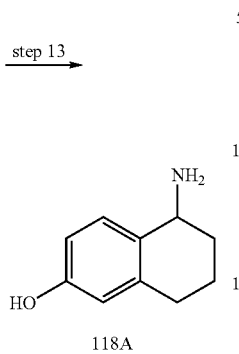

118A

Step 1: Using the procedure of step 6 from Example 32, the following intermediates were synthesized:

| Number | Compound | MS (M + 1) |
| --- | --- | --- |
| 117A | ![structure with NOH, HO on tetralone] | 178 |
| 117B | ![structure with NOH, MeO on tetralone] | 192 |

Step 2: To a solution of compound 117A (1.08 g, 6.09 mmol) dissolved in EtOH (20 ml) was added 10% palladium on carbon catalyst (0.25 g) and 1.73 M HCl in EtOH (10.6 ml, 18.3 mmol). The reaction mixture was shaken on a Parr shaker under 50 psi of hydrogen pressure for 16 h. The catalyst was removed by filtration through celite and washed with EtOH. The filtrate was concentrated to give 1.14 g (5.71 mmol, 93%) of the product 118A as a beige solid. MS (M–NH$_2$): m/e 147.

The following intermediate was synthesized by using a similar procedure:

| Number | Compound | MS (M + 1) |
| --- | --- | --- |
| 118B | ![NH2 tetralin with MeO] | 161 M-NH$_2$ |

EXAMPLE 35

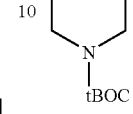

119 step 1 →

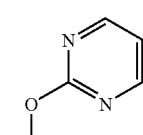

120A step 2 →

[structure 121A: pyrimidinyloxy-piperidine NH]

121A

Step 1: To a solution of compound 119 (3.00 g, 14.9 mmol) dissolved in dry DMF (60 ml) under a N$_2$ atmosphere was added NaH (60 wt % in oil, 1.19 g, 29.8 mmol). The reaction mixture was stirred at RT for 30 min, then 2-chloropyrimidine (3.41 g, 29.8 mmol) was added. The reaction mixture was heated at 80° C. for 16 h and then cooled to RT. The solvent was evaporated. Water (75 ml) was added and the aqueous solution was extracted with CH$_2$Cl$_2$. The combined organic extract was dried (MgSO$_4$), filtered, and concentrated. Purification by silica gel chromatography (eluant: 1%-4% MeOH—CH$_2$Cl$_2$) gave 2.49 g (8.91 mmol, 60%) of the product 120A as a yellowish-orange solid. MS (M+1): m/e 280.

The following intermediates were synthesized by using a similar procedure:

| Number | Compound | MS (M + 1) |
| --- | --- | --- |
| 120B | [pyrazinyloxy-piperidine-tBOC] | 280 |

-continued

| Number | Compound | MS (M + 1) |
|---|---|---|
| 120C | | 310 |

-continued

| Number | Compound | MS (M + 1) |
|---|---|---|
| 121B | | 180 |
| 121C | | 210 |

Step 2: Using the procedure of step 3 from Example 31, the following intermediates were synthesized:

EXAMPLE 36

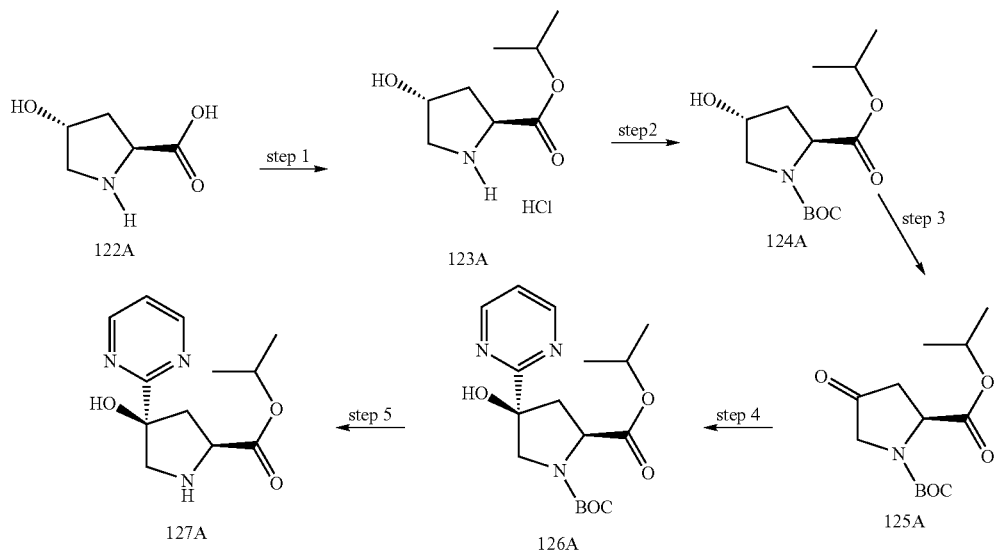

| Number | Compound | MS (M + 1) |
|---|---|---|
| 121A | | 180 |

Step 1: Trans-4-hydroxy-L-proline 122A (10.48 g, 80 mmol) was refluxed in a 5-6 M solution of HCl in 2-propanol (200 ml) for 2 h. The solvent was evaporated to give 16.33 g of the product 123A as a white solid (97% yield). MS (M+1) 174.

Step 2: 123A (16.33 g, 78.1 mmol) was suspended in dichloromethane (460 ml). Et$_3$N (30 ml) and di-tert-butyl dicarbonate (20.33 g) were added, and the mixture was stirred for 20 h at RT. The reaction mixture was washed twice with equivolume 1 N HCl, once with saturated NaHCO$_3$, and once with saturated NaCl. The organic solution was dried (anhydrous Na$_2$SO$_4$), filtered, and concentrated to give the product 124A as an amber oil (19.7 g, 92% yield). MS (M+1): m/e 274.

Step 3: Using the procedure of step 5 from Example 32, compound 125A was synthesized. MS (M+1): m/e 272.

Step 4: A 5-gram vial of CeCl₃ from Aldrich was cracked open and quickly added to a flame-dried, 125-ml, round-bottomed flask under an Ar atmosphere. Anhydrous THF was added, and the mixture was sonicated for 1 h and stirred an additional 1 h. The ketone 125A was dissolved in dry THF (5 ml) and added to the CeCl₃/THF mixture and stirred at RT for 1 h. In a separate round bottom flask, 2-pyrimidyl tri-n-butylstannane was dissolved in dry THF (18 ml) under an Ar atmosphere and cooled to −78° C. A 2.5M solution of n-butyllithium in hexanes (4 ml) was added dropwise to the pyrimidyl stannane, and the mixture turned thick and brown. After stirring for 1 h at −78° C., this cold mixture was transferred via cannula to the ketone 125A/CeCl₃ mixture also cooled to −78° C. The resulting reaction mixture was stirred at −78° C. for 3 h and then stirred at −50° C. for 30 min. The mixture was again cooled to −78° C. and quenched dropwise with 1 M citric acid (200 ml). The aqueous solution was extracted with hexane and then Et₂O. The combined organic extract was dried (MgSO₄), filtered, and concentrated. Purification by silica gel chromatography gave 0.95 g of the product 126A (27% yield). MS (M+1): m/e 352.

The following intermediates were synthesized by using a similar procedure:

| Number | Compound | MS (M + 1) |
|---|---|---|
| 126B | [structure] | 351 |
| 126C | [structure] | 280 |

Step 5: Using the procedure of step 3 from Example 31, the following intermediates were synthesized:

| Number | Compound | MS (M + 1) |
|---|---|---|
| 127A | [structure] | 252 |
| 127B | [structure] | 251 |
| 127C | [structure] | 180 |

EXAMPLE 37

[structure 128]

2,4,6-Trifluorobenzylamine 128 was prepared according to the literature procedure of A. Marfat et al, WO 9845268.

EXAMPLE 38

[structure 129]

step 1

-continued

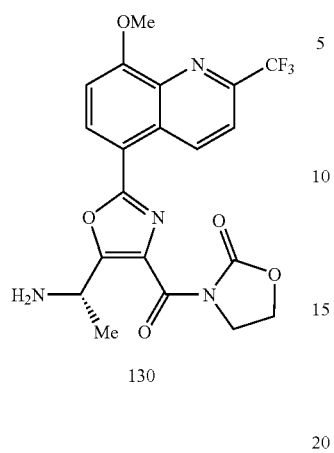

130

Step 1: Compound 129 (0.24 g, 0.5 mmol) was mixed with Et₃N (0.1 ml, 0.7 mmol) in dry THF (4 ml) and cooled to −78° C. Trimethylacetyl chloride (0.08 ml, 0.6 mmol) was added, and the resulting mixture was stirred at 0° C. for 20 min, then cooled to −78° C. again. In a separate flask, oxazolidinone (0.07 g, 0.8 mmol) was dissolved in dry THF (2 ml), cooled to −78° C., and 1.6 ml of a 1.6 M n-BuLi solution in hexane was added. After stirring at −78° C. for 15 min, the mixture was cannulated into the above mixed anhydride solution. The resulting solution was then slowly warmed up to RT. The reaction mixture was quenched with saturated NH₄Cl solution (2 ml). EtOAc (50 ml) was added, and the organic solution was washed with 1 N HCl solution, saturated NaHCO₃ solution, and brine. The organic solution was dried (Na₂SO₄), filtered, and concentrated. Purification by flash chromatography gave the product which was treated with 2 N HCl in ether (50 ml) at RT overnight. The precipitate was collected by filtration and dried in a vacuum oven at 50° C. overnight to give 0.15 gram of the product 130 as the HCl salt. MS (M+1): m/e 451.

EXAMPLE 39

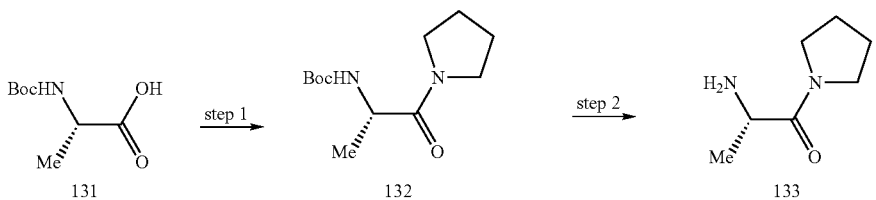

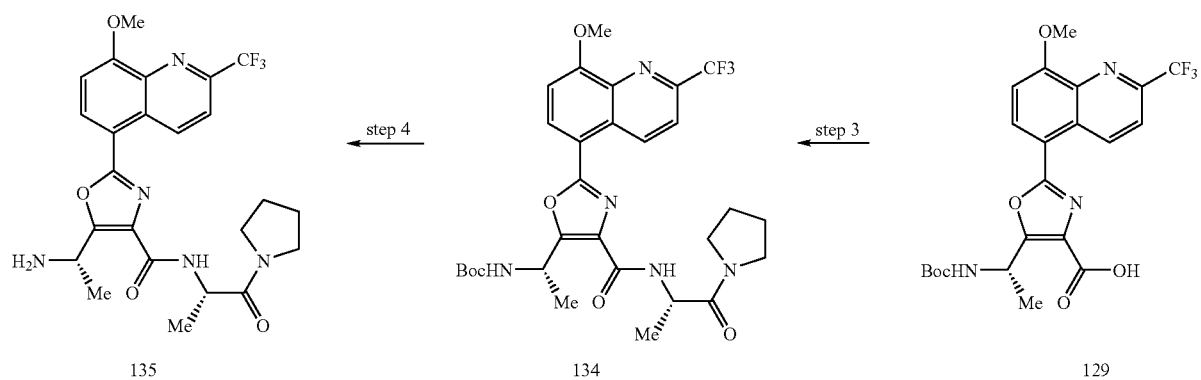

Step 1: Compound 131 (1.15 g, 6 mmol) was mixed with Et₃N (0.9 ml, 6.4 mmol) in dry THF (20 ml), and cooled to −30° C. Trimethylacetyl chloride (0.75 ml, 6 mmol) was added, and the resulting mixture was stirred at −10° C. for 20 min. Pyrrolidine (0.85 ml, 10 mmol) was added, and the resulting mixture was stirred at 0° C. for 30 min. The reaction mixture was diluted with EtOAc (150 ml) and washed with 1 N HCl solution, saturated NaHCO₃ solution, and brine. The organic solution was dried (MgSO₄), filtered, and concentrated to give the product 132.

Step 2: Using the procedure of step 3 from Example 31, intermediate 133 was synthesized.

Step 3: To a solution of compound 129 (0.48 g, 1 mmol) dissolved in DMF (4 ml) and CH₂Cl₂ (10 ml) at RT was added DIPEA (1 ml) and HATU (0.6 g). After 5 min, compound 133 (HCl salt, 0.23 g, 1.3 mmol) was added. The reaction mixture was stirred at RT for 30 min, then the mixture was diluted with EtOAc (75 ml) and washed with 1 N HCl (50 ml), saturated NaHCO₃ (50 ml), and brine. The organic solution was dried (Na₂SO₄), filtered, and concentrated. Purification by silica gel chromatography gave the product 134.

Step 4: Using the procedure of step 3 from Example 31, compound 135 was synthesized. MS (M+1): m/e 506.

EXAMPLE 40

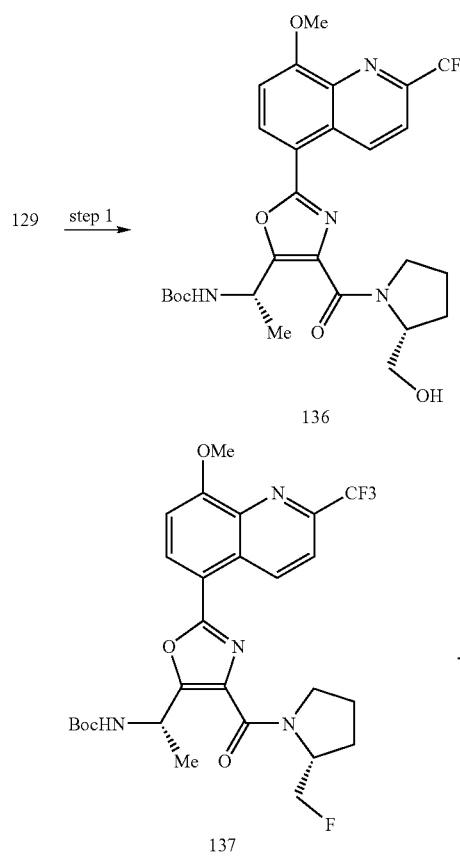

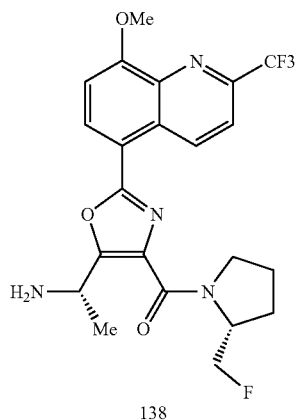

Step 1: Using the procedure for step 3 from Example 39, compound 136 was synthesized.

Step 2: To a solution of compound 136 (0.2 g, 0.35 mmol) dissolved in dry CH₂Cl₂ (6 ml) was added DAST (0.1 ml, 0.7 mmol). The reaction mixture was stirred at RT for 2 days, then quenched with saturated NaHCO₃ (2 ml). The mixture was diluted with CH₂Cl₂ (75 ml) and washed with water then 1 N HCl solution. The organic solution was dried (MgSO₄), filtered, and concentrated. Purification by silica gel chromatography gave the product 137.

Step 3: Using the procedure of step 3 from Example 31, compound 138 was synthesized. MS (M+1): m/e 467

EXAMPLE 41

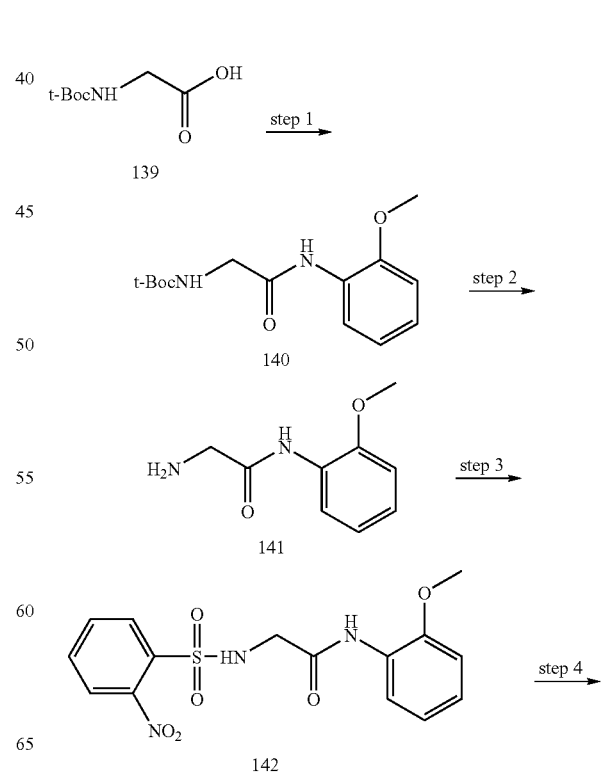

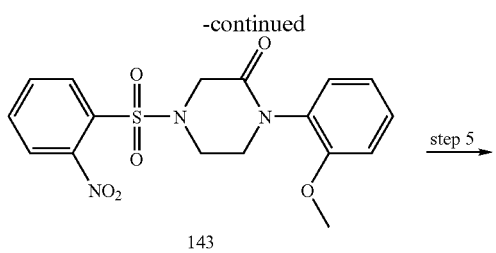

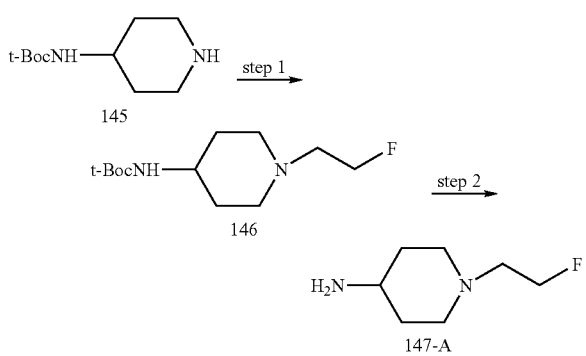

EXAMPLE 42

Step 1: Using the procedure of step 2 from Example 32, intermediate 140 was synthesized. MS (M+1): m/e 281.

Step 2: Using the procedure of step 3 from Example 31, intermediate 141 was synthesized. MS (M+1): m/e 181.

Step 3: To a solution of compound 141 (1.9 g, 8.2 mmol, a TFA salt) and Et$_3$N (2.5 g, 24.6 mmol) in CH$_2$Cl$_2$ (32 ml) at 0° C. was added a solution of 2-nitrophenylsulphonyl chloride (1.99 g, 9 mmol) in CH$_2$Cl$_2$ (8 ml) over a period of 5 min. The reaction mixture was stirred at 0° C. for 2 h, and then saturated NaHCO$_3$ solution was added. The product was extracted with CH$_2$Cl$_2$, washed with brine (1×70 ml), dried over Na$_2$SO$_4$, filtered, and concentrated to give an oily residue. Purification by silica gel chromatography (Biotage System, eluant: 40:1 CH$_2$Cl$_2$:MeOH) gave 3.11 g (8.4 mmol, 100%) of the product 142 as an off white solid. MS (M+1): m/e 366.

Step 4: The combined reaction mixture of compound 142 (730 mg, 2 mmol), K$_2$CO$_3$ (2.76 g, 20 mmol) and 1,2-dibromoethane (3.74 g, 20 mmol) in DMF (6 ml) was heated at 60° C. for 17 h, and then quenched with water. The product was extracted with EtOAc (3×30 ml), and the combined extract was washed with brine (3×60 ml), dried over Na$_2$SO$_4$, filtered, and concentrated to give an oily residue. Purification by preparative silica gel chromatography (eluant: EtOAc) gave 640 mg (1.64 mmol, 82%) of the product 143 as an oil. MS (M+1): m/e 392.

Step 5: To a solution of compound 143 (640 mg, 1.64 mmol) in CH$_3$CN (13 ml) was added Cs$_2$CO$_3$ (1.6 g, 4.92 mmol) and PhSH (216 mg, 1.97 mmol). The reaction mixture was stirred at RT for 1 h, filtered, and the solid was washed with CH$_2$Cl$_2$. The filtrate was concentrated to give a yellow oil. Purification by silica gel chromatography (Biotage System, eluant: 20:1 CH$_2$Cl$_2$:MeOH (with 4% NH$_3$) gave 210 mg (1 mmol, 61%) of the product 144A as a colorless oil. MS (M+1): m/e 207.

The following intermediates were synthesized by using a similar procedure:

| Number | Compound | MS |
|---|---|---|
| 144B | | 242 |
| 144C | | 209 |

Step 1: To a solution of amine 145 (400 mg, 2 mmol) and Et$_3$N (202 mg, 2 mmol) in EtOH (10 ml) was added 1-bromo-2-fluoroethane (1.27 g, 10 mmol). The reaction mixture, charged in a pressurized tube, was heated at 70° C. for 3 days. Mass spectroscopy was used to monitor the reaction. The reaction mixture was concentrated, and then water was added. The product was extracted with CH$_2$Cl$_2$ (3×40 ml), washed with brine (3×50 ml), dried over Na$_2$SO$_4$, filtered, and concentrated to give of the product 146 (1.75 mmol, 87%) as an oil, which was used without further purification. MS (M+1): m/e 247.

Step 2: Using the procedure of step 3 from Example 31, the following compounds were synthesized:

EXAMPLE 43

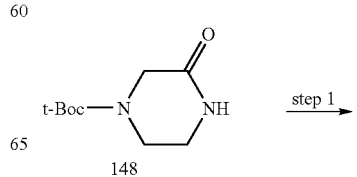

-continued

Step 1: To a solution of amide 148 (1.4 g, 7 mmol) in DMF (28 ml) was added NaH (554 mg, 23.1 mmol, 60% in oil) in portions over a period of 8 min. The reaction mixture was stirred at RT for 50 min, then EtI (3.28 g, 21 mmol) was added over a period of 2 min. The reaction mixture was stirred at RT for 15 h and then quenched with ice-water. The product was extracted with EtOAc/CH$_2$Cl$_2$, washed with brine (3×30 ml), dried over Na$_2$SO$_4$, filtered, and concentrated to give an oily residue. Purification by silica gel chromatography (Biotage System, eluant: 100:1 CH$_2$Cl$_2$:MeOH) gave 1.19 g of the product 149 (5.2 mmol, 74%) as an oil. MS (M+1): m/e 229.

Step 2: Using the procedure of step 3 from Example 31, the following compounds were synthesized:

| Number | Compound | MS |
|---|---|---|
| 150A | | 129 |
| 150B | | 115 |
| 150C | | 143 |
| 150D | | 157 |
| 150E | | 191 |
| 150F | | 143 |
| 150G | | 155 |
| 150H | | 159 |
| 150I | | 247 |

EXAMPLE 44

-continued

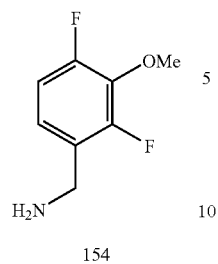

154

Step 1: Using the procedure of step 1 from Example 2, intermediate 152 was synthesized.
Step 2: Using the procedure of step 2 from Example 2, intermediate 153 was synthesized.
Step 3: Using the procedure of step 2 from Example 3, intermediate 154 was synthesized. MS (M+1): m/e 174.

EXAMPLE 45

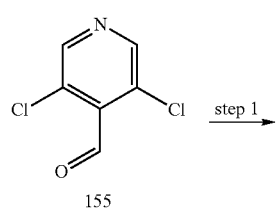

155

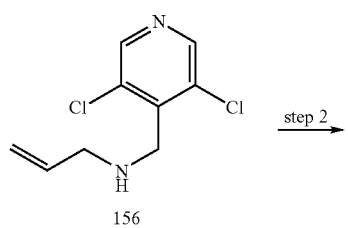

156

157

Step 1: 3,5-Dichloro-4-pyridinecarboxaldehyde (155, 0.44 g, 2.5 mmol) was mixed with allylamine (0.56 ml, 7.5 mmol), NaB(OAc)$_3$H (1.1 g, 5 mmol) and HOAc (0.15 ml) in 1,2-dichloroethane (10 ml). The reaction mixture was stirred at RT for 20 h and then poured into saturated NaHCO$_3$ solution (10 ml). The resulting-mixture was stirred at RT for 30 min, and the product was extracted with ether (3×40 ml). The combined organic extract was dried (Na$_2$SO$_4$), filtered, concentrated, and then purified by silica gel chromatography to give 0.46 g of the product 156 as an oil. MS (M+1): m/e 217.

Step 2: Compound 156 (0.32 g, 1.47 mmol) was mixed with tetrakis (triphenylphosphine) palladium (0) (20 mg) and N,N-dimethylbarbituric acid (0.73 g, 4.4 mmol) in CH$_2$Cl$_2$ (35 ml). The reaction mixture was heated at reflux for 15 h. CH$_2$Cl$_2$ (35 ml) was added, and the organic solution was washed with saturated NaHCO$_3$ solution, dried (MgSO$_4$), filtered, and concentrated. Purification by silica gel chromatography gave 0.25 g of the product 157 as an oil. MS (M+1): m/e 177.

EXAMPLE 46

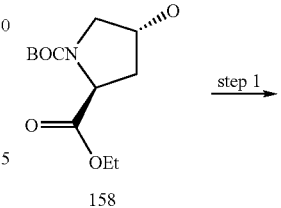

158

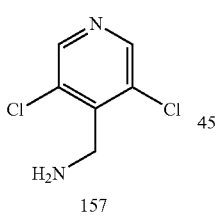

159

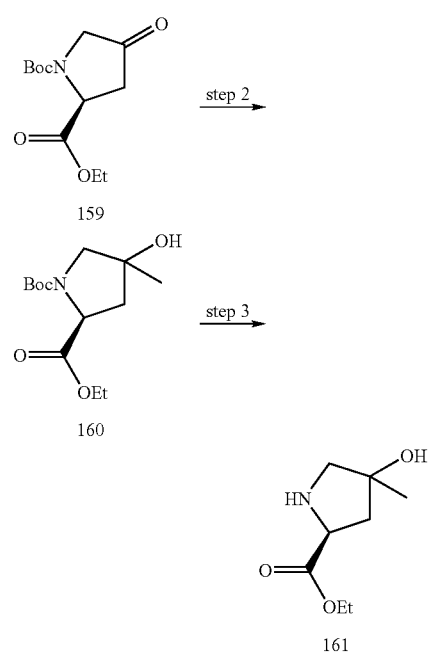

160

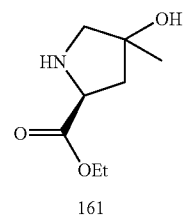

161

Step 1: To a solution of N-Boc-L-hydroxyproline ethyl ester 158 (7.0 g, 27 mmol) dissolved in CH$_2$Cl$_2$ (20 ml) was added 15% Dess-Martin reagent in CH$_2$Cl$_2$ solution (112 g). The reaction mixture was stirred at RT for 15 h. CH$_2$Cl$_2$ (100 ml) was added, and the organic solution was washed with 6% NaHCO$_3$ solution, dried, filtered, and concentrated. Purification by silica gel chromatography gave 6.5 g of the product 159 as an oil. MS (M+1): m/e 258.

Step 2: To a solution of compound 159 (1.1 g, 4.28 mmol) dissolved in dry THF (25 ml) and cooled to −78° C. was added CH$_3$MgBr solution (3.7 ml, 1.7 M in toluene/THF) dropwise. The reaction mixture was stirred at −78° C. for 1 h, then slowly warmed up to −25° C. The reaction was quenched by the addition of 5% HCl solution and then warmed up to RT. The resulting mixture was extracted with EtOAc (2×40 ml). The combined organic extract was dried (Na$_2$SO$_4$), filtered, and concentrated. Purification by silica gel chromatography gave 0.30 g of the product 160 as an oil. MS (M+1): m/e 274.

Step 3: Using the procedure of step 3 from Example 31, compound 161 was synthesized. MS (M+1): m/e 174.

EXAMPLE 47

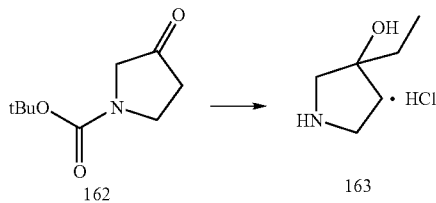

Anhydrous CeCl₃ (1.85 g, 7.5 mmol) was suspended in THF (25 ml) under N₂ and stirred overnight at RT. EtMgBr (2.5 ml of 3.0 M in THF, 7.5 mmol) was added dropwise, and the reaction mixture was stirred at RT for 1 h. A solution of ketone 162 (463 mg, 2.5 mmol) dissolved in THF (5 ml) was added dropwise to the suspension, and the resulting mixture was stirred at RT for 2 h. The reaction mixture was treated with EtOAc (5 ml) for 30 min at 20° C. and 2 M HCl, respectively, followed by extraction with EtOAc (2×100 ml). The combined organic extract was washed with brine, dried (MgSO₄), filtered, and concentrated to give the crude intermediate. This intermediate was dissolved in minimal EtOAc and HCl (10 ml of 2 M in Et₂O) was added. The reaction mixture was stirred at RT overnight to give the product 163 as a precipitate. The precipitate was filtered, washed with EtOAc, and dried in vacuo to give the product 163 as brown solid (276 mg, 73%). (M+1): m/e 116.

EXAMPLE 48

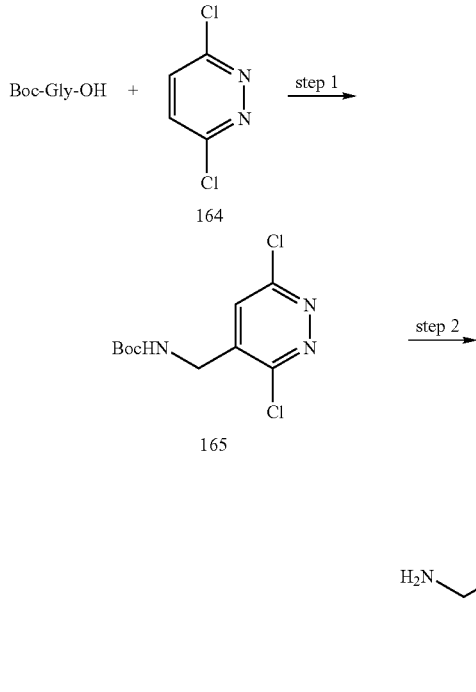

Step 1: Compound 164 was synthesized according to the procedure of Cowden, *Organic Letters* (2003), 5(23), 4497-4499.

Step 2: Using the procedure of step 3 from Example 31, compound 166 was synthesized. MS (M+1): m/e 178.

EXAMPLE 49

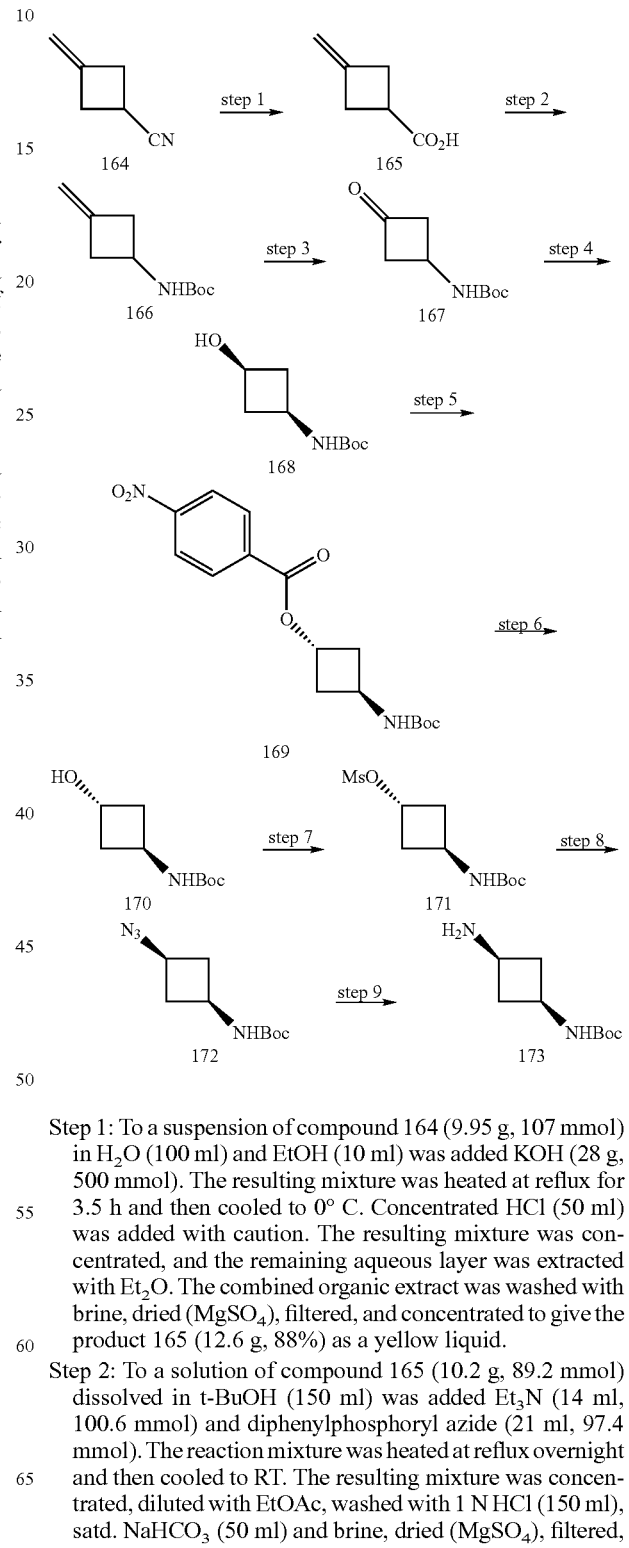

Step 1: To a suspension of compound 164 (9.95 g, 107 mmol) in H₂O (100 ml) and EtOH (10 ml) was added KOH (28 g, 500 mmol). The resulting mixture was heated at reflux for 3.5 h and then cooled to 0° C. Concentrated HCl (50 ml) was added with caution. The resulting mixture was concentrated, and the remaining aqueous layer was extracted with Et₂O. The combined organic extract was washed with brine, dried (MgSO₄), filtered, and concentrated to give the product 165 (12.6 g, 88%) as a yellow liquid.

Step 2: To a solution of compound 165 (10.2 g, 89.2 mmol) dissolved in t-BuOH (150 ml) was added Et₃N (14 ml, 100.6 mmol) and diphenylphosphoryl azide (21 ml, 97.4 mmol). The reaction mixture was heated at reflux overnight and then cooled to RT. The resulting mixture was concentrated, diluted with EtOAc, washed with 1 N HCl (150 ml), satd. NaHCO₃ (50 ml) and brine, dried (MgSO₄), filtered, and concentrated. Purification by silica gel chromatography (eluant: 1:6 EtOAc:hexane) gave the product 166 (4.05 g, 25%) as a white solid.

Step 3: To a solution of compound 166 (3.0 g, 16.4 mmol) dissolved in MeOH (200 ml), and cooled to −78° C. was bubbled ozone until the light blue color persisted. Triphenyl phosphine (9.3 g, 35.5 mmol) was added, and the reaction mixture was stirred at RT overnight. The resulting mixture was concentrated. Purification by silica gel chromatography (eluant: 1:3 EtOAc:hexane) gave the product 167 (2.95 g, 97%) as a white solid. MS (M+1): m/e 186.

Step 4: To a solution of compound 167 (3.4 g, 18.4 mmol) dissolved in THF (70 ml), and cooled to −78° C. was added L-selectride (1.0 M in THF, 22.4 ml, 22.4 mmol) dropwise. The reaction mixture was stirred at −78° C. for 2 h. Water was added, and the resulting mixture was warmed up to RT. The solution was concentrated, and water was added. The aqueous solution was extracted with EtOAc. The combined organic extract was washed with brine, dried (MgSO$_4$), filtered, and concentrated. Purification by silica gel chromatography (eluant: 1:1 EtOAc:hexane) gave the product 168 (2.74 g, 80%) as a white foam. MS (M+1): m/e 188.

Step 5: To a solution of compound 168 (1.0 g, 5.35 mmol) and p-nitrobenzoic acid (0.98 g, 5.88 mmol) dissolved in THF (25 ml) was added triphenylphosphine (2.1 g, 8.0 mmol) and DEAD (1.27 ml, 8.0 mmol) sequentially. The reaction mixture was stirred at RT overnight. The resulting solution was concentrated. Purification by silica gel chromatography (eluant: 1:5 EtOAc:hexane) gave the product 169 (1.53 g, 85%) as a white solid. MS (M+1): m/e 237.

Step 6: To a solution of compound 169 (1.53 g, 4.55 mmol) dissolved in MeOH (30 ml) at 0° C. was added K$_2$CO$_3$ (0.24 g, 1.8 mmol). The resulting suspension was stirred at 0° C. for 2 h and then concentrated. Purification by silica gel chromatography (eluant: 1:5 EtOAc:hexane) gave the product 170 (0.71 g, 83%) as a white solid. MS (M+Na$^+$): m/e 210.

Step 7: To a solution of compound 170 (0.85 g, 4.5 mmol) dissolved in CH$_2$Cl$_2$ (40 ml) at 0° C. was added Et$_3$N (0.94 ml g, 6.7 mmol) and mesyl chloride (0.45 ml, 5.8 mmol). The resulting solution was stirred at 0° C. for 2 h. Water was added, and the resulting mixture warmed up to RT. The aqueous layer was extracted with CH$_2$Cl$_2$. The combined organic extract was washed with brine, dried (MgSO$_4$), filtered, and concentrated to give the product 171 (1.0 g, 83%) as a white solid. MS (M+Na$^+$): m/e 288.

Step 8: To a solution of compound 171 (1.0 g, 3.8 mmol) dissolved in DMF (4 ml) was added NaN$_3$ (378 mg, 5.8 mmol). The reaction mixture was heated at 85° C. overnight. The resulting solution was cooled to RT, concentrated, and water was added. The aqueous layer was extracted with EtOAc. The combined organic extract was washed with brine, dried (MgSO$_4$), filtered, and concentrated to give the product 172 (0.78 g, 98%) as a white solid. MS (M+H$^+$): m/e 213.

Step 9: To a solution of compound 172 (0.78 g, 3.8 mmol) dissolved in THF (30 ml) and H$_2$O (3 ml) was added triphenylphosphine (3.86 g, 14.7 mmol). The resulting solution was heated at reflux for 2 h, cooled to RT, and then concentrated. Purification by silica gel chromatography (eluant: 1:10 4% NH$_3$MeOH:CH$_2$Cl$_2$ then 1:2 4% NH$_3$-MeOH:CH$_2$Cl$_2$) gave the product 173 (0.68 g, 100%) as a white foam. MS (M+1): m/e 187.

EXAMPLE 50

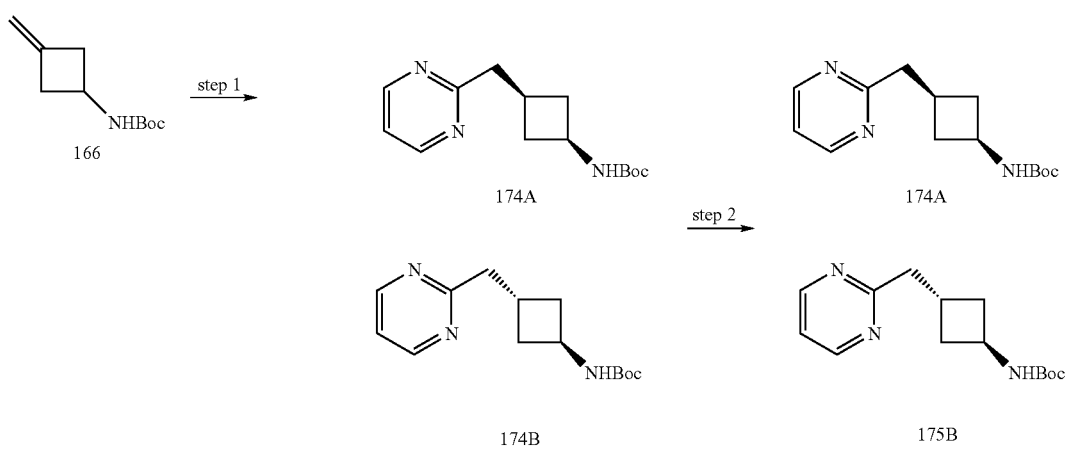

Step 1: To compound 166 (1.0 g, 5.46 mmol was added 9-BBN (0.5 N in THF, 16.4 ml, 8.2 mmol) dropwise. The reaction mixture was stirred at RT overnight. The resulting mixture was cooled to 0° C., and 2-bromopyrimidine (1.3 g, 9.2 mmol), Pd(dppf)$_2$Cl$_2$ (446 mg, 0.55 mmol), K$_2$CO$_3$ (1.13 g, 8.19 mmol), DMF (6 ml), and water (0.44 ml) were added. The reaction mixture was stirred at RT overnight. 0.5 N NaOH (50 ml) was added and the mixture extracted with CH$_2$Cl$_2$. The combined organic extract was washed with brine, dried (MgSO$_4$), filtered, and concentrated. Purification by silica gel chromatography (eluant: 1:3 EtOAc:hexane) gave a 4:1 mixture of 174A and 174B (0.8 g, 56%) as a white solid.

Step 2: Using the procedure of step 3 from Example 31, compounds 175A and 175B were synthesized.

EXAMPLE 51

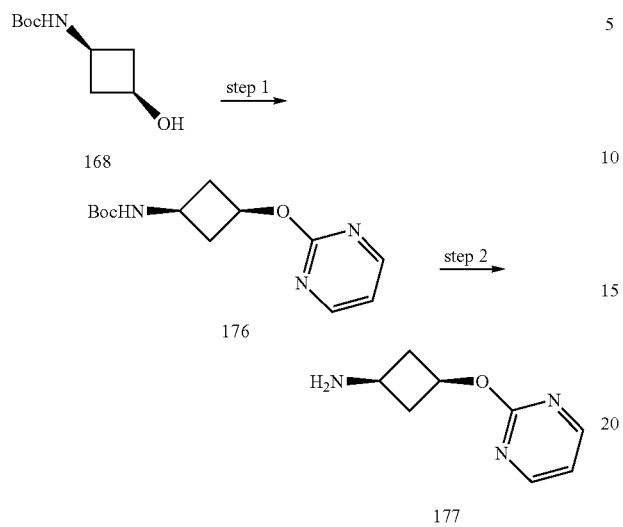

Step 1: To a solution of compound 168 (374 mg, 2.0 mmol) dissolved in DMF (5 ml) was added NaH (60% dispersion in mineral oil, 0.2 g, 5 mmol). The reaction mixture was stirred at RT for 30 min. 2-Bromopyrimidine (350 g, 2.2 mmol) was added, and the resulting solution was stirred at RT for 4 h. The reaction mixture was concentrated, and EtOAc and satd. $NaHCO_3$ (aq) were added. The aqueous layer was separated and extracted with EtOAc. The combined organic extract was washed with brine, dried ($MgSO_4$), filtered, and concentrated. Purification by silica gel chromatography (eluant: 1:1 EtOAc:hexane) gave the product 176 (0.25 g, 47%) as a white solid. MS (M+1): m/e 266.

Step 2: Using the procedure of step 3 from Example 31, compound 177 was synthesized.

EXAMPLE 52

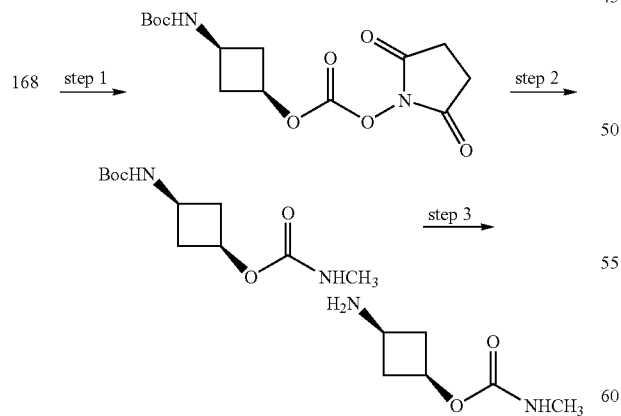

Step 1: To a solution of compound 168 (374 mg, 2.0 mmol) dissolved in $CH_3CN$ (8 ml) was added N,N'-disuccinimidyl carbonate (769 mg, 3.0 mmol) and $Et_3N$ (0.84 ml, 6.0 mmol). The reaction mixture was heated at 85° C. for 1 h. The resulting solution was concentrated, and EtOAc and satd. $NaHCO_3$ (aq) were added. The aqueous layer was separated and extracted with EtOAc. The combined organic extract was washed with brine, dried ($MgSO_4$), filtered, and concentrated to give the product 178 (0.25 g, 47%) as a white solid. MS (M+Na⁺): m/e 288.

Step 2: To a solution of compound 178 (164 mg, 0.5 mmol) dissolved in $CH_3CN$ (8 ml) was added methylamine hydrochloride salt (68 mg, 1.0 mmol), $Et_3N$ (0.45 ml, 3.3 mmol), and DMAP (2 mg). The reaction mixture was stirred at RT overnight. EtOAc and satd. $NaHCO_3$ (aq) were added. The aqueous layer was separated and extracted with EtOAc. The combined organic extract was washed with brine, dried ($MgSO_4$), filtered, and concentrated. Purification by silica gel chromatography (eluant: 1:50 $MeOH:CH_2Cl_2$) gave the product 179 (60 mg, 49%) as a white solid. MS(M+H⁺−100): m/e 145.

Step 3: Using the procedure of step 3 from Example 31, compound 177 was synthesized.

EXAMPLE 53

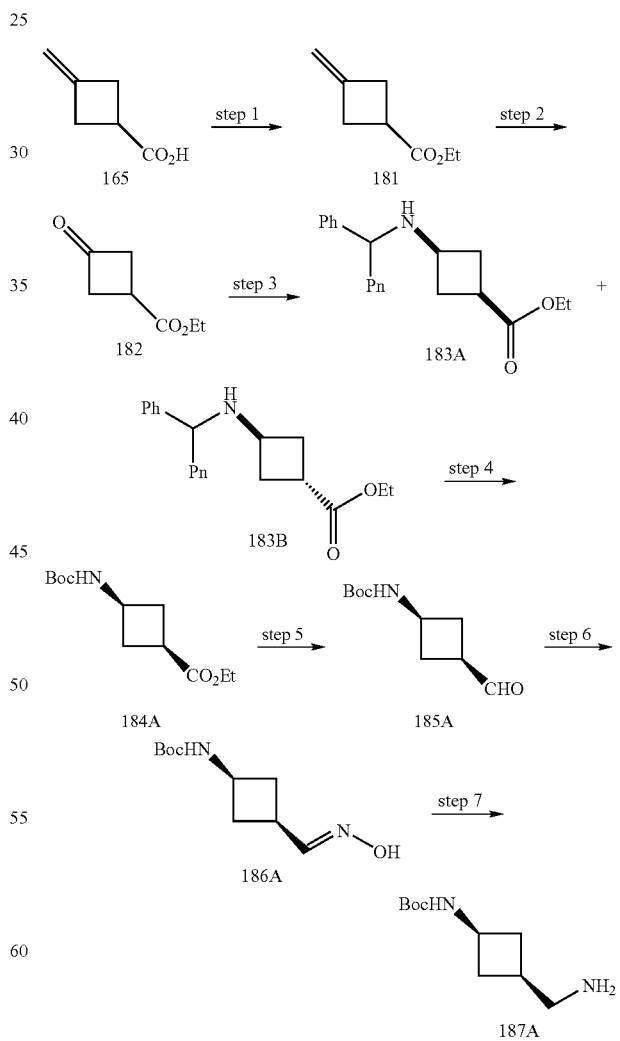

Step 1: To a suspension of compound 165 (6.22 g, 55.5 mmol) in DMF (60 ml) was added EtI (26.0 g, 166 mmol) and Cs$_2$CO$_3$ (36 g, 111 mmol). The reaction mixture was stirred at RT overnight, then diluted with Et$_2$O (200 ml) and washed with water (60 ml×3). The aqueous layer was extracted with Et$_2$O. The combined organic extract was washed with brine, dried (MgSO$_4$), filtered, and concentrated to give the product 181 (7.2 g, 93%) as a light yellow oil.

Step 2: Using the procedure for step 3 from Example 49, intermediate 182 was synthesized.

Step 3: Using the procedure for step 1 from Example 45, intermediate 183 was synthesized. Purification of 183 by silica gel chromatography (eluant: 1:20 EtOAc:hexane) gave the product 183A, cis-isomer (2.07 g, 29%) as a colorless liquid; a mixture of cis and trans isomer (183A and 183B) (2.54 g, 35%) as a colorless liquid. MS (M+1): m/e 233.

Step 4: To a solution of compound 183A (2.0 g, 6.5 mmol) dissolved in EtOH (25 ml) was added 4 N HCl in dioxane (0.25 ml) and Pd(OH)$_2$ catalyst (1.1 g). The reaction mixture was placed on a Parr shaker under 50 psi of hydrogen pressure overnight. The resulting mixture was filtered through celite. The filtrate was concentrated to give the amine HCl salt (2.3 g). The amine HCl salt (1.04 g) was suspended in CH$_2$Cl$_2$ (20 ml), and Et$_3$N (3.2 ml, 23.2 mmol) and Boc$_2$O (0.76 g, 3.48 mmol) were added. The resulting mixture was stirred at RT overnight, diluted with EtOAc and washed with 1 N HCl. The aqueous layer was separated and extracted with EtOAc. The combined organic extract was washed with brine, dried (MgSO$_4$), filtered, and concentrated. Purification by silica gel chromatography (eluant: 1:6 EtOAc:hexane) gave the product 184A (0.34 g, 48%, two steps) as a white solid. MS (M+Na$^+$): m/e 266.

Step 5: To a solution of compound 184A (0.15 g, 0.64 mmol) dissolved in CH$_2$Cl$_2$ (6 ml), and cooled to −78° C. was added a solution of DIBAL (1.0 M in CH$_2$Cl$_2$, 1.6 ml, 1.6 mmol) dropwise. The reaction mixture was stirred at −78° C. to −40° C. for 2 h. The resulting solution was warmed to RT, 10% potassium sodium tartrate solution (4 ml) was added, and stirred for 30 min. The mixture was filtered, and the filter cake was washed with CH$_2$Cl$_2$. The filtrate was washed with brine, dried (MgSO$_4$), filtered, and concentrated. Purification by silica gel chromatography (eluant: 1:6 EtOAc:hexane) gave the product 185A (60 mg, 47%) as a colorless film. MS (M+Na$^+$): m/e 222.

Step 6: Using the procedure for step 6 from Example 32, intermediate 186A was synthesized. MS (M+1): m/e 215.

Step 7: To a solution of compound 186A dissolved in THF (2 ml) was added 1 M. LAH (0.3 ml, 0.3 mmol) dropwise under a N$_2$ atmosphere. The reaction mixture was stirred at RT overnight. The resulting solution was cooled to 0° C., and H$_2$O (50 µl), 15% NaOH (aq) (30 µl), and H$_2$O (0.5 ml) were added. The resulting slurry was stirred at RT for 30 min and filtered through a pad of celite. The filtrate was diluted with CH$_2$Cl$_2$ and washed with brine, dried (MgSO$_4$), filtered, and concentrated to give the product 187A (34 mg, 97%) as a white solid. MS (M+1): m/e 201.

EXAMPLE 54

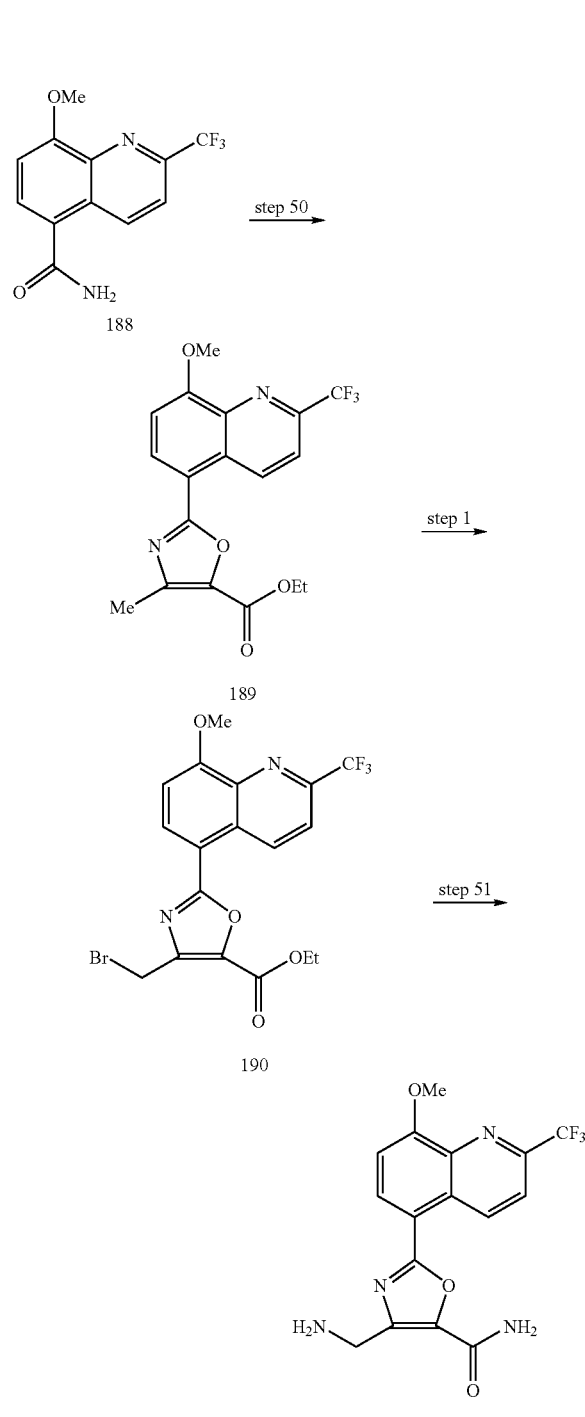

Step 1: Compound 188 (8.80 g, 32 mmol) and ethyl 2-chloroacetoacetate (27.2 g, 23 ml, 160 mmol) were mixed together and heated at 180° C. for 7 h. Excess ethyl 2-chloroacetoacetate was removed by vacuum distillation. The residue was suspended in MeOH (200 ml) and stirred at 60° C. for 40 min, then at RT overnight. The solid was collected by vacuum filtration, washed with MeOH, and dried under vacuum to give 8.5 g (74%) of the product 189 as a beige solid. MS (M+1): m/e 381.

Step 2: Using the procedure for step 1 from Example 2, intermediate 190 was synthesized. MS (M+1): m/e 459.

Step 3: Compound 190 (0.20 g, 0.44 mmol) was suspended in 7 M $NH_3$ in MeOH (10 ml) and heated at 55° C. for 16 h. The reaction mixture was cooled to RT and concentrated. Purification by reverse phase chromatography gave 35 mg (22%) of the title compound 191. MS (M+1): m/e 367.

EXAMPLE 55 collected by vacuum filtration, washed with water, and dried under vacuum to give 1.7 g (92%) of the product 194. MS (M+1): m/e 422.

Step 4: To a solution of compound 194 (1.7 g, 4 mmol) dissolved in toluene (30 ml) was added trimethylphosphine (1 M in toluene, 4.4 ml, 4.4 mmol). The reaction mixture was stirred at RT for 1 h and then cooled to −20° C. 2-(tert-butoxycarbonyl-oxyimino)-2-phnylacetonitrile (BOC-ON) (1.18 g, 4.8 mmol) was added. The reaction mixture was warmed to RT and stirred for 16 h. $CH_2Cl_2$ was added and the organic solution was washed with water. The organic solution was dried ($MgSO_4$), filtered, and con-

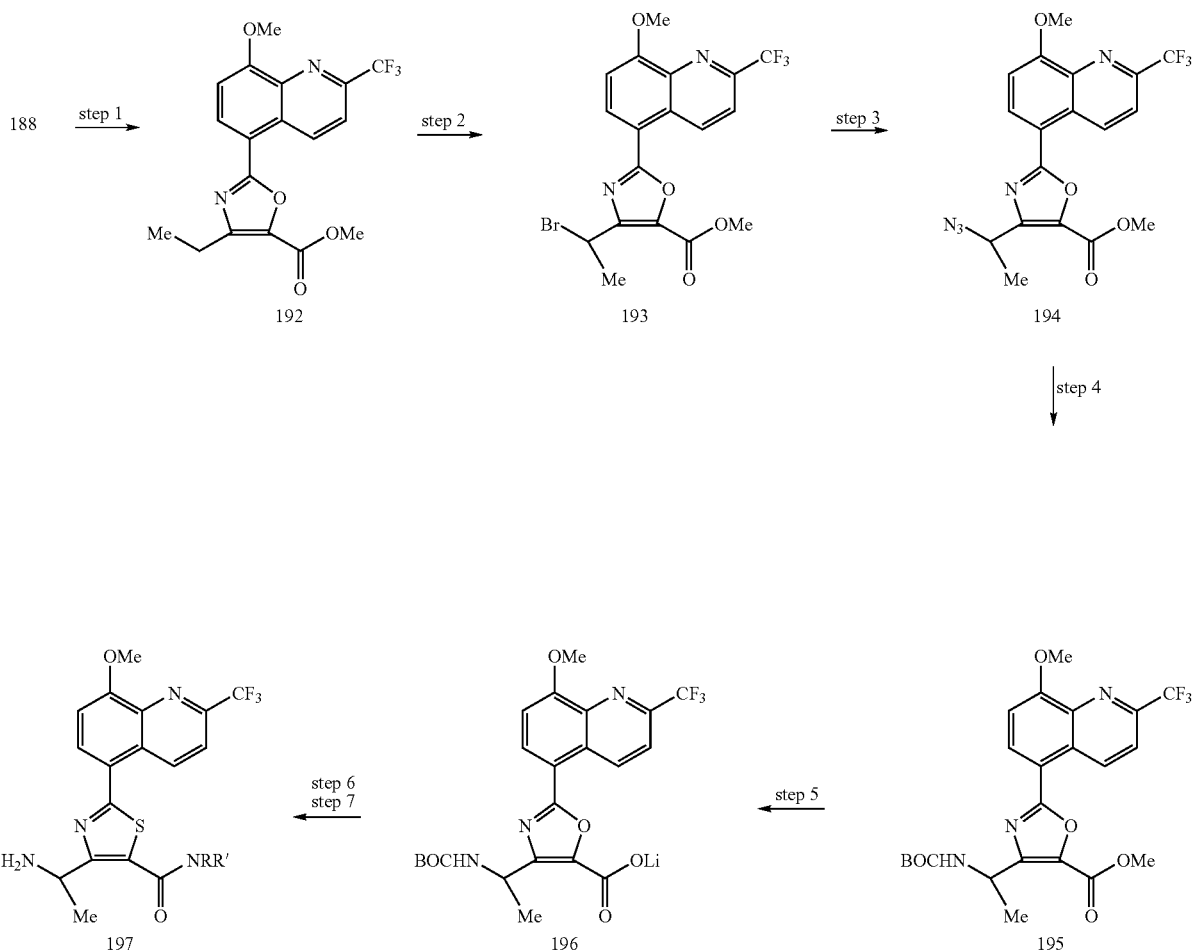

Step 1: Using the procedure for step 1 from Example 50, intermediate 192 was synthesized. MS (M+1): m/e 381.

Step 2: Using the procedure for step 1 from Example 2, intermediate 193 was synthesized.

Step 3: To a solution of compound 193 (2.0 g, 4 mmol) dissolved in DMSO (20 ml) was added $NaN_3$ (0.29 g, 4.4 mmol). The reaction mixture was stirred at RT for 24 h. Water was added and a precipitate formed. The solid was centrated. Purification by silica gel chromatography gave 1.26 g (64%) of the product 195. MS (M+1): m/e 496.

Step 5: Using the procedure for step 1 from Example 32, intermediate 196 was synthesized. MS (M+1): m/e 482.

Step 6 and Step 7: Using the procedure for step 2 from Example 32 and then step 3 from Example 31, the following compounds were synthesized.

| Number | Compound | MS (M + 1) |
|---|---|---|
| 197A | 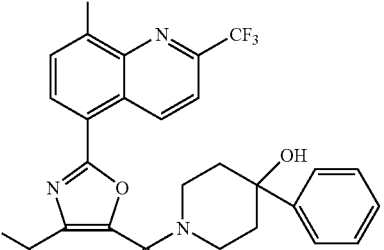 | 541 |
| 197B | 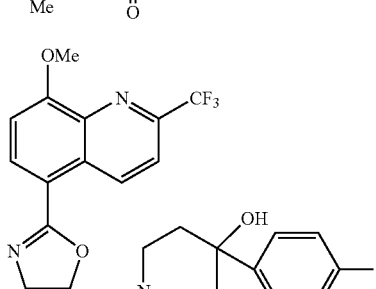 | 575 |
EXAMPLE 56
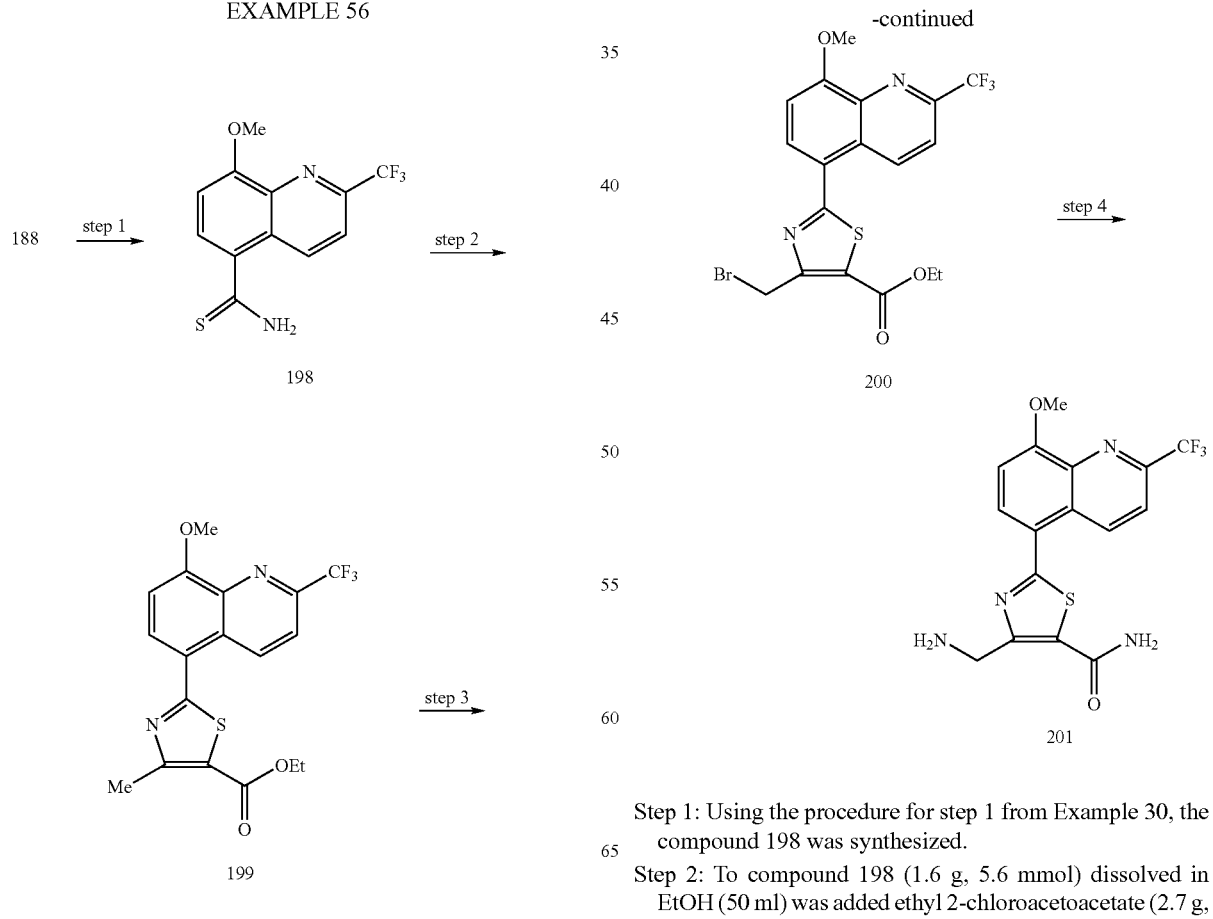
Step 1: Using the procedure for step 1 from Example 30, the compound 198 was synthesized.
Step 2: To compound 198 (1.6 g, 5.6 mmol) dissolved in EtOH (50 ml) was added ethyl 2-chloroacetoacetate (2.7 g, 2.3 ml, 16.8 mmol). The reaction mixture was heated at 65° C. for 16 h and then cooled to RT. The solid was collected by vacuum filtration and washed with MeOH. Purification by silica gel chromatography gave the product 199.

Step 3: Using the procedure for step 1 from Example 2, intermediate 200 was synthesized. MS (M+1): m/e 477.

Step 4: Using the procedure for step 3 from Example 54, title compound 201 was synthesized. MS (M+1): m/e 383.

EXAMPLE 57

Step 1: Using the procedure for step 1 from Example 54, compound 202 was synthesized.

Step 2: Using the procedure for step 1 from Example 2, compound 203 was synthesized.

Step 3: Using the procedure for step 3 from Example 55, compound 204 was synthesized.

Step 4: Using the procedure for step 4 from Example 55, compound 205 was synthesized.

Step 5: Using the procedure for step 1 from Example 32, intermediate 206 was synthesized.

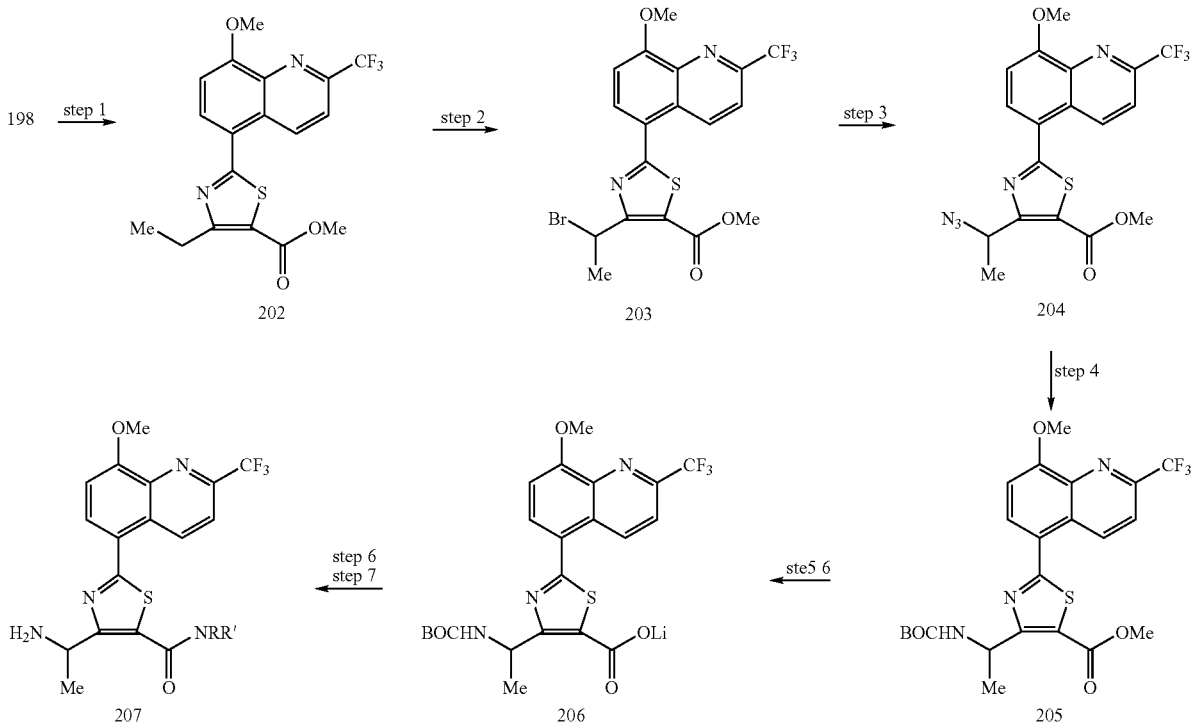

Step 6 and Step 7: Using the procedure for step 2 from Example 32 and then step 3 from Example 31, the following compounds were synthesized.

| Number | Compound | MS (M + 1) |
|---|---|---|
| 207A | (structure shown: 8-OMe, 2-CF3 quinoline linked to thiazole with H2N-CH(Me)- and C(O)-N-piperidine-4-OH-4-phenyl) | 557 |

-continued
| Number | Compound | MS (M + 1) |
|---|---|---|
| 207B | 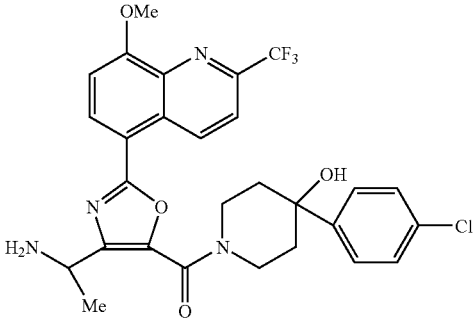 | 591 |
| 207C | 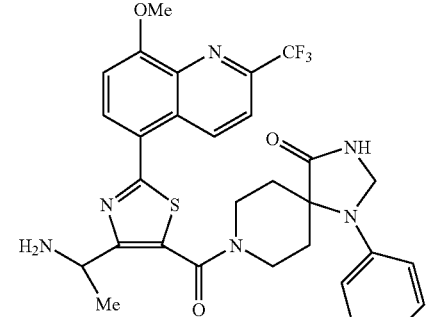 | 611 |
| 207D | 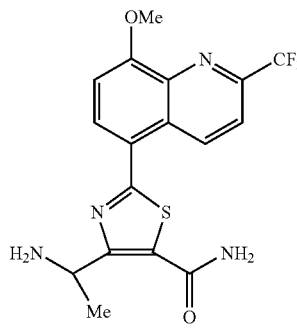 | 397 |

EXAMPLE 58

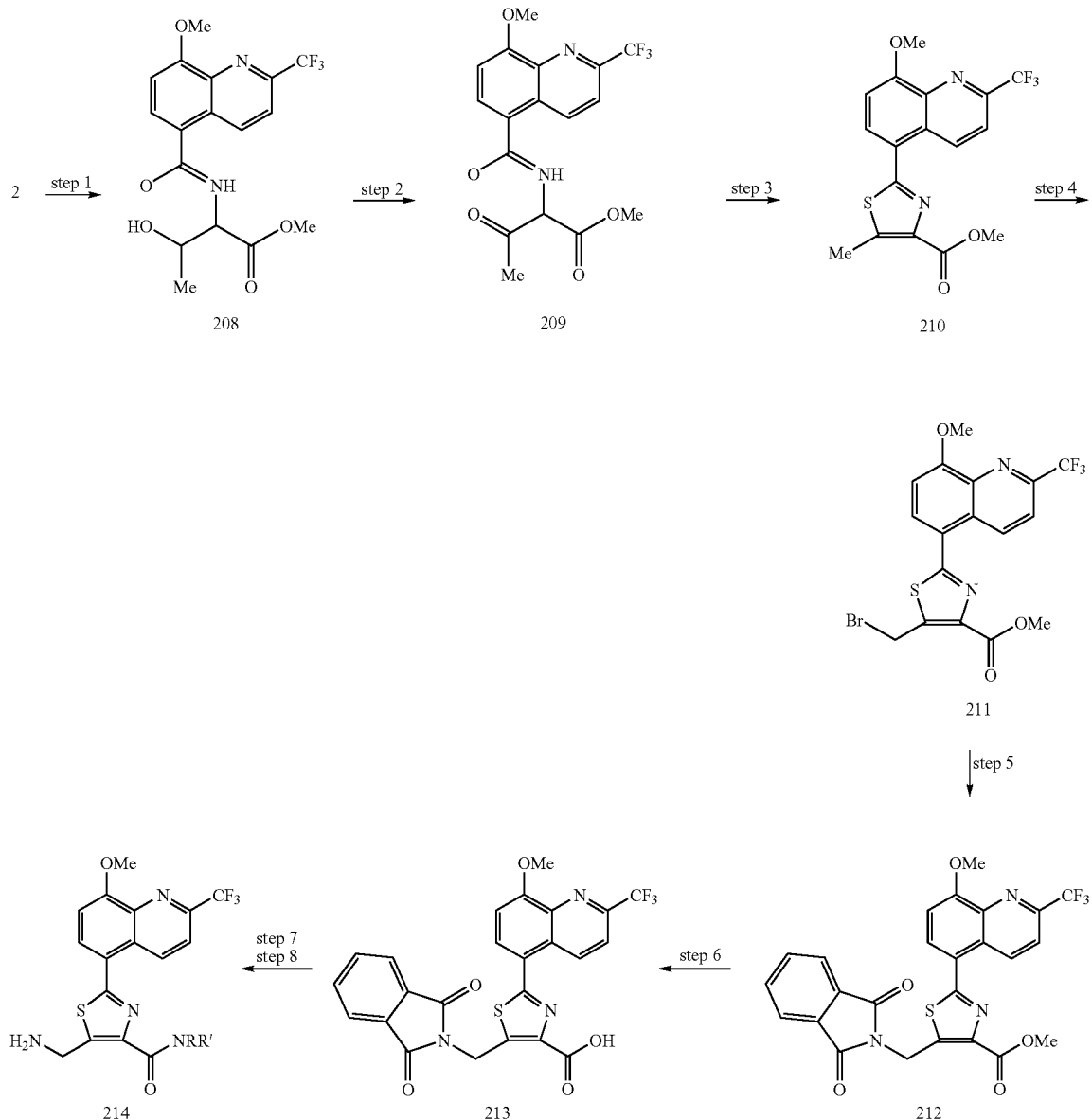

Step 1: To a suspension of threonine-OMe-HCl (10.2 g, 0.06 mol) in CH$_2$Cl$_2$ (200 ml) was added Hunig's base (14.1 g, 19 ml, 0.11 mol) and the mixture cooled to 0° C. Compound 2 (15.0 g, 0.05 mol) dissolved in CH$_2$Cl$_2$ (150 ml) was added dropwise via addition funnel. The reaction mixture was stirred at 0° C. for 15 min, then at RT for 60 min. The solvent was evaporated and dilute HCl solution was added. The solid was collected by vacuum filtration and washed with MeOH. A second crop was collected by vacuum filtration of the filtrate. The combined solid was dried under vacuum to give 19.3 g (100%) of the product 208.

Step 2: To a solution of compound 208 (7.7 g, 20 mmol) dissolved in DMSO (50 ml) and toluene (50 ml) and cooled to 0° C. was added EDCI (9.6 g, 50 mmol) and dichloroacetic acid (3.3 g, 2.1 ml, 25 mmol). The reaction mixture was stirred at 0° C. for 5 min, then at RT for 45 min. Na$_2$S$_2$O$_3$ (7 g) dissolved in water (600 ml) and hexane (300 ml) was added. The reaction mixture was stirred at RT for 15 min. The solid was collected by vacuum filtration and washed with water, 1:1 water:MeOH, and then 1:1 ether:hexane. The filtrate was filtered to give additional solid. The combined solid was dried under vacuum to give 7.2 g (94%) of the product 209.

Step 3: Using the procedure for step 1 from Example 30, the compound 210 was synthesized.

Step 4: Using the procedure for step 1 from Example 2, the compound 211 was synthesized.

Step 5: Using the procedure for step 2 from Example 2, the compound 212 was synthesized.

Step 6: Using the procedure for step 3 from Example 2, the compound 213 was synthesized.

Step 7 and Step 8: Using the procedures for step 1 and step 2 from Example 3, the following compounds were synthesized.
| Number | Compound | MS (M + 1) |
|---|---|---|
| 214A | 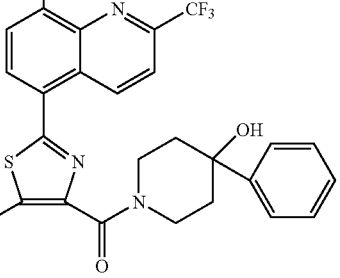 | 543 |
| 214B | 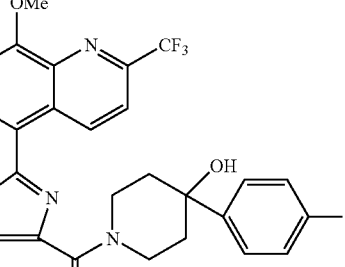 | 577 |
| 214C | 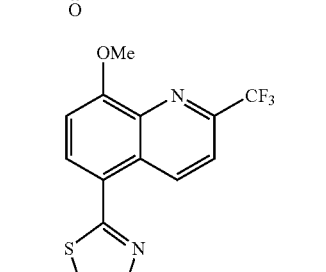 | 383 |
EXAMPLE 59
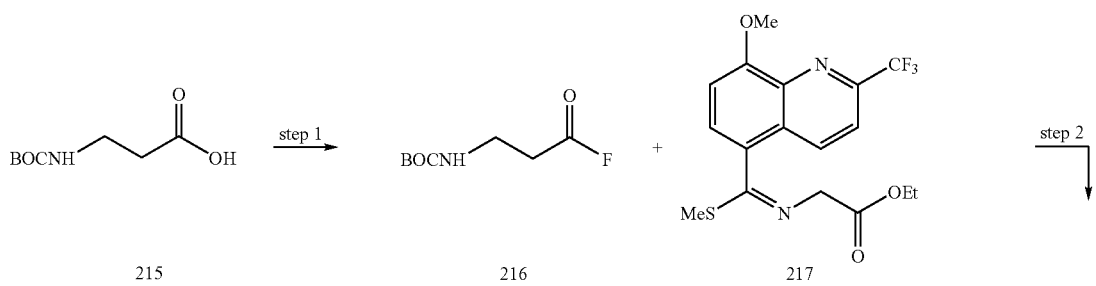

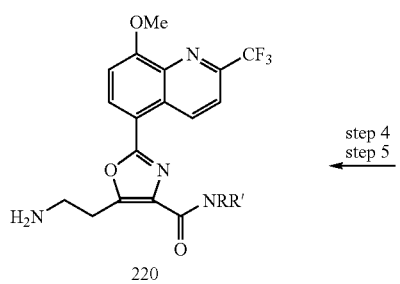

220

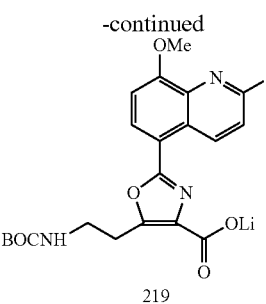

219

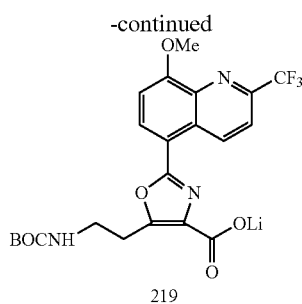

218

Step 1: To a solution of compound 215 (1.89 g, 10 mmol) in anhydrous CH$_2$Cl$_2$ (25 ml) at −20° C. was added pyridine (790 mg, 10 mmol), followed by the addition of cyanuric fluoride (3.6 ml, 40 mmol) over a period of 5 min. After 2 h at −20° C., the reaction mixture was quenched with ice-water and extracted with CH$_2$Cl$_2$. The combined extract was washed with brine, dried over Na$_2$SO$_4$, filtered, and concentrated to give 1.15 g (6 mmol, 60%) of the product 216 as a colorless liquid.

Step 2: To a solution of compound 217 (1.54 g, 3.98 mmol) and 216 (920 mg, 4.81 mmol) in anhydrous THF (16 ml) at −78° C. was added KN(TMS)$_2$ (20 ml, 20 mmol) over a period of 5 min. After 1 h at −78° C., the cold bath was removed and the reaction mixture was stirred for another 30 min, quenched with water, and extracted with EtOAc. The combined extract was washed with brine, dried over Na$_2$SO$_4$, filtered, and concentrated to give an oily residue. Purification by silica gel chromatography (Biotage System, eluant: 3:1 hexane:EtOAc) gave 0.89 g (2.1 mmol, 54%) of the product 218 as a white powder. MS (M+1): m/e 510.

Step 3: Using the procedure for step 1 from Example 32, intermediate 219 was synthesized. MS (M+1): m/e 482.

Step 4 and Step 5: Using the procedure for step 2 from Example 32 and then step 3 from Example 31, the following compounds were synthesized:

| Number | Compound | MS |
|---|---|---|
| 220A | | 507 |

-continued

| Number | Compound | MS |
|---|---|---|
| 220B | | 558 |
| 220C | | 605 |

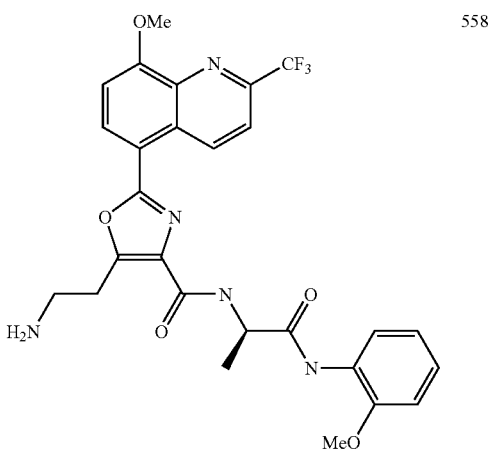

-continued
| Number | Compound | MS |
|---|---|---|
| 220D | 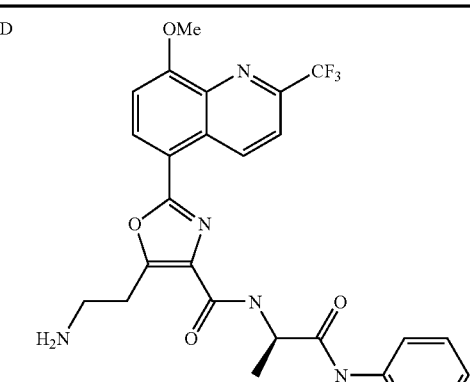 | 572 |
-continued
| Number | Compound | MS |
|---|---|---|
| 220E | | 537 |
EXAMPLE 60
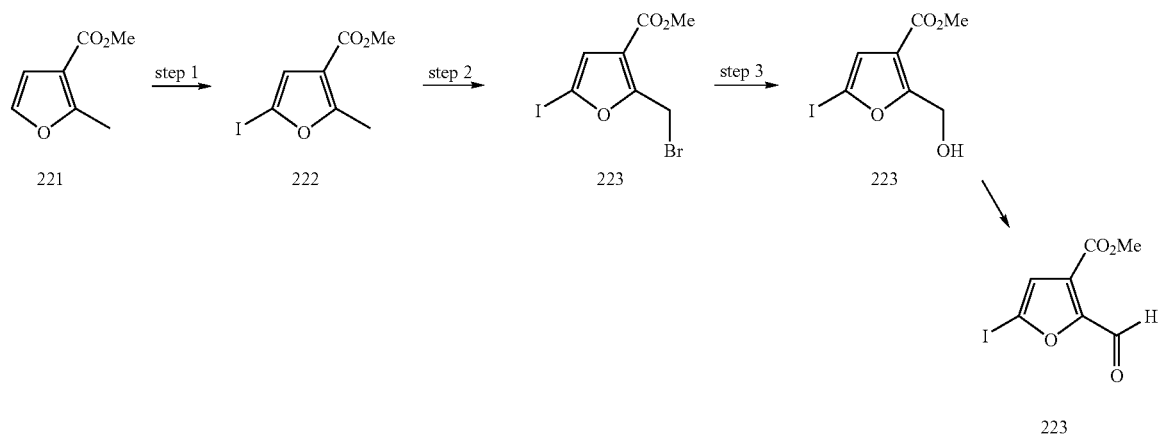
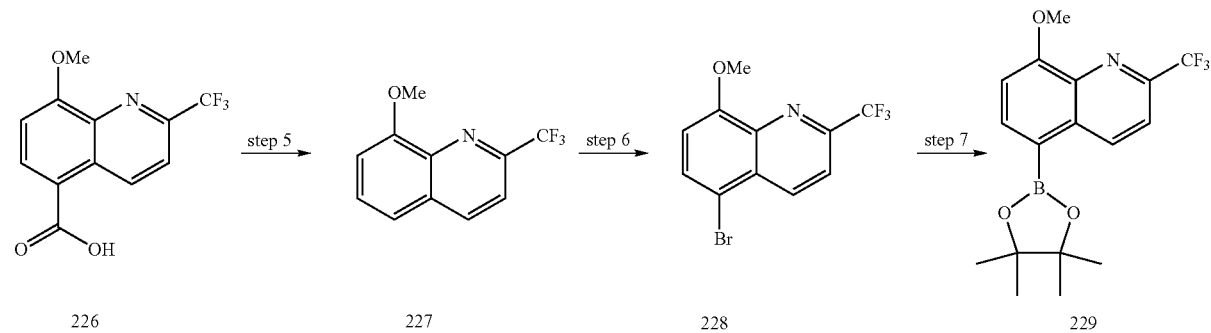

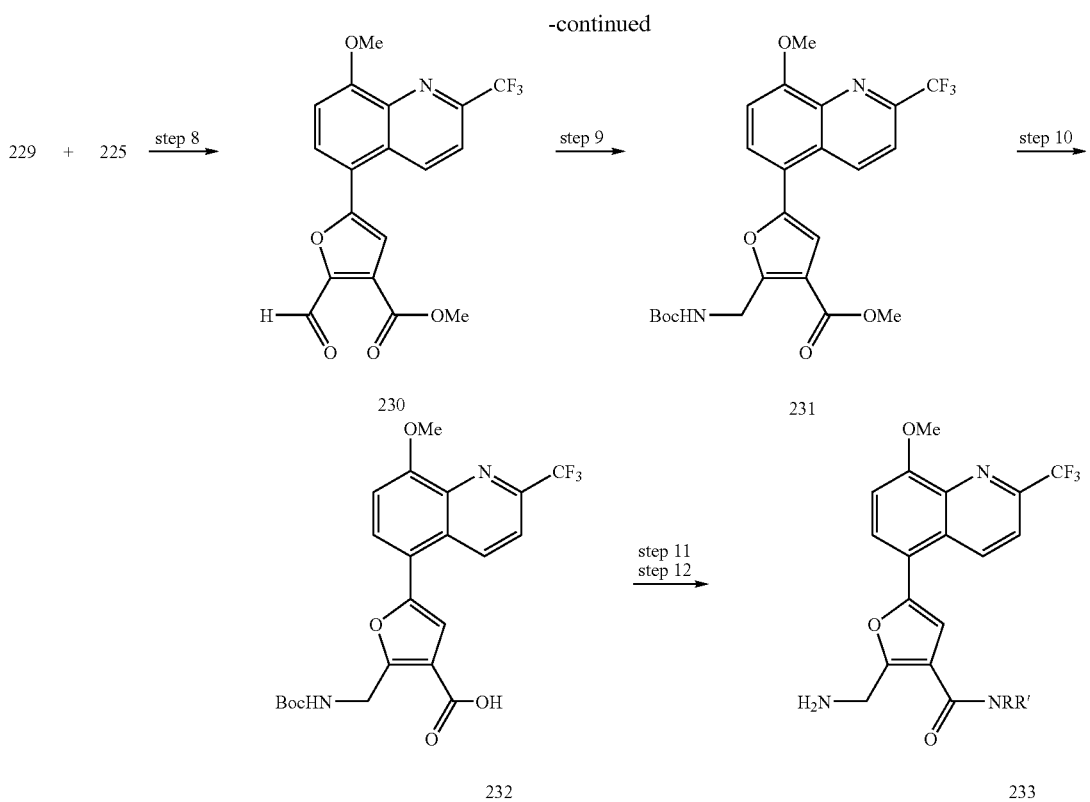

Step 1: To a solution of compound 221 (6.01 g, 42.9 mmol) dissolved in DMF (50 ml) was added N-iodosuccinimide (10.27 g, 45.6 mmol). The solution was heated at 40° C. overnight. The reaction was followed by taking $^1$H NMR of small amounts of the reaction mixture. Additional N-iodosuccinimide (1.34 g, 5.96 mmol) was added, and the resulting solution was stirred at RT for 2 days. The solution was diluted with EtOAc (150 ml) and washed with 0.5 N Na$_2$S$_2$O$_3$ (50 ml×2). The combined aqueous wash was extracted with EtOAc (100 ml×2). The combined organic extract was dried (MgSO$_4$), filtered, and concentrated. The residue was purified by silica gel chromatography (eluant: 1:20 EtOAc:hexane) to give the product 222 (8.35 g, 73%) as a light yellow liquid. MS (M+1): m/e 367.

Step 2 and Step 3: To a solution of compound 222 (8.33 g, 31.3 mmol) dissolved in CCl$_4$ (100 ml) was added NBS (11.1 g, 62.3 mmol) and benzoylperoxide (1.3 g, 5.36 mmol). The reaction mixture was heated at reflux for 16 h and then cooled to RT. CH$_2$Cl$_2$ was added (400 ml) and the organic solution was washed with 0.5 N Na$_2$S$_2$O$_3$ (150 ml×2). The aqueous washes were combined and extracted with CH$_2$Cl$_2$ (100 ml×3). The combined organic extract was washed with brine, dried (MgSO$_4$), filtered, and concentrated. The residue was dissolved in acetone (300 ml) and water (150 ml), and Ag$_2$CO$_3$ (10.3 g, 37.4 mmol) was added. The reaction mixture was heated at reflux overnight and then cooled to RT. The mixture was filtered through a pad of celite. The filtrate was concentrated, and the remaining aqueous solution was extracted with EtOAc. The combined organic extract was washed with brine, dried (MgSO$_4$), filtered, and concentrated. The residue was purified by silica gel chromatography (eluant: 1:3 EtOAc:hexane) to give the product 224 (5.25 g, 60%) as a light yellow liquid. MS (M+1): m/e 283.

Step 4: To a solution of compound 224 (4.57 g, 16.2 mmol) dissolved in CH$_2$Cl$_2$ (100 ml) was added Dess-Martin reagent (14 g, 33 mmol). The reaction mixture was stirred at RT overnight. The resulting solution was washed with 1 N NaOH (150 ml). The aqueous layer was separated and extracted with CH$_2$Cl$_2$. The combined organic extract was washed with brine, dried (MgSO$_4$), filtered, and concentrated. The residue was purified by silica gel chromatography (eluant: 1:5 EtOAc:hexane) to give the product 225 (5.25 g, 60%) as a white solid. MS (M+1): m/e 281.

Step 5: To a solution of compound 226 (14 g, 51.7 mmol) dissolved in quinoline (100 ml) was added copper (17 g, 268 mmol). The reaction mixture was heated at 180° C. for 6 h and then cooled to RT. The resulting mixture was filtered through a pad of celite and the filter cake was washed with EtOAc. The filtrate was washed with 4 N HCl (800 ml). The aqueous layer was separated and extracted with EtOAc. The combined organic extract was washed with brine, dried (MgSO$_4$), filtered, and concentrated. The residue was purified by silica gel chromatography (eluant: 1:10 EtOAc:hexanes) to give the product 227 (9.25 g, 79%) as a white solid. MS (M+1): m/e 228.

Step 6: To a solution of compound 227 (9.1 g, 40.0 mmol) dissolved in MeOH (200 ml) was added bromine (2.1 ml, 41.0 mmol). The reaction mixture was heated at 40° C. for 2 h and then cooled to RT and concentrated. The residue was purified by silica gel chromatography (eluant: 1:6 EtOAc:hexane) to give the product 228 (12.1 g, 99%) as a white solid. MS (M+1): m/e 306.

Step 7: Pd$_2$(dba)$_3$ (1.69 g, 1.85 mmol) and 1.0 M PCy$_3$ in THF (3.87 ml, 3.87 mmol) were added to a 500 ml three-neck reaction flask (evacuated and backfilled with N$_2$). Dioxane (200 ml) was added and the mixture was evacuated and refilled with N$_2$ again. The resulting mixture was stirred at RT for 30 min. Bromide 228 (5.91 g, 19.4 mmol), bis(pinocolo)diboron (6.88 g, 27.1 mmol), and KOAc (6.89 g, 70.0 mmol) were added sequentially. The reaction mixture was heated at 85° C. overnight and then cooled to RT. The resulting mixture was filtered through a pad of celite and the filter cake was washed with EtOAc. The filtrate was washed with H$_2$O (100 ml). The aqueous layer was separated and extracted with EtOAc. The combined organic extract was washed with brine, dried (MgSO$_4$), filtered, and concentrated. The residue was purified by silica gel chromatography (eluant: 1:15 EtOAc:hexane) to give the product 229 (5.35 g, 78%) as a white solid. MS (M+1): m/e 354.

Step 8: Boronic ester 229 (5.35 g, 15.15 mmol), 2-iodofuran 225 (4.27 g, 1.5.25 mmol), palladium acetate (172 mg, 0.77 mmol), S-Phos (682 mg, 1.65 mmol), and K$_3$PO$_4$ (12.5 g, 54.3 mmol) were combined in a 100 ml round bottom flask. The mixture was suspended in THF (100 ml), degassed, and refilled with N$_2$. Water (0.55 ml, 30 mmol) was added. The resulting mixture was stirred at RT under a N$_2$ atmosphere overnight. The reaction mixture was filtered through celite and the filter cake was washed with EtOAc. The filtrate was concentrated, and the residue was purified by silica gel chromatography (eluant 1:3 EtOAc:hexane) to give the product 230 (3.00 g, 46%) as a yellow solid. MS (M+1): m/e 433.

Step 9: To a solution of compound 230 (1.1 g, 2.90 mmol) dissolved in CH$_3$CN (60 ml) and CH$_2$Cl$_2$ (15 ml) was added BocNH$_2$ (1.02 g, 8.71 mmol), Et$_3$SiH (1.4 ml, 8.76 mmol), and TFA (0.43 ml, 5.79 mmol) sequentially. The reaction mixture was stirred at RT overnight. The resulting solution was diluted with CH$_2$Cl$_2$ and washed with 1 N NaOH (40 ml). The aqueous layer was separated and extracted with CH$_2$Cl$_2$. The combined organic extract was washed with brine, dried (MgSO$_4$), filtered, and concentrated. The residue was purified by silica gel chromatography (eluant: 1:3 EtOAc:hexane) to give the product 231 (0.95 g, 68%) as a yellow solid. MS (M+1): m/e 481.

Step 10: Using the procedure for step 1 from Example 32, compound 232 was synthesized. MS (M+1): m/e 467.

Step 11 and Step 12: Using the procedure for step 2 from Example 32 and for step 3 from Example 31, the following compounds were synthesized:

| Number | Compound | MS |
| --- | --- | --- |
| 233A | (structure) | 492 |
| 233B | (structure) | 525 |
| 233C | (structure) | 496 |
| 233D | (structure) | 512 |
| 233E | (structure) | 506 |

-continued
| Number | Compound | MS |
|---|---|---|
| 233F | 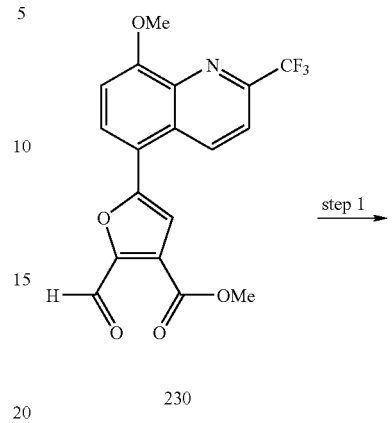 | 508 |
| 233G | | 520 |
| 233H | | 482 |
EXAMPLE 61
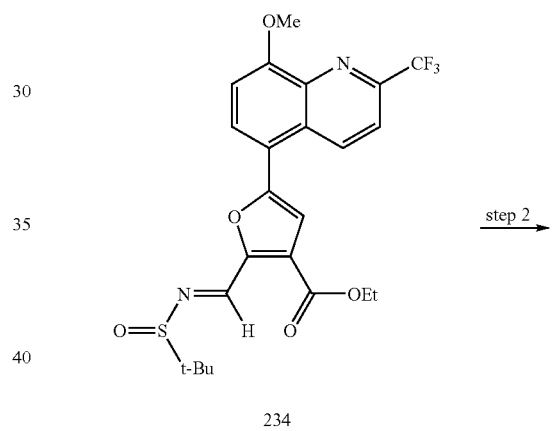
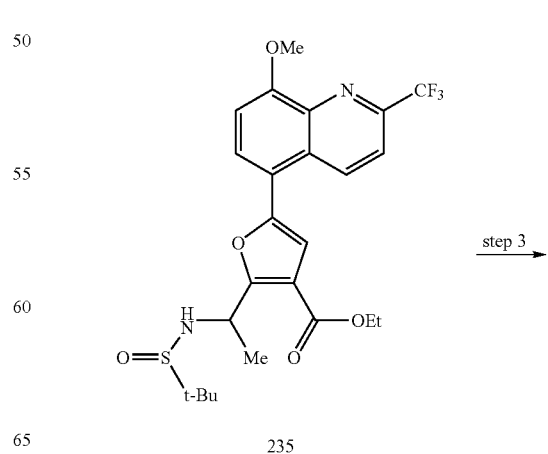

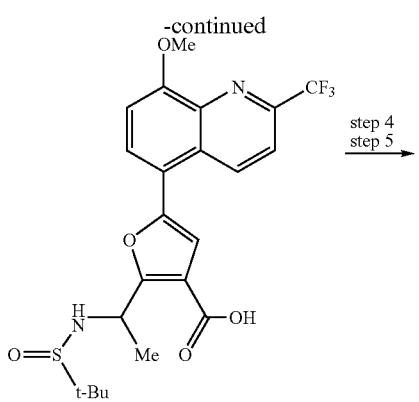

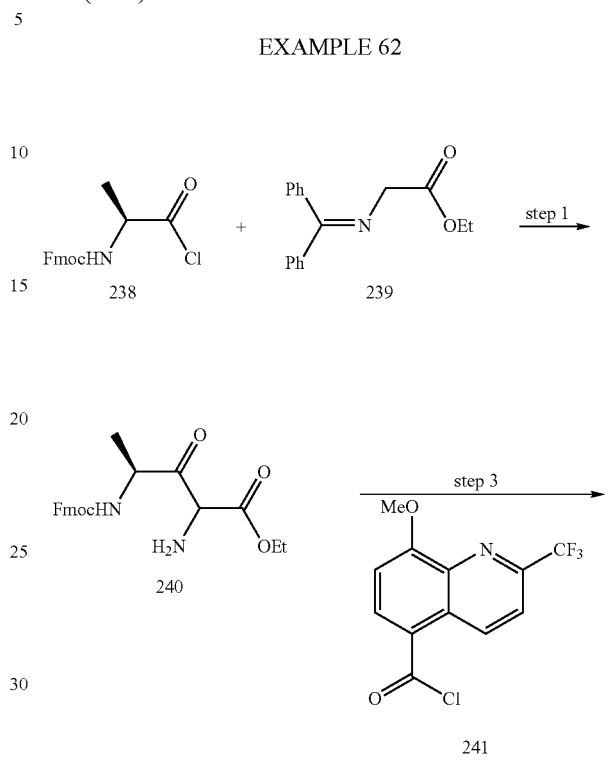

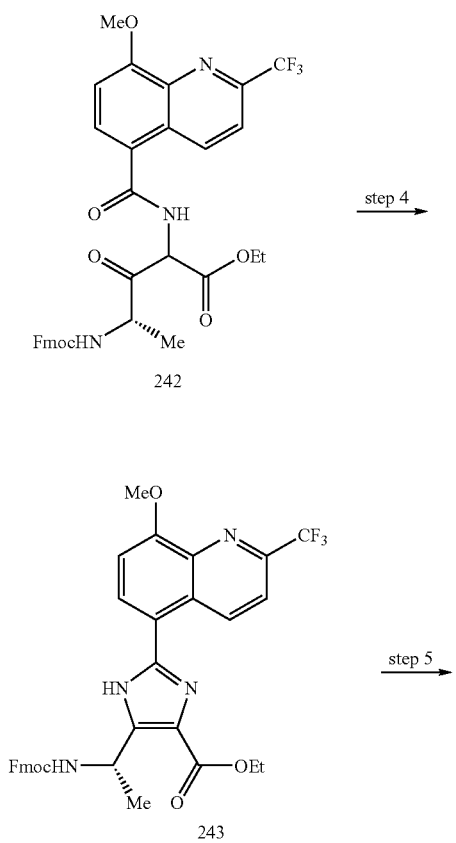

Step 1: Starting aldehyde 230 (1.21 g, 2.79 mmol), t-(R)-butanesulfinylamide (400 mg, 3.30 mmol), and titanium ethoxide (5.6 ml, 27 mmol) were mixed in dry THF (40 ml), degassed, and refluxed under a N₂ atmosphere overnight. The reaction mixture was cooled to RT and poured into brine (40 ml) with vigorous stirring. The resulting mixture was filtered through celite. The filtrate was extracted with EtOAc. The combined organic extract was washed with brine, dried (MgSO₄), filtered, and concentrated. The residue was purified by silica gel chromatography (Biotage, 40S+, eluant: 1:3 EtOAc:hexane) to give the product 234 (1.05 g, 76%) as a yellow solid. MS (M+1): m/e 497.

Step 2: To a solution of compound 234 (0.60 g, 1.2 mmol) dissolved in dry THF (40 ml) under a N₂ atmosphere and cooled to −40° C. was added a solution of MeMgBr (3 M in Et₂O, 0.5 ml, 1.5 mmol) dropwise. The reaction mixture was stirred at −40° C. for 5 h and warmed up overnight. The mixture was diluted with EtOAc, poured into saturated NH₄Cl (aq) and filtered through celite. The aqueous layer was separated and extracted with CH₂Cl₂. The combined organic extract was washed with brine, dried (MgSO₄), filtered, and concentrated. The residue was purified by silica gel chromatography (Biotage, 40S+, eluant: 1:1 EtOAc:hexane) to give the separated isomer 235A (0.41 g, 66%) as a yellow solid MS (M+1): m/e 513, and isomer 235B (0.10 g, 16%) as a yellow solid MS: (M+1): m/e 513.

Step 3: Using the procedure of step 1 from Example 32, the isomers 236A (from 235A) and 236B (from 235B) were synthesized. MS (M+1): m/e 485.

Step 4 and Step 5: Using the procedure of step 2 from Example 32 and then step 3 from Example 31, the compounds 237A (from 236A) and 237B (from 236B) were synthesized. MS (M+1): m/e 472.

EXAMPLE 62

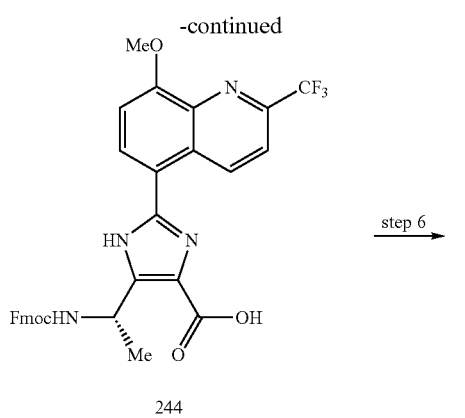

244

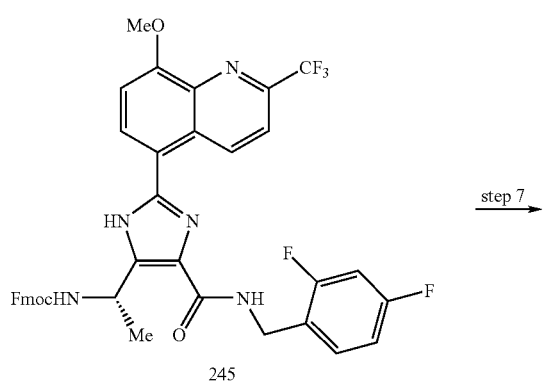

245

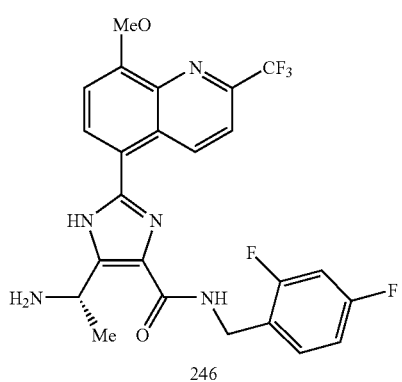

246

Step 1: Solid t-BuOK (2.20 g, 20 mmol) was dissolved in dry THF (50 ml) and cooled to −78° C. Compound 239 (5.34 g, 20 mmol) dissolved in dry THF (20 ml) was added while the reaction mixture was maintained at −78° C. After stirring at −78° C. for 30 min, the solution was cannulated into a vigorously stirred solution of compound 238 (20 mmol) dissolved in dry THF (50 ml) and also cooled to −78° C. The reaction mixture was stirred at −78° C. for 30 min, then 3 N aqueous HCl solution (50 ml) was added, and the reaction mixture was stirred at RT for 1 h. The resulting mixture was concentrated, and the aqueous solution was washed with Et$_2$O (2×75 ml). The aqueous solution was concentrated by co-evaporation with toluene at temperature <40° C. The residue was dried under vacuum overnight, then suspended in MeOH (500 ml) and stirred at RT. The insoluble salt was removed by filtration. The filtrate was concentrated, and dried in a vacuum oven at 50° C. overnight to give the product 240 (6.6 g, 76%, HCl salt) as a solid. MS (M+1): m/e 397.

Step 2: To a solution of compound 241 (10 mmol) dissolved in dry THF (60 ml) and cooled to −78° C. was added compound 240 (4.3 g, 10 mmol) dissolved in dry DMF (30 ml) and then Et$_3$N (2.7 ml, 20 mmol). The reaction mixture was stirred at RT for 3 days. The resulting mixture was concentrated and the residue was dissolved in EtOAc/Et$_2$O. The organic solution was washed with 1 N HCl, 10% NaHCO$_3$, and brine, dried (Na$_2$SO$_4$), filtered, and concentrated. Purification by silica gel chromatography gave 242 (4.2 g, 65%) as pale solid. MS (M+1): m/e 650.

Step 3: Compound 242 (2.0 g, 3 mmol) was dissolved in dry p-xylene (60 ml) and 7 N NH$_3$/MeOH (2 ml) and TFA (2.2 ml) was added. The reaction mixture was heated at 150° C. for 2 h and then 0.5 N NH$_3$/dioxane (15 ml) and AcOH (2 ml) were added. The resulting mixture was heated at 160° C. with azeotropic removal of water overnight, cooled to RT, and concentrated. Purification by silica gel chromatography (20% EtOAc in CH$_2$Cl$_2$) gave the product 243 (0.51 g, 27%) as a light-yellow solid. MS (M+1): m/e 631.

Step 4: Compound 243 (0.46 g, 0.73 mmol) was dissolved in AcOH (20 ml) and concentrated HCl (10 ml) and was heated to reflux for 24 h. The resulting mixture was concentrated and water (50 ml) was added. The precipitate was collected by filtration, washed with water, and dried in a vacuum oven at 50° C. overnight, to give the product 244 (0.41 g, 93%). MS (M+1): m/e 603.

Step 5: To a solution of compound 244 (0.12 g, 0.2 mmol) dissolved in dry DMF (0.5 ml) and CH$_2$Cl$_2$ (3 ml) was added 2,4-difluorobenzylamine (0.05 ml, 0.4 mmol), DIPEA (0.07 ml, 0.4 mmol), and HATU (0.114 g, 0.3 mmol). The resulting mixture was stirred at RT overnight and then concentrated. The residue was dissolved in DMF (2 ml) and purified by Gilson reverse phase prep HPLC to give the product 245 (0.081 g, 56%). MS (M+1): m/e 728.

Step 6: Compound 245 (0.080 g, 0.11 mmol) was dissolved in Et$_2$NH (2 ml) and CH$_3$CN (2 ml) and stirred at RT for 30 min. The resulting mixture was concentrated, and the residue was purified by Gilson reverse phase prep HPLC. The product was treated with HCl in ether, then dried in a vacuum oven at 50° C. overnight to give the product 246 (0.052 g, 94%) as a di-HCl salt. MS (M+1): m/e 506.

EXAMPLE 63

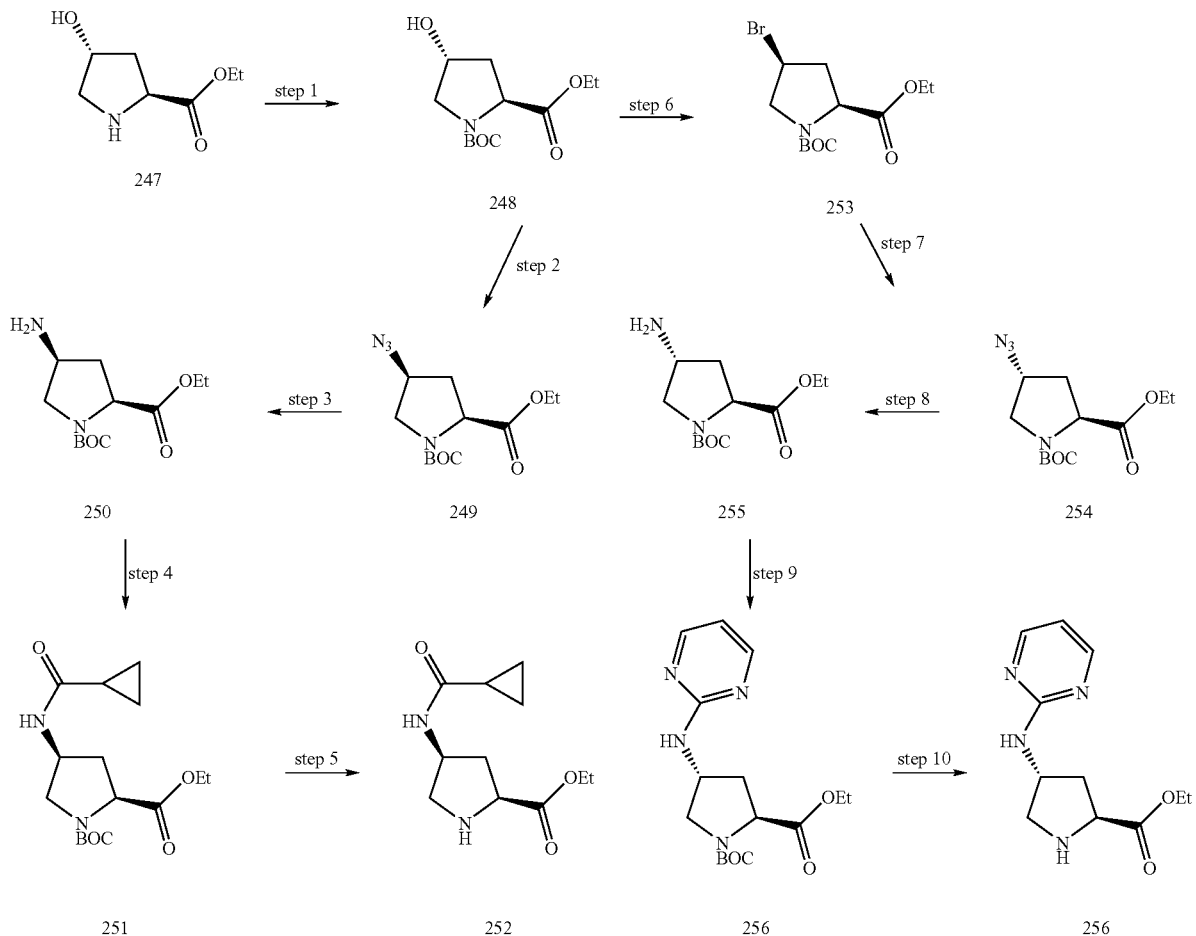

Step 1: To a solution of compound 247 (38 g, 0.19 mol) dissolved in CH₂Cl₂ (450 ml) and cooled to 0° C. was added Et₃N (35 ml, 0.25 mol) and t-Boc anhydride (54 g, 0.25 mol). The reaction mixture was stirred at RT overnight. The resulting mixture was diluted with CH₂Cl₂, washed with 1 N HCl solution, dried (Na₂SO₄), filtered, and concentrated. Purification by silica gel chromatography gave the product 248 (47 g, 96%). MS (M+1): m/e 260.

Step 2: To a solution of compound 248 (1.55 g, 6 mmol) dissolved in dry THF (60 ml) and cooled to 0° C. was added triphenylphosphine (2.0 g, 7.8 mmol), diethyl azodicarboxylate (1.3 ml, 7.8 mmol) dropwise, and then diphenylphosphoryl azide (1.7 ml, 7.8 mmol). The reaction mixture was stirred at RT overnight, then diluted with ether. The organic solution was washed with saturated NaHCO₃ and brine, dried (Na₂SO₄), filtered, and concentrated. Purification by silica gel chromatography (eluant: 15-20% EtOAc in hexane) gave compound 249 (1.7 g, 100%). MS (M+1): m/e 285.

Step 3: To a solution of compound 249 (0.5 g, 1.76 mmol) dissolved in THF (40 ml) was added 10% Pd/C catalyst (0.25 g). The reaction mixture was stirred under H₂ (1 atm) at RT overnight. The resulting mixture was filtered, and the filtrate was concentrated to give the product 250 (0.45 g, 100%). MS (M+1): m/e 259.

Step 4 and 5: To a solution of compound 250 (0.13 g, 0.5 mmol) dissolved in CH₂Cl₂ (1 ml) was added DIPEA (0.2 ml) and cyclopropanecarbonyl chloride (0.053 ml, 0.5 mmol). The reaction mixture was stirred at RT for 2 h. The resulting mixture was diluted with EtOAc. The organic solution was washed with 1 N HCl, saturated NaHCO₃, and brine, dried, filtered, and concentrated. Purification by silica gel chromatography gave the product 251. Compound 251 was treated with 4 N HCl in dioxane at RT for 4 h. The resulting mixture was concentrated, and the residue was dried under vacuum for 2 days to give the product 252 as the HCl salt (0.1 g, 76%). MS (M+1): m/e 227.

Step 6: To a solution of compound 248 (3.1 g, 12 mmol) dissolved in dry THF (100 ml) and cooled to 0° C. was added triphenylphosphine (4.0 g, 15 mmol), DEAD (2.5 ml, 15 mmol) dropwise, and LiBr (5 g, 57 mmol). Within 2 min, all the LiBr dissolved. The resulting clear yellow solution was stirred at RT overnight. The reaction mixture was diluted with EtOAc, washed with water, dried (Na₂SO₄), filtered, and concentrated. Purification by silica gel chromatography gave the product 253 (2.15 g, 56%). MS (M+1): m/e 323.

Step 7: To a solution of compound 253 (2.1 g, 6.5 mmol) dissolved in DMSO (15 ml) was added NaN₃ (0.46 g, 7 mmol). The resulting mixture was stirred at RT for 2 days. Water was added to the mixture and product was extracted with ether (3×40 ml). The combined organic layer was washed with brine, dried ($Na_2SO_4$), filtered, and concentrated to give the product 254.

Step 8: Using the procedure of step 3, compound 255 was synthesized. MS (M+1): m/e 259.

Step 9: To a solution of compound 255 (0.26 g, 1 mmol) dissolved in DMF (2 ml) was added $Et_3N$ (0.28 ml, 2 mmol) and 2-bromopyrimidine (0.16 g, 1 mmol). The reaction mixture was heated at 100° C. overnight then cooled to RT. The resulting mixture was diluted with DMSO (3 ml) and purification by reverse phase Gilson prep HPLC gave the product 256 (0.18 g, 54%). MS (M+1): m/e 337.

Step 10: Using the procedure of step 5, compound 257 was synthesized. MS (M+1): m/e 237.

EXAMPLE 64

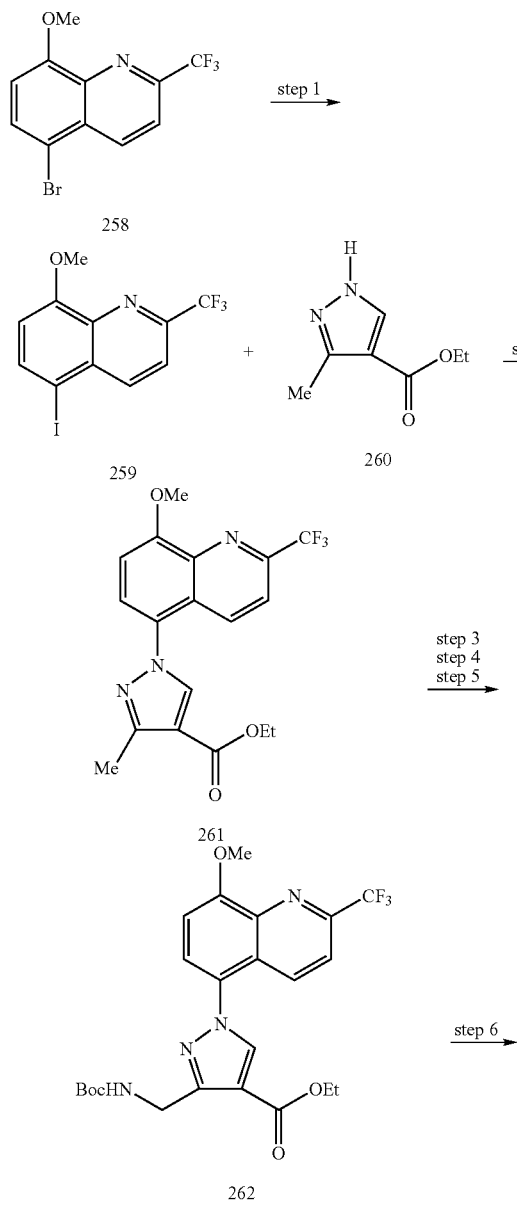

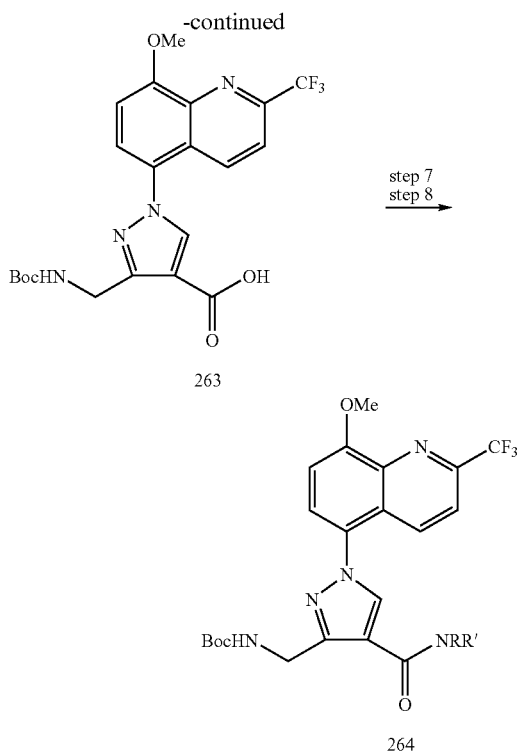

Step 1: Compound 258 (4.14 g, 13.6 mmol), CuI (288 mg, 0.37 mmol), NaI (4.32 g, 28.8 mmol), and sym-dimethylethylenediamine (0.38 ml, 0.72 mmol) were suspended in toluene (12 ml). The reaction mixture was heated in a sealed tube at 125° C. for 48 h. The resulting mixture was cooled to RT and filtered through celite. The filtrate was concentrated, and the residue was purified by silica gel chromatography (eluant: 1:10 EtOAc:hexane) to give the product 259 (4.06 g, 85%) as a beige liquid. MS (M+1): m/e 354.

Step 2: Compound 259 (3.55 g, 10.0 mmol), pyrazole 260 (2.31 g, 15 mmol), trans-1,2-di(methylamine)cyclohexane (450 mg, 3.17 mmol), CuI (190 mg, 1.0 mmol), and $K_2CO_3$ (4.14 g, 30 mmol) were suspended in toluene (40 ml). The reaction mixture was heated in a sealed tube at 125° C. for 10 days. The resulting mixture was cooled to RT and filtered through celite. The filtrate was concentrated and the residue was purified by silica gel chromatography (eluant: 1:1 EtOAc:hexane) to give the starting compound 259 (2.1 g, 46%) and the product 261 (1.29 g, 45%) as a white solid. MS (M+1): m/e 380.

Steps 3, 4, and 5: Using procedures similar to that of step 1 from Example 2, step 3 from Example 55, and step 4 from Example 55, intermediate 262 was synthesized. MS (M+1): m/e 495.

Step 6: Using a procedure similar to that of step 1 from Example 32, compound 263 was synthesized. MS (M+1): m/e 467.

Steps 7 and 8: Using procedures similar to that of step 2 from Example 32 and step 3 from Example 31, the following compounds were synthesized.

| Number | Compound | MS |
|---|---|---|
| 264A | MeO-quinoline-CF3 with pyrazole-CH2NH2, C(O)NH-CH2-(2,4-difluorophenyl) | 492 |
| 264B | MeO-quinoline-CF3 with pyrazole-CH2NH2, C(O)NH-CH2-(1-naphthyl) | 506 |

EXAMPLE 65

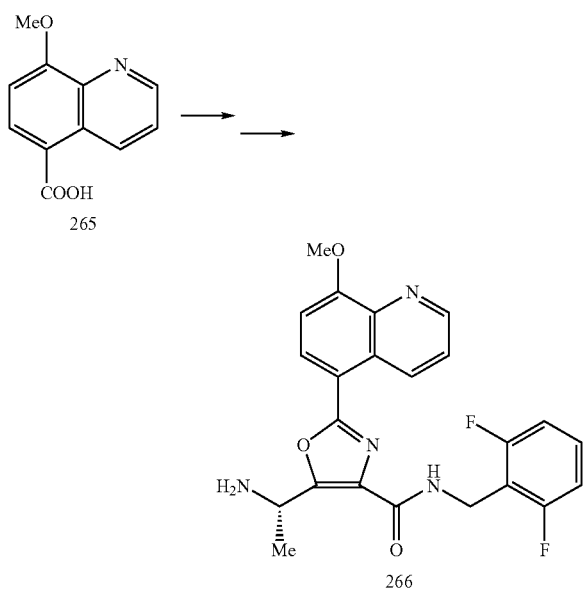

Using procedures from Examples 5 and 6, compound 266 was synthesized. MS (M+1): m/e 439.

The pharmacological activity of the compounds of the invention was measured by the following assays.

PDE4 Screening Assay

1. Human PDE4 Enzyme

The neutrophils were isolated from human blood using a standard procedure, then homogenized with a glass-glass homogenizer in a buffer containing 20 mM Tris/HCl (pH 8.0), protease inhibitor cocktail tablet (Cat. No. 1836145/Boehringer Mannheim), 2 mM EDTA, 1% Triton X-100 and 0.5% deoxycholate. After stirring for 2 h at 4° C., the samples were centrifuged at 100,000 g for 1 h. The supernatants were collected, filtered and applied to Mono Q column chromatography. The fractions containing the activity of hydrolyzing cAMP were determined and pooled as the enzymatic source of the PDE4 screening assay.

2. PDE4 Assay and Compound Screening

The PDE4 assays were performed using Phosphodiesterase [$^3$H]cAMP SPA enzyme assay kits and its procedures (Cat. No. TRKQ 7090, Amersham). The assay procedures are described briefly as follows. The diluted PDE4 enzyme, 10× assay buffer and water were mixed at a ratio of 1:1:6 (10 µl/10 µl/60 µl). 80 µl aliquots of this mixture were added into the test wells of a 96-well Microlite plate (Cat. No. 7416, ThermoLabsystems). Enzyme dilution buffer, instead of the diluted enzyme, and water were added into the wells of negative control (background). 10 µl test compounds in 10% DMSO, standard inhibitor in 10% DMSO or 10% DMSO (for positive and negative controls) were added into the corresponding wells, respectively. After a 10 min incubation at RT, the reactions were initiated by addition of 10 µl pre-diluted [$^3$H]cAMP into each well, then incubated at 30° C. for 30 min. The reactions were stopped by addition of 50 µl SPA beads into the test wells, then counted in a β-counter over 30 min ~24 hr.

10× Assay Buffer: 500 mM Tris/HCl pH 7.5, 83 mM MgCl$_2$, 17 mM EGTA

[$^3$H]cAMP: [3H] cAMP (40-60 Ci/mmol) is diluted at a 1:200 ratio with water. The final concentration is 0.005 µCi/µl Yttrium SPA Beads: 500 mg of beads was reconstituted with 28 ml of water, stored at 4° C.

PDE10 and 11 Screening Assay

PDE10 (human recombinant PDE10A2, expressed in Sf9 insect cells by the baculovirus expression technique) was assayed using [$^3$H]cGMP PDE SPA Assay kit (Amersham) at a final concentration of cGMP of 0.7 µM. PDE11 (human recombinant PDE11A3, expressed in Sf9 insect cells by the baculovirus expression technique) was assayed using [$^3$H] cAMP PDE SPA Assay kit (Amersham) at a final concentration of cAMP of 0.0125 µM. Compounds were evaluated at 0.1-10,000 nM in 2% DMSO and 0.1% BSA from a stock solution of 4 mM in 100% DMSO. All assays were performed in duplicate, and each set of experiments was performed at least twice. Analysis of dose-response data and calculation of IC$_{50}$ values were performed using GraphPad Prism.

PBMC (Peripheral Blood Mononuclear Cell) Preparation and TNF Inhibition Assay

This protocol was modified from Prabhaker et al. (Int. J. Immunopharmac, Vol 16, No 10 pp 805-816, 1994. Smithkline Beecham Pharmaceuticals).

1. Human blood was collected from internal donors. The plasma was separated from red blood cells by mixing with 6% dextran (4 ml for a 15-ml blood) and a 40 min-incubation at 37° C.

2. 10 ml plasma was then layered on 9 ml Ficoll-paque (Cat. No. 17-1440-03, Amersham) in a centrifuge tube.
3. After a centrifugation at 1500 rpm for 45 min, PBMC was removed from the interface.
4. PBMC was washed twice with PBS and counted.
5. PBMC was suspended in RPMI medium containing 2.5% heat-inactivated FCS (Hyclone laboratories Inc. Logan, Utah, USA), Penicillin and streptomycin, and the cell volume was adjusted to $1 \times 10^6$ cell/ml.
6. 0.5 ml cells were transferred into each well of a 24 well plate.
7. After one hour incubation at 37° C., the cells were pre-treated for 1 h with 5 µl 10% DMSO (control) and 5 µl test compounds at various concentrations (100 fold stock solutions in 10% DMSO).
8. LPS was added to stimulate TNF production at a final concentration of 100 ng/ml (*E. coli* 055:13S, SIGMA).
9. The cells were stimulated for 14-16 h at 37° C.
10. The supernatants were removed and transferred to new tubes. TNF alpha levels were assayed by ELISA using Human TNF-α ELISA kit (Cat. No. KHC3012, Biosource) and its procedures with an optimal dilution. (1:10→1:100 dilution).

In vivo TNFα Assay

C57Bl/6 mice were injected with 25 ug of LPS (LPS O55-B5, Sigma: L2880) by the intraperitoneal route. One hour prior to injection of the LPS, mice were treated orally with the PDE4 compounds at the selected doses. Ninety min after the LPS challenge, the mice were euthanized, and blood was collected through a heparinized syringe tip into Capijet T-MGA tubes. The blood was centrifuged for 10 min in a microcentrifuge at maximum speed (~13,000 rpm), and the serum was collected and analyzed for TNFα protein using an R&D ELISA kit.

Lipopolysaccharide (LPS) in vivo Assay

Male Sprague/Dawley rats (200-250 g) were purchased from Charles River Laboratories. Prior to use, the animals were permitted unrestricted access to food and water. Test compounds were delivered by gavage 5 hours prior to LPS-challenge. Compounds were suspended in a 0.4% methylcellulose vehicle with the same vehicle being given to control animals.

LPS-treatment: Animals were anethesized by inhalation of isoflurane, supplemented with oxygen (flow rate 1.0 ml/min). Once anesthetized, animals were placed supine and the trachea visualized using a small laryngoscope. Animals then received either 0.1 ml of saline or 0.1 ml of a 100 µg/ml lipopolysaccharide solution (LPS; *E. coli*) in saline by use of a Penn-Century Microspray needle (Penn-Century, Philadelphia, Pa.). Animals were allowed to recover on a heat pad, returned to housing and permitted access to food and water ad libitium. Sixteen hours after LPS-challenge, animals were anesthetized with an intra-peritoneal injection of the combination of ketamine/xylazine (10:1, 200 mg/kg ketamine, 20 mg/kg xylazine). After reaching anesthesia, animals were surgically prepared for bronchial lavage by inserting a tracheal cannula. Animals were lavaged with 2×2 ml of phosphate buffered saline, pH 7.2 (PBS). Routine recovery of BAL fluids did not significantly differ between animals with >80% of instilled volume recovered. Afterwards, animals were euthanized by surgically opening the thoracic cavity and cutting the diaphragm to assure lung collapse. Bronchial lavage (BAL) fluid was analyzed for cellular contents as described below.

BAL samples: Bronchial lavage (BAL) fluid was spun at 350×g for 10 min at 4° C. One ml of supernatant was removed and stored at −20° C. until analyzed for cytokine levels. Remaining fluid was aspirated and the cell pellet lysed for residual erythrocytes and resuspended in PBS, pH 7.2 containing 10 ug/ml of DNase I. Afterwards, the cell suspension was centrifuged at 350×g for 10 mins at 4° C., the supernatant aspirated and the cell pellet resuspended in 1 ml of PBS with 10 ug/ml DNase 1 and 5% heat inactivated fetal bovine serum. Cytospin slide preparations were made and stained with Hema3™ staining system (Fisher Scientific, Springfield N.J.). Differential cell counts were performed using standard histological parameters and at least 200 cells were enumerated. Total cell counts were performed using a Neubauer chamber.

Assay Procedure for Testing of Dermatitis in Dogs:

Five dogs are selected for each treatment group. Administration of experimental medications begins and continues through the end of the animal phase of the experiment. After three days, all dogs are sedated using medetomadine intravenously. An approximately 5 cm by 13 cm area is shaved on the lateral thorax of each dog. 1 cc of lidocaine is injected subcutaneously, and then two 8 mm punch biopsies are taken to act as Time 0 controls. Biopsy sites are closed with simple interrupted sutures of 3-0 Nylon suture.

Ten intradermal injections are given (five rows of two injections)—two injections are of phosphate buffered saline (PBS), and the remaining eight injections are of rabbit IgG antibody to dog IgE. Each injection is 0.05 ml. The total dose of anti-IgE per injection is 7 µg, as previously determined to be optimal. After injection, sites are observed and sampled. After injection and between all future samples, all dogs wear a protective garment (Quick Cover incision cover, Four Flags over Aspen) to prevent disturbance of the injection and/or biopsy sites.

The test compounds are compounds of formula I; the negative control is phosphate buffered saline (PBS); the positive control is commercially available prednisone tablets. Tablets are given orally by placement in the back of the mouth. Liquids are given by syringe to place the test article toward the back of the mouth. The dog's mouth may be held closed to ensure that all of the test article is swallowed. Plasma samples are analyzed for the concentration of test compound from the dogs treated with the active compounds. Samples from the negative control and prednisone treated dogs need not be analyzed.

Anti-IgE Site Observations: Sites of anti-IgE injection are examined and evaluated for erythema and wheal formation. At the 20 min observation time, the two PBS sites and the two 6 hr. biopsy sites are measured. At the other post-injection times, the two PBS sites and the corresponding biopsy sites are measured. If the size of the reaction is not consistent across sites in the same dog, then all sites that have not been previously biopsied will be measured. Wheals will be measured by calipers in two orthogonal dimensions as well as measured for thickness.

Collection of Skin Samples: Two 8 mm punch biopsies are taken of the sites injected with anti-IgE. One biopsy is placed in RNA isolation buffer and the other biopsy is bisected. One half goes into a standard 10% formalin solution for routine histopathological analysis and the other is deposited in Optimal Cutting Temperature Medium and quick frozen in liquid nitrogen, then maintained at −70° C. for immunohistochemical staining with Luna's stain for eosinophils, and Alcian Blue with Nuclear Fast Red counterstain for mast cells. Using manual or computerized morphometric analysis, the extent of infiltration by the following specific leukocytes is quantitated: CD 1a+c, IgE, CD3, 4+8, TCR alpha/beta and gamma/ delta, TNF alpha, and TSLP. Cytokine analysis is to determine the presence of the following: TNF alpha, IL4, IL13, IL2, IFN gamma, and Thymic stromal lymphopoietin.

Allergic Brown Norway (BN) Rat Model:

Inbred male BN rats weighing 150 to 200 g were obtained from Charles River Laboratory (Wilmington, Mass.). Prior to use, the animals were allowed food and water ad libitum. The test compounds were administered 5 h prior to antigen challenge either by oral or inhalational route, as detailed in the "delivery of test compounds" section.

Sensitization and Antigen Bronchoprovocation

The animals were divided into two main groups viz. an alum group and an antigen group. In the antigen group, animals were sensitized by an intra-peritoneal (i.p.) injection of 1 ml alum-precipitated antigen containing 20 µg of ovalbumin (OVA, grade III; Sigma chemical Co., St Louis, Mo.) and 8 mg of $Al(OH)_3$ suspended in 0.9% saline vehicle. A booster injection of this alum-OVA mixture was given again 7 days later. Animals belonging to the alum group received injections containing alum only. Seven days after the second injection, animals were exposed to aerosolized antigen bronchoprovocation which was performed by placing the rats in an enclosed plexiglass chamber (21 liters) and exposing the rats to aerosolized OVA (1%) for 30 min. The aerosolized OVA was produced by an ultrasonic nebulizer (DeVilbiss, Somerset, Pa., USA; Model Ultra-Neb 99) at a flow rate of approximately 8 liters/min. Twenty four hours after aerosolized OVA challenge, the animals were euthanized with an overdose of pentobarbital sodium. The trachea was exteriorized and intubated, and the lungs were lavaged with two aliquots of 3 ml of physiological saline. The bronchoalveolar lavage fluid (BALF) thus collected was subjected to cell enumeration. Ten microliter of the BALF was utilized to manually enumerate the total white cells using a hemocytometer. One hundred microliter of BALF was used to prepare cytocentrifuge which was stained with Hema3™ staining system (Fisher Scientific, Springfield, N.J.) to identify and enumerate differential white blood cells such as eosinophils, neutrophils, mononuclear cells and epithelial cells. A total of 200 cells were enumerated from each cytocentrifuge. The ability of the compound to inhibit recruitment of inflammatory cells into the airways is reported.

Delivery of Test Compounds:

Oral administration: the compounds were dissolved in 0.4% methylcellulose and delivered to animals orally @ 3 ml/kg. An equivalent volume of 0.4% methylcellulose was given to both negative (alum group) and positive (antigen) control groups.

Intra-tracheal administration: the appropriate dose of the compound was mixed with lactose powder to achieve a final amount of 3 mg, which was delivered intra-tracheally to anesthetized animals. Animals were held in an upright position for 3-4 min and were allowed to recover from anesthesia before returning to their cages.

Using the procedures described above in the PDE 4, PDE10 and PDE11 screening assays, compounds of formula I were found to have $IC_{50}$ values for PDE4 in a range of 0.01 to 500 nM, with preferred compounds having a range of 0.01 to 100 nM, more preferably 0.01 to 10 nM, and most preferably 0.01 to 3 nM. Compounds of formula I are preferably selective PDE4 inhibitors compared to PDE10 and PDE11: preferably the $IC_{50}$ values for PDE10 and PDE 11 are 100 to 300 times the values for PDE4.

Representative compounds of formula I have the following $IC_{50}$ values for PDE4:

| Compound No. | $IC_{50}$ (nM) |
|---|---|
| 13-106 | 0.14 |
| 26-42 | 0.07 |
| 26-92 | 0.01 |
| 26-177 | 3 |
| 26-241 | 0.2 |
| 26-293 | 0.5 |
| 26-417 | 1.4 |
| 26-444 | 0.03 |
| 38-3 | 1.8 |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally or via inhalation.

Preferably, the pharmaceutical preparation is in unit dosage form. In such form, the preparation is subdivided into unit doses containing appropriate quantities of the active component, e.g., an effective amount to achieve the desired purpose.

The quantity of active compound of formula I in a unit dose of preparation may be varied or adjusted from about 0.1 mg to 1000 mg, more preferably from about 1 mg to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen for compounds of formula I is oral administration of from 10 mg to 2000 mg/day preferably 10 to 1000 mg/day, in two to four divided doses to provide relief from allergic and inflammatory diseases or the other disease or conditions listed above.

The doses and dosage regimen of the additional agents administered in the combinations of the invention will be determined by the attending clinician in view of the approved doses and dosage regimen in the literature, e.g., the package insert, taking into consideration the age, sex and condition of the patient and the severity of the disease.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound represented by the structural formula

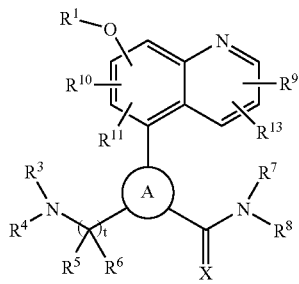

I or a pharmaceutically acceptable salt thereof, wherein

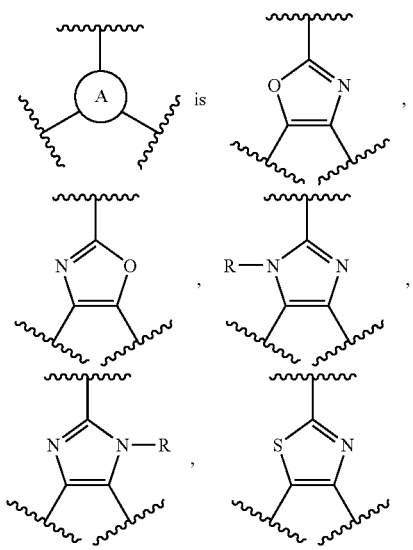

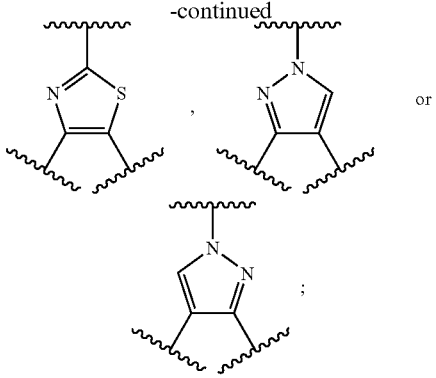

R is H or alkyl;

X is O or S;

$R^1$ is H, alkyl, cycloalkyl, cycloalkyl($C_1$-$C_4$)alkyl-, —$CH_2F$, —$CHF_2$, —$CF_3$, —C(O)alkyl or —C(O)NR$^{18}$R$^{19}$;

$R^3$ and $R^4$ are independently selected from the group consisting of H, alkyl, hydroxyalkyl and —C(O)Oalkyl;

$R^5$ and $R^6$ are independently selected from the group consisting of H, alkyl, hydroxyalkyl, alkoxyalkyl, mercaptoalkyl, —$CH_2F$, —$CHF_2$, —$CF_3$, —C(O)OH, —C(O)Oalkyl and —C(O)NR$^{43}$R$^{44}$;

t is 1 or 2;

$R^7$ is H, alkyl, alkenyl, hydroxyalkyl, cycloalkyl, alkoxyalkyl, aminoalkyl, ($R^{17}$-phenyl)alkyl or —$CH_2$—C(O)—O-alkyl;

$R^8$ is H, alkyl, alkenyl, alkoxy, alkoxyalkyl, hydroxyalkyl, dihydroxyalkyl, alkyl-NR$^{18}$R$^{19}$, cyanoalkyl, haloalkyl, R$^{23}$-heteroaryl, R$^{23}$-heteroarylalkyl, R$^{36}$-heterocycloalkyl, (R$^{36}$-heterocycloalkyl)alkyl, R$^{17}$-phenyl, (R$^{17}$-phenyl)alkyl, R$^{17}$-naphthyl, (R$^{17}$-naphthyl)alkyl, R$^{17}$-benzyloxy, -alkyl-C(O)—NR$^{18}$R$^{19}$, -alkyl-C(O)—N(R$^{30}$)—(R$^{23}$-heteroaryl), -alkyl-C(O)—(R$^{17}$-phenyl), -alkyl-C(O)—(R$^{36}$-heterocycloalkyl); -alkyl-N(R$^{30}$)—C(O)Oalkyl, -alkyl-N(R$^{30}$)—C(O)—NR$^{18}$R$^{19}$, -alkyl-N(R$^{30}$)—C(O)alkyl, -alkyl-N(R$^{30}$)—C(O)-(fluoroalkyl), -alkyl-N(R$^{30}$)—C(O)—(R$^{39}$-cycloalkyl), -alkyl-N(R$^{30}$)—C(O)—(R$^{17}$-phenyl), -alkyl-N(R$^{30}$)—C(O)—(R$^{23}$-heteroaryl), -alkyl-N(R$^{30}$)—C(O)-alkylene-(R$^{23}$-heteroaryl), -alkyl-NH—SO$_2$—NR$^{18}$R$^{19}$, -alkyl-N(R$^{30}$)—(R$^{17}$-phenyl), -alkyl-N(R$^{30}$)—(R$^{23}$-heteroaryl), -alkyl-O—(R$^{17}$-phenyl), -alkyl-O—(R$^{23}$-heteroaryl), -alkyl-N(R$^{30}$)—SO$_2$-alkyl, alkylthioalkyl, alkyl-SO$_2$-alkyl-, (R$^{35}$-phenylalkyl)-S-alkyl-, (hydroxyalkyl)-S-alkyl-, (alkoxyalkyl)-S-alkyl-, -alkyl-CO$_2$-alkyl, R$^{45}$-hydroxyalkyl, dihydroxyalkyl substituted by R$^{17}$-benzyloxy, dihydroxyalkyl substituted by R$^{17}$-phenyl, alkoxyalkyl substituted by R$^{17}$-phenyl, (R$^{17}$-phenyl)alkyl substituted by —CO$_2$alkyl, (R$^{17}$-phenyl)alkyl substituted by —C(O)N(R$^{30}$)$_2$, alkyl substituted by (R$^{23}$-heteroaryl) and —C(O)NR$^{37}$R$^{38}$, haloalkyl substituted by CO$_2$alkyl, R$^{12}$-cycloalkyl, (R$^{12}$-cycloalkyl)alkyl,

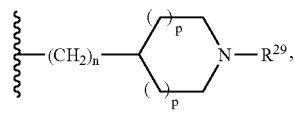

or $R^7$ and $R^8$ and the nitrogen to which they are attached together form a ring system selected from the group consisting of

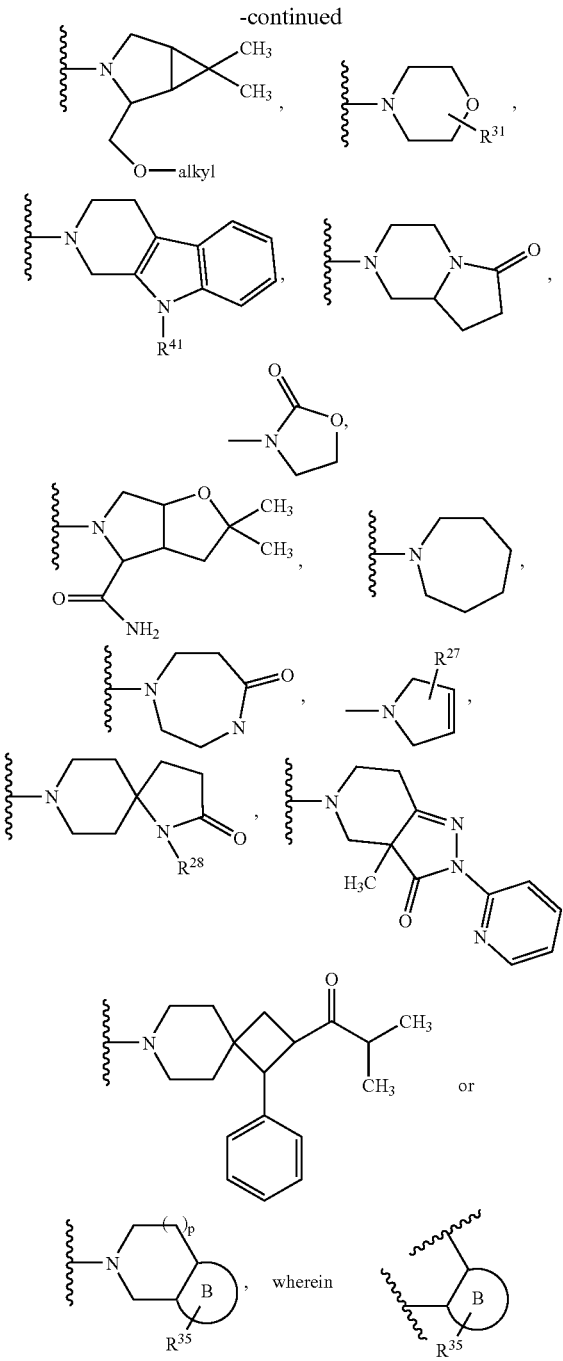

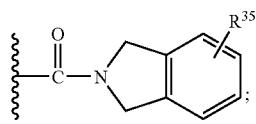

comprises an $R^{35}$-substituted 5 or 6-membered heteroaryl group fused to the piperidinyl or pyrrolidinyl ring;

p is 0 or 1;

q is 0 or 1;

the dotted line represents an optional double bond;

$R^9$ is H, halo, alkyl, cycloalkyl, —$CH_2F$, —$CHF_2$ or $CF_3$;

$R^{10}$, $R^{11}$, and $R^{13}$ are independently selected from the group consisting of H and halo;

$R^{12}$ is 1-3 substituents independently selected from the group consisting of H, alkyl, hydroxy, alkoxy, hydroxyalkyl, alkoxyalkyl, —C(O)Oalkyl, —$(CH_2)_n$—N$(R^{30})$—C(O)-cycloalkyl, —$(CH_2)_n$—N$(R^{30})$—C(O)alkyl, —$(CH_2)_n$—N$(R^{30})$C(O)Oalkyl, —$(CH_2)_n$—N$(R^{30})$—$(R^{23}$-heteroaryl), —$(CH_2)_n$—N$(R^{30})$—C(O)—NR$^{18}$R$^{19}$, —$(CH_2)_n$—C(O)—NR$^{18}$R$^{19}$, $R^{17}$-phenyl, $R^{35}$-heteroarylalkyl, $R^{35}$-heteroaryloxy, —C(O)-heterocycloalkyl, —O—C(O)-heterocycloalkyl, —O—C(O)—NR$^{18}$R$^{19}$, —NH—$SO_2$-alkyl, —NH—C(=NH)$NH_2$, and

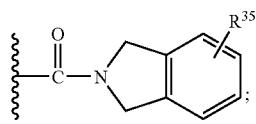

or two $R^{12}$ substituents on the same carbon form =O, =NOR$^{30}$ or =$CH_2$;

$R^{14}$ is 1 or 2 substituents independently selected from the group consisting of H, OH, halo, alkyl, alkoxy, hydroxyalkyl, alkoxyalkyl, —$CF_3$, CN, $R^{17}$-phenyl, ($R^{17}$-phenyl)alkyl, —NR$^{18}$R$^{19}$, alkyl-NR$^{18}$R$^{19}$, —$(CH_2)_n$—C(O)OH, —$(CH_2)_n$—C(O)Oalkyl, —$(CH_2)_n$—C(O)alkyl, —$(CH_2)_n$—C(O)($R^{35}$-phenyl), —$(CH_2)_n$—C(O)($R^{23}$-heteroaryl), —$(CH_2)_n$—C(O)NR$^{18}$R$^{19}$, ($CH_2)_n$—C(O)N($R^{30}$)—$(CH_2)_n$—($R^{23}$-heteroaryl), —$(CH_2)_n$—N($R^{30}$)—C(O)alkyl, —$(CH_2)_n$—N($R^{30}$)—C(O)-(fluoroalkyl), —$(CH_2)_n$—N($R^{30}$)—C(O)-(cycloalkyl), —$(CH_2)_n$—N($R^{30}$)—C(O)($R^{35}$-phenyl), —$(CH_2)_n$—N($R^{30}$)—C(O)($R^{23}$-heteroaryl), —$(CH_2)_n$—N($R^{30}$)C(O)NR$^{18}$R$^{19}$, —$(CH_2)_n$—N($R^{30}$)—C(O)Oalkyl, —$(CH_2)_n$—N($R^{30}$)cycloalkyl, —$(CH_2)_n$—N($R^{30}$)($R^{17}$-phenyl), —$(CH_2)_n$—N($R^{30}$)($R^{23}$-heteroaryl), —$(CH_2)_n$—N($R^{18}$)$SO_2$alkyl, —$(CH_2)_n$—N($R^{20}$)$SO_2$—($R^{17}$-phenyl), —$(CH_2)_n$—N($R^{30}$)$SO_2$—$CF_3$, —$CH_2S(O)_{0-2}$($R^{35}$-phenyl), —$(CH_2)_n$—OC(O)N($R^{30}$)alkyl, $R^{23}$-heteroaryl, ($R^{23}$-heteroaryl)alkyl, ($R^{23}$-heteroaryl)oxy, ($R^{23}$-heteroaryl)amino, —CH(OH)—($R^{17}$-phenyl), —CH(OH)—($R^{23}$-heteroaryl), —C(=NOR$^{30}$)—($R^{17}$-phenyl), —C(=NOR$^{30}$)—($R^{23}$-heteroaryl), morpholinyl, thiomorpholinyl,

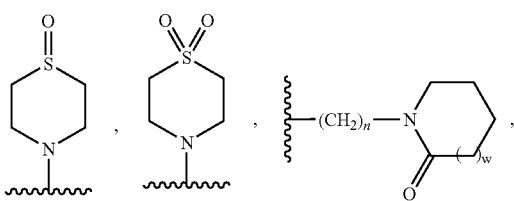

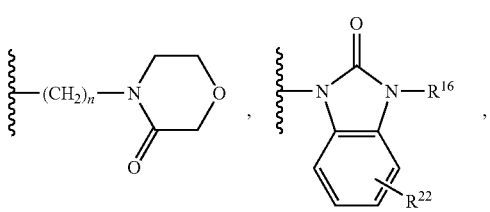

-continued

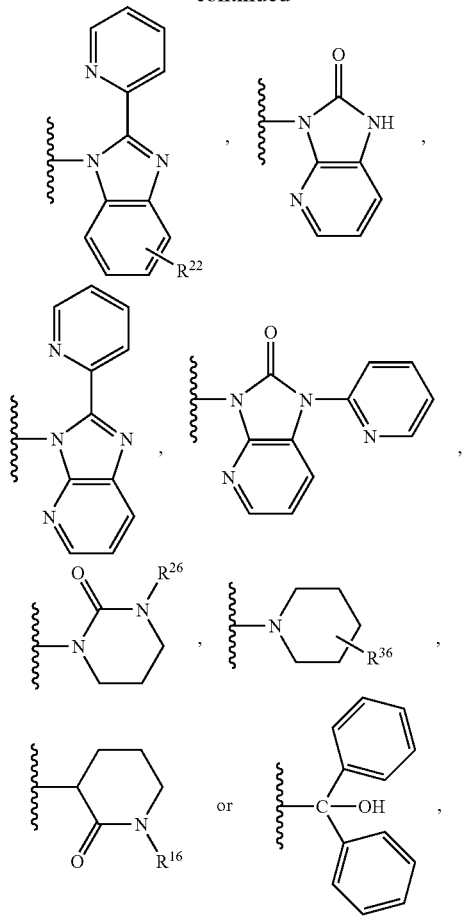

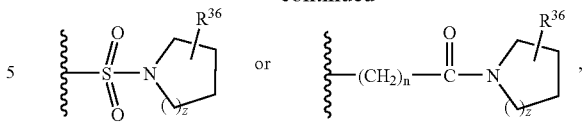

w is 0 or 1;

or two R¹⁴ substituents and the carbon to which they are both attached form —C(=NOR³⁰)— or —C(O)—;

each n is independently 0, 1, 2 or 3;

R¹⁵ is H, alkyl, cycloalkyl, (cycloalkyl)alkyl, hydroxyalkyl, alkoxyalkyl, haloalkyl, —C(O)Oalkyl, —C(O)O(R³⁰-cycloalkyl), -alkyl-C(O)O-alkyl, —C(O)O-alkylene-(R³⁵-phenyl), R¹⁷-phenyl, (R¹⁷-phenyl)alkyl, —CH—(R¹⁷-phenyl)₂, R²³-heteroaryl, —(CH₂)ₙ—C(O)NR¹⁸R¹⁹, —SO₂-alkyl, —SO₂-cycloalkyl, —SO₂—CF₃, —SO₂—(R³⁵-phenyl), —SO₂—NR¹⁸R¹⁹, —C(O)alkyl, —C(O)-(fluoroalkyl), —C(O)—C(CH₃)(CF₃)₂, —C(O)—(R¹⁷-phenyl), —C(O)—(R²³-heteroaryl), —C(O)-hydroxyalkyl, —C(O)alkoxyalkyl, —C(O)—(R³⁹-cycloalkyl), —C(O)-alkylene-(R¹⁷-phenyl), —C(O)-alkylene-R²³-heteroaryl), —C(O)-alkylene-S—C(O)alkyl, —C(=S)—(R¹⁷-phenyl), hydroxyalkyl substituted by R¹⁷-phenyl, hydroxyalkyl substituted by R²³-heteroaryl, alkoxyalkyl substituted by R¹⁷-phenyl, alkoxyalkyl substituted by R²³-heteroaryl,

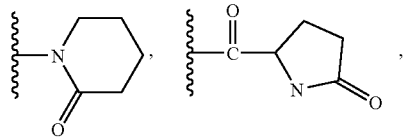

wherein z is 0, 1 or 2;

R¹⁶ is 1 to 4 substituents independently selected from the group consisting of H, alkyl, R¹⁷-phenyl, (R¹⁷-phenyl)alkyl, (R²³-heteroaryl)alkyl, hydroxyalkyl, alkoxyalkyl and —(O)Oalkyl, or two R¹⁶ groups and the carbon to which they are both attached form —C(O)—;

R¹⁷ is 1 to 3 substituents independently selected from the group consisting of H, halo, alkyl, cycloalkyl, —OH, hydroxyalkyl, alkoxy, alkoxyalkyl, —CN, —CF₃, —OCF₃, —OCHF₂, —OCH₂F, —C(O)OH, —C(O)Oalkyl, —C(O)O—(R³⁶-phenyl), —C(O)alkyl, —C(O)—(R³⁵-phenyl), —SOalkyl, —SO₂alkyl, —O₂—CF₃, alkylthio, —NR⁴³R⁴⁴, -alkyl-NR⁴³R⁴⁴, R³⁵-phenyl, R³⁵-phenoxy, R³⁵-heteroaryl, R³⁵-heteroaryloxy, R³⁶-heterocycloalkyl, —C(O)—(R³⁶-heterocycloalkyl), hydroxyalkyl-NH—, —C(O)N(R³⁰)₂, —N(R⁴³)—(R³⁵-cycloalkyl) and —C(=NOR³⁰); or two R¹⁷ substituents on adjacent carbon atoms together form —O—CH₂—O—, —O—(CH₂)₂—O—, —(CH₂)₂—O— or —O—CH₂—O—CH₂—;

R¹⁸ and R¹⁹ are independently selected from the group consisting of H, alkyl, hydroxyalkyl, alkoxyalkyl, haloalkyl, R¹⁷-phenyl, (R¹⁷-phenyl)alkyl, naphthyl and cycloalkyl;

R²⁰ is H, alkyl, or cycloalkyl;

R²² is 1 to 4 substituents independently selected from the group consisting of H, alkyl, hydroxy, alkoxy, halo, —CF₃, —NH₂ and R³⁵-phenyl;

R²³ is 1 to 4 substituents independently selected from the group consisting of H, alkyl, hydroxy, alkoxy, halo, —CF₃, —NR¹⁸R¹⁹, —CN, —C(O)Oalkyl, —SO₂-alkyl, —NHSO₂-alkyl, R³⁵-phenyl, R³⁵-heteroaryl, morpholinyl, and —(CH₂)ₙ—C(O)—N(R³⁰)₂;

R²⁴ is H, OH or alkoxy; or when the optional double bond is present, R²⁴ and the adjacent carbon atom form the double bond;

R²⁵ is H or R³⁵-phenyl;

R²⁷ is 1 to 3 substituents independently selected from the group consisting of H, halo, OH, alkyl, alkoxy, hydroxyalkyl, alkoxyalkyl, haloalkyl, —CN, —C(O)OH, —C(O)Oalkyl, —C(O)N(R³⁰)(R¹⁸), —C(O)—(R³⁶-hetercycloalkyl), R¹⁷-phenyl, (R¹⁷-phenyl)-alkyl, R²³-heteroaryl, (R²³-heteroaryl)alkyl, (R²³-heteroaryl)oxy, (R²³-heteroaryl)amino NR¹⁸R¹⁹, NR¹⁸R¹⁹-alkyl, —(CH₂)ₙ—N(R³⁰)—C(O)alkyl, —(CH₂)ₙ—N(R³⁰)—C(O)-(fluoroalkyl), —(CH₂)ₙ—N(R³⁰)—C(O)alkoxyalkyl, —(CH₂)ₙ—N(R³⁰)—C(O)(cycloalkyl), —(CH₂)ₙ—N(R³⁰)—(R²³-heteroaryl), —(CH₂)ₙ—N(R³⁰)—C(O)—(R²³-heteroaryl), —(CH₂)ₙ—N(R³⁰)—C(O)O-alkyl, —(CH₂)ₙ—N(R³⁰)—C(O)O—(CF₃alkyl), —(CH₂)ₙ—N(R³⁰)—C(O)O—(R³⁹-cycloalkyl), —(CH₂)ₙ—N(R³⁰)—C(O)O-alkylene-cycloalkyl, —(CH₂)ₙ—N(R³⁰)—C(O)—N(R³⁰)(R²⁰), —(CH₂)ₙ—N(R³⁰)—SO₂-alkyl, —(CH₂)ₙ—N(R³⁰)—SO₂—CF₃, —(CH₂)ₙ—N(R³⁰)—SO₂—N(R³⁰)₂ and

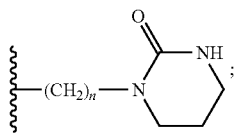

or two R$^{27}$ groups and the carbon to which they are both attached form —C(=NOR$^{30}$)— or —C(O)—;

R$^{28}$ is H, alkyl, R$^{35}$-benzyl or -alkyl-C(O)O-alkyl;

R$^{29}$ is alkyl, haloalkyl, —C(O)Oalkyl, —C(O)alkyl, —C(O)CF$_3$, —C(O)—(R$^{12}$-cycloalkyl), —C(O)—(R$^{17}$-phenyl), —C(O)—(R$^{23}$-heteroaryl), —C(O)—(R$^{36}$-hetercycloalkyl), —SO$_2$-alkyl, —SO$_2$—(R$^{35}$-phenyl), —C(O)NR$^{18}$R$^{19}$, R$^{35}$-phenyl, (R$^{35}$-phenyl)alkyl or R$^{23}$-heteroaryl;

R$^{30}$ is independently selected from the group consisting of H, alkyl, R$^{35}$-benzyl and R$^{35}$-phenyl;

R$^{31}$ is H, alkyl, R$^{36}$-benzyl or phenoxyalkyl;

R$^{33}$ is H, OH or alkoxy;

R$^{34}$ is H, alkyl, hydroxyalkyl, alkoxyalkyl or —C(O)Oalkyl;

R$^{35}$ is 1 to 3 substituents independently selected from the group consisting of H, halo, alkyl, OH, —CF$_3$, alkoxy, —CO$_2$alkyl and —N(R$^{43}$)(R$^{44}$);

R$^{36}$ is 1 or 2 substituents independently selected from the group consisting of H, alkyl, R$^{17}$-phenyl, —OH, hydroxyalkyl, alkoxyalkyl, —C(O)Oalkyl and —NR$^{18}$R$^{19}$; or two R$^{36}$ groups and the carbon to which they are both attached form —C(=NOR$^{30}$)— or —C(O)—;

R$^{37}$ and R$^{38}$ are independently selected from the group consisting of H and alkyl, or R$^{37}$ and R$^{38}$ together are —(CH$_2$)$_3$— or —(CH$_2$)$_4$—, and together with the nitrogen to which they are attached, form a ring;

R$^{39}$ is H, OH, alkyl, alkoxy, or CF$_3$;

R$^{40}$ is —OR$^{30}$ or —NHC(O)alkyl;

R$^{41}$ is H or —SO$_2$alkyl;

R$^{42}$ is —(CH$_2$)$_n$—(R$^{35}$-phenyl), —(CH$_2$)$_n$—(R$^{23}$-heteroaryl), —C(O)Oalkyl or —C(O)alkyl;

R$^{43}$ and R$^{44}$ are independently selected from the group consisting of H and alkyl; and R$^{45}$ is 1 or 2 substituents independently selected from the group consisting of halo, alkoxyalkyl, —CO$_2$alkyl, R$^{17}$-phenyl, R$^{23}$-heteroaryl and cycloalkyl.

2. A compound of claim 1 wherein X is O.

3. A compound of claim 2 wherein

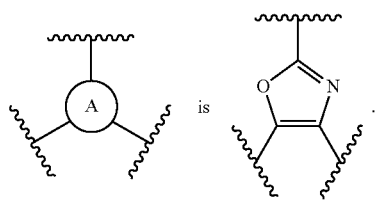

4. A compound of claim 3 wherein R$^{10}$, R$^{11}$ and R$^{13}$ are each H; R$^1$ is H, alkyl, cycloalkyl or —CF$_3$; and R$^9$ is H, alkyl or —CF$_3$.

5. A compound of claim 4 wherein R$^{10}$, R$^{11}$ and R$^{13}$ are each H, R$^1$ is alkyl, and R$^9$ is —CF$_3$.

6. A compound of claim 5 wherein t is 1, R$^5$ is H, R$^6$ is H, alkyl or hydroxyalkyl, and R$^3$ and R$^4$ are each H or alkyl.

7. A compound of claim 6 wherein R$^7$ is H, alkyl, cycloalkyl, hydroxyalkyl or alkoxyalkyl, and R$^8$ is R$^{12}$-cycloalkyl, (R$^{12}$-cycloalkyl)alkyl, R$^{45}$-hydroxyalkyl, R$^{17}$-phenyl, (R$^{17}$-phenyl)alkyl, R$^{23}$-heteroaryl, (R$^{23}$-heteroaryl)alkyl, -alkyl-N(R$^{30}$)—C(O)—NR$^{18}$R$^{19}$, -alkyl-N(R$^{30}$)—C(O)alkyl, -alkyl-N(R$^{30}$)—C(O)—(R$^{17}$-phenyl), -alkyl-N(R$^{30}$)—C(O)—(R$^{23}$-heteroaryl), -alkyl-N(R$^{30}$)—(R$^{23}$-heteroaryl),

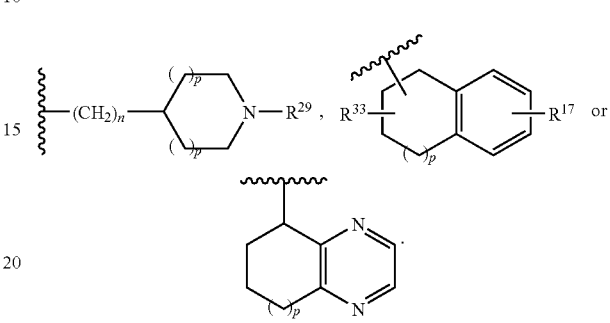

8. A compound of claim 7 wherein R$^8$ is R$^{12}$-cycloalkyl, R$^{45}$-hydroxyalkyl, (R$^{17}$-phenyl)alkyl, R$^{23}$-heteroaryl, (R$^{23}$-heteroaryl)alkyl, -alkyl-N(R$^{30}$)—(R$^{23}$-heteroaryl), -alkyl-N(R$^{30}$)—C(O)alkyl,

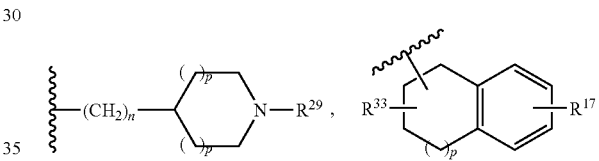

wherein p is 0, or

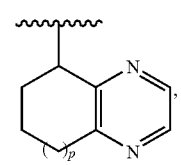

wherein p is 1.

9. A compound of claim 8 wherein R$^{12}$ is OH, —(CH$_2$)$_n$—N(R$^{30}$)—C(O)-cycloalkyl Or —(CH$_2$)$_n$—N(R$^{30}$)—(R$^{23}$-heteroaryl), R$^{45}$ is R$^{17}$-phenyl, or R$^{29}$ is heteroaryl, —C(O)alkyl or —C(O)cycloalkyl.

10. A compound of claim 6 wherein R$^7$ and R$^8$ and the nitrogen to which they are attached form

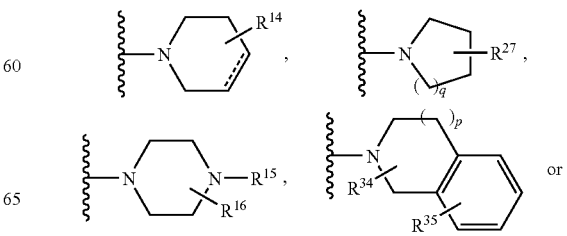

-continued

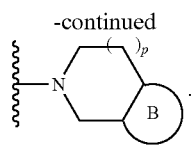

11. A compound of claim 10 wherein $R^7$ and $R^8$ form

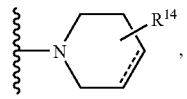

the optional double bond is not present, and $R^{14}$ is selected from the group consisting of H, OH, alkoxy, —$(CH_2)_n$—N$(R^{30})(R^{23}$-heteroaryl), $R^{23}$-heteroaryl and $(R^{23}$-heteroaryl)-alkyl; or wherein $R^7$ and $R^8$ form

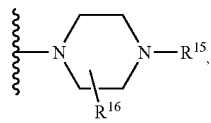

$R^{15}$ is selected from the group consisting of alkyl, $R^{17}$-phenyl, $R^{23}$-heteroaryl, —C(O)alkyl, —C(O)(fluoroalkyl), —C(O)—$(R^{23}$-heteroaryl), —C(O)-alkoxyalkyl, —C(O)—$(R^{38}$-cycloalkyl), —$SO_2$-alkyl, —$SO_2$—$NR^{18}R^{19}$ and

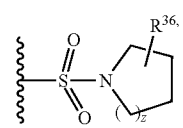

and $R^{16}$ is selected from the group consisting of H and alkyl, or two $R^{16}$ groups and the carbon to which they are attached form —C(O)—.

12. A compound of claim 10 wherein $R^7$ and $R^8$ form

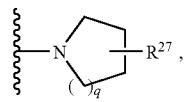

q is 1, and $R^{27}$ is 1, 2 or 3 substituents independently selected from the group consisting of H, OH, alkyl, alkoxy, alkoxyalkyl, $R^{17}$-phenyl, —C(O)OH, —C(O)Oalkyl, $R^{23}$-heteroaryl, $(R^{23}$-heteroaryl)amino and —$(CH_2)_n$—N$(R^{30})$—C(O)(cycloalkyl) wherein n is 0.

13. A compound of claim 10 wherein $R^7$ and $R^8$ form

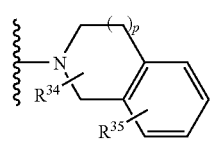

wherein p is 0, $R^{34}$ is H, and $R^{35}$ is 1 or 2 substituents independently selected from the group consisting of H, OH, halo and alkyl.

14. A compound of claim 10 wherein $R^7$ and $R^8$ form

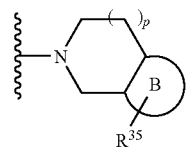

wherein p is 0, B is a pyrazolyl or thiazolyl ring, and $R^{35}$ is 1 or 2 substituents independently selected from the group consisting of H and alkyl.

15. A compound of claim 7 wherein $R^7$ is H or alkyl and $R^8$ is ($R^{17}$-phenyl)alkyl, $R^{45}$-hydroxyalkyl or -alkyl-N$(R^{30})$—($R^{23}$-heteroaryl), wherein $R^{45}$ is $R^{17}$-phenyl; heteroaryl is pyridinyl, pyrimidinyl, pyrazinyl, indolyl, benzothienyl or benzofuranyl; $R^{17}$ is 1 to 3 substituents independently selected from the group consisting of halogen, OH, alkoxy and alkyl; and $R^{23}$ is 1 or 2 substituents independently selected from the group consisting of H, alkyl, alkoxy and halogen.

16. A compound of claim 1 selected from the group consisting of

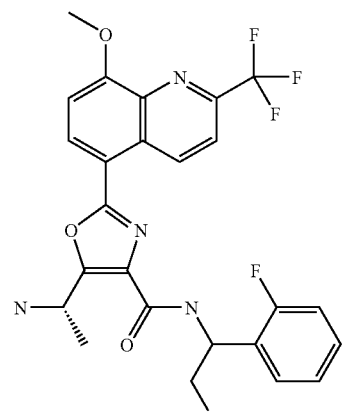

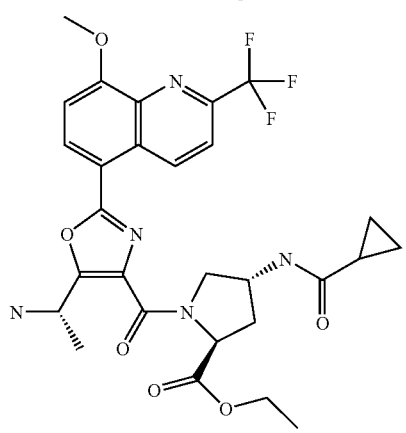

-continued

847
-continued
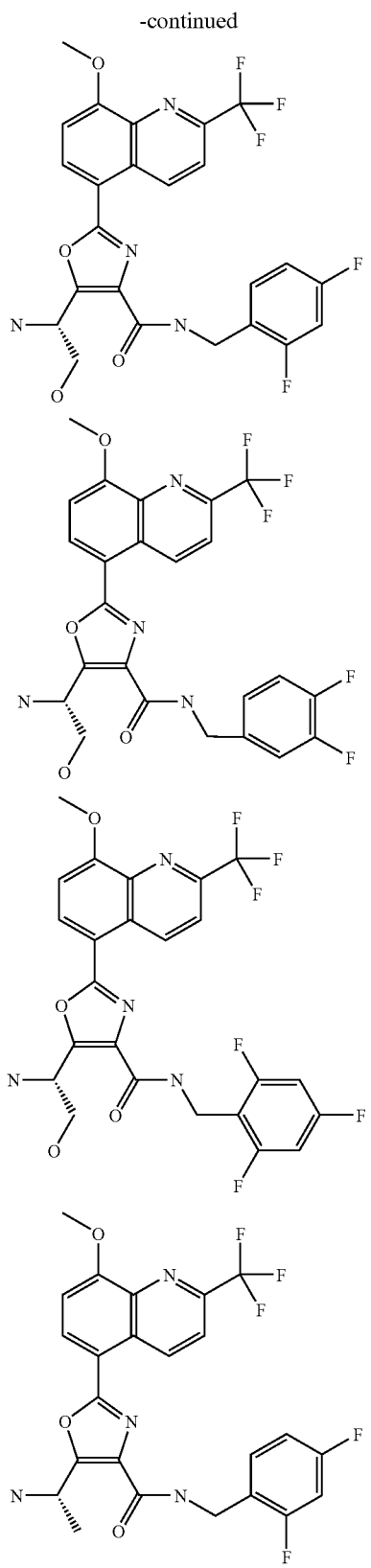
848
-continued
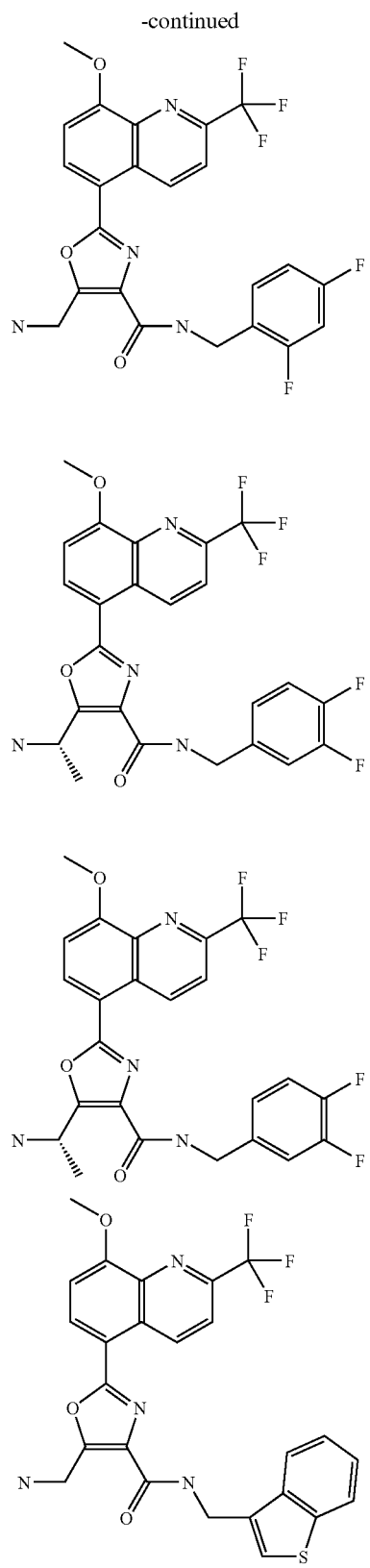

849
-continued
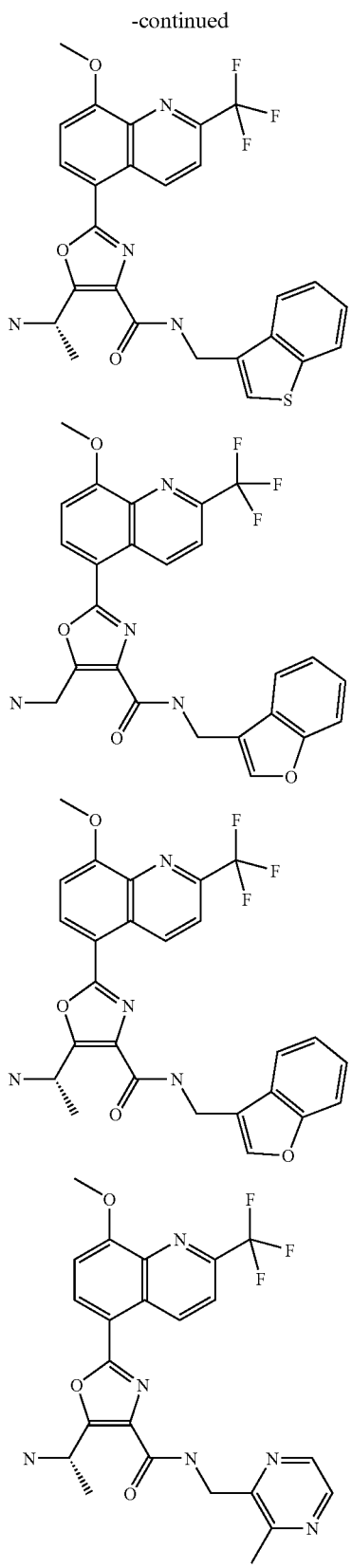
850
-continued
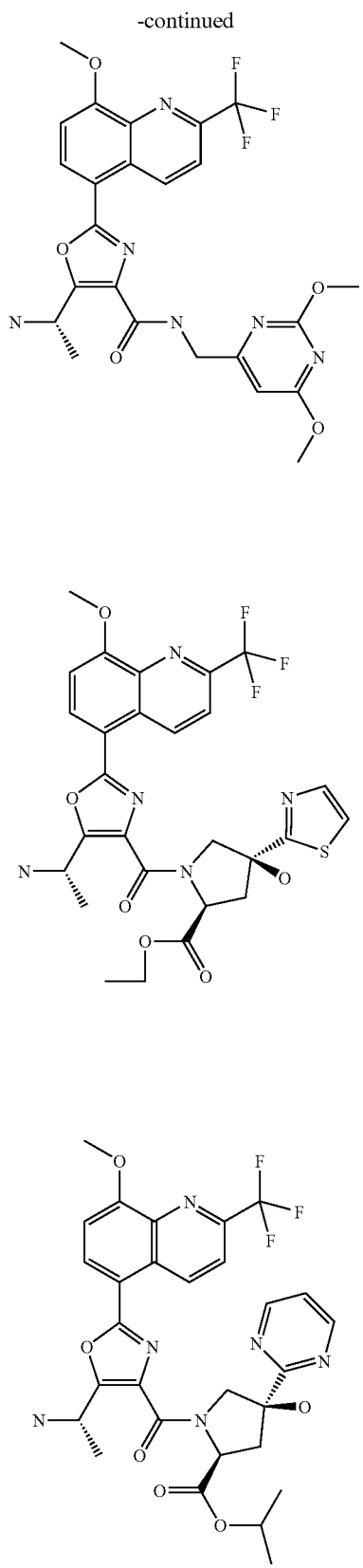

851
-continued
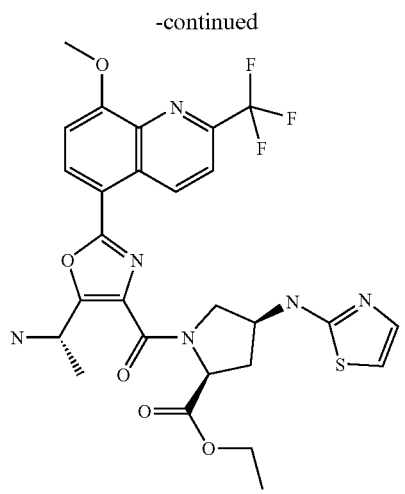
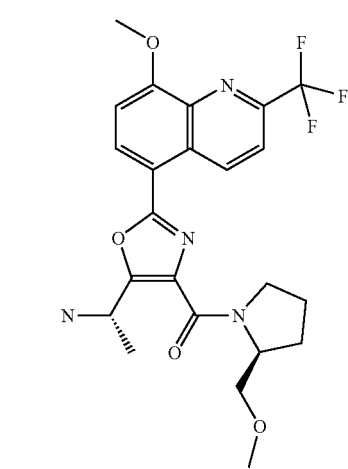
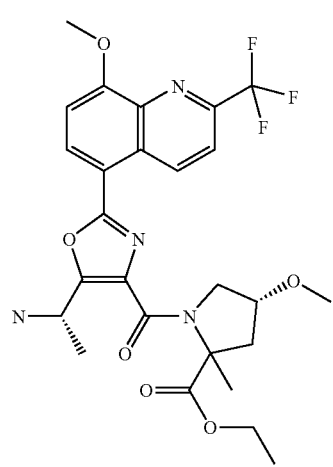
852
-continued
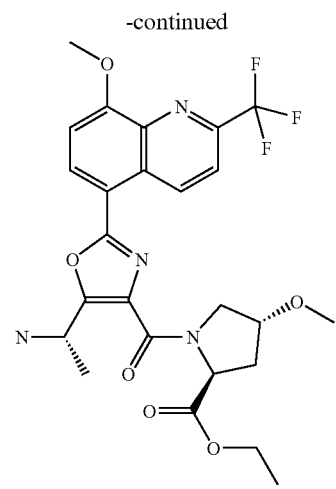
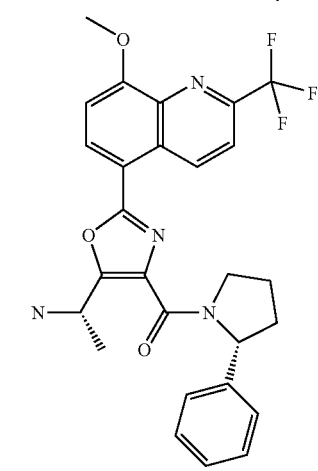
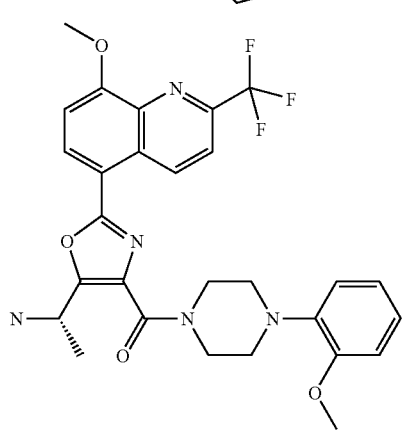
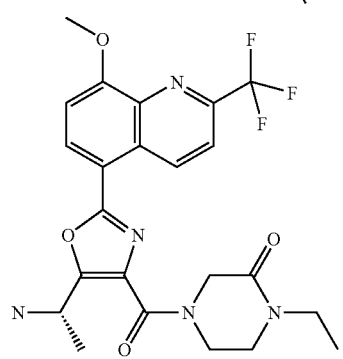

853
-continued
854
-continued
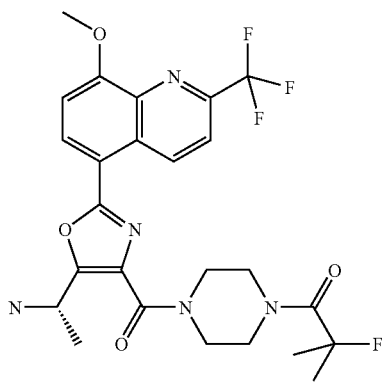
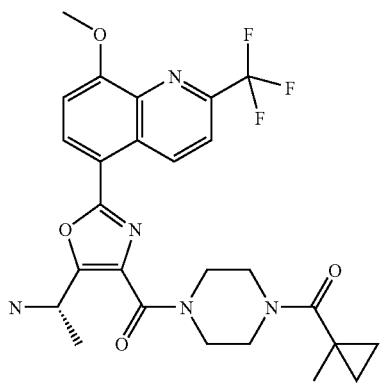

855
-continued
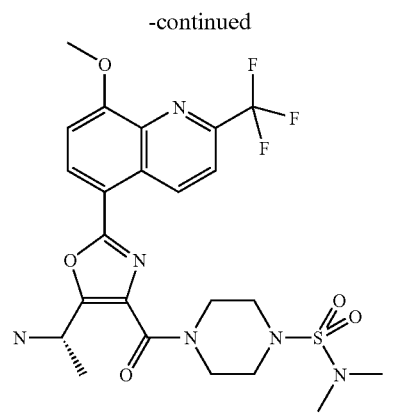
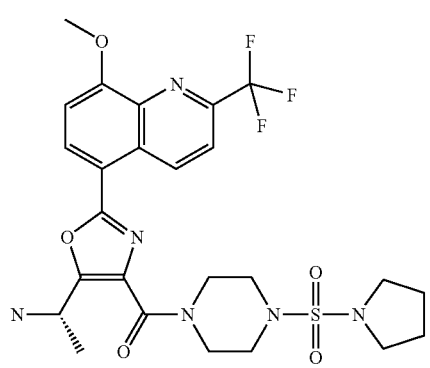
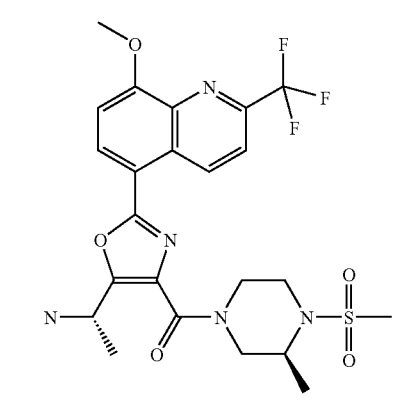
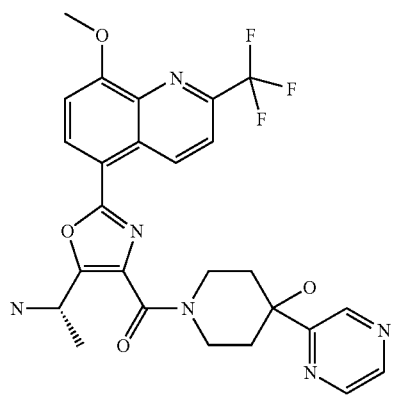
856
-continued
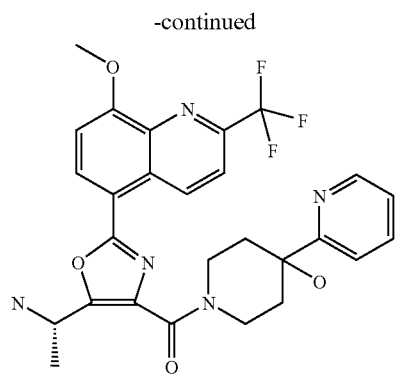
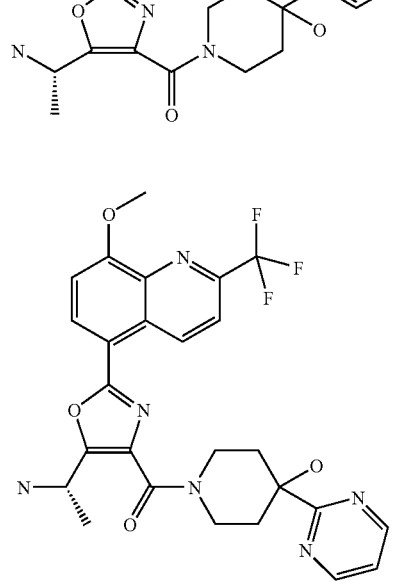
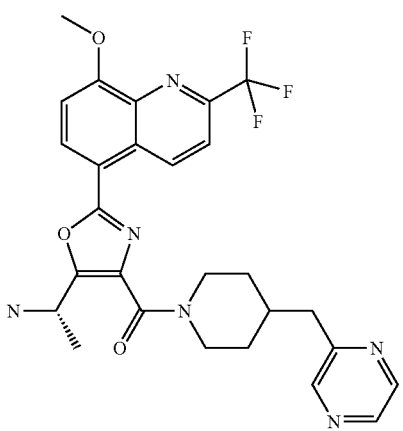
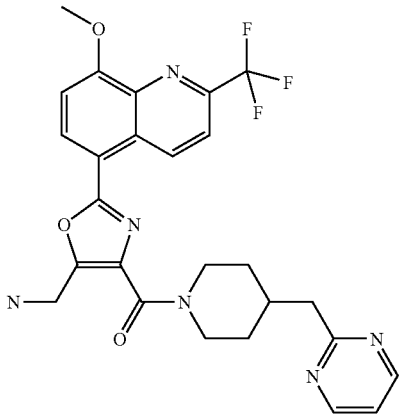

857 858
-continued -continued
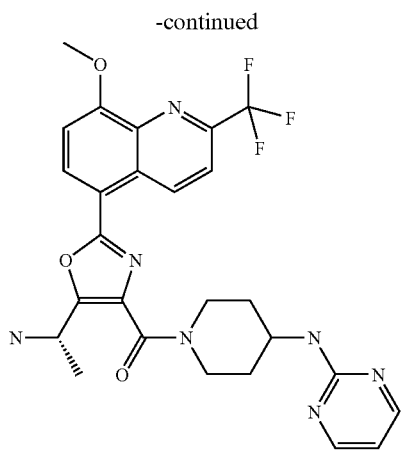
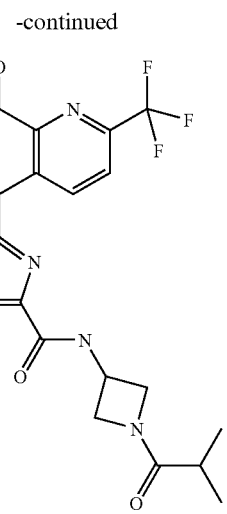
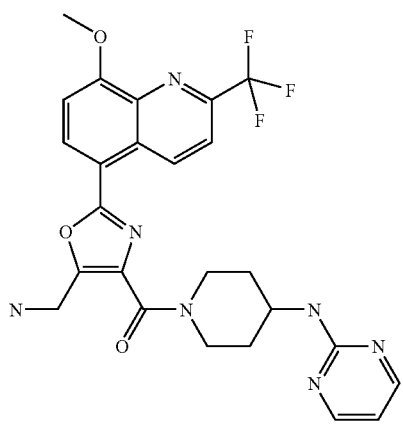
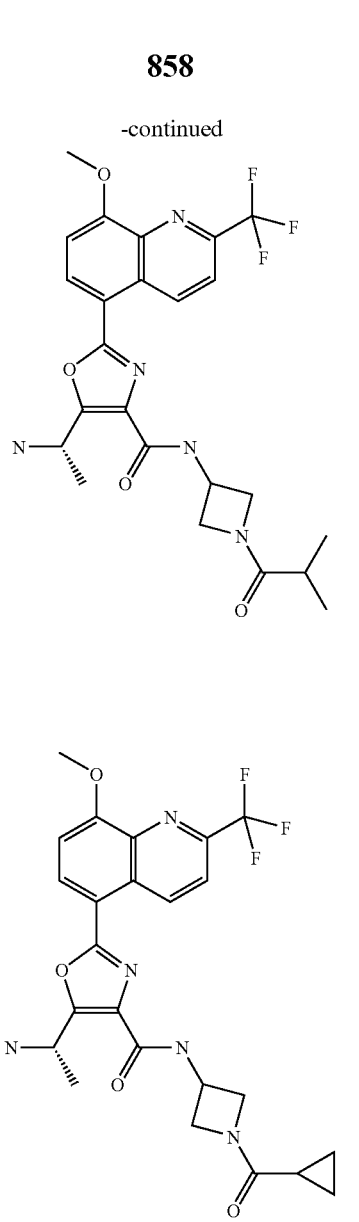
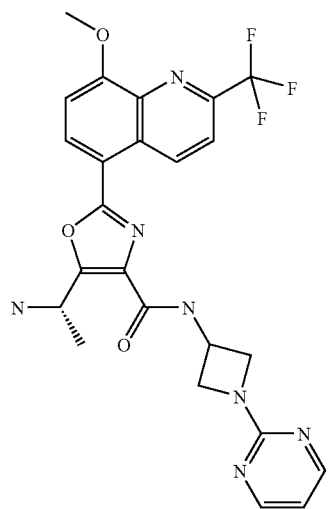
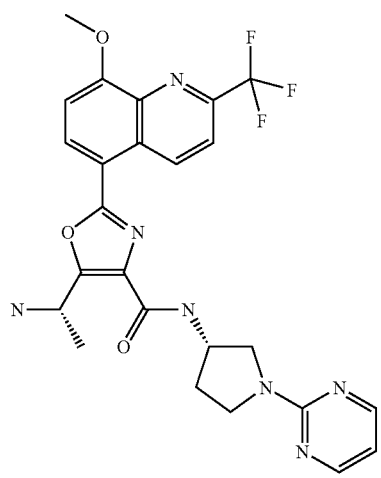

859 860
-continued -continued
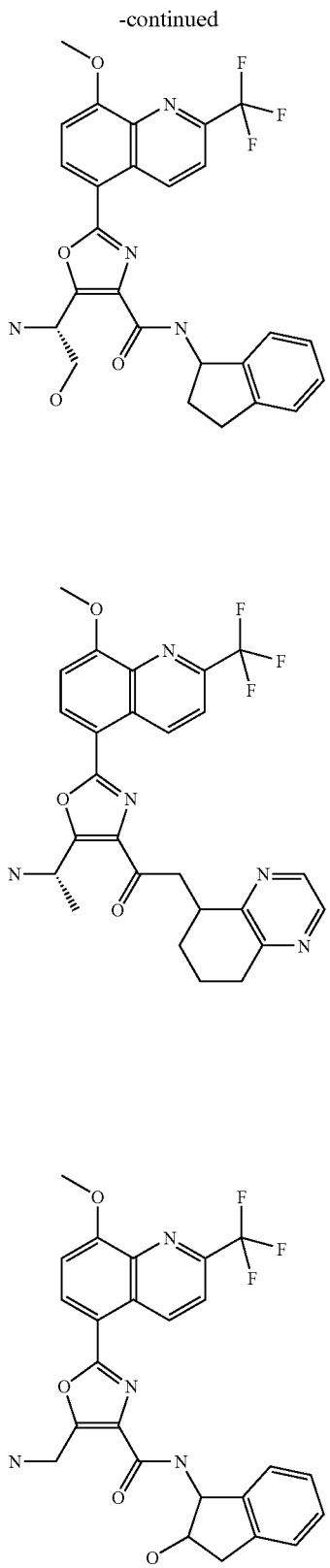
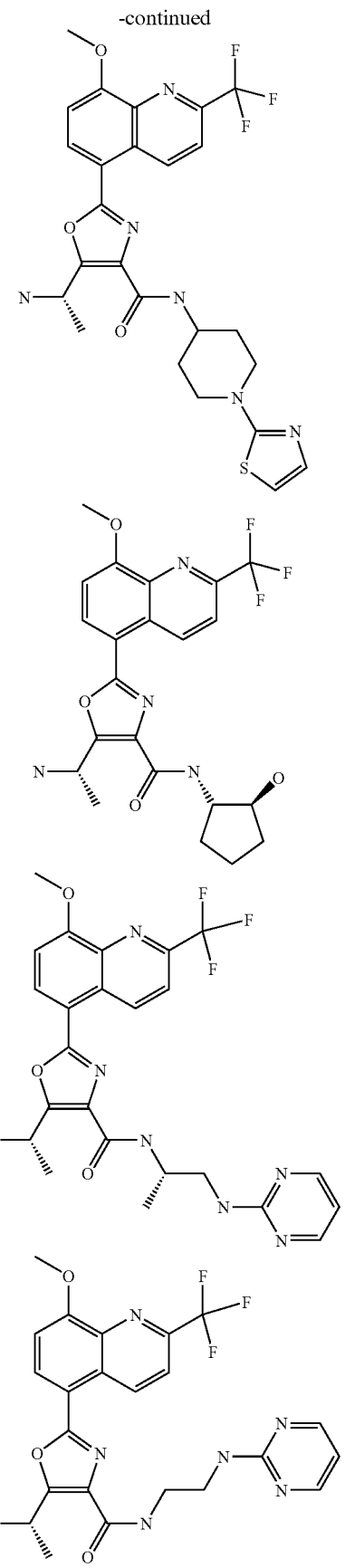

861
-continued
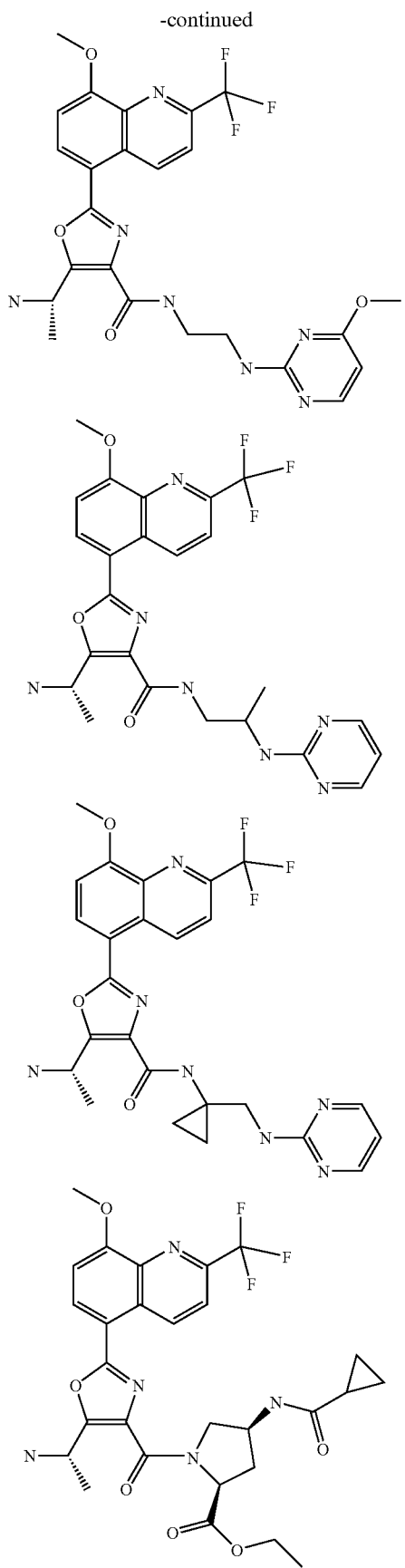
862
-continued
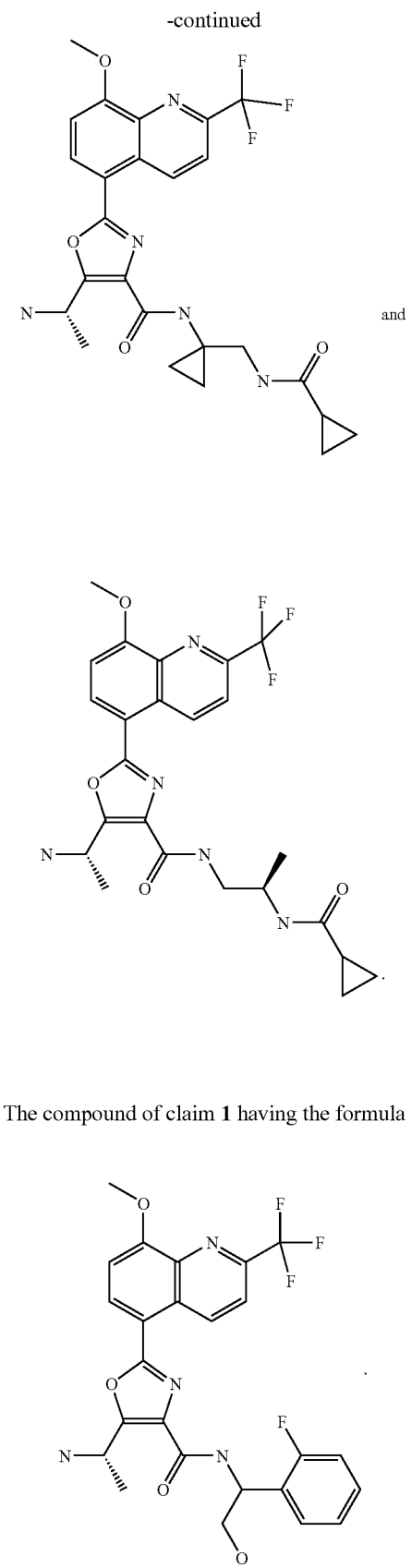
and
17. The compound of claim 1 having the formula
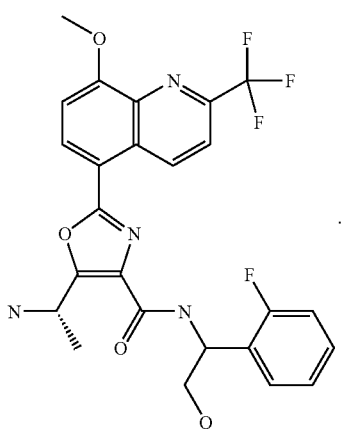

18. The compound of claim 1 having the formula
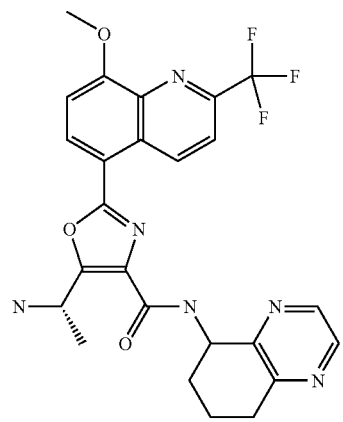
19. The compound of claim 1 having the formula
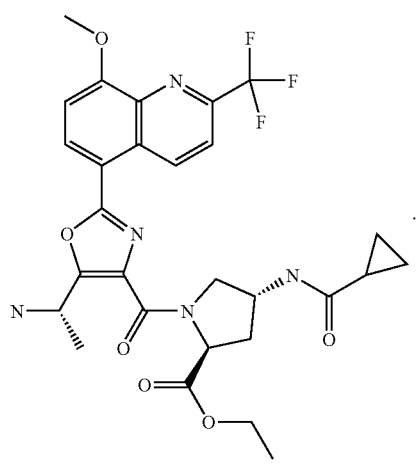
20. The compound of claim 1 having the formula
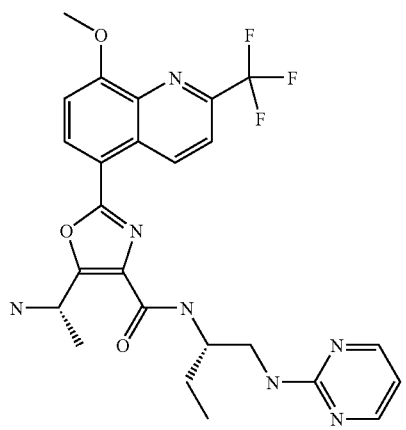
21. The compound of claim 1 having the formula
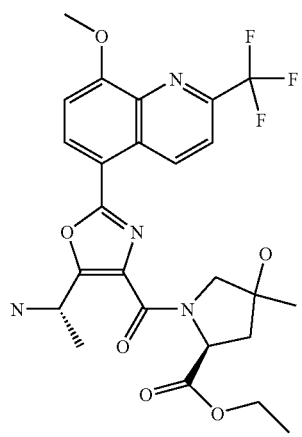
22. The compound of claim 1 having the formula
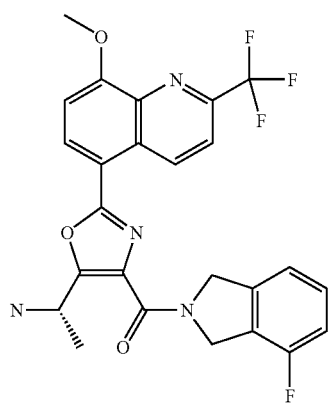
23. The compound of claim 1 having the formula
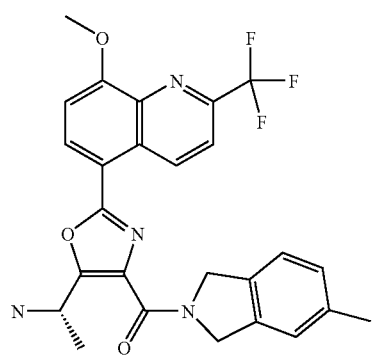

24. The compound of claim 1 having the formula

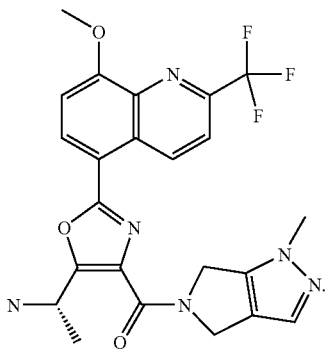

25. The compound of claim 1 having the formula

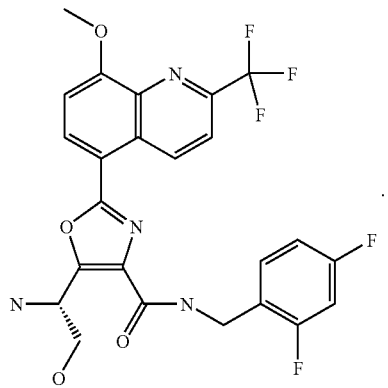

26. A pharmaceutical composition comprising an effective amount of a compound of claim 1 and a pharmaceutically acceptable carrier.

27. A method of treating a PDE4 mediated disease, where the disease is selected from COPD asthma, depression or multiple sclerosis comprising administering an effective amount of a compound of claim 1 to a patient in need of such treatment.

28. The method of claim 27 for treating dermatitis in dogs.

29. The method of claim 27 further comprising administering to said patient the compound of formula I in combination with at least one other medicament selected from the group consisting of disease modifying antirheumatic drugs, nonsteroidal anitinflammatory drugs, COX-2 selective inhibitors, COX-1 inhibitors, Immunosuppressives, steroids, biological response modifiers and other anti-inflammatory agents or therapeutics useful for the treatment of PDE4 mediated diseases.

* * * * *